(12) United States Patent
Boloor et al.

(10) Patent No.: US 9,815,828 B2
(45) Date of Patent: *Nov. 14, 2017

(54) HISTONE DEMETHYLASE INHIBITORS

(71) Applicant: CELGENE QUANTICEL RESEARCH, INC., San Diego, CA (US)

(72) Inventors: Amogh Boloor, San Diego, CA (US); Young K. Chen, San Marcos, CA (US); Michael Brennan Wallace, San Diego, CA (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/402,100

(22) Filed: Jan. 9, 2017

(65) Prior Publication Data
US 2017/0114055 A1    Apr. 27, 2017

Related U.S. Application Data

(63) Continuation of application No. 15/220,118, filed on Jul. 26, 2016, now Pat. No. 9,586,902, which is a continuation of application No. 14/963,754, filed on Dec. 9, 2015, now Pat. No. 9,447,046, which is a continuation of application No. 14/751,007, filed on Jun. 25, 2015, now Pat. No. 9,242,968.

(60) Provisional application No. 62/017,201, filed on Jun. 25, 2014.

(51) Int. Cl.
| | |
|---|---|
| *C07D 401/12* | (2006.01) |
| *C07D 405/12* | (2006.01) |
| *C07D 405/14* | (2006.01) |
| *C07D 409/14* | (2006.01) |
| *C07D 417/14* | (2006.01) |
| *C07D 213/79* | (2006.01) |
| *C07D 403/12* | (2006.01) |
| *C07D 403/14* | (2006.01) |
| *C07D 413/12* | (2006.01) |
| *C07D 417/12* | (2006.01) |
| *C07D 409/12* | (2006.01) |

(52) U.S. Cl.
CPC ......... *C07D 417/14* (2013.01); *C07D 213/79* (2013.01); *C07D 401/12* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 7,897,612 B2 | 3/2011 | Fitch et al. | |
| 8,034,811 B2 | 10/2011 | Fensholdt et al. | |
| 8,952,151 B2 | 2/2015 | Chen et al. | |
| 9,085,534 B2 | 7/2015 | Chen et al. | |
| 9,242,968 B2 | 1/2016 | Boloor et al. | |
| 2004/0106599 A1 | 6/2004 | Delorme et al. | |
| 2014/0080802 A1 | 3/2014 | Holson et al. | |
| 2014/0171432 A1 | 6/2014 | Kanouni et al. | |
| 2015/0291529 A1 | 10/2015 | Chen et al. | |

FOREIGN PATENT DOCUMENTS

| | | | |
|---|---|---|---|
| WO | 2006/002383 A2 | 1/2006 | |
| WO | 2012/052390 A1 | 4/2012 | |
| WO | 2013/143597 A1 | 10/2013 | |
| WO | 2014/089368 A1 | 6/2014 | |
| WO | 2014/100818 A1 | 6/2014 | |

OTHER PUBLICATIONS

Berge et al., "Pharmaceutical Salts," Journal of Pharmaceutical Sciences 66(1):1-19 (Jan. 1977).
Bundgard et al., Design of Prodrugs, pp. 7-9, 21-24 (1985).
Higuchi et al., "Pro-drugs as Novel Delivery Systems," A.C.S. Symposium Series, vol. 14 (1975).
Klose et al., "JmjC-domain-containing proteins and histone demethylation," Nature Reviews Genetics 7:715-727 (Sep. 2006).
Lachner et al., "An epigenetic road map for histone lysine methylation," Journal of Cell Sicence 116:2117-2124 (Jun. 1, 2003).
Lin et al., Loss of the retinoblastoma binding protein 2 (RBP2) histone demethylase suppresses tumorigenesis in mice lacking RB1 or Men1.PNAS108(33):13379-13386 (2011).
Mangueron et al., "The key to development: interpreting the histone code?," Current Opinion Genet. Dev. 15:163-176 (2005).
International Preliminary Report on Patentability, dated Jul. 2, 2015, issued in PCT/US2013/077539, filed Dec. 23, 2013.
International Search Report and Written Opinion, dated Apr. 28, 2014, issued in PCT/US2013/077539, filed Dec. 23, 2013.
International Search Report and Written Opinion, dated Sep. 30, 2015, issued in PCT/US2015/37812, filed Jun. 25, 2015.
Stahl et al., Handbook of Pharmaceutical Salts. Verlag Helvetica Chimica Acta, Zurich (2002).

*Primary Examiner* — Timothy R Rozof
(74) *Attorney, Agent, or Firm* — Wiley Rein LLP

(57) ABSTRACT

The present disclosure relates generally to compositions and methods for treating cancer and neoplastic disease. Provided herein are substituted pyridine derivative compounds and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like.

36 Claims, No Drawings

HISTONE DEMETHYLASE INHIBITORS

CROSS-REFERENCE

This application is a continuation of U.S. patent application Ser. No. 15/220,118, filed Jul. 26, 2016, which is a continuation of U.S. patent application Ser. No. 14/963,754, filed Dec. 9, 2015, which is a continuation of U.S. patent application Ser. No. 14/751,007, filed Jun. 25, 2015, which claims the benefit of U.S. Provisional Application No. 62/017,201, filed Jun. 25, 2014, which are incorporated herein by reference in their entirety.

BACKGROUND

A need exists in the art for an effective treatment of cancer and neoplastic disease.

BRIEF SUMMARY OF THE INVENTION

Provided herein are substituted pyridine derivative compounds and pharmaceutical compositions comprising said compounds. The subject compounds and compositions are useful for inhibition of histone demethylase. Furthermore, the subject compounds and compositions are useful for the treatment of cancer, such as prostate cancer, breast cancer, bladder cancer, lung cancer and/or melanoma and the like. The substituted pyridine derivative compounds described herein are based upon a disubstituted pyridine ring bearing at the 4-position a carboxylic acid, a carboxylic acid ester, or a carboxylic acid bioisostere thereof, and at the 3-position a substituted amino group.

One embodiment provides a compound, or a stereoisomer or pharmaceutically acceptable salt thereof, having the structure of Formula (I):

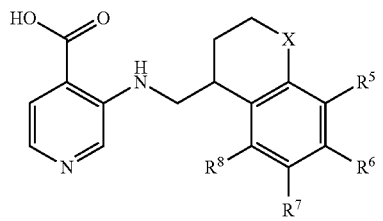

wherein,

X is O or $CH_2$;

each $R^5$, $R^6$, $R^7$ and $R^8$ is independently chosen from hydrogen, optionally substituted heterocyclyl, optionally substituted heterocyclyloxy, optionally substituted heterocyclylalkyl, optionally substituted heterocyclylalkoxy, optionally substituted $C_6$-$C_{10}$ aryl-$SO_2$—, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—;

with the provision that at least one of $R^5$, $R^6$, $R^7$ or $R^8$ is not hydrogen.

One embodiment provides a compound, or a stereoisomer or pharmaceutically acceptable salt thereof, having the structure of Formula (II):

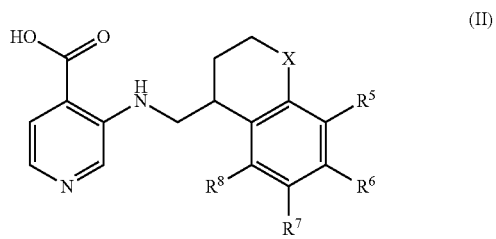

wherein,

X is O or $CH_2$;

$R^6$ is chosen from optionally substituted heterocyclyl, optionally substituted heterocyclyloxy, optionally substituted heterocyclylalkyl, optionally substituted heterocyclylalkoxy, optionally substituted $C_6$-$C_{10}$ aryl-$SO_2$—, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—; and each $R^5$, $R^7$ and $R^8$ is independently chosen from hydrogen, halogen, —OH, —CN, optionally substituted $C_1$-$C_6$ alkyl, optionally substituted $C_1$-$C_6$ alkoxy, optionally substituted $C_3$-$C_7$ carbocyclyl, optionally substituted $C_3$-$C_7$ carbocyclyloxy, optionally substituted $C_4$-$C_{12}$ carbocyclylalkyl, optionally substituted $C_4$-$C_{12}$ carbocyclylalkoxy, optionally substituted $C_1$-$C_6$ alkynyl, optionally substituted $C_1$-$C_6$ alkenyl, optionally substituted $C_6$-$C_{10}$ aryl, optionally substituted $C_6$-$C_{10}$ aryloxy, optionally substituted $C_6$-$C_{10}$ aryl-S—, optionally substituted $C_7$-$C_{14}$ aralkoxy, optionally substituted heteroaryl, and optionally substituted heteroaryloxy, optionally substituted heterocyclyl, optionally substituted heterocyclyloxy, substituted heterocyclylalkyl, optionally substituted heterocyclylalkoxy, optionally substituted $C_6$-$C_{10}$ aryl-$SO_2$—, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—;

with the provision that at least one of $R^5$, $R^7$ and $R^8$ is hydrogen.

One embodiment provides the compound of Formula (II), or pharmaceutically acceptable salt thereof, having the structure of Formula (IIa):

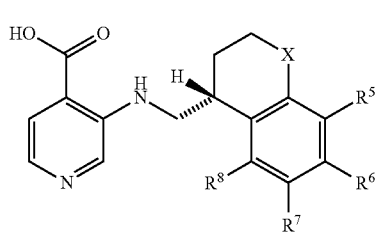

(IIa)

wherein,

X is O or CH$_2$;

R$^6$ is chosen from optionally substituted heterocyclyl, optionally substituted heterocyclyloxy, optionally substituted heterocyclylalkyl, optionally substituted heterocyclylalkoxy, optionally substituted C$_6$-C$_{10}$ aryl-SO$_2$—, optionally substituted heteroaryl-S—, or —N(R$^1$)(R$^2$), wherein R$^1$ is hydrogen or optionally substituted alkyl, and R$^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—; and each R$^5$, R$^7$ and R$^8$ is independently chosen from hydrogen, halogen, —OH, —CN, optionally substituted C$_1$-C$_6$ alkyl, optionally substituted C$_1$-C$_6$ alkoxy, optionally substituted C$_3$-C$_7$ carbocyclyl, optionally substituted C$_3$-C$_7$ carbocyclyloxy, optionally substituted C$_4$-C$_{12}$ carbocyclylalkyl, optionally substituted C$_4$-C$_{12}$ carbocyclylalkoxy, optionally substituted C$_1$-C$_6$ alkynyl, optionally substituted C$_1$-C$_6$ alkenyl, optionally substituted C$_6$-C$_{10}$ aryl, optionally substituted C$_6$-C$_{10}$ aryloxy, optionally substituted C$_6$-C$_{10}$ aryl-S—, optionally substituted C$_7$-C$_{14}$ aralkoxy, optionally substituted heteroaryl, and optionally substituted heteroaryloxy, optionally substituted heterocyclyl, optionally substituted heterocyclyloxy, substituted heterocyclylalkyl, optionally substituted heterocyclylalkoxy, optionally substituted C$_6$-C$_{10}$ aryl-SO$_2$—, optionally substituted heteroaryl-S—, or —N(R$^1$)(R$^2$), wherein R$^1$ is hydrogen or optionally substituted alkyl, and R$^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—;

with the provision that at least one of R$^5$, R$^7$ and R$^8$ is hydrogen.

One embodiment provides a compound, or a stereoisomer or pharmaceutically acceptable salt thereof, having the structure of Formula (III):

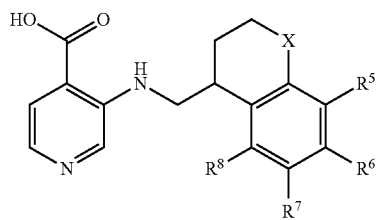

(III)

wherein,

X is O or CH$_2$;

at least one of R$^5$, R$^6$, R$^7$ and R$^8$ is chosen from optionally substituted heterocyclyl, optionally substituted heterocyclyloxy, optionally substituted heterocyclylalkyl, optionally substituted heterocyclylalkoxy, optionally substituted C$_6$-C$_{10}$ aryl-SO$_2$—, optionally substituted heteroaryl-S—, or —N(R$^1$)(R$^2$), wherein R$^1$ is hydrogen or optionally substituted alkyl, and R$^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—; and the remaining R$^5$, R$^6$, R$^7$ and R$^8$ groups are independently chosen from hydrogen, halogen, —OH, —CN, optionally substituted C$_1$-C$_6$ alkyl, optionally substituted C$_1$-C$_6$ alkoxy, optionally substituted C$_3$-C$_7$ carbocyclyl, optionally substituted C$_3$-C$_7$ carbocyclyloxy, optionally substituted C$_4$-C$_{12}$ carbocyclylalkyl, optionally substituted C$_4$-C$_{12}$ carbocyclylalkoxy, optionally substituted C$_1$-C$_6$ alkynyl, optionally substituted C$_1$-C$_6$ alkenyl, optionally substituted C$_6$-C$_{10}$ aryl, optionally substituted C$_6$-C$_{10}$ aryloxy, optionally substituted C$_6$-C$_{10}$ aryl-S—, optionally substituted C$_7$-C$_{14}$ aralkoxy, optionally substituted heteroaryl, and optionally substituted heteroaryloxy, optionally substituted heterocyclyl, optionally substituted heterocyclyloxy, substituted heterocyclylalkyl, optionally substituted heterocyclylalkoxy, optionally substituted C$_6$-C$_{10}$ aryl-SO$_2$—, optionally substituted heteroaryl-S—, or —N(R$^1$)(R$^2$), wherein R$^1$ is hydrogen or optionally substituted alkyl, and R$^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

One embodiment provides a compound, or a stereoisomer or pharmaceutically acceptable salt thereof, having the structure of Formula (V):

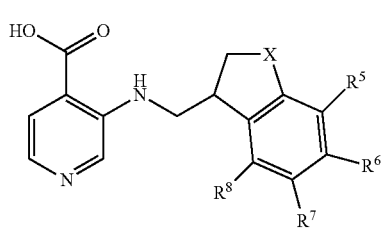

(V)

wherein,

X is O or $CH_2$;

$R^6$ is chosen from optionally substituted heterocyclyl, optionally substituted heterocyclyloxy, optionally substituted heterocyclylalkyl, optionally substituted heterocyclylalkoxy, optionally substituted $C_6$-$C_{10}$ aryl-$SO_2$—, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—; and each $R^5$, $R^7$ and $R^8$ is independently chosen from hydrogen, halogen, —OH, —CN, optionally substituted $C_1$-$C_6$ alkyl, optionally substituted $C_1$-$C_6$ alkoxy, optionally substituted $C_3$-$C_7$ carbocyclyl, optionally substituted $C_3$-$C_7$ carbocyclyloxy, optionally substituted $C_4$-$C_{12}$ carbocyclylalkyl, optionally substituted $C_4$-$C_{12}$ carbocyclylalkoxy, optionally substituted $C_1$-$C_6$ alkynyl, optionally substituted $C_1$-$C_6$ alkenyl, optionally substituted $C_6$-$C_{10}$ aryl, optionally substituted $C_6$-$C_{10}$ aryloxy, optionally substituted $C_6$-$C_{10}$ aryl-S—, optionally substituted $C_7$-$C_{14}$ aralkoxy, optionally substituted heteroaryl, and optionally substituted heteroaryloxy, optionally substituted heterocyclyl, optionally substituted heterocyclyloxy, substituted heterocyclylalkyl, optionally substituted heterocyclylalkoxy, optionally substituted $C_6$-$C_{10}$ aryl-$SO_2$—, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—;

with the provision that at least one of $R^5$, $R^7$ and $R^8$ is hydrogen.

One embodiment provides a pharmaceutical composition comprising a pharmaceutically acceptable carrier and a substituted pyridine derivative compound as described herein, or a stereoisomer or pharmaceutically acceptable salt thereof.

One embodiment provides a method of inhibiting a histone demethylase enzyme comprising contacting the histone demethylase enzyme with a substituted pyridine derivative compound as described herein, or a stereoisomer thereof.

One embodiment provides a method of treating cancer in a subject in need thereof, comprising administering to the subject a composition comprising a substituted pyridine derivative compound as described herein, or a stereoisomer, or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the $NH_2$ radical.

"Cyano" refers to the —CN radical.

"Nitro" refers to the —$NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Hydrazine" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises two to ten carbon atoms (e.g., $C_2$-$C_{10}$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (isobutyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$) S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$) S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula O—$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$) S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$) S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

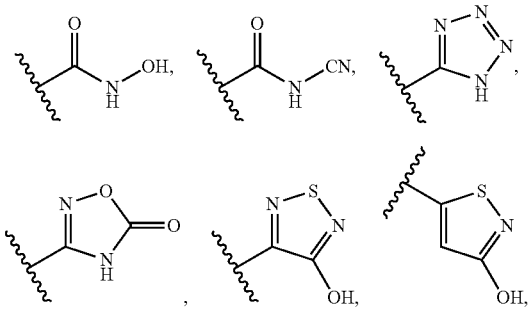

(e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "stereoisomer" refers to a compound made up of the same atoms bonded by the same bonds but having different three-dimensional structures, which are not interchangeable. It is contemplated that the disclosure provided herein encompasses the various stereoisomers and mixtures thereof and includes "enantiomers," which refers to two stereoisomers whose molecular structures are nonsuperimposeable mirror images of one another.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. 000000Some examples of tautomeric equilibrium include:

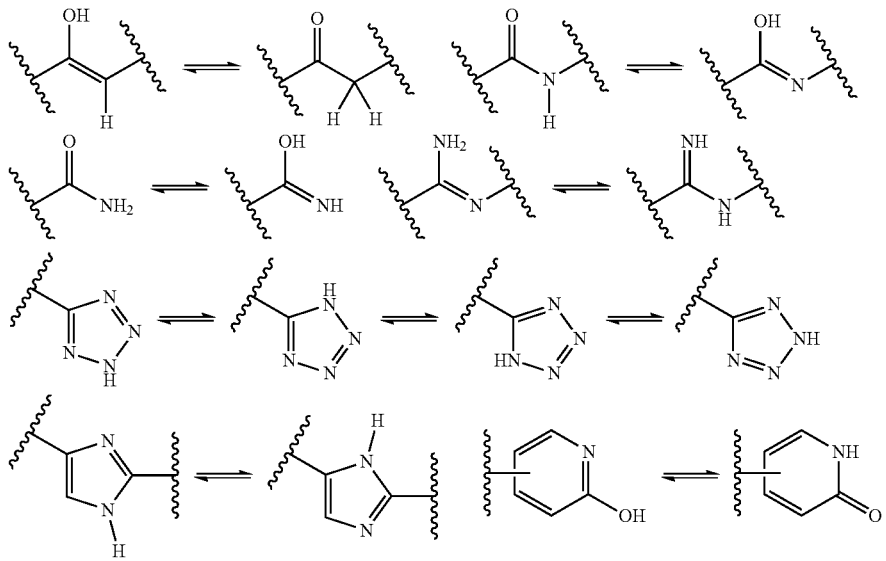

-continued

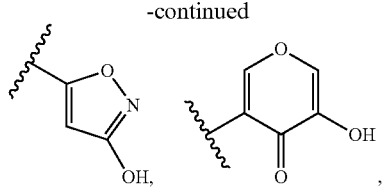

and the like.

The compounds, or their pharmaceutically acceptable salts, in some instances, contain one or more asymmetric centers and thus give rise to enantiomers, diastereomers, and other stereoisomeric forms that are defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers "Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted pyridine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Pyridine Derivative Compounds

Substituted pyridine derivative compounds are described herein that inhibit a histone demethylase enzyme. These compounds, and compositions comprising these compounds, are useful for the treatment of cancer and neoplastic disease. The compounds described herein, in some embodiments, are useful for treating prostate cancer, breast cancer, bladder cancer, lung cancer and/or melanoma and the like.

One embodiment provides a compound, or a stereoisomer or pharmaceutically acceptable salt thereof, having the structure of Formula (I):

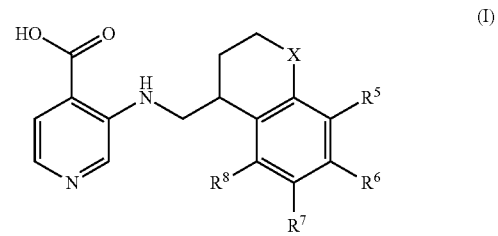

wherein,
X is O or $CH_2$;
each $R^5$, $R^6$, $R^7$ and $R^8$ is independently chosen from hydrogen, optionally substituted heterocyclyl, optionally substituted heterocyclyloxy, optionally substituted heterocyclylalkyl, optionally substituted heterocyclylalkoxy, optionally substituted $C_6$-$C_{10}$ aryl-$SO_2$—, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—;

with the provision that at least one of $R^5$, $R^6$, $R^7$ or $R^8$ is not hydrogen.

Another embodiment provides the compound, or a stereoisomer or pharmaceutically acceptable salt thereof, of Formula (I), wherein X is O. Another embodiment provides the compound, or a stereoisomer or pharmaceutically acceptable salt thereof, of Formula (I), wherein X is $CH_2$. Another embodiment provides the compound, or a stereoisomer or pharmaceutically acceptable salt thereof, of Formula (I), wherein $R^5$ is hydrogen. Another embodiment provides the compound, or a stereoisomer or pharmaceutically acceptable salt thereof, of Formula (I), wherein $R^7$ is hydrogen. Another embodiment provides the compound, or a stereoisomer or pharmaceutically acceptable salt thereof, of Formula (I), wherein $R^8$ is hydrogen. Another embodiment provides the compound, or a stereoisomer or pharmaceutically acceptable salt thereof, of Formula (I), wherein $R^7$ and $R^8$ are hydrogen. Another embodiment provides the compound, or a stereoisomer or pharmaceutically acceptable salt thereof, of Formula (I), wherein $R^6$ is not hydrogen.

One embodiment provides a compound, or a stereoisomer or pharmaceutically acceptable salt thereof, having the structure of Formula (II):

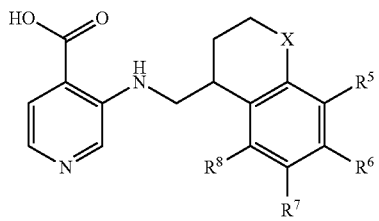

(II)

wherein,

X is O or $CH_2$;

$R^6$ is chosen from optionally substituted heterocyclyl, optionally substituted heterocyclyloxy, optionally substituted heterocyclylalkyl, optionally substituted heterocyclylalkoxy, optionally substituted $C_6$-$C_{10}$ aryl-$SO_2$—, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—; and each $R^5$, $R^7$ and $R^8$ is independently chosen from hydrogen, halogen, —OH, —CN, optionally substituted $C_1$-$C_6$ alkyl, optionally substituted $C_1$-$C_6$ alkoxy, optionally substituted $C_3$-$C_7$ carbocyclyl, optionally substituted $C_3$-$C_7$ carbocyclyloxy, optionally substituted $C_4$-$C_{12}$ carbocyclylalkyl, optionally substituted $C_4$-$C_{12}$ carbocyclylalkoxy, optionally substituted $C_1$-$C_6$ alkynyl, optionally substituted $C_1$-$C_6$ alkenyl, optionally substituted $C_6$-$C_{10}$ aryl, optionally substituted $C_6$-$C_{10}$ aryloxy, optionally substituted $C_6$-$C_{10}$ aryl-S—, optionally substituted $C_7$-$C_{14}$ aralkoxy, optionally substituted heteroaryl, and optionally substituted heteroaryloxy, optionally substituted heterocyclyl, optionally substituted heterocyclyloxy, substituted heterocyclylalkyl, optionally substituted heterocyclylalkoxy, optionally substituted $C_6$-$C_{10}$ aryl-$SO_2$—, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—;

with the provision that at least one of $R^5$, $R^7$ and $R^8$ is hydrogen.

Another embodiment provides the compound, or a stereoisomer or pharmaceutically acceptable salt thereof, of Formula (II), wherein X is O. Another embodiment provides the compound, or a stereoisomer or pharmaceutically acceptable salt thereof, of Formula (II), wherein X is $CH_2$. Another embodiment provides the compound, or a stereoisomer or pharmaceutically acceptable salt thereof, of Formula (II), wherein each $R^5$, $R^7$ and $R^8$ is independently chosen from hydrogen, halogen, —OH, —CN, optionally substituted $C_1$-$C_6$ alkyl, or optionally substituted $C_1$-$C_6$ alkoxy.

Another embodiment provides the compound, or a stereoisomer or pharmaceutically acceptable salt thereof, of Formula (II), wherein $R^5$ is hydrogen. Another embodiment provides the compound, or a stereoisomer or pharmaceutically acceptable salt thereof, of Formula (II), wherein $R^7$ is hydrogen. Another embodiment provides the compound, or a stereoisomer or pharmaceutically acceptable salt thereof, of Formula (II), wherein $R^8$ is hydrogen. Another embodiment provides the compound, or a stereoisomer or pharmaceutically acceptable salt thereof, of Formula (II), wherein $R^7$ and $R^8$ are hydrogen. Another embodiment provides the compound, or a stereoisomer or pharmaceutically acceptable salt thereof, of Formula (II), wherein $R^6$ is not hydrogen.

Another embodiment provides the compound, or a stereoisomer or pharmaceutically acceptable salt thereof, of Formula (II), wherein $R^6$ is optionally substituted heterocyclyl. Another embodiment provides the compound, or a stereoisomer or pharmaceutically acceptable salt thereof, of Formula (II), wherein $R^6$ is optionally substituted heterocyclyloxy. Another embodiment provides the compound, or a stereoisomer or pharmaceutically acceptable salt thereof, of Formula (II), wherein $R^6$ is optionally substituted heterocyclylalkyl. Another embodiment provides the compound, or a stereoisomer or pharmaceutically acceptable salt thereof, of Formula (II), wherein $R^6$ is optionally substituted heterocyclylalkoxy. Another embodiment provides the compound, or a stereoisomer or pharmaceutically acceptable salt thereof, of Formula (II), wherein $R^6$ is optionally substituted $C_6$-$C_{10}$ aryl-$SO_2$—, or optionally substituted heteroaryl-S—.

Another embodiment provides the compound, or a stereoisomer or pharmaceutically acceptable salt thereof, of Formula (II), wherein $R^6$ is —N($R^1$)($R^2$), wherein $R^1$ is hydrogen and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—. Another embodiment provides the compound, or a stereoisomer or pharmaceutically acceptable salt thereof, of Formula (II), wherein $R^6$ is —N($R^1$)($R^2$), wherein $R^1$ is optionally substituted alkyl and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—. Another embodiment provides the compound, or a stereoisomer or pharmaceutically acceptable salt thereof, of Formula (II), wherein $R^6$ is —N($R^1$)($R^2$), and $R^2$ is optionally substituted alkyl. Another embodiment provides the compound, or a stereoisomer or pharmaceutically acceptable salt thereof, of Formula (II), wherein $R^6$ is —N($R^1$)($R^2$), and $R^2$ is optionally substituted aryl. Another embodiment provides the compound, or a stereoisomer or pharmaceutically acceptable salt thereof, of Formula (II), wherein $R^6$ is —N($R^1$)($R^2$), and $R^2$ is optionally substituted heteroaryl. Another embodiment provides the compound, or a stereoisomer or pharmaceutically acceptable salt thereof, of Formula (II), wherein $R^6$ is —N($R^1$)($R^2$), and $R^2$ is optionally substituted heterocyclyl. Another embodiment provides the compound, or a stereoisomer or pharmaceutically acceptable salt thereof, of Formula (II), wherein $R^6$ is —N($R^1$)($R^2$), and $R^2$ is optionally substituted cycloalkyl. Another embodiment provides the compound, or a stereoisomer or pharmaceutically acceptable salt thereof, of Formula (II), wherein $R^6$ is —N($R^1$)($R^2$), and $R^2$ is optionally substituted cycloalkylalkyl. Another embodiment provides the compound, or a stereoisomer or pharmaceutically acceptable salt thereof, of Formula (II), wherein $R^6$ is —N($R^1$)($R^2$), and $R^2$ is optionally substituted aryl-CO—. Another embodiment provides the compound, or a stereoisomer or pharmaceutically acceptable salt thereof, of Formula (II), wherein $R^6$ is —N($R^1$)($R^2$), and $R^2$ is optionally substituted heteroaryl-CO—. Another embodiment provides the compound, or a stereoisomer or pharmaceutically acceptable salt thereof, of Formula (II), wherein $R^6$ is —N($R^1$)($R^2$), and $R^2$ is optionally substituted cycloalkyl-CO—. Another embodiment provides the compound, or a stereoisomer or pharmaceutically acceptable salt thereof, of Formula (II), wherein $R^6$ is —N($R^1$)($R^2$), and $R^2$ is optionally substituted alkyl-CO—.

One embodiment provides the compound of Formula (II), or pharmaceutically acceptable salt thereof, having the structure of Formula (IIa):

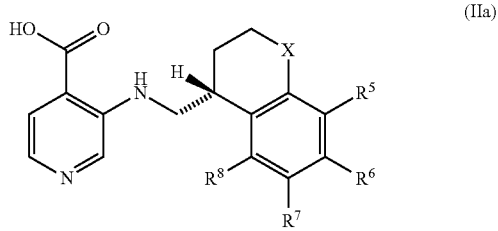

(IIa)

wherein,

X is O or $CH_2$;

$R^6$ is chosen from optionally substituted heterocyclyl, optionally substituted heterocyclyloxy, optionally substituted heterocyclylalkyl, optionally substituted heterocyclylalkoxy, optionally substituted $C_6$-$C_{10}$ aryl-$SO_2$—, optionally substituted heteroaryl-S—, or —N($R^1$)($R^2$), wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—; and each $R^5$, $R^7$ and $R^8$ is independently chosen from hydrogen, halogen, —OH, —CN, optionally substituted $C_1$-$C_6$ alkyl, optionally substituted $C_1$-$C_6$ alkoxy, optionally substituted $C_3$-$C_7$ carbocyclyl, optionally substituted $C_3$-$C_7$ carbocyclyloxy, optionally substituted $C_4$-$C_{12}$ carbocyclylalkyl, optionally substituted $C_4$-$C_{12}$ carbocyclylalkoxy, optionally substituted $C_1$-$C_6$ alkynyl, optionally substituted $C_1$-$C_6$ alkenyl, optionally substituted $C_6$-$C_{10}$ aryl, optionally substituted $C_6$-$C_{10}$ aryloxy, optionally substituted $C_6$-$C_{10}$ aryl-S—, optionally substituted $C_7$-$C_{14}$ aralkoxy, optionally substituted heteroaryl, and optionally substituted heteroaryloxy, optionally substituted heterocyclyl, optionally substituted heterocyclyloxy, substituted heterocyclylalkyl, optionally substituted heterocyclylalkoxy, optionally substituted $C_6$-$C_{10}$ aryl-$SO_2$—, optionally substituted heteroaryl-S—, or —N($R^1$)($R^2$), wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—;

with the provision that at least one of $R^5$, $R^7$ and $R^8$ is hydrogen.

Another embodiment provides the compound of Formula (IIa), or pharmaceutically acceptable salt thereof, wherein X is O. Another embodiment provides the compound of Formula (IIa), or pharmaceutically acceptable salt thereof, wherein X is $CH_2$.

Another embodiment provides the compound of Formula (IIa), or pharmaceutically acceptable salt thereof, wherein $R^5$ is hydrogen. Another embodiment provides the compound of Formula (IIa), or pharmaceutically acceptable salt thereof, wherein $R^7$ is hydrogen. Another embodiment provides the compound of Formula (IIa), or pharmaceutically acceptable salt thereof, wherein $R^8$ is hydrogen. Another embodiment provides the compound of Formula (IIa), or pharmaceutically acceptable salt thereof, wherein $R^5$, $R^7$ and $R^8$ are hydrogen. Another embodiment provides the compound of Formula (IIa), or pharmaceutically acceptable salt thereof, wherein X is O; and $R^5$, $R^7$ and $R^8$ are hydrogen.

Another embodiment provides the compound of Formula (IIa), or pharmaceutically acceptable salt thereof, wherein $R^6$ is optionally substituted heterocyclyl, or optionally substituted heterocyclyloxy.

Another embodiment provides the compound of Formula (IIa), or pharmaceutically acceptable salt thereof, wherein $R^6$ is optionally substituted $C_6$-$C_{10}$ aryl-$SO_2$—, or optionally substituted heteroaryl-S—.

Another embodiment provides the compound of Formula (IIa), or pharmaceutically acceptable salt thereof, wherein $R^6$ is —$N(R^1)(R^2)$, wherein $R^1$ is hydrogen; and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

Another embodiment provides the compound of Formula (IIa), or pharmaceutically acceptable salt thereof, wherein $R^6$ is —$N(R^1)(R^2)$, wherein $R^1$ is optionally substituted alkyl; and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

Another embodiment provides the compound of Formula (IIa), or pharmaceutically acceptable salt thereof, wherein $R^5$, $R^7$ and $R^8$ are hydrogen; $R^6$ is —$N(R^1)(R^2)$, wherein $R^1$ is optionally substituted alkyl; and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

Another embodiment provides the compound of Formula (IIa), or pharmaceutically acceptable salt thereof, wherein $R^5$, $R^7$ and $R^8$ are hydrogen; $R^6$ is —$N(R^1)(R^2)$, wherein $R^1$ is optionally substituted alkyl; and $R^2$ is optionally substituted aryl.

Another embodiment provides the compound of Formula (IIa), or pharmaceutically acceptable salt thereof, wherein $R^5$, $R^7$ and $R^8$ are hydrogen; $R^6$ is —$N(R^1)(R^2)$, wherein $R^1$ is optionally substituted alkyl; and $R^2$ is optionally substituted heteroaryl.

Another embodiment provides the compound of Formula (IIa), or pharmaceutically acceptable salt thereof, wherein $R^5$, $R^7$ and $R^8$ are hydrogen; $R^6$ is —$N(R^1)(R^2)$, wherein $R^1$ is optionally substituted alkyl; and $R^2$ is optionally substituted heterocyclyl, optionally substituted cycloalkyl, optionally substituted cycloalkylalkyl, optionally substituted aryl-CO—, optionally substituted cycloalkyl-CO—, or optionally substituted alkyl-CO—.

Another embodiment provides the compound of Formula (IIa), or pharmaceutically acceptable salt thereof, wherein $R^5$, $R^7$ and $R^8$ are hydrogen; $R^6$ is —$N(R^1)(R^2)$, wherein $R^1$ is an optionally substituted C1-C3 alkyl; and $R^2$ is optionally substituted aryl. Another embodiment provides the compound of Formula (IIa), or pharmaceutically acceptable salt thereof, wherein X is O; $R^5$, $R^7$ and $R^8$ are hydrogen; $R^6$ is —$N(R^1)(R^2)$, wherein $R^1$ is an optionally substituted C1-C3 alkyl; and $R^2$ is optionally substituted aryl.

Another embodiment provides the compound of Formula (IIa), or pharmaceutically acceptable salt thereof, wherein $R^5$, $R^7$ and $R^8$ are hydrogen; $R^6$ is —$N(R^1)(R^2)$, wherein $R^1$ is a $CH_3$ group; and $R^2$ is optionally substituted aryl. Another embodiment provides the compound of Formula (IIa), or pharmaceutically acceptable salt thereof, wherein X is O; $R^5$, $R^7$ and $R^8$ are hydrogen; $R^6$ is —$N(R^1)(R^2)$, wherein $R^1$ is a $CH_3$ group; and $R^2$ is optionally substituted aryl.

Another embodiment provides the compound of Formula (IIa), or pharmaceutically acceptable salt thereof, wherein $R^5$, $R^7$ and $R^8$ are hydrogen; $R^6$ is —$N(R^1)(R^2)$, wherein $R^1$ is optionally substituted alkyl; and $R^2$ is optionally substituted aryl substituted with at least one substituent selected from optionally substituted C1-C5 alkyl, optionally substituted C2-C5 alkenyl, halogen, cyano, hydroxy, amino, optionally substituted C1-C5 alkoxy, optionally substituted alkylamino, optionally substituted dialkylamino, optionally substituted heterocyclyl, optionally substituted heteroaryl, optionally substituted cycloalkyl, optionally substituted cycloalkylalkyl, optionally substituted cycloalkylalkoxy, or optionally substituted cycloalkoxy. Another embodiment provides the compound of Formula (IIa), or pharmaceutically acceptable salt thereof, wherein X is O; $R^5$, $R^7$ and $R^8$ are hydrogen; $R^6$ is —$N(R^1)(R^2)$, wherein $R^1$ is optionally substituted alkyl; and $R^2$ is optionally substituted aryl substituted with at least one substituent selected from optionally substituted C1-C5 alkyl, optionally substituted C2-C5 alkenyl, halogen, cyano, hydroxy, amino, optionally substituted C1-C5 alkoxy, optionally substituted alkylamino, optionally substituted dialkylamino, optionally substituted heterocyclyl, optionally substituted heteroaryl, optionally substituted cycloalkyl, optionally substituted cycloalkylalkyl, optionally substituted cycloalkylalkoxy, or optionally substituted cycloalkoxy.

Another embodiment provides the compound of Formula (IIa), or pharmaceutically acceptable salt thereof, wherein $R^5$, $R^7$ and $R^8$ are hydrogen; $R^6$ is —$N(R^1)(R^2)$, wherein $R^1$ is optionally substituted alkyl; and $R^2$ is optionally substituted aryl substituted with at least one substituent selected from optionally substituted C1-C5 alkyl, halogen, optionally substituted C1-C5 alkoxy, optionally substituted heterocyclyl, optionally substituted heteroaryl, optionally substituted cycloalkyl, optionally substituted cycloalkylalkyl, optionally substituted cycloalkylalkoxy, or optionally substituted cycloalkoxy. Another embodiment provides the compound of Formula (IIa), or pharmaceutically acceptable salt thereof, wherein X is O; $R^5$, $R^7$ and $R^8$ are hydrogen; $R^6$ is —$N(R^1)(R^2)$, wherein $R^1$ is optionally substituted alkyl; and $R^2$ is optionally substituted aryl substituted with at least one substituent selected from optionally substituted C1-C5 alkyl, halogen, optionally substituted C1-C5 alkoxy, optionally substituted heterocyclyl, optionally substituted heteroaryl, optionally substituted cycloalkyl, optionally substituted cycloalkylalkyl, optionally substituted cycloalkylalkoxy, or optionally substituted cycloalkoxy.

Another embodiment provides the compound of Formula (IIa), or pharmaceutically acceptable salt thereof, wherein $R^5$, $R^7$ and $R^8$ are hydrogen; $R^6$ is —$N(R^1)(R^2)$, wherein $R^1$ is optionally substituted alkyl; and $R^2$ is optionally substituted aryl substituted with at least one substituent selected from optionally substituted heterocyclyl, optionally substituted heteroaryl, optionally substituted cycloalkyl, optionally substituted cycloalkylalkyl, optionally substituted cycloalkylalkoxy, or optionally substituted cycloalkoxy. Another embodiment provides the compound of Formula (IIa), or pharmaceutically acceptable salt thereof, wherein X is O; $R^5$, $R^7$ and $R^8$ are hydrogen; $R^6$ is —$N(R^1)(R^2)$, wherein $R^1$ is optionally substituted alkyl; and $R^2$ is optionally substituted aryl substituted with at least one substituent selected from optionally substituted heterocyclyl, optionally substituted heteroaryl, optionally substituted cycloalkyl, optionally substituted cycloalkylalkyl, optionally substituted cycloalkylalkoxy, or optionally substituted cycloalkoxy.

Another embodiment provides the compound of Formula (IIa), or pharmaceutically acceptable salt thereof, wherein $R^5$, $R^7$ and $R^8$ are hydrogen; $R^6$ is —N($R^1$)($R^2$), wherein $R^1$ is optionally substituted alkyl; and $R^2$ is optionally substituted aryl substituted with at least one substituent selected from optionally substituted C1-C5 alkyl, halogen, or optionally substituted C1-C5 alkoxy. Another embodiment provides the compound of Formula (IIa), or pharmaceutically acceptable salt thereof, wherein X is O; $R^5$, $R^7$ and $R^8$ are hydrogen; $R^6$ is —N($R^1$)($R^2$), wherein $R^1$ is optionally substituted alkyl; and $R^2$ is optionally substituted aryl substituted with at least one substituent selected from optionally substituted C1-C5 alkyl, halogen, or optionally substituted C1-C5 alkoxy.

Another embodiment provides the compound of Formula (IIa), or pharmaceutically acceptable salt thereof, wherein $R^5$, $R^7$ and $R^8$ are hydrogen; $R^6$ is —N($R^1$)($R^2$), wherein $R^1$ is optionally substituted alkyl; and $R^2$ is optionally substituted aryl substituted with at least one optionally substituted C1-C5 alkyl. Another embodiment provides the compound of Formula (IIa), or pharmaceutically acceptable salt thereof, wherein X is O; $R^5$, $R^7$ and $R^8$ are hydrogen; $R^6$ is —N($R^1$)($R^2$), wherein $R^1$ is optionally substituted alkyl; and $R^2$ is optionally substituted aryl substituted with at least one optionally substituted C1-C5 alkyl.

Another embodiment provides the compound of Formula (IIa), or pharmaceutically acceptable salt thereof, wherein X is O; $R^5$, $R^7$ and $R^8$ are hydrogen; $R^6$ is —N($R^1$)($R^2$), wherein $R^1$ is a $CH_3$ group; and $R^2$ is optionally substituted aryl substituted with at least one substituent selected from optionally substituted C1-C5 alkyl, halogen, or optionally substituted C1-C5 alkoxy.

Another embodiment provides the compound of Formula (IIa), or pharmaceutically acceptable salt thereof, having the structure:

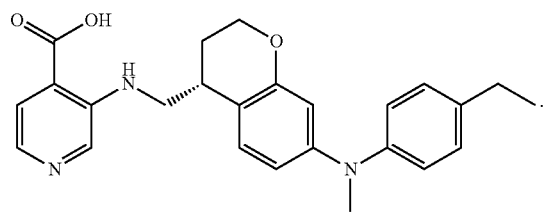 [SMILES: CCc1ccc(N(C)c2ccc3c(c2)OCC[C@H]3CNc2cnccc2C(=O)O)cc1]

Another embodiment provides the compound of Formula (IIa), or pharmaceutically acceptable salt thereof, having the structure:

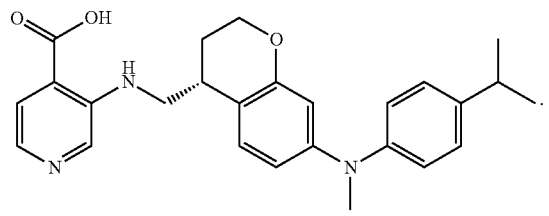

Another embodiment provides the compound of Formula (IIa), or pharmaceutically acceptable salt thereof, having the structure:

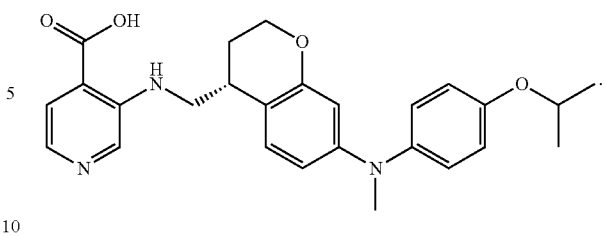

Another embodiment provides the compound of Formula (IIa), or pharmaceutically acceptable salt thereof, selected from:

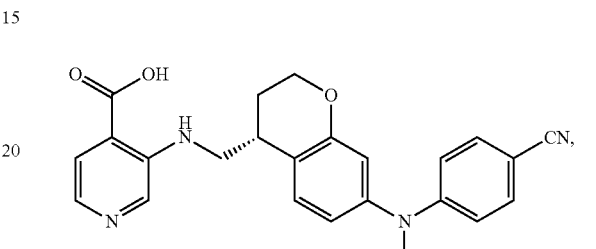

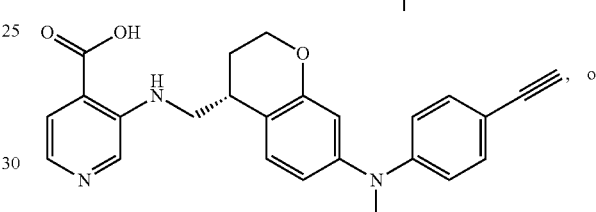

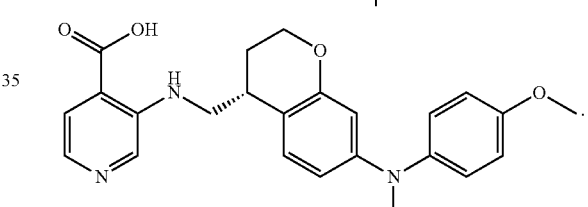

Another embodiment provides the compound of Formula (IIa), or pharmaceutically acceptable salt thereof, selected from:

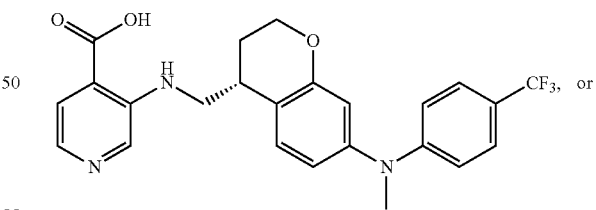

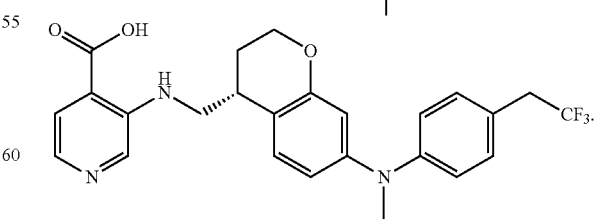

Another embodiment provides the compound of Formula (IIa), or pharmaceutically acceptable salt thereof, selected from:

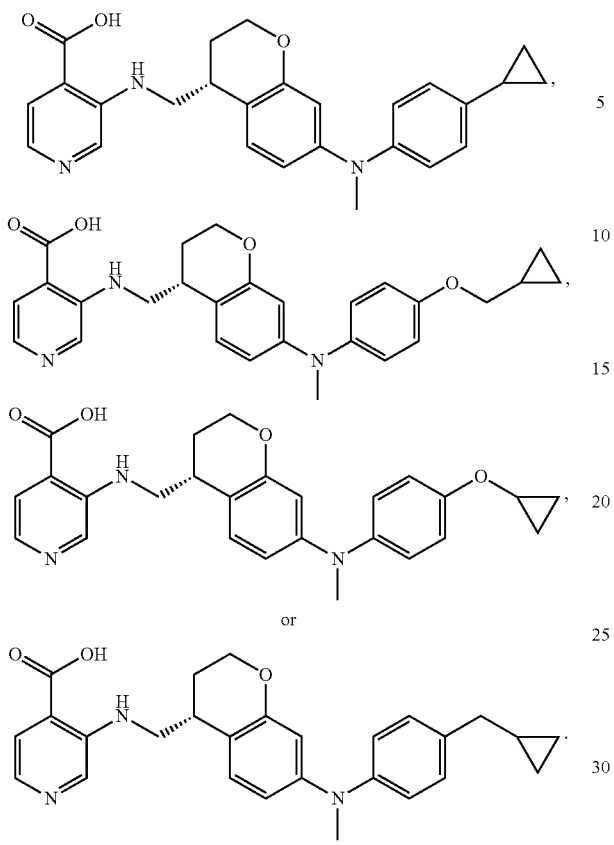

Another embodiment provides the compound of Formula (IIa), or pharmaceutically acceptable salt thereof, selected from:

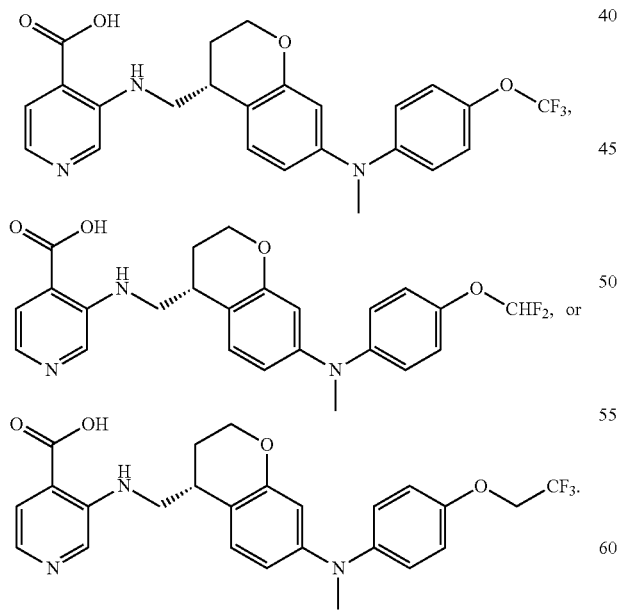

One embodiment provides a compound, or a stereoisomer or pharmaceutically acceptable salt thereof, having the structure of Formula (III):

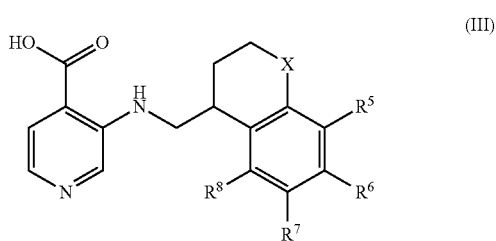

(III)

wherein,

X is O or CH$_2$;

at least one of R$^5$, R$^6$, R$^7$ and R$^8$ is chosen from optionally substituted heterocyclyl, optionally substituted heterocyclyloxy, optionally substituted heterocyclylalkyl, optionally substituted heterocyclylalkoxy, optionally substituted C$_6$-C$_{10}$ aryl-SO$_2$—, optionally substituted heteroaryl-S—, or —N(R$^1$)(R$^2$), wherein R$^1$ is hydrogen or optionally substituted alkyl, and R$^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—; and the remaining R$^5$, R$^6$, R$^7$ and R$^8$ groups are independently chosen from hydrogen, halogen, —OH, —CN, optionally substituted C$_1$-C$_6$ alkyl, optionally substituted C$_1$-C$_6$ alkoxy, optionally substituted C$_3$-C$_7$ carbocyclyl, optionally substituted C$_3$-C$_7$ carbocyclyloxy, optionally substituted C$_4$-C$_{12}$ carbocyclylalkyl, optionally substituted C$_4$-C$_{12}$ carbocyclylalkoxy, optionally substituted C$_1$-C$_6$ alkynyl, optionally substituted C$_1$-C$_6$ alkenyl, optionally substituted C$_6$-C$_{10}$ aryl, optionally substituted C$_6$-C$_{10}$ aryloxy, optionally substituted C$_6$-C$_{10}$ aryl-S—, optionally substituted C$_7$-C$_{14}$ aralkoxy, optionally substituted heteroaryl, and optionally substituted heteroaryloxy, optionally substituted heterocyclyl, optionally substituted heterocyclyloxy, substituted heterocyclylalkyl, optionally substituted heterocyclylalkoxy, optionally substituted C$_6$-C$_{10}$ aryl-SO$_2$—, optionally substituted heteroaryl-S—, or —N(R$^1$)(R$^2$), wherein R$^1$ is hydrogen or optionally substituted alkyl, and R$^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

Another embodiment provides the compound, or a stereoisomer or pharmaceutically acceptable salt thereof, of Formula (III), wherein X is O. Another embodiment provides the compound, or a stereoisomer or pharmaceutically acceptable salt thereof, of Formula (III), wherein X is CH$_2$. Another embodiment provides the compound, or a stereoisomer or pharmaceutically acceptable salt thereof, of Formula (III), wherein each R$^5$, R$^7$ and R$^8$ is independently chosen from hydrogen, halogen, —OH, —CN, optionally substituted C$_1$-C$_6$ alkyl, or optionally substituted C$_1$-C$_6$ alkoxy.

Another embodiment provides the compound, or a stereoisomer or pharmaceutically acceptable salt thereof, of Formula (III), wherein $R^5$ is hydrogen. Another embodiment provides the compound, or a stereoisomer or pharmaceutically acceptable salt thereof, of Formula (III), wherein $R^7$ is hydrogen. Another embodiment provides the compound, or a stereoisomer or pharmaceutically acceptable salt thereof, of Formula (III), wherein $R^8$ is hydrogen. Another embodiment provides the compound, or a stereoisomer or pharmaceutically acceptable salt thereof, of Formula (III), wherein $R^7$ and $R^8$ are hydrogen. Another embodiment provides the compound, or a stereoisomer or pharmaceutically acceptable salt thereof, of Formula (III), wherein $R^6$ is not hydrogen.

Another embodiment provides the compound, or a stereoisomer or pharmaceutically acceptable salt thereof, of Formula (III), wherein $R^6$ is optionally substituted heterocyclyl. Another embodiment provides the compound, or a stereoisomer or pharmaceutically acceptable salt thereof, of Formula (III), wherein $R^6$ is optionally substituted heterocyclyloxy. Another embodiment provides the compound, or a stereoisomer or pharmaceutically acceptable salt thereof, of Formula (III), wherein $R^6$ is optionally substituted heterocyclylalkyl. Another embodiment provides the compound, or a stereoisomer or pharmaceutically acceptable salt thereof, of Formula (III), wherein $R^6$ is optionally substituted heterocyclylalkoxy. Another embodiment provides the compound, or a stereoisomer or pharmaceutically acceptable salt thereof, of Formula (III), wherein $R^6$ is optionally substituted $C_6$-$C_{10}$ aryl-$SO_2$—, or optionally substituted heteroaryl-S—.

Another embodiment provides the compound, or a stereoisomer or pharmaceutically acceptable salt thereof, of Formula (III), wherein $R^6$ is —N($R^1$)($R^2$), wherein $R^1$ is hydrogen and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—. Another embodiment provides the compound, or a stereoisomer or pharmaceutically acceptable salt thereof, of Formula (III), wherein $R^6$ is —N($R^1$)($R^2$), wherein $R^1$ is optionally substituted alkyl and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—. Another embodiment provides the compound, or a stereoisomer or pharmaceutically acceptable salt thereof, of Formula (III), wherein $R^6$ is —N($R^1$)($R^2$), and $R^2$ is optionally substituted alkyl. Another embodiment provides the compound, or a stereoisomer or pharmaceutically acceptable salt thereof, of Formula (III), wherein $R^6$ is —N($R^1$)($R^2$), and $R^2$ is optionally substituted aryl. Another embodiment provides the compound, or a stereoisomer or pharmaceutically acceptable salt thereof, of Formula (III), wherein $R^6$ is —N($R^1$)($R^2$), and $R^2$ is optionally substituted heteroaryl. Another embodiment provides the compound, or a stereoisomer or pharmaceutically acceptable salt thereof, of Formula (III), wherein $R^6$ is —N($R^1$)($R^2$), and $R^2$ is optionally substituted heterocyclyl. Another embodiment provides the compound, or a stereoisomer or pharmaceutically acceptable salt thereof, of Formula (III), wherein $R^6$ is —N($R^1$)($R^2$), and $R^2$ is optionally substituted cycloalkyl. Another embodiment provides the compound, or a stereoisomer or pharmaceutically acceptable salt thereof, of Formula (III), wherein $R^6$ is —N($R^1$)($R^2$), and $R^2$ is optionally substituted cycloalkylalkyl. Another embodiment provides the compound, or a stereoisomer or pharmaceutically acceptable salt thereof, of Formula (III), wherein $R^6$ is —N($R^1$)($R^2$), and $R^2$ is optionally substituted aryl-CO—. Another embodiment provides the compound, or a stereoisomer or pharmaceutically acceptable salt thereof, of Formula (III), wherein $R^6$ is —N($R^1$)($R^2$), and $R^2$ is optionally substituted heteroaryl-CO—. Another embodiment provides the compound, or a stereoisomer or pharmaceutically acceptable salt thereof, of Formula (III), wherein $R^6$ is —N($R^1$)($R^2$), and $R^2$ is optionally substituted cycloalkyl-CO—. Another embodiment provides the compound, or a stereoisomer or pharmaceutically acceptable salt thereof, of Formula (III), wherein $R^6$ is —N($R^1$)($R^2$), and $R^2$ is optionally substituted alkyl-CO—.

One embodiment provides a compound, or a stereoisomer or pharmaceutically acceptable salt thereof, having the structure of Formula (IV):

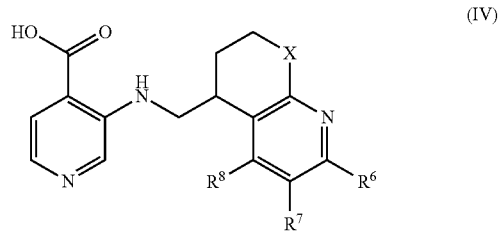

wherein,

X is O or $CH_2$;

$R^6$ is an optionally substituted aryl, optionally substituted heteroaryl, or —N($R^1$)($R^2$), wherein $R^1$ is hydrogen or optionally substituted alkyl, and $R^2$ is chosen from optionally substituted aryl or optionally substituted heteroaryl; and each $R^7$ and $R^8$ is independently chosen from hydrogen, halogen, —OH, —CN, optionally substituted $C_1$-$C_6$ alkyl, or optionally substituted $C_1$-$C_6$ alkoxy.

One embodiment provides a compound, or a stereoisomer or pharmaceutically acceptable salt thereof, having the structure of Formula (V):

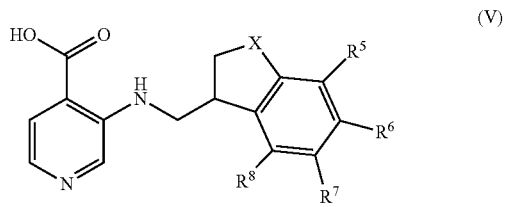

wherein,

X is O or $CH_2$;

$R^6$ is chosen from optionally substituted heterocyclyl, optionally substituted heterocyclyloxy, optionally substituted heterocyclylalkyl, optionally substituted heterocyclylalkoxy, optionally substituted $C_6$-$C_{10}$ aryl-$SO_2$—, optionally substituted heteroaryl-S—, or —N($R^1$)($R^2$), wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—; and each $R^5$, $R^7$ and $R^8$ is independently chosen from hydrogen, halogen, —OH, —CN, optionally substituted $C_1$-$C_6$ alkyl, optionally substituted $C_1$-$C_6$ alkoxy, optionally substituted $C_3$-$C_7$ carbocyclyl, optionally substituted $C_3$-$C_7$ carbocyclyloxy, optionally substituted $C_4$-$C_{12}$ carbocyclylalkyl, optionally substituted $C_4$-$C_{12}$ carbocyclylalkoxy, optionally substituted $C_1$-$C_6$ alkynyl, optionally substituted $C_1$-$C_6$ alkenyl, optionally substituted $C_6$-$C_{10}$ aryl, optionally substituted $C_6$-$C_{10}$ aryloxy, optionally substituted $C_6$-$C_{10}$ aryl-S—, optionally substituted $C_7$-$C_{14}$ aralkoxy, optionally substituted heteroaryl, and optionally substituted heteroaryloxy, optionally substituted heterocyclyl, optionally substituted heterocyclyloxy, substituted heterocyclylalkyl, optionally substituted heterocyclylalkoxy, optionally substituted $C_6$-$C_{10}$ aryl-$SO_2$—, optionally substituted heteroaryl-S—, or —N($R^1$)($R^2$), wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—;

with the provision that at least one of $R^5$, $R^7$ and $R^8$ is hydrogen.

Another embodiment provides the compound, or a stereoisomer or pharmaceutically acceptable salt thereof, of Formula (V), wherein X is O. Another embodiment provides the compound, or a stereoisomer or pharmaceutically acceptable salt thereof, of Formula (V), wherein X is $CH_2$.

Another embodiment provides the compound, or a stereoisomer or pharmaceutically acceptable salt thereof, of Formula (V), wherein $R^5$ is hydrogen. Another embodiment provides the compound, or a stereoisomer or pharmaceutically acceptable salt thereof, of Formula (V), wherein $R^7$ is hydrogen. Another embodiment provides the compound, or a stereoisomer or pharmaceutically acceptable salt thereof, of Formula (V), wherein $R^8$ is hydrogen. Another embodiment provides the compound, or a stereoisomer or pharmaceutically acceptable salt thereof, of Formula (V), wherein $R^5$, $R^7$ and $R^8$ are hydrogen.

Another embodiment provides the compound, or a stereoisomer or pharmaceutically acceptable salt thereof, of Formula (V), wherein $R^6$ is optionally substituted heterocyclyl, or optionally substituted heterocyclyloxy.

Another embodiment provides the compound, or a stereoisomer or pharmaceutically acceptable salt thereof, of Formula (V), wherein $R^6$ is optionally substituted $C_6$-$C_{10}$ aryl-$SO_2$—, or optionally substituted heteroaryl-S—.

Another embodiment provides the compound, or a stereoisomer or pharmaceutically acceptable salt thereof, of Formula (V), wherein $R^6$ is —N($R^1$)($R^2$), wherein $R^1$ is hydrogen; and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

Another embodiment provides the compound, or a stereoisomer or pharmaceutically acceptable salt thereof, of Formula (V), wherein $R^6$ is —N($R^1$)($R^2$), wherein $R^1$ is optionally substituted alkyl; and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

Another embodiment provides the compound, or a stereoisomer or pharmaceutically acceptable salt thereof, of Formula (V), wherein $R^5$, $R^7$ and $R^8$ are hydrogen; and $R^6$ is —N($R^1$)($R^2$), wherein $R^1$ is optionally substituted alkyl; and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—. Another embodiment provides the compound, or a stereoisomer or pharmaceutically acceptable salt thereof, of Formula (V), wherein $R^5$, $R^7$ and $R^8$ are hydrogen; and $R^6$ is —N($R^1$)($R^2$), wherein $R^1$ is optionally substituted alkyl; and $R^2$ is optionally substituted aryl.

Another embodiment provides the compound, or a stereoisomer or pharmaceutically acceptable salt thereof, of Formula (V), wherein $R^5$, $R^7$ and $R^8$ are hydrogen; and $R^6$ is —N($R^1$)($R^2$), wherein $R^1$ is optionally substituted alkyl; and $R^2$ is optionally substituted heteroaryl.

Another embodiment provides the compound, or a stereoisomer or pharmaceutically acceptable salt thereof, of Formula (V), wherein $R^5$, $R^7$ and $R^8$ are hydrogen; and $R^6$ is —N($R^1$)($R^2$), wherein $R^1$ is optionally substituted alkyl; and $R^2$ is optionally substituted heterocyclyl, optionally substituted cycloalkyl, optionally substituted cycloalkylalkyl, optionally substituted aryl-CO—, optionally substituted cycloalkyl-CO—, or optionally substituted alkyl-CO—.

Another embodiment provides the compound, or a stereoisomer or pharmaceutically acceptable salt thereof, of Formula (V), wherein $R^5$, $R^7$ and $R^8$ are hydrogen; and $R^6$ is —N($R^1$)($R^2$), wherein $R^1$ is optionally substituted C1-C3 alkyl; and $R^2$ is optionally substituted heterocyclyl, optionally substituted cycloalkyl, optionally substituted cycloalkylalkyl, optionally substituted aryl-CO—, optionally substituted cycloalkyl-CO—, or optionally substituted alkyl-CO—.

Another embodiment provides the compound, or a stereoisomer or pharmaceutically acceptable salt thereof, of Formula (V), wherein $R^5$, $R^7$ and $R^8$ are hydrogen; and $R^6$ is —N($R^1$)($R^2$), wherein $R^1$ is a $CH_3$ group; and $R^2$ is optionally substituted heterocyclyl, optionally substituted cycloalkyl, optionally substituted cycloalkylalkyl, optionally substituted aryl-CO—, optionally substituted cycloalkyl-CO—, or optionally substituted alkyl-CO—.

Another embodiment provides the compound, or a stereoisomer or pharmaceutically acceptable salt thereof, of Formula (V), wherein $R^5$, $R^7$ and $R^8$ are hydrogen; and $R^6$ is —N($R^1$)($R^2$), wherein $R^1$ is optionally substituted alkyl; and $R^2$ is an optionally substituted aryl substituted with at least one substituent selected from optionally substituted C1-C5 alkyl, optionally substituted C2-C5 alkenyl, halogen, cyano, hydroxy, amino, optionally substituted C1-C5 alkoxy, optionally substituted alkylamino, optionally substituted dialkylamino, optionally substituted heterocyclyl, optionally substituted heteroaryl, optionally substituted cycloalkyl, optionally substituted cycloalkylalkyl, optionally substituted cycloalkylalkoxy, or optionally substituted cycloalkoxy.

Another embodiment provides the compound, or a stereoisomer or pharmaceutically acceptable salt thereof, of Formula (V), wherein $R^5$, $R^7$ and $R^8$ are hydrogen; and $R^6$ is —$N(R^1)(R^2)$, wherein $R^1$ is optionally substituted alkyl; and $R^2$ is an optionally substituted aryl substituted with at least one substituent selected from optionally substituted C1-C5 alkyl, halogen, optionally substituted C1-C5 alkoxy, optionally substituted heterocyclyl, optionally substituted heteroaryl, optionally substituted cycloalkyl, optionally substituted cycloalkylalkyl, optionally substituted cycloalkylalkoxy, or optionally substituted cycloalkoxy.

Another embodiment provides the compound, or a stereoisomer or pharmaceutically acceptable salt thereof, of Formula (V), wherein $R^5$, $R^7$ and $R^8$ are hydrogen; and $R^6$ is —$N(R^1)(R^2)$, wherein $R^1$ is optionally substituted alkyl; and $R^2$ is an optionally substituted aryl substituted with at least one substituent selected from optionally substituted heterocyclyl, optionally substituted heteroaryl, optionally substituted cycloalkyl, optionally substituted cycloalkylalkyl, optionally substituted cycloalkylalkoxy, or optionally substituted cycloalkoxy.

Another embodiment provides the compound, or a stereoisomer or pharmaceutically acceptable salt thereof, of Formula (V), wherein $R^5$, $R^7$ and $R^8$ are hydrogen; and $R^6$ is —$N(R^1)(R^2)$, wherein $R^1$ is optionally substituted alkyl; and $R^2$ is an optionally substituted aryl substituted with at least one substituent selected from optionally substituted C1-C5 alkyl, halogen, or optionally substituted C1-C5 alkoxy.

Another embodiment provides the compound, or a stereoisomer or pharmaceutically acceptable salt thereof, of Formula (V), wherein $R^5$, $R^7$ and $R^8$ are hydrogen; and $R^6$ is —$N(R^1)(R^2)$, wherein $R^1$ is optionally substituted alkyl; and $R^2$ is an optionally substituted aryl substituted with at least one optionally substituted C1-C5 alkyl.

Another embodiment provides the compound, or a stereoisomer or pharmaceutically acceptable salt thereof, of Formula (V), wherein X is O; $R^5$, $R^7$ and $R^8$ are hydrogen; and $R^6$ is —$N(R^1)(R^2)$, wherein $R^1$ is a $CH_3$ group; and $R^2$ is an optionally substituted aryl substituted with at least one substituent selected from optionally substituted C1-C5 alkyl, halogen, or optionally substituted C1-C5 alkoxy.

Another embodiment provides the compound, or a stereoisomer or pharmaceutically acceptable salt thereof, of Formula (V), wherein X is $CH_2$; $R^5$, $R^7$ and $R^8$ are hydrogen; and $R^6$ is —$N(R^1)(R^2)$, wherein $R^1$ is a $CH_3$ group; and $R^2$ is an optionally substituted aryl substituted with at least one substituent selected from optionally substituted C1-C5 alkyl, halogen, or optionally substituted C1-C5 alkoxy.

Another embodiment provides the compound, or a stereoisomer or pharmaceutically acceptable salt thereof, of Formula (V), wherein X is O; $R^5$, $R^7$ and $R^8$ are hydrogen; and $R^6$ is —$N(R^1)(R^2)$, wherein $R^1$ is a $CH_3$ group; and $R^2$ is an optionally substituted aryl.

Another embodiment provides the compound, or a stereoisomer or pharmaceutically acceptable salt thereof, of Formula (V), wherein X is $CH_2$; $R^5$, $R^7$ and $R^8$ are hydrogen; and $R^6$ is —$N(R^1)(R^2)$, wherein $R^1$ is a $CH_3$ group; and $R^2$ is an optionally substituted aryl.

One embodiment provides a compound, or a stereoisomer or pharmaceutically acceptable salt thereof, chosen from:

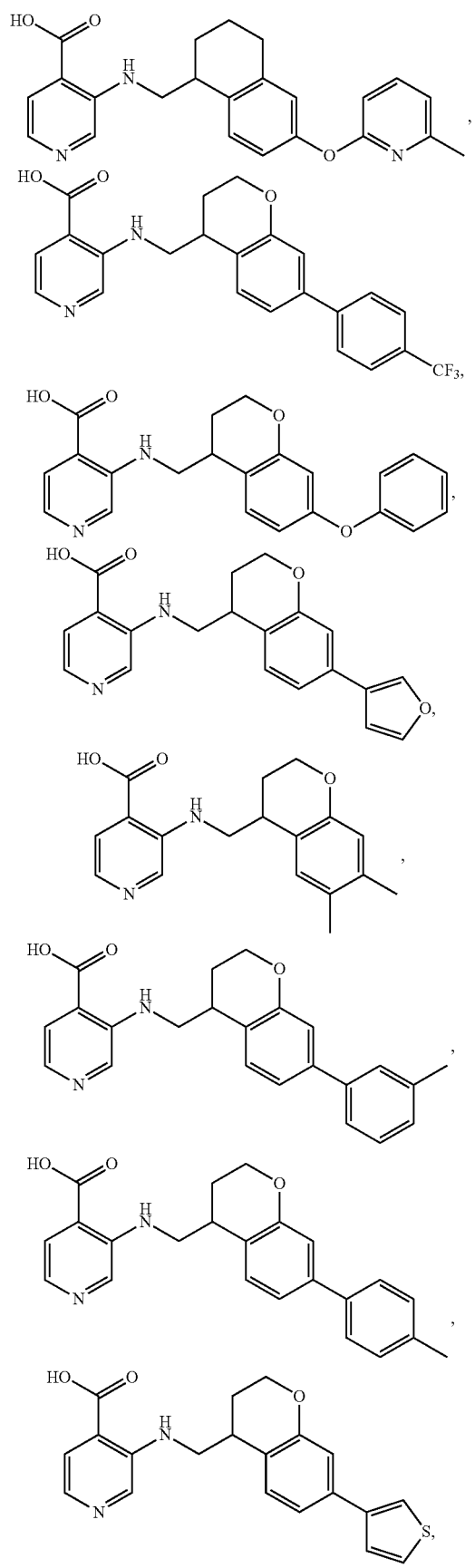

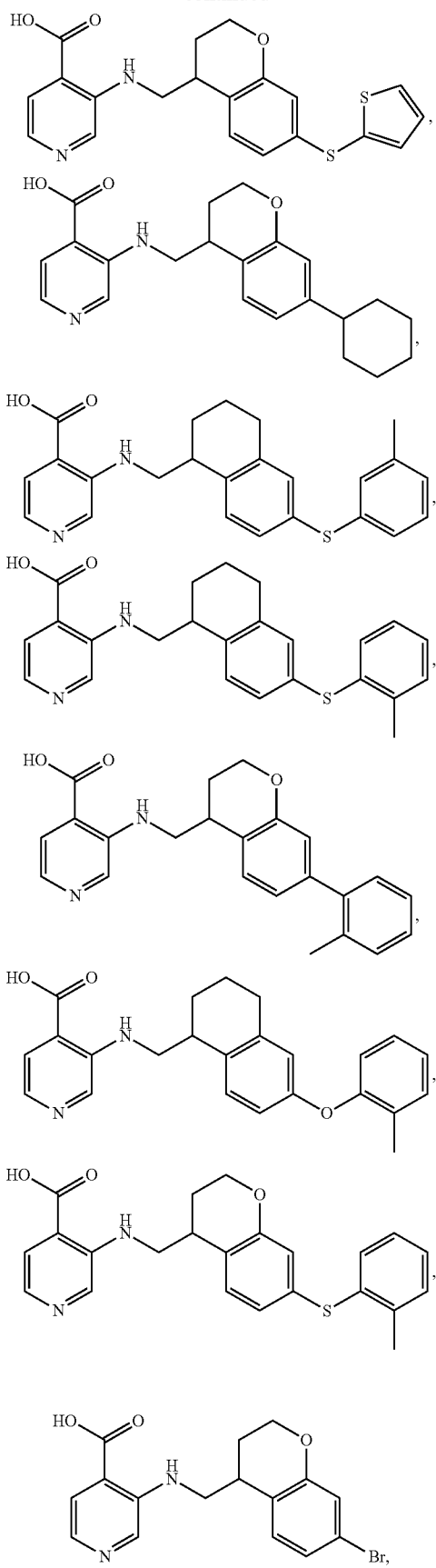
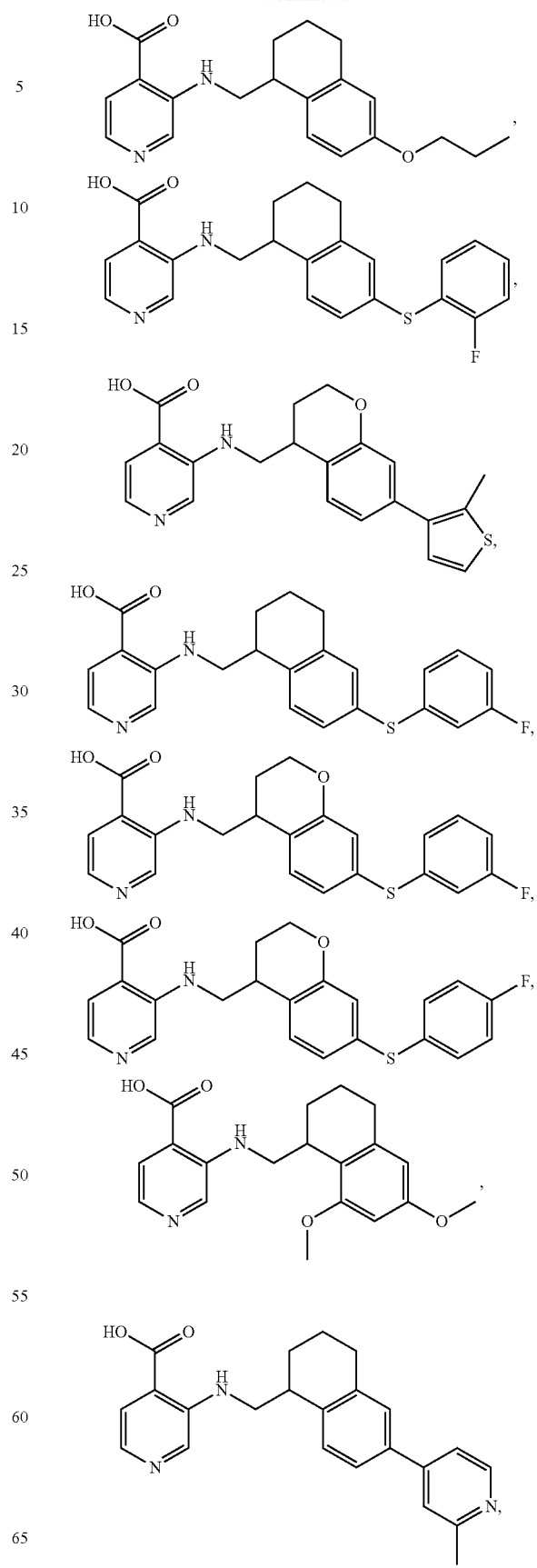

-continued
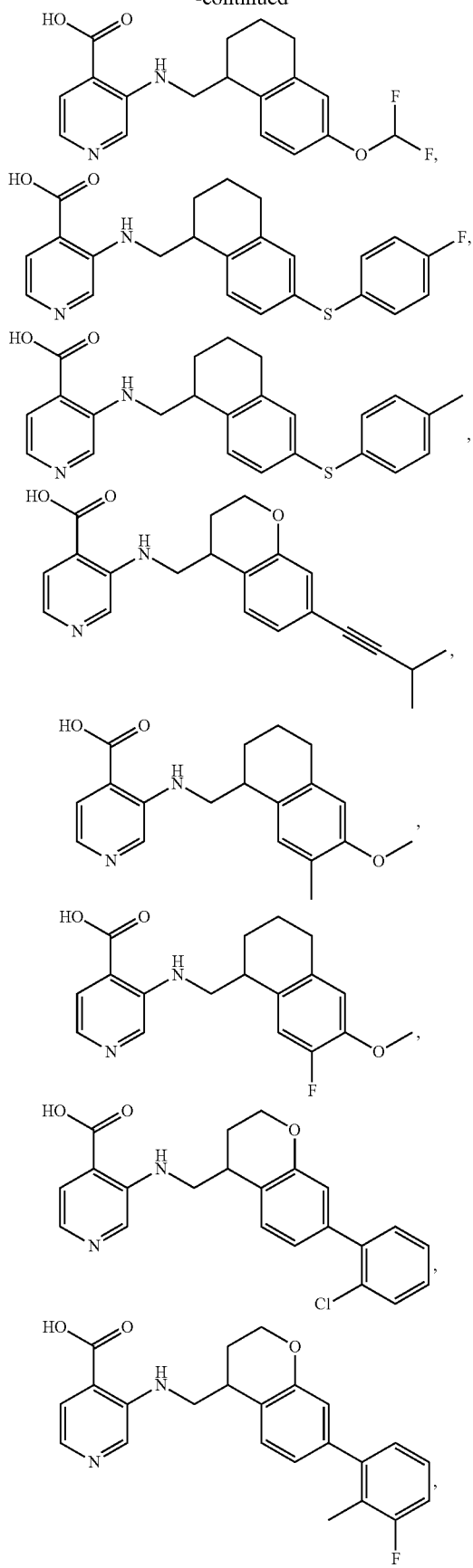
-continued
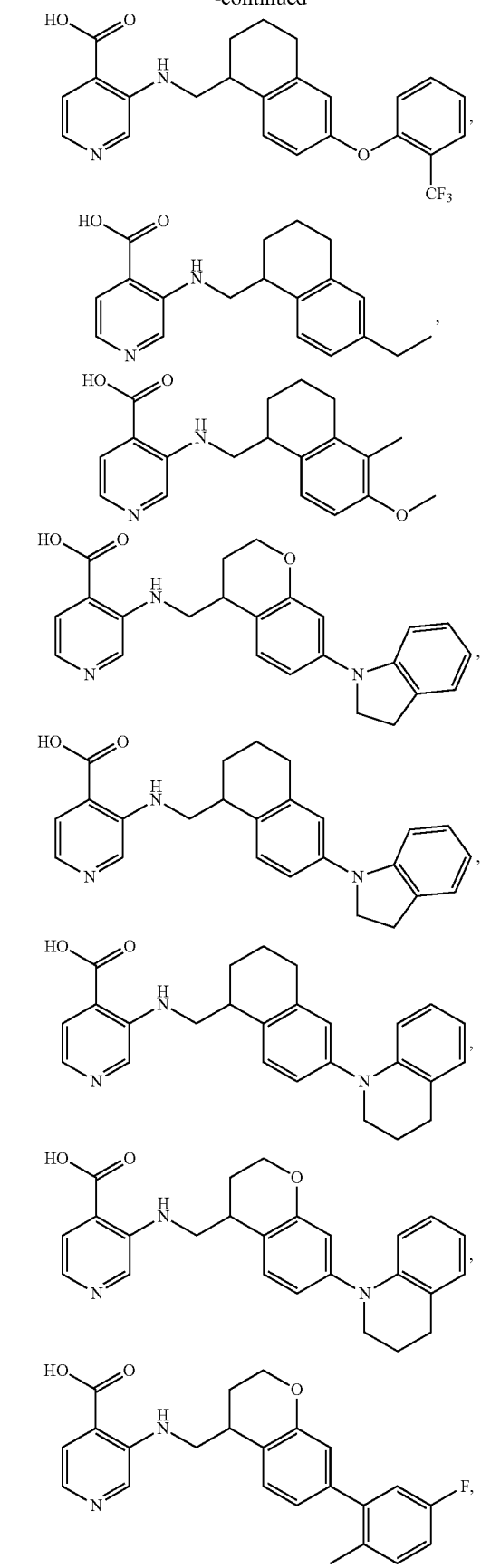

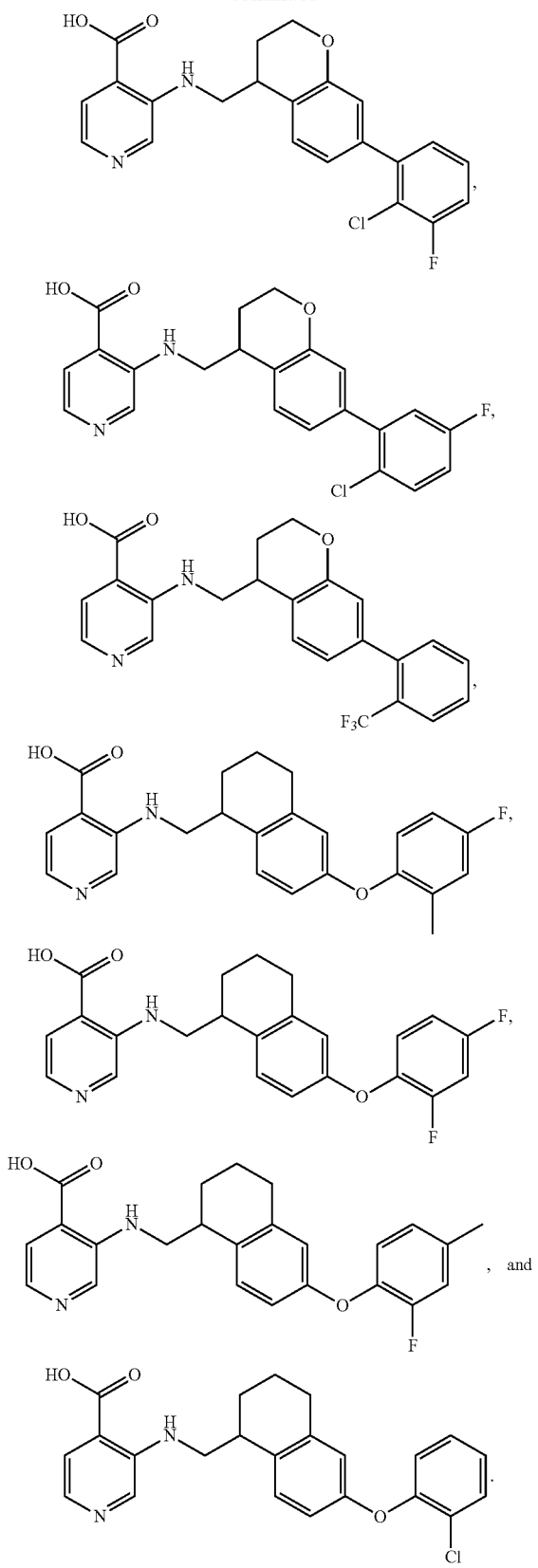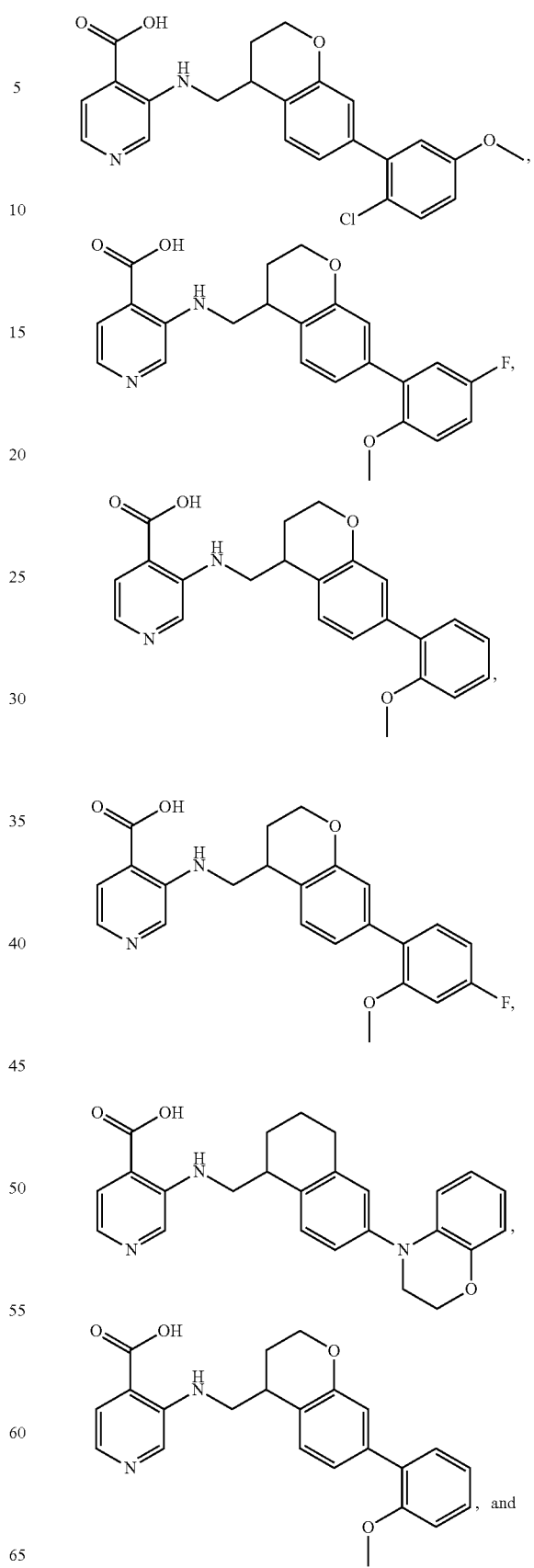
One embodiment provides a compound, or a stereoisomer or pharmaceutically acceptable salt thereof, chosen from:

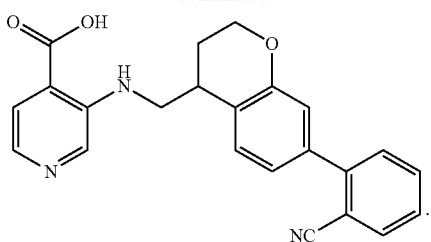 [SMILES: N#Cc1ccccc1-c1ccc2c(c1)OCCC2CNc1cnccc1C(=O)O]
One embodiment provides a compound, or a stereoisomer or pharmaceutically acceptable salt thereof, chosen from:
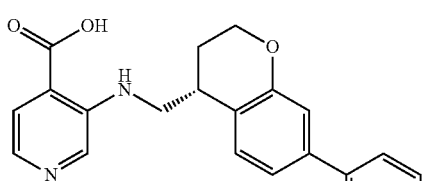
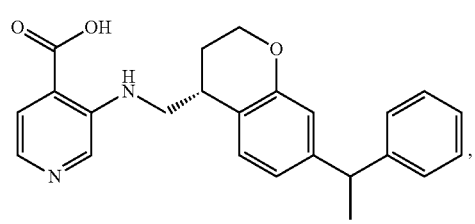
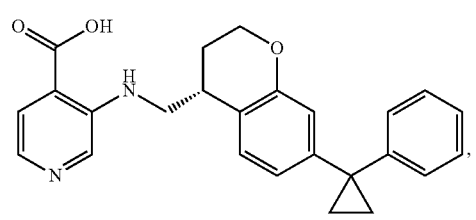
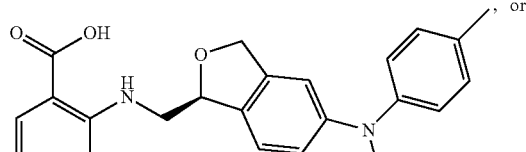
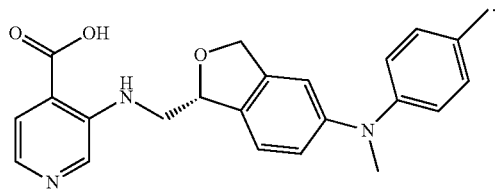
One embodiment provides a compound, or a stereoisomer or pharmaceutically acceptable salt thereof, chosen from:
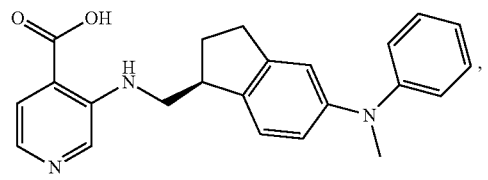
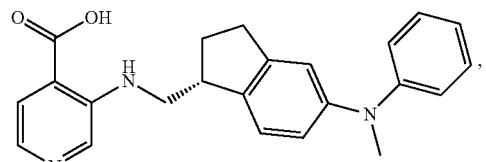
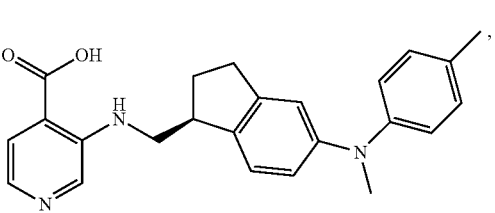
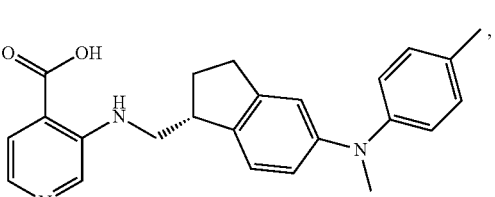
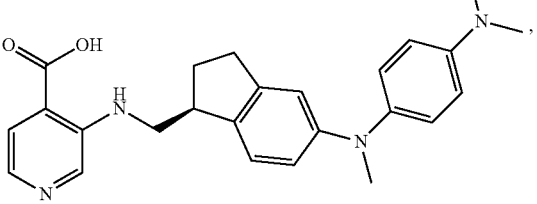

-continued
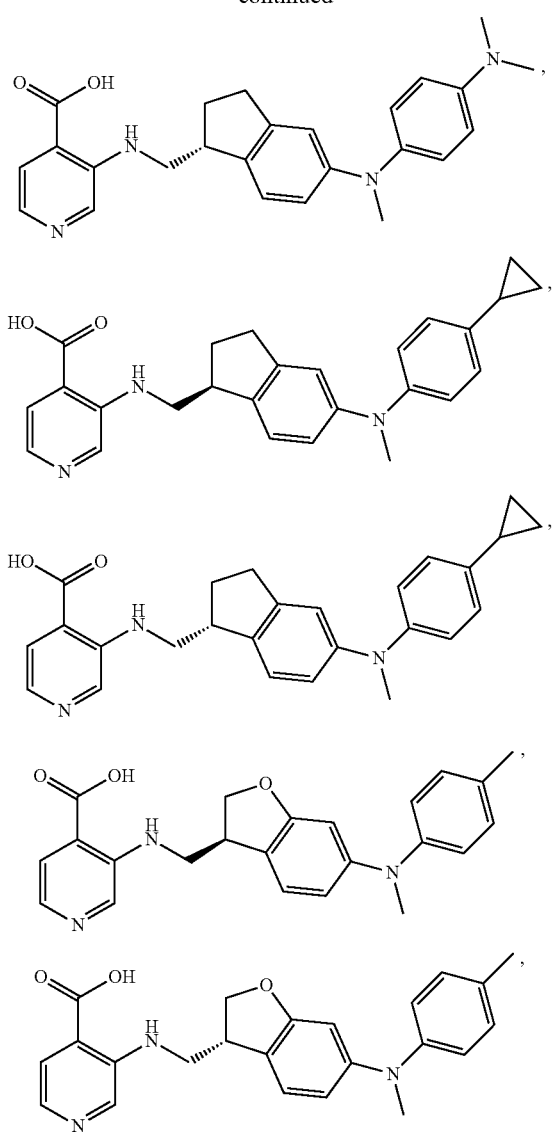
-continued
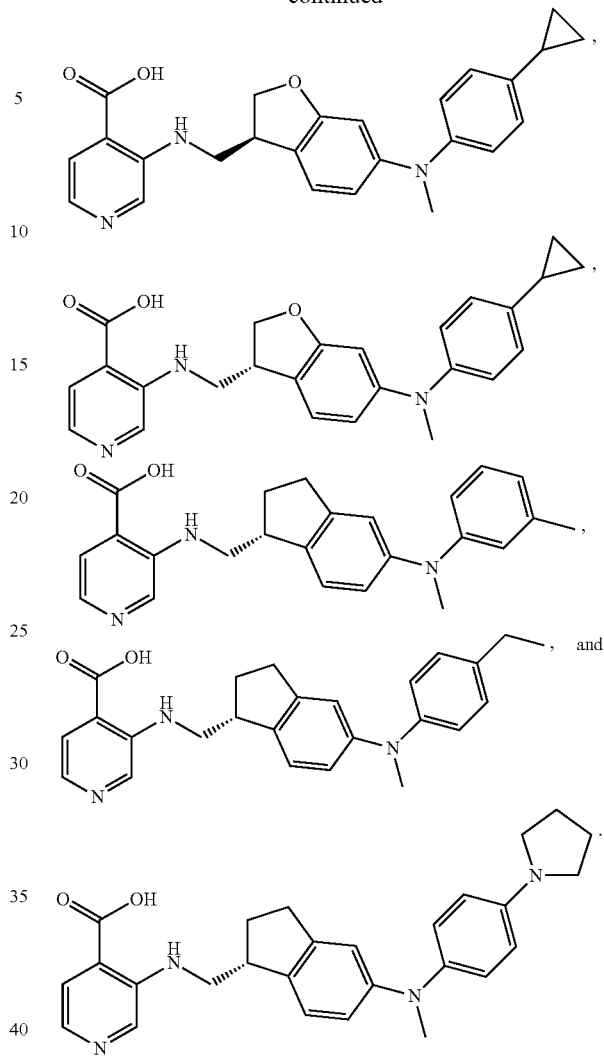
In some embodiments, the substituted pyridine derivative compound as described herein, or a stereoisomer or pharmaceutically acceptable salt thereof, has the structure provided in Table 1.
TABLE 1
| Chemical Synthesis Example | Structure | Comments |
|---|---|---|
| 1 | 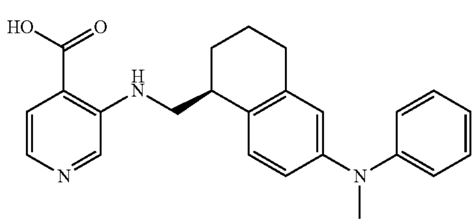 [SMILES: CN(c1ccccc1)c1ccc2c(c1)CCC[C@@H]2CNc1cnccc1C(=O)O] | 3-({[(1S)-6-[methyl(phenyl)amino]-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 2 | 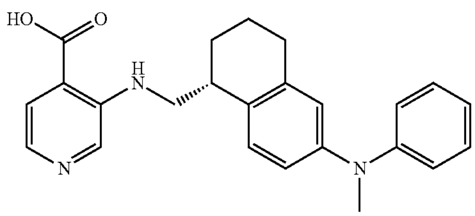 [SMILES: CN(c1ccccc1)c1ccc2c(c1)CCC[C@H]2CNc1cnccc1C(=O)O] | 3-({[(1S)-6-[methyl(phenyl)amino]-1,2,3,4-tetrahydronaphthalen-1-yl]methyl}amino)pyridine-4-carboxylic acid |
| 3 | 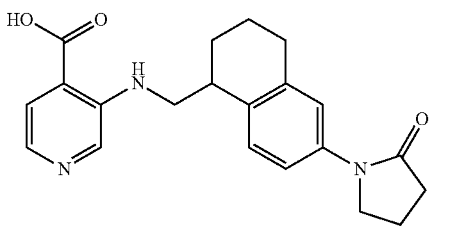 [SMILES: O=C(O)c1ccncc1NCC1CCCc2cc(N3CCCC3=O)ccc21] | 3-({[6-(2-oxopyrrolidin-1-yl)-1,2,3,4-tetrahydronaphthalen-1-yl]methyl}amino)pyridine-4-carboxylic acid |
| 4 | 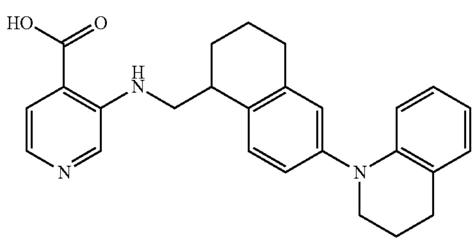 [SMILES: O=C(O)c1ccncc1NCC1CCCc2cc(N3CCCc4ccccc43)ccc21] | 3-({[6-(1,2,3,4-tetrahydroquinolin-1-yl)-1,2,3,4-tetrahydronaphthalen-1-yl]methyl}amino)pyridine-4-carboxylic acid |
| 5 | 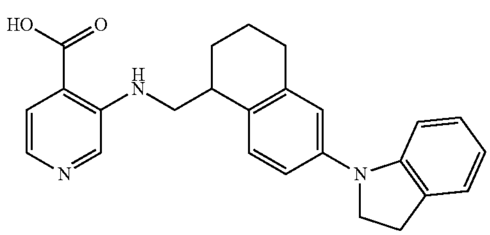 [SMILES: O=C(O)c1ccncc1NCC1CCCc2cc(N3CCc4ccccc43)ccc21] | 3-({[6-(2,3-dihydro-1H-indol-1-yl)-1,2,3,4-tetrahydronaphthalen-1-yl]methyl}amino)pyridine-4-carboxylic acid |
| 6 | 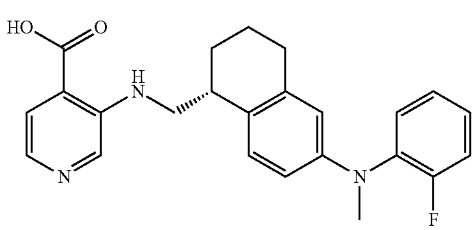 | 3-({[(1R)-6-[(2-fluorophenyl)(methyl)amino]-1,2,3,4-tetrahydronaphthalen-1-yl]methyl}amino)pyridine-4-carboxylic acid |
| 7 | 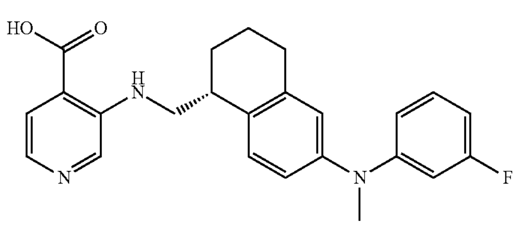 | 3-({[(1R)-6-[(3-fluorophenyl)(methyl)amino]-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 8 | 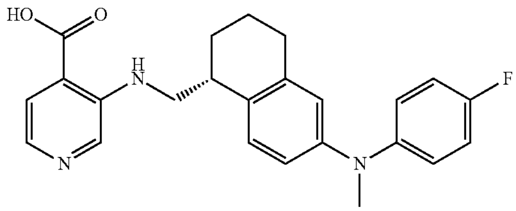 [SMILES: CN(c1ccc(F)cc1)c1ccc2c(c1)CCC[C@H]2CNc1cnccc1C(=O)O] | 3-({[(1R)-6-[(4-fluorophenyl)(methyl)amino]-1,2,3,4-tetrahydronaphthalen-1-yl]methyl}amino)pyridine-4-carboxylic acid |
| 9 | 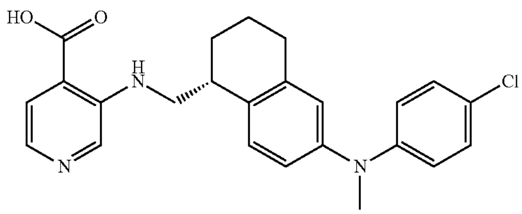 [SMILES: CN(c1ccc(Cl)cc1)c1ccc2c(c1)CCC[C@H]2CNc1cnccc1C(=O)O] | 3-({[(1R)-6-[(4-chlorophenyl)(methyl)amino]-1,2,3,4-tetrahydronaphthalen-1-yl]methyl}amino)pyridine-4-carboxylic acid |
| 10 | 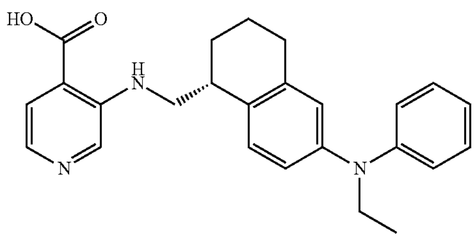 [SMILES: CCN(c1ccccc1)c1ccc2c(c1)CCC[C@H]2CNc1cnccc1C(=O)O] | 3-({[(1R)-6-[ethyl(phenyl)amino]-1,2,3,4-tetrahydronaphthalen-1-yl]methyl}amino)pyridine-4-carboxylic acid |
| 11 | 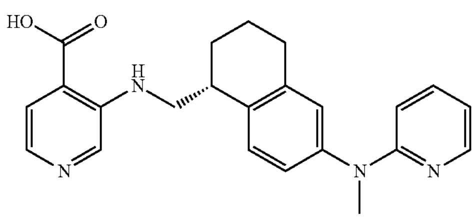 | 3-({[(1R)-6-[methyl(pyridin-2-yl)amino]-1,2,3,4-tetrahydronaphthalen-1-yl]methyl}amino)pyridine-4-carboxylic acid |
| 12 | 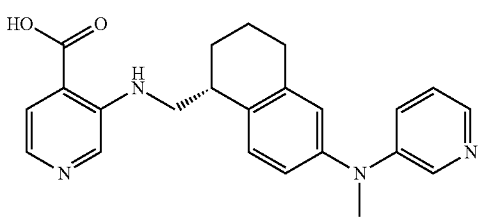 [SMILES: CN(c1cccnc1)c1ccc2c(c1)CCC[C@H]2CNc1cnccc1C(=O)O] | 3-({[(1R)-6-[methyl(pyridin-3-yl)amino]-1,2,3,4-tetrahydronaphthalen-1-yl]methyl}amino)pyridine-4-carboxylic acid |
| 13 | 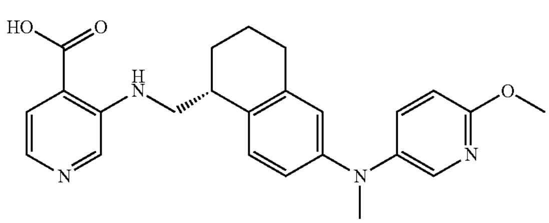 | 3-({[(1R)-6-[(6-methoxypyridin-3-yl)(methyl)amino]-1,2,3,4-tetrahydronaphthalen-1-yl]methyl}amino)pyridine-4-carboxylic acid |
| 14 | 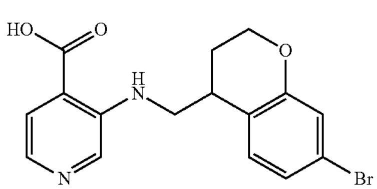 [SMILES: O=C(O)c1ccncc1NCC1CCOc2cc(Br)ccc21] | 3-{[(7-bromo-3,4-dihydro-2H-1-benzopyran-4-yl)methyl]amino}pyridine-4-carboxylic acid |

TABLE 1-continued

| Chemical Synthesis Example | Structure | Comments |
|---|---|---|
| 15 | 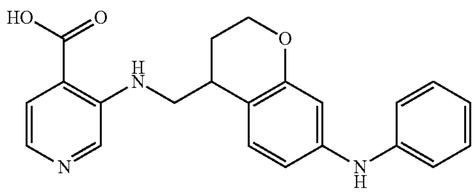 [SMILES: O=C(O)c1ccncc1NCC1CCOc2cc(Nc3ccccc3)ccc21] | 3-({[7-(phenylamino)-3,4-dihydro-2H-1-benzopyran-4-yl]methyl}amino)pyridine-4-carboxylic acid |
| 16 | 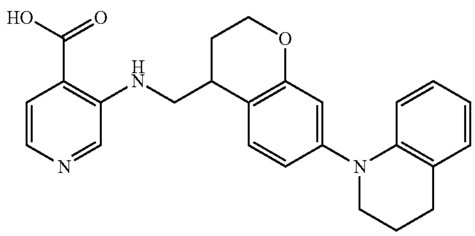 | 3-({[7-(1,2,3,4-tetrahydroquinolin-1-yl)-3,4-dihydro-2H-1-benzopyran-4-yl]methyl}amino)pyridine-4-carboxylic acid |
| 17 | 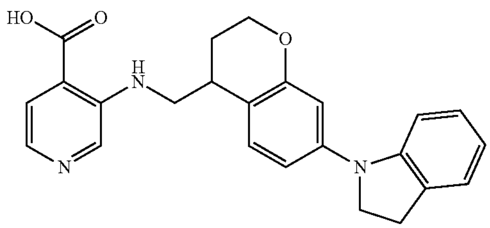 [SMILES: O=C(O)c1ccncc1NCC1CCOc2cc(N3CCc4ccccc43)ccc21] | 3-({[7-(2,3-dihydro-1H-indol-1-yl)-3,4-dihydro-2H-1-benzopyran-4-yl]methyl}amino)pyridine-4-carboxylic acid |
| 18 | 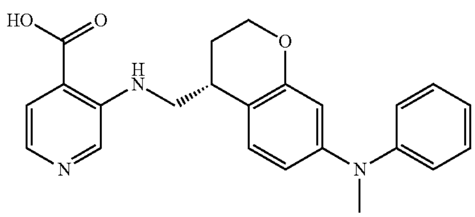 | 3-({[(4R)-7-[methyl(phenyl)amino]-3,4-dihydro-2H-1-benzopyran-4-yl]methyl}amino)pyridine-4-carboxylic acid |
| 19 | 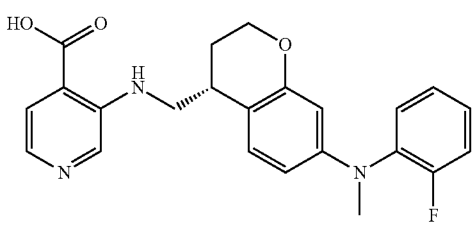 [SMILES: CN(c1ccc2c(c1)OCC[C@H]2CNc1cnccc1C(=O)O)c1ccccc1F] | 3-({[(4R)-7-[(2-fluorophenyl)(methyl)amino]-3,4-dihydro-2H-1-benzopyran-4-yl]methyl}amino)pyridine-4-carboxylic acid |
| 20 | 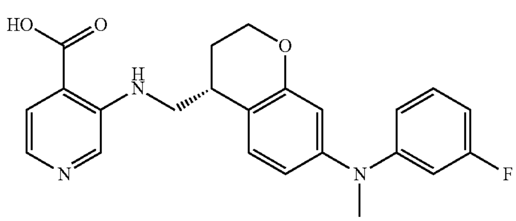 [SMILES: CN(c1cccc(F)c1)c1ccc2c(c1)OCC[C@H]2CNc1cnccc1C(=O)O] | 3-({[(4R)-7-[(3-fluorophenyl)(methyl)amino]-3,4-dihydro-2H-1-benzopyran-4-yl]methyl}amino)pyridine-4-carboxylic acid |
| 21 | 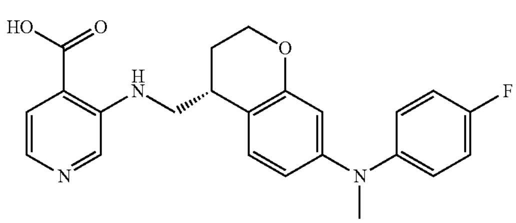 [SMILES: CN(c1ccc(F)cc1)c1ccc2c(c1)OCC[C@H]2CNc1cnccc1C(=O)O] | 3-({[(4R)-7-[(4-fluorophenyl)(methyl)amino]-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 22 | 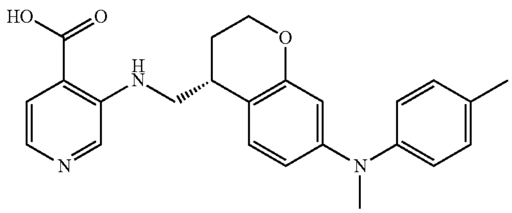 [SMILES: Cc1ccc(N(C)c2ccc3c(c2)OCC[C@H]3CNc2cnccc2C(=O)O)cc1] | 3-({[(4R)-7-[methyl(4-methylphenyl)amino]-3,4-dihydro-2H-1-benzopyran-4-yl]methyl}amino)pyridine-4-carboxylic acid |
| 23 | 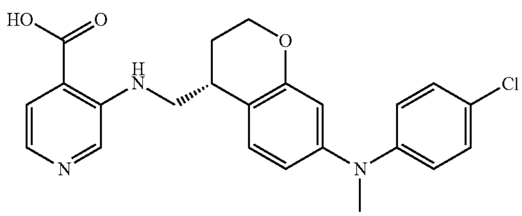 | 3-({[(4R)-7-[(4-chlorophenyl)(methyl)amino]-3,4-dihydro-2H-1-benzopyran-4-yl]methyl}amino)pyridine-4-carboxylic acid |
| 24 | 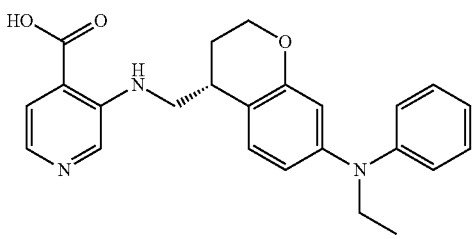 [SMILES: CCN(c1ccccc1)c1ccc2c(c1)OCC[C@H]2CNc1cnccc1C(=O)O] | 3-({[(4R)-7-[ethyl(phenyl)amino]-3,4-dihydro-2H-1-benzopyran-4-yl]methyl}amino)pyridine-4-carboxylic acid |
| 25 | 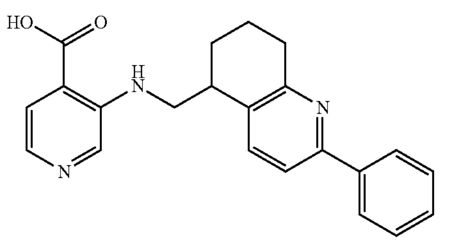 [SMILES: O=C(O)c1ccncc1NCC1CCCc2nc(-c3ccccc3)ccc21] | 3-{[(2-phenyl-5,6,7,8-tetrahydroquinolin-5-yl)methyl]amino}pyridine-4-carboxylic acid |
| 26 | 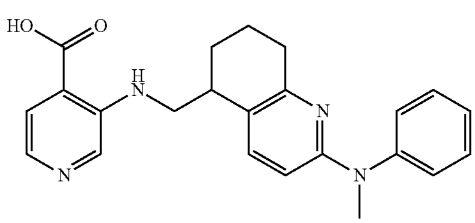 | 3-[({2-[methyl(phenyl)amino]-5,6,7,8-tetrahydroquinolin-5-yl}methyl)amino]pyridine-4-carboxylic acid |
| 27 | 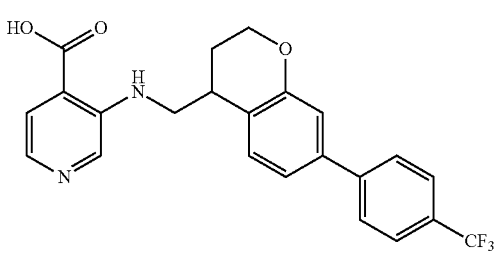 [SMILES: O=C(O)c1ccncc1NCC1CCOc2cc(-c3ccc(C(F)(F)F)cc3)ccc21] | 3-[({7-[4-(trifluoromethyl)phenyl]-3,4-dihydro-2H-1-benzopyran-4-yl}methyl)amino]pyridine-4-carboxylic acid |

TABLE 1-continued

| Chemical Synthesis Example | Structure | Comments |
|---|---|---|
| 28 | 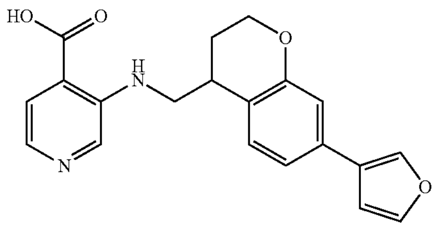 [SMILES: O=C(O)c1ccncc1NCC1CCOc2cc(-c3ccoc3)ccc21] | 3-({[7-(furan-3-yl)-3,4-dihydro-2H-1-benzopyran-4-yl]methyl}amino)pyridine-4-carboxylic acid |
| 29 | 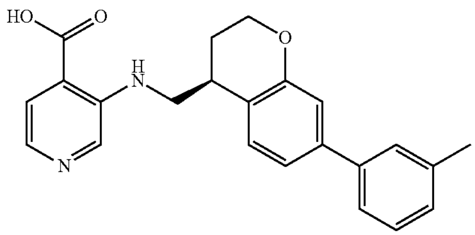 [SMILES: Cc1cccc(-c2ccc3c(c2)OCC[C@@H]3CNc2cnccc2C(=O)O)c1] | 3-({[(4S)-7-(3-methylphenyl)-3,4-dihydro-2H-1-benzopyran-4-yl]methyl}amino)pyridine-4-carboxylic acid |
| 30 | 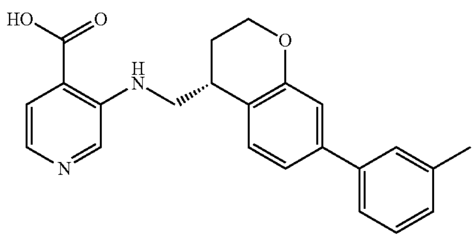 [SMILES: Cc1cccc(-c2ccc3c(c2)OCC[C@H]3CNc2cnccc2C(=O)O)c1] | 3-({[(4R)-7-(3-methylphenyl)-3,4-dihydro-2H-1-benzopyran-4-yl]methyl}amino)pyridine-4-carboxylic acid |
| 31 | 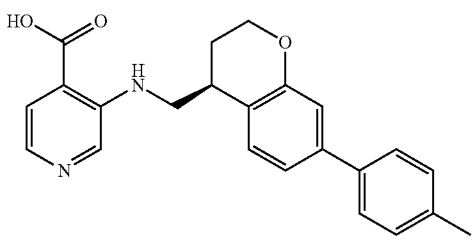 [SMILES: Cc1ccc(-c2ccc3c(c2)OCC[C@@H]3CNc2cnccc2C(=O)O)cc1] | 3-({[(4S)-7-(4-methylphenyl)-3,4-dihydro-2H-1-benzopyran-4-yl]methyl}amino)pyridine-4-carboxylic acid |
| 32 | 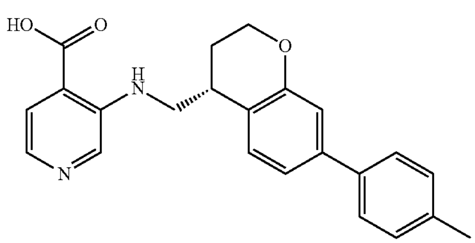 [SMILES: Cc1ccc(-c2ccc3c(c2)OCC[C@H]3CNc2cnccc2C(=O)O)cc1] | 3-({[(4R)-7-(4-methylphenyl)-3,4-dihydro-2H-1-benzopyran-4-yl]methyl}amino)pyridine-4-carboxylic acid |
| 33 | 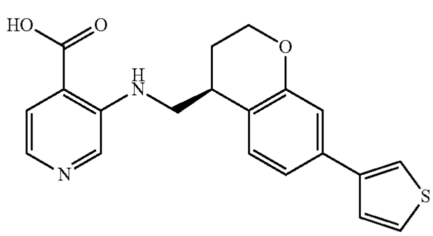 [SMILES: O=C(O)c1ccncc1NC[C@H]1CCOc2cc(-c3ccsc3)ccc21] | 3-({[(4S)-7-(thiophen-3-yl)-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 34 | 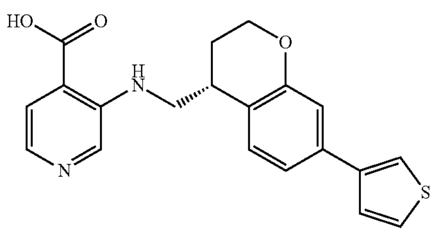 [SMILES: O=C(O)c1ccncc1NC[C@@H]1CCOc2cc(-c3ccsc3)ccc21] | 3-({[(4R)-7-(thiophen-3-yl)-3,4-dihydro-2H-1-benzopyran-4-yl]methyl}amino)pyridine-4-carboxylic acid |
| 35 | 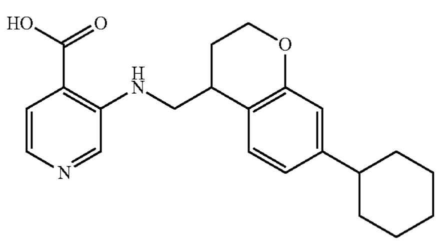 [SMILES: O=C(O)c1ccncc1NCC1CCOc2cc(C3CCCCC3)ccc21] | 3-({[(4R)-7-cyclohexyl-3,4-dihydro-2H-1-benzopyran-4-yl]methyl}amino)pyridine-4-carboxylic acid |
| 36 | 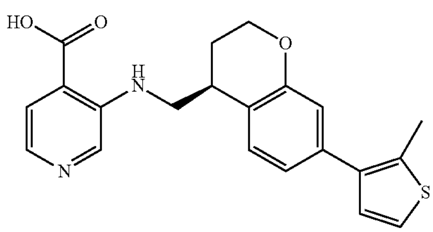 [SMILES: Cc1sccc1-c1ccc2c(c1)OCC[C@@H]2CNc1cnccc1C(=O)O] | 3-({[(4S)-7-(2-methylthiophen-3-yl)-3,4-dihydro-2H-1-benzopyran-4-yl]methyl}amino)pyridine-4-carboxylic acid |
| 37 | 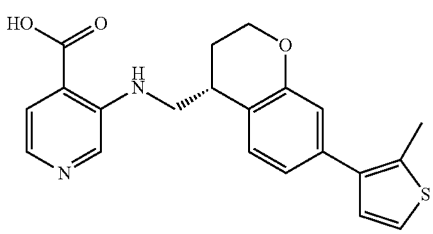 [SMILES: Cc1sccc1-c1ccc2c(c1)OCC[C@H]2CNc1cnccc1C(=O)O] | 3-({[(4R)-7-(2-methylthiophen-3-yl)-3,4-dihydro-2H-1-benzopyran-4-yl]methyl}amino)pyridine-4-carboxylic acid |
| 38 | 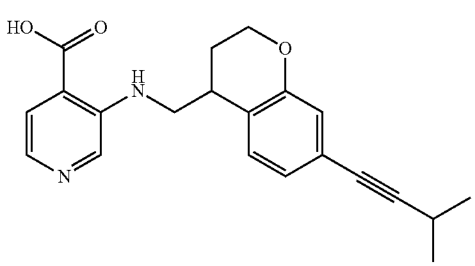 [SMILES: CC(C)C#Cc1ccc2c(c1)OCCC2CNc1cnccc1C(=O)O] | 3-({[7-(3-methylbut-1-yn-1-yl)-3,4-dihydro-2H-1-benzopyran-4-yl]methyl}amino)pyridine-4-carboxylic acid |
| 39 | 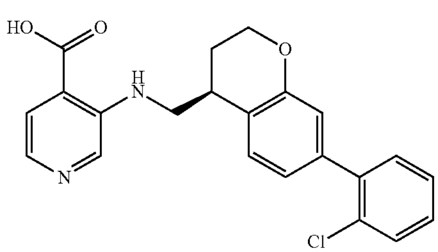 [SMILES: O=C(O)c1ccncc1NC[C@H]1CCOc2cc(-c3ccccc3Cl)ccc21] | 3-({[(4S)-7-(2-chlorophenyl)-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 40 | 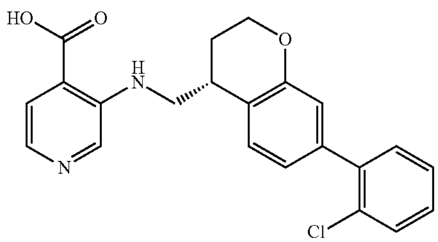 [SMILES: O=C(O)c1ccncc1NC[C@@H]1CCOc2cc(-c3ccccc3Cl)ccc21] | 3-({[(4R)-7-(2-chlorophenyl)-3,4-dihydro-2H-1-benzopyran-4-yl]methyl}amino)pyridine-4-carboxylic acid |
| 41 | 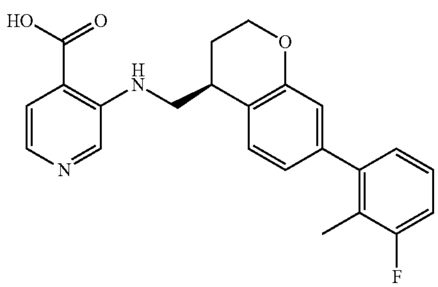 [SMILES: Cc1c(F)cccc1-c1ccc2c(c1)OCC[C@@H]2CNc1cnccc1C(=O)O] | 3-({[(4S)-7-(3-fluoro-2-methylphenyl)-3,4-dihydro-2H-1-benzopyran-4-yl]methyl}amino)pyridine-4-carboxylic acid |
| 42 | 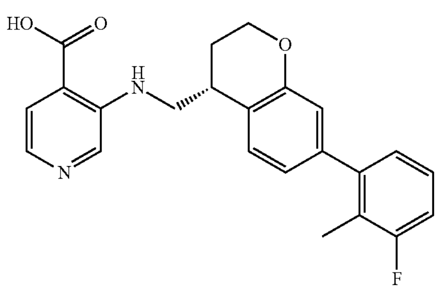 [SMILES: Cc1c(F)cccc1-c1ccc2c(c1)OCC[C@H]2CNc1cnccc1C(=O)O] | 3-({[(4R)-7-(3-fluoro-2-methylphenyl)-3,4-dihydro-2H-1-benzopyran-4-yl]methyl}amino)pyridine-4-carboxylic acid |
| 43 | 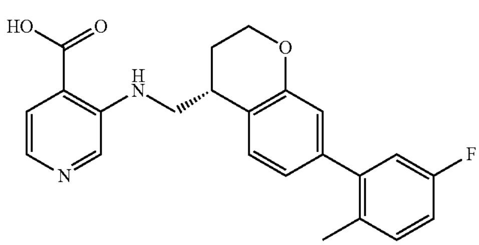 [SMILES: Cc1ccc(F)cc1-c1ccc2c(c1)OCC[C@H]2CNc1cnccc1C(=O)O] | 3-({[(4R)-7-(5-fluoro-2-methylphenyl)-3,4-dihydro-2H-1-benzopyran-4-yl]methyl}amino)pyridine-4-carboxylic acid |
| 44 | 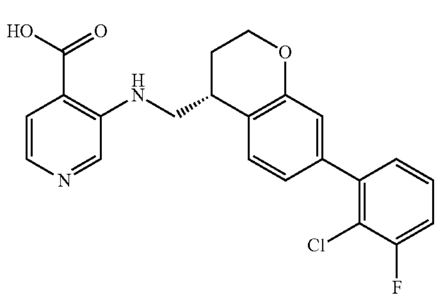 [SMILES: O=C(O)c1ccncc1NC[C@@H]1CCOc2cc(-c3cccc(F)c3Cl)ccc21] | 3-({[(4R)-7-(2-chloro-3-fluorophenyl)-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 45 | 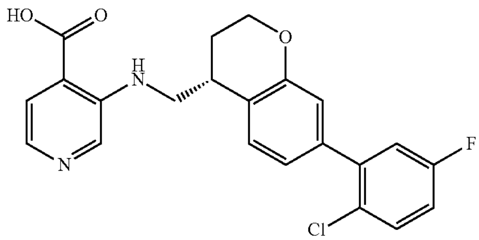 [SMILES: O=C(O)c1ccncc1NC[C@@H]1CCOc2cc(-c3cc(F)ccc3Cl)ccc21] | 3-({[(4R)-7-(2-chloro-5-fluorophenyl)-3,4-dihydro-2H-1-benzopyran-4-yl]methyl}amino)pyridine-4-carboxylic acid |
| 46 | 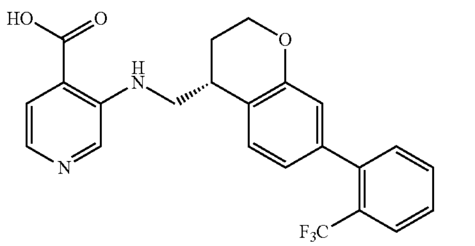 [SMILES: O=C(O)c1ccncc1NC[C@@H]1CCOc2cc(-c3ccccc3C(F)(F)F)ccc21] | 3-({[(4R)-7-[2-(trifluoromethyl)phenyl]-3,4-dihydro-2H-1-benzopyran-4-yl]methyl}amino)pyridine-4-carboxylic acid |
| 47 | 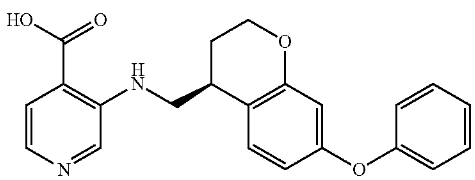 [SMILES: O=C(O)c1ccncc1NC[C@H]1CCOc2cc(Oc3ccccc3)ccc21] | 3-({[(4S)-7-phenoxy-3,4-dihydro-2H-1-benzopyran-4-yl]methyl}amino)pyridine-4-carboxylic acid |
| 48 | 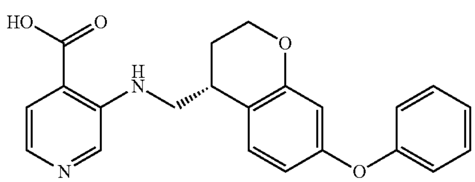 [SMILES: O=C(O)c1ccncc1NC[C@@H]1CCOc2cc(Oc3ccccc3)ccc21] | 3-({[(4R)-7-phenoxy-3,4-dihydro-2H-1-benzopyran-4-yl]methyl}amino)pyridine-4-carboxylic acid |
| 49 | 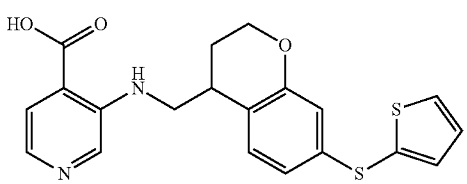 [SMILES: O=C(O)c1ccncc1NCC1CCOc2cc(Sc3cccs3)ccc21] | 3-({[7-(thiophen-2-ylsulfanyl)-3,4-dihydro-2H-1-benzopyran-4-yl]methyl}amino)pyridine-4-carboxylic acid |
| 50 | 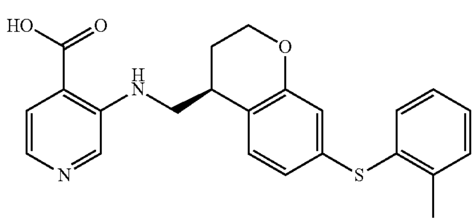 | 3-({[(4S)-7-[(2-methylphenyl)sulfanyl]-3,4-dihydro-2H-1-benzopyran-4-yl]methyl}amino)pyridine-4-carboxylic acid |
| 51 | 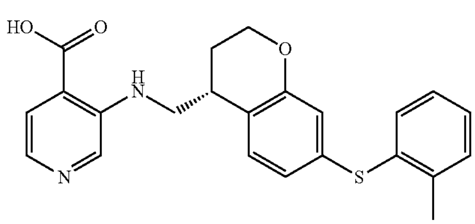 [SMILES: Cc1ccccc1Sc1ccc2c(c1)OCC[C@H]2CNc1cnccc1C(=O)O] | 3-({[(4R)-7-[(2-methylphenyl)sulfanyl]-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 52 | 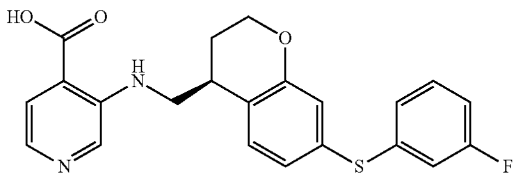 [SMILES: O=C(O)c1ccncc1NC[C@H]1CCOc2cc(Sc3cccc(F)c3)ccc21] | 3-({[(4S)-7-[(3-fluorophenyl)sulfanyl]-3,4-dihydro-2H-1-benzopyran-4-yl]methyl}amino)pyridine-4-carboxylic acid |
| 53 | 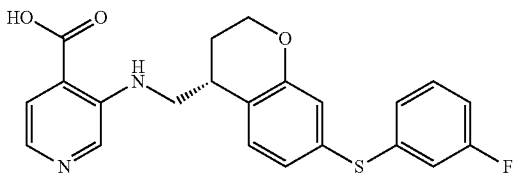 [SMILES: O=C(O)c1ccncc1NC[C@@H]1CCOc2cc(Sc3cccc(F)c3)ccc21] | 3-({[(4R)-7-[(3-fluorophenyl)sulfanyl]-3,4-dihydro-2H-1-benzopyran-4-yl]methyl}amino)pyridine-4-carboxylic acid |
| 54 | 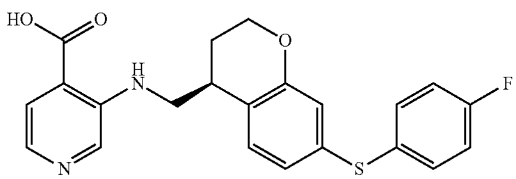 [SMILES: O=C(O)c1ccncc1NC[C@H]1CCOc2cc(Sc3ccc(F)cc3)ccc21] | 3-({[(4S)-7-[(4-fluorophenyl)sulfanyl]-3,4-dihydro-2H-1-benzopyran-4-yl]methyl}amino)pyridine-4-carboxylic acid |
| 55 | 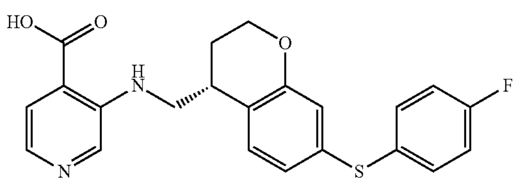 [SMILES: O=C(O)c1ccncc1NC[C@@H]1CCOc2cc(Sc3ccc(F)cc3)ccc21] | 3-({[(4R)-7-[(4-fluorophenyl)sulfanyl]-3,4-dihydro-2H-1-benzopyran-4-yl]methyl}amino)pyridine-4-carboxylic acid |
| 56 | 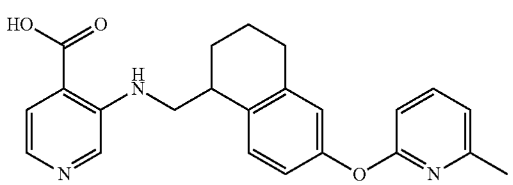 [SMILES: Cc1cccc(Oc2ccc3c(c2)CCCC3CNc2cnccc2C(=O)O)n1] | 3-[({6-[(6-methylpyridin-2-yl)oxy]-1,2,3,4-tetrahydronaphthalen-1-yl}methyl)amino]pyridine-4-carboxylic acid |
| 57 | 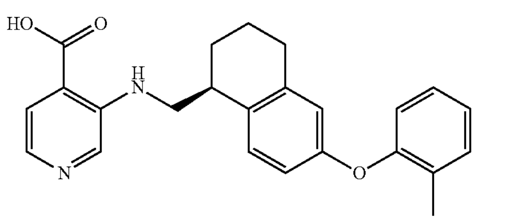 | 3-({[(1S)-6-(2-methylphenoxy)-1,2,3,4-tetrahydronaphthalen-1-yl]methyl}amino)pyridine-4-carboxylic acid |
| 58 | 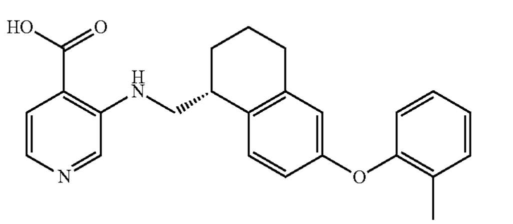 [SMILES: Cc1ccccc1Oc1ccc2c(c1)CCC[C@H]2CNc1cnccc1C(=O)O] | 3-({[(1R)-6-(2-methylphenoxy)-1,2,3,4-tetrahydronaphthalen-1-yl]methyl}amino)pyridine-4-carboxylic acid |
| 59 | 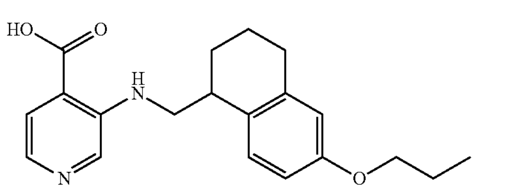 [SMILES: CCCOc1ccc2c(c1)CCCC2CNc1cnccc1C(=O)O] | 3-{[(6-propoxy-1,2,3,4-tetrahydronaphthalen-1-yl)methyl]amino}pyridine-4-carboxylic acid |

TABLE 1-continued

| Chemical Synthesis Example | Structure | Comments |
|---|---|---|
| 60 | 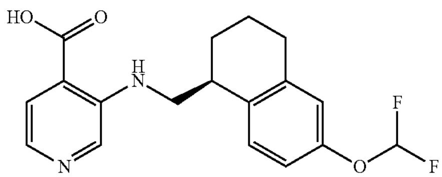 [SMILES: O=C(O)c1ccncc1NC[C@H]1CCCc2cc(OC(F)F)ccc21] | 3-({[(1S)-6-(difluoromethoxy)-1,2,3,4-tetrahydronaphthalen-1-yl]methyl}amino)pyridine-4-carboxylic acid |
| 61 | 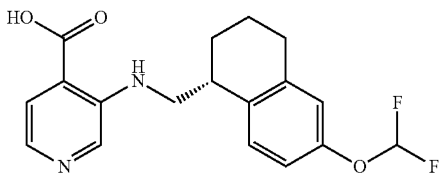 [SMILES: O=C(O)c1ccncc1NC[C@@H]1CCCc2cc(OC(F)F)ccc21] | 3-({[(1R)-6-(difluoromethoxy)-1,2,3,4-tetrahydronaphthalen-1-yl]methyl}amino)pyridine-4-carboxylic acid |
| 62 | 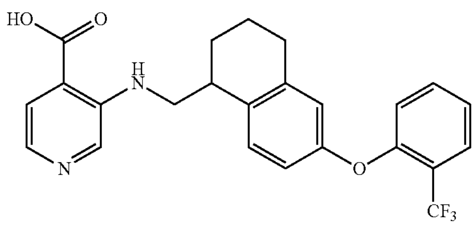 [SMILES: O=C(O)c1ccncc1NCC1CCCc2cc(Oc3ccccc3C(F)(F)F)ccc21] | 3-[({6-[2-(trifluoromethyl)phenoxy]-1,2,3,4-tetrahydronaphthalen-1-yl}methyl)amino]pyridine-4-carboxylic acid |
| 63 | 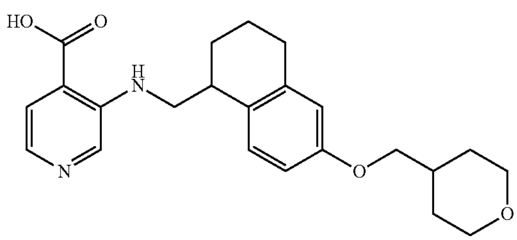 [SMILES: O=C(O)c1ccncc1NCC1CCCc2cc(OCC3CCOCC3)ccc21] | 3-({[6-(oxan-4-ylmethoxy)-1,2,3,4-tetrahydronaphthalen-1-yl]methyl}amino)pyridine-4-carboxylic acid |
| 64 | 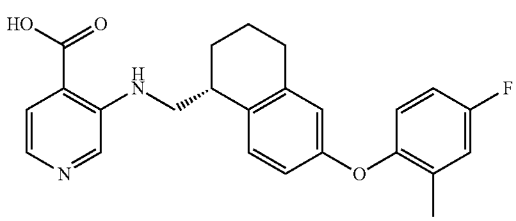 [SMILES: Cc1cc(F)ccc1Oc1ccc2c(c1)CCC[C@H]2CNc1cnccc1C(=O)O] | 3-({[(1R)-6-(4-fluoro-2-methylphenoxy)-1,2,3,4-tetrahydronaphthalen-1-yl]methyl}amino)pyridine-4-carboxylic acid |
| 65 | 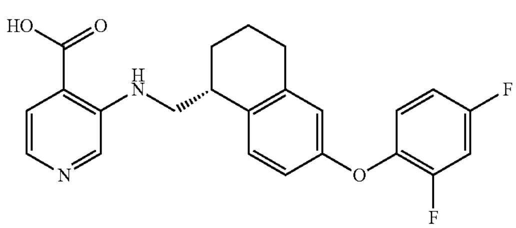 [SMILES: O=C(O)c1ccncc1NC[C@@H]1CCCc2cc(Oc3ccc(F)cc3F)ccc21] | 3-({[(1R)-6-(2,4-difluorophenoxy)-1,2,3,4-tetrahydronaphthalen-1-yl]methyl}amino)pyridine-4-carboxylic acid |
| 66 | 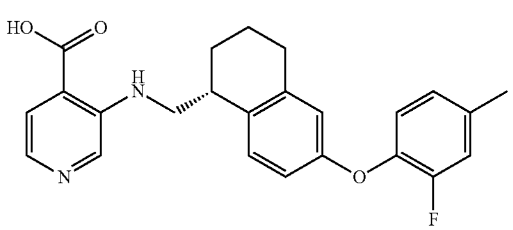 [SMILES: Cc1ccc(Oc2ccc3c(c2)CCC[C@H]3CNc2cnccc2C(=O)O)c(F)c1] | 3-({[(1R)-6-(2-fluoro-4-methylphenoxy)-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 67 | 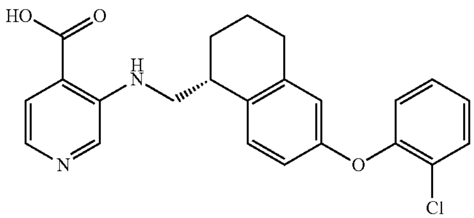 [SMILES: O=C(O)c1ccncc1NC[C@@H]1CCCc2cc(Oc3ccccc3Cl)ccc21] | 3-({[(1R)-6-(2-chlorophenoxy)-1,2,3,4-tetrahydronaphthalen-1-yl]methyl}amino)pyridine-4-carboxylic acid |
| 68 | 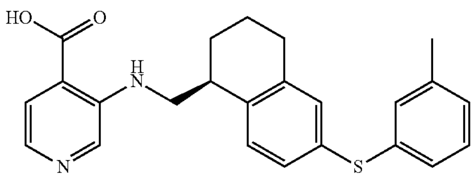 [SMILES: Cc1cccc(Sc2ccc3c(c2)CCC[C@@H]3CNc2cnccc2C(=O)O)c1] | 3-({[(1S)-6-[(3-methylphenyl)sulfanyl]-1,2,3,4-tetrahydronaphthalen-1-yl]methyl}amino)pyridine-4-carboxylic acid |
| 69 | 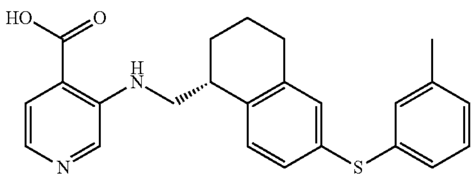 [SMILES: Cc1cccc(Sc2ccc3c(c2)CCC[C@H]3CNc2cnccc2C(=O)O)c1] | 3-({[(1R)-6-[(3-methylphenyl)sulfanyl]-1,2,3,4-tetrahydronaphthalen-1-yl]methyl}amino)pyridine-4-carboxylic acid |
| 70 | 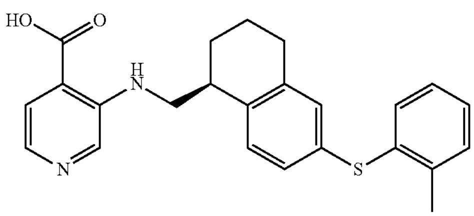 [SMILES: Cc1ccccc1Sc1ccc2c(c1)CCC[C@@H]2CNc1cnccc1C(=O)O] | 3-({[(1S)-6-[(2-methylphenyl)sulfanyl]-1,2,3,4-tetrahydronaphthalen-1-yl]methyl}amino)pyridine-4-carboxylic acid |
| 71 | 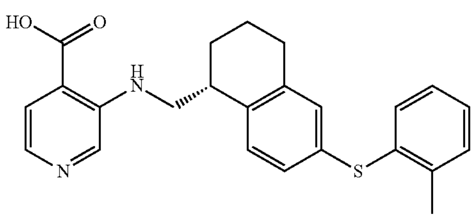 [SMILES: Cc1ccccc1Sc1ccc2c(c1)CCC[C@H]2CNc1cnccc1C(=O)O] | 3-({[(1R)-6-[(2-methylphenyl)sulfanyl]-1,2,3,4-tetrahydronaphthalen-1-yl]methyl}amino)pyridine-4-carboxylic acid |
| 72 | 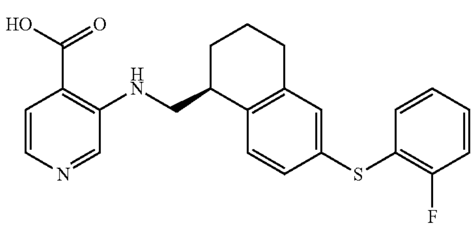 [SMILES: O=C(O)c1ccncc1NC[C@H]1CCCc2cc(Sc3ccccc3F)ccc21] | 3-({[(1S)-6-[(2-fluorophenyl)sulfanyl]-1,2,3,4-tetrahydronaphthalen-1-yl]methyl}amino)pyridine-4-carboxylic acid |
| 73 | 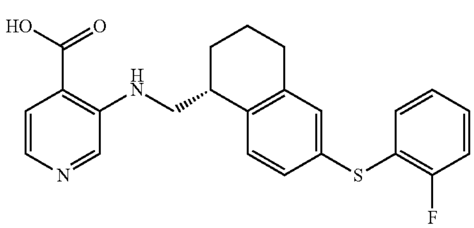 [SMILES: O=C(O)c1ccncc1NC[C@@H]1CCCc2cc(Sc3ccccc3F)ccc21] | 3-({[(1R)-6-[(2-fluorophenyl)sulfanyl]-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 74 | 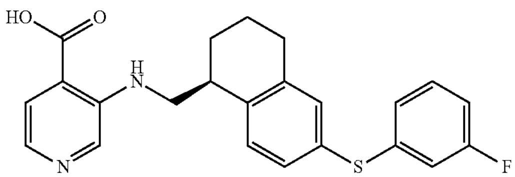 [SMILES: O=C(O)c1ccncc1NC[C@H]1CCCc2cc(Sc3cccc(F)c3)ccc21] | 3-({[(1S)-6-[(3-fluorophenyl)sulfanyl]-1,2,3,4-tetrahydronaphthalen-1-yl]methyl}amino)pyridine-4-carboxylic acid |
| 75 | 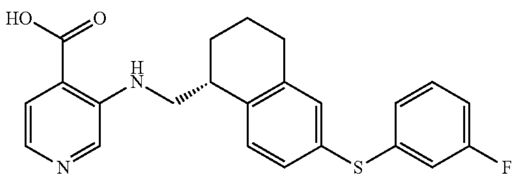 [SMILES: O=C(O)c1ccncc1NC[C@@H]1CCCc2cc(Sc3cccc(F)c3)ccc21] | 3-({[(1R)-6-[(3-fluorophenyl)sulfanyl]-1,2,3,4-tetrahydronaphthalen-1-yl]methyl}amino)pyridine-4-carboxylic acid |
| 76 | 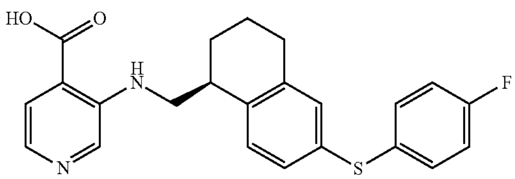 [SMILES: O=C(O)c1ccncc1NC[C@H]1CCCc2cc(Sc3ccc(F)cc3)ccc21] | 3-({[(1S)-6-[(4-fluorophenyl)sulfanyl]-1,2,3,4-tetrahydronaphthalen-1-yl]methyl}amino)pyridine-4-carboxylic acid |
| 77 | 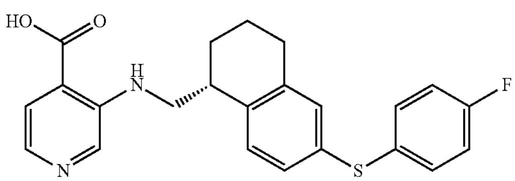 | 3-({[(1R)-6-[(4-fluorophenyl)sulfanyl]-1,2,3,4-tetrahydronaphthalen-1-yl]methyl}amino)pyridine-4-carboxylic acid |
| 78 | 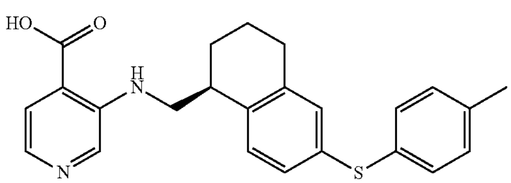 [SMILES: Cc1ccc(Sc2ccc3c(c2)CCC[C@@H]3CNc2cnccc2C(=O)O)cc1] | 3-({[(1S)-6-[(4-methylphenyl)sulfanyl]-1,2,3,4-tetrahydronaphthalen-1-yl]methyl}amino)pyridine-4-carboxylic acid |
| 79 | 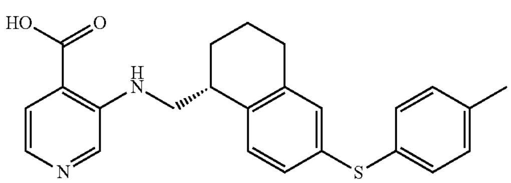 [SMILES: Cc1ccc(Sc2ccc3c(c2)CCC[C@H]3CNc2cnccc2C(=O)O)cc1] | 3-({[(1R)-6-[(4-methylphenyl)sulfanyl]-1,2,3,4-tetrahydronaphthalen-1-yl]methyl}amino)pyridine-4-carboxylic acid |
| 80 | 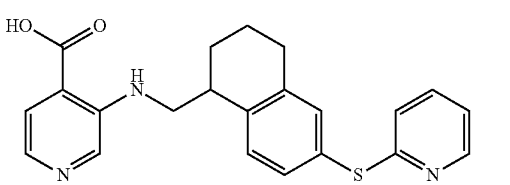 [SMILES: O=C(O)c1ccncc1NCC1CCCc2cc(Sc3ccccn3)ccc21] | 3-({[6-(pyridin-2-ylsulfanyl)-1,2,3,4-tetrahydronaphthalen-1-yl]methyl}amino)pyridine-4-carboxylic acid |
| 81 | 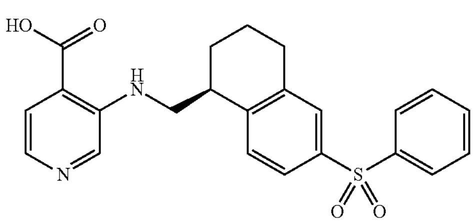 [SMILES: O=C(O)c1ccncc1NC[C@H]1CCCc2cc(S(=O)(=O)c3ccccc3)ccc21] | 3-({[(1S)-6-(benzenesulfonyl)-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 82 | 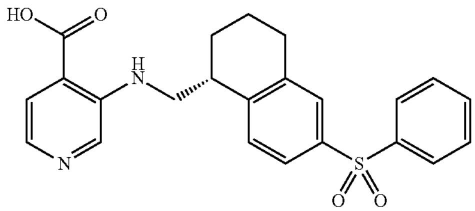 [SMILES: O=C(O)c1ccncc1NC[C@@H]1CCCc2cc(S(=O)(=O)c3ccccc3)ccc21] | 3-({[(1R)-6-(benzenesulfonyl)-1,2,3,4-tetrahydronaphthalen-1-yl]methyl}amino)pyridine-4-carboxylic acid |
| 83 | 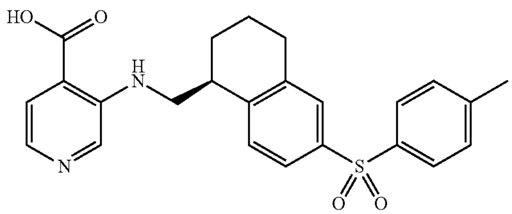 [SMILES: Cc1ccc(S(=O)(=O)c2ccc3c(c2)CCC[C@@H]3CNc2cnccc2C(=O)O)cc1] | 3-({[(1S)-6-(4-methylbenzenesulfonyl)-1,2,3,4-tetrahydronaphthalen-1-yl]methyl}amino)pyridine-4-carboxylic acid |
| 84 | 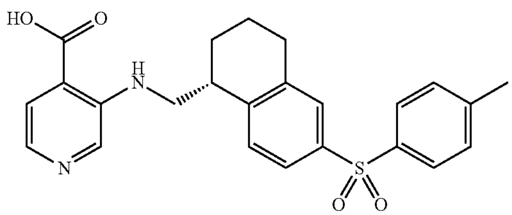 [SMILES: Cc1ccc(S(=O)(=O)c2ccc3c(c2)CCC[C@H]3CNc2cnccc2C(=O)O)cc1] | 3-({[(1R)-6-(4-methylbenzenesulfonyl)-1,2,3,4-tetrahydronaphthalen-1-yl]methyl}amino)pyridine-4-carboxylic acid |
| 85 | 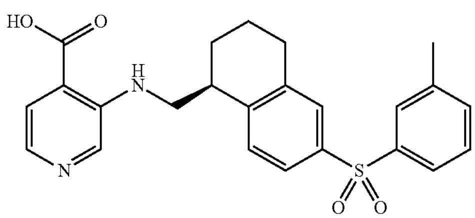 [SMILES: Cc1cccc(S(=O)(=O)c2ccc3c(c2)CCC[C@@H]3CNc2cnccc2C(=O)O)c1] | 3-({[(1S)-6-(3-methylbenzenesulfonyl)-1,2,3,4-tetrahydronaphthalen-1-yl]methyl}amino)pyridine-4-carboxylic acid |
| 86 | 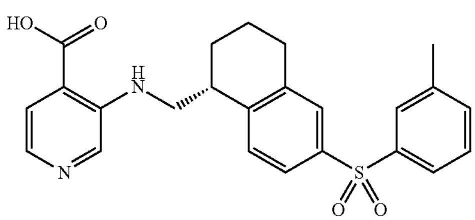 [SMILES: Cc1cccc(S(=O)(=O)c2ccc3c(c2)CCC[C@H]3CNc2cnccc2C(=O)O)c1] | 3-({[(1R)-6-(3-methylbenzenesulfonyl)-1,2,3,4-tetrahydronaphthalen-1-yl]methyl}amino)pyridine-4-carboxylic acid |
| 87 | 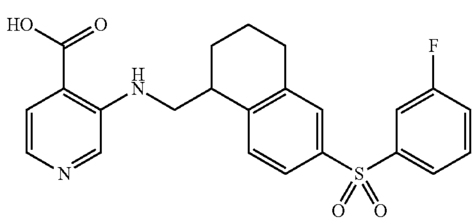 [SMILES: O=C(O)c1ccncc1NCC1CCCc2cc(S(=O)(=O)c3cccc(F)c3)ccc21] | 3-({[6-(3-fluorobenzenesulfonyl)-1,2,3,4-tetrahydronaphthalen-1-yl]methyl}amino)pyridine-4-carboxylic acid |
| 88 | 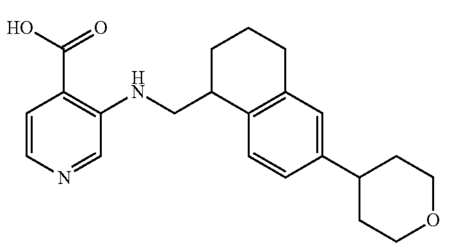 [SMILES: O=C(O)c1ccncc1NCC1CCCc2cc(C3CCOCC3)ccc21] | 3-({[6-(oxan-4-yl)-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 89 | 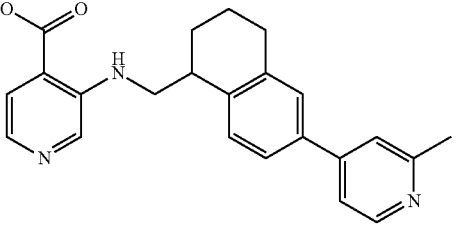 | 3-({[6-(2-methylpyridin-4-yl)-1,2,3,4-tetrahydronaphthalen-1-yl]methyl}amino)pyridine-4-carboxylic acid, hydrochloride |
| 90 | 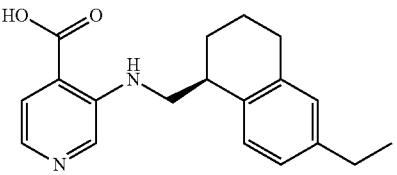 [SMILES: CCc1ccc2c(c1)CCC[C@@H]2CNc1cnccc1C(=O)O] | 3-({[(1S)-6-ethyl-1,2,3,4-tetrahydronaphthalen-1-yl]methyl}amino)pyridine-4-carboxylic acid |
| 91 | 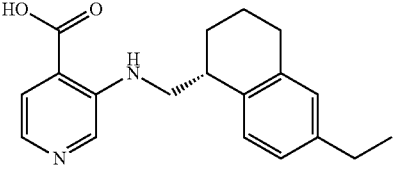 [SMILES: CCc1ccc2c(c1)CCC[C@H]2CNc1cnccc1C(=O)O] | 3-({[(1R)-6-ethyl-1,2,3,4-tetrahydronaphthalen-1-yl]methyl}amino)pyridine-4-carboxylic acid |
| 92 | 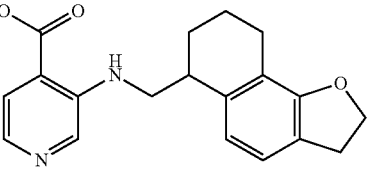 | 3-({2H,3H,6H,7H,8H,9H-naphtho[1,2-b]furan-6-ylmethyl}amino)pyridine-4-carboxylic acid |
| 93 | 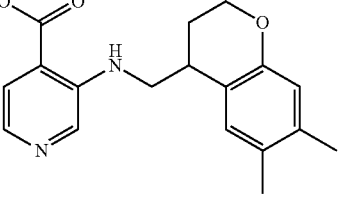 | 3-{[(6,7-dimethyl-3,4-dihydro-2H-1-benzopyran-4-yl)methyl]amino}pyridine-4-carboxylic acid |
| 94 | 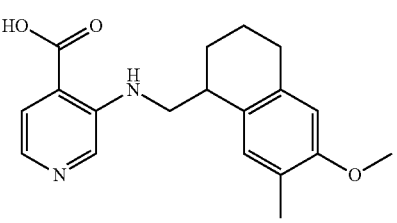 [SMILES: COc1cc2c(cc1C)C(CNc1cnccc1C(=O)O)CCC2] | 3-{[(6-methoxy-7-methyl-1,2,3,4-tetrahydronaphthalen-1-yl)methyl]amino}pyridine-4-carboxylic acid |
| 95 | 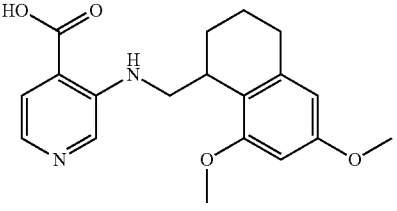 [SMILES: COc1cc2c(c(OC)c1)C(CNc1cnccc1C(=O)O)CCC2] | 3-{[(6,8-dimethoxy-1,2,3,4-tetrahydronaphthalen-1-yl)methyl]amino}pyridine-4-carboxylic acid |

TABLE 1-continued

| Chemical Synthesis Example | Structure | Comments |
|---|---|---|
| 96 | 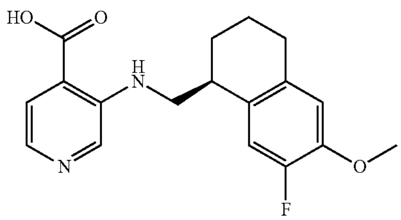 [SMILES: COc1cc2c(cc1F)[C@@H](CNc1cnccc1C(=O)O)CCC2] | 3-({[(1S)-7-fluoro-6-methoxy-1,2,3,4-tetrahydronaphthalen-1-yl]methyl}amino)pyridine-4-carboxylic acid |
| 97 | 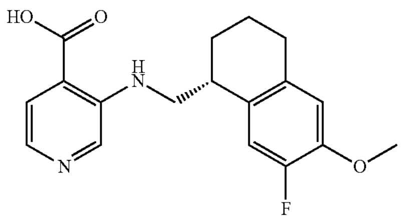 [SMILES: COc1cc2c(cc1F)[C@H](CNc1cnccc1C(=O)O)CCC2] | 3-({[(1R)-7-fluoro-6-methoxy-1,2,3,4-tetrahydronaphthalen-1-yl]methyl}amino)pyridine-4-carboxylic acid |
| 98 | 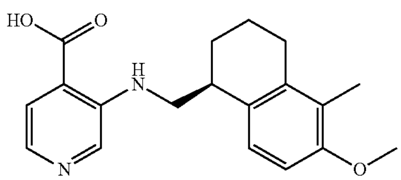 [SMILES: COc1ccc2c(c1C)CCC[C@@H]2CNc1cnccc1C(=O)O] | 3-({[(1S)-6-methoxy-5-methyl-1,2,3,4-tetrahydronaphthalen-1-yl]methyl}amino)pyridine-4-carboxylic acid |
| 99 | 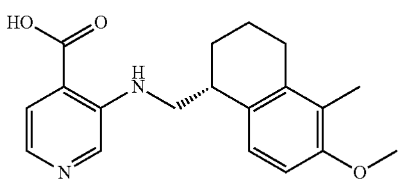 [SMILES: COc1ccc2c(c1C)CCC[C@H]2CNc1cnccc1C(=O)O] | 3-({[(1R)-6-methoxy-5-methyl-1,2,3,4-tetrahydronaphthalen-1-yl]methyl}amino)pyridine-4-carboxylic acid |
| 100 | 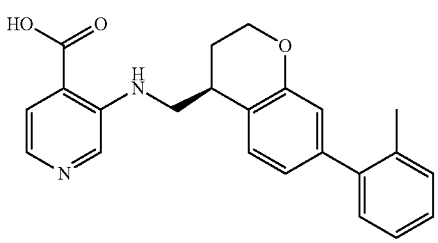 [SMILES: Cc1ccccc1-c1ccc2c(c1)OCC[C@@H]2CNc1cnccc1C(=O)O] | 3-({[(4S)-7-(2-methylphenyl)-3,4-dihydro-2H-1-benzopyran-4-yl]methyl}amino)pyridine-4-carboxylic acid |
| 101 | 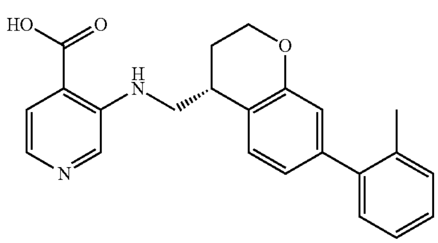 [SMILES: Cc1ccccc1-c1ccc2c(c1)OCC[C@H]2CNc1cnccc1C(=O)O] | 3-({[(4R)-7-(2-methylphenyl)-3,4-dihydro-2H-1-benzopyran-4-yl]methyl}amino)pyridine-4-carboxylic acid |
| 102 | 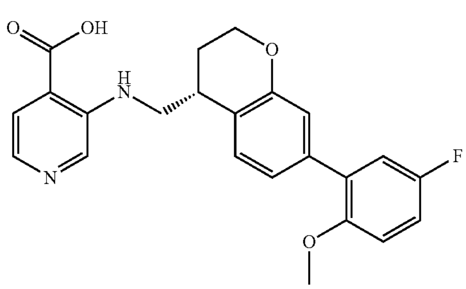 [SMILES: COc1ccc(F)cc1-c1ccc2c(c1)OCC[C@H]2CNc1cnccc1C(=O)O] | 3-({[(4R)-7-(5-fluoro-2-methoxyphenyl)-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 103 | 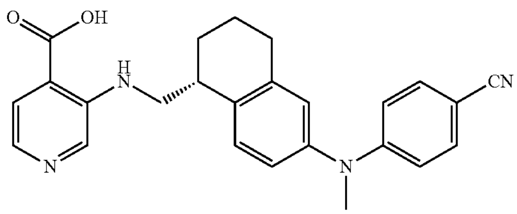 [SMILES: CN(c1ccc(C#N)cc1)c1ccc2c(c1)CCC[C@H]2CNc1cnccc1C(=O)O] | 3-({[(1R)-6-[(4-cyanophenyl)(methyl)amino]-1,2,3,4-tetrahydronaphthalen-1-yl]methyl}amino)pyridine-4-carboxylic acid |
| 104 | 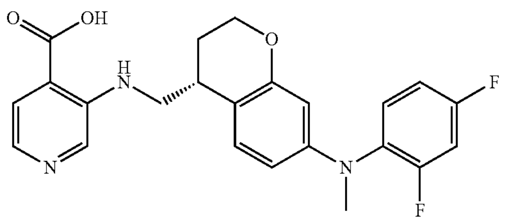 [SMILES: CN(c1ccc2c(c1)OCC[C@H]2CNc1cnccc1C(=O)O)c1ccc(F)cc1F] | 3-({[(4R)-7-[(2,4-difluorophenyl)(methyl)amino]-3,4-dihydro-2H-1-benzopyran-4-yl]methyl}amino)pyridine-4-carboxylic acid |
| 105 | 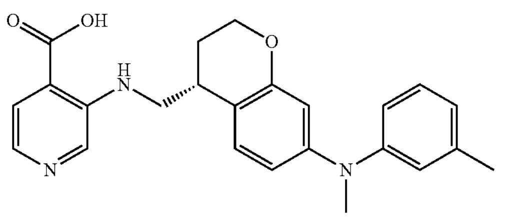 | 3-({[(4R)-7-[methyl(3-methylphenyl)amino]-3,4-dihydro-2H-1-benzopyran-4-yl]methyl}amino)pyridine-4-carboxylic acid |
| 106 | 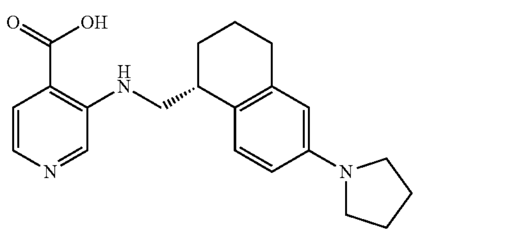 [SMILES: O=C(O)c1ccncc1NC[C@@H]1CCCc2cc(N3CCCC3)ccc21] | 3-({[(1R)-6-(pyrrolidin-1-yl)-1,2,3,4-tetrahydronaphthalen-1-yl]methyl}amino)pyridine-4-carboxylic acid |
| 107 | 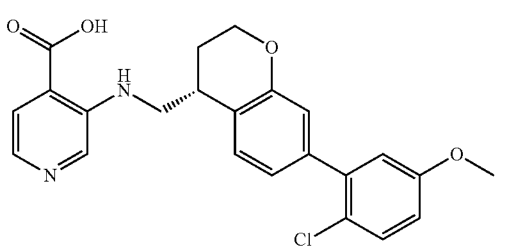 [SMILES: COc1ccc(Cl)c(-c2ccc3c(c2)OCC[C@H]3CNc2cnccc2C(=O)O)c1] | 3-({[(4R)-7-(2-chloro-5-methoxyphenyl)-3,4-dihydro-2H-1-benzopyran-4-yl]methyl}amino)pyridine-4-carboxylic acid |
| 108 | 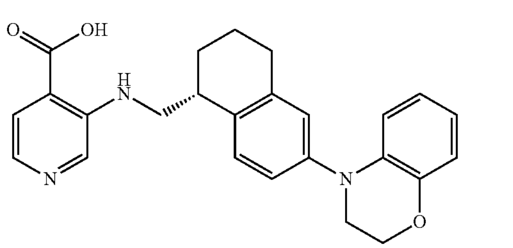 | 3-({[(1R)-6-(3,4-dihydro-2H-1,4-benzoxazin-4-yl)-1,2,3,4-tetrahydronaphthalen-1-yl]methyl}amino)pyridine-4-carboxylic acid |

| Chemical Synthesis Example | Structure | Comments |
|---|---|---|
| 109 | 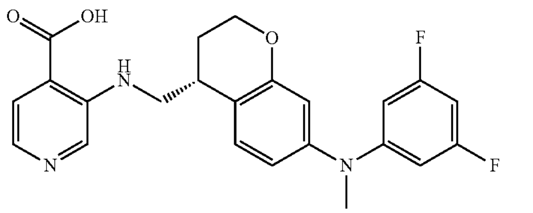 [SMILES: CN(c1cc(F)cc(F)c1)c1ccc2c(c1)OCC[C@H]2CNc1cnccc1C(=O)O] | 3-({[(4R)-7-[(3,5-difluorophenyl)(methyl)amino]-3,4-dihydro-2H-1-benzopyran-4-yl]methyl}amino)pyridine-4-carboxylic acid |
| 110 | 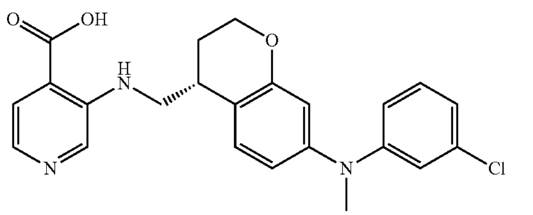 [SMILES: CN(c1cccc(Cl)c1)c1ccc2c(c1)OCC[C@H]2CNc1cnccc1C(=O)O] | 3-({[(4R)-7-[(3-chlorophenyl)(methyl)amino]-3,4-dihydro-2H-1-benzopyran-4-yl]methyl}amino)pyridine-4-carboxylic acid |
| 111 | 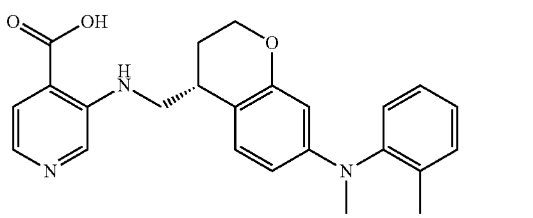 | 3-({[(4R)-7-[methyl(2-methylphenyl)amino]-3,4-dihydro-2H-1-benzopyran-4-yl]methyl}amino)pyridine-4-carboxylic acid |
| 112 | 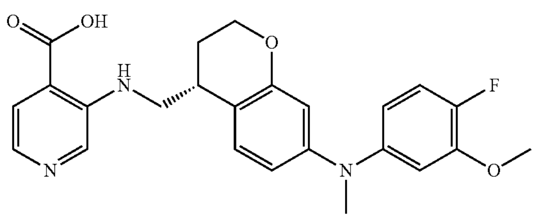 | 3-({[(4R)-7-[(4-fluoro-3-methoxyphenyl)(methyl)amino]-3,4-dihydro-2H-1-benzopyran-4-yl]methyl}amino)pyridine-4-carboxylic acid |
| 113 | 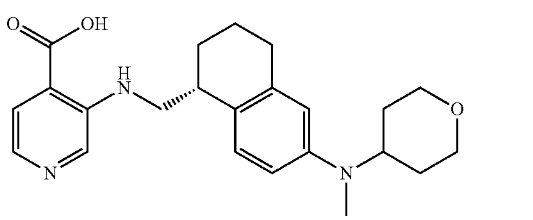 [SMILES: CN(c1ccc2c(c1)CCC[C@H]2CNc1cnccc1C(=O)O)C1CCOCC1] | 3-({[(1R)-6-[methyl(oxan-4-yl)amino]-1,2,3,4-tetrahydronaphthalen-1-yl]methyl}amino)pyridine-4-carboxylic acid |
| 114 | 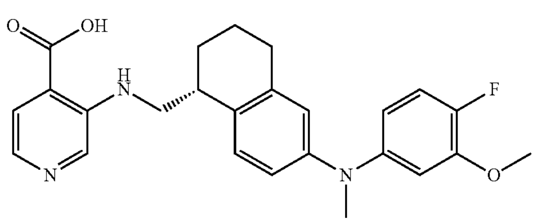 [SMILES: COc1cc(N(C)c2ccc3c(c2)CCC[C@H]3CNc2cnccc2C(=O)O)ccc1F] | 3-({[(1R)-6-[(4-fluoro-3-methoxyphenyl)(methyl)amino]-1,2,3,4-tetrahydronaphthalen-1-yl]methyl}amino)pyridine-4-carboxylic acid |
| 115 | 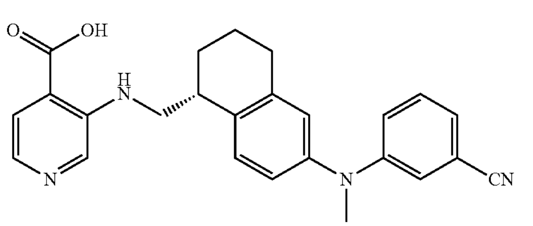 [SMILES: CN(c1cccc(C#N)c1)c1ccc2c(c1)CCC[C@H]2CNc1cnccc1C(=O)O] | 3-({[(1R)-6-[(3-cyanophenyl)(methyl)amino]-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 116 | 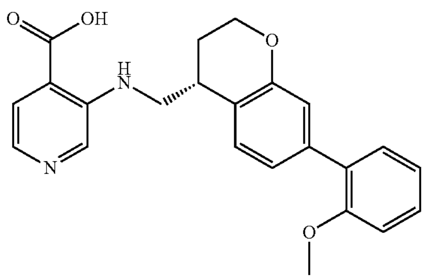 [SMILES: COc1ccccc1-c1ccc2c(c1)OCC[C@H]2CNc1cnccc1C(=O)O] | 3-({[(4R)-7-(2-methoxyphenyl)-3,4-dihydro-2H-1-benzopyran-4-yl]methyl}amino)pyridine-4-carboxylic acid |
| 117 | 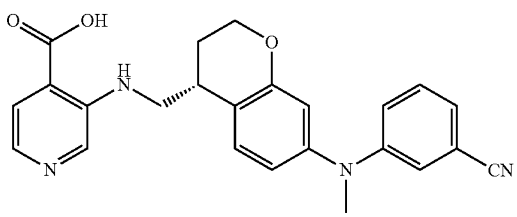 [SMILES: CN(c1cccc(C#N)c1)c1ccc2c(c1)OCC[C@H]2CNc1cnccc1C(=O)O] | 3-({[(4R)-7-[(3-cyanophenyl)(methyl)amino]-3,4-dihydro-2H-1-benzopyran-4-yl]methyl}amino)pyridine-4-carboxylic acid |
| 118 | 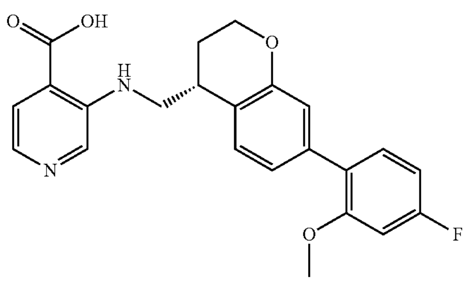 [SMILES: COc1cc(F)ccc1-c1ccc2c(c1)OCC[C@H]2CNc1cnccc1C(=O)O] | 3-({[(4R)-7-(4-fluoro-2-methoxyphenyl)-3,4-dihydro-2H-1-benzopyran-4-yl]methyl}amino)pyridine-4-carboxylic acid |
| 119 | 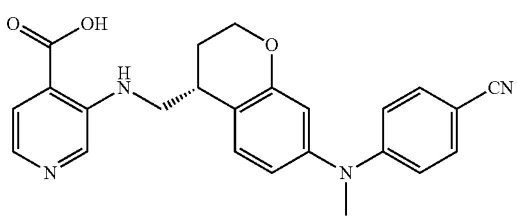 [SMILES: CN(c1ccc(C#N)cc1)c1ccc2c(c1)OCC[C@H]2CNc1cnccc1C(=O)O] | 3-({[(4R)-7-[(4-cyanophenyl)(methyl)amino]-3,4-dihydro-2H-1-benzopyran-4-yl]methyl}amino)pyridine-4-carboxylic acid |
| 120 | 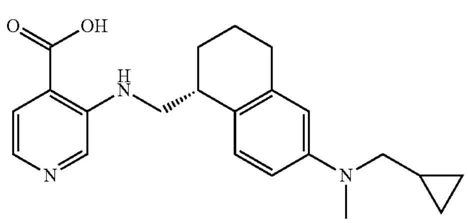 [SMILES: CN(CC1CC1)c1ccc2c(c1)CCC[C@H]2CNc1cnccc1C(=O)O] | 3-({[(1R)-6-[(cyclopropylmethyl)(methyl)amino]-1,2,3,4-tetrahydronaphthalen-1-yl]methyl}amino)pyridine-4-carboxylic acid |
| 121 | 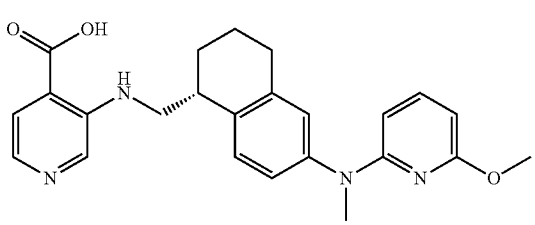 [SMILES: COc1cccc(N(C)c2ccc3c(c2)CCC[C@H]3CNc2cnccc2C(=O)O)n1] | 3-({[(1R)-6-[methyl(6-methoxypyridin-2-yl)amino]-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 122 | 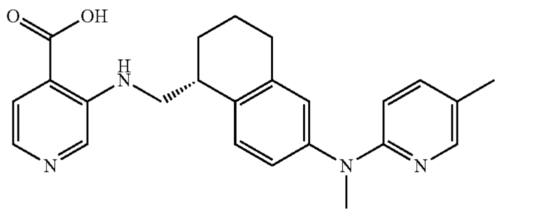 | 3-({[(1R)-6-[methyl(5-methylpyridin-2-yl)amino]-1,2,3,4-tetrahydronaphthalen-1-yl]methyl}amino)pyridine-4-carboxylic acid |
| 123 | 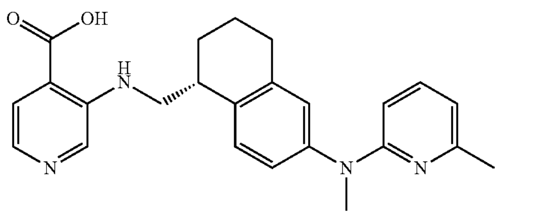 | 3-({[(1R)-6-[methyl(6-methylpyridin-2-yl)amino]-1,2,3,4-tetrahydronaphthalen-1-yl]methyl}amino)pyridine-4-carboxylic acid |
| 124 | 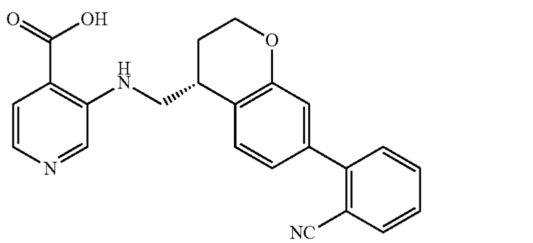 | 3-({[(4R)-7-(2-cyanophenyl)-3,4-dihydro-2H-1-benzopyran-4-yl]methyl}amino)pyridine-4-carboxylic acid |
| 125 | 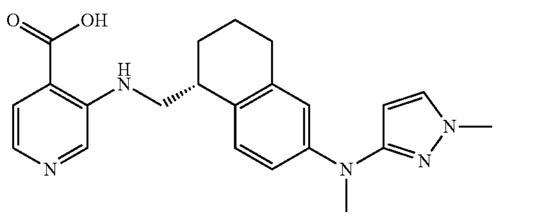 [SMILES: CN(c1ccc2c(c1)CCC[C@H]2CNc1cnccc1C(=O)O)c1ccn(C)n1] | 3-({[(1R)-6-[methyl(1-methyl-1H-pyrazol-3-yl)amino]-1,2,3,4-tetrahydronaphthalen-1-yl]methyl}amino)pyridine-4-carboxylic acid |
| 126 | 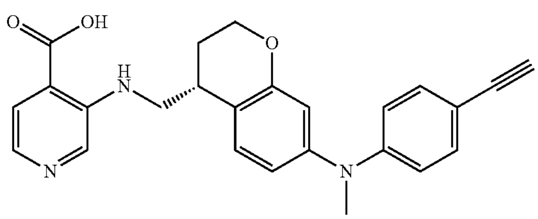 [SMILES: C#Cc1ccc(N(C)c2ccc3c(c2)OCC[C@H]3CNc2cnccc2C(=O)O)cc1] | 3-({[(4R)-7-[(4-ethynylphenyl)(methyl)amino]-3,4-dihydro-2H-1-benzopyran-4-yl]methyl}amino)pyridine-4-carboxylic acid |
| 127 | 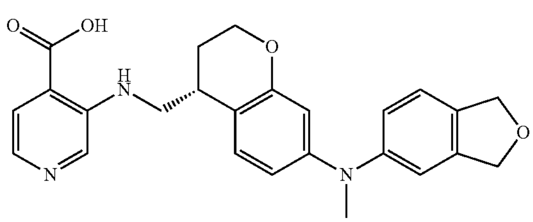 [SMILES: CN(c1ccc2c(c1)COC2)c1ccc2c(c1)OCC[C@H]2CNc1cnccc1C(=O)O] | 3-({[(4R)-7-[(1,3-dihydro-2-benzofuran-5-yl)(methyl)amino]-3,4-dihydro-2H-1-benzopyran-4-yl]methyl}amino)pyridine-4-carboxylic acid |
| 128 | 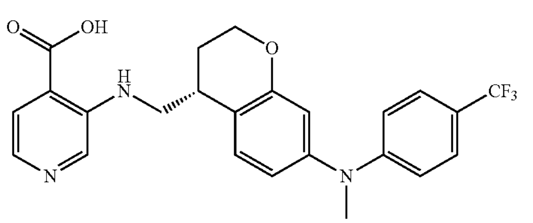 [SMILES: CN(c1ccc(C(F)(F)F)cc1)c1ccc2c(c1)OCC[C@H]2CNc1cnccc1C(=O)O] | 3-({[(4R)-7-{methyl[4-(trifluoromethyl)phenyl]amino}-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 129 | 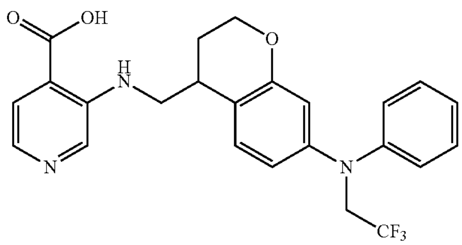 [SMILES: O=C(O)c1ccncc1NCC1CCOc2cc(N(CC(F)(F)F)c3ccccc3)ccc21] | 3-[({7-[phenyl(2,2,2-trifluoroethyl)amino]-3,4-dihydro-2H-1-benzopyran-4-yl}methyl)amino]pyridine-4-carboxylic acid |
| 130 | 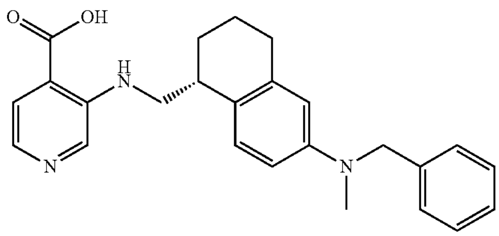 | 3-({[(1R)-6-[benzyl(methyl)amino]-1,2,3,4-tetrahydronaphthalen-1-yl]methyl}amino)pyridine-4-carboxylic acid |
| 131 | 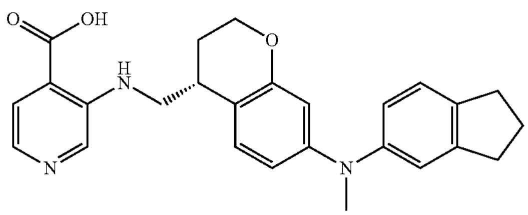 [SMILES: CN(c1ccc2c(c1)CCC2)c1ccc2c(c1)OCC[C@H]2CNc1cnccc1C(=O)O] | 3-({[(4R)-7-[(2,3-dihydro-1H-inden-5-yl)(methyl)amino]-3,4-dihydro-2H-1-benzopyran-4-yl]methyl}amino)pyridine-4-carboxylic acid |
| 132 | 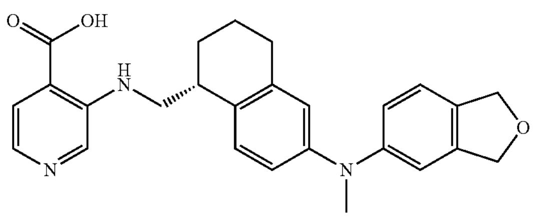 | 3-({[(1R)-6-[(1,3-dihydro-2-benzofuran-5-yl)(methyl)amino]-1,2,3,4-tetrahydronaphthalen-1-yl]methyl}amino)pyridine-4-carboxylic acid |
| 133 | 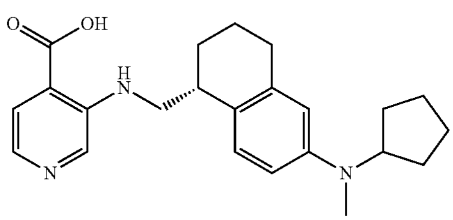 [SMILES: CN(c1ccc2c(c1)CCC[C@H]2CNc1cnccc1C(=O)O)C1CCCC1] | 3-({[(1R)-6-[cyclopentyl(methyl)amino]-1,2,3,4-tetrahydronaphthalen-1-yl]methyl}amino)pyridine-4-carboxylic acid |
| 134 | 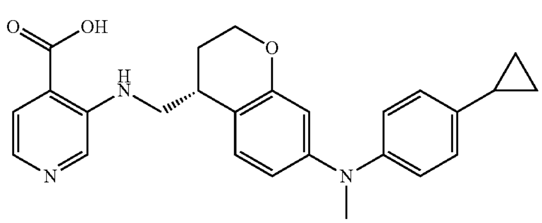 [SMILES: CN(c1ccc(C2CC2)cc1)c1ccc2c(c1)OCC[C@H]2CNc1cnccc1C(=O)O] | 3-({[(4R)-7-[(4-cyclopropylphenyl)(methyl)amino]-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 135 | 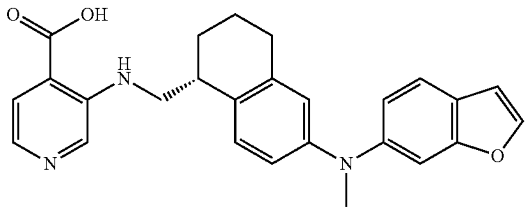 | 3-({[(1R)-6-[(1-benzofuran-6-yl)(methyl)amino]-1,2,3,4-tetrahydronaphthalen-1-yl]methyl}amino)pyridine-4-carboxylic acid |
| 136 | 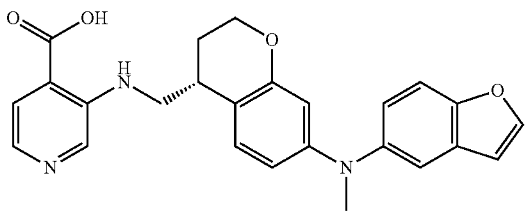 | 3-({[(4R)-7-[(1-benzofuran-5-yl)(methyl)amino]-3,4-dihydro-2H-1-benzopyran-4-yl]methyl}amino)pyridine-4-carboxylic acid |
| 137 | 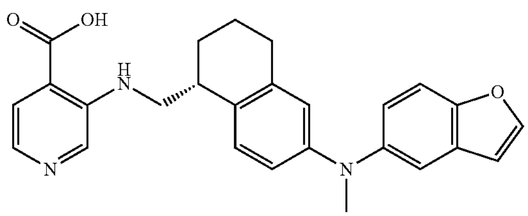 [SMILES: CN(c1ccc2c(c1)CCC[C@H]2CNc1cnccc1C(=O)O)c1ccc2occc2c1] | 3-({[(1R)-6-[(1-benzofuran-5-yl)(methyl)amino]-1,2,3,4-tetrahydronaphthalen-1-yl]methyl}amino)pyridine-4-carboxylic acid |
| 138 | 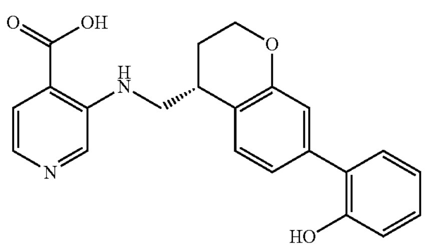 | 3-({[(4R)-7-(2-hydroxyphenyl)-3,4-dihydro-2H-1-benzopyran-4-yl]methyl}amino)pyridine-4-carboxylic acid |
| 139 | 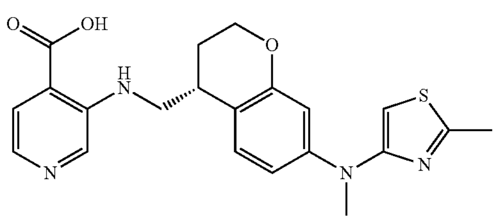 [SMILES: Cc1nc(N(C)c2ccc3c(c2)OCC[C@H]3CNc2cnccc2C(=O)O)cs1] | 3-({[(4R)-7-[methyl(2-methyl-1,3-thiazol-4-yl)amino]-3,4-dihydro-2H-1-benzopyran-4-yl]methyl}amino)pyridine-4-carboxylic acid |
| 140 | 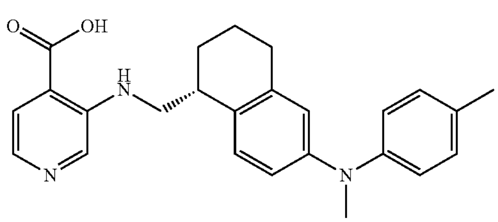 | 3-({[(1R)-6-[methyl(4-methylphenyl)amino]-1,2,3,4-tetrahydronaphthalen-1-yl]methyl}amino)pyridine-4-carboxylic acid |
| 141 | 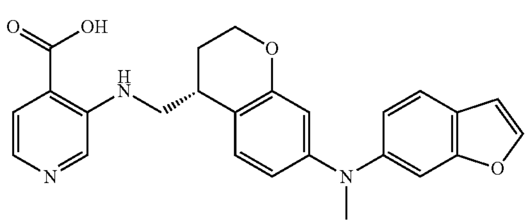 | 3-({[(4R)-7-[(1-benzofuran-6-yl)(methyl)amino]-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 142 | 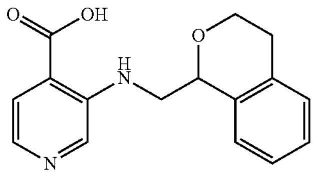 [SMILES: O=C(O)c1ccncc1NCC1OCCc2ccccc21] | 3-[(3,4-dihydro-1H-2-benzopyran-1-ylmethyl)amino]pyridine-4-carboxylic acid |
| 143 | 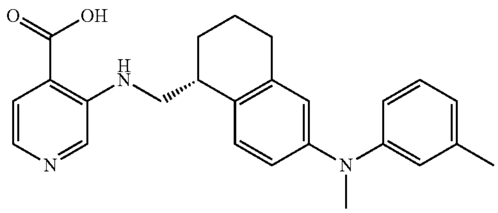 | 3-({[(1R)-6-[methyl(3-methylphenyl)amino]-1,2,3,4-tetrahydronaphthalen-1-yl]methyl}amino)pyridine-4-carboxylic acid |
| 144 | 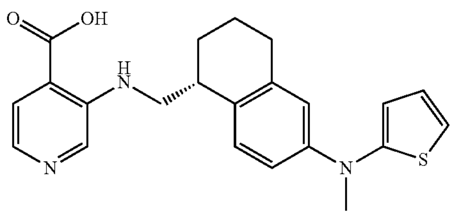 [SMILES: CN(c1ccc2c(c1)CCC[C@H]2CNc1cnccc1C(=O)O)c1cccs1] | 3-({[(1R)-6-[methyl(thiophen-2-yl)amino]-1,2,3,4-tetrahydronaphthalen-1-yl]methyl}amino)pyridine-4-carboxylic acid |
| 145 | 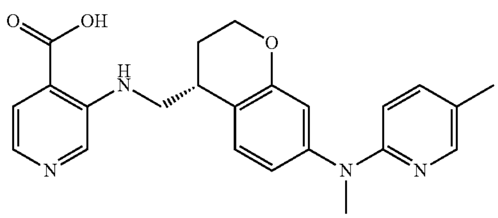 [SMILES: Cc1ccc(N(C)c2ccc3c(c2)OCC[C@H]3CNc2cnccc2C(=O)O)nc1] | 3-({[(4R)-7-[methyl(5-methylpyridin-2-yl)amino]-3,4-dihydro-2H-1-benzopyran-4-yl]methyl}amino)pyridine-4-carboxylic acid |
| 146 | 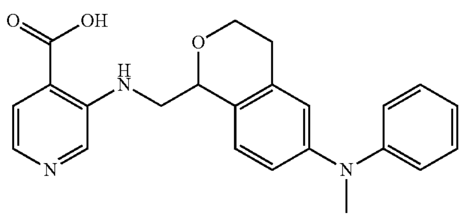 | 3-[({6-[methyl(phenyl)amino]-3,4-dihydro-1H-2-benzopyran-1-yl}methyl)amino]pyridine-4-carboxylic acid |
| 147 | 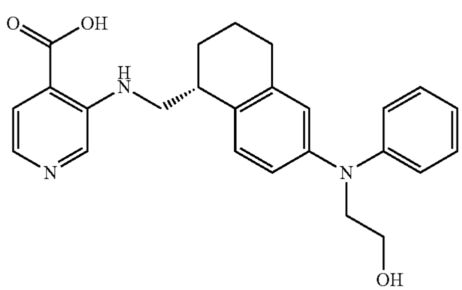 [SMILES: O=C(O)c1ccncc1NC[C@@H]1CCCc2cc(N(CCO)c3ccccc3)ccc21] | 3-({[(1R)-6-[(2-hydroxyethyl)(phenyl)amino]-1,2,3,4-tetrahydronaphthalen-1-yl]methyl}amino)pyridine-4-carboxylic acid |
| 148 | 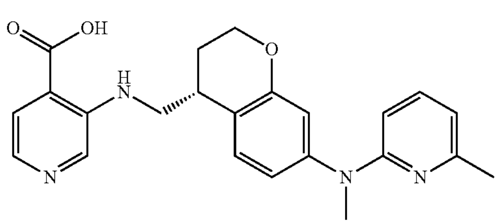 | 3-({[(4R)-7-[methyl(6-methylpyridin-2-yl)amino]-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 149 | 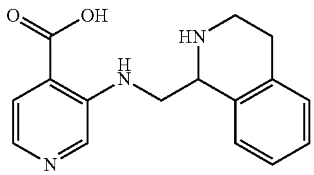 [SMILES: O=C(O)c1ccncc1NCC1NCCc2ccccc21] | 3-[(1,2,3,4-tetrahydroisoquinolin-1-ylmethyl)amino]pyridine-4-carboxylic acid |
| 150 | 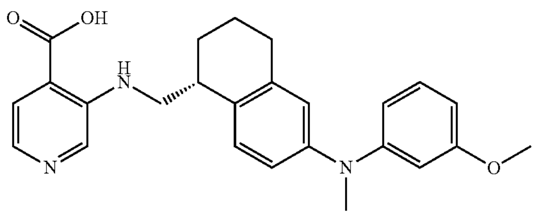 [SMILES: COc1cccc(N(C)c2ccc3c(c2)CCC[C@H]3CNc2cnccc2C(=O)O)c1] | 3-({[(1R)-6-[(3-methoxyphenyl)(methyl)amino]-1,2,3,4-tetrahydronaphthalen-1-yl]methyl}amino)pyridine-4-carboxylic acid |
| 151 | 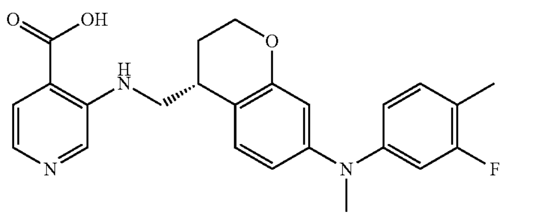 [SMILES: Cc1ccc(N(C)c2ccc3c(c2)OCC[C@H]3CNc2cnccc2C(=O)O)cc1F] | 3-({[(4R)-7-[(3-fluoro-4-methylphenyl)(methyl)amino]-3,4-dihydro-2H-1-benzopyran-4-yl]methyl}amino)pyridine-4-carboxylic acid |
| 152 | 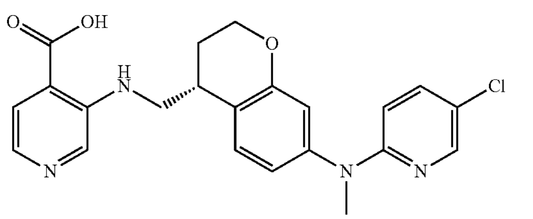 [SMILES: CN(c1ccc2c(c1)OCC[C@H]2CNc1cnccc1C(=O)O)c1ccc(Cl)cn1] | 3-({[(4R)-7-[(5-chloropyridin-2-yl)(methyl)amino]-3,4-dihydro-2H-1-benzopyran-4-yl]methyl}amino)pyridine-4-carboxylic acid |
| 153 | 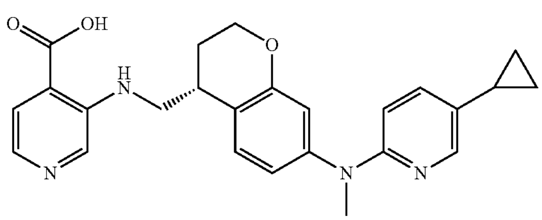 [SMILES: CN(c1ccc2c(c1)OCC[C@H]2CNc1cnccc1C(=O)O)c1ccc(C2CC2)cn1] | 3-({[(4R)-7-[(5-cyclopropylpyridin-2-yl)(methyl)amino]-3,4-dihydro-2H-1-benzopyran-4-yl]methyl}amino)pyridine-4-carboxylic acid |
| 154 | 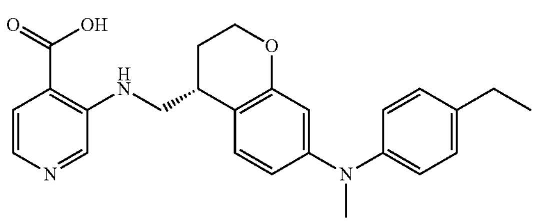 [SMILES: CCc1ccc(N(C)c2ccc3c(c2)OCC[C@H]3CNc2cnccc2C(=O)O)cc1] | 3-({[(4R)-7-[(4-ethylphenyl)(methyl)amino]-3,4-dihydro-2H-1-benzopyran-4-yl]methyl}amino)pyridine-4-carboxylic acid |
| 155 | 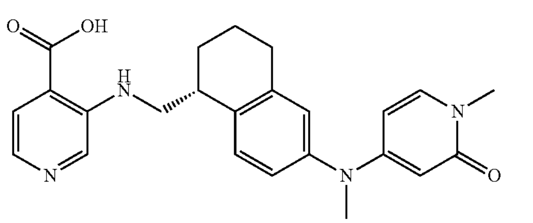 [SMILES: CN(c1ccc2c(c1)CCC[C@H]2CNc1cnccc1C(=O)O)c1ccn(C)c(=O)c1] | 3-({[(1R)-6-[methyl(1-methyl-2-oxo-1,2-dihydropyridin-4-yl)amino]-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 156 | 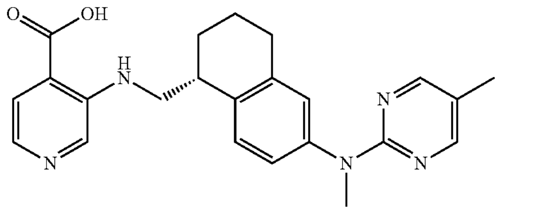 [SMILES: Cc1cnc(N(C)c2ccc3c(c2)CCC[C@H]3CNc2cnccc2C(=O)O)nc1] | 3-({[(1R)-6-[methyl(5-methylpyrimidin-2-yl)amino]-1,2,3,4-tetrahydronaphthalen-1-yl]methyl}amino)pyridine-4-carboxylic acid |
| 157 | 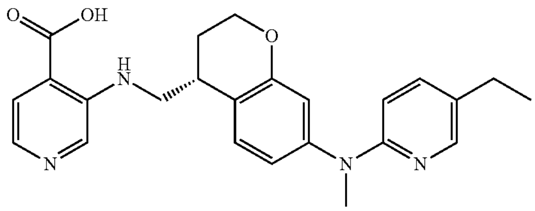 | 3-({[(4R)-7-[(5-ethylpyridin-2-yl)(methyl)amino]-3,4-dihydro-2H-1-benzopyran-4-yl]methyl}amino)pyridine-4-carboxylic acid |
| 158 | 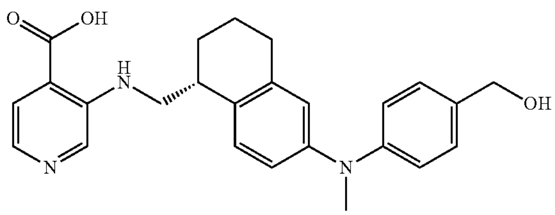 | 3-({[(1R)-6-{[4-(hydroxymethyl)phenyl](methyl)amino}-1,2,3,4-tetrahydronaphthalen-1-yl]methyl}amino)pyridine-4-carboxylic acid |
| 159 | 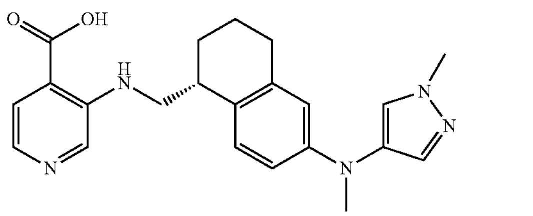 [SMILES: CN(c1ccc2c(c1)CCC[C@H]2CNc1cnccc1C(=O)O)c1cnn(C)c1] | 3-({[(1R)-6-[methyl(1-methyl-1H-pyrazol-4-yl)amino]-1,2,3,4-tetrahydronaphthalen-1-yl]methyl}amino)pyridine-4-carboxylic acid |
| 160 | 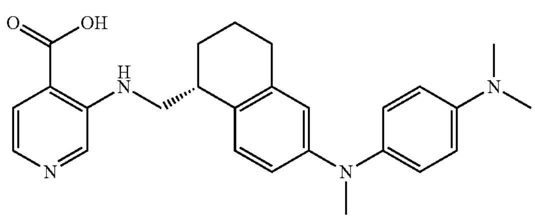 [SMILES: CN(C)c1ccc(N(C)c2ccc3c(c2)CCC[C@H]3CNc2cnccc2C(=O)O)cc1] | 3-({[(1R)-6-{[4-(dimethylamino)phenyl](methyl)amino}-1,2,3,4-tetrahydronaphthalen-1-yl]methyl}amino)pyridine-4-carboxylic acid |
| 161 | 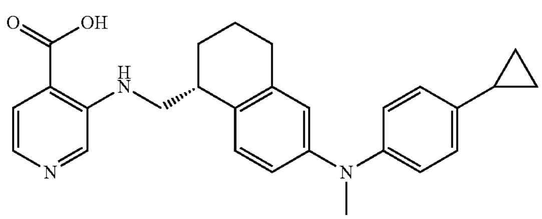 [SMILES: CN(c1ccc(C2CC2)cc1)c1ccc2c(c1)CCC[C@H]2CNc1cnccc1C(=O)O] | 3-({[(1R)-6-[(4-cyclopropylphenyl)(methyl)amino]-1,2,3,4-tetrahydronaphthalen-1-yl]methyl}amino)pyridine-4-carboxylic acid |
| 162 | 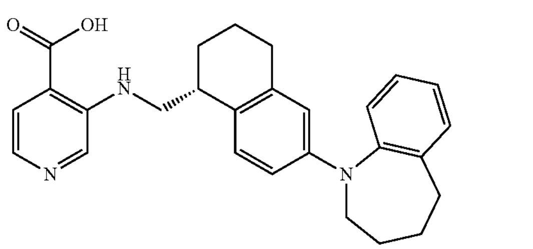 [SMILES: O=C(O)c1ccncc1NC[C@@H]1CCCc2cc(N3CCCCc4ccccc43)ccc21] | 3-({[(1R)-6-(2,3,4,5-tetrahydro-1H-1-benzazepin-1-yl)-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 163 | 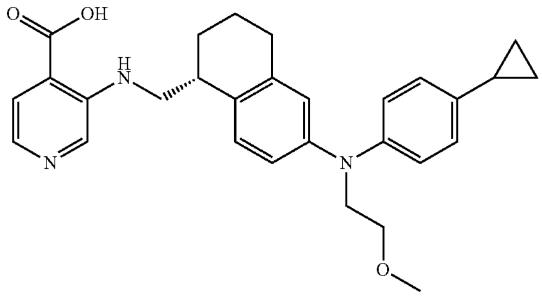 [SMILES: COCCN(c1ccc(C2CC2)cc1)c1ccc2c(c1)CCC[C@H]2CNc1cnccc1C(=O)O] | 3-({[(1R)-6-[(4-cyclopropylphenyl)(2-methoxyethyl)amino]-1,2,3,4-tetrahydronaphthalen-1-yl]methyl}amino)pyridine-4-carboxylic acid |
| 164 | 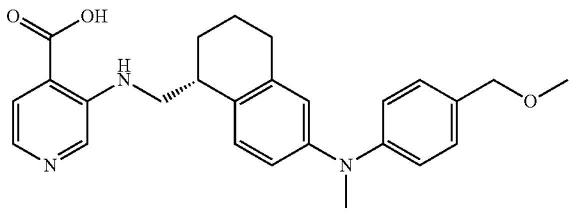 | 3-({[(1R)-6-{[4-(methoxymethyl)phenyl](methyl)amino}-1,2,3,4-tetrahydronaphthalen-1-yl]methyl}amino)pyridine-4-carboxylic acid |
| 165 | 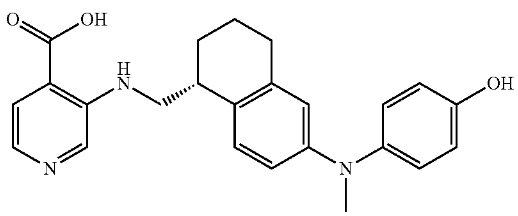 | 3-({[(1R)-6-[(4-hydroxyphenyl)(methyl)amino]-1,2,3,4-tetrahydronaphthalen-1-yl]methyl}amino)pyridine-4-carboxylic acid |
| 166 | 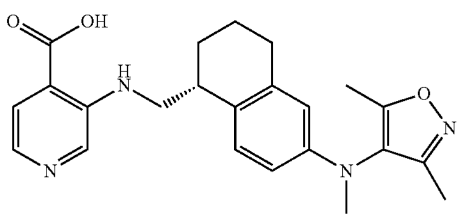 [SMILES: Cc1noc(C)c1N(C)c1ccc2c(c1)CCC[C@H]2CNc1cnccc1C(=O)O] | 3-({[(1R)-6-[(dimethyl-1,2-oxazol-4-yl)(methyl)amino]-1,2,3,4-tetrahydronaphthalen-1-yl]methyl}amino)pyridine-4-carboxylic acid |
| 167 | 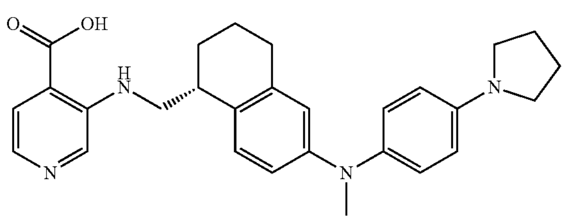 | 3-({[(1R)-6-{methyl[4-(pyrrolidin-1-yl)phenyl]amino}-1,2,3,4-tetrahydronaphthalen-1-yl]methyl}amino)pyridine-4-carboxylic acid |
| 168 | 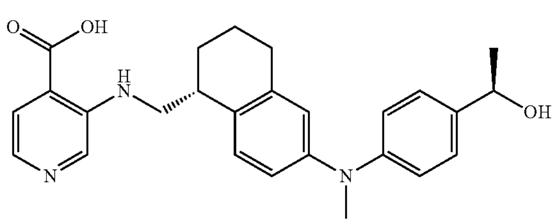 [SMILES: C[C@@H](O)c1ccc(N(C)c2ccc3c(c2)CCC[C@H]3CNc2cnccc2C(=O)O)cc1] | 3-({[(1R)-6-({4-[(1R)-1-hydroxyethyl]phenyl}(methyl)amino)-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 169 | 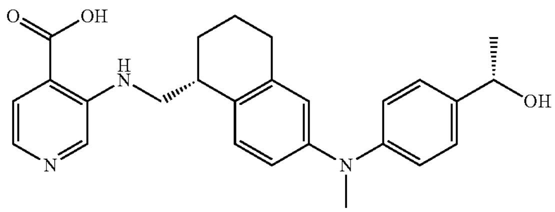 [SMILES: C[C@H](O)c1ccc(N(C)c2ccc3c(c2)CCC[C@H]3CNc2cnccc2C(=O)O)cc1] | 3-({[(1R)-6-({4-[(1S)-1-hydroxyethyl]phenyl}(methyl)amino)-1,2,3,4-tetrahydronaphthalen-1-yl]methyl}amino)pyridine-4-carboxylic acid |
| 170 | 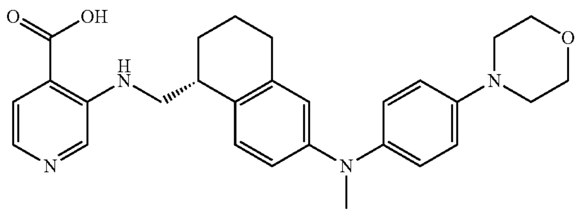 | 3-({[(1R)-6-{methyl[4-(morpholin-4-yl)phenyl]amino}-1,2,3,4-tetrahydronaphthalen-1-yl]methyl}amino)pyridine-4-carboxylic acid |
| 171 | 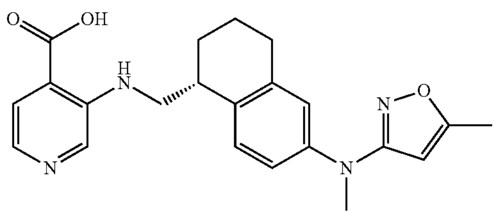 [SMILES: Cc1cc(N(C)c2ccc3c(c2)CCC[C@H]3CNc2cnccc2C(=O)O)no1] | 3-({[(1R)-6-[methyl(5-methyl-1,2-oxazol-3-yl)amino]-1,2,3,4-tetrahydronaphthalen-1-yl]methyl}amino)pyridine-4-carboxylic acid |
| 172 | 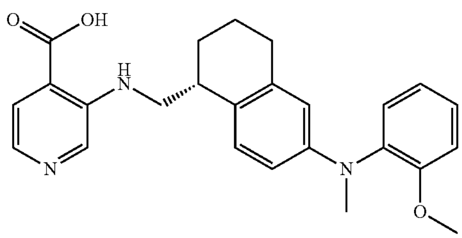 [SMILES: COc1ccccc1N(C)c1ccc2c(c1)CCC[C@H]2CNc1cnccc1C(=O)O] | 3-({[(1R)-6-[(2-methoxyphenyl)(methyl)amino]-1,2,3,4-tetrahydronaphthalen-1-yl]methyl}amino)pyridine-4-carboxylic acid |
| 173 | 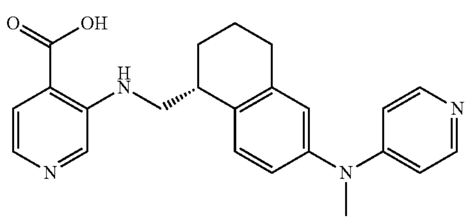 [SMILES: CN(c1ccncc1)c1ccc2c(c1)CCC[C@H]2CNc1cnccc1C(=O)O] | 3-({[(1R)-6-[methyl(pyridin-4-yl)amino]-1,2,3,4-tetrahydronaphthalen-1-yl]methyl}amino)pyridine-4-carboxylic acid |
| 174 | 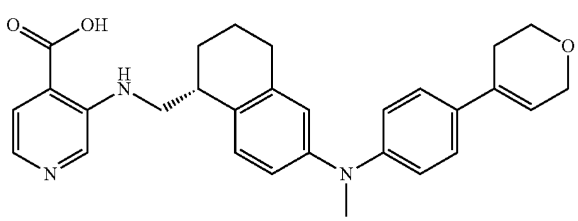 | 3-({[(1R)-6-{[4-(3,6-dihydro-2H-pyran-4-yl)phenyl](methyl)amino}-1,2,3,4-tetrahydronaphthalen-1-yl]methyl}amino)pyridine-4-carboxylic acid |
| 175 | 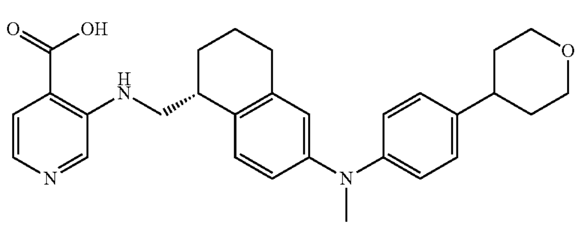 | 3-({[(1R)-6-{methyl[4-(oxan-4-yl)phenyl]amino}-1,2,3,4-tetrahydronaphthalen-1-yl]methyl}amino)pyridine-4-carboxylic acid |

TABLE 1-continued

| Chemical Synthesis Example | Structure | Comments |
|---|---|---|
| 176 | 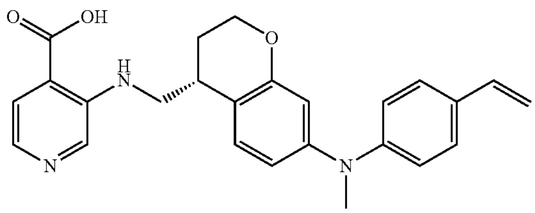 [SMILES: C=Cc1ccc(N(C)c2ccc3c(c2)OCC[C@H]3CNc2cnccc2C(=O)O)cc1] | 3-({[(4R)-7-[(4-ethenylphenyl)(methyl)amino]-3,4-dihydro-2H-1-benzopyran-4-yl]methyl}amino)pyridine-4-carboxylic acid |
| 177 | 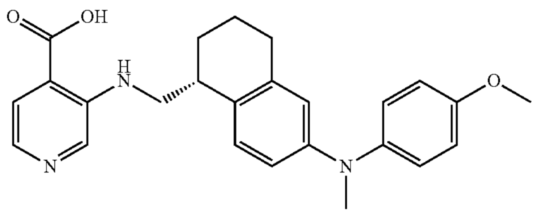 [SMILES: COc1ccc(N(C)c2ccc3c(c2)OCC[C@H]3CNc2cnccc2C(=O)O)cc1] | 3-({[(1R)-6-[(4-methoxyphenyl)(methyl)amino]-1,2,3,4-tetrahydronaphthalen-1-yl]methyl}amino)pyridine-4-carboxylic acid |
| 178 | 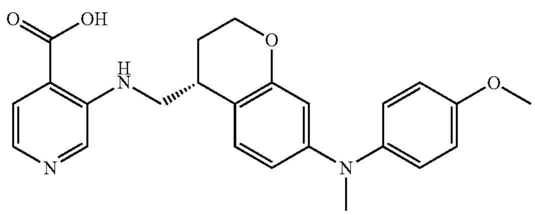 | 3-({[(4R)-7-[(4-methoxyphenyl)(methyl)amino]-3,4-dihydro-2H-1-benzopyran-4-yl]methyl}amino)pyridine-4-carboxylic acid |
| 179 | 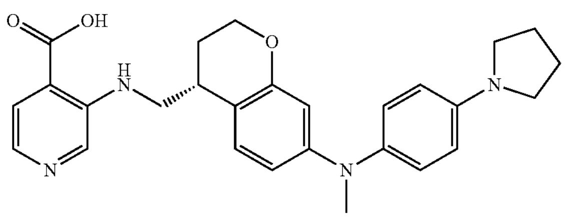 [SMILES: CN(c1ccc(N2CCCC2)cc1)c1ccc2c(c1)OCC[C@H]2CNc1cnccc1C(=O)O] | 3-({[(4R)-7-{methyl[4-(pyrrolidin-1-yl)phenyl]amino}-3,4-dihydro-2H-1-benzopyran-4-yl]methyl}amino)pyridine-4-carboxylic acid |
| 180 | 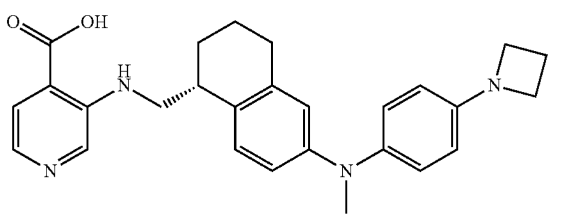 [SMILES: CN(c1ccc(N2CCC2)cc1)c1ccc2c(c1)CCC[C@H]2CNc1cnccc1C(=O)O] | 3-({[(1R)-6-{[4-(azetidin-1-yl)phenyl](methyl)amino}-1,2,3,4-tetrahydronaphthalen-1-yl]methyl}amino)pyridine-4-carboxylic acid |
| 181 | 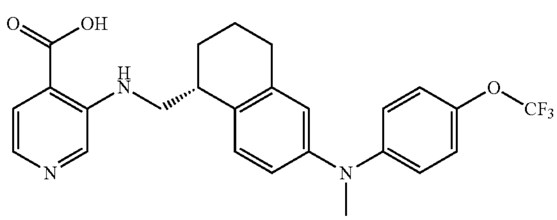 [SMILES: CN(c1ccc(OC(F)(F)F)cc1)c1ccc2c(c1)CCC[C@H]2CNc1cnccc1C(=O)O] | 3-({[(1R)-6-{methyl[4-(trifluoromethoxy)phenyl]amino}-1,2,3,4-tetrahydronaphthalen-1-yl]methyl}amino)pyridine-4-carboxylic acid |
| 182 | 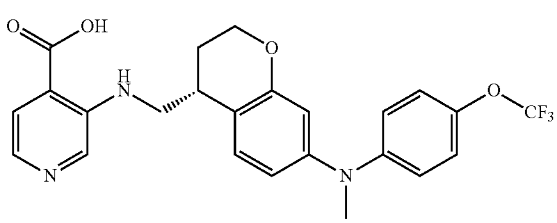 [SMILES: CN(c1ccc(OC(F)(F)F)cc1)c1ccc2c(c1)OCC[C@H]2CNc1cnccc1C(=O)O] | 3-({[(4R)-7-{methyl[4-(trifluoromethoxy)phenyl]amino}-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 183 | 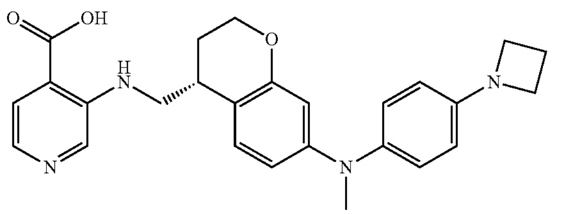 [SMILES: CN(c1ccc(N2CCC2)cc1)c1ccc2c(c1)OCC[C@H]2CNc1cnccc1C(=O)O] | 3-({[(4R)-7-{[4-(azetidin-1-yl)phenyl](methyl)amino}-3,4-dihydro-2H-1-benzopyran-4-yl]methyl}amino)pyridine-4-carboxylic acid |
| 184 | 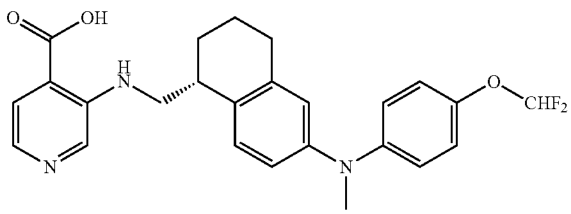 [SMILES: CN(c1ccc(OC(F)F)cc1)c1ccc2c(c1)CCC[C@H]2CNc1cnccc1C(=O)O] | 3-({[(1R)-6-{[4-(difluoromethoxy)phenyl](methyl)amino}-1,2,3,4-tetrahydronaphthalen-1-yl]methyl}amino)pyridine-4-carboxylic acid |
| 185 | 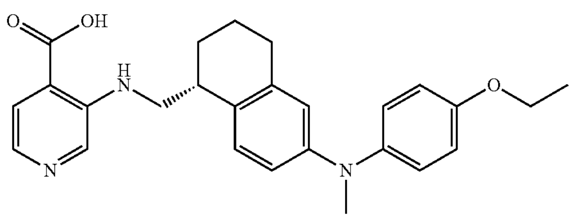 | 3-({[(1R)-6-[(4-ethoxyphenyl)(methyl)amino]-1,2,3,4-tetrahydronaphthalen-1-yl]methyl}amino)pyridine-4-carboxylic acid |
| 186 | 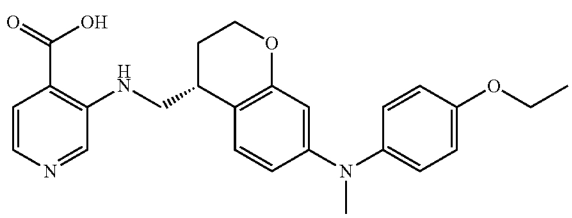 | 3-({[(4R)-7-[(4-ethoxyphenyl)(methyl)amino]-3,4-dihydro-2H-1-benzopyran-4-yl]methyl}amino)pyridine-4-carboxylic acid |
| 187 | 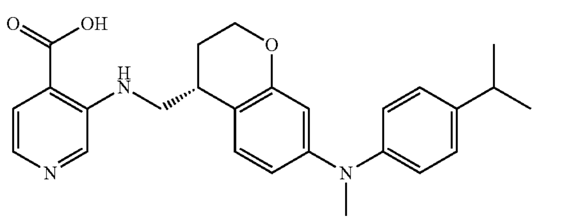 [SMILES: CC(C)c1ccc(N(C)c2ccc3c(c2)OCC[C@H]3CNc2cnccc2C(=O)O)cc1] | 3-({[(4R)-7-{methyl[4-(propan-2-yl)phenyl]amino}-3,4-dihydro-2H-1-benzopyran-4-yl]methyl}amino)pyridine-4-carboxylic acid |
| 188 | 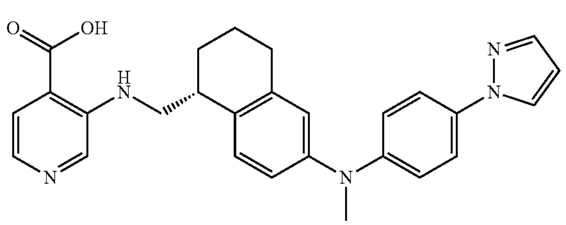 | 3-({[(1R)-6-{methyl[4-(1H-pyrazol-1-yl)phenyl]amino}-1,2,3,4-tetrahydronaphthalen-1-yl]methyl}amino)pyridine-4-carboxylic acid |
| 189 | 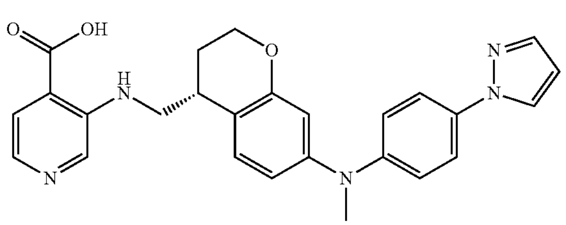 [SMILES: CN(c1ccc(-n2cccn2)cc1)c1ccc2c(c1)OCC[C@H]2CNc1cnccc1C(=O)O] | 3-({[(4R)-7-{methyl[4-(1H-pyrazol-1-yl)phenyl]amino}-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 190 | 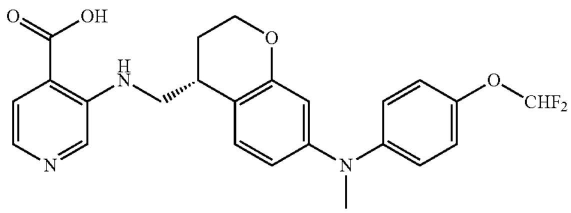 | 3-({[(4R)-7-{[4-(difluoromethoxy)phenyl](methyl)amino}-3,4-dihydro-2H-1-benzopyran-4-yl]methyl}amino)pyridine-4-carboxylic acid |
| 191 | 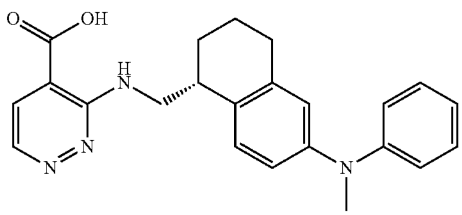 | 3-({[(1R)-6-[methyl(phenyl)amino]-1,2,3,4-tetrahydronaphthalen-1-yl]methyl}amino)pyridazine-4-carboxylic acid |
| 192 | 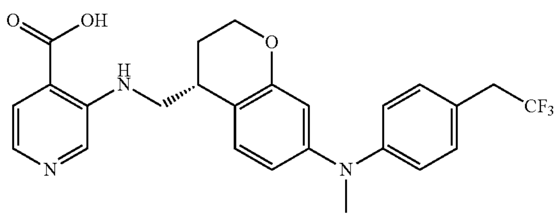 [SMILES: CN(c1ccc(CC(F)(F)F)cc1)c1ccc2c(c1)OCC[C@H]2CNc1cnccc1C(=O)O] | 3-({[(4R)-7-{methyl[4-(2,2,2-trifluoroethyl)phenyl]amino}-3,4-dihydro-2H-1-benzopyran-4-yl]methyl}amino)pyridine-4-carboxylic acid |
| 193 | 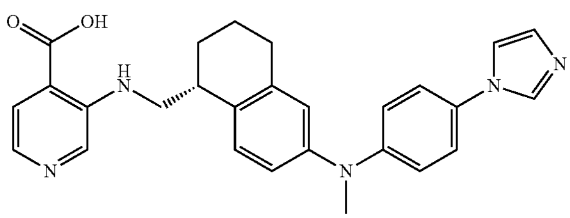 [SMILES: CN(c1ccc(-n2ccnc2)cc1)c1ccc2c(c1)CCC[C@H]2CNc1cnccc1C(=O)O] | 3-({[(1R)-6-{[4-(1H-imidazol-1-yl)phenyl](methyl)amino}-1,2,3,4-tetrahydronaphthalen-1-yl]methyl}amino)pyridine-4-carboxylic acid |
| 194 | 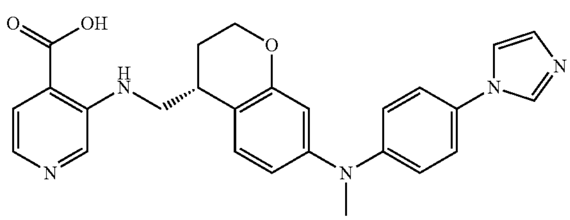 [SMILES: CN(c1ccc(-n2ccnc2)cc1)c1ccc2c(c1)OCC[C@H]2CNc1cnccc1C(=O)O] | 3-({[(4R)-7-{[4-(1H-imidazol-1-yl)phenyl](methyl)amino}-3,4-dihydro-2H-1-benzopyran-4-yl]methyl}amino)pyridine-4-carboxylic acid |
| 195 | 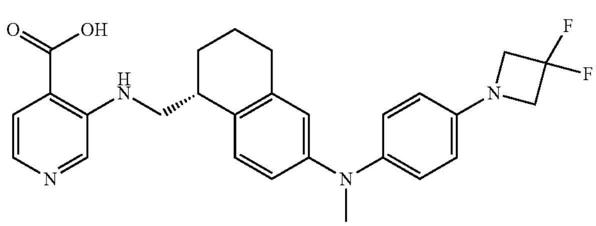 | 3-({[(1R)-6-{[4-(3,3-difluoroazetidin-1-yl)phenyl](methyl)amino}-1,2,3,4-tetrahydronaphthalen-1-yl]methyl}amino)pyridine-4-carboxylic acid |
| 196 | 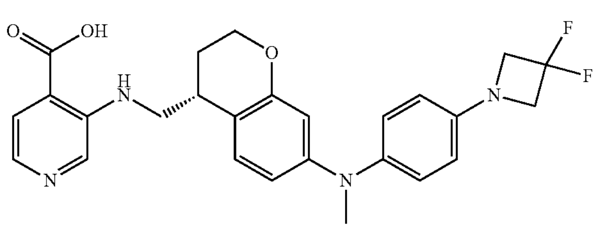 [SMILES: CN(c1ccc(N2CC(F)(F)C2)cc1)c1ccc2c(c1)CCC[C@H]2CNc1cnccc1C(=O)O] | 3-({[(4R)-7-{[4-(3,3-difluoroazetidin-1-yl)phenyl](methyl)amino}-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 197 | 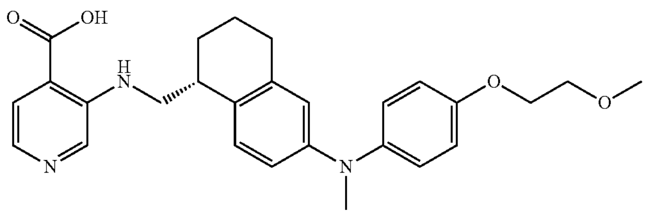 [SMILES: COCCOc1ccc(N(C)c2ccc3c(c2)CCC[C@H]3CNc2cnccc2C(=O)O)cc1] | 3-({[(1R)-6-{[4-(2-methoxyethoxy)phenyl](methyl)amino}-1,2,3,4-tetrahydronaphthalen-1-yl]methyl}amino)pyridine-4-carboxylic acid |
| 198 | 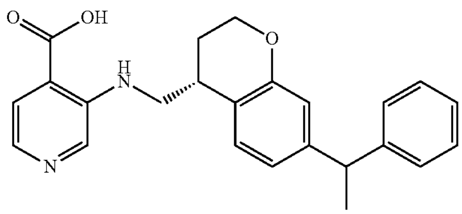 | 3-({[(4R)-7-(1-phenylethyl)-3,4-dihydro-2H-1-benzopyran-4-yl]methyl}amino)pyridine-4-carboxylic acid |
| 199 | 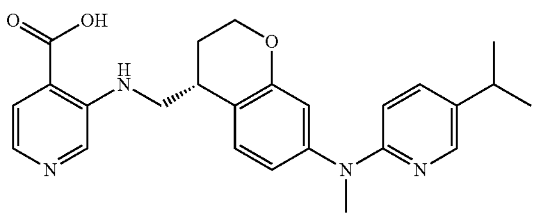 | 3-({[(4R)-7-{methyl[5-(propan-2-yl)pyridin-2-yl]amino}-3,4-dihydro-2H-1-benzopyran-4-yl]methyl}amino)pyridine-4-carboxylic acid |
| 200 | 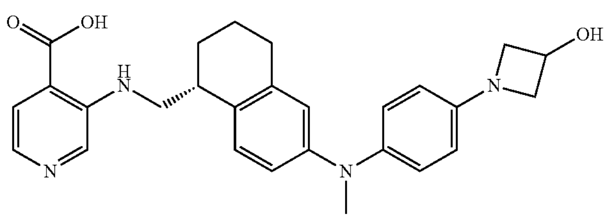 [SMILES: CN(c1ccc(N2CC(O)C2)cc1)c1ccc2c(c1)CCC[C@H]2CNc1cnccc1C(=O)O] | 3-({[(1R)-6-{[4-(3-hydroxyazetidin-1-yl)phenyl](methyl)amino}-1,2,3,4-tetrahydronaphthalen-1-yl]methyl}amino)pyridine-4-carboxylic acid |
| 201 | 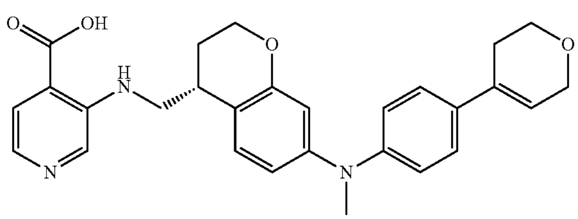 | 3-({[(4R)-7-{[4-(3,6-dihydro-2H-pyran-4-yl)phenyl](methyl)amino}-3,4-dihydro-2H-1-benzopyran-4-yl]methyl}amino)pyridine-4-carboxylic acid |
| 202 | 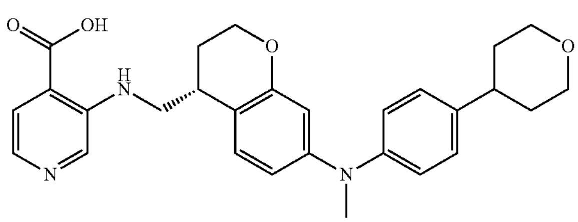 [SMILES: CN(c1ccc(C2CCOCC2)cc1)c1ccc2c(c1)OCC[C@H]2CNc1cnccc1C(=O)O] | 3-({[(4R)-7-{methyl[4-(oxan-4-yl)phenyl]amino}-3,4-dihydro-2H-1-benzopyran-4-yl]methyl}amino)pyridine-4-carboxylic acid |
| 203 | 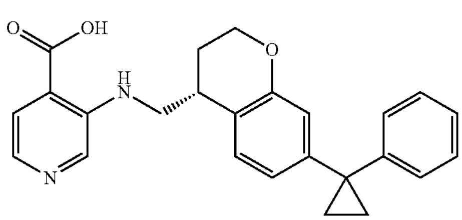 [SMILES: O=C(O)c1ccncc1NC[C@@H]1CCOc2cc(C3(c4ccccc4)CC3)ccc21] | 3-({[(4R)-7-(1-phenylcyclopropyl)-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 204 | 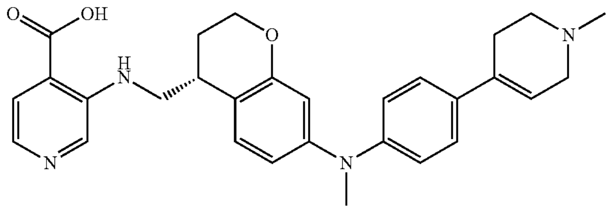 [SMILES: CN1CC=C(c2ccc(N(C)c3ccc4c(c3)OCC[C@H]4CNc3cnccc3C(=O)O)cc2)CC1] | 3-({[(4R)-7-{methyl[4-(1-methyl-1,2,3,6-tetrahydropyridin-4-yl)phenyl]amino}-3,4-dihydro-2H-1-benzopyran-4-yl]methyl}amino)pyridine-4-carboxylic acid |
| 205 | 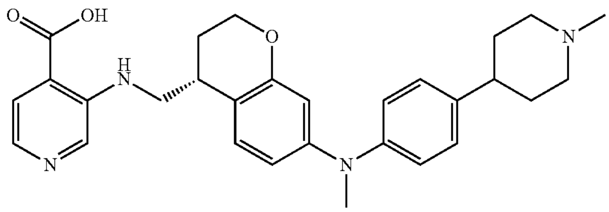 [SMILES: CN1CCC(c2ccc(N(C)c3ccc4c(c3)OCC[C@H]4CNc3cnccc3C(=O)O)cc2)CC1] | 3-({[(4R)-7-{methyl[4-(1-methylpiperidin-4-yl)phenyl]amino}-3,4-dihydro-2H-1-benzopyran-4-yl]methyl}amino)pyridine-4-carboxylic acid |
| 206 | 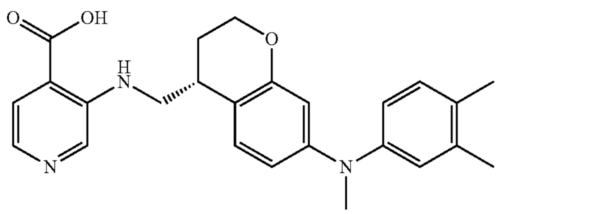 [SMILES: Cc1ccc(N(C)c2ccc3c(c2)OCC[C@H]3CNc2cnccc2C(=O)O)cc1C] | 3-({[(4R)-7-[(3,4-dimethylphenyl)(methyl)amino]-3,4-dihydro-2H-1-benzopyran-4-yl]methyl}amino)pyridine-4-carboxylic acid |
| 207 | 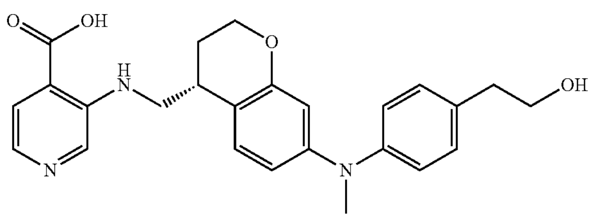 [SMILES: CN(c1ccc(CCO)cc1)c1ccc2c(c1)OCC[C@H]2CNc1cnccc1C(=O)O] | 3-({[(4R)-7-{[4-(2-hydroxyethyl)phenyl](methyl)amino}-3,4-dihydro-2H-1-benzopyran-4-yl]methyl}amino)pyridine-4-carboxylic acid |
| 208 | 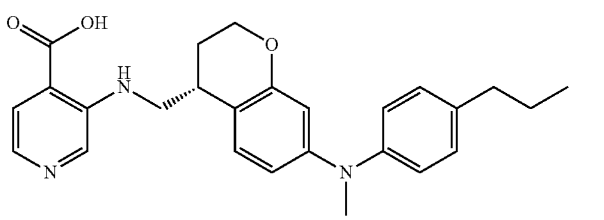 | 3-({[(4R)-7-[methyl(4-propylphenyl)amino]-3,4-dihydro-2H-1-benzopyran-4-yl]methyl}amino)pyridine-4-carboxylic acid |
| 209 | 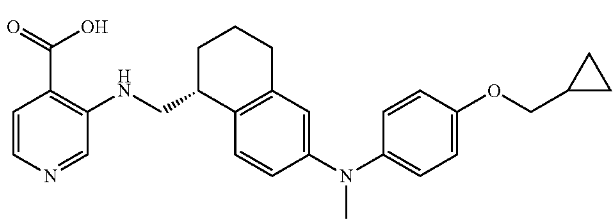 [SMILES: CN(c1ccc(OCC2CC2)cc1)c1ccc2c(c1)CCC[C@H]2CNc1cnccc1C(=O)O] | 3-({[(1R)-6-{[4-(cyclopropylmethoxy)phenyl](methyl)amino}-1,2,3,4-tetrahydronaphthalen-1-yl]methyl}amino)pyridine-4-carboxylic acid |
| 210 | 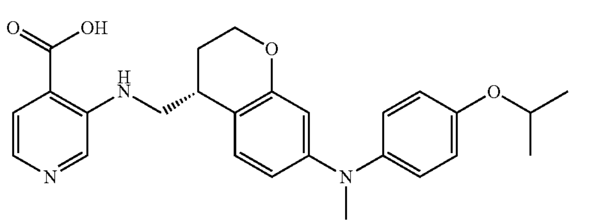 [SMILES: CC(C)Oc1ccc(N(C)c2ccc3c(c2)OCC[C@H]3CNc2cnccc2C(=O)O)cc1] | 3-({[(4R)-7-{methyl[4-(propan-2-yloxy)phenyl]amino}-3,4-dihydro-2H-1-benzopyran-4-yl]methyl}amino)pyridine-4-carboxylic acid |

TABLE 1-continued

| Chemical Synthesis Example | Structure | Comments |
|---|---|---|
| 211 | 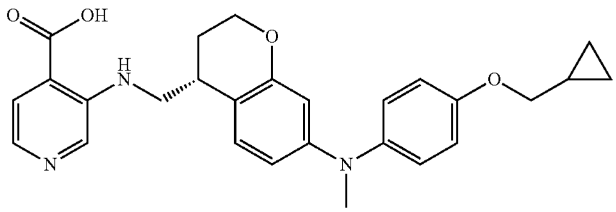 | 3-({[(4R)-7-{[4-(cyclopropylmethoxy)phenyl](methyl)amino}-3,4-dihydro-2H-1-benzopyran-4-yl]methyl}amino)pyridine-4-carboxylic acid |
| 212 | 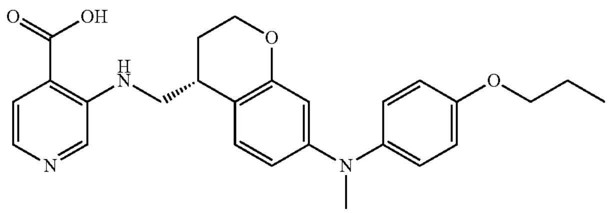 [SMILES: CCCOc1ccc(N(C)c2ccc3c(c2)OCC[C@H]3CNc2cnccc2C(=O)O)cc1] | 3-({[(4R)-7-[methyl(4-propoxyphenyl)amino]-3,4-dihydro-2H-1-benzopyran-4-yl]methyl}amino)pyridine-4-carboxylic acid |
| 213 | 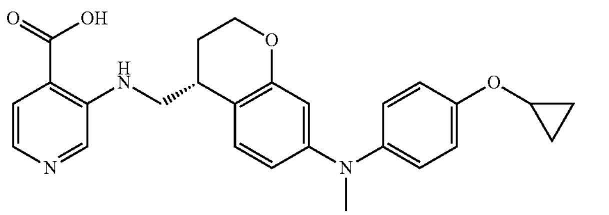 [SMILES: CN(c1ccc(OC2CC2)cc1)c1ccc2c(c1)OCC[C@H]2CNc1cnccc1C(=O)O] | 3-({[(4R)-7-[(4-cyclopropoxyphenyl)(methyl)amino]-3,4-dihydro-2H-1-benzopyran-4-yl]methyl}amino)pyridine-4-carboxylic acid |
| 214 | 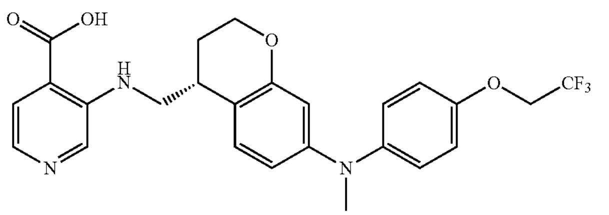 [SMILES: CN(c1ccc(OCC(F)(F)F)cc1)c1ccc2c(c1)OCC[C@H]2CNc1cnccc1C(=O)O] | 3-({[(4R)-7-{methyl[4-(2,2,2-trifluoroethoxy)phenyl]amino}-3,4-dihydro-2H-1-benzopyran-4-yl]methyl}amino)pyridine-4-carboxylic acid |
| 215 | 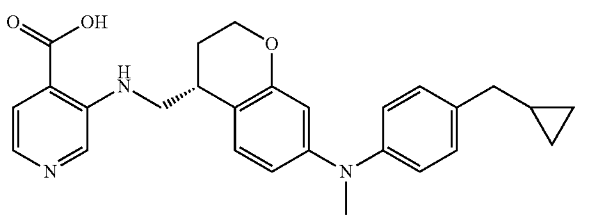 [SMILES: CN(c1ccc(CC2CC2)cc1)c1ccc2c(c1)OCC[C@H]2CNc1cnccc1C(=O)O] | 3-({[(4R)-7-{[4-(cyclopropylmethyl)phenyl](methyl)amino}-3,4-dihydro-2H-1-benzopyran-4-yl]methyl}amino)pyridine-4-carboxylic acid |
| 216 | 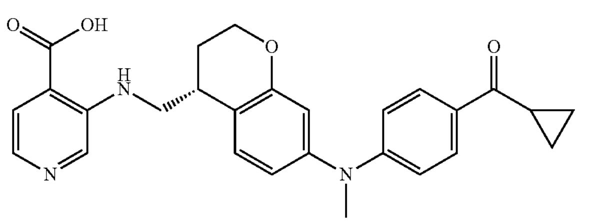 [SMILES: CN(c1ccc(C(=O)C2CC2)cc1)c1ccc2c(c1)OCC[C@H]2CNc1cnccc1C(=O)O] | 3-({[(4R)-7-[(4-cyclopropanecarbonylphenyl)(methyl)amino]-3,4-dihydro-2H-1-benzopyran-4-yl]methyl}amino)pyridine-4-carboxylic acid |
| 217 | 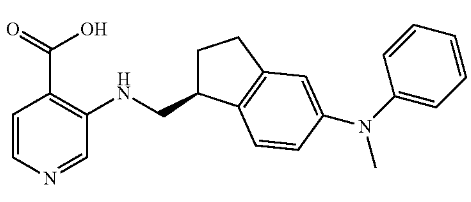 [SMILES: CN(c1ccccc1)c1ccc2c(c1)CC[C@@H]2CNc1cnccc1C(=O)O] | 3-({[(1S)-5-[methyl(phenyl)amino]-2,3-dihydro-1H-inden-1-yl]methyl}amino)pyridine-4-carboxylic acid |

TABLE 1-continued

| Chemical Synthesis Example | Structure | Comments |
|---|---|---|
| 218 | 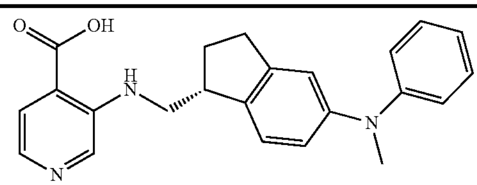 | 3-({[(1R)-5-[methyl(phenyl)amino]-2,3-dihydro-1H-inden-1-yl]methyl}amino)pyridine-4-carboxylic acid |
| 219 | 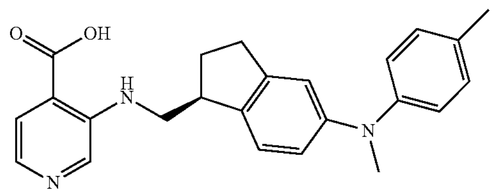 [SMILES: Cc1ccc(N(C)c2ccc3c(c2)CC[C@@H]3CNc2cnccc2C(=O)O)cc1] | 3-({[(1S)-5-[methyl(4-methylphenyl)amino]-2,3-dihydro-1H-inden-1-yl]methyl}amino)pyridine-4-carboxylic acid |
| 220 | 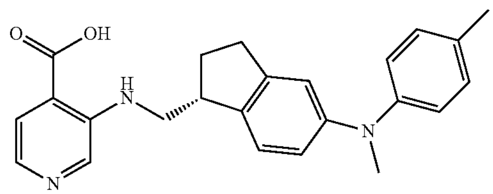 | 3-({[(1R)-5-[methyl(4-methylphenyl)amino]-2,3-dihydro-1H-inden-1-yl]methyl}amino)pyridine-4-carboxylic acid |
| 221 | 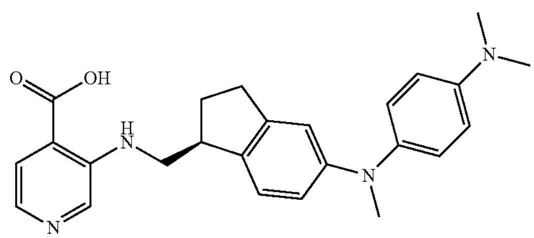 [SMILES: CN(C)c1ccc(N(C)c2ccc3c(c2)CC[C@@H]3CNc2cnccc2C(=O)O)cc1] | 3-({[(1S)-5-{[4-(dimethylamino)phenyl](methyl)amino}-2,3-dihydro-1H-inden-1-yl]methyl}amino)pyridine-4-carboxylic acid |
| 222 | 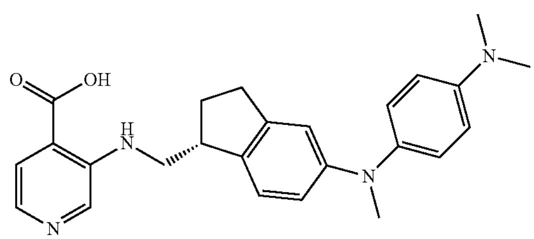 [SMILES: CN(C)c1ccc(N(C)c2ccc3c(c2)CC[C@H]3CNc2cnccc2C(=O)O)cc1] | 3-({[(1R)-5-{[4-(dimethylamino)phenyl](methyl)amino}-2,3-dihydro-1H-inden-1-yl]methyl}amino)pyridine-4-carboxylic acid |
| 223 | 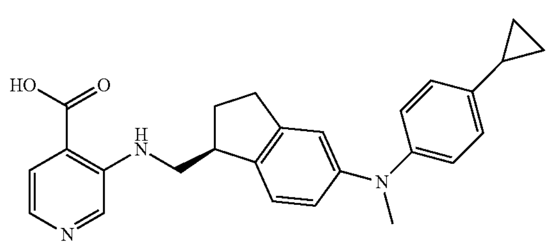 [SMILES: CN(c1ccc(C2CC2)cc1)c1ccc2c(c1)CC[C@@H]2CNc1cnccc1C(=O)O] | 3-({[(1S)-5-[(4-cyclopropylphenyl)(methyl)amino]-2,3-dihydro-1H-inden-1-yl]methyl}amino)pyridine-4-carboxylic acid |
| 224 | 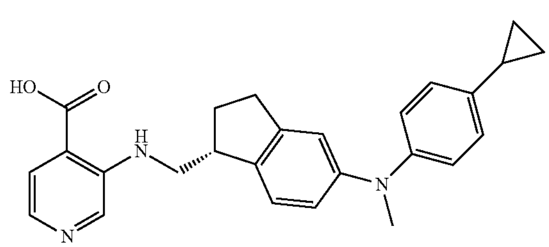 [SMILES: CN(c1ccc(C2CC2)cc1)c1ccc2c(c1)CC[C@H]2CNc1cnccc1C(=O)O] | 3-({[(1R)-5-[(4-cyclopropylphenyl)(methyl)amino]-2,3-dihydro-1H-inden-1-yl]methyl}amino)pyridine-4-carboxylic acid |

TABLE 1-continued

| Chemical Synthesis Example | Structure | Comments |
|---|---|---|
| 225 | 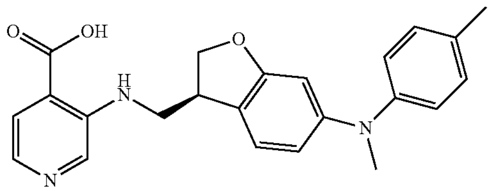 | 3-({[(3S)-6-[methyl(4-methylphenyl)amino]-2,3-dihydro-1-benzofuran-3-yl]methyl}amino)pyridine-4-carboxylic acid |
| 226 | 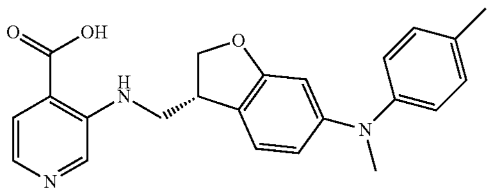 | 3-({[(3R)-6-[methyl(4-methylphenyl)amino]-2,3-dihydro-1-benzofuran-3-yl]methyl}amino)pyridine-4-carboxylic acid |
| 227 | 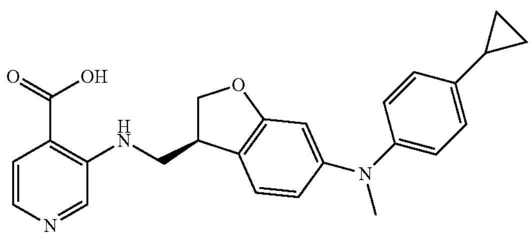 [SMILES: CN(c1ccc(C2CC2)cc1)c1ccc2c(c1)OC[C@@H]2CNc1cnccc1C(=O)O] | 3-({[(3S)-6-[(4-cyclopropylphenyl)(methyl)amino]-2,3-dihydro-1-benzofuran-3-yl]methyl}amino)pyridine-4-carboxylic acid |
| 228 | 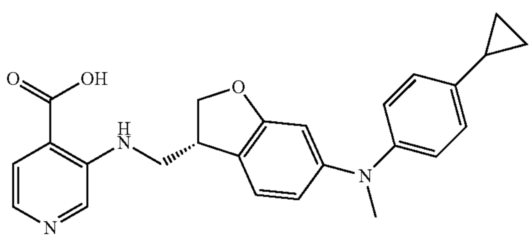 [SMILES: CN(c1ccc(C2CC2)cc1)c1ccc2c(c1)OC[C@H]2CNc1cnccc1C(=O)O] | 3-({[(3R)-6-[(4-cyclopropylphenyl)(methyl)amino]-2,3-dihydro-1-benzofuran-3-yl]methyl}amino)pyridine-4-carboxylic acid |
| 229 | 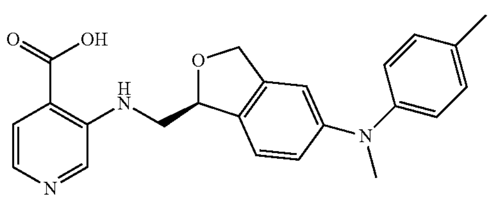 | 3-({[(1S)-5-[methyl(4-methylphenyl)amino]-1,3-dihydro-2-benzofuran-1-yl]methyl}amino)pyridine-4-carboxylic acid |
| 230 | 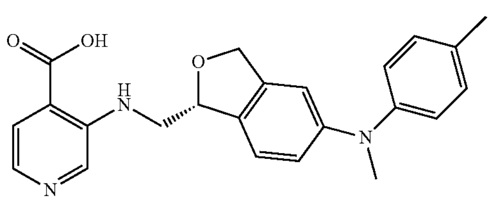 [SMILES: Cc1ccc(N(C)c2ccc3c(c2)CO[C@H]3CNc2cnccc2C(=O)O)cc1] | 3-({[(1R)-5-[methyl(4-methylphenyl)amino]-1,3-dihydro-2-benzofuran-1-yl]methyl}amino)pyridine-4-carboxylic acid |
| 231 | 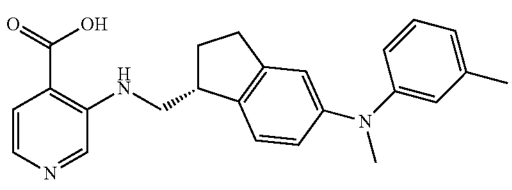 [SMILES: Cc1cccc(N(C)c2ccc3c(c2)CC[C@H]3CNc2cnccc2C(=O)O)c1] | 3-({[(1R)-5-[methyl(3-methylphenyl)amino]-2,3-dihydro-1H-inden-1-yl]methyl}amino)pyridine-4-carboxylic acid |

TABLE 1-continued

| Chemical Synthesis Example | Structure | Comments |
|---|---|---|
| 231 | 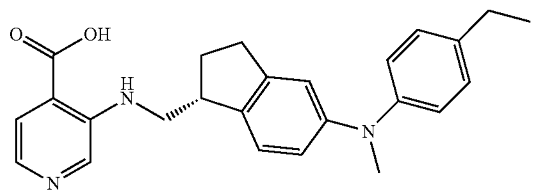 [SMILES: CCc1ccc(N(C)c2ccc3c(c2)CC[C@H]3CNc2cnccc2C(=O)O)cc1] | 3-({[(1R)-5-[(4-ethylphenyl)(methyl)amino]-2,3-dihydro-1H-inden-1-yl]methyl}amino)pyridine-4-carboxylic acid |
| 232 | 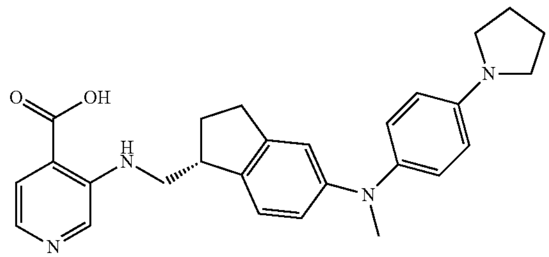 [SMILES: CN(c1ccc(N2CCCC2)cc1)c1ccc2c(c1)CC[C@H]2CNc1cnccc1C(=O)O] | 3-({[(1R)-5-{methyl[4-(pyrrolidin-1-yl)phenyl]amino}-2,3-dihydro-1H-inden-1-yl]methyl}amino)pyridine-4-carboxylic acid |

In some embodiments, the substituted pyridine derivative compound as described herein, or a stereoisomer of pharmaceutically acceptable salt thereof, has the structure provided in Table 2.

TABLE 2

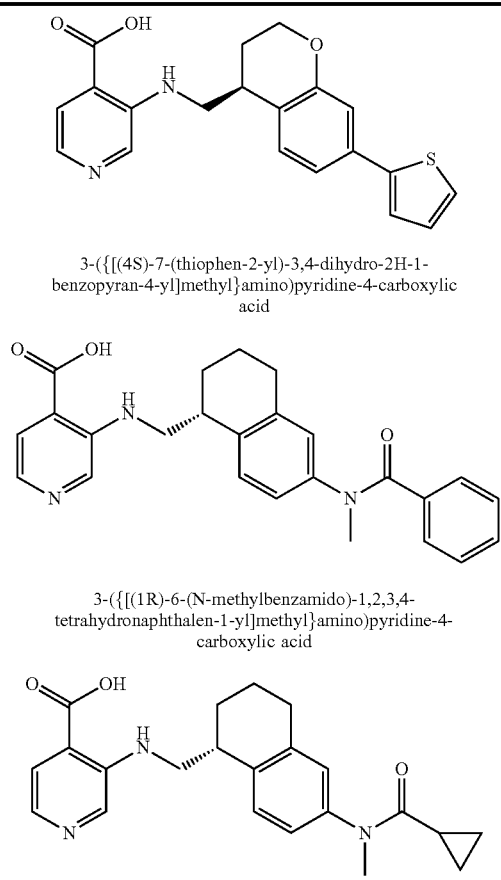

3-({[(4S)-7-(thiophen-2-yl)-3,4-dihydro-2H-1-benzopyran-4-yl]methyl}amino)pyridine-4-carboxylic acid 3-({[(1R)-6-(N-methylbenzamido)-1,2,3,4-tetrahydronaphthalen-1-yl]methyl}amino)pyridine-4-carboxylic acid 3-({[(1R)-6-(N-methylcyclopropaneamido)-1,2,3,4-tetrahydronaphthalen-1-yl]methyl}amino)pyridine-4-carboxylic acid

TABLE 2-continued 3-({[(1R)-6-(N-methylcyclopentaneamido)-1,2,3,4-tetrahydronaphthalen-1-yl]methyl}amino)pyridine-4-carboxylic acid 3-({[(1R)-6-(dimethylamino)-1,2,3,4-tetrahydronaphthalen-1-yl]methyl}amino)pyridine-4-carboxylic acid 3-({[(4S)-7-[1-(cyclopropylmethyl)-1H-pyrazol-4-yl]-3,4-dihydro-2H-1-benzopyran-4-yl]methyl}amino)pyridine-4-carboxylic acid TABLE 2-continued

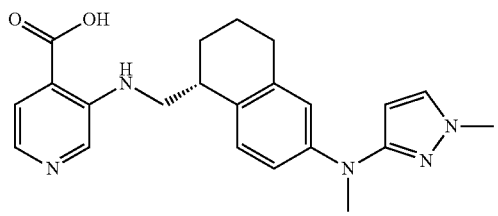 [SMILES: CN(c1ccc2c(c1)CCC[C@H]2CNc1cnccc1C(=O)O)c1ccn(C)n1]

3-({[(1R)-6-[methyl(1-methyl-1H-pyrazol-3-yl)amino]-1,2,3,4-tetrahydronaphthalen-1-yl]methyl}amino)pyridine-4-carboxylic acid

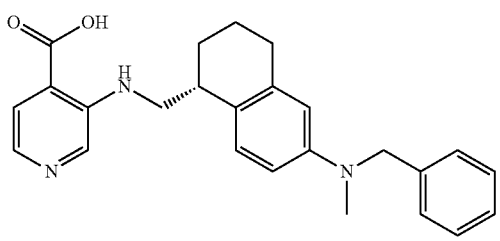

3-({[(1R)-6-[benzyl(methyl)amino]-1,2,3,4-tetrahydronaphthalen-1-yl]methyl}amino)pyridine-4-carboxylic acid

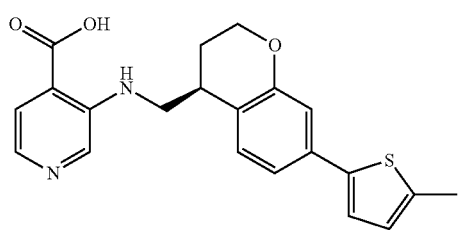 [SMILES: Cc1ccc(-c2ccc3c(c2)OCC[C@@H]3CNc2cnccc2C(=O)O)s1]

3-({[(4S)-7-(5-methylthiophen-2-yl)-3,4-dihydro-2H-1-benzopyran-4-yl]methyl}amino)pyridine-4-carboxylic acid

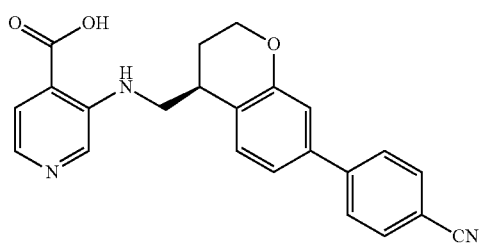 [SMILES: N#Cc1ccc(-c2ccc3c(c2)OCC[C@@H]3CNc2cnccc2C(=O)O)cc1]

3-({[(4S)-7-(4-cyanophenyl)-3,4-dihydro-2H-1-benzopyran-4-yl]methyl}amino)pyridine-4-carboxylic acid

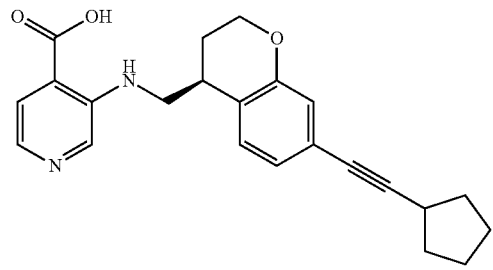 [SMILES: O=C(O)c1ccncc1NC[C@H]1CCOc2cc(C#CC3CCCC3)ccc21]

3-({[(4S)-7-(2-cyclopentylethynyl)-3,4-dihydro-2H-1-benzopyran-4-yl]methyl}amino)pyridine-4-carboxylic acid TABLE 2-continued

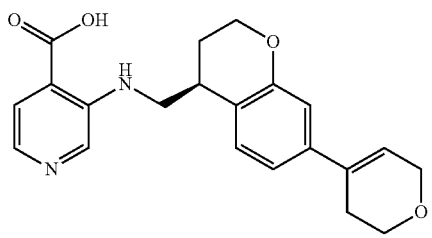 [SMILES: O=C(O)c1ccncc1NC[C@H]1CCOc2cc(C3=CCOCC3)ccc21]

3-({[(4S)-7-(3,6-dihydro-2H-pyran-4-yl)-3,4-dihydro-2H-1-benzopyran-4-yl]methyl}amino)pyridine-4-carboxylic acid

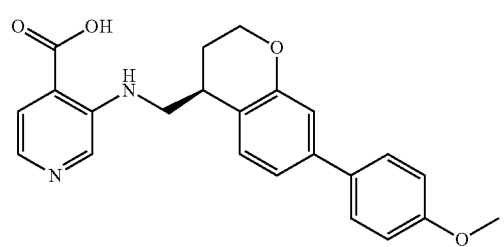 [SMILES: COc1ccc(-c2ccc3c(c2)OCC[C@@H]3CNc2cnccc2C(=O)O)cc1]

3-({[(4S)-7-(4-methoxyphenyl)-3,4-dihydro-2H-1-benzopyran-4-yl]methyl}amino)pyridine-4-carboxylic acid

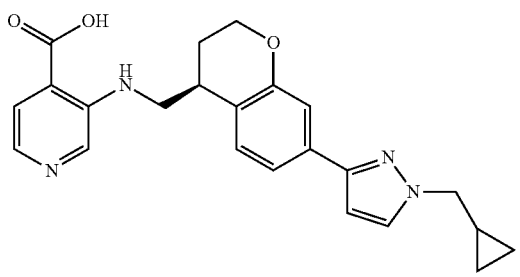 [SMILES: O=C(O)c1ccncc1NC[C@H]1CCOc2cc(-c3ccn(CC4CC4)n3)ccc21]

3-({[(4S)-7-[1-(cyclopropylmethyl)-1H-pyrazol-3-yl]-3,4-dihydro-2H-1-benzopyran-4-yl]methyl}amino)pyridine-4-carboxylic acid

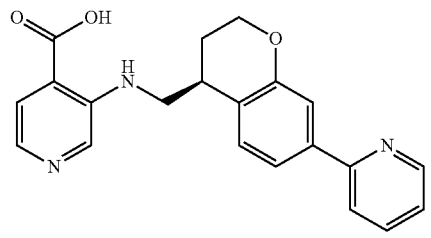

3-({[(4S)-7-(pyridin-2-yl)-3,4-dihydro-2H-1-benzopyran-4-yl]methyl}amino)pyridine-4-carboxylic acid

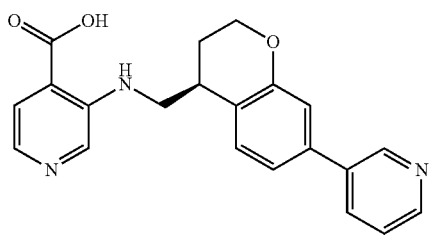 [SMILES: O=C(O)c1ccncc1NC[C@H]1CCOc2cc(-c3cccnc3)ccc21]

3-({[(4S)-7-(pyridin-3-yl)-3,4-dihydro-2H-1-benzopyran-4-yl]methyl}amino)pyridine-4-carboxylic acid TABLE 2-continued

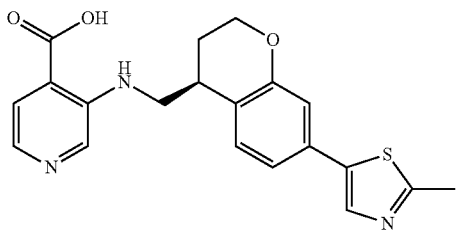 [SMILES: Cc1ncc(-c2ccc3c(c2)OCC[C@@H]3CNc2cnccc2C(=O)O)s1]

3-({[(4S)-7-(2-methyl-1,3-thiazol-5-yl)-3,4-dihydro-2H-1-benzopyran-4-yl]methyl}amino)pyridine-4-carboxylic acid

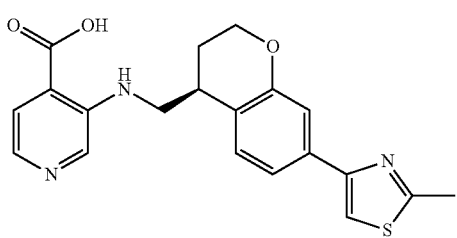 [SMILES: Cc1nc(-c2ccc3c(c2)OCC[C@@H]3CNc2cnccc2C(=O)O)cs1]

3-({[(4S)-7-(2-methyl-1,3-thiazol-4-yl)-3,4-dihydro-2H-1-benzopyran-4-yl]methyl}amino)pyridine-4-carboxylic acid

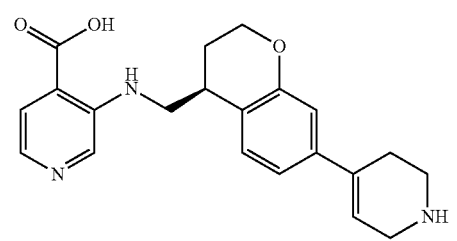 [SMILES: O=C(O)c1ccncc1NC[C@H]1CCOc2cc(C3CCNCC3)ccc21]

3-({[(4S)-7-(1,2,3,6-tetrahydropyridin-4-yl)-3,4-dihydro-2H-1-benzopyran-4-yl]methyl}amino)pyridine-4-carboxylic acid

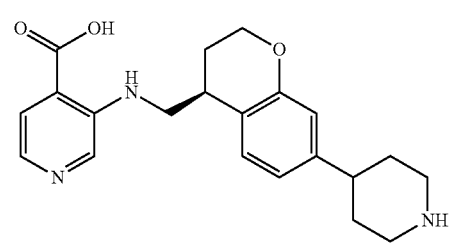

3-({[(4S)-7-(piperidin-4-yl)-3,4-dihydro-2H-1-benzopyran-4-yl]methyl}amino)pyridine-4-carboxylic acid

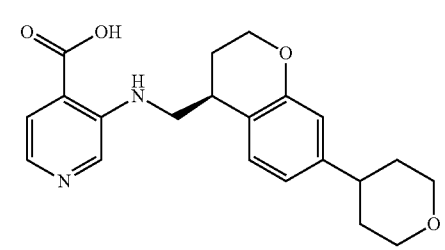 [SMILES: O=C(O)c1ccncc1NC[C@H]1CCOc2cc(C3CCOCC3)ccc21]

3-({[(4S)-7-(oxan-4-yl)-3,4-dihydro-2H-1-benzopyran-4-yl]methyl}amino)pyridine-4-carboxylic acid TABLE 2-continued

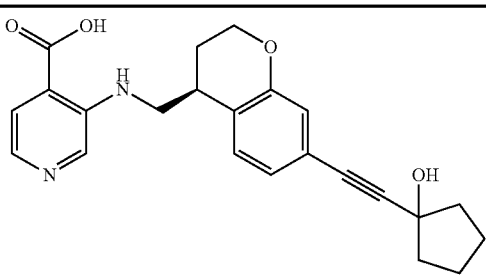

3-({[(4S)-7-[2-(1-hydroxycyclopentyl)ethynyl]-3,4-dihydro-2H-1-benzopyran-4-yl]methyl}amino)pyridine-4-carboxylic acid

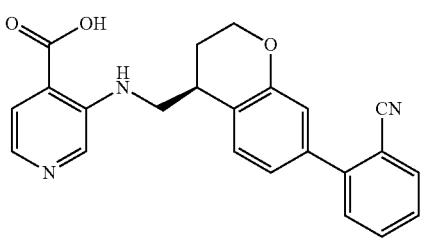

3-({[(4S)-7-(2-cyanophenyl)-3,4-dihydro-2H-1-benzopyran-4-yl]methyl}amino)pyridine-4-carboxylic acid

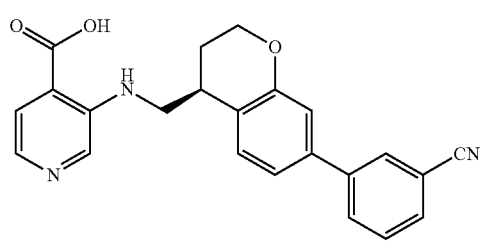 [SMILES: N#Cc1cccc(-c2ccc3c(c2)OCC[C@@H]3CNc2cnccc2C(=O)O)c1]

3-({[(4S)-7-(3-cyanophenyl)-3,4-dihydro-2H-1-benzopyran-4-yl]methyl}amino)pyridine-4-carboxylic acid

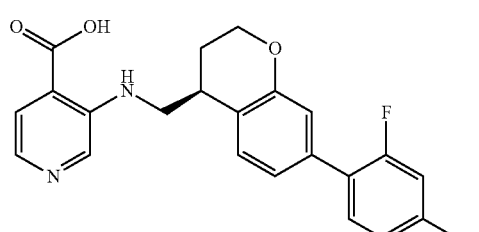

3-({[(4S)-7-(4-cyano-2-fluorophenyl)-3,4-dihydro-2H-1-benzopyran-4-yl]methyl}amino)pyridine-4-carboxylic acid

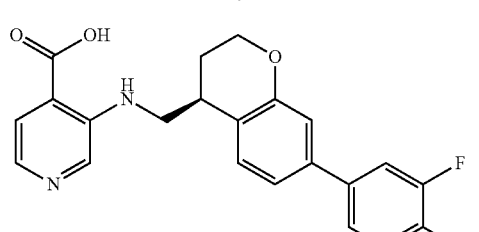

3-({[(4S)-7-(4-cyano-3-fluorophenyl)-3,4-dihydro-2H-1-benzopyran-4-yl]methyl}amino)pyridine-4-carboxylic acid TABLE 2-continued

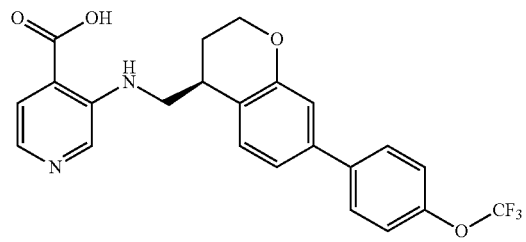 [SMILES: O=C(O)c1ccncc1NC[C@H]1CCOc2cc(-c3ccc(OC(F)(F)F)cc3)ccc21]

3-({[(4S)-7-[4-(trifluoromethoxy)phenyl]-3,4-dihydro-
2H-1-benzopyran-4-yl]methyl}amino)pyridine-4-
carboxylic acid

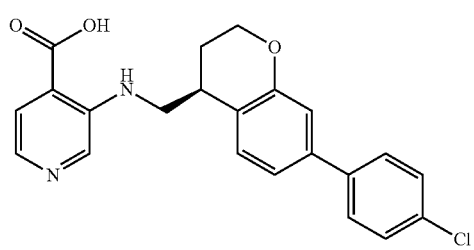 [SMILES: O=C(O)c1ccncc1NC[C@H]1CCOc2cc(-c3ccc(Cl)cc3)ccc21]

3-({[(4S)-7-(4-chlorophenyl)-3,4-dihydro-2H-1-
benzopyran-4-yl]methyl}amino)pyridine-4-carboxylic
acid

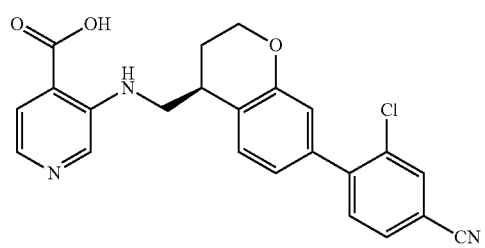

3-({[(4S)-7-(2-chloro-4-cyanophenyl)-3,4-dihydro-
2H-1-benzopyran-4-yl]methyl}amino)pyridine-4-
carboxylic acid

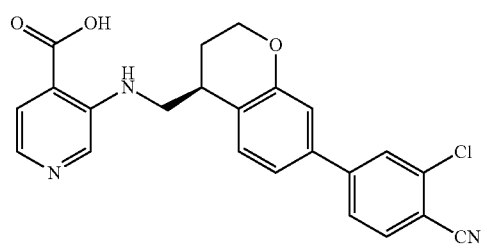 [SMILES: N#Cc1ccc(-c2ccc3c(c2)OCC[C@@H]3CNc2cnccc2C(=O)O)cc1Cl]

3-({[(4S)-7-(3-chloro-4-cyanophenyl)-3,4-dihydro-
2H-1-benzopyran-4-yl]methyl}amino)pyridine-4-
carboxylic acid

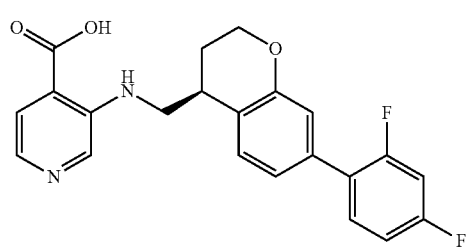 [SMILES: O=C(O)c1ccncc1NC[C@H]1CCOc2cc(-c3ccc(F)cc3F)ccc21]

3-({[(4S)-7-(2,4-difluorophenyl)-3,4-dihydro-2H-1-
benzopyran-4-yl]methyl}amino)pyridine-4-carboxylic
acid TABLE 2-continued

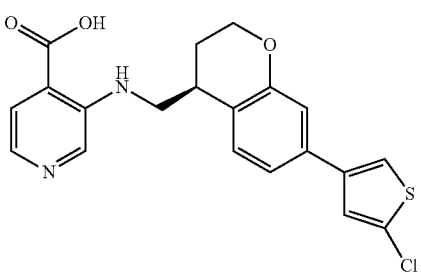 [SMILES: O=C(O)c1ccncc1NC[C@H]1CCOc2cc(-c3csc(Cl)c3)ccc21]

3-({[(4S)-7-(5-chlorothiophen-3-yl)-3,4-dihydro-2H-
1-benzopyran-4-yl]methyl}amino)pyridine-4-
carboxylic acid

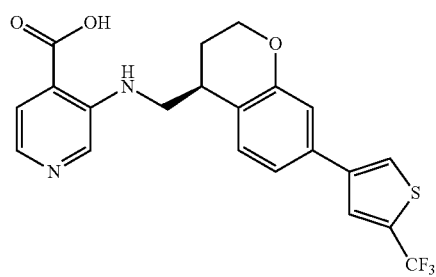 [SMILES: O=C(O)c1ccncc1NC[C@H]1CCOc2cc(-c3csc(C(F)(F)F)c3)ccc21]

3-({[(4S)-7-[5-(trifluoromethyl)thiophen-3-yl]-3,4-
dihydro-2H-1-benzopyran-4-
yl]methyl}amino)pyridine-4-carboxylic acid

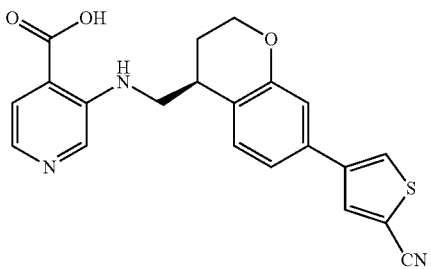 [SMILES: N#Cc1cc(-c2ccc3c(c2)OCC[C@@H]3CNc2cnccc2C(=O)O)cs1]

3-({[(4S)-7-(5-cyanothiophen-3-yl)-3,4-dihydro-2H-1-
benzopyran-4-yl]methyl}amino)pyridine-4-carboxylic
acid

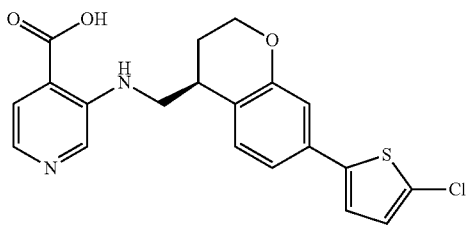 [SMILES: O=C(O)c1ccncc1NC[C@H]1CCOc2cc(-c3ccc(Cl)s3)ccc21]

3-({[(4S)-7-(5-chlorothiophen-2-yl)-3,4-dihydro-2H-
1-benzopyran-4-yl]methyl}amino)pyridine-4-
carboxylic acid

TABLE 2-continued

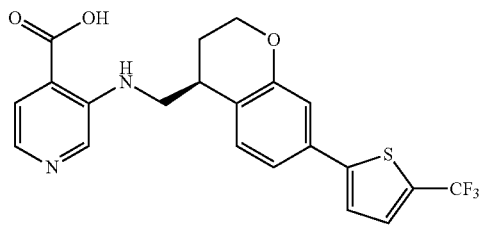 [SMILES: O=C(O)c1ccncc1NC[C@H]1CCOc2cc(-c3ccc(C(F)(F)F)s3)ccc21]

3-({[(4S)-7-[5-(trifluoromethyl)thiophen-2-yl]-3,4-dihydro-2H-1-benzopyran-4-yl]methyl}amino)pyridine-4-carboxylic acid

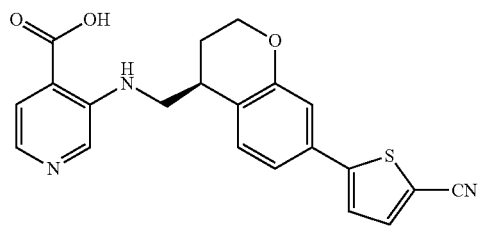 [SMILES: N#Cc1ccc(-c2ccc3c(c2)OCC[C@@H]3CNc2cnccc2C(=O)O)s1]

3-({[(4S)-7-(5-cyanothiophen-2-yl)-3,4-dihydro-2H-1-benzopyran-4-yl]methyl}amino)pyridine-4-carboxylic acid

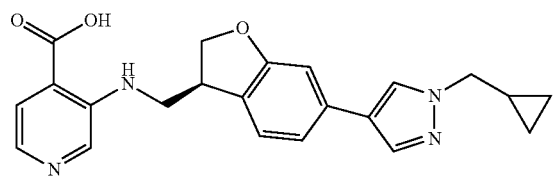 [SMILES: O=C(O)c1ccncc1NC[C@H]1COc2cc(-c3cnn(CC4CC4)c3)ccc21]

3-({[(3S)-6-[1-(cyclopropylmethyl)-1H-pyrazol-4-yl]-2,3-dihydro-1-benzofuran-3-yl]methyl}amino)pyridine-4-carboxylic acid

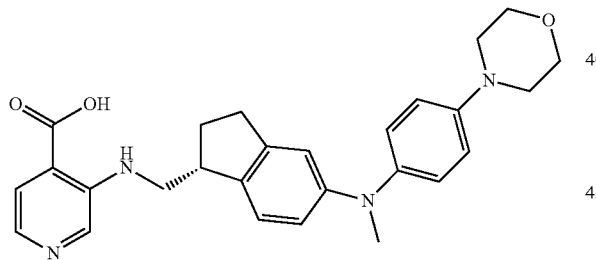

3-({[(1R)-5-{methyl[4-(morpholin-4-yl)phenyl]amino}-2,3-dihydro-1H-inden-1-yl]methyl}amino)pyridine-4-carboxylic acid

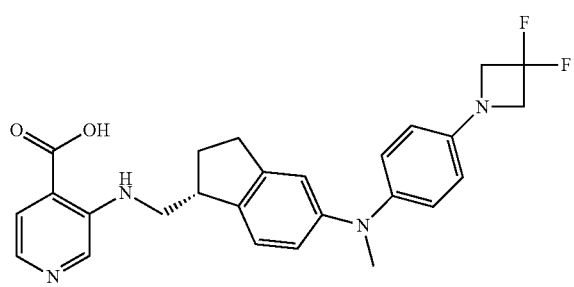 [SMILES: CN(c1ccc(N2CC(F)(F)C2)cc1)c1ccc2c(c1)CC[C@H]2CNc1cnccc1C(=O)O]

3-({[(1R)-5-{4-(3,3-difluoroazetidin-1-yl)phenyl](methyl)amino}-2,3-dihydro-1H-inden-1-yl]methyl}amino)pyridine-4-carboxylic acid

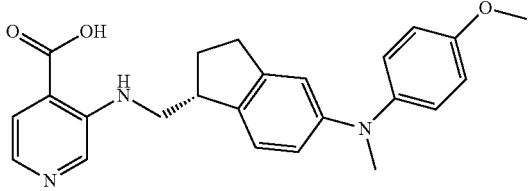 [SMILES: COc1ccc(N(C)c2ccc3c(c2)CC[C@H]3CNc2cnccc2C(=O)O)cc1]

3-({[(1R)-5-[(4-methoxyphenyl)(methyl)amino]-2,3-dihydro-1H-inden-1-yl]methyl}amino)pyridine-4-carboxylic acid

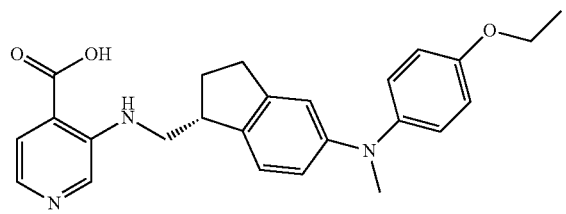 [SMILES: CCOc1ccc(N(C)c2ccc3c(c2)CC[C@H]3CNc2cnccc2C(=O)O)cc1]

3-({[(1R)-5-[(4-ethoxyphenyl)(methyl)amino]-2,3-dihydro-1H-inden-1-yl]methyl}amino)pyridine-4-carboxylic acid

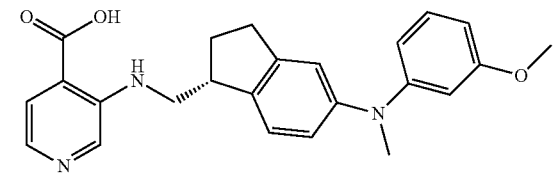 [SMILES: COc1cccc(N(C)c2ccc3c(c2)CC[C@H]3CNc2cnccc2C(=O)O)c1]

3-({[(1R)-5-[(3-methoxyphenyl)(methyl)amino]-2,3-dihydro-1H-inden-1-yl]methyl}amino)pyridine-4-carboxylic acid

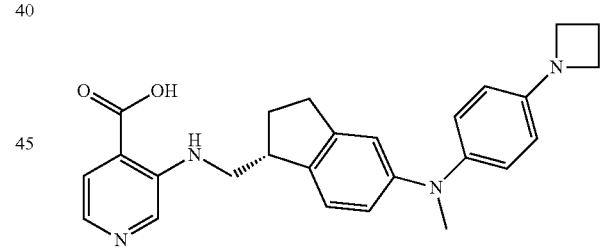

3-({[(1R)-5-{[4-(azetidin-1-yl)phenyl](methyl)amino}-2,3-dihydro-1H-inden-1-yl]methyl}amino)pyridine-4-carboxylic acid

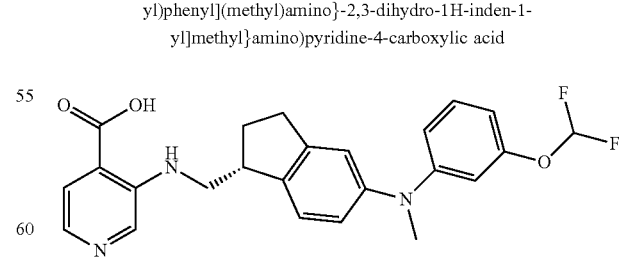

3-({[(1R)-5-{[3-(difluoromethoxy)phenyl](methyl)amino}-2,3-dihydro-1H-inden-1-yl]methyl}amino)pyridine-4-carboxylic acid TABLE 2-continued

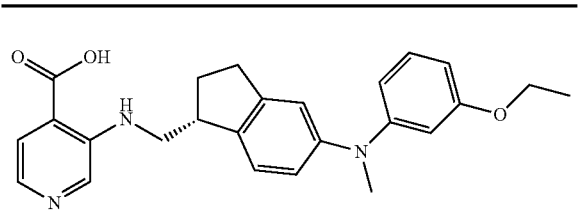

3-({[(1R)-5-[(3-ethoxyphenyl)(methyl)amino]-2,3-dihydro-1H-inden-1-yl]methyl}amino)pyridine-4-carboxylic acid

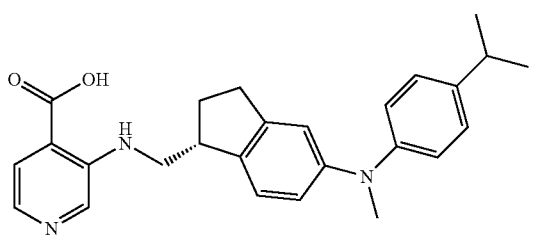 [SMILES: CC(C)c1ccc(N(C)c2ccc3c(c2)CC[C@H]3CNc2cnccc2C(=O)O)cc1]

3-({[(1R)-5-{methyl[4-(propan-2-yl)phenyl]amino}-2,3-dihydro-1H-inden-1-yl]methyl}amino)pyridine-4-carboxylic acid

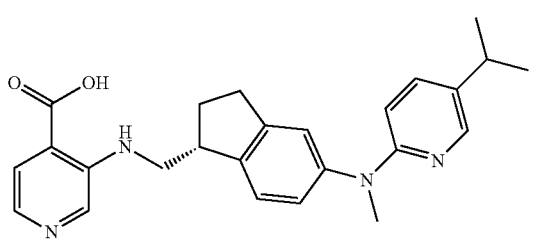 [SMILES: CC(C)c1ccc(N(C)c2ccc3c(c2)CC[C@H]3CNc2cnccc2C(=O)O)nc1]

3-({[(1R)-5-{methyl[5-(propan-2-yl)pyridin-2-yl]amino}-2,3-dihydro-1H-inden-1-yl]methyl}amino)pyridine-4-carboxylic acid

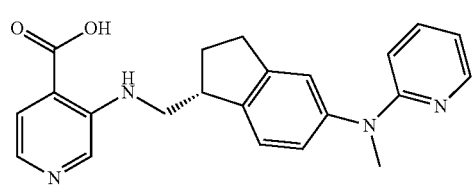 [SMILES: CN(c1ccc2c(c1)CC[C@H]2CNc1cnccc1C(=O)O)c1ccccn1]

3-({[(1R)-5-[methyl(pyridin-2-yl)amino]-2,3-dihydro-1H-inden-1-yl]methyl}amino)pyridine-4-carboxylic acid

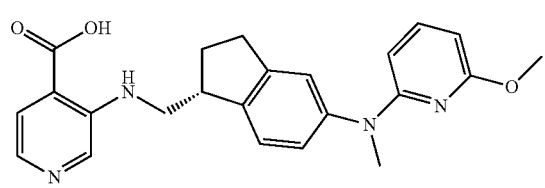 [SMILES: COc1cccc(N(C)c2ccc3c(c2)CC[C@H]3CNc2cnccc2C(=O)O)n1]

3-({[(1R)-5-[(6-methoxypyridin-2-yl)(methyl)amino]-2,3-dihydro-1H-inden-1-yl]methyl}amino)pyridine-4-carboxylic acid TABLE 2-continued

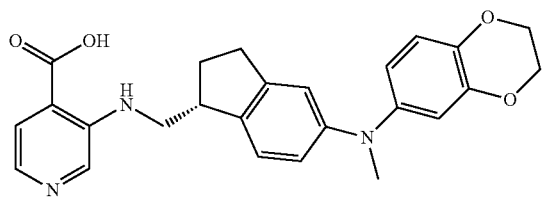 [SMILES: CN(c1ccc2c(c1)CC[C@H]2CNc1cnccc1C(=O)O)c1ccc2c(c1)OCCO2]

3-({[(1R)-5-[(2,3-dihydro-1,4-benzodioxin-6-yl)(methyl)amino]-2,3-dihydro-1H-inden-1-yl]methyl}amino)pyridine-4-carboxylic acid

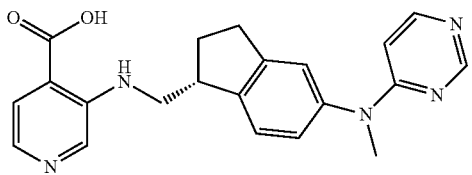 [SMILES: CN(c1ccc2c(c1)CC[C@H]2CNc1cnccc1C(=O)O)c1ccncn1]

3-({[(1R)-5-[methyl(pyrimidin-4-yl)amino]-2,3-dihydro-1H-inden-1-yl]methyl}amino)pyridine-4-carboxylic acid

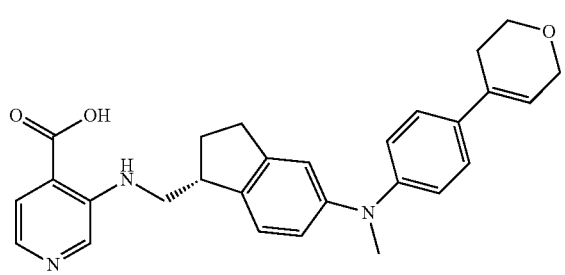 [SMILES: CN(c1ccc(C2=CCOCC2)cc1)c1ccc2c(c1)CC[C@H]2CNc1cnccc1C(=O)O]

3-({[(1R)-5-{[4-(3,6-dihydro-2H-pyran-4-yl)phenyl](methyl)amino}-2,3-dihydro-1H-inden-1-yl]methyl}amino)pyridine-4-carboxylic acid

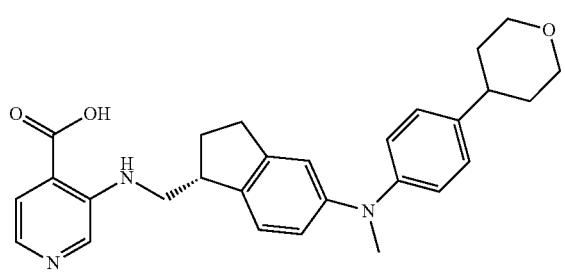 [SMILES: CN(c1ccc(C2CCOCC2)cc1)c1ccc2c(c1)CC[C@H]2CNc1cnccc1C(=O)O]

3-({[(1R)-5-{methyl[4-(oxan-4-yl)phenyl]amino}-2,3-dihydro-1H-inden-1-yl]methyl}amino)pyridine-4-carboxylic acid

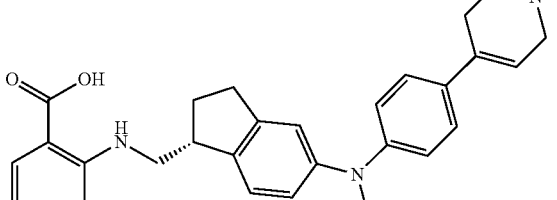

3-({[(1R)-5-{methyl[4-(1-methyl-1,2,3,6-tetrahydropyridin-4-yl)phenyl]amino}-2,3-dihydro-1H-inden-1-yl]methyl}amino)pyridine-4-carboxylic acid TABLE 2-continued

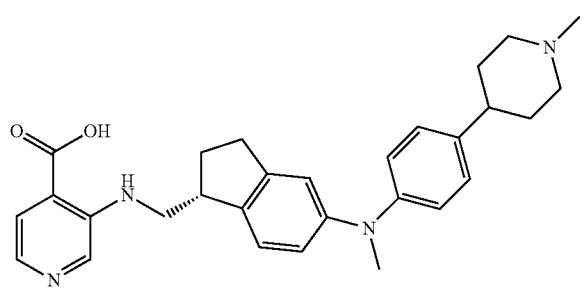 [SMILES: CN1CCC(c2ccc(N(C)c3ccc4c(c3)CC[C@H]4CNc3cnccc3C(=O)O)cc2)CC1]

3-({[(1R)-5-{methyl[4-(1-methylpiperidin-4-yl)phenyl]amino}-2,3-dihydro-1H-inden-1-yl]methyl}amino)pyridine-4-carboxylic acid

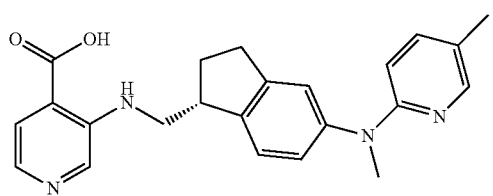 [SMILES: Cc1ccc(N(C)c2ccc3c(c2)CC[C@H]3CNc2cnccc2C(=O)O)nc1]

3-({[(1R)-5-[methyl(5-methylpyridin-2-yl)amino]-2,3-dihydro-1H-inden-1-yl]methyl}amino)pyridine-4-carboxylic acid

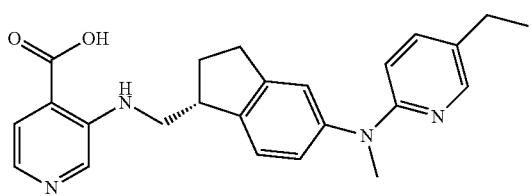 [SMILES: CCc1ccc(N(C)c2ccc3c(c2)CC[C@H]3CNc2cnccc2C(=O)O)nc1]

3-({[(1R)-5-[(5-ethylpyridin-2-yl)(methyl)amino]-2,3-dihydro-1H-inden-1-yl]methyl}amino)pyridine-4-carboxylic acid

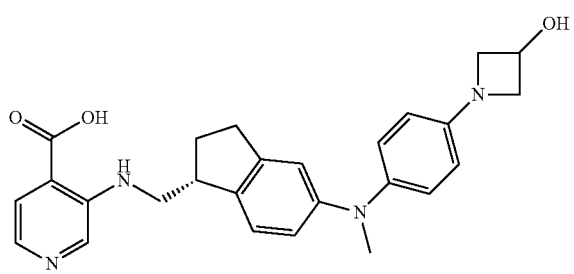 [SMILES: CN(c1ccc(N2CC(O)C2)cc1)c1ccc2c(c1)CC[C@H]2CNc1cnccc1C(=O)O]

3-({[(1R)-5-{[4-(3-hydroxyazetidin-1-yl)phenyl](methyl)amino}-2,3-dihydro-1H-inden-1-yl]methyl}amino)pyridine-4-carboxylic acid

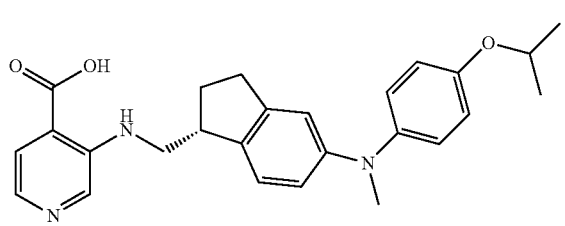 [SMILES: CC(C)Oc1ccc(N(C)c2ccc3c(c2)CC[C@H]3CNc2cnccc2C(=O)O)cc1]

3-({[(1R)-5-{methyl[4-(propan-2-yloxy)phenyl]amino}-2,3-dihydro-1H-inden-1-yl]methyl}amino)pyridine-4-carboxylic acid

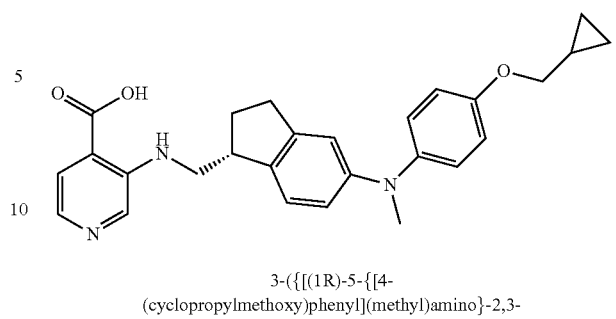

3-({[(1R)-5-{[4-(cyclopropylmethoxy)phenyl](methyl)amino}-2,3-dihydro-1H-inden-1-yl]methyl}amino)pyridine-4-carboxylic acid

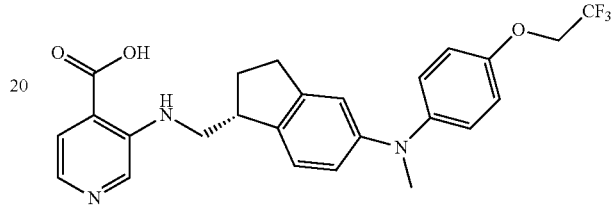

3-({[(1R)-5-{methyl[4-(2,2,2-trifluoroethoxy)phenyl]amino}-2,3-dihydro-1H-inden-1-yl]methyl}amino)pyridine-4-carboxylic acid

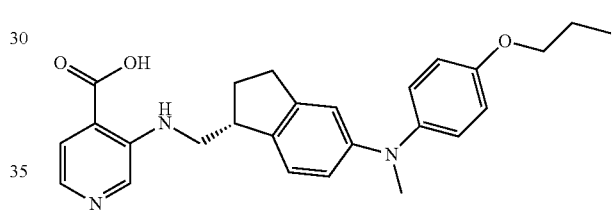

3-({[(1R)-5-[methyl(4-propoxyphenyl)amino]-2,3-dihydro-1H-inden-1-yl]methyl}amino)pyridine-4-carboxylic acid

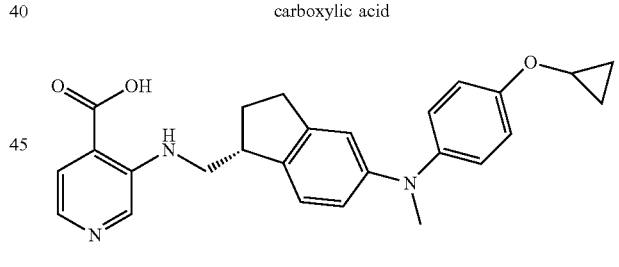

3-({[(1R)-5-[(4-cyclopropoxyphenyl)(methyl)amino]-2,3-dihydro-1H-inden-1-yl]methyl}amino)pyridine-4-carboxylic acid

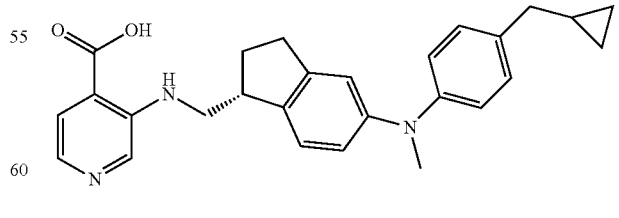

3-({[(1R)-5-{[4-(cyclopropylmethyl)phenyl](methyl)amino}-2,3-dihydro-1H-inden-1-yl]methyl}amino)pyridine-4-carboxylic acid TABLE 2-continued

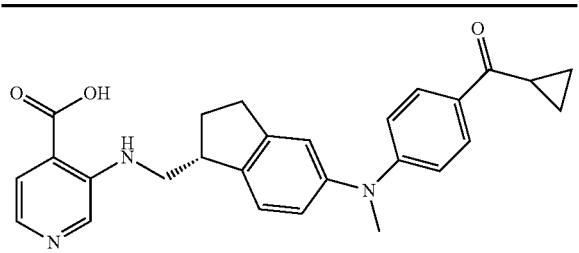

3-({[(1R)-5-[(4-cyclopropanecarbonylphenyl)(methyl)amino]-2,3-dihydro-1H-inden-1-yl]methyl}amino)pyridine-4-carboxylic acid

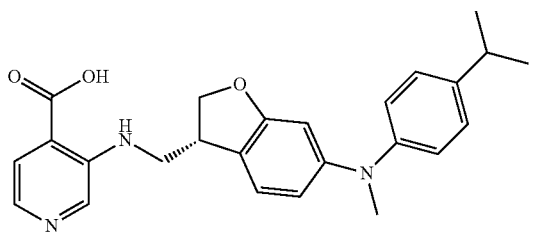 [SMILES: CC(C)c1ccc(N(C)c2ccc3c(c2)OC[C@H]3CNc2cnccc2C(=O)O)cc1]

3-({[(3R)-6-{methyl[4-(propan-2-yl)phenyl]amino}-2,3-dihydro-1-benzofuran-3-yl]methyl}amino)pyridine-4-carboxylic acid

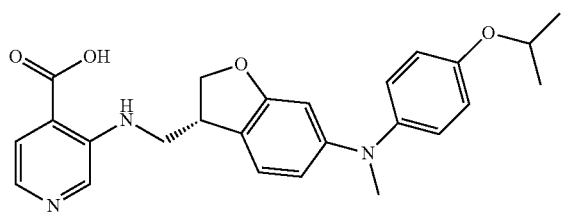

3-({[(3R)-6-{methyl[4-(propan-2-yloxy)phenyl]amino}-2,3-dihydro-1-benzofuran-3-yl]methyl}amino)pyridine-4-carboxylic acid

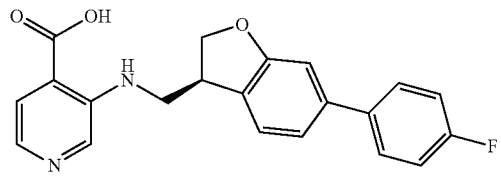 [SMILES: O=C(O)c1ccncc1NC[C@H]1COc2cc(-c3ccc(F)cc3)ccc21]

3-({[(3S)-6-(4-fluorophenyl)-2,3-dihydro-1-benzofuran-3-yl]methyl}amino)pyridine-4-carboxylic acid

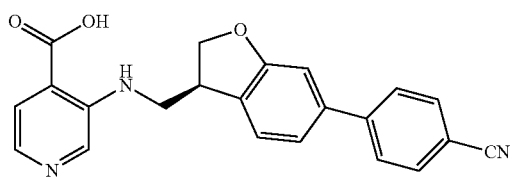 [SMILES: N#Cc1ccc(-c2ccc3c(c2)OC[C@@H]3CNc2cnccc2C(=O)O)cc1]

3-({[(3S)-6-(4-cyanophenyl)-2,3-dihydro-1-benzofuran-3-yl]methyl}amino)pyridine-4-carboxylic acid TABLE 2-continued

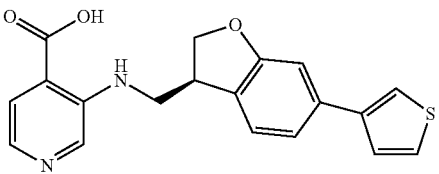 [SMILES: O=C(O)c1ccncc1NC[C@H]1COc2cc(-c3ccsc3)ccc21]

3-({[(3S)-6-(thiophen-3-yl)-2,3-dihydro-1-benzofuran-3-yl]methyl}amino)pyridine-4-carboxylic acid

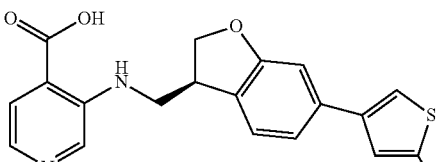

3-({[(3S)-6-(5-methylthiophen-3-yl)-2,3-dihydro-1-benzofuran-3-yl]methyl}amino)pyridine-4-carboxylic acid

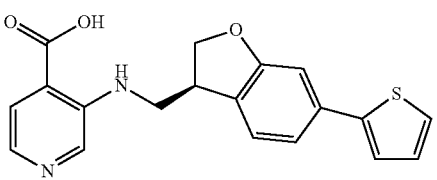 [SMILES: O=C(O)c1ccncc1NC[C@H]1COc2cc(-c3cccs3)ccc21]

3-({[(3S)-6-(thiophen-2-yl)-2,3-dihydro-1-benzofuran-3-yl]methyl}amino)pyridine-4-carboxylic acid

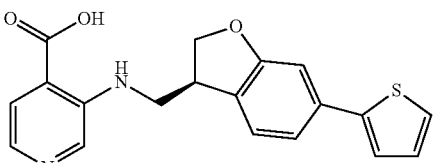

3-({[(3S)-6-(5-methylthiophen-2-yl)-2,3-dihydro-1-benzofuran-3-yl]methyl}amino)pyridine-4-carboxylic acid

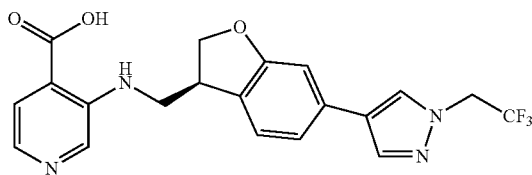 [SMILES: O=C(O)c1ccncc1NC[C@H]1COc2cc(-c3cnn(CC(F)(F)F)c3)ccc21]

3-({[(3S)-6-[1-(2,2,2-trifluoroethyl)-1H-pyrazol-4-yl]-2,3-dihydro-1-benzofuran-3-yl]methyl}amino)pyridine-4-carboxylic acid Preparation of the Substituted Pyridine Derivative Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted pyridine and pyridazine derivative compounds described herein is P. H. Stahl & C. G. Wermuth "Handbook of Pharmaceutical Salts", Verlag Helvetica Chimica Acta, Zurich, 2002.

The substituted pyridine derivative compounds are prepared by the general synthetic routes described below in Schemes 1-3.

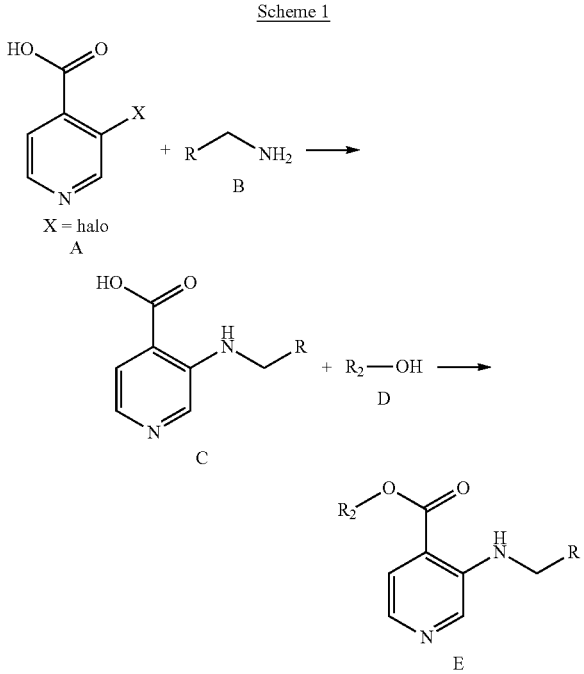

Referring to Scheme 1, compound A and an amine compound B are mixed and treated under a variety of conditions to form compound C. For example, the mixture of compound A and an amine B can be subjected to microwave irradiation in an appropriate solvent, at temperatures ranging from 120° C. to 172° C. The ester compound E can be prepared from compound C and an alcohol D using a coupling reagent, such as HATU, in the presence of a base.

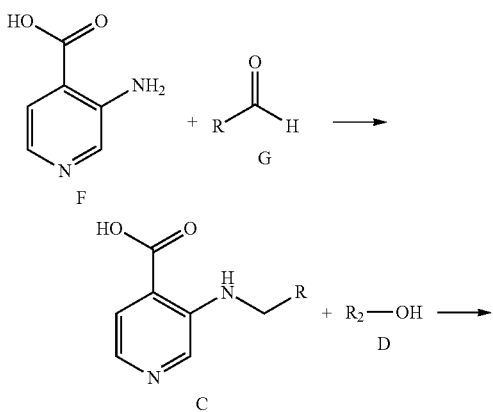

-continued

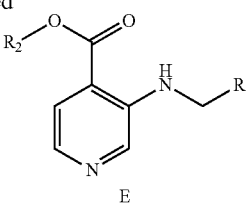

E

Referring to Scheme 2, compound F and an aldehyde compound G are mixed and treated under reductive amination conditions to form compound C. The ester compound E can be prepared from compound C and an alcohol D using a coupling reagent, such as HATU, in the presence of a base.

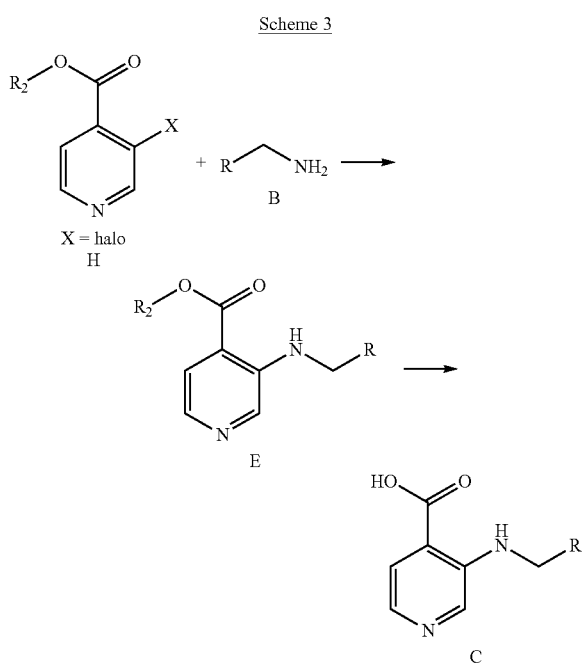

Referring to Scheme 3, compound H and an amine compound B are mixed and treated under a variety of conditions to form compound E. For example, the mixture of compound H and an amine B can be subjected to a Buchwald reaction under microwave irradiation in an appropriate solvent, at temperatures ranging from 100° C. to 120° C. The ester compound E can be hydrolyzed to give compound C, using basic conditions such as 1N aq. NaOH.

Pharmaceutical Compositions

In certain embodiments, the substituted pyridine derivative compound as described herein is administered as a pure chemical. In other embodiments, the substituted pyridine derivative compound as described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)), the disclosure of which is hereby incorporated herein by reference, in its entirety.

Accordingly, provided herein is a pharmaceutical composition comprising at least one substituted pyridine derivative compound, or a stereoisomer, prodrug, pharmaceutically acceptable salt, hydrate, solvate, or N-oxide thereof, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formulas (I), (II), (IIa) (III), (IV) or (V) or a tautomer, stereoisomer, geometric isomer, N-oxide, or pharmaceutically acceptable salt thereof.

In certain embodiments, the substituted pyridine derivative compound as described by Formulas (I), (II), (IIa) (III), (IV) or (V) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, $21^{st}$ Ed. Mack Pub. Co., Easton, Pa. (2005)).

The dose of the composition comprising at least one substituted pyridine derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

For the substituted pyridine derivative compounds described herein oral doses typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenosyl methionine (SAM) to histones. Histone methylation is known to participate in a diverse range of biological processes including heterochromatin formation, X-chromosome inactivation, and transcriptional regulation (Lachner et al., (2003) J. Cell Sci. 116:2117-2124; Margueron et al., (2005) Curr. Opin. Genet. Dev. 15:163-176).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas mono-methylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 family of proteins are a family of histone-demethylases known to demethylate tri- and di-methylated H3-K9, and were the first identified histone tri-methyl demethylases. In particular, ectopic expression of JMJD2 family members was found to dramatically decrease levels of tri- and di-methylated H3-K9, while increasing levels of mono-methylated H3-K9, which delocalized Heterochromatin Protein 1 (HP1) and reduced overall levels of heterochromatin in vivo. Members of the JMJD2 subfamily of jumonji proteins include JMJD2C and its homologues JMJD2A, JMJD2B, JMJD2D and JMJD2E. Common structural features found in the JMJD2 subfamily of Jumonji proteins include the JmjN, JmjC, PHD and Tdr sequences.

JMJD2C, also known as GASC1 and KDM4C, is known to demethylate tri-methylated H3K9 and H3K36. Histone demethylation by JMJD2C occurs via a hydroxylation reaction dependent on iron and $\alpha$-ketoglutarate, wherein oxidative decarboxylation of $\alpha$-ketoglutarate by JMJD2C produces carbon dioxide, succinate, and ferryl and ferryl subsequently hydroxylates a methyl group of lysine H3K9, releasing formaldehyde. JMJD2C is known to modulate regulation of adipogenesis by the nuclear receptor PPAR$\gamma$ and is known to be involved in regulation of self-renewal in embryonic stem cells.

JARID Family

As used herein, a "JARID protein" includes proteins in the JARID1 subfamily (e.g., JARID1A, JARID1B, JARID1C and JARID1D proteins) and the JARID2 subfamily, as well as homologues thereof. A further description and listing of JARID proteins can be found in Klose et al. (2006) Nature Reviews/Genetics 7:715-727. The JARID1 family contains several conserved domains: JmjN, ARID, JmjC, PHD and a C5HC2 zing finger.

JARID1A, also called KDM5A or RBP2, was initially found as a binding partner of retinoblastoma (Rb) protein. JARID1A was subsequently found to function as a demethylase of tri- and di-methylated H3K4, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastome binding protein 2 (RBP2) histone demethylase suppresses tumorigenesis in mice lacking Rb1 or Men1 (Lin et al. Proc. Natl. Acad. Sci. USA, Aug. 16, 2011, 108(33), 13379-86; doi: 10.1073/pnas.1110104108) and the authors of the study concluded that RBP2-inhibitory drugs would have anti-cancer activity.

JARID1B, also referred to as KDM5B and PLU1, was originally found in experiments to discover genes regulated by the HER2 tyrosine kinase. JARID1B has consistently been found to be expressed in breast cancer cell lines, although restriction of JARID1B has been found in normal adult tissues, with the exception of the testis. In addition, 90% of invasive ductal carcinomas have been found to express JARID1B. In addition, JARID1B has been found to be up-regulated in prostate cancers, while having more limited expression in benign prostate, and has also been found to be up-regulated in bladder cancer and lung cancer (both SCLC and NSCLC). JARID1B has also been found to repress tumor suppressor genes such as BRCA1, CAV1 and 14-3-3$\sigma$, and knockdown of JARID1B was found to increase the levels of tri-methylated H3K4 at these genes.

UTX/UTY Family

UTX/UTY family includes KDM6A, KDM6B, and UTY. KDM6A, also referred to as UTX, and KDM6B, also referred to as JMJD3, act on di- and trimethylated H3K27 and are important for development whereas the substrate and role of UTY remains to be elucidated. Both KDM6A (UTX) and KDM6B (JMJD3) have demonstrated tumor-supressive characteristics by functioning as antagonists to the oncogenic polycomb (PcG) proteins. PcG proteins are important repressive histone marks that catalyze the tri- and dimethylation of H3K27 The PcG genes have been characterized as oncogenes that are frequently overexpressed or amplified in cancer.

In an additional embodiment is the method for inhibiting a histone-demethylase enzyme comprising contacting the enzyme with a substituted pyridine derivative compound as disclosed herein, wherein the histone-demethylase enzyme comprises a JmjC domain. In an additional embodiment is the method for inhibiting a histone-demethylase enzyme comprising contacting the enzyme with a substituted pyridine derivative compound as disclosed herein, wherein the histone-demethylase enzyme is selected from JARID1A, JARID1B, or JMJD2C. In an additional embodiment is the method for inhibiting a histone-demethylase enzyme comprising contacting the enzyme with a substituted pyridine derivative compound as disclosed herein, wherein the histone-demethylase enzyme is selected from JARID1A, JARID1B, JMJD2C, and JMJD3. In one embodiment is the method for inhibiting the histone-demethylase enzyme JMJD3 comprising contacting the JMJD3 enzyme with a substituted pyridine derivative compound as disclosed herein. In one embodiment is the method for inhibiting the histone-demethylase enzyme JMJD2C comprising contacting the JMJD2C enzyme with a substituted pyridine derivative compound as disclosed herein.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, provided herein is a method of treating a disease regulated by histone methylation and/or demethylation in a subject in need thereof by modulating the activity of a demethylase comprising a JmjC domain (e.g., a histone demethylase such as a JHDM protein (s)).

In one embodiment is provided a method of treating cancer in a patient in need thereof comprising administering to the patient a composition comprising a compound of Formula (I), (II), (IIa) (III), (IV) or (V) or a pharmaceutically acceptable salt thereof. In a further embodiment is the method for treating cancer in a patient wherein the cancer is selected from prostate cancer, breast cancer, bladder cancer, lung cancer or melanoma.

In an additional embodiment is a method for inhibiting the growth of a tumor comprising exposing the tumor to a composition comprising a compound of Formula (I), (II), (IIa) (III), (IV) or (V) or a pharmaceutically acceptable salt thereof, wherein the tumor is characterized by a loss of retinoblastoma gene (RB1) function.

In an additional embodiment is a method for inhibiting the growth of a tumor comprising exposing the tumor to a composition comprising a compound of Formula (I), (II), (IIa) (III), (IV) or (V) or a pharmaceutically acceptable salt thereof, wherein the tumor is characterized by a loss of multiple endocrine neoplasia type 1 gene (Men1) function.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation 1a 6-bromo-1,2,3,4-tetrahydronaphthalen-1-one

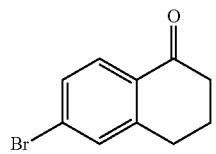 [SMILES: O=C1CCCc2cc(Br)ccc21]

A solution of $NaNO_2$ (2.35 g, 34 mmol) in water (10 mL) was added dropwise to the solution of 6-amino-1,2,3,4-tetrahydronaphthalen-1-one (5.0 g, 31 mmol) in 25% HBr (16 mL) at 0° C. The suspension was then transferred to a stirred mixture of CuBr (8.9 g, 62 mmol) in 48% HBr (30 mL) at 0° C. The resulting mixture was allowed to warm to rt and stirred for 1 h. The mixture was extracted with EtOAc, dried ($Na_2SO_4$), and concentrated. The residue was purified by silica gel chromatography (0%-60% EtOAc/Hex) to give 5.6 g (80%) of the title compound as a light yellow oil. $^1H$ NMR (400 MHz, $CDCl_3$): δ 2.10-2.16 (2H, m), 2.64 (2H, t, J=6.4 Hz), 2.94 (2H, t, J=6.0 Hz), 7.42 (1H, s), 7.44 (1H, s), 7.87 (1H, d, J=8.9 Hz). [M+H] calc'd for $C_{10}H_9BrO$, 225, 227; found 225, 227.

Preparation 1b

6-[methyl(phenyl)amino]-1,2,3,4-tetrahydronaphthalen-1-one

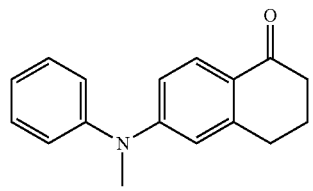 [SMILES: CN(c1ccccc1)c1ccc2c(c1)CCCC2=O]

To a solution of 6-bromo-1,2,3,4-tetrahydronaphthalen-1-one (2.0 g, 8.9 mmol) in toluene (20 mL) was added N-methylaniline (960 mg, 8.9 mmol), $Cs_2CO_3$ (4.4 g, 13.4 mmol), BINAP (310 mg, 0.5 mmol) and $Pd(OAc)_2$ (110 mg, 0.5 mmol). The mixture was stirred overnight at 100° C. under nitrogen. The mixture was filtered and concentrated, and the residue was purified by silica gel chromatography (30%-80% EtOAc/Hex) to give 1.52 g (68%) of the title compound as a light brown oil. [M+H] calc'd for $C_{17}H_{17}NO$, 252; found 252.

Preparation 1c 5-(aminomethyl)-N-methyl-N-phenyl-7,8-dihydronaphthalen-2-amine, hydrochloride

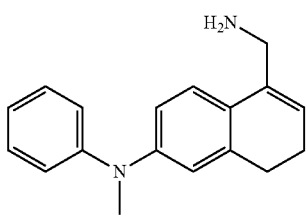 [SMILES: CN(c1ccccc1)c1ccc2c(c1)CCC=C2CN]

To a solution of Preparation 1b (1.52 g, 6.0 mmol) and ZnI$_2$ (150 mg) in toluene (20 mL) was added TMSCN (1.2 g, 12 mmol) at rt. The mixture was heated at 60° C. for 2 h. The reaction mixture was cooled to rt and diluted with addition of THF (20 mL). A solution of LAH (5 mL, 2.4 M in THF, 12 mmol) was added slowly at rt, and the solution stirred for 0.5 h. The reaction was quenched with the addition of EtOAc (10 mL), and then water (1 mL) and aqueous 1 M NaOH (1 mL). The solution was dried (Na$_2$SO$_4$) and concentrated to give 1.52 g (89%) of the crude 1-(aminomethyl)-6-[methyl(phenyl)amino]-1,2,3,4-tetrahydronaphthalen-1-ol as a white solid. Into a solution of this intermediate (1.52 g, 5.4 mmol) in methanol (20 mL) was bubbled dry HCl gas for 2 min, while the reaction was cooled so as to not allow the temperature to exceed 30° C. The mixture was then stirred at rt for 1 h. The methanol was evaporated under reduced pressure to give 1.4 g (98%) of the title compound as the HCl salt. [M+H] calc'd for C$_{18}$H$_{20}$N$_2$, 265; found 265.

Preparation 1d 5-(aminomethyl)-N-methyl-N-phenyl-5,6,7,8-tetrahydronaphthalen-2-amine

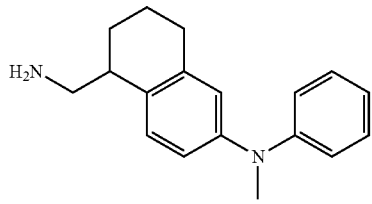 [SMILES: CN(c1ccccc1)c1ccc2c(c1)CCCC2CN]

To a solution of Preparation 1c (1.4 g, 5.3 mmol) in MeOH (30 mL) and conc. HCl (three drops) was added 10% Pd/C (200 mg) at rt under N$_2$. The suspension was stirred at rt for 16 h under hydrogen at 50 psi. The reaction mixture was filtered through Celite, adjusted to pH=8~9 with sat. Na$_2$CO$_3$, dried (Na$_2$SO$_4$), and concentrated to give 830 mg (59%) of the title compound as a yellow oil. [M+H] calc'd for C$_{18}$H$_{22}$N$_2$, 267; found 267.

Preparation 1e methyl 3-[({6-[methyl(phenyl)amino]-1,2,3,4-tetrahydronaphthalen-1-yl}methyl)amino]pyridine-4-carboxylate

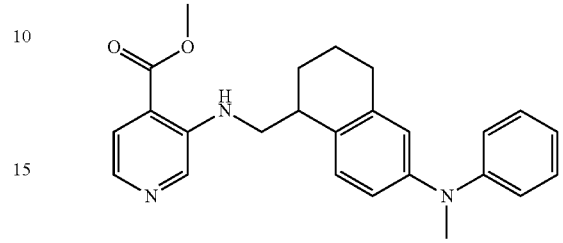

To a solution of Preparation 1d (500 mg, 1.88 mmol) in DMA (12 mL) was added methyl 3-fluoroisonicotinate (300 mg, 1.93 mmol). The reaction mixture was stirred at 170° C. for 1 h in a microwave. The reaction mixture was poured into water and extracted with EtOAc. Organics were washed with brine, dried (Na$_2$SO$_4$), and concentrated. The residue was purified by silica gel chromatography (20-80% EtOAc/Hex) to give 200 mg (26%) of the title compound as a yellow oil. [M+H] calc'd for C$_{25}$H$_{27}$N$_3$O$_2$, 402; found 402.

Preparation 1f methyl 3-({[(1S)-6-[methyl(phenyl)amino]-1,2,3,4-tetrahydronaphthalen-1-yl]methyl}amino)pyridine-4-carboxylate, and

Preparation 2f methyl 3-({[(1R)-6-[methyl(phenyl)amino]-1,2,3,4-tetrahydronaphthalen-1-yl]methyl}amino)pyridine-4-carboxylate 1f

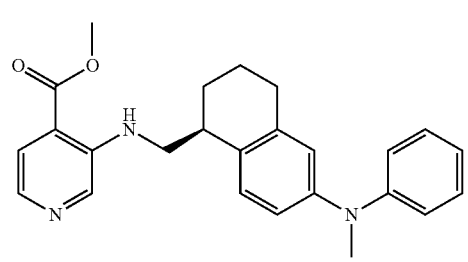

2f

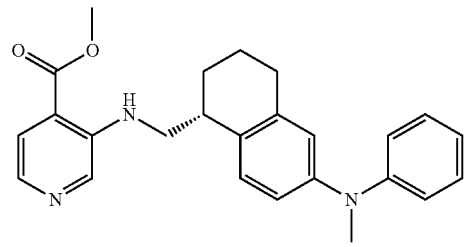 [SMILES: COC(=O)c1ccncc1NCC1CCCc2cc(N(C)c3ccccc3)ccc21]

Preparation 1e (200 mg) was separated by chiral HPLC (Column: Chiralcel IA, 250 mm*4.6 mm 5um; Mobile phase: Hex:EtOH=85:15; F: 1.0 mL/min; W: 230 nm; T=30°

C.) to give 95 mg (47%) of Preparation 1f (6.54 min) and 92 mg (46%) of Preparation 2f (7.91 min), each as a yellow oil.

Example 1

3-({[(1S)-6-[methyl(phenyl)amino]-1,2,3,4-tetrahydronaphthalen-1-yl]methyl}amino)pyridine-4-carboxylic acid

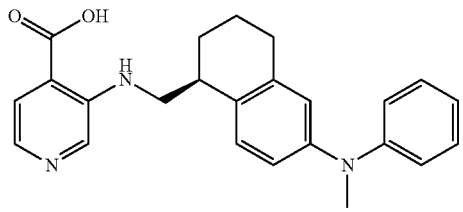 [SMILES: CN(c1ccccc1)c1ccc2c(c1)CCC[C@@H]2CNc1cnccc1C(=O)O]

To a solution of Preparation 1f (95 mg, 0.24 mmol) in THF (6 mL) and H$_2$O (2 mL) was added LiOH.H$_2$O (31 mg, 0.72 mmol) at rt, and the reaction mixture was stirred overnight. The reaction mixture was concentrated to remove THF, and the residue was diluted with water and acidified to pH=3~4 with 1.0 N aqueous HCl solution. The precipitate was collected by filtration and washed with EtOAc/ether. The solid was dried under vacuum to give 52 mg (56%) of the title compound as a yellow solid. $^1$H NMR (400 MHz, DMSO-d$_6$): δ 1.64-1.67 (1H, m), 1.77-1.84 (3H, m), 2.65-2.68 (2H, d, J=5.6 Hz), 3.04-3.07 (1H, m), 3.21 (3H, s), 3.41-3.47 (1H, m), 3.56-3.60 (1H, m), 6.78-6.92 (5H, m), 7.21-7.25 (3H, m), 7.55 (1H, d, J=5.2 Hz), 7.82 (1H, d, J=5.2 Hz), 8.36 (1H, s). [M+H] Calc'd for C$_{24}$H$_{25}$N$_3$O$_2$, 388; Found, 388.

Example 2

3-({[(1R)-6-[methyl(phenyl)amino]-1,2,3,4-tetrahydronaphthalen-1-yl]methyl}amino)pyridine-4-carboxylic acid

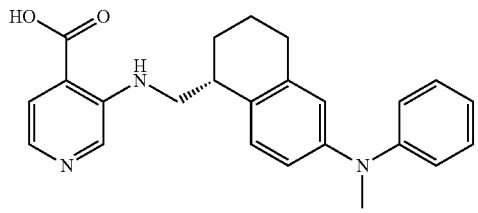 [SMILES: CN(c1ccccc1)c1ccc2c(c1)CCC[C@H]2CNc1cnccc1C(=O)O]

The title compound was prepared in 53% yield from Preparation 2f according to the procedure for Example 1. $^1$H NMR (400 MHz, DMSO-d$_6$): δ 1.64-1.68 (1H, m), 1.77-1.84 (3H, m), 2.65-2.68 (2H, d, J=5.6 Hz), 3.04-3.07 (1H, m), 3.21 (3H, s), 3.41-3.47 (1H, m), 3.56-3.60 (1H, m), 6.78-6.92 (5H, m), 7.21-7.25 (3H, m), 7.56 (1H, d, J=4.8 Hz), 7.82 (1H, d, J=5.2 Hz), 8.36 (1H, s). [M+H] calc'd for C$_{24}$H$_{25}$N$_3$O$_2$, 388; found 388.

Preparation 3a (6-bromo-3,4-dihydronaphthalen-1-yl)methanamine, hydrochloride

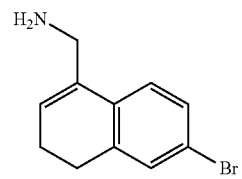 [SMILES: NCC1=CCCc2cc(Br)ccc21]

To a solution of 6-bromo-1,2,3,4-tetrahydronaphthalen-1-one (5.00 g, 22.0 mmol) and ZnI$_2$ (300 mg) in toluene (50 mL) was added TMSCN (4.36 g, 44.0 mmol) at rt. The mixture was heated at 60° C. overnight. The reaction mixture was cooled to rt, and a solution of LAH (20.0 mL, 2.4 M in THF, 44.0 mmol) was added slowly. The reaction stirred at 40° C. for 2 h. The reaction was cooled to 0° C. was quenched with addition of EtOAc (10 mL) at 0° C., and then water (5 mL) and aqueous 10% NaOH (5 mL). The mixture was filtered through Celite and concentrated to give the 4.5 g (79%) of the crude 1-(aminomethyl)-6-bromo-1,2,3,4-tetrahydronaphthalen-1-ol intermediate as a brown oil. To a solution of this intermediate (4.5 g, 17.4 mmol) in toluene (100 mL) was added 4N HCl/dioxane (20 mL) solution, and the mixture was stirred at reflux for 10 min. The mixture was cooled to room temperature and concentrated to give 3.6 g (75%) of the title compound as a tan solid. [M+H] calc'd for C$_{11}$H$_{12}$BrN, 237, 239; found 237, 239.

Preparation 3b tert-butyl N-[(6-bromo-3,4-dihydronaphthalen-1-yl)methyl]carbamate

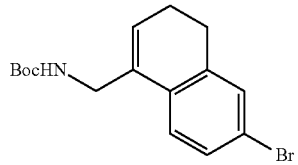 [SMILES: CC(C)(C)OC(=O)NCC1=CCCc2cc(Br)ccc21]

To a solution of Preparation 3a (1.05 g, 3.84 mmol) in DCM (10 mL) was added TEA (1.6 mL, 11.5 mmol), Boc$_2$O (2.1 g, 9.6 mmol) and DMAP (94 mg, 0.77 mmol). The mixture was stirred at rt for 1 h. The reaction was concentrated, and the residue was purified by silica gel chromatography (20-60% EtOAc/Hex) to give 900 mg (69%) of the title compound as a white solid. $^1$H NMR (400 MHz, CDCl$_3$): δ 1.44 (9H, s), 2.24-2.29 (2H, m), 2.70-2.74 (2H, m), 4.12 (2H, d, J=4.8 Hz), 4.56 (1H, br s), 6.03 (1H, t, J=4.4 Hz), 7.10 (1H, d, J=8.0 Hz), 7.26-7.32 (2H, m).

Preparation 3c tert-butyl N-{[6-(2-oxopyrrolidin-1-yl)-3,4-dihydronaphthalen-1-yl]methyl}carbamate

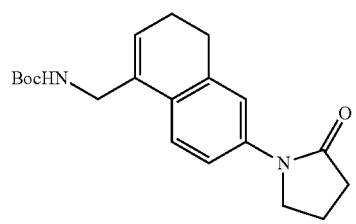 [SMILES: CC(C)(C)OC(=O)NCC1=CCCc2cc(N3CCCC3=O)ccc21]

To a solution of Preparation 3b (900 mg, 2.67 mmol) in dioxane (10 mL) was added 2-pyrrolidinone (680 mg, 8.0 mmol), $Cs_2CO_3$ (1.3 g, 4.0 mmol), BINAP (283 mg, 0.45 mmol) and $Pd(OAc)_2$ (60 mg, 0.27 mmol). The mixture was stirred at 100° C. for 4 h under nitrogen. The mixture was filtered and concentrated, and the residue was purified by silica gel chromatography (30-80% EtOAc/Hex) to give 470 mg (51%) of the title compound as a white solid. $^1$H NMR (400 MHz, DMSO-$d_6$): δ 1.38 (9H, s), 2.01-2.08 (2H, m), 2.18-2.23 (2H, m), 2.45-2.50 (2H, m), 2.68 (2H, t, J=8.0 Hz), 3.81 (2H, t, J=7.0 Hz), 3.92 (2H, d, J=4.8 Hz), 5.86 (1H, s), 7.02 (1H, t, J=5.4 Hz), 7.22 (1H, d, J=8.8 Hz), 7.42 (1H, d, J=8.4 Hz), 7.48 (1H, s).

Preparation 3d

1-[5-(aminomethyl)-7,8-dihydronaphthalen-2-yl]pyrrolidin-2-one, hydrochloride

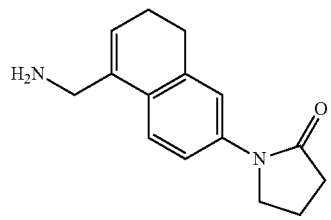 [SMILES: NCC1=CCCc2cc(N3CCCC3=O)ccc21]

A solution of Preparation 3c (470 mg, 1.37 mmol) in 4 N HCl/dioxane (10 mL) was stirred overnight at rt. The mixture was concentrated to 330 mg (99%) of the title compound as a tan oil. $^1$H NMR (400 MHz, MeOD-$d_4$): δ 2.19-2.23 (2H, m), 2.38-2.41 (2H, m), 2.63 (2H, t, J=8.2 Hz), 2.84 (2H, t, J=8.2 Hz), 3.96 (2H, t, J=7.0 Hz), 4.02 (2H, s), 6.26 (1H, t, J=4.4 Hz), 7.31 (1H, d, J=8.8 Hz), 7.52 (1H, s), 7.54 (1H, d, J=6.8 Hz). [M+H] calc'd for $C_{15}H_{18}N_2O$, 243; found 243.

Preparation 3e

1-[5-(aminomethyl)-5,6,7,8-tetrahydronaphthalen-2-yl]pyrrolidin-2-one

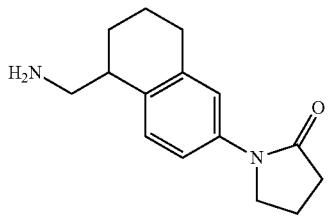 [SMILES: NCC1CCCc2cc(N3CCCC3=O)ccc21]

To a solution of Preparation 3d (330 mg, 1.36 mmol) in MeOH (10 mL) and conc. HCl (one drop) was added 10% Pd/C (50 mg) at rt under $N_2$. The suspension was stirred overnight under hydrogen at 50 psi. The reaction mixture was filtered through Celite, adjusted to pH=8~9 with sat. $Na_2CO_3$, dried ($Na_2SO_4$), and concentrated to give 240 mg (72%) of the title compound as a white solid. [M+H] calc'd for $C_{15}H_{20}N_2O$, 245; found 245.

Preparation 3f methyl 3-({[6-(2-oxopyrrolidin-1-yl)-1,2,3,4-tetrahydronaphthalen-1-yl]methyl}amino)pyridine-4-carboxylate

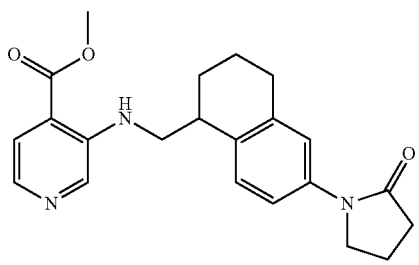 [SMILES: COC(=O)c1ccncc1NCC1CCCc2cc(N3CCCC3=O)ccc21]

The title compound was prepared in 15% yield from Preparation 3e according to the general procedure for Preparation 1e. [M+H] calc'd for $C_{22}H_{25}N_3O_3$, 380; found 380.

Example 3

3-({[6-(2-oxopyrrolidin-1-yl)-1,2,3,4-tetrahydronaphthalen-1-yl]methyl}amino)pyridine-4-carboxylic acid

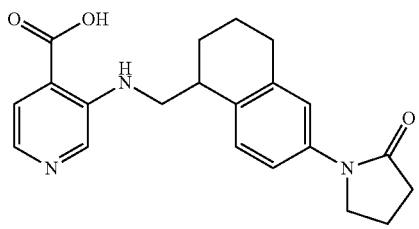 [SMILES: O=C(O)c1ccncc1NCC1CCCc2cc(N3CCCC3=O)ccc21]

The title compound was prepared in 92% yield from Preparation 3f according to the general procedure for Example 1. $^1$H NMR (400 MHz, DMSO-$d_6$): δ 1.65-1.69 (1H, m), 1.78-1.84 (3H, m), 2.00-2.07 (2H, m), 2.44-2.50 (2H, m), 2.70-2.73 (2H, m), 3.06-3.10 (1H, m), 3.38-3.45 (1H, m), 3.54-3.58 (1H, m), 3.79 (2H, t, J=7.0 Hz), 7.29 (1H, d, J=8.0 Hz), 7.34 (1H, s), 7.41 (1H, d, J=8.0 Hz), 7.55 (1H, d, J=5.2 Hz), 7.81 (1H, d, J=5.2 Hz), 8.34 (1H, s). [M+H] calc'd for $C_{21}H_{23}N_3O_3$, 366; found 366.

Preparation 4a 6-(1,2,3,4-tetrahydroquinolin-1-yl)-1,2,3,4-tetrahydronaphthalen-1-one

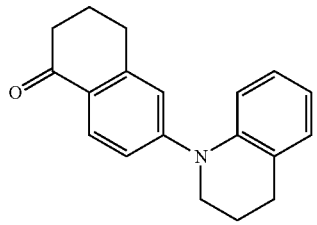 [SMILES: O=C1CCCc2cc(N3CCCc4ccccc43)ccc21]

To a solution of 5-oxo-5,6,7,8-tetrahydronaphthalen-2-yl 4-methylbenzene-1-sulfonate (1.0 g, 3.4 mmol) in THF (20 mL) was added 1,2,3,4-tetrahydroquinoline (0.55 g, 4.1 mmol), Pd(OAc)$_2$ (92 mg, 0.41 mmol), BINAP (383 mg, 0.61 mmol) and Cs$_2$CO$_3$ (1.7 g, 5.1 mmol). The mixture was heated to reflux under nitrogen overnight. The mixture was filtered and concentrated, and the residue was purified by silica gel chromatography (10% EtOAc/hexanes) to give 0.72 g (76%) of the title compound as a brown oil. $^1$H NMR (400 MHz, CDCl$_3$): δ 7.94 (d, J=8.4 Hz, 1H), 7.18-7.04 (m, 4H), 6.97 (d, J=2.4 Hz, 1H), 6.90 (dt, J=7.6 Hz, 1.2 Hz, 1H), 3.69 (t, J=6.0 Hz, 2H), 2.87 (t, J=6.0 Hz, 2H), 2.77 (t, J=6.4 Hz, 2H), 2.61 (t, J=6.4 Hz, 2H), 2.14-2.08 (m, 2H), 2.05-1.98 (m, 2H). [M+H] calc'd for $C_{19}H_{19}NO$, 278; found 278.

Preparation 4b

[6-(1,2,3,4-tetrahydroquinolin-1-yl)-3,4-dihydronaphthalen-1-yl]methanamine, hydrochloride

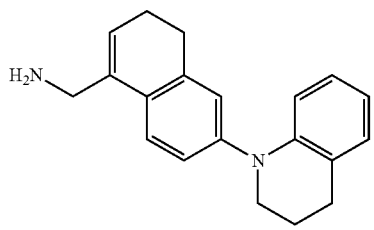

The title compound was prepared in 65% yield from Preparation 4a according to the general procedure for Preparation 3a. [M+H] calc'd for $C_{20}H_{22}N_2$, 291; found 291.

Preparation 4c

[6-(1,2,3,4-tetrahydroquinolin-1-yl)-1,2,3,4-tetrahydronaphthalen-1-yl]methanamine

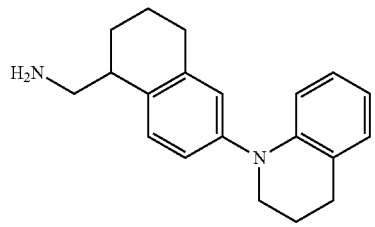

The title compound was prepared in 96% yield from Preparation 4b according to the general procedure for Preparation 3e, except that the reaction was heated at 50° C. [M+H] calc'd for $C_{20}H_{24}N_2$, 293; found 293.

Preparation 4d methyl 3-({[6-(1,2,3,4-tetrahydroquinolin-1-yl)-1,2,3,4-tetrahydronaphthalen-1-yl]methyl}amino)pyridine-4-carboxylate

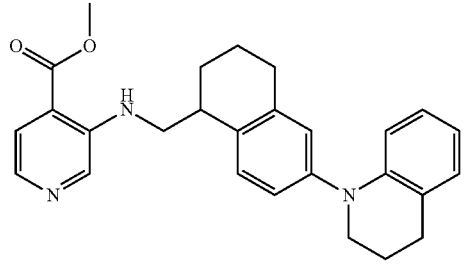

To a solution of Preparation 4c (0.49 g, 1.7 mmol) in toluene (10 mL) was added methyl 3-bromoisonicotinate (0.36 g, 1.7 mmol), Pd$_2$(dba)$_3$ (31 mg, 0.033 mmol), Xantphos (58 mg, 0.1 mmol) and Cs$_2$CO$_3$ (0.76 g, 2.3 mmol). The mixture was heated to reflux under nitrogen overnight. The mixture was filtered and concentrated, and the residue was purified by silica gel chromatography (10-30% EtOAc/Hex) to give 0.35 g (49%) of the title compound as a pale yellow solid. $^1$H NMR (400 MHz, CDCl$_3$): δ 8.34 (s, 1H), 7.91 (d, J=5.2 Hz, 1H), 7.63 (d, J=5.2 Hz, 1H), 7.61-7.58 (m, 1H), 7.21 (d, J=8.0 Hz, 1H), 7.05-6.99 (m, 2H), 6.93 (dd, J=8.0 Hz 7.6 Hz, 1H), 6.75 (d, J=8.4 Hz, 1H), 6.68 (t, J=7.6 Hz, 1H), 3.90 (s, 3H), 3.64-3.58 (m, 3H), 3.47-3.40 (m, 1H), 3.19-3.13 (m, 1H), 2.84 (t, J=6.4 Hz, 2H), 2.78-2.74 (m, 2H), 2.06-2.00 (m, 2H), 1.97-1.75 (m, 4H). [M+H] calc'd for $C_{27}H_{29}N_3O_2$, 428; found 428.

Example 4

3-({[6-(1,2,3,4-tetrahydroquinolin-1-yl)-1,2,3,4-tetrahydronaphthalen-1-yl]methyl}amino)pyridine-4-carboxylic acid

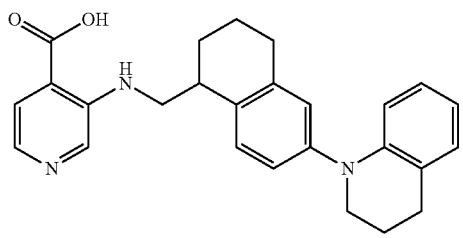

The title compound was prepared in 21% yield from Preparation 4d according to the general procedure for Example 1. $^1$H NMR (400 MHz, DMSO-$d_6$): δ 8.35 (s, 1H), 7.82 (d, J=4.4 Hz, 1H), 7.56 (d, J=4.4 Hz, 1H), 7.31 (d, J=7.2 Hz, 1H), 7.01-6.93 (m, 3H), 6.86 (dd, J=7.6 Hz, 8.0 Hz, 1H), 6.61 (dd, J=7.6 Hz, 7.2 Hz, 1H), 6.55 (d, J=8.0 Hz, 1H), 3.62-3.51 (m, 3H), 3.47-3.40 (m, 1H), 3.11-3.06 (m, 1H), 2.78-2.66 (m, 4H), 1.94-1.78 (m, 6H). [M+H] calc'd for $C_{26}H_{27}N_3O_2$, 414; found 414.

Preparation 5a 6-(2,3-dihydro-1H-indol-1-yl)-1,2,3,4-tetrahydronaphthalen-1-one

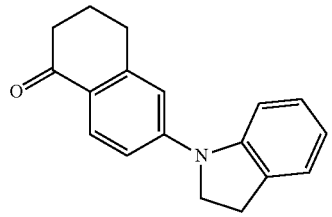 [SMILES: O=C1CCCc2cc(N3CCc4ccccc43)ccc21]

The title compound was prepared in 93% yield using indoline according to the general procedure for Preparation 4a. [M+H] calc'd for $C_{18}H_{17}NO$, 264; found 264.

Preparation 5b

[6-(2,3-dihydro-1H-indol-1-yl)-3,4-dihydronaphthalen-1-yl]methanamine, hydrochloride

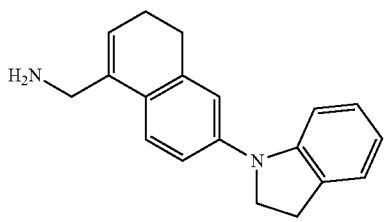 [SMILES: NCC1=CCCc2cc(N3CCc4ccccc43)ccc21]

The title compound was prepared in 77% yield from Preparation 5a according to the general procedure for Preparation 3a. [M+H] calc'd for $C_{19}H_{20}N_2$, 277; found 277.

Preparation 5c

[6-(2,3-dihydro-1H-indol-1-yl)-1,2,3,4-tetrahydronaphthalen-1-yl]methanamine

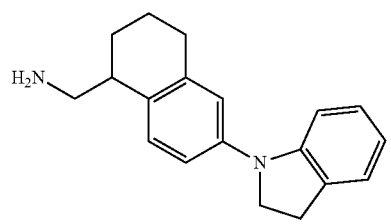

The title compound was prepared in 97% yield from Preparation 5b according to the general procedure for Preparation 3e, except the reaction was heated at 50° C. [M+H] calc'd for $C_{19}H_{22}N_2$, 279; found 279.

Preparation 5d methyl 3-({[6-(2,3-dihydro-1H-indol-1-yl)-1,2,3,4-tetrahydronaphthalen-1-yl]methyl}amino)pyridine-4-carboxylate

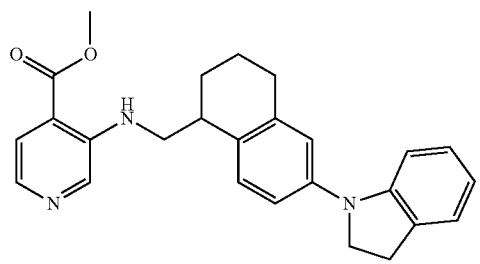 [SMILES: COC(=O)c1ccncc1NCC1CCCc2cc(N3CCc4ccccc43)ccc21]

The title compound was prepared in 24% yield from Preparation 5c according to the general procedure for Preparation 1e. [M+H] calc'd for $C_{26}H_{27}N_3O_2$, 414; found 414.

Example 5

3-({[6-(2,3-dihydro-1H-indol-1-yl)-1,2,3,4-tetrahydronaphthalen-1-yl]methyl}amino)pyridine-4-carboxylic acid

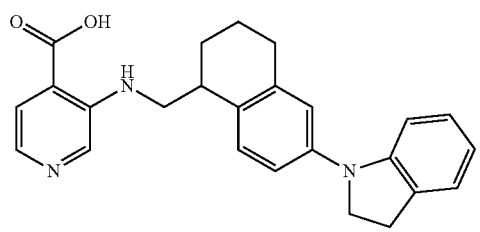 [SMILES: O=C(O)c1ccncc1NCC1CCCc2cc(N3CCc4ccccc43)ccc21]

The title compound was prepared in 78% yield from Preparation 5d according to the general procedure for Example 1. ¹H NMR (400 MHz, DMSO-$d_6$): δ 1.67-2.88 (4H, m), 2.71-2.77 (2H, m), 3.03-3.10 (3H, m), 3.42-3.49 (1H, m), 3.56-3.58 (1H, m), 3.88 (2H, t, J=8.4 Hz), 6.67-6.71 (1H, m), 6.93-6.94 (1H, m), 7.02-7.04 (3H, m), 7.15 (1H, d, J=7.2 Hz), 7.29 (1H, d, J=8.4 Hz), 7.59 (1H, d, J=8.1 Hz), 8.84 (1H, d, J=4.8 Hz), 8.39 (1H, s). [M+H] calc'd for $C_{25}H_{25}N_3O_2$, 400; found 400.

Preparation 6a 6-bromo-3,4-dihydronaphthalene-1-carboxamide

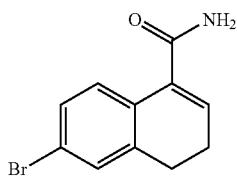 [SMILES: NC(=O)C1=CCCc2cc(Br)ccc21]

To a solution of 6-bromo-1,2,3,4-tetrahydronaphthalen-1-one (5.46 g, 24.3 mmol) and $ZnI_2$ (50 mg) in toluene (50 mL) was added TMSCN (4.82 mL, 48.6 mmol), and the solution stirred at 60° C. overnight. The reaction was cooled to rt, and $H_2SO_4$ (5.6 mL) was added. Then AcOH (34 mL), $H_2SO_4$ (25 mL) and $H_2O$ (4 mL) were added to the reaction, and it was heated to 105° C. for 3 h. The mixture was cooled and poured over ice-water (250 mL). The precipitate was collected by filtration, washed with water, and dried under vacuum to give 4.88 g (80%) of the title compound as an off-white solid. ¹H NMR (400 MHz, DMSO-$d_6$): δ 2.25-2.33 (2H, m), 2.72 (2H, t, J=8.0 Hz), 6.51 (1H, t, J=4.6 Hz), 7.20 (1H, br s), 7.35-7.40 (3H, m), 7.65 (1H, br s). [M+H] calc'd for $C_{11}H_{10}BrNO$, 252, 254; found 252, 254.

Preparation 6b (1R)-6-bromo-1,2,3,4-tetrahydronaphthalene-1-carboxamide

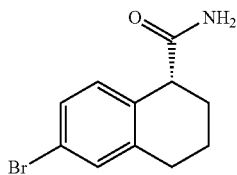 [SMILES: NC(=O)[C@@H]1CCCc2cc(Br)ccc21]

To a solution of Preparation 6a (4.88 g, 19.4 mmol) in MeOH (75 mL) and THF (75 mL) was added Ru(OAc)$_2$[s-binap] (82 mg, 0.097 mmol). The mixture was heated at 40° C. under hydrogen at 120 psi overnight. The solution was concentrated to give the crude title compound (ee >80%). Re-crystallization from ACN gave 3.8 g (77%) of the title compound (ee >96%) as a white solid. ¹H NMR (400 MHz, DMSO-$d_6$): δ 1.55-1.62 (1H, m), 1.85-1.94 (3H, m), 2.67-2.74 (2H, m), 3.56 (1H, t, J=6.6 Hz), 6.98 (1H, br s), 7.02 (1H, d, J=8.9 Hz), 7.25-7.29 (2H, m), 7.47 (1H, br s). [M+H] calc'd for $C_{11}H_{12}BrNO$, 254, 256; found 254, 256. Analytical Column: Chiralcel: AS-H, Mobile phase: Hex:EtOH=60:40.

Preparation 6c

[(1R)-6-bromo-1,2,3,4-tetrahydronaphthalen-1-yl]methanamine

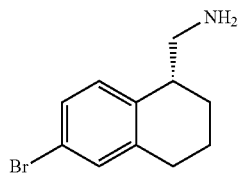 [SMILES: NC[C@@H]1CCCc2cc(Br)ccc21]

To a solution of Preparation 6b (2.5 g, 9.84 mmol) in THF (40 mL) was added $BH_3$.THF (39.4 mL, 1.0 M in THF, 39.4 mmol) at rt, and the solution was heated at 55° C. overnight. The solution was cooled and quenched with 10% $H_2SO_4$ (8 mL) and stirred for 6 h. The solution was made basic with aq. $NH_4OH$ and extracted (3×) with EtOAc. Organics were dried ($Na_2SO_4$) and concentrated to give 2.36 g (100%) of the crude title compound as a brown oil. [M+H] calc'd for $C_{11}H_{14}BrN$, 240, 242; found 240, 242.

Preparation 6d tert-butyl N-{[(1R)-6-bromo-1,2,3,4-tetrahydronaphthalen-1-yl]methyl}carbamate

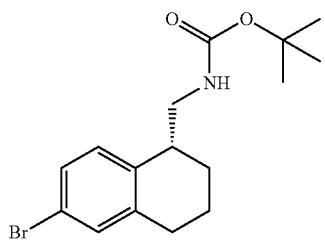 [SMILES: CC(C)(C)OC(=O)NC[C@@H]1CCCc2cc(Br)ccc21]

To a solution of Preparation 6c (2.36 g, 9.83 mmol) and DIEA (2.23 mL, 12.8 mmol) in DCM (50 mL) was added (Boc)$_2$O (2.58 g, 11.8 mmol), and the reaction stirred at rt for 2 h. The solution was washed with brine, dried (MgSO$_4$), and concentrated. Purification by silica gel chromatography (10-60% EtOAc/Hex) gave 3.02 g (90%) of the title compound as a white solid. ¹H NMR (400 MHz, CDCl$_3$): δ 1.45 (9H, s), 1.72-1.85 (4H, m), 2.69-2.75 (2H, m), 2.88-2.96 (1H, m), 3.21-3.27 (1H, m), 3.35-3.42 (1H, m), 4.61 (1H, br s), 7.08 (1H, d, J=7.4 Hz), 7.22-7.27 (2H, m). [M+H] calc'd for $C_{16}H_{22}BrNO_2$, 340, 342; found 340, 342.

Preparation 6e tert-butyl N-{[(1R)-6-[(2-fluorophenyl)(methyl)amino]-1,2,3,4-tetrahydronaphthalen-1-yl]methyl}carbamate

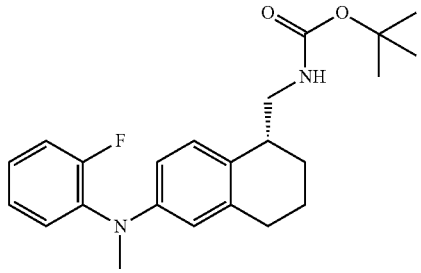 [SMILES: CN(c1ccc2c(c1)CCC[C@H]2CNC(=O)OC(C)(C)C)c1ccccc1F]

To a suspension of Preparation 6d (150 mg, 0.442 mmol), 2-fluoro-N-methylaniline (83 mg, 0.66 mmol), BINAP (14 mg, 0.022 mmol) and Cs$_2$CO$_3$ (216 mg, 0.664 mmol) in toluene (10 mL) was added Pd(OAc)$_2$ (3 mg, 0.01 mmol) at rt under N$_2$. The reaction was stirred at 105° C. overnight. The mixture was filtered and concentrated. Purification by silica gel chromatography (PE:EtOAc=8:1) gave 105 mg (62%) of the title compound as a brown oil. [M+H] calc'd for C$_{23}$H$_{29}$FN$_2$O$_2$, 385; found 385.

Preparation 6f (5R)-5-(aminomethyl)-N-(2-fluorophenyl)-N-methyl-5,6,7,8-tetrahydronaphthalen-2-amine

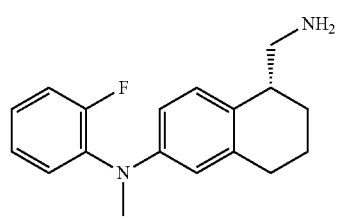 [SMILES: CN(c1ccc2c(c1)CCC[C@H]2CN)c1ccccc1F]

To a solution of Preparation 6e (105 mg, 0.273 mmol) in EtOAc (5 mL) was added HCl/EtOAc (5 mL, 1.0 M), and the reaction was stirred at rt for 30 min. The solution was concentrated, re-dissolved in EtOAc, and washed with sat. Na$_2$CO$_3$. The organic layer was dried (Na$_2$SO$_4$) and concentrated to give 79 mg (100%) of the title compound as a yellow oil. [M+H] calc'd for C$_{18}$H$_{21}$FN$_2$, 285; found 285.

Preparation 6g methyl 3-({[(1R)-6-[(2-fluorophenyl)(methyl)amino]-1,2,3,4-tetrahydronaphthalen-1-yl]methyl}amino)pyridine-4-carboxylic acid

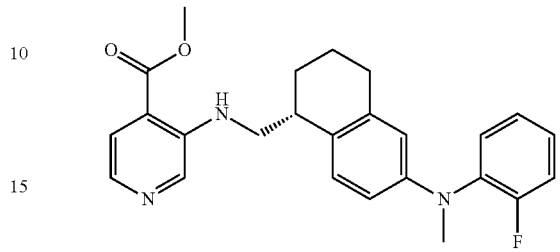

The title compound was prepared in 60% yield from Preparation 6f according to the general procedure for Preparation 4d. [M+H] calc'd for C$_{25}$H$_{26}$FN$_3$O$_2$, 420; found 420.

Example 6

3-({[(1R)-6-[(2-fluorophenyl)(methyl)amino]-1,2,3,4-tetrahydronaphthalen-1-yl]methyl}amino)pyridine-4-carboxylic acid The title compound was prepared in 79% yield from Preparation 6g according to the general procedure for Example 1. $^1$H NMR (400 MHz, DMSO-d$_6$): δ 1.62-1.83 (4H, m), 2.61-2.63 (2H, m), 2.98-3.02 (1H, m), 3.20 (3H, s), 3.34-3.41 (1H, m), 3.50-3.55 (1H, m), 6.44-6.48 (2H, m), 7.13 (1H, d, J=8.4 Hz), 7.22-7.33 (4H, m), 7.56 (1H, d, J=5.2 Hz), 7.82 (1H, d, J=4.8 Hz), 8.34 (1H, s). [M+H] calc'd for C$_{24}$H$_{24}$FN$_3$O$_2$, 406; found 406.

Preparation 7a tert-butyl N-{[(1R)-6-[(3-fluorophenyl)(methyl)amino]-1,2,3,4-tetrahydronaphthalen-1-yl]methyl}carbamate

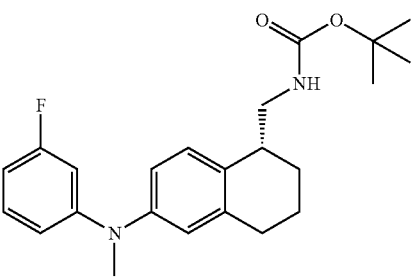 [SMILES: CN(c1cccc(F)c1)c1ccc2c(c1)CCC[C@H]2CNC(=O)OC(C)(C)C]

The title compound was prepared in 56% yield from Preparation 6d and 3-fluoro-N-methylaniline according to the general procedure for Preparation 6e. [M+H] calc'd for $C_{23}H_{29}FN_2O_2$, 385; found 385.

Preparation 7b (5R)-5-(aminomethyl)-N-(3-fluorophenyl)-N-methyl-5,6,7,8-tetrahydronaphthalen-2-amine

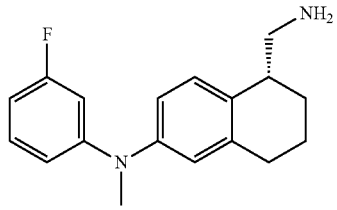 [SMILES: CN(c1cccc(F)c1)c1ccc2c(c1)CCC[C@H]2CN]

The title compound was prepared in quantitative yield from Preparation 7a according to the general procedure for Preparation 6f. [M+H] calc'd for $C_{18}H_{21}FN_2$, 285; found 285.

Preparation 7c methyl 3-({[(1R)-6-[(3-fluorophenyl)(methyl)amino]-1,2,3,4-tetrahydronaphthalen-1-yl]methyl}amino)pyridine-4-carboxylic acid

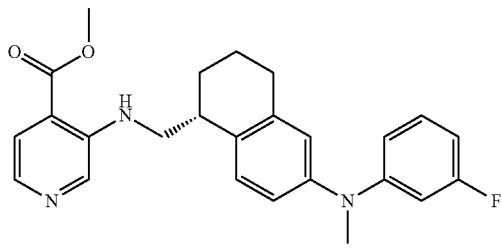 [SMILES: COC(=O)c1ccncc1NC[C@@H]1CCCc2cc(N(C)c3cccc(F)c3)ccc21]

The title compound was prepared in 66% yield from Preparation 7b according to the general procedure for Preparation 4d. [M+H] calc'd for $C_{25}H_{26}FN_3O_2$, 420; found 420.

Example 7

3-({[(1R)-6-[(3-fluorophenyl)(methyl)amino]-1,2,3,4-tetrahydronaphthalen-1-yl]methyl}amino)pyridine-4-carboxylic acid

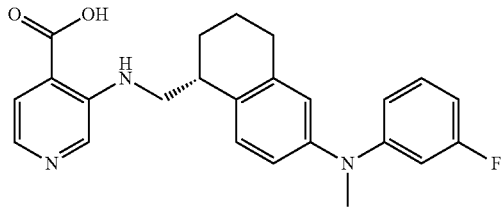 [SMILES: CN(c1cccc(F)c1)c1ccc2c(c1)CCC[C@H]2CNc1cnccc1C(=O)O]

The title compound was prepared in 76% yield from Preparation 7c according to the general procedure for Example 1. $^1$H NMR (400 MHz, DMSO-$d_6$): δ 1.67-1.86 (4H, m), 2.69-2.72 (2H, m), 3.09-3.12 (1H, m), 3.31 (3H, s), 3.44-3.50 (1H, m), 3.59-3.64 (1H, m), 6.51-6.58 (3H, m), 6.92-6.95 (2H, m), 7.14-7.20 (1H, m), 7.33 (1H, d, J=8.0 Hz), 7.58 (1H, d, J=5.2 Hz), 7.84 (1H, d, J=5.2 Hz), 8.38 (1H, s). [M+H] calc'd for $C_{24}H_{24}FN_3O_2$, 406; found 406.

Preparation 8a tert-butyl N-{[(1R)-6-[(4-fluorophenyl)(methyl)amino]-1,2,3,4-tetrahydronaphthalen-1-yl]methyl}carbamate

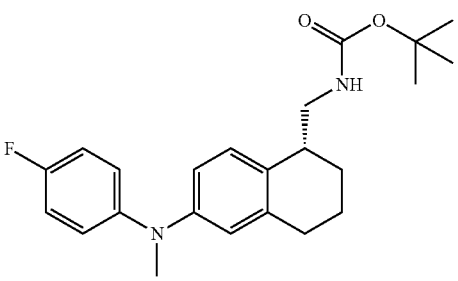 [SMILES: CN(c1ccc(F)cc1)c1ccc2c(c1)CCC[C@H]2CNC(=O)OC(C)(C)C]

The title compound was prepared in 76% yield from Preparation 6d and 4-fluoro-N-methylaniline according to the general procedure for Preparation 6e. [M+H] calc'd for $C_{23}H_{29}FN_2O_2$, 385; found 385.

Preparation 8b (5R)-5-(aminomethyl)-N-(4-fluorophenyl)-N-methyl-5,6,7,8-tetrahydronaphthalen-2-amine

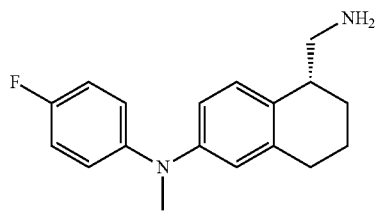 [SMILES: CN(c1ccc(F)cc1)c1ccc2c(c1)CCC[C@H]2CN]

The title compound was prepared in quantitative yield from Preparation 8a according to the general procedure for Preparation 6f. [M+H] calc'd for $C_{18}H_{21}FN_2$, 285; found 285.

Preparation 8c methyl 3-({[(1R)-6-[(4-fluorophenyl)(methyl)amino]-1,2,3,4-tetrahydronaphthalen-1-yl]methyl}amino)pyridine-4-carboxylic acid

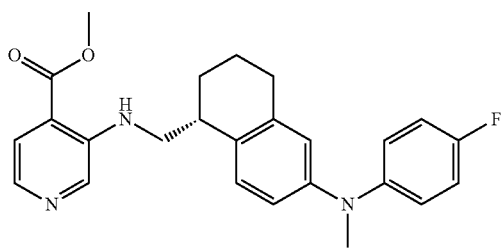 [SMILES: COC(=O)c1ccncc1NC[C@@H]1CCCc2cc(N(C)c3ccc(F)cc3)ccc21]

The title compound was prepared in 42% yield from Preparation 8b according to the general procedure for Preparation 4d. [M+H] calc'd for $C_{25}H_{26}FN_3O_2$, 420; found 420.

Example 8

3-({[(1R)-6-[(4-fluorophenyl)(methyl)amino]-1,2,3,4-tetrahydronaphthalen-1-yl]methyl}amino)pyridine-4-carboxylic acid

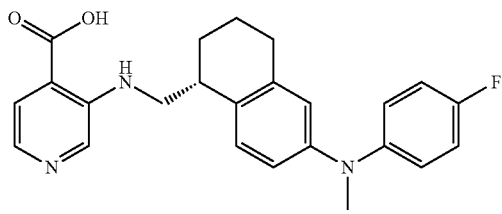 [SMILES: CN(c1ccc(F)cc1)c1ccc2c(c1)CCC[C@H]2CNc1cnccc1C(=O)O]

The title compound was prepared in 78% yield from Preparation 8c according to the general procedure for Example 1. $^1$H NMR (400 MHz, DMSO-$d_6$): δ 1.63-1.67 (1H, m), 1.75-1.85 (3H, m), 2.63-2.68 (2H, m), 3.02-3.06 (1H, m), 3.19 (3H, s), 3.39-3.45 (1H, m), 3.53-3.59 (1H, m), 6.68-6.73 (2H, m), 6.97-7.02 (2H, m), 7.07-7.13 (2H, m), 7.20 (1H, d, J=8.3 Hz), 7.56 (1H, d, J=5.0 Hz), 7.69 (1H, br s), 7.82 (1H, d, J=5.0 Hz), 8.34 (1H, s), 13.36 (1H, br s). [M+H] calc'd for $C_{24}H_{24}FN_3O_2$, 406; found 406.

Preparation 9a tert-butyl N-{[(1R)-6-[(4-chlorophenyl)(methyl)amino]-1,2,3,4-tetrahydronaphthalen-1-yl]methyl}carbamate

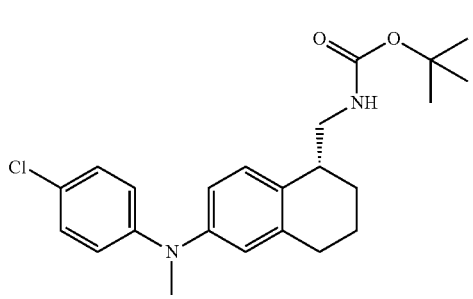 [SMILES: CN(c1ccc(Cl)cc1)c1ccc2c(c1)CCC[C@H]2CNC(=O)OC(C)(C)C]

To a solution of Preparation 6d (200 mg, 0.59 mmol) in toluene (5 mL) was added 4-chloro-N-methylaniline (100 mg, 0.7 mmol), $Pd_2(dba)_3$ (27 mg, 0.03 mmol), Xantphos (51 mg, 0.15 mmol) and NaOtBu (68 mg, 0.7 mmol). The mixture was heated at 96° C. in a microwave for 1 h. The mixture was filtered and concentrated, and the residue was purified by silica gel chromatography (0-10% MeOH/DCM) to give 168 mg (76%) of the title compound as a pale yellow solid. [M+H] calc'd for $C_{23}H_{29}ClN_2O_2$, 401; found 401.

Preparation 9b (5R)-5-(aminomethyl)-N-(4-chlorophenyl)-N-methyl-5,6,7,8-tetrahydronaphthalen-2-amine

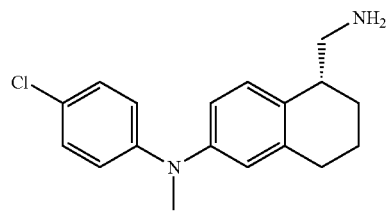 [SMILES: CN(c1ccc(Cl)cc1)c1ccc2c(c1)CCC[C@H]2CN]

Preparation 9a (168 mg, 0.42 mmol) was stirred in 50% TFA/DCM for 1 h. The solution was concentrated, and the residue was dissolved in EtOAc and washed with sat. NaHCO$_3$, dried (Na$_2$SO$_4$) and concentrated to give 126 mg (quantitative) clear oil. [M+H] calc'd for $C_{18}H_{21}ClN_2$, 301. found 301.

Preparation 9c methyl 3-({[(1R)-6-[(4-chlorophenyl)(methyl)amino]-1,2,3,4-tetrahydronaphthalen-1-yl]methyl}amino)pyridine-4-carboxylic acid

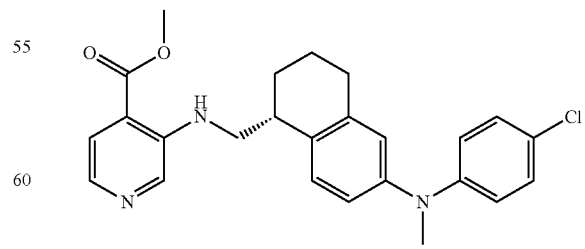

The title compound was prepared in 12% yield from Preparation 9b according to the general procedure for Preparation 4d. [M+H] calc'd for $C_{25}H_{26}ClN_3O_2$, 436; found 436.

Example 9

3-({[(1R)-6-[(4-chlorophenyl)(methyl)amino]-1,2,3,4-tetrahydronaphthalen-1-yl]methyl}amino)pyridine-4-carboxylic acid

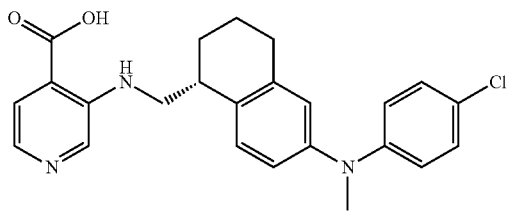 [SMILES: CN(c1ccc(Cl)cc1)c1ccc2c(c1)CCC[C@H]2CNc1cnccc1C(=O)O]

The title compound was prepared in 76% yield from Preparation 9c according to the general procedure for Example 1. $^1$H NMR (400 MHz, MeOD): δ 1.73-1.79 (1H, m), 1.90-1.97 (3H, m), 2.73-2.81 (2H, m), 3.12-3.15 (1H, s), 3.23 (3H, s), 3.42-3.48 (1H, m), 3.54-3.59 (1H, m), 6.81-6.85 (4H, m), 7.15 (2H, dd, J=6.8, 2.2 Hz), 7.21 (1H, d, J=8.1 Hz), 7.76-7.82 (2H, m), 8.21 (1H, s). [M+H] calc'd for $C_{24}H_{24}ClN_3O_2$, 422; found 422.

Preparation 10a tert-butyl N-{[(1R)-6-[ethyl(phenyl)amino]-1,2,3,4-tetrahydronaphthalen-1-yl]methyl}carbamate

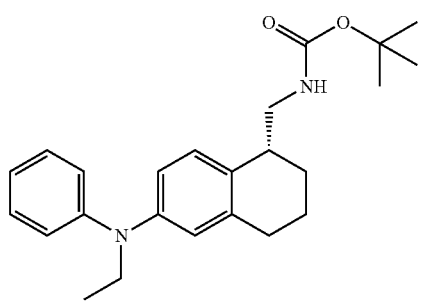 [SMILES: CCN(c1ccccc1)c1ccc2c(c1)CCC[C@H]2CNC(=O)OC(C)(C)C]

The title compound was prepared in 59% yield from Preparation 6d and N-ethylaniline according to the general procedure for Preparation 9a. [M+H] calc'd for $C_{24}H_{32}N_2O_2$, 381; found 381.

Preparation 10b (5R)-5-(aminomethyl)-N-ethyl-N-phenyl-5,6,7,8-tetrahydronaphthalen-2-amine

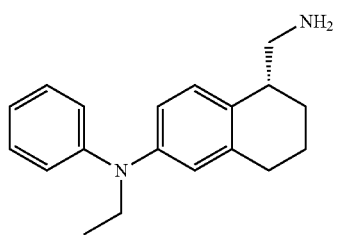 [SMILES: CCN(c1ccccc1)c1ccc2c(c1)CCC[C@H]2CN]

The title compound was prepared in quantitative yield from Preparation 10a according to the general procedure for Preparation 9b. [M+H] calc'd for $C_{19}H_{24}N_2$, 281; found 281.

Preparation 10c methyl 3-({[(1R)-6-[ethyl(phenyl)amino]-1,2,3,4-tetrahydronaphthalen-1-yl]methyl}amino)pyridine-4-carboxylate

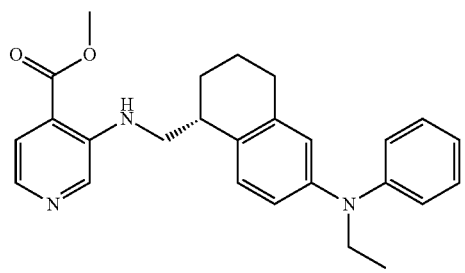 [SMILES: CCN(c1ccccc1)c1ccc2c(c1)CCC[C@H]2CNc1cnccc1C(=O)OC]

The title compound was prepared in 82% yield from Preparation 10b according to the general procedure for Preparation 4d. [M+H] calc'd for $C_{26}H_{29}N_3O_2$, 416; found 416.

Example 10

3-({[(1R)-6-[ethyl(phenyl)amino]-1,2,3,4-tetrahydronaphthalen-1-yl]methyl}amino)pyridine-4-carboxylic acid

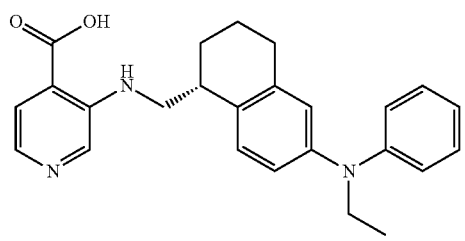 [SMILES: CCN(c1ccccc1)c1ccc2c(c1)CCC[C@H]2CNc1cnccc1C(=O)O]

The title compound was prepared in 90% yield from Preparation 10c according to the general procedure for Example 1. $^1$H NMR (400 MHz, DMSO-d$_6$): δ 1.11 (3H, t, J=7.0 Hz), 1.63-1.83 (4H, m), 2.62-2.70 (2H, m), 3.03-3.07 (1H, m), 3.39-3.46 (1H, m), 3.55-3.61 (1H, m), 3.70 (2H, q, J=7.0 Hz), 6.75-6.89 (5H, m), 7.19-7.25 (3H, m), 7.56 (1H, d, J=5.0 Hz), 7.69 (1H, br s), 7.82 (1H, d, J=5.0 Hz), 8.34 (1H, s), 13.47 (1H, br s). [M+H] calc'd for $C_{25}H_{27}N_3O_2$, 402; found 402.

Preparation 11a tert-butyl N-{[(1R)-6-[methyl(pyridin-2-yl)amino]-1,2,3,4-tetrahydronaphthalen-1-yl]methyl}carbamate

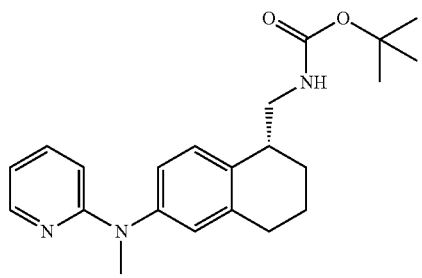 [SMILES: CN(c1ccc2c(c1)CCC[C@H]2CNC(=O)OC(C)(C)C)c1ccccn1]

The title compound was prepared in 41% yield from Preparation 6d and N-methyl-2-pyridinamine according to the general procedure for Preparation 6e. [M+H] calc'd for $C_{22}H_{29}N_3O_2$, 368; found 368.

Preparation 11b

N-[(5R)-5-(aminomethyl)-5,6,7,8-tetrahydronaphthalen-2-yl]-N-methylpyridin-2-amine

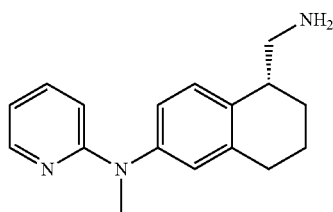 [SMILES: CN(c1ccc2c(c1)CCC[C@H]2CN)c1ccccn1]

The title compound was prepared in 99% yield from Preparation 11a according to the general procedure for Preparation 6f. [M+H] calc'd for $C_{17}H_{21}N_3$, 268; found 268.

Preparation 11c methyl 3-({[(1R)-6-[methyl(pyridin-2-yl)amino]-1,2,3,4-tetrahydronaphthalen-1-yl]methyl}amino)pyridine-4-carboxylate

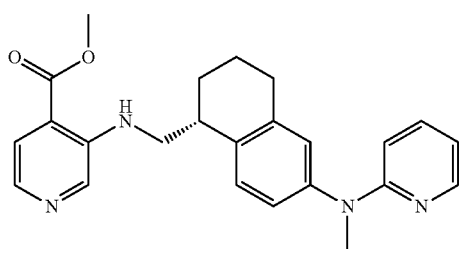 [SMILES: COC(=O)c1ccncc1NC[C@@H]1CCCc2cc(N(C)c3ccccn3)ccc21]

The title compound was prepared in 42% yield from Preparation 11b according to the general procedure for Preparation 4d. [M+H] calc'd for $C_{24}H_{26}N_4O_2$, 403; found 403.

Example 11

3-({[(1R)-6-[methyl(pyridin-2-yl)amino]-1,2,3,4-tetrahydronaphthalen-1-yl]methyl}amino)pyridine-4-carboxylic acid

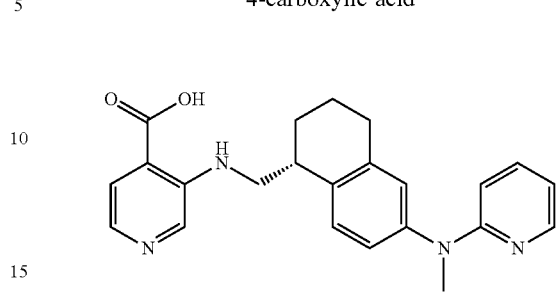

The title compound was prepared in 32% yield from Preparation 11c according to the general procedure for Example 1. $^1$H NMR (400 MHz, DMSO-$d_6$): δ 1.67-1.71 (1H, m), 1.80-1.88 (3H, m), 2.70-2.74 (2H, m), 3.02-3.05 (1H, m), 3.23-3.29 (1H, m), 3.40 (3H, s), 3.47-3.50 (1H, m), 6.48 (1H, d, J=8.8 Hz), 6.61-6.64 (1H, m), 7.00 (1H, s), 7.02 (1H, d, J=8.0 Hz), 7.37-7.41 (2H, m), 7.54 (1H, d, J=4.8 Hz), 7.68 (1H, d, J=4.8 Hz), 8.05 (1H, s), 8.13 (1H, d, J=4.8 Hz), 9.19 (1H, br s). [M+H] calc'd for $C_{23}H_{24}N_4O_2$, 389; found 389.

Preparation 12a tert-butyl N-{[(1R)-6-[methyl(pyridin-3-yl)amino]-1,2,3,4-tetrahydronaphthalen-1-yl]methyl}carbamate

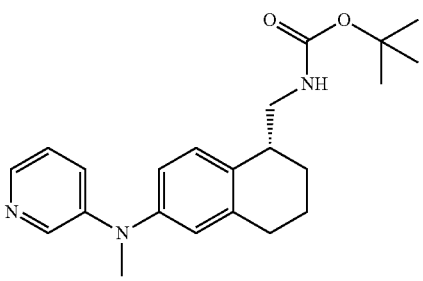 [SMILES: CN(c1cccnc1)c1ccc2c(c1)CCC[C@H]2CNC(=O)OC(C)(C)C]

The title compound was prepared in 77% yield from Preparation 6d and N-methyl-3-pyridinamine according to the general procedure for Preparation 9a. [M+H] calc'd for $C_{22}H_{29}N_3O_2$, 368; found 368.

Preparation 12b

N-[(5R)-5-(aminomethyl)-5,6,7,8-tetrahydronaphthalen-2-yl]-N-methylpyridin-3-amine

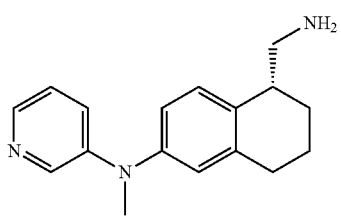 [SMILES: CN(c1cccnc1)c1ccc2c(c1)CCC[C@H]2CN]

The title compound was prepared in 88% yield from Preparation 12a according to the general procedure for Preparation 9b. [M+H] calc'd for $C_{17}H_{21}N_3$, 268; found 268.

Preparation 12c methyl 3-({[(1R)-6-[methyl(pyridin-3-yl)amino]-1,2,3,4-tetrahydronaphthalen-1-yl]methyl}amino)pyridine-4-carboxylate

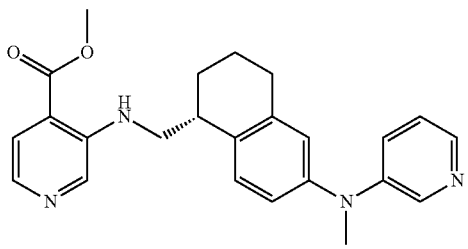 [SMILES: COC(=O)c1ccncc1NC[C@@H]1CCCc2cc(N(C)c3cccnc3)ccc21]

The title compound was prepared in 27% yield from Preparation 12b according to the general procedure for Preparation 4d. [M+H] calc'd for $C_{24}H_{26}N_4O_2$, 403; found 403.

Example 12

3-({[(1R)-6-[methyl(pyridin-3-yl)amino]-1,2,3,4-tetrahydronaphthalen-1-yl]methyl}amino)pyridine-4-carboxylic acid

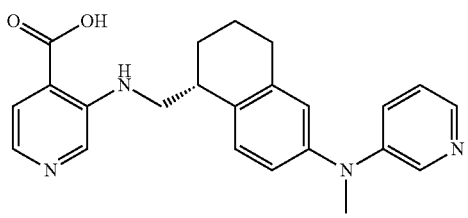 [SMILES: CN(c1cccnc1)c1ccc2c(c1)CCC[C@H]2CNc1cnccc1C(=O)O]

The title compound was prepared in 62% yield from Preparation 12c according to the general procedure for Example 1. $^1$H NMR (400 MHz, MeOD): δ 1.75-1.79 (1H, m), 1.93-1.99 (3H, m), 2.72-2.81 (2H, m), 3.19-3.23 (1H, m), 3.33 (3H, s), 3.50-3.63 (2H, m), 6.91-6.97 (2H, m), 7.30-7.38 (3H, m), 7.76-7.82 (2H, m), 7.92 (1H, br s), 8.04 (1H, br s), 8.15 (1H, s). [M+H] calc'd for $C_{23}H_{24}N_4O_2$, 389; found 389.

Preparation 13a tert-butyl N-{[(1R)-6-[(6-methoxypyridin-3-yl)(methyl)amino]-1,2,3,4-tetrahydronaphthalen-1-yl]methyl}carbamate

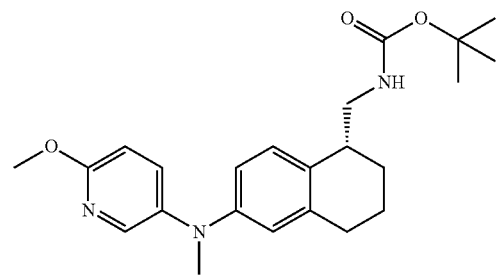 [SMILES: COc1ccc(N(C)c2ccc3c(c2)CCC[C@H]3CNC(=O)OC(C)(C)C)cn1]

The title compound was prepared in 64% yield from Preparation 6d and 6-methoxy-N-methylpyridin-3-amine according to the general procedure for Preparation 9a. [M+H] calc'd for $C_{23}H_{31}N_3O_3$, 398; found 398.

Preparation 13b

N-[(5R)-5-(aminomethyl)-5,6,7,8-tetrahydronaphthalen-2-yl]-6-methoxy-N-methylpyridin-3-amine

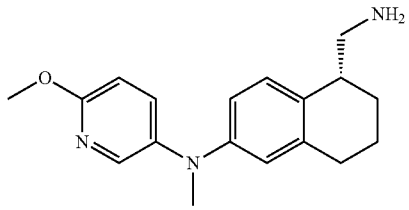 [SMILES: COc1ccc(N(C)c2ccc3c(c2)CCC[C@H]3CN)cn1]

The title compound was prepared in 98% yield from Preparation 13a according to the general procedure for Preparation 9b. [M+H] calc'd for $C_{18}H_{23}N_3O$, 298; found 298.

Example 13

3-({[(1R)-6-[(6-methoxypyridin-3-yl)(methyl)amino]-1,2,3,4-tetrahydronaphthalen-1-yl]methyl}amino)pyridine-4-carboxylic acid

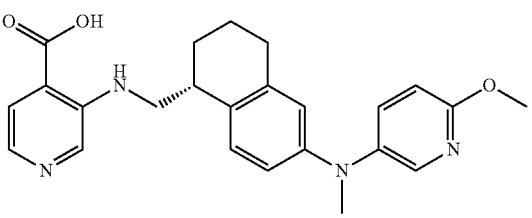

3-Fluoroisonicotinic acid (52 mg, 0.36 mmol), Preparation 13b (108 mg, 0.36 mmol) and DIEA (64 μL, 0.36 mmol) were combined in DMA (2 mL), and the solution was heated at 168° C. in a microwave for 1 h. The solution was concentrated and purified by prep-HPLC (35-85% ACN/water with 0.1% formic acid) to give 58 mg (39%) of the title compound as a pale yellow solid. $^1$H NMR (400 MHz, DMSO-$d_6$): δ 1.61-1.80 (4H, m), 2.61-2.67 (2H, m), 2.99-3.04 (1H, m), 3.18 (3H, s), 3.40-3.55 (2H, m), 3.83 (3H, s), 6.54-6.60 (2H, m), 6.79 (1H, d, J=8.7 Hz), 7.15 (1H, d, J=8.5 Hz), 7.46 (1H, d, J=8.7 Hz), 7.55 (1H, d, J=5.0 Hz), 7.72 (1H, br s), 7.82 (1H, d, J=5.0 Hz), 7.95 (1H, s), 8.34 (1H, s), 13.29 (1H, br s). [M+H] calc'd for $C_{24}H_{26}N_4O_3$, 419; found 419.

Preparation 14a (7-bromo-2H-chromen-4-yl)methanamine, hydrochloride

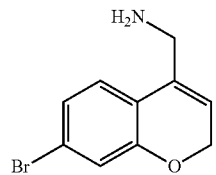

To a solution of 7-bromochroman-4-one (5.00 g, 22.0 mmol) and $ZnI_2$ (30 mg) in toluene (50 mL) was added TMSCN (4.36 g, 44.0 mmol), and the mixture was heated at 60° C. overnight. The reaction mixture was cooled to rt, and a solution of LAH (20.0 mL, 2.4 M in THF, 44.0 mmol) was added slowly. The mixture was stirred at 40° C. for 2 h. The reaction was quenched with the addition of EtOAc (10 mL) at 0° C., followed by water (5 mL) and aqueous 10% NaOH (5 mL). The reaction mixture was diluted with EtOAc, dried (MgSO$_4$), filtered through Celite, and concentrated to give 4.5 g (79%) of the crude 4-(aminomethyl)-7-bromo-3,4-dihydro-2H-1-benzopyran-4-ol intermediate as a yellow oil.

To a solution of this intermediate (4.50 g, 17.4 mmol) in toluene (100 mL) was added 4N HCl/dioxane (20 mL) solution, and the mixture was stirred at reflux for 10 min. The mixture was cooled to rt and concentrated. The residue was precipitated from cold EtOAc and collected to give 3.6 g (75%) of the title compound as a yellow solid. [M+H] calc'd for $C_{10}H_{10}BrNO$, 240, 242; found 240, 242.

Preparation 14b (7-bromo-3,4-dihydro-2H-1-benzopyran-4-yl)methanamine

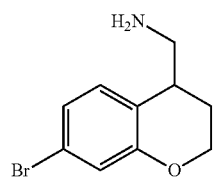 [SMILES: NCC1CCOc2cc(Br)ccc21]

To a solution of Preparation 14a (2.0 g, 7.2 mmol) in MeOH (20 mL) and AcOH (2 mL) was added Raney Ni (200 mg) at rt. The suspension was stirred for overnight at under hydrogen at 50 psi. The reaction mixture was filtered, and the pH was adjusted to 7-8 with sat. Na$_2$CO$_3$. The solution was dried (Na$_2$SO$_4$) and concentrated to give 1.32 g (75%) of the title compound as a brown oil. [M+H] Calc'd for $C_{10}H_{12}BrNO$, 242, 244; Found, 242, 244.

Preparation 14c methyl 3-{[(7-bromo-3,4-dihydro-2H-1-benzopyran-4-yl)methyl]amino}pyridine-4-carboxylate

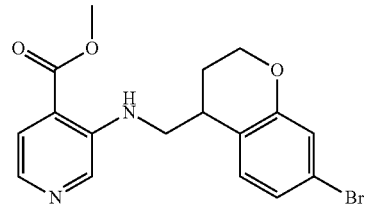 [SMILES: COC(=O)c1ccncc1NCC1CCOc2cc(Br)ccc21]

The title compound was prepared in 44% yield from Preparation 9b according to the general procedure for Preparation 1e. [M+H] Calc'd for $C_{17}H_{17}BrN_2O_3$, 377, 379; Found, 377, 379.

Example 14

3-{[(7-bromo-3,4-dihydro-2H-1-benzopyran-4-yl)methyl]amino}pyridine-4-carboxylic acid

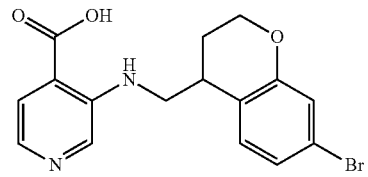 [SMILES: O=C(O)c1ccncc1NCC1CCOc2cc(Br)ccc21]

The title compound was prepared in 59% yield from Preparation 14c according to the general procedure for Example 1. $^1$H NMR (400 MHz, DMSO-$d_6$): δ 1.87-2.01 (2H, m), 3.10-3.14 (1H, m), 3.49-3.55 (1H, m), 3.66-3.71 (1H, m), 4.16-4.23 (2H, m), 6.99-7.04 (2H, m), 7.27 (1H, d, J=8.0 Hz), 7.57 (1H, d, J=4.8 Hz), 7.85 (1H, d, J=5.2 Hz), 8.42 (1H, s). [M+H] Calc'd for $C_{16}H_{15}BrN_2O_3$, 363, 365; Found, 363, 365.

Preparation 15a methyl 3-({[7-(phenylamino)-3,4-dihydro-2H-1-benzopyran-4-yl]methyl}amino)pyridine-4-carboxylate

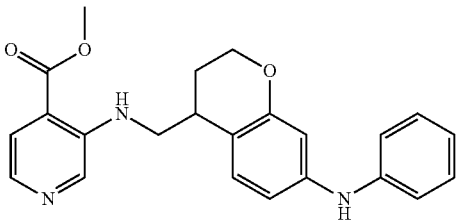 [SMILES: COC(=O)c1ccncc1NCC1CCOc2cc(Nc3ccccc3)ccc21]

A suspension of Preparation 14c (100 mg, 0.26 mmol), aniline (25.0 mg, 0.26 mmol), Cs$_2$CO$_3$ (130 mg, 0.40 mmol), Pd(OAc)$_2$ (2.0 mg, 0.007 mmol) and BINAP (9.0 mg, 0.013 mmol) in toluene (10 mL) was stirred at 100° C. under N$_2$ overnight. The reaction was filtered and concentrated. Purification by silica gel chromatography (PE:EA=1:1) gave 54 mg (52%) of the title compound as a brown oil. [M+H] calc'd for C$_{23}$H$_{23}$N$_3$O$_3$, 390; found 390.

Example 15

3-({[7-(phenylamino)-3,4-dihydro-2H-1-benzopyran-4-yl]methyl}amino)pyridine-4-carboxylic acid

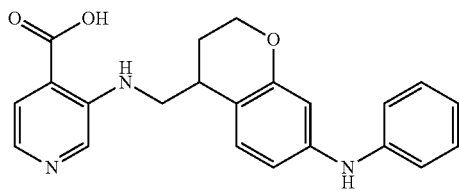 [SMILES: O=C(O)c1ccncc1NCC1CCOc2cc(Nc3ccccc3)ccc21]

The title compound was prepared in 71% yield from Preparation 15a according to the general procedure for Example 1. $^1$H NMR (400 MHz, DMSO-d$_6$): δ 1.86-1.88 (1H, m), 1.96-1.99 (1H, m), 3.04-3.05 (1H, m), 3.3.43-3.48 (1H, m), 3.63-3.67 (1H, m), 4.12-4.17 (2H, m), 6.47 (1H, s), 6.48-6.61 (1H, m), 6.78-6.82 (1H, m), 7.04 (2H, d, J=8.0 Hz), 7.11-7.23 (3H, m), 7.58 (1H, d, J=4.8 Hz), 7.84 (1H, d, J=4.8 Hz), 8.08 (1H, s), 8.38 (1H, s). [M+H] calc'd for C$_{22}$H$_{21}$N$_3$O$_3$, 376; found 376.

Preparation 16a tert-butyl [(7-bromo-2H-chromen-4-yl)methyl]carbamate

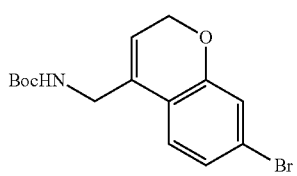

To a solution of Preparation 14a (3.6 g, 13 mmol) in DMF (30 mL) was added TEA (5.5 mL, 39 mmol) and (Boc)$_2$O (3.40 g, 15.6 mmol). The mixture was stirred at rt for 2 h. The reaction was concentrated and the residue was purified by silica gel chromatography (PE:EtOAc=4:1) to give 3.19 g (72%) of the title compound as a yellow solid. $^1$H NMR (400 MHz, CDCl$_3$): δ 6.97-7.03 (m, 3H), 5.72-5.75 (m, 1H), 4.76-4.79 (m, 2H), 4.67 (br s, 1H), 4.08-4.15 (m, 2H), 1.45 (s, 9H). [M+H] calc'd for C$_{15}$H$_{18}$BrNO$_3$, 340, 342; found 340, 342.

Preparation 16b tert-butyl N-{[7-(1,2,3,4-tetrahydroquinolin-1-yl)-2H-chromen-4-yl]methyl}carbamate

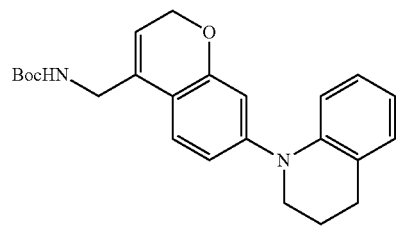 [SMILES: CC(C)(C)OC(=O)NCC1=CCOc2cc(N3CCCc4ccccc43)ccc21]

To a solution of Preparation 16a (500 mg, 1.47 mmol) in THF (15 mL) was added 1,2,3,4-tetrahydroquinoline (215 mg, 1.62 mmol), Cs$_2$CO$_3$ (719 g, 2.21 mmol), BINAP (220 mg, 0.35 mmol) and Pd(OAc)$_2$ (40 mg, 0.18 mmol). The mixture was refluxed for overnight under nitrogen. The mixture was filtered and concentrated, and the residue was purified by silica gel chromatography (PE: EtOAc=5:1) to give 360 mg (62%) of the title compound as a yellow oil. [M+H] calc'd for C$_{24}$H$_{28}$N$_2$O$_3$, 393; found 393.

Preparation 16c

[7-(1,2,3,4-tetrahydroquinolin-1-yl)-2H-chromen-4-yl]methanamine, hydrochloride

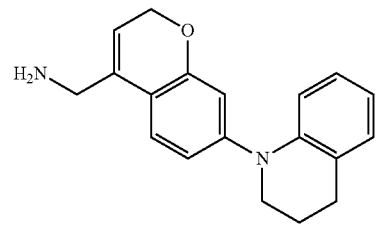

A solution of Preparation 16b (360 mg, 0.918 mmol) in 4N HCl/EtOAc (20 mL) was stirred overnight at rt. The mixture was concentrated to give the crude title compound as a yellow solid. [M+H] calc'd for C$_{19}$H$_{20}$N$_2$O, 293; found 293.

Preparation 16d

[7-(1,2,3,4-tetrahydroquinolin-1-yl)-3,4-dihydro-2H-1-benzopyran-4-yl]methanamine

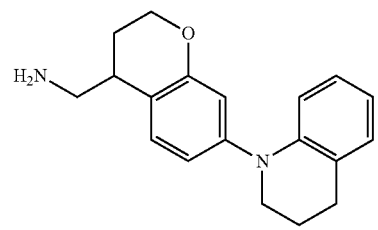 [SMILES: NCC1CCOc2cc(N3CCCc4ccccc43)ccc21]

To a solution of Preparation 16c (300 mg, 0.913 mmol) in MeOH (20 mL) and conc. HCl (one drop) was added 10% Pd/C (30 mg) under N₂. The suspension was stirred at rt under 50 psi of hydrogen overnight. The reaction mixture was filtered, adjusted to pH=7~8 with sat. K₂CO₃, dried (Na₂SO₄), and concentrated to give 240 mg (90%) of the title compound as a yellow oil. [M+H] calc'd for $C_{19}H_{22}N_2O$, 295; found 295.

Preparation 16e methyl 3-({[7-(1,2,3,4-tetrahydroquinolin-1-yl)-3,4-dihydro-2H-1-benzopyran-4-yl]methyl}amino)pyridine-4-carboxylate

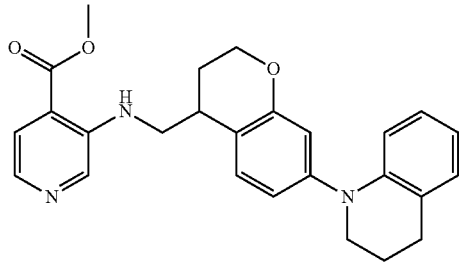

To a solution of Preparation 16d (240 mg, 0.816 mmol) in toluene (10 mL) was added methyl 3-bromoisonicotinate (176 mg, 0.816 mmol), Pd₂(dba)₃ (15 mg, 0.016 mmol), Xantphos (29 mg, 0.049 mmol) and Cs₂CO₃ (373 mg, 1.14 mmol). The mixture was heated to reflux under nitrogen overnight. The mixture was filtered and concentrated, and the residue was purified by silica gel chromatography (PE:EtOAc=2:1) to give 90 mg (26%) of the title compound as a yellow oil. [M+H] calc'd for $C_{26}H_{27}N_3O_3$, 430; found 430.

Example 16

3-({[7-(1,2,3,4-tetrahydroquinolin-1-yl)-3,4-dihydro-2H-1-benzopyran-4-yl]methyl}amino)pyridine-4-carboxylic acid

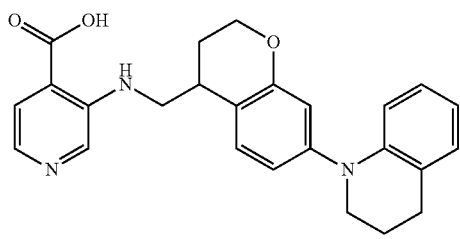 [SMILES: O=C(O)c1ccncc1NCC1CCOc2cc(N3CCCc4ccccc43)ccc21]

The title compound was prepared in 86% yield from Preparation 16f according to the general procedure for Example 1. ¹H NMR (400 MHz, DMSO-d₆): δ 1.87-2.02 (4H, m), 2.75 (2H, t, J=6.0 Hz), 3.08-3.12 (1H, m), 3.51-3.68 (3H, m), 3.68-3.72 (1H, m), 4.13-4.23 (2H, m), 6.58 (1H, s), 6.65 (2H, d, J=7.6 Hz), 6.70-6.73 (1H, m), 6.89 (1H, t, J=7.2 Hz), 7.00 (1H, d, J=7.2 Hz), 7.28 (1H, d, J=8.4 Hz), 7.58 (1H, d, J=4.8 Hz), 7.84 (1H, d, J=5.2 Hz), 8.41 (1H, s). [M+H] calc'd for $C_{25}H_{25}N_3O_3$, 416; found 416.

Preparation 17a tert-butyl N-{[7-(2,3-dihydro-1H-indol-1-yl)-2H-chromen-4-yl]methyl}carbamate

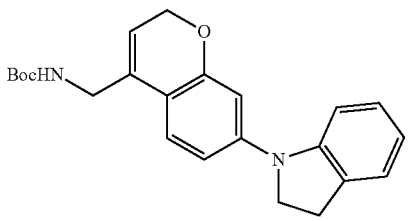 [SMILES: CC(C)(C)OC(=O)NCC1=CCOc2cc(N3CCc4ccccc43)ccc21]

The title compound was prepared in 59% yield from Preparation 16a and indoline according to the general procedure for Preparation 16c. [M+H] calc'd for $C_{23}H_{26}N_2O_3$, 379; found 379.

Preparation 17b

[7-(2,3-dihydro-1H-indol-1-yl)-2H-chromen-4-yl]methanamine, hydrochloride

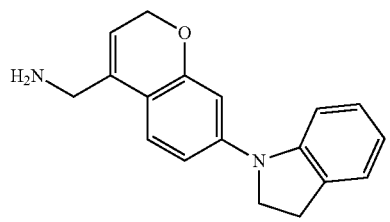 [SMILES: NCC1=CCOc2cc(N3CCc4ccccc43)ccc21]

The title compound was prepared in 84% yield from Preparation 17a according to the general procedure for Preparation 16c. [M+H] calc'd for $C_{18}H_{18}N_2O$, 279; found 279.

Preparation 17c

[7-(2,3-dihydro-1H-indol-1-yl)-3,4-dihydro-2H-1-benzopyran-4-yl]methanamine

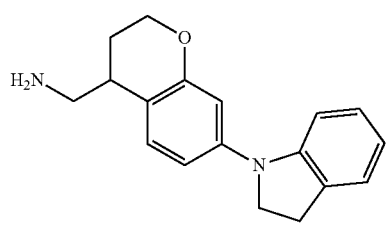 [SMILES: NCC1CCOc2cc(N3CCc4ccccc43)ccc21]

The title compound was prepared in 86% yield from Preparation 17b according to the general procedure for Preparation 16d. [M+H] calc'd for $C_{18}H_{20}N_2O$, 281; found 281.

Preparation 17d methyl 3-({[7-(2,3-dihydro-1H-indol-1-yl)-3,4-di-hydro-2H-1-benzopyran-4-yl]methyl}amino)pyridine-4-carboxylate

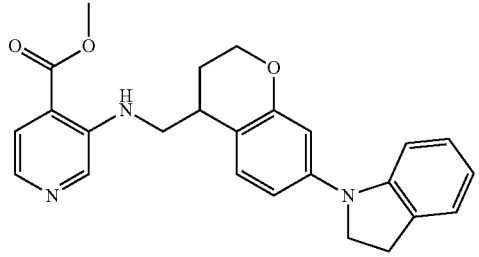 [SMILES: COC(=O)c1ccncc1NCC1CCOc2cc(N3CCc4ccccc43)ccc21]

To a solution of Preparation 17c (350 mg, 1.25 mmol) in DMA (6 mL) was added methyl 3-fluoroisonicotinate (195 mg, 1.25 mmol), and the reaction mixture was stirred at 170° C. for 1 h in a microwave. The reaction mixture was poured into water and extracted with EtOAc. Organics were washed with brine, dried ($Na_2SO_4$) and concentration. Purification by silica gel chromatography (PE:EtOAc=2:1) gave 79 mg (15%) of the title compound as a yellow gum. [M+H] calc'd for $C_{25}H_{25}N_3O_3$, 416; found 416.

Example 17

3-({[7-(2,3-dihydro-1H-indol-1-yl)-3,4-dihydro-2H-1-benzopyran-4-yl]methyl}amino)pyridine-4-carboxylic acid

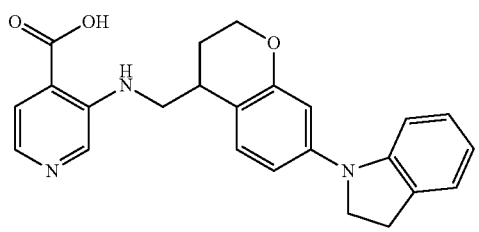 [SMILES: O=C(O)c1ccncc1NCC1CCOc2cc(N3CCc4ccccc43)ccc21]

The title compound was prepared in 43% yield from Preparation 17d according to the general procedure for Example 1. $^1$H NMR (400 MHz, DMSO-$d_6$): δ 1.87-1.90 (1H, m), 1.97-2.01 (1H, m), 3.03-3.09 (3H, m), 3.43-3.48 (1H, m), 3.63-3.68 (1H, m), 3.86 (2H, t, J=9.0 Hz), 4.13-4.21 (2H, m), 6.58 (1H, s), 6.67-6.71 (1H, m), 6.77-6.80 (1H, m), 7.02-7.05 (2H, m), 7.15 (1H, d, J=7.2 Hz), 7.26 (1H, d, J=8.4 Hz), 7.56 (1H, d, J=4.8 Hz), 7.81 (1H, d, J=5.2 Hz), 8.35 (1H, s). [M+H] calc'd for $C_{24}H_{23}N_3O_3$, 402; found 402.

Preparation 18a 7-bromo-2H-chromene-4-carboxamide

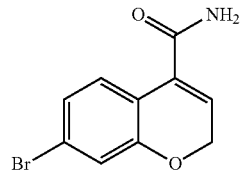 [SMILES: NC(=O)C1=CCOc2cc(Br)ccc21]

To a solution of 7-bromochroman-4-one (2.0 g, 8.8 mmol) and $AlCl_3$ (118 mg, 0.9 mmol) in toluene (10 mL) was added TMSCN (1.3 mL, 9.7 mmol). The solution was stirred at 40° C. for 1.5 h. The reaction was cooled to rt, and $H_2SO_4$ (1.0 mL) was added, followed by AcOH (13 mL) and more $H_2SO_4$ (4.3 mL). The reaction was heated to 130° C. and stirred for 6 h. The reaction was cooled, poured over $H_2O$ (100 mL) and filtered. The filter cake dissolved in THF (50 mL) and filtered. The combined organic solutions were concentrated to give 1.0 g (45%) of the crude title compound as an off-white solid. [M+H] calc'd for $C_{10}H_8BrNO_2$, 254, 256; found 254, 256.

Preparation 18b (4R)-7-bromo-3,4-dihydro-2H-1-benzopyran-4-carboxamide

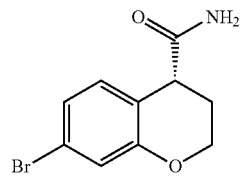 [SMILES: NC(=O)[C@@H]1CCOc2cc(Br)ccc21]

To a solution of Preparation 18a (6.0 g, 23.6 mmol) in MeOH (70 mL) and THF (70 mL) was added $Ru(OAc)_2$[s-binap] (100 mg). The mixture was heated at 80° C. overnight with 5.0 MPa $H_2$. The solution was concentrated to get the crude title compound (ee >90%). This was re-crystallized from EtOAc to give 3.5 g (58%, ee >95%) as a white solid. [M+H] calc'd for $C_{10}H_{10}BrNO_2$, 256, 258; found 256, 258. Analytical Column: Chiralcel: AS-H, Mobile phase: $CO_2$:MeOH=70:30.

Preparation 18c

[(4R)-7-bromo-3,4-dihydro-2H-1-benzopyran-4-yl]methanamine

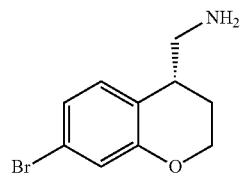 [SMILES: NC[C@@H]1CCOc2cc(Br)ccc21]

To a solution of Preparation 18b (500 mg, 2.0 mmol) in THF (10 mL) was added BH$_3$.THF (9.8 mL, 1.0 M, 9.8 mmol) at rt. The mixture was heated at 45° C. for 3 h. The reaction was diluted with water (10 mL), basified to pH 9 with sat. Na$_2$CO$_3$, and then extracted with EtOAc (3×50 mL). Organics were washed with brine (50 mL), dried (Na$_2$SO$_4$), and concentrated to give 500 mg of the crude title compound as a yellow oil. [M+H] calc'd for C$_{10}$H$_{12}$BrNO, 242, 244; found 242, 244.

Preparation 18d tert-butyl N-{[(4R)-7-bromo-3,4-dihydro-2H-1-benzopyran-4-yl]methyl}carbamate

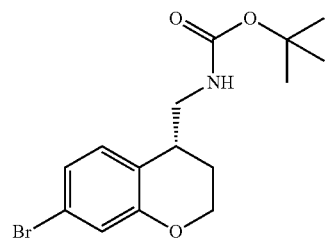 [SMILES: CC(C)(C)OC(=O)NC[C@@H]1CCOc2cc(Br)ccc21]

To a solution of Preparation 18c (2.0 mmol) and TEA (0.8 mL, 5.9 mmol) in DCM (10 mL) was added Boc$_2$O (510 mg, 2.3 mmol) at 0° C., and the reaction was stirred at rt overnight. The solution was concentrated and purified by silica gel chromatography (PE:EtOAc=10:1) to give 270 mg (41%) of the title compound as a yellow oil. [M+H] calc'd for C$_{15}$H$_{20}$BrNO$_3$, 342, 344; found 342, 344.

Preparation 18e tert-butyl N-{[(4R)-7-[methyl(phenyl)amino]-3,4-dihydro-2H-1-benzopyran-4-yl]methyl}carbamate

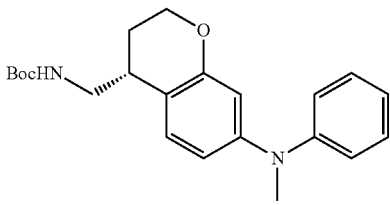 [SMILES: CN(c1ccccc1)c1ccc2c(c1)OCC[C@H]2CNC(=O)OC(C)(C)C]

The title compound was prepared in 57% yield from Preparation 18d and N-methylaniline according to the general procedure for Preparation 6e. [M+H] calc'd for C$_{22}$H$_{28}$N$_2$O$_3$, 369; found 369.

Preparation 18f (4R)-4-(aminomethyl)-N-methyl-N-phenyl-3,4-dihydro-2H-1-benzopyran-7-amine

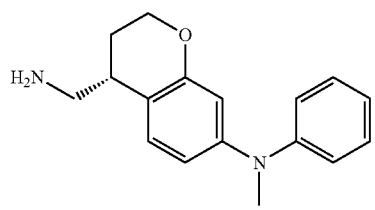 [SMILES: CN(c1ccccc1)c1ccc2c(c1)OCC[C@H]2CN]

The title compound was prepared in quantitative yield from Preparation 18e according to the general procedure for Preparation 6f. [M+H] calc'd for C$_{17}$H$_{20}$N$_2$O, 269; found 269.

Preparation 18g methyl 3-({[(4R)-7-[methyl(phenyl)amino]-3,4-dihydro-2H-1-benzopyran-4-yl]methyl}amino)pyridine-4-carboxylate

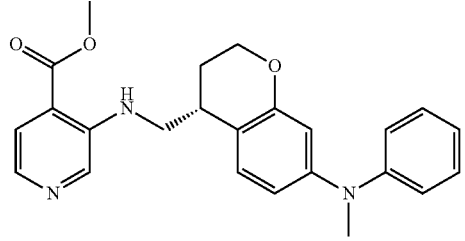 [SMILES: COC(=O)c1ccncc1NC[C@@H]1CCOc2cc(N(C)c3ccccc3)ccc21]

The title compound was prepared in 68% yield from Preparation 18f according to the general procedure for Preparation 16f. [M+H] calc'd for C$_{24}$H$_{25}$N$_3$O$_3$, 404; found 404.

Example 18

3-({[(4R)-7-[methyl(phenyl)amino]-3,4-dihydro-2H-1-benzopyran-4-yl]methyl}amino)pyridine-4-carboxylic acid

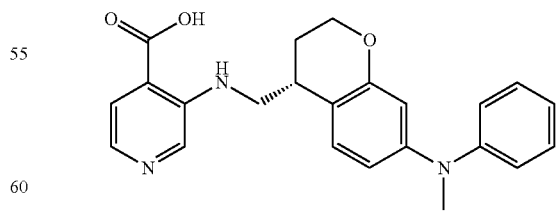

The title compound was prepared in 32% yield from Preparation 18g according to the general procedure for Example 1. $^1$H NMR (400 MHz, DMSO-d$_6$): δ 1.87-1.88 (1H, m), 1.96-1.97 (1H, m), 3.06-3.09 (1H, m), 3.20 (3H, s), 3.44-3.52 (1H, m), 3.64-3.66 (1H, m), 4.12-4.18 (2H, m), 6.36 (1H, d, J=2.1 Hz), 6.48 (1H, d, J=8.4 Hz), 6.91-7.01 (3H, m), 7.17-7.29 (3H, m), 7.56 (1H, d, J=5.1 Hz), 7.83 (1H, d, J=5.1 Hz), 8.40 (1H, s). [M+H] calc'd for $C_{23}H_{23}N_3O_3$, 390; found 390.

Preparation 19a tert-butyl N-{[(4R)-7-[(2-fluorophenyl)(methyl)amino]-3,4-dihydro-2H-1-benzopyran-4-yl]methyl}carbamate

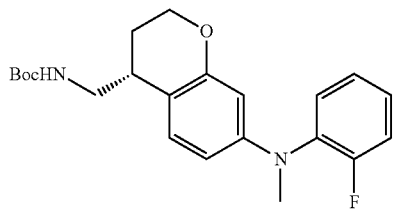 [SMILES: CN(c1ccc2c(c1)OCC[C@H]2CNC(=O)OC(C)(C)C)c1ccccc1F]

The title compound was prepared in 65% yield from Preparation 18d and 2-fluoro-N-methylaniline according to the general procedure for Preparation 6e. [M+H] calc'd for $C_{22}H_{27}FN_2O_3$, 387; found 387.

Preparation 19b (4R)-4-(aminomethyl)-N-(2-fluorophenyl)-N-methyl-3,4-dihydro-2H-1-benzopyran-7-amine

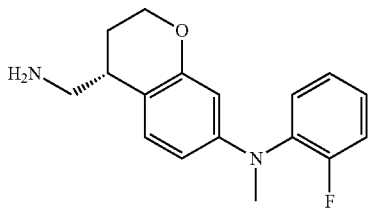 [SMILES: CN(c1ccc2c(c1)OCC[C@H]2CN)c1ccccc1F]

The title compound was prepared in quantitative yield from Preparation 19a according to the general procedure for Preparation 6f. [M+H] calc'd for $C_{17}H_{19}FN_2O$, 287; found 287.

Preparation 19c methyl 3-({[(4R)-7-[(2-fluorophenyl)(methyl)amino]-3,4-dihydro-2H-1-benzopyran-4-yl]methyl}amino)pyridine-4-carboxylate

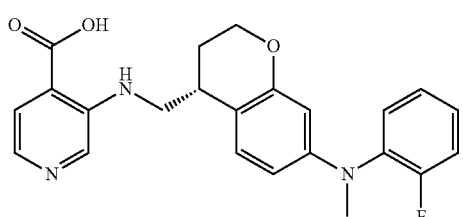

The title compound was prepared in 50% yield from Preparation 19b according to the general procedure for Preparation 16e. [M+H] calc'd for $C_{24}H_{24}FN_3O_3$, 422; found 422.

Example 19

3-({[(4R)-7-[(2-fluorophenyl)(methyl)amino]-3,4-dihydro-2H-1-benzopyran-4-yl]methyl}amino)pyridine-4-carboxylic acid

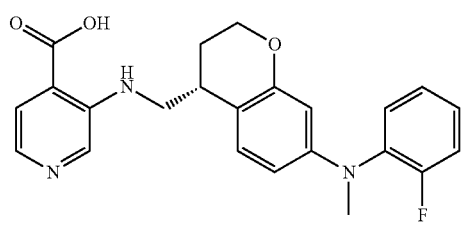

The title compound was prepared in 88% yield from Preparation 19c according to the general procedure for Example 1. $^1$H NMR (400 MHz, DMSO-$d_6$): δ 1.81-1.85 (1H, m), 1.93-1.99 (1H, m), 2.99-3.02 (1H, m), 3.18 (3H, s), 3.41-3.44 (1H, m), 3.58-3.63 (1H, m), 4.08-4.14 (2H, m), 6.04 (1H, s), 6.18 (1H, dd, J=1.2, 7.2 Hz), 7.10 (1H, d, J=8.4 Hz), 7.24-7.34 (4H, m), 7.56 (1H, d, J=5.2 Hz), 7.82 (1H, d, J=4.8 Hz), 8.35 (1H, s). [M+H] calc'd for $C_{23}H_{22}FN_3O_3$, 408; found 408.

Preparation 20a tert-butyl N-{[(4R)-7-[(3-fluorophenyl)(methyl)amino]-3,4-dihydro-2H-1-benzopyran-4-yl]methyl}carbamate

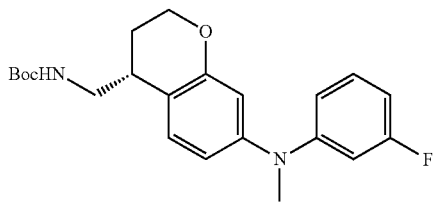 [SMILES: CN(c1cccc(F)c1)c1ccc2c(c1)OCC[C@H]2CNC(=O)OC(C)(C)C]

The title compound was prepared in 83% yield from Preparation 18d and 3-fluoro-N-methylaniline according to the general procedure for Preparation 6e. [M+H] calc'd for $C_{22}H_{27}FN_2O_3$, 387; found 387.

Preparation 20b (4R)-4-(aminomethyl)-N-(3-fluorophenyl)-N-methyl-3,4-dihydro-2H-1-benzopyran-7-amine

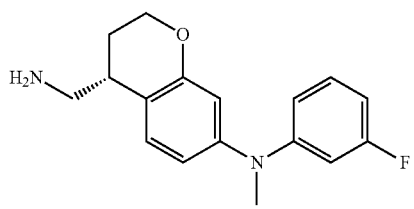 [SMILES: CN(c1cccc(F)c1)c1ccc2c(c1)OCC[C@H]2CN]

The title compound was prepared in quantitative yield from Preparation 20a according to the general procedure for Preparation 6f. [M+H] calc'd for $C_{17}H_{19}FN_2O$, 287; found 287.

Preparation 20c methyl 3-({[(4R)-7-[(3-fluorophenyl)(methyl)amino]-3,4-dihydro-2H-1-benzopyran-4-yl]methyl}amino)pyridine-4-carboxylate

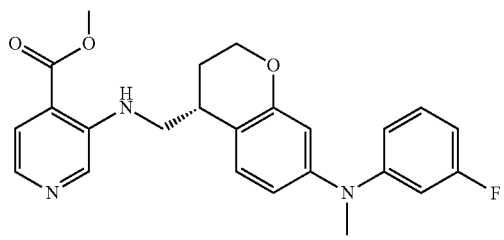 [SMILES: COC(=O)c1ccncc1NC[C@@H]1CCOc2cc(N(C)c3cccc(F)c3)ccc21]

The title compound was prepared in 12% yield from Preparation 20b according to the general procedure for Preparation 16e. [M+H] calc'd for $C_{24}H_{24}FN_3O_3$, 422; found 422.

Example 20

3-({[(4R)-7-[(3-fluorophenyl)(methyl)amino]-3,4-dihydro-2H-1-benzopyran-4-yl]methyl}amino)pyridine-4-carboxylic acid

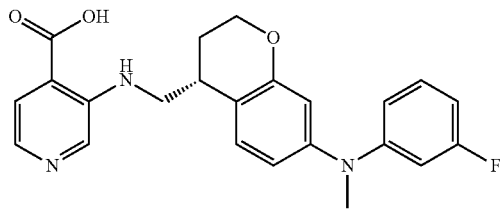

The title compound was prepared in 46% yield from Preparation 20c according to the general procedure for Example 1. $^1$H NMR (400 MHz, THF-$d_8$): δ 8.30 (s, 1H), 7.74 (brs, 2H), 7.48 (d, J=4.0 Hz, 1H), 7.14 (d, J=8.0 Hz, 1H), 7.03-6.97 (m, 1H), 6.59-6.45 (m, 4H), 6.36 (t, J=8.0 Hz, 1H), 4.13-4.02 (m, 2H), 3.65-3.59 (m, 1H), 3.42-3.34 (m, 1H), 3.14 (s, 3H), 3.08-3.02 (m, 1H), 2.00-1.86 (m, 2H). [M+H] calc'd for $C_{23}H_{22}FN_3O_3$, 408; found 408.

Preparation 21a tert-butyl N-{[(4R)-7-[(4-fluorophenyl)(methyl)amino]-3,4-dihydro-2H-1-benzopyran-4-yl]methyl}carbamate

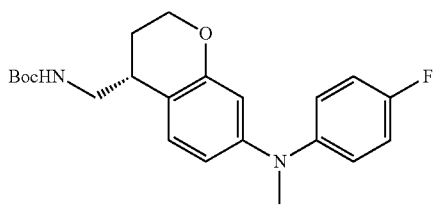 [SMILES: CN(c1ccc(F)cc1)c1ccc2c(c1)OCC[C@H]2CNC(=O)OC(C)(C)C]

The title compound was prepared in 55% yield from Preparation 18d and 4-fluoro-N-methylaniline according to the general procedure for Preparation 6e. [M+H] calc'd for $C_{22}H_{27}FN_2O_3$, 387; found 387.

Preparation 21b (4R)-4-(aminomethyl)-N-(4-fluorophenyl)-N-methyl-3,4-dihydro-2H-1-benzopyran-7-amine

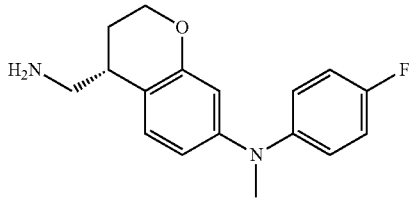 [SMILES: CN(c1ccc(F)cc1)c1ccc2c(c1)OCC[C@H]2CN]

The title compound was prepared in quantitative yield from Preparation 21a according to the general procedure for Preparation 6f. [M+H] calc'd for $C_{17}H_{19}FN_2O$, 287; found 287.

Preparation 21c methyl 3-({[(4R)-7-[(4-fluorophenyl)(methyl)amino]-3,4-dihydro-2H-1-benzopyran-4-yl]methyl}amino)pyridine-4-carboxylate

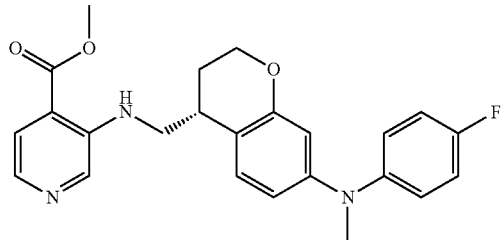

The title compound was prepared in 83% yield from Preparation 21b according to the general procedure for Preparation 16e. [M+H] calc'd for $C_{24}H_{24}FN_3O_3$, 422; found 422.

Example 21

3-({[(4R)-7-[(4-fluorophenyl)(methyl)amino]-3,4-dihydro-2H-1-benzopyran-4-yl]methyl}amino)pyridine-4-carboxylic acid

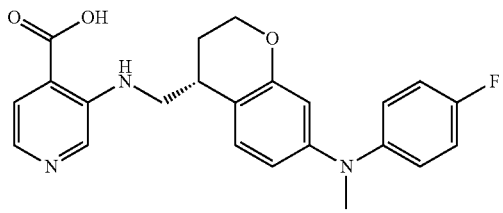 [SMILES: CN(c1ccc(F)cc1)c1ccc2c(c1)OCC[C@H]2CNc1cnccc1C(=O)O]

The title compound was prepared in 83% yield from Preparation 21c according to the general procedure for Example 1. $^1$H NMR (400 MHz, DMSO-d$_6$): δ 1.82-1.87 (1H, m), 1.94-1.99 (1H, m), 3.03-3.06 (1H, m), 3.17 (3H, s), 3.43-3.49 (1H, m), 3.63-3.67 (1H, m), 4.09-4.20 (2H, m), 6.26 (1H, s), 6.38 (1H, d, J=8.4 Hz), 7.04-7.08 (2H, m), 7.11-7.16 (3H, m), 7.56 (1H, d, J=5.2 Hz), 7.83 (1H, d, J=4.8 Hz), 8.39 (1H, s). [M+H] calc'd for $C_{23}H_{22}FN_3O_3$, 408; found 408.

Preparation 22a tert-butyl N-{[(4R)-7-[methyl(4-methylphenyl)amino]-3,4-dihydro-2H-1-benzopyran-4-yl]methyl}carbamate

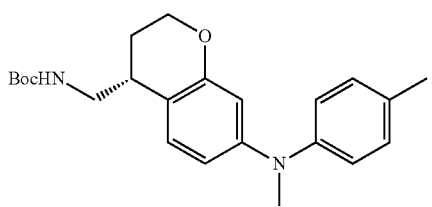 [SMILES: Cc1ccc(N(C)c2ccc3c(c2)OCC[C@H]3CNC(=O)OC(C)(C)C)cc1]

The title compound was prepared in 45% yield from Preparation 18d and 4-methyl-N-methylaniline according to the general procedure for Preparation 6e. [M+H] calc'd for $C_{23}H_{30}N_2O_3$, 383; found 383.

Preparation 22b (4R)-4-(aminomethyl)-N-methyl-N-(4-methylphenyl)-3,4-dihydro-2H-1-benzopyran-7-amine

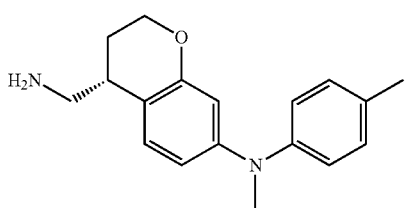

The title compound was prepared in quantitative yield from Preparation 22a according to the general procedure for Preparation 6f. [M+H] calc'd for $C_{18}H_{22}N_2O$, 283; found 283.

Preparation 22c methyl 3-({[(4R)-7-[methyl(4-methylphenyl)amino]-3,4-dihydro-2H-1-benzopyran-4-yl]methyl}amino)pyridine-4-carboxylate

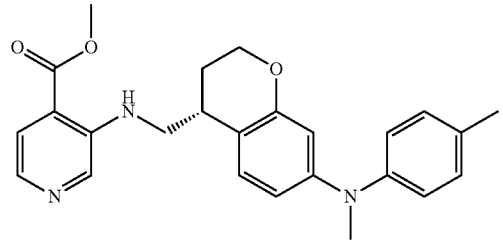 [SMILES: COC(=O)c1ccncc1NC[C@@H]1CCOc2cc(N(C)c3ccc(C)cc3)ccc21]

The title compound was prepared in 29% yield from Preparation 22b according to the general procedure for Preparation 16e. [M+H] calc'd for $C_{25}H_{27}N_3O_3$, 418; found 418.

Example 22

3-({[(4R)-7-[methyl(4-methylphenyl)amino]-3,4-dihydro-2H-1-benzopyran-4-yl]methyl}amino)pyridine-4-carboxylic acid

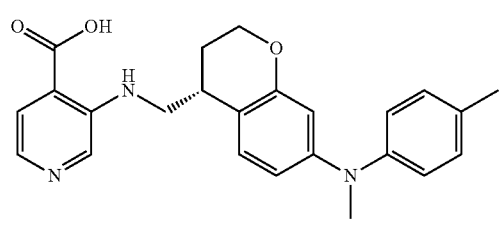 [SMILES: Cc1ccc(N(C)c2ccc3c(c2)OCC[C@H]3CNc2cnccc2C(=O)O)cc1]

The title compound was prepared in 79% yield from Preparation 22c according to the general procedure for Example 1. $^1$H NMR (400 MHz, DMSO-d$_6$): δ 1.84-1.86 (1H, m), 1.95-1.99 (1H, m), 2.26 (3H, s), 3.02-3.05 (1H, m), 3.16 (3H, s), 3.42-3.48 (1H, m), 3.62-3.66 (1H, m), 4.08-4.16 (2H, m), 6.25 (1H, s), 6.38-6.40 (1H, m), 6.95 (2H, d, J=8.0 Hz), 7.10-7.14 (3H, m), 7.56 (1H, d, J=5.2 Hz), 7.84 (1H, d, J=5.2 Hz), 8.38 (1H, s). [M+H] calc'd for $C_{24}H_{25}N_3O_3$, 404; found 404.

Preparation 23a tert-butyl N-{[(4R)-7-[(4-chlorophenyl)(methyl)amino]-3,4-dihydro-2H-1-benzopyran-4-yl]methyl}carbamate

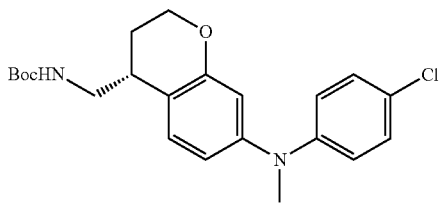 [SMILES: CN(c1ccc(Cl)cc1)c1ccc2c(c1)OCC[C@H]2CNC(=O)OC(C)(C)C]

The title compound was prepared in 65% yield from Preparation 18d and 4-chloro-N-methylaniline according to the general procedure for Preparation 6e. [M+H] calc'd for $C_{22}H_{27}ClN_2O_3$, 403; found 403.

Preparation 23b (4R)-4-(aminomethyl)-N-(4-chlorophenyl)-N-methyl-3,4-dihydro-2H-1-benzopyran-7-amine

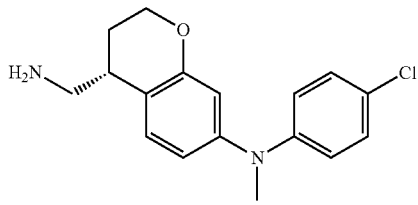 [SMILES: CN(c1ccc(Cl)cc1)c1ccc2c(c1)OCC[C@H]2CN]

The title compound was prepared in quantitative yield from Preparation 23a according to the general procedure for Preparation 6f. [M+H] calc'd for $C_{17}H_{19}ClN_2O$, 303; found 303.

Preparation 23c methyl 3-({[(4R)-7-[(4-chlorophenyl)(methyl)amino]-3,4-dihydro-2H-1-benzopyran-4-yl]methyl}amino)pyridine-4-carboxylate

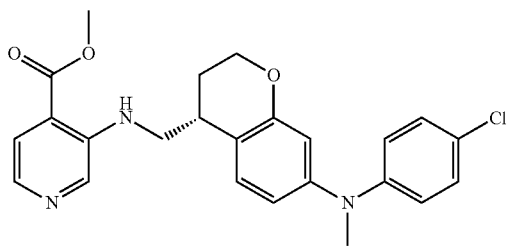 [SMILES: COC(=O)c1ccncc1NC[C@@H]1CCOc2cc(N(C)c3ccc(Cl)cc3)ccc21]

The title compound was prepared in 18% yield from Preparation 21b according to the general procedure for Preparation 16e. [M+H] calc'd for $C_{24}H_{24}ClN_3O_3$, 438; found 438.

Example 23

3-({[(4R)-7-[(4-chlorophenyl)(methyl)amino]-3,4-dihydro-2H-1-benzopyran-4-yl]methyl}amino)pyridine-4-carboxylic acid

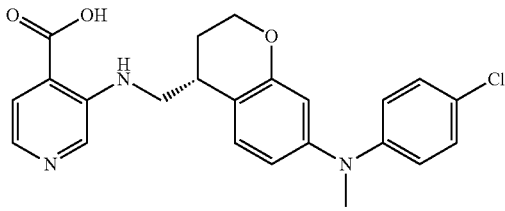 [SMILES: CN(c1ccc(Cl)cc1)c1ccc2c(c1)OCC[C@H]2CNc1cnccc1C(=O)O]

The title compound was prepared in 51% yield from Preparation 23c according to the general procedure for Example 1. $^1$H NMR (400 MHz, DMSO-$d_6$): δ 8.39 (s, 1H), 7.84 (d, J=4.8 Hz, 1H), 7.56 (d, J=4.8 Hz, 1H), 7.27-7.23 (m, 3H), 6.92 (d, J=8.8 Hz, 2H), 6.56 (dd, J=8.0 Hz, 2.0 Hz, 1H), 6.45 (d, J=2.0 Hz, 1H), 4.23-4.12 (m, 2H), 3.71-3.66 (m, 1H), 3.52-3.46 (m, 1H), 3.20 (s, 3H), 3.11-3.07 (m, 1H), 2.02-1.95 (m, 1H), 1.89-1.86 (m, 1H). [M+H] calc'd for $C_{23}H_{22}ClN_3O_3$, 424; found 424.

Preparation 24a tert-butyl N-{[(4R)-7-[ethyl(phenyl)amino]-3,4-dihydro-2H-1-benzopyran-4-yl]methyl}carbamate

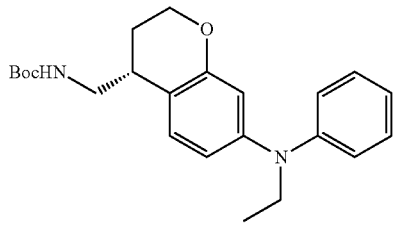 [SMILES: CCN(c1ccccc1)c1ccc2c(c1)OCC[C@H]2CNC(=O)OC(C)(C)C]

The title compound was prepared in 68% yield from Preparation 18d and N-ethylaniline according to the general procedure for Preparation 6e. [M+H] calc'd for $C_{23}H_{30}N_2O_3$, 383; found 383.

Preparation 24b (4R)-4-(aminomethyl)-N-ethyl-N-phenyl-3,4-dihydro-2H-1-benzopyran-7-amine

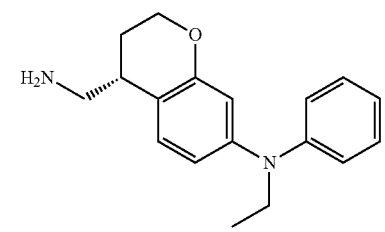 [SMILES: CCN(c1ccccc1)c1ccc2c(c1)OCC[C@H]2CN]

The title compound was prepared in quantitative yield from Preparation 24a according to the general procedure for Preparation 6f. [M+H] calc'd for $C_{18}H_{22}N_2O$, 283; found 283.

Preparation 24c methyl 3-({[(4R)-7-[ethyl(phenyl)amino]-3,4-dihydro-2H-1-benzopyran-4-yl]methyl}amino)pyridine-4-carboxylate

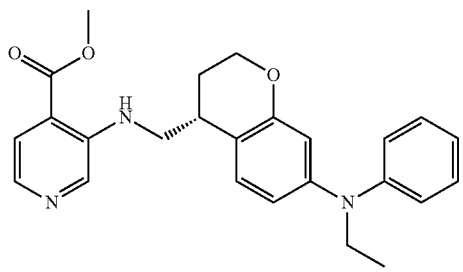

The title compound was prepared in 33% yield from Preparation 22b according to the general procedure for Preparation 16e. [M+H] calc'd for $C_{25}H_{27}N_3O_3$, 418; found 418.

Example 24

3-({[(4R)-7-[ethyl(phenyl)amino]-3,4-dihydro-2H-1-benzopyran-4-yl]methyl}amino)pyridine-4-carboxylic acid

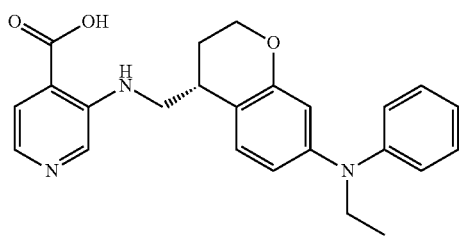

The title compound was prepared in 58% yield from Preparation 24c according to the general procedure for Example 1. $^1$H NMR (400 MHz, DMSO-$d_6$): δ 1.10 (3H, t, J=6.8 Hz), 1.83-1.87 (1H, m), 1.95-2.00 (1H, m), 3.05-3.08 (1H, m), 3.45-3.51 (1H, m), 3.65-3.72 (3H, m), 4.10-4.18 (2H, m), 6.33 (1H, s), 6.4 (1H, d, J=8.0 Hz), 6.91-6.98 (3H, m), 7.17 (1H, d, J=8.4 Hz), 7.26 (2H, t, J=7.6 Hz), 7.57 (1H, d, J=4.4 Hz), 7.84 (1H, d, J=4.8 Hz), 8.40 (1H, s). [M+H] calc'd for $C_{24}H_{25}N_3O_3$, 404; found 404.

Preparation 25a 2-hydroxy-5,6,7,8-tetrahydroquinolin-5-one

A mixture of 3-amino-2-cyclohexen-1-one (25.0 g, 224.9 mmol) and methyl propiolate (23.6 g, 281 mmol) was heated to reflux for 1 h. The mixture was cooled and the solid was collected by filtration, washing with THF, to give 7.8 g (21%) of the title compound as a yellow solid. [M+H] calc'd for $C_9H_9NO_2$, 164; found 164.

Preparation 25b 2-chloro-5,6,7,8-tetrahydroquinolin-5-one

To the suspension of Preparation 25a (7.8 g, 47.7 mmol) in ACN (120 mL) was added $POCl_3$ (14.6 g, 95.3 mmol) dropwise. The reaction mixture was heated to reflux for 2 h and then concentrated. The residue was dissolved in $H_2O$, basified to pH 8 with 2N NaOH, and extracted with EtOAc. Organics were concentrated and purified by silica gel chromatography (PE:EtOAc=4:1) to give 7.1 g (82%) of the title compound as an off-white solid. [M+H] calc'd for $C_9H_8ClNO$, 182; found 182.

Preparation 25c 2-phenyl-5,6,7,8-tetrahydroquinolin-5-one

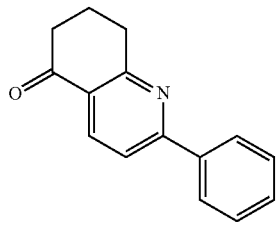 [SMILES: O=C1CCCc2nc(-c3ccccc3)ccc21]

The suspension of Preparation 25b (0.82 g, 4.5 mmol), phenylboronic acid (1.1 g, 9.1 mmol), $Pd(Ph_3P)_4$ (0.25 g, 0.23 mmol), and $Na_2CO_3$ (1.5 g, 13.6 mmol) in dioxane (30 mL) and $H_2O$ (2 mL) was heated to reflux overnight under $N_2$. The reaction mixture was cooled, filtered, and concentrated. Purification by silica gel chromatography (PE:E- tOAc=9:1) gave 1.1 g (85%) of the title compound as a white solid. [M+H] calc'd for $C_{15}H_{13}NO_2$, 224; found 224.

Preparation 25d (2-phenyl-7,8-dihydroquinolin-5-yl)methanamine, $H_2SO_4$ salt

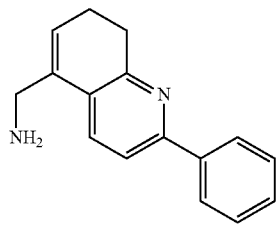 [SMILES: NCC1=CCCc2nc(-c3ccccc3)ccc21]

To a solution of Preparation 25c (1.0 g, 4.6 mmol) and $ZnI_2$ (20 mg) in toluene (20 mL) was added TMSCN (0.91 g, 9.2 mmol) at rt. The solution was heated at 110° C. overnight. The reaction was cooled to 0° C., and LAH (3.9 mL, 2.4 M, 9.2 mmol) was added, and the reaction stirred for 2 h. The reaction was quenched with addition of EtOAc (20 mL) at 0° C., followed by water (0.4 mL) and aqueous 10% NaOH (0.4 mL). The mixture was filtered and concentrated. The resulting solid was washed with MTBE to give 0.55 g (47%) of the 5-(aminomethyl)-2-phenyl-5,6,7,8-tetrahydroquinolin-5-ol intermediated as a brown solid.

To a solution of 5-(aminomethyl)-2-phenyl-5,6,7,8-tetrahydroquinolin-5-ol (0.55 g, 2.2 mmol) in toluene (80 mL) was added conc. $H_2SO_4$ (24 drops), and the solution was stirred at 150° C. under a Dean-Stark condenser. The solution was cooled to rt and concentrated to give the crude title compound. [M+H] calc'd for $C_{16}H_{16}N_2$, 237; found 237.

Preparation 25e (2-phenyl-5,6,7,8-tetrahydroquinolin-5-yl)methanamine

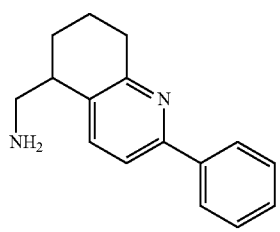 [SMILES: NCC1CCCc2nc(-c3ccccc3)ccc21]

To a solution of Preparation 25d (2.2 mmol) in MeOH (20 mL) and AcOH (2 mL) under $N_2$ was added 10% Pd/C (270 mg) at rt. The mixture was heated to 50° C. overnight under $H_2$. The reaction was filtered through Celite and concentrated. The residue was diluted with EtOAc, washed with sat. $K_2CO_3$ solution, dried ($Na_2SO_4$), and concentrated to 0.52 g of the crude title compound as a brown oil. [M+H] calc'd for $C_{16}H_{18}N_2$, 239; found 239.

Preparation 25f methyl 3-({[(4R)-7-[ethyl(phenyl)amino]-3,4-dihydro-2H-1-benzopyran-4-yl]methyl}amino)pyridine-4-carboxylate

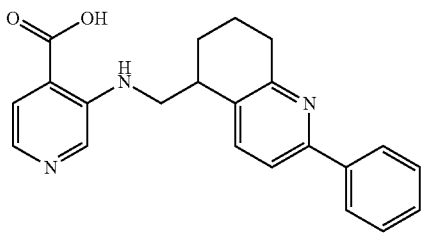 [SMILES: O=C(O)c1ccncc1NCC1CCCc2nc(-c3ccccc3)ccc21]

The title compound was prepared in 54% yield from Preparation 25e according to the general procedure for Preparation 4d. [M+H] Calc'd for $C_{23}H_{23}N_3O_2$, 374; Found, 374.

Example 25

3-({[(4R)-7-[ethyl(phenyl)amino]-3,4-dihydro-2H-1-benzopyran-4-yl]methyl}amino)pyridine-4-carboxylic acid The title compound was prepared in 41% yield from Preparation 25f according to the general procedure for Example 1. $^1$H NMR (400 MHz, DMSO-$d_6$): δ 1.79-2.00 (m, 4H), 2.88-2.94 (m, 2H), 3.22-3.23 (m, 1H), 3.50-3.56 (m, 1H), 3.64-3.68 (m, 1H), 7.41 (d, J=7.6 Hz, 1H), 7.47 (t, J=7.6 Hz, 2H), 7.57 (d, J=4.8 Hz, 1H), 7.72 (d, J=8.0 Hz, 1H), 7.81 (d, J=8.0 Hz, 1H), 7.85 (d, J=4.8 Hz, 1H), 8.05 (d, J=7.6 Hz, 2H), 8.43 (s, 1H). [M+H] Calc'd for $C_{22}H_{21}N_3O_2$, 360; Found, 360.

Preparation 26a

2-[methyl(phenyl)amino]-5,6,7,8-tetrahydroquinolin-5-one

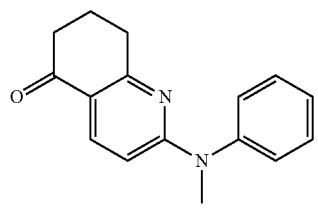 [SMILES: CN(c1ccccc1)c1ccc2c(n1)CCCC2=O]

To a solution of Preparation 25b (4.5 g, 24.7 mmol) in toluene (100 mL) was added N-methylaniline (5.3 g, 49.4 mmol), Pd$_2$(dba)$_3$ (456 mg, 0.49 mmol), Xantphos (0.86 g, 1.48 mmol) and Cs$_2$CO$_3$ (11.3 g, 34.6 mmol). The mixture was heated to reflux under nitrogen overnight. The mixture was filtered and concentrated. The residue was purified by silica gel chromatography (PE:EtOAc=20:1 to 10:1) to give 1.6 g (26%) of the title compound as an off-white solid. [M+H] calc'd for C$_{16}$H$_{16}$N$_2$O, 253. found 253.

Preparation 26b 5-(aminomethyl)-N-methyl-N-phenyl-7,8-dihydroquinolin-2-amine, hydrochloride

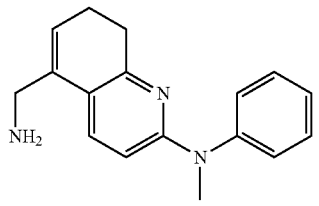 [SMILES: CN(c1ccccc1)c1ccc2c(n1)CCC=C2CN]

The title compound was prepared in 51% yield from Preparation 26a according to the general procedure for Preparation 25d. [M+H] calc'd for C$_{17}$H$_{19}$N$_2$, 266; found 266.

Preparation 26c 5-(aminomethyl)-N-methyl-N-phenyl-5,6,7,8-tetrahydroquinolin-2-amine

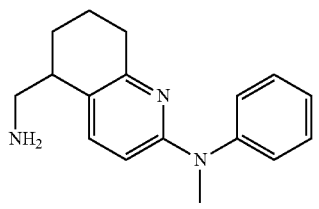 [SMILES: CN(c1ccccc1)c1ccc2c(n1)CCCC2CN]

The title compound was prepared in quantitative yield from Preparation 26b according to the general procedure for Preparation 25e. [M+H] calc'd for C$_{17}$H$_{21}$N$_2$, 268; found 268.

Preparation 26d methyl 3-[({2-[methyl(phenyl)amino]-5,6,7,8-tetrahydroquinolin-5-yl}methyl)amino]pyridine-4-carboxylate

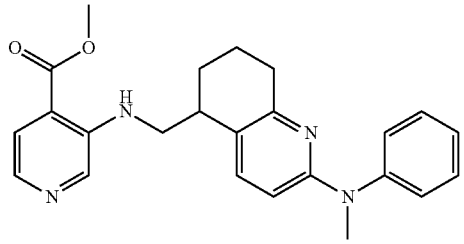 [SMILES: COC(=O)c1ccncc1NCC1CCCc2nc(N(C)c3ccccc3)ccc21]

The title compound was prepared in 30% yield from Preparation 26c according to the general procedure for Preparation 4d. [M+H] Calc'd for C$_{24}$H$_{26}$N$_4$O$_2$, 403; Found, 403.

Example 26

3-[({2-[methyl(phenyl)amino]-5,6,7,8-tetrahydroquinolin-5-yl}methyl)amino]pyridine-4-carboxylic acid

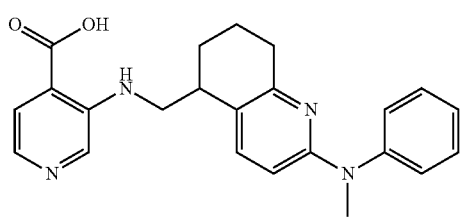 [SMILES: CN(c1ccccc1)c1ccc2c(n1)CCCC2CNc1cnccc1C(=O)O]

The title compound was prepared in 47% yield from Preparation 26d according to the general procedure for Example 1. $^1$H NMR (400 MHz, DMSO-d$_6$): δ 1.72-1.93 (m, 4H), 2.67-2.73 (m, 2H), 2.98-3.02 (m, 1H), 3.37 (s, 3H), 3.40-3.43 (m, 1H), 3.50-3.54 (m, 1H), 6.35 (d, J=8.4 Hz, 1H), 7.18 (t, J=7.2 Hz, 1H), 7.25 (d, J=7.2 Hz, 2H), 7.39 (d, J=7.2 Hz, 2H), 7.41 (d, J=8.4 Hz, 1H), 7.55 (d, J=4.8 Hz, 1H), 7.82 (d, J=4.8 Hz, 1H), 8.34 (s, 1H). [M+H] Calc'd for C$_{23}$H$_{24}$N$_4$O$_2$, 389; Found, 389.

Preparation 27a

7-[4-(trifluoromethyl)phenyl]-3,4-dihydro-2H-1-benzopyran-4-one

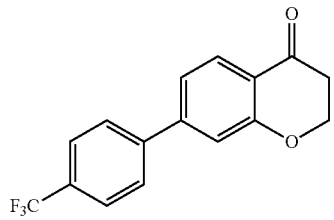 [SMILES: O=C1CCOc2cc(-c3ccc(C(F)(F)F)cc3)ccc21]

To a solution of 7-bromo-4-chromanone (1.0 g, 4.4 mmol) in DMF (15 mL) was added [4-(trifluoromethyl)phenyl]boronic acid (1.25 g, 6.6 mmol), Pd(PPh$_3$)$_4$ (580 mg, 0.5 mmol) and K$_2$CO$_3$ (1.22 g, 8.8 mmol). The mixture was stirred at 105° C. for 4 h under nitrogen. The mixture was filtered and concentrated, and the residue was purified by silica gel chromatography (PE:EtOAc=4:1) to give 830 mg (61%) of the title compound as white solid. [M+H] Calc'd for C$_{16}$H$_{11}$F$_3$O$_2$, 293; Found, 293.

Preparation 27b

{7-[4-(trifluoromethyl)phenyl]-2H-chromen-4-yl}methanamine, hydrochloride

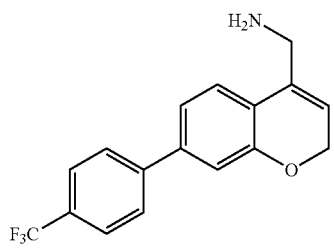 [SMILES: NCC1=CCOc2cc(-c3ccc(C(F)(F)F)cc3)ccc21]

The title compound was prepared in 41% yield from Preparation 27a according to the general procedure for Preparation 3a. [M+H] Calc'd for C$_{17}$H$_{14}$F$_3$NO, 306; Found, 306.

Preparation 27c

{7-[4-(trifluoromethyl)phenyl]-3,4-dihydro-2H-1-benzopyran-4-yl}methanamine

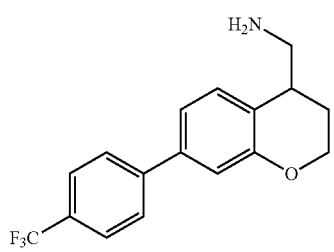 [SMILES: NCC1CCOc2cc(-c3ccc(C(F)(F)F)cc3)ccc21]

The title compound was prepared in 80% yield from Preparation 27b according to the general procedure for Preparation 3e. [M+H] Calc'd for C$_{17}$H$_{16}$F$_3$NO, 308; Found, 308.

Preparation 27d methyl 3-[({7-[4-(trifluoromethyl)phenyl]-3,4-dihydro-2H-1-benzopyran-4-yl}methyl)amino]pyridine-4-carboxylate

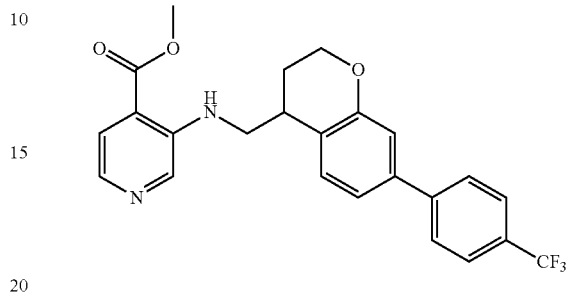

To a solution of Preparation 27c (260 mg, 0.85 mmol) in DMA (10 mL) was added methyl 3-fluoroisonicotinate (330 mg, 2.2 mmol) at rt. The reaction mixture was stirred at 170° C. for 1 h in a microwave. The reaction mixture was poured into water, and extracted with EtOAc. The organic layer was washed with brine, dried (Na$_2$SO$_4$), and concentrated. Purification by silica gel chromatography gave 28 mg (7%) of the title compound as yellow solid. [M+H] Calc'd for C$_{24}$H$_{21}$F$_3$N$_2$O$_3$, 443; Found, 443.

Example 27

3-[({7-[4-(trifluoromethyl)phenyl]-3,4-dihydro-2H-1-benzopyran-4-yl}methyl)amino]pyridine-4-carboxylic acid

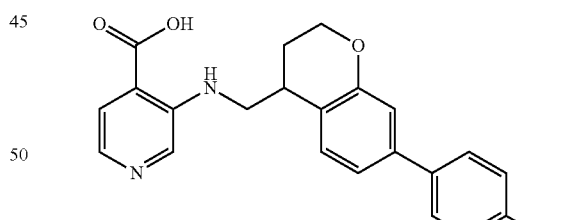

The title compound was prepared in 59% yield from Preparation 38a according to the general procedure for Example 1. $^1$H NMR (400 MHz, DMSO-d$_6$): δ 1.94-1.96 (1H, m), 2.02-2.03 (1H, m), 3.17-3.22 (1H, m), 3.50-3.56 (1H, m), 3.71-3.74 (1H, m), 4.21-4.27 (2H, m), 7.14 (1H, s), 7.23 (1H, d, J=7.2 Hz), 7.45 (1H, d, J=8.4 Hz), 7.58 (1H, d, J=4.8 Hz), 7.77-7.87 (5H, m), 8.41 (1H, s). [M+H] Calc'd for C$_{23}$H$_{19}$F$_3$N$_2$O$_3$, 429; Found, 429.

Preparation 28a 7-(furan-3-yl)-3,4-dihydro-2H-1-benzopyran-4-one

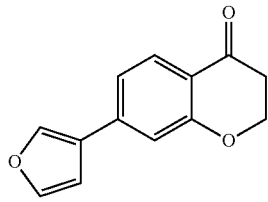 [SMILES: O=C1CCOc2cc(-c3ccoc3)ccc21]

To a solution of 6-bromo-1,2,3,4-tetrahydronaphthalen-1-one (1.5 g, 6.6 mmol) in dioxane (6 mL) was added 2-(furan-3-yl)-4,4,5,5-tetramethyl-1,3,2-dioxaborolane (1.92 g, 9.9 mmol), Pd(dppf)Cl$_2$DCM (540 mg, 0.66 mmol) and sat. NaHCO$_3$ (2 mL). The mixture was stirred at 100° C. for 4 h under nitrogen. The mixture was cooled to rt and diluted with EtOAc, filtered, and concentrated. The residue was purified by silica gel chromatography (4:1 PE:EtOAc) to give 1.18 g (83%) of the title compound as white solid. $^1$H NMR (400 MHz, CDCl$_3$): δ 2.82 (2H, t, J=6.2 Hz), 4.56 (2H, t, J=6.4 Hz), 6.71 (1H, s), 7.07 (1H, s), 7.14 (1H, d, J=8.4 Hz), 7.50 (1H, s), 7.81 (1H, s), 7.88 (1H, d, J=8.4 Hz). [M+H] Calc'd for C$_{13}$H$_{10}$O$_3$, 215; Found, 215.

Preparation 28b

[7-(furan-3-yl)-2H-chromen-4-yl]methanamine, hydrochloride

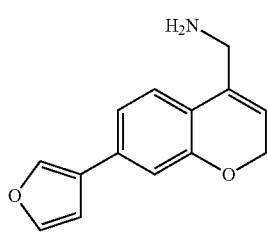 [SMILES: NCC1=CCOc2cc(-c3ccoc3)ccc21]

The title compound was prepared in 87% yield from Preparation 28a according to the general procedure for Preparation 3a. [M+H] Calc'd for C$_{14}$H$_{13}$NO$_2$, 228; Found, 228.

Preparation 28c

[7-(furan-3-yl)-3,4-dihydro-2H-1-benzopyran-4-yl]methanamine

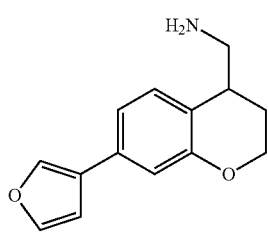 [SMILES: NCC1CCOc2cc(-c3ccoc3)ccc21]

The title compound was prepared in 57% yield from Preparation 28b according to the general procedure for Preparation 3e. [M+H] Calc'd for C$_{14}$H$_{15}$NO$_2$, 230; Found, 230.

Preparation 28d methyl 3-({[7-(furan-3-yl)-3,4-dihydro-2H-1-benzopyran-4-yl]methyl}amino)pyridine-4-carboxylate

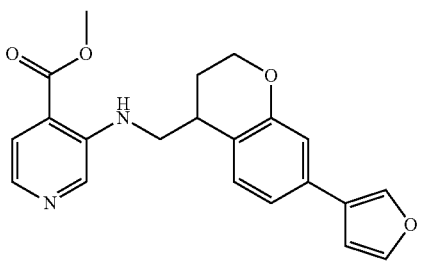 [SMILES: COC(=O)c1ccncc1NCC1CCOc2cc(-c3ccoc3)ccc21]

The title compound was prepared in 14% yield from Preparation 28c according to the general procedure for Preparation 1e. [M+H] Calc'd for C$_{21}$H$_{20}$N$_2$O$_4$, 365; Found, 365.

Example 28

3-({[7-(furan-3-yl)-3,4-dihydro-2H-1-benzopyran-4-yl]methyl}amino)pyridine-4-carboxylic acid

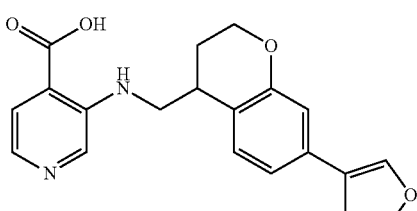

The title compound was prepared in 71% yield from Preparation 28d according to the general procedure for Example 1. $^1$H NMR (300 MHz, DMSO-d$_6$): δ 1.89-1.91 (1H, m), 1.97-2.00 (1H, m), 3.11-3.16 (1H, m), 3.48-3.56 (1H, m), 3.67-3.72 (1H, m), 4.17-4.23 (2H, m), 6.92 (1H, s), 7.03 (1H, s), 7.10 (1H, d, J=8.1 Hz), 7.29 (1H, d, J=8.1 Hz), 7.56 (1H, d, J=5.1 Hz), 7.70 (1H, s), 7.84 (1H, d, J=5.1 Hz), 8.14 (1H, s), 8.43 (1H, s). [M+H] Calc'd for C$_{20}$H$_{18}$N$_2$O$_4$, 351; Found, 351.

Preparation 29a 7-(3-methylphenyl)-3,4-dihydro-2H-1-benzopyran-4-one

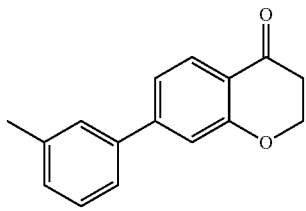 [SMILES: Cc1cccc(-c2ccc3c(c2)OCCC3=O)c1]

To a suspension of 6-bromo-1,2,3,4-tetrahydronaphthalen-1-one (2.0 g, 8.9 mmol), 3-methylbenzeneboronic acid (1.8 g, 13.2 mmol), $Na_2CO_3$ (2.8 g, 26.4 mmol) in dioxane (40 mL) and water (2 mL) was added $Pd(PPh_3)_4$ (509 mg, 0.4 mmol) at rt under $N_2$. The reaction was stirred at 100° C. overnight. The reaction was filtered and concentrated. Purification by silica gel chromatography (PE:EtOAc=12:1) gave 2.0 g (96%) of the title compound as a white oil. $^1$H NMR (300 MHz, $CDCl_3$): δ 2.44 (3H, s), 2.86 (2H, t, J=6.6 Hz), 4.59 (2H, t, J=6.6 Hz), 7.20-7.29 (3H, m), 7.36-7.44 (3H, m), 7.87 (1H, d, J=8.1 Hz). [M+H] Calc'd for $C_{16}H_{14}O_2$, 239; Found, 239.

Preparation 29b

[7-(3-methylphenyl)-2H-chromen-4-yl]methanamine

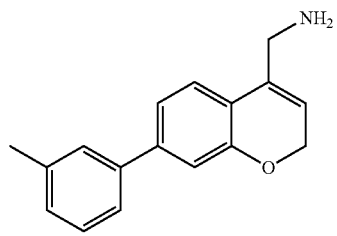 [SMILES: Cc1cccc(-c2ccc3c(c2)OCC=C3CN)c1]

The title compound was prepared in 29% yield from Preparation 29a according to the general procedure for Preparation 3a. [M+H] Calc'd for $C_{17}H_{17}NO$, 252; Found, 252.

Preparation 29c

[7-(3-methylphenyl)-3,4-dihydro-2H-1-benzopyran-4-yl]methanamine

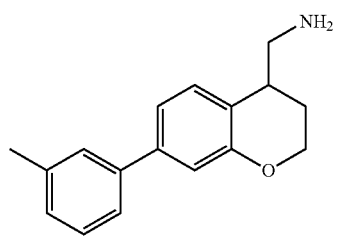 [SMILES: Cc1cccc(-c2ccc3c(c2)OCCC3CN)c1]

The title compound was prepared in 99% yield from Preparation 29b according to the general procedure for Preparation 3e. [M+H] Calc'd for $C_{17}H_{19}NO$, 254; Found, 254.

Preparation 29d methyl 3-({[(4S)-7-(3-methylphenyl)-3,4-dihydro-2H-1-benzopyran-4-yl]methyl}amino)pyridine-4-carboxylate; and

Preparation 30d methyl 3-({[(4R)-7-(3-methylphenyl)-3,4-dihydro-2H-1-benzopyran-4-yl]methyl}amino)pyridine-4-carboxylate

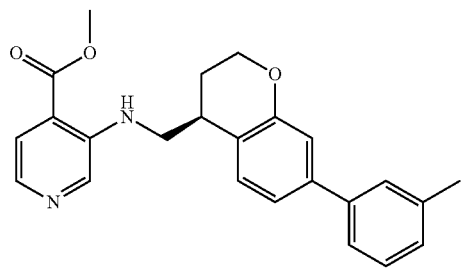

29d

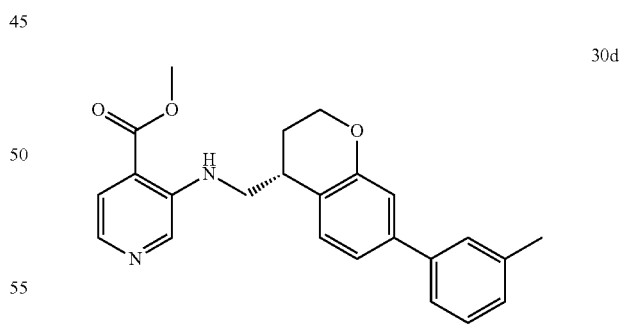

30d

The racemate of the title compounds (200 mg) was prepared in 22% yield from Preparation 29c according to the general procedure for Preparation 1e. [M+H] Calc'd for $C_{24}H_{24}N_2O_3$, 389; Found, 389.

Separation by chiral HPLC (Column: Chiralcel IA Sum 4.6*250 mm, Mobile phase: Hex:EtOH=50:50; F: 1.0 mL/min; W: 230 nm; T: 30° C.) gave 50 mg (25%) of Preparation 30d (9.211 min) and 52 mg (26%) of Preparation 29d (11.640 min), each as a yellow oil.

Example 29

3-({[(4S)-7-(3-methylphenyl)-3,4-dihydro-2H-1-benzopyran-4-yl]methyl}amino)pyridine-4-carboxylic acid

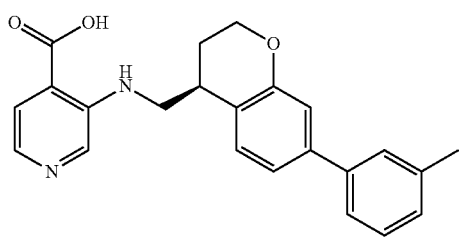 [SMILES: Cc1cccc(-c2ccc3c(c2)OCC[C@@H]3CNc2cnccc2C(=O)O)c1]

The title compound was prepared in 89% yield from Preparation 29d according to the general procedure for Example 1. ¹H NMR (300 MHz, DMSO-$d_6$): δ 1.90-1.94 (1H, m), 2.00-2.04 (1H, m), 2.36 (3H, s), 3.17-3.20 (1H, m), 3.51-3.58 (1H, m), 3.71-3.77 (1H, m), 4.21-4.25 (2H, m), 7.03 (1H, d, J=0.9 Hz), 7.13-7.16 (2H, m), 7.29-7.43 (4H, m), 7.58 (1H, d, J=5.1 Hz), 7.86 (1H, d, J=5.1 Hz), 8.45 (1H, s). [M+H] Calc'd for $C_{23}H_{22}N_2O_3$, 375; Found, 375.

Example 30

3-({[(4R)-7-(3-methylphenyl)-3,4-dihydro-2H-1-benzopyran-4-yl]methyl}amino)pyridine-4-carboxylic acid

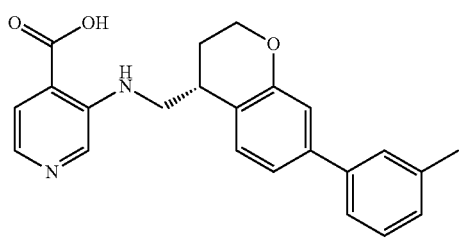 [SMILES: Cc1cccc(-c2ccc3c(c2)OCC[C@H]3CNc2cnccc2C(=O)O)c1]

The title compound was prepared in 90% yield from Preparation 30d according to the general procedure for Example 1. ¹H NMR (300 MHz, DMSO-$d_6$): δ 1.90-1.94 (1H, m), 2.00-2.04 (1H, m), 2.36 (3H, s), 3.17-3.20 (1H, m), 3.51-3.58 (1H, m), 3.71-3.77 (1H, m), 4.21-4.25 (2H, m), 7.03 (1H, d, J=0.9 Hz), 7.13-7.16 (2H, m), 7.29-7.43 (4H, m), 7.58 (1H, d, J=5.1 Hz), 7.86 (1H, d, J=5.1 Hz), 8.45 (1H, s). [M+H] Calc'd for $C_{23}H_{22}N_2O_3$, 375; Found, 375.

Preparation 31a 7-(4-methylphenyl)-3,4-dihydro-2H-1-benzopyran-4-one

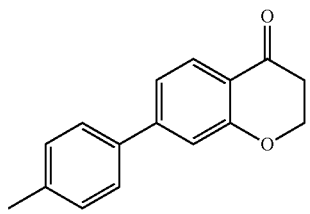 [SMILES: Cc1ccc(-c2ccc3c(c2)OCCC3=O)cc1]

The title compound was prepared in 95% yield from 4-methylbenzeneboronic acid according to the general procedure for Preparation 27a. ¹H NMR (400 MHz, CDCl₃): δ 2.40 (3H, s), 2.82 (2H, t, J=6.6 Hz), 4.56 (2H, t, J=6.4 Hz), 7.17 (1H, s), 7.23-7.27 (3H, m), 7.49 (2H, d, J=8.0 Hz), 7.92 (1H, d, J=8.4 Hz). [M+H] Calc'd for $C_{16}H_{14}O_2$, 239; Found, 239.

Preparation 31b

[7-(4-methylphenyl)-2H-chromen-4-yl]methanamine, hydrochloride

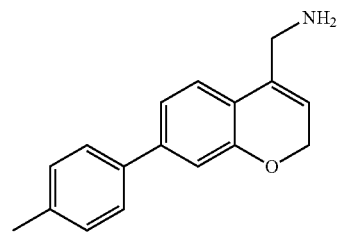 [SMILES: Cc1ccc(-c2ccc3c(c2)OCC=C3CN)cc1]

The title compound was prepared in 51% yield from Preparation 31a according to the general procedure for Preparation 3a. [M+H] Calc'd for $C_{17}H_{17}NO$, 252; Found, 252.

Preparation 31c

[7-(4-methylphenyl)-3,4-dihydro-2H-1-benzopyran-4-yl]methanamine

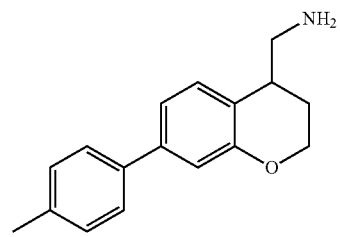 [SMILES: Cc1ccc(-c2ccc3c(c2)OCCC3CN)cc1]

The title compound was prepared in 72% yield from Preparation 31b according to the general procedure for Preparation 3e. [M+H] Calc'd for $C_{17}H_{19}NO$, 254; Found, 254.

Preparation 31d methyl 3-({[(4S)-7-(4-methylphenyl)-3,4-dihydro-2H-1-benzopyran-4-yl]methyl}amino)pyridine-4-carboxylate; and

Preparation 32d methyl 3-({[(4R)-7-(4-methylphenyl)-3,4-dihydro-2H-1-benzopyran-4-yl]methyl}amino)pyridine-4-carboxylate

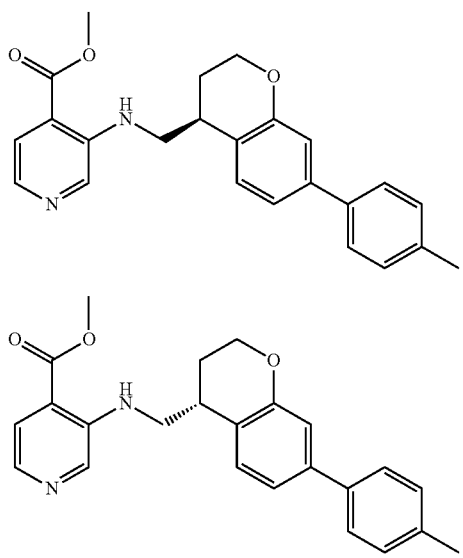

The racemate of the title compounds (370 mg) was prepared in 30% yield from Preparation 29c according to the general procedure for Preparation 1e. [M+H] Calc'd for $C_{24}H_{24}N_2O_3$, 389; Found, 389.

Separation by chiral HPLC (Column: Chiralcel IA, 250 mm*4.6 mm, 5 um; Mobile phase: Hex:EtOH=50:50; F: 1.0 mL/min; W: 230 nm; T=30° C.) give 160 mg (43%) of Preparation 32d (10.07 min) and 135 mg (36%) of Preparation 31d (12.88 min), each as a yellow oil.

Example 31

3-({[(4S)-7-(4-methylphenyl)-3,4-dihydro-2H-1-benzopyran-4-yl]methyl}amino)pyridine-4-carboxylic acid

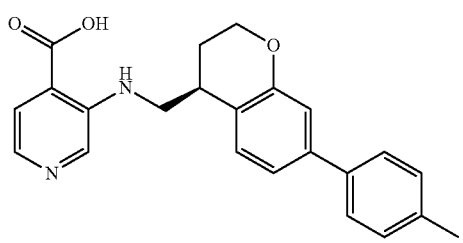 [SMILES: Cc1ccc(-c2ccc3c(c2)OCC[C@@H]3CNc2cnccc2C(=O)O)cc1]

The title compound was prepared in 59% yield from Preparation 31d according to the general procedure for Example 1. $^1$H NMR (300 MHz, DMSO-$d_6$): δ 1.90-1.92 (1H, m), 1.99-2.04 (1H, m), 2.32 (3H, s), 3.20-3.25 (1H, m), 3.59-3.64 (1H, m), 3.73-3.77 (1H, m), 4.16-4.25 (2H, m), 7.03 (1H, s), 7.11 (1H, d, J=7.5 Hz), 7.22 (2H, d, J=7.5 Hz), 7.37 (1H, d, J=7.8 Hz), 7.49 (2H, d, J=7.8 Hz), 8.03 (1H, d, J=5.7 Hz), 8.13 (1H, d, J=5.4 Hz), 8.30 (1H, bs), 8.61 (1H, s). [M+H] Calc'd for $C_{23}H_{22}N_2O_3$, 375; Found, 375.

Example 32

3-({[(4R)-7-(4-methylphenyl)-3,4-dihydro-2H-1-benzopyran-4-yl]methyl}amino)pyridine-4-carboxylic acid

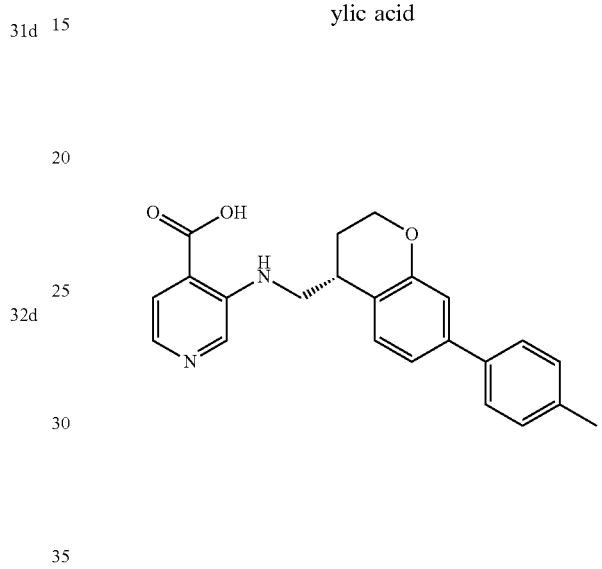

The title compound was prepared in 71% yield from Preparation 32d according to the general procedure for Example 1. $^1$H NMR (300 MHz, DMSO-$d_6$): δ 1.90-1.92 (1H, m), 1.99-2.04 (1H, m), 2.32 (3H, s), 3.20-3.25 (1H, m), 3.59-3.64 (1H, m), 3.73-3.77 (1H, m), 4.16-4.25 (2H, m), 7.02 (1H, s), 7.11 (1H, d, J=8.1 Hz), 7.21 (2H, d, J=8.1 Hz), 7.36 (1H, d, J=8.4 Hz), 7.48 (2H, d, J=7.8 Hz), 8.03 (1H, d, J=5.7 Hz), 8.14 (1H, d, J=5.7 Hz), 8.30 (1H, bs), 8.61 (1H, s). [M+H] Calc'd for $C_{23}H_{22}N_2O_3$, 375; Found, 375.

Preparation 33a 7-(thiophen-3-yl)-3,4-dihydro-2H-1-benzopyran-4-one

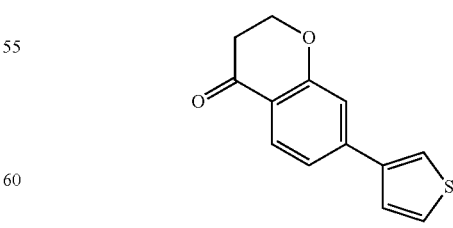

The title compound was prepared in 85% yield from 3-thienylboronic acid according to the general procedure for Preparation 27a. [M+H] Calc'd for $C_{13}H_{10}O_2S$, 231; Found, 231.

Preparation 33b

[7-(thiophen-3-yl)-2H-chromen-4-yl]methanamine, hydrochloride

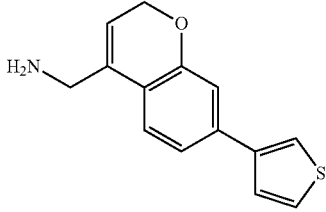 [SMILES: NCC1=CCOc2cc(-c3ccsc3)ccc21]

The title compound was prepared in 77% yield from Preparation 33a according to the general procedure for Preparation 3a. [M+H] Calc'd for $C_{14}H_{13}NOS$, 244; Found, 244.

Preparation 33c

[7-(thiophen-3-yl)-3,4-dihydro-2H-1-benzopyran-4-yl]methanamine

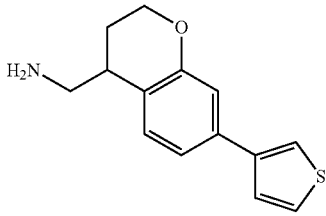 [SMILES: NCC1CCOc2cc(-c3ccsc3)ccc21]

The title compound was prepared in 99% yield from Preparation 33b according to the general procedure for Preparation 3e. [M+H] Calc'd for $C_{14}H_{15}NOS$, 246; Found, 246.

Preparation 33d methyl 3-({[(4S)-7-(thiophen-3-yl)-3,4-dihydro-2H-1-benzopyran-4-yl]methyl}amino)pyridine-4-carboxylate; and

Preparation 34d methyl 3-({[(4R)-7-(thiophen-3-yl)-3,4-dihydro-2H-1-benzopyran-4-yl]methyl}amino)pyridine-4-carboxylate

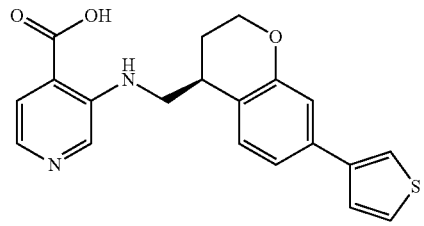 [SMILES: O=C(O)c1ccncc1NC[C@H]1CCOc2cc(-c3ccsc3)ccc21]

33d

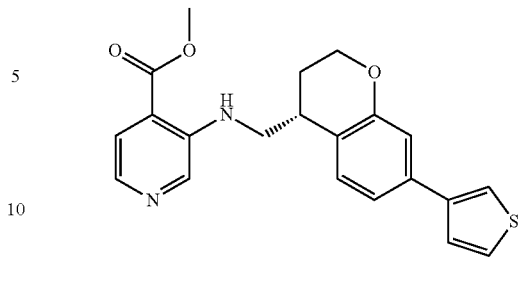

34d

The racemate of the title compounds (250 mg) was prepared in 16% yield from Preparation 33c according to the general procedure for Preparation 1e.
Separation by chiral HPLC (Column: Chiralcel: AS 5 um 4.6*250 mm, Mobile phase: Hex:EtOH=80:20, F: 1.0 mL/min, W: 230 nm, T: 30° C.) gave 83 mg (33%) of Preparation 34d (9.489 min) and 76 mg (30%) of Preparation 33d (11.968 min), each as a yellow solid.

Example 33

3-({[(4S)-7-(thiophen-3-yl)-3,4-dihydro-2H-1-benzopyran-4-yl]methyl}amino)pyridine-4-carboxylic acid

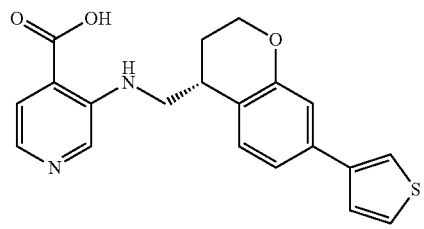 [SMILES: O=C(O)c1ccncc1NC[C@@H]1CCOc2cc(-c3ccsc3)ccc21]

The title compound was prepared in 64% yield from Preparation 33d according to the general procedure for Example 1. $^1$H NMR (400 MHz, DMSO-d$_6$): δ 1.90-1.92 (1H, m), 1.99-2.03 (1H, m), 3.14-3.18 (1H, m), 3.52-3.58 (1H, m), 3.71-3.75 (1H, m), 4.19-4.25 (2H, m), 7.14 (1H, s), 7.22 (1H, d, J=8.0 Hz), 7.34 (1H, d, J=8.0 Hz), 7.52-7.62 (3H, m), 7.85-7.87 (2H, m), 8.45 (1H, s). [M+H] Calc'd for $C_{20}H_{18}N_2O_3S$, 367; Found, 367.

Example 34

3-({[(4R)-7-(thiophen-3-yl)-3,4-dihydro-2H-1-benzopyran-4-yl]methyl}amino)pyridine-4-carboxylic acid The title compound was prepared in 62% yield from Preparation 34d according to the general procedure for Example 1. ¹H NMR (400 MHz, DMSO-d₆): δ 1.92-1.93 (1H, m), 1.99-2.03 (1H, m), 3.16-3.17 (1H, m), 3.55-3.57 (1H, m), 3.71-3.75 (1H, m), 4.20-4.24 (2H, m), 7.13 (1H, s), 7.22 (1H, d, J=8.4 Hz), 7.34 (1H, d, J=8.0 Hz), 7.52-7.61 (3H, m), 7.85-7.86 (2H, m), 8.44 (1H, s). [M+H] Calc'd for $C_{20}H_{18}N_2O_3S$, 367; Found, 367.

Preparation 35a tert-butyl N-{[7-(cyclohex-1-en-1-yl)-2H-chromen-4-yl]methyl}carbamate

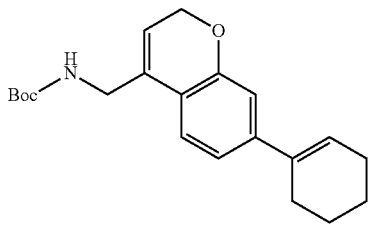 [SMILES: CC(C)(C)OC(=O)NCC1=CCOc2cc(C3=CCCCC3)ccc21]

To a solution of Preparation 3b (600 mg, 1.76 mmol) in dioxane (25 mL) was added compound 1-cyclohexen-yl-boronic acid pinacol ester (404 mg, 1.94 mmol), Pd(PPh₃)₄ (204 mg, 1.76 mmol), Na₂CO₃ (8.0 mL, 2.0 mol/L, 14 mmol). The mixture was stirred at 80° C. for overnight under nitrogen. The mixture was filtered and concentrated. The residue was purified by silica gel chromatography (PE:EtOAc=5:1) to give 450 mg (75%) of the title compound as a light red solid. [M+H] Calc'd for $C_{21}H_{27}NO_3$, 342; Found, 342.

Preparation 35b tert-butyl N-[(7-cyclohexyl-3,4-dihydro-2H-1-benzopyran-4-yl)methyl]carbamate

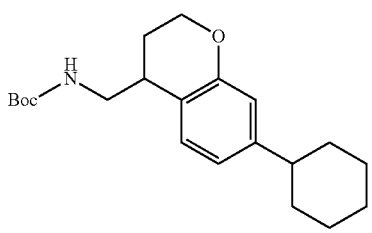 [SMILES: CC(C)(C)OC(=O)NCC1CCOc2cc(C3CCCCC3)ccc21]

The title compound was prepared in 88% yield from Preparation 35a according to the general procedure for Preparation 3e. [M+H] Calc'd for $C_{21}H_{31}NO_3$, 346; Found, 346.

Preparation 35c: (7-cyclohexyl-3,4-dihydro-2H-1-benzopyran-4-yl)methanamine

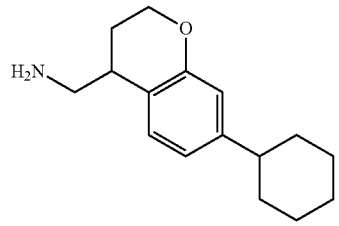 [SMILES: NCC1CCOc2cc(C3CCCCC3)ccc21]

To a solution of Preparation 35b (400 mg, 1.16 mmol) in EtOAc (10 mL) was added EtOAc/HCl (10 mL, 1.0 M), and the reaction mixture was stirred at rt for 4 h. The reaction mixture was concentrated, and the residue was taken up in sat. aq. K₂CO₃ (20 mL) and extracted with EtOAc (3×10 mL). Organics were dried (Na₂SO₄) and concentrated to give 289 mg (quantitative) of the title compound as a pale brown oil. [M+H] Calc'd for $C_{16}H_{23}NO$, 246; Found, 246.

Preparation 35d methyl 3-({[(4R)-7-cyclohexyl-3,4-dihydro-2H-1-benzopyran-4-yl]methyl}amino)pyridine-4-carboxylate

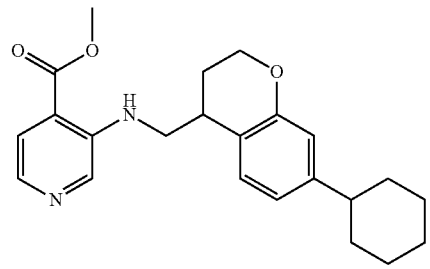 [SMILES: COC(=O)c1ccncc1NCC1CCOc2cc(C3CCCCC3)ccc21]

The title compound was prepared in 20% yield from Preparation 35c according to the general procedure for Preparation 1e. [M+H] Calc'd for $C_{23}H_{28}N_2O_3$, 381; Found, 381.

Example 35

3-({[(4R)-7-cyclohexyl-3,4-dihydro-2H-1-benzopyran-4-yl]methyl}amino)pyridine-4-carboxylic acid

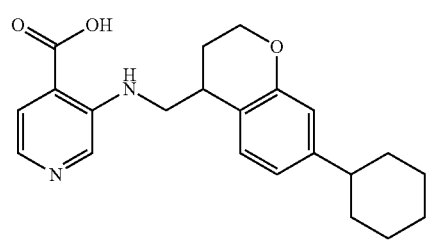 [SMILES: O=C(O)c1ccncc1NCC1CCOc2cc(C3CCCCC3)ccc21]

The title compound was prepared in 48% yield from Preparation 35d according to the general procedure for Example 1. $^1$H NMR (300 MHz, DMSO-$d_6$): δ 1.31-1.37 (5H, m), 1.66-1.97 (7H, m), 2.36-2.39 (1H, m), 3.06-3.08 (1H, m), 3.46-3.48 (1H, m), 3.64-3.69 (1H, m), 4.14-4.17 (2H, m), 6.60 (1H, s), 6.71 (1H, d, J=7.2 Hz), 7.20 (1H, d, J=8.1 Hz), 7.57 (1H, d, J=4.8 Hz), 7.85 (1H, d, J=4.8 Hz), 8.41 (1H, s). [M+H] Calc'd for $C_{22}H_{26}N_2O_3$, 367; Found, 367.

Preparation 36a methyl 3-({[7-(2-methylthiophen-3-yl)-3,4-dihydro-2H-1-benzopyran-4-yl]methyl}amino)pyridine-4-carboxylate

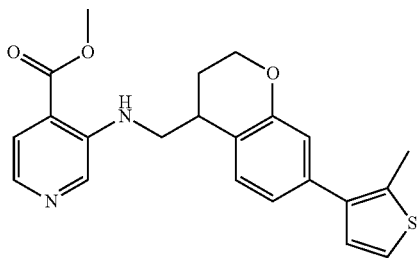 [SMILES: COC(=O)c1ccncc1NCC1CCOc2cc(-c3ccsc3C)ccc21]

To a solution of Preparation 14c (285 mg, 0.756 mmol) in DME (15 mL) was added compound 2-methylthiophene-3-boronic acid (161 mg, 1.13 mmol), Pd(PPh$_3$)$_4$ (88 mg, 0.76 mmol) and Na$_2$CO$_3$ (1.2 mL, 2 N, 2.4 mmol). The mixture was stirred at reflux overnight under nitrogen. The mixture was diluted with EtOAc, filtered, and concentrated. The residue was purified by silica gel chromatography (PE:EtOAc=1:1) to give 117 mg (39%) of the title compound as a yellow oil. [M+H] Calc'd for $C_{22}H_{22}N_2O_3S$, 395; Found, 395.

Preparation 36b methyl 3-({[(4S)-7-(2-methylthiophen-3-yl)-3,4-dihydro-2H-1-benzopyran-4-yl]methyl}amino)pyridine-4-carboxylate; and Preparation 37b methyl 3-({[(4R)-7-(2-methylthiophen-3-yl)-3,4-dihydro-2H-1-benzopyran-4-yl]methyl}amino)pyridine-4-carboxylate

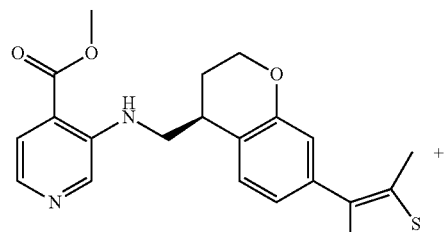

36b

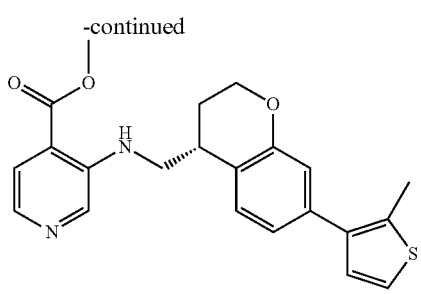

37b

Preparation 36a (117 mg) was separated by chiral HPLC (Column: Chiralcel OD, 250 mm*4.6 mm 5 um; Mobile phase: Hex:EtOH:DEA=70:30:0.2; F: 1.0 mL/min; W: 230 nm; T=30° C.) gave 47 mg (31%) of Preparation 36b (8.686 min) and 44 mg (29%) of Preparation 37b (10.759 min), each as a yellow oil.

Example 36

3-({[(4S)-7-(2-methylthiophen-3-yl)-3,4-dihydro-2H-1-benzopyran-4-yl]methyl}amino)pyridine-4-carboxylic acid

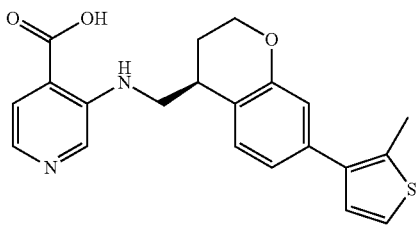 [SMILES: Cc1sccc1-c1ccc2c(c1)OCC[C@@H]2CNc1cnccc1C(=O)O]

The title compound was prepared in 91% yield from Preparation 36b according to the general procedure for Example 1. $^1$H NMR (400 MHz, DMSO-$d_6$): δ 1.89-1.93 (1H, m), 2.00-2.05 (1H, m), 2.46 (3H, s), 3.19-3.22 (1H, m), 3.57-3.62 (1H, m), 3.76-3.80 (1H, m), 4.17-4.28 (2H, m), 6.82 (1H, s), 6.91-6.93 (1H, m), 7.07 (1H, d, J=5.2 Hz), 7.32-7.39 (2H, m), 7.92-7.96 (2H, m), 8.07-8.09 (1H, m), 8.56 (1H, s). [M+H] Calc'd for $C_{21}H_{20}N_2O_3S$, 381; Found, 381.

Example 37

3-({[(4R)-7-(2-methylthiophen-3-yl)-3,4-dihydro-2H-1-benzopyran-4-yl]methyl}amino)pyridine-4-carboxylic acid

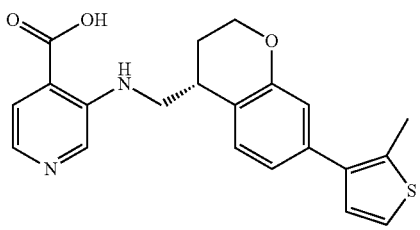 [SMILES: Cc1sccc1-c1ccc2c(c1)OCC[C@H]2CNc1cnccc1C(=O)O]

The title compound was prepared in 95% yield from Preparation 37b according to the general procedure for Example 1. $^1$H NMR (400 MHz, DMSO-$d_6$): δ 1.90-1.93 (1H, m), 2.01-2.04 (1H, m), 2.46 (3H, s), 3.16-3.21 (1H, m), 3.51-3.59 (1H, m), 3.72-3.77 (1H, m), 4.19-4.25 (2H, m), 6.82 (1H, s), 6.91-6.93 (1H, m), 7.07 (1H, d, J=5.2 Hz), 7.32-7.38 (2H, m), 7.65 (1H, d, J=5.2 Hz), 7.88 (1H, d, J=5.2 Hz), 8.47 (1H, s). [M+H] Calc'd for $C_{21}H_{20}N_2O_3S$, 381; Found, 381.

Preparation 38a methyl 3-({[7-(3-methylbut-1-yn-1-yl)-3,4-dihydro-2H-1-benzopyran-4-yl]methyl}amino)pyridine-4-carboxylic acid

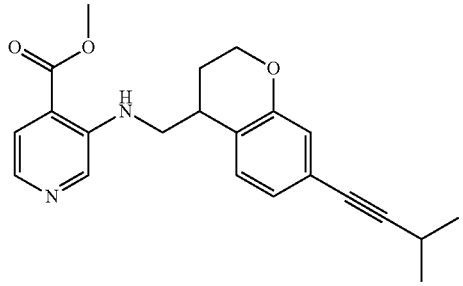 [SMILES: COC(=O)c1ccncc1NCC1CCOc2cc(C#CC(C)C)ccc21]

To a suspension of Preparation 14c (50 mg, 0.13 mmol), 3-methyl-1-butyne (27 mg, 0.40 mmol), PPh$_3$ (17 mg, 0.065 mmol) and CuI (5 mg, 0.026 mmol) in TEA (10 mL) was added Pd$_2$(dba)$_3$ (12 mg, 0.013 mmol) at rt under N$_2$. The reaction was stirred at reflux overnight. The reaction was concentrated and purified by prep-HPLC to give 25 mg (52%) of the title compound as a yellow oil. [M+H] Calc'd for $C_{22}H_{24}N_2O_3$, 365; Found, 365.

Example 38

3-({[7-(3-methylbut-1-yn-1-yl)-3,4-dihydro-2H-1-benzopyran-4-yl]methyl}amino)pyridine-4-carboxylic acid

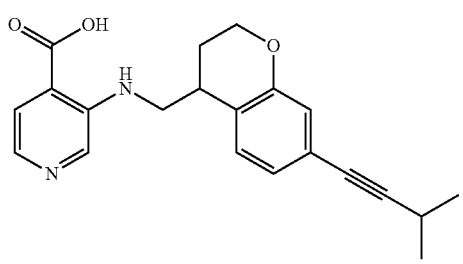 [SMILES: CC(C)C#Cc1ccc2c(c1)OCCC2CNc1cnccc1C(=O)O]

The title compound was prepared in 83% yield from Preparation 38a according to the general procedure for Example 1. $^1$H NMR (400 MHz, DMSO-$d_6$): δ 1.19-1.26 (6H, m), 1.87-1.99 (2H, m), 2.75-2.82 (1H, m), 3.12-3.15 (1H, m), 3.48-3.54 (1H, m), 3.66-3.71 (1H, m), 4.15-4.21 (2H, m), 6.73 (1H, d, J=1.2 Hz), 6.84 (1H, dd, J=1.2, 8.0 Hz), 7.26 (1H, d, J=8.0 Hz), 7.57 (1H, d, J=4.4 Hz), 7.84 (1H, d, J=4.4 Hz), 8.41 (1H, s). [M+H] Calc'd for $C_{21}H_{22}N_2O_3$, 351; Found, 351.

Preparation 39a methyl 3-({[(4S)-7-(2-chlorophenyl)-3,4-dihydro-2H-1-benzopyran-4-yl]methyl}amino)pyridine-4-carboxylate; and Preparation 40a methyl 3-({[(4R)-7-(2-chlorophenyl)-3,4-dihydro-2H-1-benzopyran-4-yl]methyl}amino)pyridine-4-carboxylate

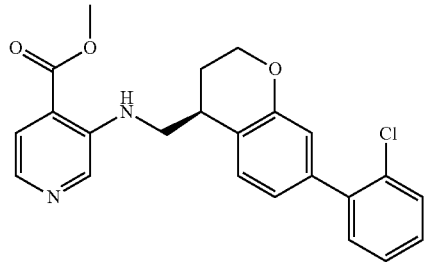

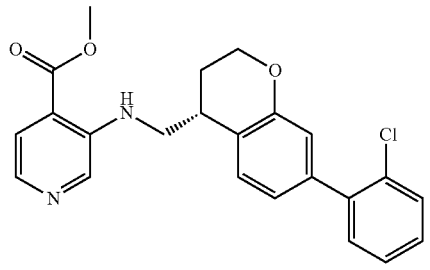

To a solution of Preparation 14c (300 mg, 0.8 mmol) in DMF (10 mL) was added 2-chlorophenylboronic acid (186 mg, 1.2 mmol), Pd(PPh$_3$)$_4$ (92 mg, 0.08 mmol) and K$_2$CO$_3$ (221 mg, 1.6 mmol). The mixture was stirred at 105° C. for 12 h under nitrogen. The mixture was filtered and concentrated, and the residue was purified by silica gel chromatography (PE:EtOAc=2:1) to give 150 mg (46%) of the racemate as colorless oil. [M+H] Calc'd for $C_{23}H_{21}ClN_2O_3$, 409; Found, 409.

Separation by chiral HPLC (Column: Chiralcel: IA 5 um 4.6*250 mm, Mobile phase: Hex:EtOH=70:30, F: 1.0 mL/min, W: 230 nm, T: 30° C.) gave 40 mg (27%) of Preparation 40a (8.862 min) and 45 mg (30%) of Preparation 39a (11.567 min), each as a yellow oil.

Example 39

3-({[(4S)-7-(2-chlorophenyl)-3,4-dihydro-2H-1-benzopyran-4-yl]methyl}amino)pyridine-4-carboxylic acid

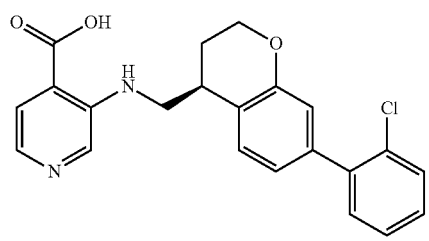 [SMILES: O=C(O)c1ccncc1NC[C@H]1CCOc2cc(-c3ccccc3Cl)ccc21]

The title compound was prepared in 90% yield from Preparation 39a according to the general procedure for Example 1. $^1$H NMR (400 MHz, CD$_3$OD): δ 1.92-1.97 (1H, m), 2.08-2.12 (1H, m), 3.18-3.21 (1H, m), 3.51-3.56 (1H, m), 3.67-3.72 (1H, m), 4.14-4.23 (2H, m), 6.73 (1H, s), 6.79 (1H, d, J=9.2 Hz), 7.19-7.25 (4H, m), 7.37 (1H, d, J=9.6 Hz), 7.13 (1H, d, J=2.0 Hz), 8.12 (1H, d, J=4.0 Hz), 8.29 (1H, s). [M+H] Calc'd for C$_{22}$H$_{19}$ClN$_2$O$_3$, 395; Found, 395.

Example 40

3-({[(4R)-7-(2-chlorophenyl)-3,4-dihydro-2H-1-benzopyran-4-yl]methyl}amino)pyridine-4-carboxylic acid

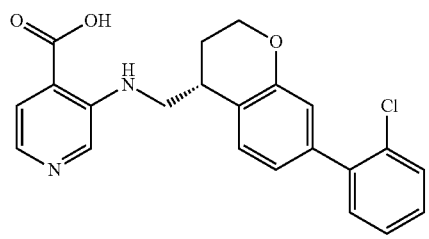

The title compound was prepared in 81% yield from Preparation 40a according to the general procedure for Example 1. $^1$H NMR (400 MHz, CD$_3$OD): δ 1.92-1.97 (1H, m), 2.08-2.12 (1H, m), 3.18-3.21 (1H, m), 3.51-3.56 (1H, m), 3.67-3.72 (1H, m), 4.14-4.23 (2H, m), 6.73 (1H, s), 6.79 (1H, d, J=9.2 Hz), 7.19-7.25 (4H, m), 7.37 (1H, d, J=9.6 Hz), 7.13 (1H, d, J=2.0 Hz), 8.12 (1H, d, J=4.0 Hz), 8.29 (1H, s). [M+H] Calc'd for C$_{22}$H$_{19}$ClN$_2$O$_3$, 395; Found, 395.

Preparation 41a methyl 3-({[(4S)-7-(3-fluoro-2-methylphenyl)-3,4-dihydro-2H-1-benzopyran-4-yl]methyl}amino)pyridine-4-carboxylate, and

Preparation 42a methyl 3-({[(4R)-7-(3-fluoro-2-methylphenyl)-3,4-dihydro-2H-1-benzopyran-4-yl]methyl}amino)pyridine-4-carboxylate

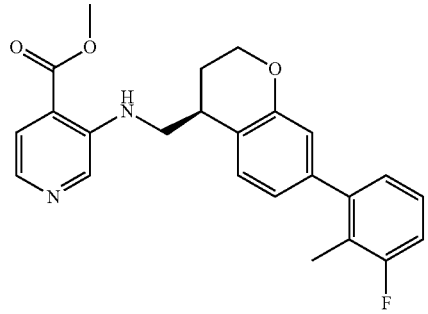

41

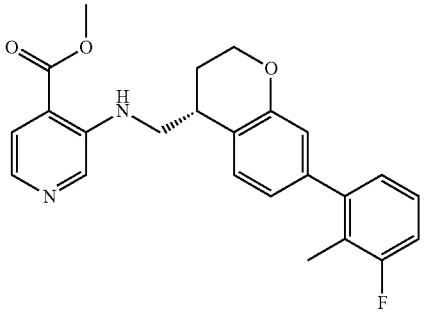

42a

To a solution of Preparation 14c (400 mg, 1.06 mmol) in dioxane (10 mL) was added 3-fluoro-2-methylphenylboronic acid (245 mg, 1.59 mmol), Pd(PPh$_3$)$_4$ (123 mg, 1.06 mmol) and Na$_2$CO$_3$ (338 mg, 3.18 mmol). The mixture was stirred at 110° C. overnight under nitrogen. The mixture was diluted with EtOAc, filtered, and concentrated. Purification by silica gel chromatography (PE:EtOAc=1:1) gave 170 mg (39%) of the title compound as a yellow oil. [M+H] Calc'd for C$_{24}$H$_{23}$FN$_2$O$_3$, 407; Found, 407.

Separation by chiral HPLC (Column: Chiralcel IC, 250*4.6 mm 5 um; Mobile phase: Hex:EtOH=70:30; F: 1.0 mL/min; W: 230 nm; T=30° C.) gave 68 mg (32%) of Preparation 41a (6.921 min) and 68 mg (32%) of Preparation 42a (7.486 min), each as a yellow oil.

Example 41

3-({[(4S)-7-(3-fluoro-2-methylphenyl)-3,4-dihydro-2H-1-benzopyran-4-yl]methyl}amino)pyridine-4-carboxylic acid

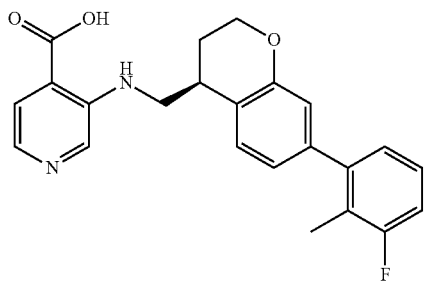 [SMILES: Cc1c(F)cccc1-c1ccc2c(c1)OCC[C@@H]2CNc1cnccc1C(=O)O]

The title compound was prepared in 81% yield from Preparation 41a according to the general procedure for Example 1. $^1$H NMR (300 MHz, DMSO-$d_6$): δ 1.91-2.05 (2H, m), 2.13 (3H, s), 3.18-3.22 (1H, m), 3.55-3.60 (1H, m), 3.74-3.79 (1H, m), 4.19-4.26 (2H, m), 6.74 (1H, s), 6.82-6.84 (1H, m), 7.04 (1H, d, J=8.0 Hz), 7.15 (1H, t, J=8.8 Hz), 7.24-7.30 (1H, m), 7.39 (1H, d, J=8.0 Hz), 7.60 (1H, d, J=5.2 Hz), 7.87 (1H, d, J=5.2 Hz), 8.46 (1H, s). [M+H] Calc'd for $C_{23}H_{21}FN_2O_3$, 393; Found, 393.

Example 42

3-({[(4R)-7-(3-fluoro-2-methylphenyl)-3,4-dihydro-2H-1-benzopyran-4-yl]methyl}amino)pyridine-4-carboxylic acid

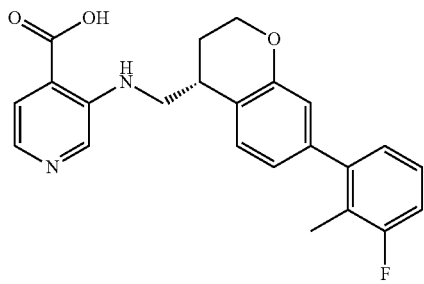 [SMILES: Cc1c(F)cccc1-c1ccc2c(c1)OCC[C@H]2CNc1cnccc1C(=O)O]

The title compound was prepared in 85% yield from Preparation 42a according to the general procedure for Example 1. $^1$H NMR (300 MHz, DMSO-$d_6$): δ 1.94-2.13 (2H, m), 2.13 (3H, s), 3.18-3.21 (1H, m), 3.54-3.60 (1H, m), 3.74-3.79 (1H, m), 4.21-4.26 (2H, m), 6.74 (1H, s), 6.82-6.84 (1H, m), 7.04 (1H, d, J=7.6 Hz), 7.15 (1H, t, J=8.8 Hz), 7.24-7.30 (1H, m), 7.39 (1H, d, J=8.0 Hz), 7.59 (1H, d, J=4.8 Hz), 7.86 (1H, d, J=5.2 Hz), 8.46 (1H, s). [M+H] Calc'd for $C_{23}H_{21}FN_2O_3$, 393; Found, 393.

Preparation 43a tert-butyl N-{[(4R)-7-(5-fluoro-2-methylphenyl)-3,4-dihydro-2H-1-benzopyran-4-yl]methyl}carbamate

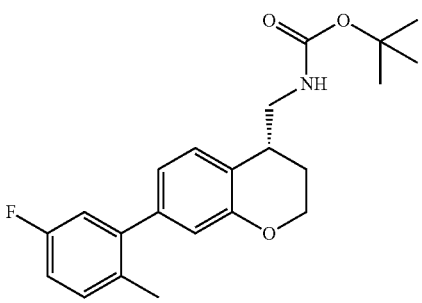 [SMILES: Cc1ccc(F)cc1-c1ccc2c(c1)OCC[C@H]2CNC(=O)OC(C)(C)C]

To a suspension of Preparation 18d (200 mg, 0.58 mmol), 5-fluoro-2-methylphenylboronic acid (135 mg, 0.88 mmol) and $Na_2CO_3$ (184 mg, 1.74 mmol) in dioxane (10 mL) and $H_2O$ (0.5 mL) was added Pd(PPh$_3$)$_4$ (67 mg, 0.06 mmol) at rt under $N_2$. The reaction was stirred at 100° C. overnight. The reaction was filtered and purified by silica gel chromatography (PE:EtOAc=10:1) to give 150 mg (70%) of the title compound as a yellow oil. [M+H] Calc'd for $C_{22}H_{26}FNO_3$, 372; Found, 372.

Preparation 43b

[(4R)-7-(5-fluoro-2-methylphenyl)-3,4-dihydro-2H-1-benzopyran-4-yl]methanamine

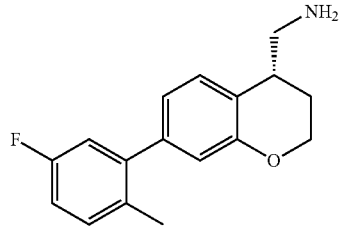 [SMILES: Cc1ccc(F)cc1-c1ccc2c(c1)OCC[C@H]2CN]

To a solution of Preparation 43a (150 mg, 0.40 mmol) in EtOAc (5 mL) was added HCl/EtOAc (8 mL, 1.0 M) at rt, and the reaction was stirred for 2 h. The solution was concentrated, re-dissolved in EtOAc, and washed with sat. $Na_2CO_3$. The organic layer was dried ($Na_2SO_4$) and concentrated to give the title compound as a yellow oil. [M+H] Calc'd for $C_{17}H_{18}FNO$, 272; Found, 272.

Preparation 43c methyl 3-({[(4R)-7-(5-fluoro-2-methylphenyl)-3,4-dihydro-2H-1-benzopyran-4-yl]methyl}amino)pyridine-4-carboxylate

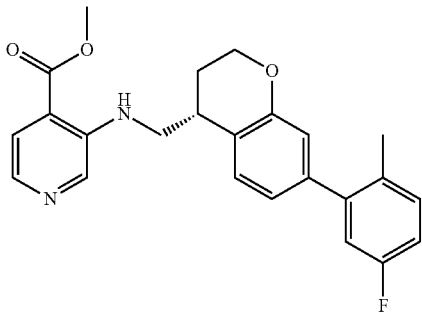 [SMILES: COC(=O)c1ccncc1NC[C@@H]1CCOc2cc(-c3cc(F)ccc3C)ccc21]

The title compound was prepared in 49% yield from Preparation 43b according to the procedure for Preparation 4d. [M+H] Calc'd for $C_{24}H_{23}FN_2O_3$, 407; Found, 407.

Example 43

3-({[(4R)-7-(5-fluoro-2-methylphenyl)-3,4-dihydro-2H-1-benzopyran-4-yl]methyl}amino)pyridine-4-carboxylic acid

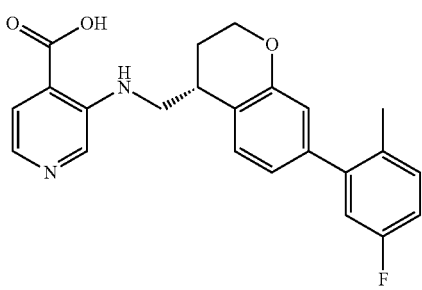 [SMILES: Cc1ccc(F)cc1-c1ccc2c(c1)OCC[C@H]2CNc1cnccc1C(=O)O]

The title compound was prepared in 89% yield from Preparation 43c according to the procedure for Example 1. $^1$H NMR (400 MHz, DMSO-$d_6$): δ 1.90-1.94 (1H, m), 2.01-2.05 (1H, m), 2.20 (3H, s), 3.17-3.21 (1H, m), 3.53-3.59 (1H, m), 3.74-3.79 (1H, m), 4.18-4.26 (2H, m), 6.75 (1H, d, J=1.6 Hz), 6.85 (1H, dd, J=1.6, 8.0 Hz), 6.98 (1H, dd, J=2.8, 9.6 Hz), 7.09 (1H, td, J=3.2, 8.8 Hz), 7.30 (1H, dd, J=5.6, 8.4 Hz), 7.39 (1H, d, J=8.0 Hz), 7.58 (1H, d, J=4.8 Hz), 7.86 (1H, d, J=3.2 Hz), 8.44 (1H, s). [M+H] Calc'd for $C_{23}H_{21}FN_2O_3$, 393; Found, 393.

Preparation 44a

[(4R)-7-(2-chloro-3-fluorophenyl)-3,4-dihydro-2H-1-benzopyran-4-yl]methanamine

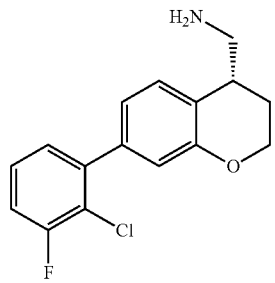 [SMILES: NC[C@@H]1CCOc2cc(-c3cccc(F)c3Cl)ccc21]

The title compound was prepared in 78% yield from 2-chloro-3-fluorophenylboronic acid and Preparation 18d according to the procedures for Preparation 43a and 43b. [M+H] Calc'd for $C_{16}H_{15}ClFNO$, 292; Found, 292.

Preparation 44b methyl 3-({[(4R)-7-(2-chloro-3-fluorophenyl)-3,4-dihydro-2H-1-benzopyran-4-yl]methyl}amino)pyridine-4-carboxylate

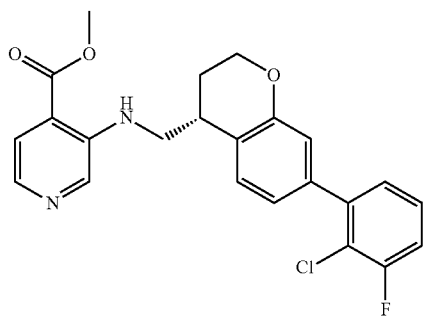 [SMILES: COC(=O)c1ccncc1NC[C@@H]1CCOc2cc(-c3cccc(F)c3Cl)ccc21]

The title compound was prepared in 28% yield from Preparation 44a according to the procedure for Preparation 4d. [M+H] Calc'd for $C_{23}H_{20}ClFN_2O_3$, 427. Found, 427.

Example 44

3-({[(4R)-7-(2-chloro-3-fluorophenyl)-3,4-dihydro-2H-1-benzopyran-4-yl]methyl}amino)pyridine-4-carboxylic acid

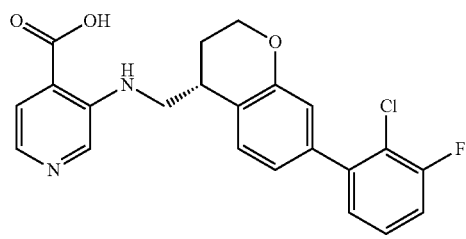 [SMILES: O=C(O)c1ccncc1NC[C@@H]1CCOc2cc(-c3cccc(F)c3Cl)ccc21]

The title compound was prepared in 48% yield from Preparation 44b according to the procedure for Example 1. $^1$H NMR (400 MHz, DMSO-$d_6$): δ 1.90-1.96 (m, 1H), 2.00-2.07 (m, 1H), 3.19-3.23 (m, 1H), 3.53-3.59 (m, 1H), 3.73-3.78 (m, 1H), 4.20-4.29 (m, 2H), 6.96 (s, 1H), 7.04 (d, J=8.0 Hz, 1H), 7.28-7.32 (m, 1H), 7.43-7.49 (m, 2H), 7.56-7.60 (m, 2H), 7.86 (d, J=5.2 Hz, 1H), 8.46 (s, 1H). [M+H] Calc'd for $C_{22}H_{18}ClFN_2O_3$, 413; Found, 413.

Preparation 45a

[(4R)-7-(2-chloro-5-fluorophenyl)-3,4-dihydro-2H-1-benzopyran-4-yl]methanamine

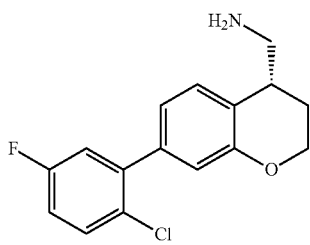 [SMILES: NC[C@@H]1CCOc2cc(-c3cc(F)ccc3Cl)ccc21]

The title compound was prepared in 77% yield from 2-chloro-5-fluorophenylboronic acid and Preparation 18d according to the procedures for Preparation 43a and 43b. [M+H] Calc'd for $C_{16}H_{15}ClFNO$, 292; Found, 292.

Preparation 45b methyl 3-({[(4R)-7-(2-chloro-5-fluorophenyl)-3,4-dihydro-2H-1-benzopyran-4-yl]methyl}amino)pyridine-4-carboxylate

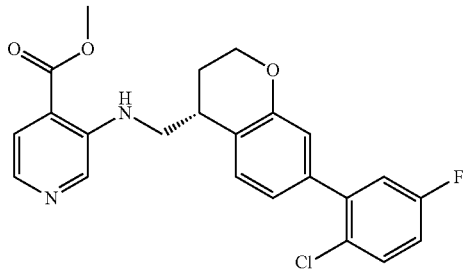 [SMILES: COC(=O)c1ccncc1NC[C@@H]1CCOc2cc(-c3cc(F)ccc3Cl)ccc21]

The title compound was prepared in 46% yield from Preparation 45a according to the procedure for Preparation 4d. [M+H] Calc'd for $C_{23}H_{20}ClFN_2O_3$, 427; Found, 427.

Example 45

3-({[(4R)-7-(2-chloro-5-fluorophenyl)-3,4-dihydro-2H-1-benzopyran-4-yl]methyl}amino)pyridine-4-carboxylic acid

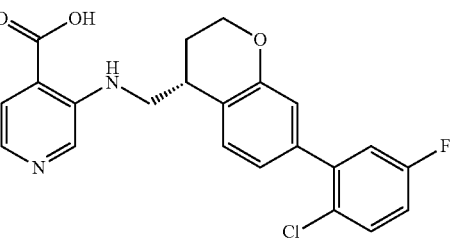

The title compound was prepared in 52% yield from Preparation 45b according to the procedure for Example 1. $^1$H NMR (400 MHz, DMSO-$d_6$): δ 1.89-1.94 (m, 1H), 1.99-2.07 (m, 1H), 3.18-3.22 (m, 1H), 3.52-3.60 (m, 1H), 3.74-3.79 (m, 1H), 4.18-4.28 (m, 2H), 6.85 (d, J=1.2 Hz, 1H), 6.94 (dd, J=7.6 Hz, 1.2 Hz, 1H), 7.24-7.29 (m, 2H), 7.43 (d, J=7.6 Hz, 1H), 7.58-7.61 (m, 2H), 7.86 (d, J=4.8 Hz, 1H), 8.46 (s, 1H). [M+H] Calc'd for $C_{22}H_{18}ClFN_2O_3$, 413; Found, 413.

Preparation 46a

[(4R)-7-[2-(trifluoromethyl)phenyl]-3,4-dihydro-2H-1-benzopyran-4-yl]methanamine

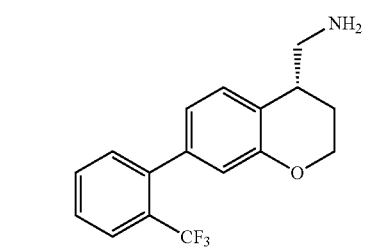 [SMILES: NC[C@@H]1CCOc2cc(-c3ccccc3C(F)(F)F)ccc21]

The title compound was prepared in 59% yield from 2-(trifluoromethyl)phenylboronic acid and Preparation 18d according to the procedures for Preparation 43a and 43b. [M+H] Calc'd for $C_{17}H_{16}F_3NO$, 308; Found, 292.

Preparation 46b methyl 3-({[(4R)-7-[2-(trifluoromethyl)phenyl]-3,4-dihydro-2H-1-benzopyran-4-yl]methyl}amino)pyridine-4-carboxyl

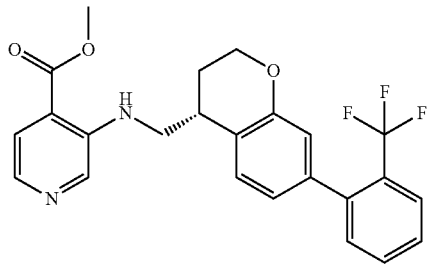 [SMILES: COC(=O)c1ccncc1NC[C@@H]1CCOc2cc(-c3ccccc3C(F)(F)F)ccc21]

The title compound was prepared in 62% yield from Preparation 45a according to the procedure for Preparation 4d. [M+H] Calc'd for $C_{24}H_{21}F_3N_2O_3$, 443; Found, 443.

Example 46

3-({[(4R)-7-[2-(trifluoromethyl)phenyl]-3,4-dihydro-2H-1-benzopyran-4-yl]methyl}amino)pyridine-4-carboxylic acid

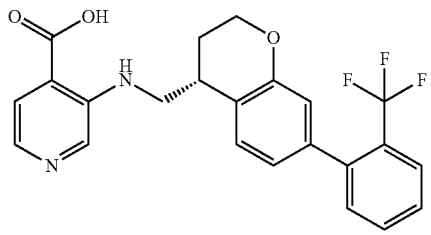 [SMILES: O=C(O)c1ccncc1NC[C@@H]1CCOc2cc(-c3ccccc3C(F)(F)F)ccc21]

The title compound was prepared in 66% yield from Preparation 46b according to the procedure for Example 1. $^1$H NMR (300 MHz, DMSO-d$_6$): δ 1.90-1.95 (1H, m), 2.01-2.05 (1H, m), 3.17-3.24 (1H, m), 3.52-3.60 (1H, m), 3.74-3.80 (1H, m), 4.20-4.26 (2H, m), 6.72 (1H, s), 6.81 (1H, d, J=7.5 Hz), 7.37-7.41 (2H, m), 7.58-7.62 (2H, m), 7.70 (1H, t, J=7.5 Hz), 7.80-7.87 (2H, m), 8.46 (1H, s). [M+H] Calc'd for $C_{23}H_{19}F_3N_2O_3$, 429; Found, 429.

Preparation 47a 3-(3-phenoxyphenoxy)propanenitrile

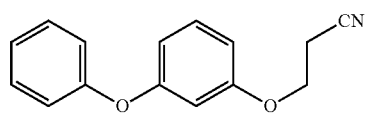 [SMILES: N#CCCOc1cccc(Oc2ccccc2)c1]

To a solution of 3-phenoxyphenol (3.0 g, 16.1 mmol) in acetonitrile (10.6 mL, 161 mmol) was added tert-BuOH (120 mg, 1.6 mmol) and K$_2$CO$_3$ (225 mg, 1.6 mmol). The mixture was refluxed for 2 days. The reaction was filtered and concentrated, and the residue was purified by HPLC to get give 2.78 g (72%) of the title compound as a colorless gum. $^1$H NMR (400 MHz, CDCl$_3$): δ 2.80 (2H, t, J=6.0 Hz), 4.15 (2H, t, J=6.0 Hz), 6.55 (1H, s), 6.64 (2H, d, J=8.0 Hz), 7.02 (2H, d, J=7.6 Hz), 7.12 (1H, t, J=7.2 Hz), 7.23 (1H, t, J=8.0 Hz) 7.35 (2H, t, J=8.0 Hz).

Preparation 47b 7-phenoxy-3,4-dihydro-2H-1-benzopyran-4-one

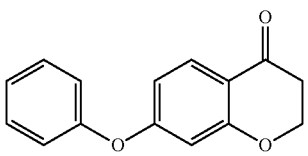 [SMILES: O=C1CCOc2cc(Oc3ccccc3)ccc21]

To a solution of Preparation 47a (2.78 g, 11.6 mmol) in TFA (4.5 mL) was slowly added TfOH (1.54 mL) under nitrogen at 0-5° C. The mixture was stirred at 0-5° C. for 3 h, and then at rt for 16 h. The reaction was cooled to 0° C. and quenched with water, stirring at rt for 3 h. The reaction was extracted with EtOAc, washed with brine, dried (Na$_2$SO$_4$), and concentrated. The residue was purified by HPLC to give 2.5 g (89%) as a yellow gum. $^1$H NMR (300 MHz, DMSO-d$_6$): δ 2.73 (2H, t, J=6.3 Hz), 4.50 (2H, t, J=6.6 Hz), 6.42 (1H, s), 6.62 (1H, d, J=8.7 Hz), 7.13 (2H, d, J=7.8 Hz), 7.26 (1H, t, J=7.2 Hz), 7.46 (2H, t, J=8.1 Hz) 7.75 (1H, d, J=8.7 Hz). [M+H] Calc'd for $C_{15}H_{12}O_3$, 241; Found, 241.

Preparation 47c (7-phenoxy-2H-chromen-4-yl)methanamine

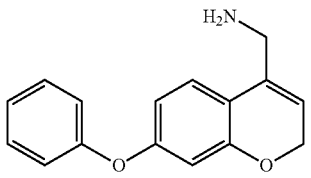 [SMILES: NCC1=CCOc2cc(Oc3ccccc3)ccc21]

The title compound was prepared in 65% yield from Preparation 47b according to the general procedure for Preparation 16a. $^1$H NMR (400 MHz, MeOD-d$_4$): δ 3.89 (2H, s), 4.72 (2H, d, J=4.0 Hz), 5.86 (1H, t, J=3.6 Hz), 6.35 (1H, s), 6.49 (1H, d, J=6.0 Hz), 6.94 (2H, d, J=3.6 Hz), 7.08 (1H, d, J=7.6 Hz), 7.15 (1H, d, J=8.8 Hz), 7.30 (2H, t, J=8.0 Hz). [M+H] Calc'd for $C_{16}H_{15}NO_2$, 254; Found, 254.

Preparation 47d (7-phenoxy-3,4-dihydro-2H-1-benzopyran-4-yl)methanamine

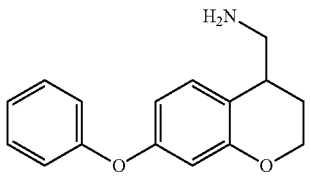 [SMILES: NCC1CCOc2cc(Oc3ccccc3)ccc21]

To a solution of Preparation 47c (1.5 g, 6.0 mmol) in MeOH (150 mL) and one drop of conc. HCl under N$_2$ was added 10% Pd/C (250 mg) at rt. The suspension was stirred for 16 h at rt under H$_2$. The reaction mixture was filtered through Celite, and the pH was adjusted to 8-9 with sat. Na$_2$CO$_3$. The solution was dried (Na$_2$SO$_4$) and concentrated to give 1.0 g (67%) of the title compound as a yellow gum. [M+H] Calc'd for C$_{16}$H$_{17}$NO$_2$, 256; Found, 256.

Preparation 47e methyl 3-{[(7-phenoxy-3,4-dihydro-2H-1-benzopyran-4-yl)methyl]amino}pyridine-4-carboxylate

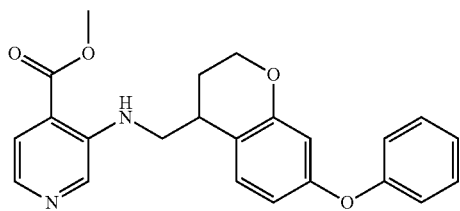 [SMILES: COC(=O)c1ccncc1NCC1CCOc2cc(Oc3ccccc3)ccc21]

The title compound was prepared in 15% yield from Preparation 47d according to the general procedure for Preparation 1e. [M+H] Calc'd for C$_{23}$H$_{22}$N$_2$O$_4$, 390; Found, 390.

Preparation 47f methyl 3-({[(4S)-7-phenoxy-3,4-dihydro-2H-1-benzopyran-4-yl]methyl}amino)pyridine-4-carboxylate;
and Preparation 48f methyl 3-({[(4R)-7-phenoxy-3,4-dihydro-2H-1-benzopyran-4-yl]methyl}amino)pyridine-4-carboxylate

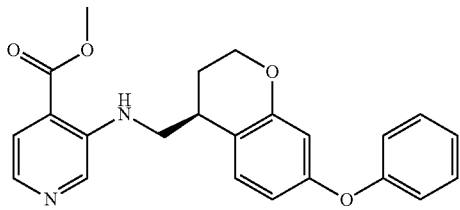

47f

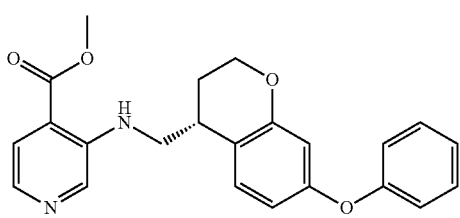

48f

Preparation 47e (120 mg) was purified by chiral HPLC (Column: Chiralcel IA, 250 mm*4.6 mm 5 um; Mobile phase: Hex:EtOH=60:40; F: 1.0 mL/min; W: 230 nm; T=30° C.) to give 43 mg (36%) of Preparation 48f (7.36 min) and 45 mg (38%) of Preparation 47f (10.26 min), each as a pale-yellow oil.

Example 47

3-({[(4S)-7-phenoxy-3,4-dihydro-2H-1-benzopyran-4-yl]methyl}amino)pyridine-4-carboxylic acid

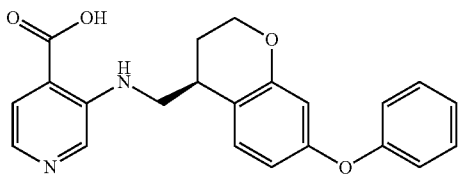 [SMILES: O=C(O)c1ccncc1NC[C@H]1CCOc2cc(Oc3ccccc3)ccc21]

The title compound was prepared in 74% yield from Preparation 47f according to the procedure for Example 1. $^1$H NMR (400 MHz, DMSO-d$_6$): δ 1.84-1.88 (1H, m), 1.95-2.03 (1H, m), 3.13-3.17 (1H, m), 3.53-3.59 (1H, m), 3.72-3.77 (1H, m), 4.14-4.25 (2H, m), 6.37 (1H, s), 6.50 (1H, d, J=8.4 Hz), 6.99 (2H, d, J=8.0 Hz), 7.12-7.16 (1H, m), 7.32-7.41 (3H, m), 7.94 (2H, s), 8.55 (1H, s). [M+H] Calc'd for C$_{22}$H$_{20}$N$_2$O$_4$, 377; Found, 377.

Example 48

3-({[(4R)-7-phenoxy-3,4-dihydro-2H-1-benzopyran-4-yl]methyl}amino)pyridine-4-carboxylic acid

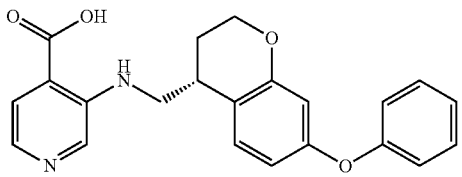 [SMILES: O=C(O)c1ccncc1NC[C@@H]1CCOc2cc(Oc3ccccc3)ccc21]

The title compound was prepared in 77% yield from Preparation 48f according to the procedure for Example 1. $^1$H NMR (400 MHz, DMSO-d$_6$): δ 1.86-1.89 (1H, m), 1.97-2.01 (1H, m), 3.14-3.16 (1H, m), 3.52-3.57 (1H, m), 3.73-3.77 (1H, m), 4.13-4.25 (2H, m), 6.37 (1H, s), 6.50 (1H, d, J=8.0 Hz), 6.99 (2H, d, J=8.0 Hz), 7.12-7.15 (1H, m), 7.32-7.41 (3H, m), 7.95 (2H, s), 8.56 (1H, s). [M+H] Calc'd for C$_{22}$H$_{20}$N$_2$O$_4$, 377; Found, 377.

Preparation 49a 7-(thiophen-2-ylsulfanyl)-3,4-dihydro-2H-1-benzopyran-4-one

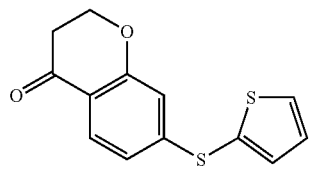 [SMILES: O=C1CCOc2cc(Sc3cccs3)ccc21]

7-Bromochroman-4-one (1.5 g, 6.6 mmol), thiophene-2-thiol (0.68 mL, 7.3 mmol), and potassium carbonate (1.37 g, 9.9 mmol) were combined in ACN (50 mL) in a sealed vessel, and the reaction was heated at 78° C. overnight. The reaction was cooled, filtered, and concentrated. Purification by silica gel chromatography (10-60% EtOAc/hexanes) gave 1.6 g (93%) of the title compound as a yellow oil. $^1$H NMR (400 MHz, DMSO-d$_6$): δ 2.75 (2H, t, J=6.4 Hz), 4.48 (2H, t, J=6.4 Hz), 6.59 (1H, d, J=1.8 Hz), 6.75 (1H, dd, J=8.4, 1.8 Hz), 7.13-7.17 (1H, m), 7.34 (1H, dd, J=3.6, 1.2 Hz), 8.58 (1H, dd, J=5.4, 1.2 Hz), 7.75 (1H, d, J=8.4 Hz). [M+H] calc'd for $C_{13}H_{10}O_2S_2$, 263; Found 263.

Preparation 49b

[7-(thiophen-2-ylsulfanyl)-2H-chromen-4-yl]methanamine, hydrochloride

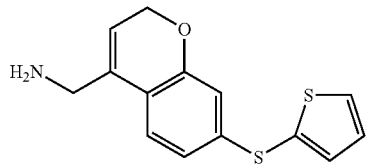 [SMILES: NCC1=CCOc2cc(Sc3cccs3)ccc21]

The title compound was prepared in 25% yield from Preparation 49a according to the general procedure for Preparation 3a. [M+H] calc'd for $C_{14}H_{13}NOS_2$, 276; Found 276.

Preparation 49c

[7-(thiophen-2-ylsulfanyl)-3,4-dihydro-2H-1-benzopyran-4-yl]methanamine

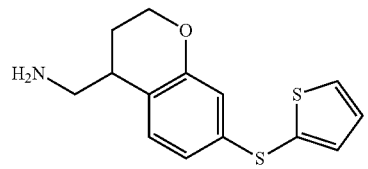 [SMILES: NCC1CCOc2cc(Sc3cccs3)ccc21]

The title compound was prepared in quantitative yield from Preparation 49b according to the general procedure for Preparation 3e. [M+H] calc'd for $C_{14}H_{15}NOS_2$, 278; Found 278.

Example 49

3-({[7-(thiophen-2-ylsulfanyl)-3,4-dihydro-2H-1-benzopyran-4-yl]methyl}amino)pyridine-4-carboxylic acid

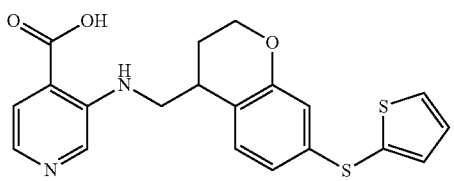 [SMILES: O=C(O)c1ccncc1NCC1CCOc2cc(Sc3cccs3)ccc21]

The title compound was prepared in 5% yield from Preparation 49c according to the general procedure for Example 13. $^1$H NMR (400 MHz, DMSO-d$_6$): δ 1.86-1.98 (2H, m), 3.06-3.10 (1H, m), 3.43-3.49 (1H, m), 3.61-3.67 (1H, m), 4.10-4.20 (2H, m), 6.50 (1H, d, J=1.8 Hz), 6.69 (1H, dd, J=8.0, 1.8 Hz), 7.17 (1H, dd, J=5.3, 3.6 Hz), 7.26 (1H, d, J=8.1 Hz), 7.39-7.42 (1H, m), 7.57 (1H, d, J=4.4 Hz), 7.81 (1H, d, J=4.4 Hz), 7.82 (1H, d, J=0.9 Hz), 8.37 (1H, s). [M+H] calc'd for $C_{20}H_{18}N_2O_3S$, 399; Found 399.

Preparation 50a tert-butyl N-({7-[(2-methylphenyl)sulfanyl]-2H-chromen-4-yl}methyl)carbamate

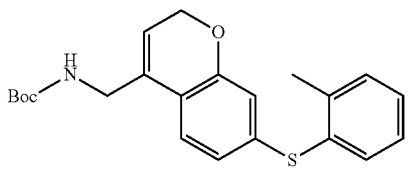 [SMILES: Cc1ccccc1Sc1ccc2c(c1)OCC=C2CNC(=O)OC(C)(C)C]

To a suspension of Preparation 16a (1.2 g, 3.5 mmol), 2-methylthiophenol (438 mg, 3.53 mmol) and Xantphos (102 mg, 0.176 mmol) in dioxane (25 mL) and DIEA (1.2 mL, 7.0 mmol) was added Pd$_2$dba$_3$ (82 mg, 0.088 mmol) at rt under N$_2$. The reaction was stirred at reflux overnight. The reaction was filtered and concentrated. Purification by silica gel chromatography (PE:EtOAc=5:1) gave 483 mg (36%) as an orange oil. [M+H] Calc'd for $C_{22}H_{25}NO_3S$, 384; Found, 384.

Preparation 50b tert-butyl N-({7-[(2-methylphenyl)sulfanyl]-3,4-dihydro-2H-1-benzopyran-4-yl}methyl)carbamate

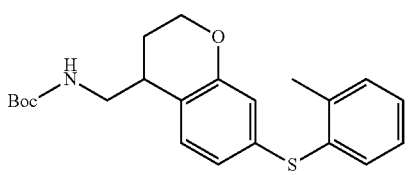 [SMILES: Cc1ccccc1Sc1ccc2c(c1)OCCC2CNC(=O)OC(C)(C)C]

To a solution of Preparation 50a (483 mg, 1.26 mmol) in MeOH (10 mL) and AcOH (2 mL) was added 10% Pd/C (150 mg) at rt. The mixture was stirred overnight with 50 psi H$_2$. The reaction was filtered and concentrated. The residue was dissolved in EtOAc, washed with sat. Na$_2$CO$_3$, dried (Na$_2$SO$_4$), and concentrated to give 450 mg (93%) of the title compound as a pale brown oil. [M+H] Calc'd for $C_{22}H_{27}NO_3S$, 386; Found, 386.

Preparation 50c

{7-[(2-methylphenyl) sulfanyl]-3,4-dihydro-2H-1-benzopyran-4-yl}methanamine

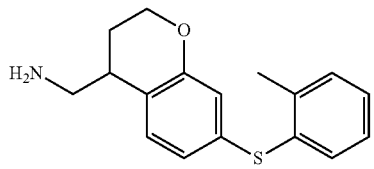 [SMILES: Cc1ccccc1Sc1ccc2c(c1)OCCC2CN]

To a solution of Preparation 50b (450 mg, 1.17 mmol) in EtOAc (10 mL) was added HCl/EtOAc (10 mL, 1.0 M), and the reaction stirred at rt overnight. The solution was concentrated, and the residue was dissolved in EtOAc, washed with sat. $Na_2CO_3$, dried ($Na_2SO_4$), and concentrated to give 320 mg (96%) of the title compound as an orange oil. [M+H] Calc'd for $C_{17}H_{19}NOS$, 286; Found, 286.

Preparation 50d methyl 3-({[(4S)-7-[(2-methylphenyl)sulfanyl]-3,4-dihydro-2H-1-benzopyran-4-yl]methyl}amino)pyridine-4-carboxylate; and

Preparation 51d methyl 3-({[(4R)-7-[(2-methylphenyl)sulfanyl]-3,4-dihydro-2H-1-benzopyran-4-yl]methyl}amino)pyridine-4-carboxylate

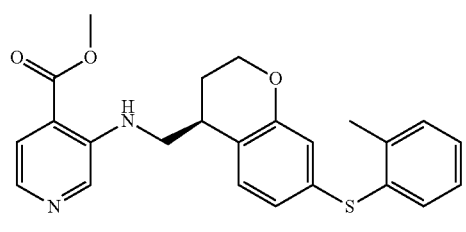

50d

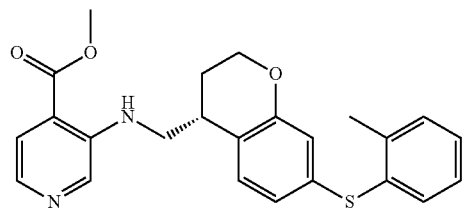

51d

The racemate (150 mg) of the title compounds was prepared in 32% yield from Preparation 50c according to the general procedure for Preparation 1e. [M+H] Calc'd for $C_{24}H_{24}N_2O_3S$, 421; Found, 421.
Separation by chiral HPLC (Column: Chiralcel: IA 5um 4.6*250 mm, Mobile phase: Hex:EtOH=50:50, F: 1.0 mL/min, W: 230 nm, T: 30° C.) gave 60 mg (40%) of Preparation 51d (7.746 min) and 62 mg (41%) of Preparation 50d (10.602 min), each as a yellow oil.

Example 50

3-({[(4S)-7-[(2-methylphenyl)sulfanyl]-3,4-dihydro-2H-1-benzopyran-4-yl]methyl}amino)pyridine-4-carboxylic acid

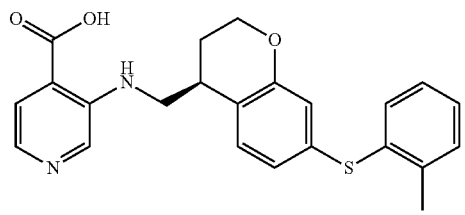 [SMILES: Cc1ccccc1Sc1ccc2c(c1)OCC[C@@H]2CNc1cnccc1C(=O)O]

The title compound was prepared in 76% yield from Preparation 56d according to the general procedure for Example 1. $^1$H NMR (400 MHz, DMSO-$d_6$): δ 1.84-1.88 (1H, m), 1.94-1.99 (1H, m), 2.31 (3H, s), 3.10-3.13 (1H, m), 3.48-3.54 (1H, m), 3.66-3.70 (1H, m), 4.12-4.22 (2H, m), 6.50 (1H, s), 6.67-6.70 (1H, m), 7.20-7.35 (5H, m), 7.57 (1H, d, J=5.2 Hz), 7.85 (1H, d, J=4.8 Hz), 8.41 (1H, s). [M+H] Calc'd for $C_{23}H_{22}N_2O_3S$, 407; Found, 407.

Example 51

3-({[(4R)-7-[(2-methylphenyl)sulfanyl]-3,4-dihydro-2H-1-benzopyran-4-yl]methyl}amino)pyridine-4-carboxylic acid

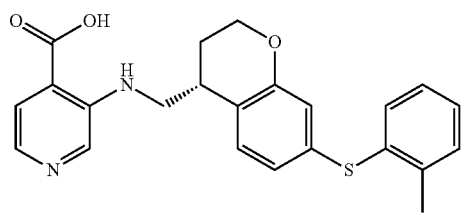 [SMILES: Cc1ccccc1Sc1ccc2c(c1)OCC[C@H]2CNc1cnccc1C(=O)O]

The title compound was prepared in 90% yield from Preparation 51d according to the general procedure for Example 1. $^1$H NMR (400 MHz, DMSO-$d_6$): δ 1.86-1.88 (1H, m), 1.96-1.98 (1H, m), 2.31 (3H, s), 3.10-3.13 (1H, m), 3.48-3.54 (1H, m), 3.66-3.71 (1H, m), 4.14-4.19 (2H, m), 6.50 (1H, s), 6.68-6.70 (1H, m), 7.22-7.35 (5H, m), 7.58 (1H, d, J=5.2 Hz), 7.85 (1H, d, J=5.2 Hz), 8.41 (1H, s). [M+H] Calc'd for $C_{23}H_{22}N_2O_3S$, 407; Found, 407.

Preparation 52a methyl 3-[({7-[(3-fluorophenyl)sulfanyl]-3,4-dihydro-2H-1-benzopyran-4-yl}methyl)amino]pyridine-4-carboxylate

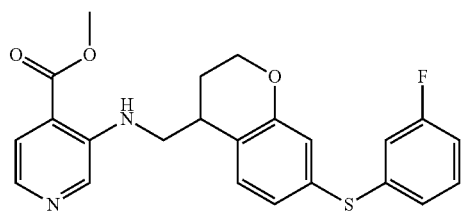

To a solution of Preparation 14c (310 mg, 0.82 mmol) in THF (5 mL) was added 3,3'-difluorodiphenyldisulfide (105 mg, 0.41 mmol), Pd(dppf)Cl$_2$ (34 mg, 0.041 mmol) and Zn (65 mg, 0.99 mmol). The mixture was stirred at reflux for overnight under nitrogen. The mixture was diluted with EtOAc, filtered, and concentrated. The residue was purified by silica gel chromatography (PE:EtOAc=1:1) to give 112 mg (32%) of the title compound as a yellow oil. [M+H] Calc'd for $C_{23}H_{21}F_2O_3S$, 425; Found, 425.

Preparation 52b methyl 3-({[(4S)-7-[(3-fluorophenyl)sulfanyl]-3,4-dihydro-2H-1-benzopyran-4-yl]methyl}amino)pyridine-4-carboxylate; and Preparation 53b methyl 3-({[(4R)-7-[(3-fluorophenyl)sulfanyl]-3,4-dihydro-2H-1-benzopyran-4-yl]methyl}amino)pyridine-4-carboxylate

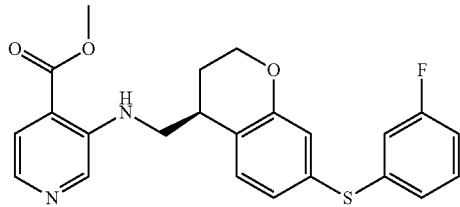

52b

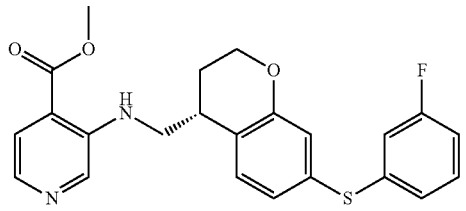 [SMILES: COC(=O)c1ccncc1NCC1CCOc2cc(Sc3cccc(F)c3)ccc21]

53b

Preparation 52a (112 mg) was separated by chiral HPLC (Column: Chiralcel IA, 250 mm*4.6 mm 5 um; Mobile phase: Hex:EtOH=50:50; F: 1.0 mL/min; W: 230 nm; T=30° C.) to give 44 mg (29%) of Preparation 53b (7.697 min) and 43 mg (29%) of Preparation 52b (10.724 min), each as a yellow oil.

Example 52

3-({[(4S)-7-[(3-fluorophenyl)sulfanyl]-3,4-dihydro-2H-1-benzopyran-4-yl]methyl}amino)pyridine-4-carboxylic acid

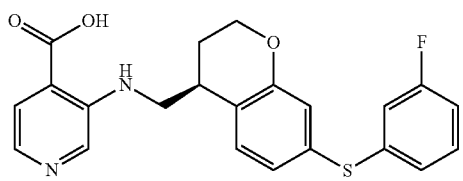

The title compound was prepared in 78% yield from Preparation 52b according to the general procedure for Example 1. $^1$H NMR (400 MHz, DMSO-d$_6$): δ 1.90-2.01 (2H, m), 3.15-3.18 (1H, m), 3.51-3.57 (1H, m), 3.69-3.74 (1H, m), 4.18-4.24 (2H, m), 6.81 (1H, s), 6.89-6.92 (1H, m), 7.07-7.14 (3H, m), 7.37-7.42 (2H, m), 7.58 (1H, d, J=4.8 Hz), 7.86 (1H, d, J=4.8 Hz), 8.43 (1H, s). [M+H] Calc'd for $C_{22}H_{19}FN_2O_3S$, 411; Found, 411.

Example 53

3-({[(4R)-7-[(3-fluorophenyl)sulfanyl]-3,4-dihydro-2H-1-benzopyran-4-yl]methyl}amino)pyridine-4-carboxylic acid

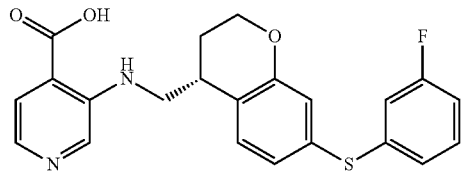 [SMILES: O=C(O)c1ccncc1NC[C@@H]1CCOc2cc(Sc3cccc(F)c3)ccc21]

The title compound was prepared in 68% yield from Preparation 53b according to the general procedure for Example 1. $^1$H NMR (400 MHz, DMSO-d$_6$): δ 1.90-2.01 (2H, m), 3.15-3.18 (1H, m), 3.51-3.57 (1H, m), 3.69-3.74 (1H, m), 4.18-4.24 (2H, m), 6.81 (1H, s), 6.89-6.91 (1H, m), 7.07-7.14 (3H, m), 7.37-7.43 (2H, m), 7.57 (1H, d, J=4.8 Hz), 7.85 (1H, d, J=5.2 Hz), 8.42 (1H, s). [M+H] Calc'd for $C_{22}H_{19}FN_2O_3S$, 411; Found, 411.

Preparation 54a methyl 3-[({7-[(4-fluorophenyl)sulfanyl]-3,4-dihydro-2H-1-benzopyran-4-yl}methyl)amino]pyridine-4-carboxylate

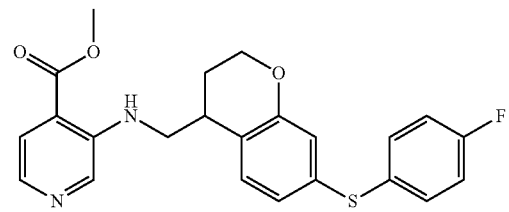 [SMILES: COC(=O)c1ccncc1NCC1CCOc2cc(Sc3ccc(F)cc3)ccc21]

The title compound was prepared in 53% yield from 3,3'-difluorodiphenyldisulfide according to the general procedure for Preparation 52a. [M+H] Calc'd for $C_{23}H_{21}F_2O_3S$, 425; Found, 425.

Preparation 54b methyl 3-({[(4S)-7-[(4-fluorophenyl)sulfanyl]-3,4-dihydro-2H-1-benzopyran-4-yl]methyl}amino)pyridine-4-carboxylate; and

Preparation 55b methyl 3-({[(4R)-7-[(4-fluorophenyl)sulfanyl]-3,4-dihydro-2H-1-benzopyran-4-yl]methyl}amino)pyridine-4-carboxylate

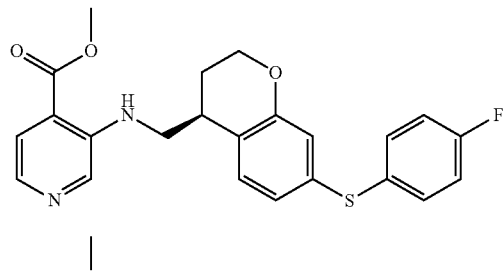

54b

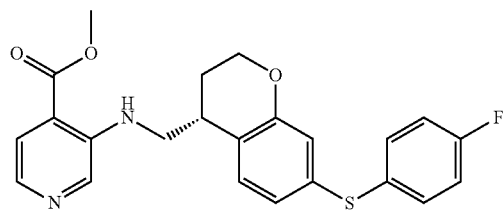

55b

Preparation 54a (179 mg) was separated by chiral HPLC (Column: Chiralcel IA, 250 mm*4.6 mm 5 um; Mobile phase: Hex:EtOH=50:50; F: 1.0 mL/min; W: 230 nm; T=30° C.) to give 70 mg (41%) of Preparation 55b (9.350 min) and 70 mg (41%) of Preparation 54b (16.515 min), each as a yellow oil.

Example 54

3-({[(4S)-7-[(4-fluorophenyl)sulfanyl]-3,4-dihydro-2H-1-benzopyran-4-yl]methyl}amino)pyridine-4-carboxylic acid

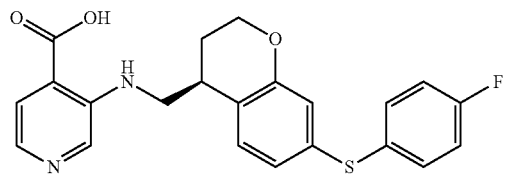

The title compound was prepared in 86% yield from Preparation 54b according to the general procedure for Example 1. $^1$H NMR (400 MHz, DMSO-d$_6$): δ 1.84-1.98 (2H, m), 3.11-3.14 (1H, m), 3.48-3.54 (1H, m), 3.66-3.70 (1H, m), 4.13-4.20 (2H, m), 6.62 (1H, s), 6.75-6.78 (1H, m), 7.24-7.32 (3H, m), 7.41-7.45 (2H, m), 7.59 (1H, d, J=5.2 Hz), 7.86 (1H, d, J=4.8 Hz), 8.42 (1H, s). [M+H] Calc'd for C$_{22}$H$_{19}$FN$_2$O$_3$S, 411; Found, 411.

Example 55

3-({[(4R)-7-[(4-fluorophenyl)sulfanyl]-3,4-dihydro-2H-1-benzopyran-4-yl]methyl}amino)pyridine-4-carboxylic acid

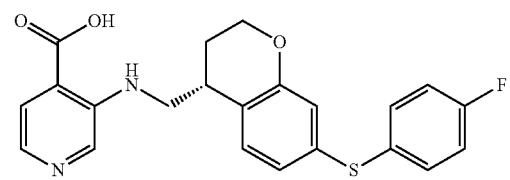

The title compound was prepared in 85% yield from Preparation 55b according to the general procedure for Example 1. $^1$H NMR (400 MHz, DMSO-d$_6$): δ 1.84-2.00 (2H, m), 3.15-3.18 (1H, m), 3.48-3.54 (1H, m), 3.66-3.70 (1H, m), 4.13-4.22 (2H, m), 6.62 (1H, s), 6.76-6.78 (1H, m), 7.24-7.32 (3H, m), 7.41-7.45 (2H, m), 7.58 (1H, d, J=5.2 Hz), 7.85 (1H, d, J=5.2 Hz), 8.41 (1H, s). [M+H] Calc'd for C$_{22}$H$_{19}$FN$_2$O$_3$S, 411; Found, 411.

Preparation 56a

6-[(6-methylpyridin-2-yl)oxy]-1,2,3,4-tetrahydronaphthalen-1-one

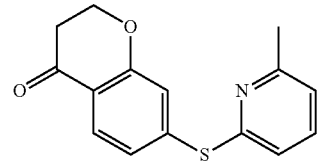 [SMILES: Cc1cccc(Sc2ccc3c(c2)OCCC3=O)n1]

A suspension of 6-hydroxy-1-tetralone (3.0 g, 18 mmol), 2-fluoro-6-methylpyridine (2.06 g, 18.5 mmol) and Cs$_2$CO$_3$ (12.1 g, 37.0 mmol) in DMF (150 mL) was stirred at 150° C. in a sealed vessel overnight under N$_2$. The reaction was poured into water (300 mL) and extracted with EtOAc (3×50 mL). Organics were dried (Na$_2$SO$_4$) and concentrated. Purification by silica gel chromatography (PE:EA=5:1) gave 1.2 g (26%) of the title compound as a red oil. [M+H] calc'd for C$_{16}$H$_{15}$NO$_2$, 254; found 254.

Preparation 56b

{6-[(6-methylpyridin-2-yl)oxy]-3,4-dihydronaphthalen-1-yl}methanamine, hydrochloride

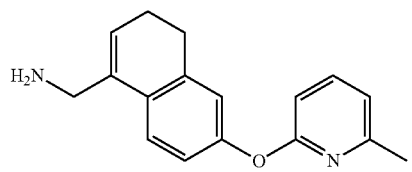 [SMILES: Cc1cccc(Oc2ccc3c(c2)CCC=C3CN)n1]

The title compound was prepared in 71% yield from Preparation 56a according to the general procedure for Preparation 3a. [M+H] calc'd for $C_{17}H_{18}N_2O$, 267; Found 267.

Preparation 56c

{6-[(6-methylpyridin-2-yl)oxy]-1,2,3,4-tetrahydronaphthalen-1-yl}methanamine

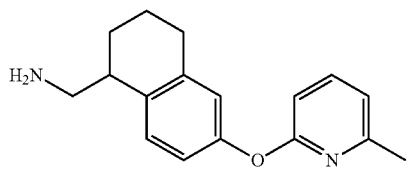 [SMILES: Cc1cccc(Oc2ccc3c(c2)CCCC3CN)n1]

The title compound was prepared in quantitative yield from Preparation 56b according to the general procedure for Preparation 3e. [M+H] calc'd for $C_{17}H_{20}N_2O$, 269; Found 269.

Preparation 56d methyl 3-[({6-[(6-methylpyridin-2-yl)oxy]-1,2,3,4-tetrahydronaphthalen-1-yl}methyl)amino]pyridine-4-carboxylic acid

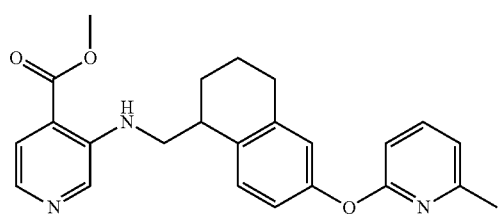 [SMILES: COC(=O)c1ccncc1NCC1CCCc2cc(Oc3cccc(C)n3)ccc21]

The title compound was prepared in 66% yield from Preparation 56c according to the procedure for Preparation 1e. [M+H] Calc'd for $C_{24}H_{25}N_3O_3$, 404; Found, 404.

Example 56

3-[({6-[(6-methylpyridin-2-yl)oxy]-1,2,3,4-tetrahydronaphthalen-1-yl}methyl)amino]pyriding-4-carboxylic acid

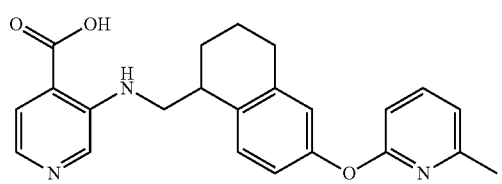 [SMILES: Cc1cccc(Oc2ccc3c(c2)CCCC3CNc2cnccc2C(=O)O)n1]

The title compound was prepared in 42% yield from Preparation 56d according to the general procedure for Example 1. $^1$H NMR (400 MHz, MeOD-d$_4$): δ 1.80-1.82 (1H, m), 1.97-2.01 (3H, m), 2.45 (3H, m), 2.81-2.85 (2H, m), 3.21-3.24 (1H, m), 3.51-3.66 (2H, m), 6.57 (1H, d, J=8.0 Hz), 6.86-6.88 (2H, m), 7.00 (1H, d, J=7.2 Hz), 7.34 (1H, d, J=9.2 Hz), 7.68 (1H, t, J=8.0 Hz), 7.83-7.89 (2H, m), 8.21 (1H, s). [M+H] Calc'd for $C_{23}H_{23}N_3O_3$, 390; Found, 390.

Preparation 57a 6-amino-1,2,3,4-tetrahydronaphthalen-1-one

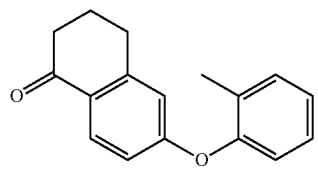 [SMILES: Cc1ccccc1Oc1ccc2c(c1)CCCC2=O]

The suspension of 6-amino-1,2,3,4-tetrahydronaphthalen-1-one (1.0 g, 4.4 mmol), o-cresol (0.72 g, 6.7 mmol), 1-pyridin-2-ylacetone (0.12 g, 0.89 mmol), $Cs_2CO_3$ (2.9 g, 8.9 mmol) and CuBr (70 mg, 0.44 mmol) in DMSO (10 mL) was stirred at 110° C. overnight under $N_2$. The reaction was poured into water and extracted with EtOAc. Organics were dried ($Na_2SO_4$) and concentrated. Purification by silica gel chromatography (PE:EtOAc=30:1 to 10:1) gave 0.77 g (69%) of the title compound as a colorless oil. $^1$H NMR (300 MHz, CDCl$_3$): δ 2.07-2.15 (m, 2H), 2.19 (s, 3H), 2.62 (t, J=6.3 Hz, 2H), 2.88 (t, J=6.0 Hz, 2H), 6.66 (s, 1H), 6.77 (dd, J=8.7 Hz, 2.7 Hz, 1H), 6.99 (d, J=8.1 Hz, 1H), 7.11-7.30 (m, 3H), 8.01 (d, J=8.7 Hz, 1H). [M+H] Calc'd for $C_{17}H_{16}O_2$, 253; Found, 253.

Preparation 57b

[6-(2-methylphenoxy)-3,4-dihydronaphthalen-1-yl]methanamine, hydrochloride

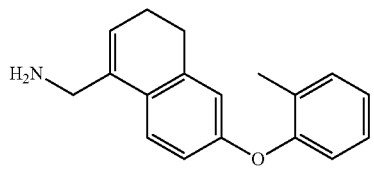

The title compound was prepared in 73% yield from Preparation 57a according to the general procedure for Preparation 3a. [M+H] Calc'd for $C_{18}H_{19}NO$, 266; Found, 266.

Preparation 57c

[6-(2-methylphenoxy)-1,2,3,4-tetrahydronaphthalen-1-yl]methanamine

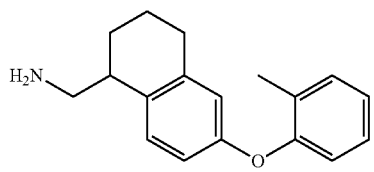 [SMILES: Cc1ccccc1Oc1ccc2c(c1)CCCC2CN]

The title compound was prepared in 93% yield from Preparation 57b according to the general procedure for Preparation 3e. [M+H] Calc'd for $C_{18}H_{21}NO$, 268; Found, 268.

Preparation 57d methyl 3-({[(1S)-6-(2-methylphenoxy)-1,2,3,4-tetrahydronaphthalen-1-yl]methyl}amino)pyridine-4-carboxylate; and Preparation 58d methyl 3-({[(1R)-6-(2-methylphenoxy)-1,2,3,4-tetrahydronaphthalen-1-yl]methyl}amino)pyridine-4-carboxylate

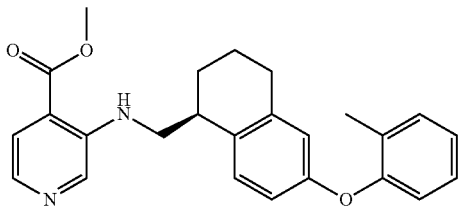

57d

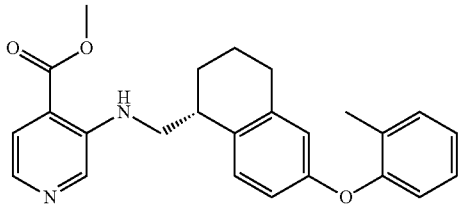

58d

The racemate (300 mg) of the title compounds was prepared in 26% yield from Preparation 72c according to the general procedure for Preparation 1e. [M+H] Calc'd for $C_{25}H_{26}N_2O_3$, 403; Found, 403.
Separation by chiral HPLC (Column: Chiralcel: IC 5 um 4.6*250 mm, Mobile phase: Hex:EtOH=70:30, F: 1.0 mL/min, W: 230 nm, T: 30° C.) gave 108 mg (36%) of Preparation 57a (6.053 min) and 108 mg (36%) of Preparation 58a (6.873 min) as a colorless oil.

Example 57

3-({[(1S)-6-(2-methylphenoxy)-1,2,3,4-tetrahydronaphthalen-1-yl]methyl}amino)pyridine-4-carboxylic acid

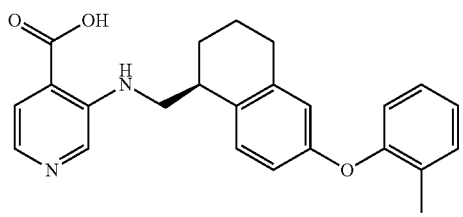 [SMILES: Cc1ccccc1Oc1ccc2c(c1)CCC[C@@H]2CNc1cnccc1C(=O)O]

The title compound was prepared in 67% yield from Preparation 57d according to the general procedure for Example 1. $^1$H NMR (400 MHz, DMSO-$d_6$): δ 1.63-1.67 (m, 1H), 1.78-1.84 (m, 3H), 2.17 (s, 3H), 2.63-2.73 (m, 2H), 3.06-3.09 (m, 1H), 3.42-3.47 (m, 1H), 3.55-3.59 (m, 1H), 6.61 (d, J=2.0 Hz, 1H), 6.65 (dd, J=6.4 Hz, 2.4 Hz, 1H), 6.86 (d, J=8.0 Hz, 1H), 7.07-7.10 (m, 1H), 7.18-7.22 (m, 1H), 7.28-7.31 (m, 2H), 7.56 (d, J=5.2 Hz, 1H), 7.83 (d, J=5.2 Hz, 1H), 8.35 (s, 1H). [M+H] Calc'd for $C_{24}H_{24}N_2O_3$, 389; Found, 389.

Example 58

3-({[(1R)-6-(2-methylphenoxy)-1,2,3,4-tetrahydronaphthalen-1-yl]methyl}amino)pyridine-4-carboxylic acid

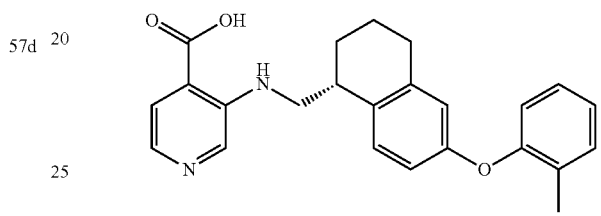

The title compound was prepared in 81% yield from Preparation 58d according to the general procedure for Example 1. $^1$H NMR (400 MHz, DMSO-$d_6$): δ 1.63-1.67 (m, 1H), 1.78-1.84 (m, 3H), 2.17 (s, 3H), 2.63-2.73 (m, 2H), 3.06-3.09 (m, 1H), 3.42-3.47 (m, 1H), 3.55-3.59 (m, 1H), 6.61 (d, J=2.0 Hz, 1H), 6.65 (dd, J=6.4 Hz, 2.4 Hz, 1H), 6.86 (d, J=8.0 Hz, 1H), 7.06-7.10 (m, 1H), 7.18-7.22 (m, 1H), 7.28-7.31 (m, 2H), 7.56 (d, J=5.2 Hz, 1H), 7.83 (d, J=5.2 Hz, 1H), 8.35 (s, 1H). [M+H] Calc'd for $C_{24}H_{24}N_2O_3$, 389; Found, 389.

Preparation 59a 6-propoxy-1,2,3,4-tetrahydronaphthalen-1-one

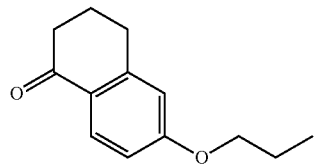

6-Hydroxy-1-tetralone (2.0 g, 12.3 mmol), bromo-propane (2.24 mL, 24.7 mmol), potassium iodide (2.05 g, 12.3 mmol) and potassium carbonate (3.41 g, 24.7 mmol) were combined in ACN (50 mL) in a sealed vessel, and the reaction was stirred at 122° C. overnight. The reaction was cooled, filtered, and concentrated. Purification by silica gel chromatography (10-50% EtOAc/hexanes) gave 2.36 g (94%) of the title compound as a clear oil. $^1$H NMR (400 MHz, DMSO-$d_6$): δ 1.04 (3H, t, J=7.4 Hz), 1.79-1.85 (2H, m), 2.09-2.14 (2H, m), 2.60 (2H, t, J=6.3 Hz), 2.88-2.93 (2H, t, J=6.5 Hz), 3.97 (2H, t, J=6.5 Hz), 6.69 (1H, d, J=2.3 Hz), 6.81 (1H, dd, J=8.8, 4.1 Hz), 7.99 (1H, d, J=8.7 Hz). [M+H] calc'd for $C_{13}H_{16}O_2$, 205; Found 205.

Preparation 59b (6-propoxy-3,4-dihydronaphthalen-1-yl)methanamine, hydrochloride

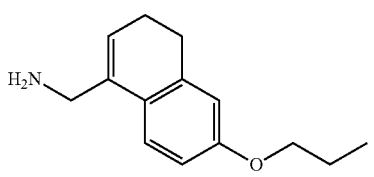 [SMILES: CCCOc1ccc2c(c1)CCC=C2CN]

The title compound was prepared in 54% yield from Preparation 59a according to the general procedure for Preparation 3a. [M+H] calc'd for $C_{14}H_{18}NO$, 218; Found 218.

Preparation 59c (6-propoxy-1,2,3,4-tetrahydronaphthalen-1-yl)methanamine

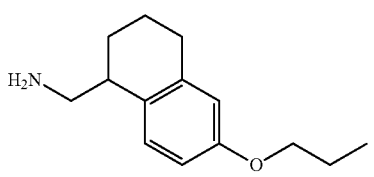 [SMILES: CCCOc1ccc2c(c1)CCCC2CN]

The title compound was prepared in quantitative yield from Preparation 59b according to the general procedure for Preparation 3e. [M+H] calc'd for $C_{14}H_{20}NO$, 220; Found 220.

Example 59

3-{[(6-propoxy-1,2,3,4-tetrahydronaphthalen-1-yl)methyl]amino}pyridine-4-carboxylic acid

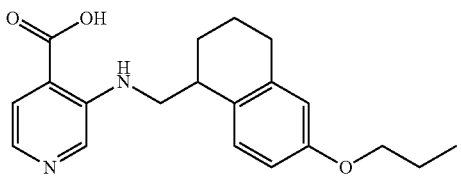 [SMILES: CCCOc1ccc2c(c1)CCCC2CNc1cnccc1C(=O)O]

The title compound was prepared in 26% yield from Preparation 59c according to the general procedure for Example 13. $^1$H NMR (400 MHz, DMSO-$d_6$): δ 0.96 (3H, t, J=7.4 Hz), 1.65-1.82 (6H, m), 2.66-2.71 (2H, m), 3.02-3.05 (1H, m), 3.38-3.55 (2H, m), 3.87 (2H, t, J=6.5 Hz), 6.64-6.71 (2H, m), 7.20 (1H, d, J=8.4 Hz), 7.55 (1H, d, J=5.0 Hz), 7.70 (1H, br s), 7.83 (1H, d, J=5.0 Hz), 8.35 (1H, s), 13.40 (1H, br s). [M+H] calc'd for $C_{20}H_{24}N_2O_3$, 341; Found 341.

Preparation 60a 6-(difluoromethoxy)-1,2,3,4-tetrahydronaphthalen-1-one

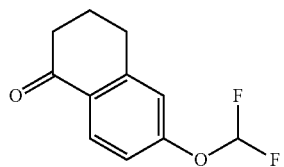 [SMILES: O=C1CCCc2cc(OC(F)F)ccc21]

A solution of 6-hydroxy-1-tetralone (5.0 g, 30.8 mmol) in DMA (75 mL) was cooled to 0° C. Freon was bubbled into the mixture for 10 min. $Cs_2CO_3$ (30.1 g, 92.5 mmol) was added, and the reaction was heated at 50° C. in a sealed vessel for 2 h. The mixture poured into ice-water and extracted with EtOAc. Organics were dried and concentrated. Purification by silica gel chromatography (PE:EtOAc=10:1 to 5:1) gave 5.1 g (78%) of the title compound as an off-white solid. $^1$H NMR (400 MHz, CDCl$_3$): δ 2.11-2.17 (m, 2H), 2.65 (t, J=6.4 Hz, 2H), 2.96 (t, J=6.0 Hz, 2H), 6.59 (t, J=73.2 Hz, 1H), 6.97 (d, J=2.0 Hz, 1H), 7.01 (dd, J=8.4 Hz, 2.0 Hz, 1H), 8.05 (d, J=8.4 Hz, 1H).

Preparation 60b

[6-(difluoromethoxy)-3,4-dihydronaphthalen-1-yl]methanamine, hydrochloride

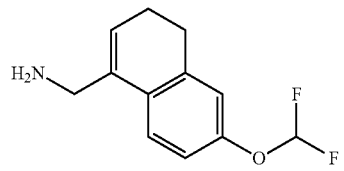 [SMILES: NCC1=CCCc2cc(OC(F)F)ccc21]

The title compound was prepared in 53% yield from Preparation 60a according to the general procedure for Preparation 3a. [M+H] calc'd for $C_{12}H_{13}F_2NO$, 226; Found 226.

Preparation 60c

[6-(difluoromethoxy)-1,2,3,4-tetrahydronaphthalen-1-yl]methanamine

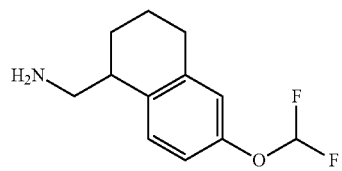 [SMILES: NCC1CCCc2cc(OC(F)F)ccc21]

The title compound was prepared in 85% yield from Preparation 60b according to the general procedure for Preparation 3e. [M+H] calc'd for $C_{12}H_{15}F_2NO$, 228; Found 228.

Preparation 60d methyl 3-({[(1S)-6-(difluoromethoxy)-1,2,3,4-tetra-hydronaphthalen-1-yl]methyl}amino)pyridine-4-carboxylate; and

Preparation 61d methyl 3-({[(1R)-6-(difluoromethoxy)-1,2,3,4-tetra-hydronaphthalen-1-yl]methyl}amino)pyridine-4-carboxylate

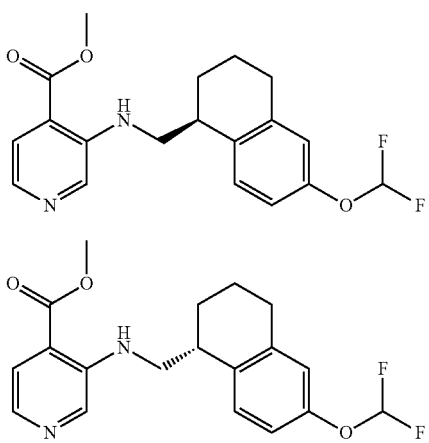

The racemate of the title compounds was prepared in 25% yield from Preparation 60c according to the general procedure for Preparation 1e.

Separation by chiral HPLC (Column: Chiralcel: IC 5 um 4.6*250 mm, Mobile phase: Hex:EtOH=70:30, F: 1.0 mL/min, W: 230 nm, T: 30° C.) gave 20% yield of Preparation 60d (6.240 min) and 16% yield of Preparation 61d (6.718 min), each as a colorless oil.

Example 60

3-({[(1S)-6-(difluoromethoxy)-1,2,3,4-tetrahydronaphthalen-1-yl]methyl}amino)pyridine-4-carboxylic acid

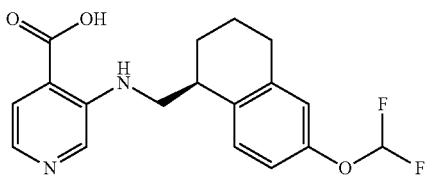 [SMILES: O=C(O)c1ccncc1NC[C@H]1CCCc2cc(OC(F)F)ccc21]

The title compound was prepared in 71% yield from Preparation 60d according to the procedure for Example 1. $^1$H NMR (400 MHz, DMSO-d$_6$): δ 1.65-1.70 (m, 1H), 1.76-1.87 (m, 3H), 2.67-2.80 (m, 2H), 3.08-3.14 (m, 1H), 3.43-3.48 (m, 1H), 3.55-3.60 (m, 1H), 6.92-6.95 (m, 2H), 7.18 (t, J=74.8 Hz, 1H), 7.36 (s, 1H), 7.56 (d, J=4.8 Hz, 1H), 7.84 (d, J=4.8 Hz, 1H), 8.38 (s, 1H). [M+H] Calc'd for C$_{18}$H$_{18}$F$_2$N$_2$O$_3$, 349; Found, 349.

Example 61

3-({[(1R)-6-(difluoromethoxy)-1,2,3,4-tetrahydronaphthalen-1-yl]methyl}amino)pyridine-4-carboxylic acid

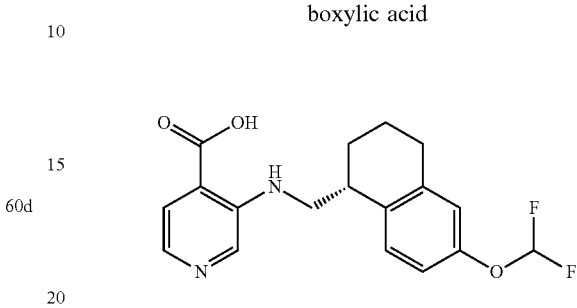

The title compound was prepared in 78% yield from Preparation 61d according to the procedure for Example 1. $^1$H NMR (400 MHz, DMSO-d$_6$): δ 1.64-1.71 (m, 1H), 1.74-1.88 (m, 3H), 2.67-2.80 (m, 2H), 3.09-3.12 (m, 1H), 3.42-3.48 (m, 1H), 3.55-3.60 (m, 1H), 6.92-6.95 (m, 2H), 7.18 (t, J=74.4 Hz, 1H), 7.36 (s, 1H), 7.56 (d, J=4.8 Hz, 1H), 7.84 (d, J=4.8 Hz, 1H), 8.38 (s, 1H). [M+H] Calc'd for C$_{18}$H$_{18}$F$_2$N$_2$O$_3$, 349; Found, 349.

Preparation 62a

6-[2-(trifluoromethyl)phenoxy]-1,2,3,4-tetrahydronaphthalen-1-one

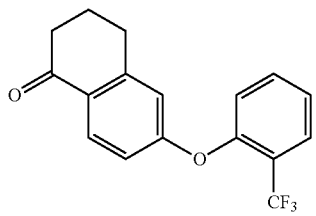 [SMILES: O=C1CCCc2cc(Oc3ccccc3C(F)(F)F)ccc21]

To a solution of 6-hydroxy-1-tetralone (2.5 g, 15.4 mmol) and 2-iodobenzotrifluoride (25 g, 92 mmol) in DMF (50 mL) was added NaH (0.74 g, 60%, 18.5 mmol) at rt. The mixture was heated to 50° C. until the solid was dissolved and then cooled. To the mixture was added CuCl (1.53 g, 15.4 mmol), followed by tris(dioxa 3,6-heptyl)amine (1.65 mL, 5.15 mmol). The mixture was heated at 145° C. overnight. The reaction was diluted with water, extracted with EtOAc, washed with brine, dried (Na$_2$SO$_4$), and concentrated. Purification by silica gel chromatography (0-20% EtOAc/hexanes) gave 850 mg (18%) of the title compound as a yellow oil. $^1$H NMR (400 MHz, CDCl$_3$): δ 2.09-2.16 (2H, m), 2.63 (2H, t, J=6.2 Hz), 2.91 (2H, t, J=6.1 Hz), 6.82 (1H, d, J=2.4 Hz), 6.86 (dd, 1H, J=8.6, 2.4 Hz), 7.05 (1H, d, J=8.2 Hz), 7.27 (1H, td, J=8.2, 0.6 Hz), 7.51-7.56 (1H, m), 7.71 (1H, dd, J=7.8, 1.2 Hz), 8.07 (1H, d, J=8.2 Hz). [M+H] calc'd for C$_{17}$H$_{13}$F$_3$O$_2$, 307; Found 307.

Preparation 62b

{6-[2-(trifluoromethyl)phenoxy]-3,4-dihydronaphthalen-1-yl}methanamine, hydrochloride

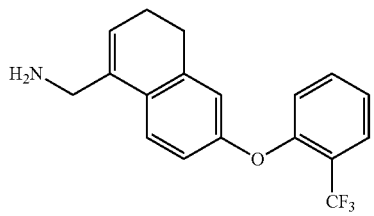 [SMILES: NCC1CCCc2cc(Oc3ccccc3C(F)(F)F)ccc21]

The title compound was prepared in 58% yield from Preparation 62a according to the general procedure for Preparation 3a. [M+H] calc'd for $C_{18}H_{16}F_3NO$, 320; Found 320.

Preparation 62c

{6-[2-(trifluoromethyl)phenoxy]-1,2,3,4-tetrahydronaphthalen-1-yl}methanamine

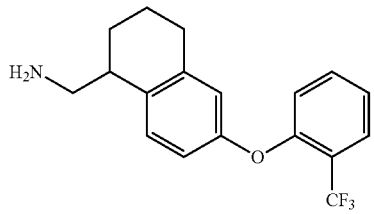

The title compound was prepared in quantitative yield from Preparation 62b according to the general procedure for Preparation 3e. $^1$H NMR (400 MHz, CD$_3$OD): δ 1.68-1.92 (4H, m), 2.68-2.72 (2H, m), 2.82-2.96 (3H, m), 6.72 (1H, d, J=2.2 Hz), 6.78 (1H, dd, J=8.3, 2.4 Hz), 6.90 (1H, d, J=8.2 Hz), 7.15-7.23 (2H, m), 7.47 (1H, t, J=7.2 Hz), 7.66 (1H, d, J=7.6 Hz). [M+H] calc'd for $C_{18}H_{18}F_3NO$, 322; Found 322.

Example 62

3-[({6-[2-(trifluoromethyl)phenoxy]-1,2,3,4-tetrahydronaphthalen-1-yl}methyl)amino]pyridine-4-carboxylic acid

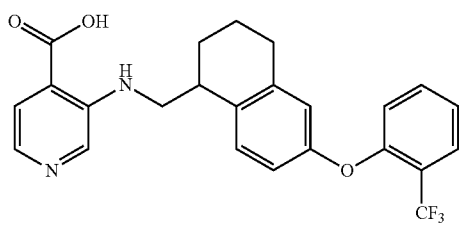 [SMILES: O=C(O)c1ccncc1NCC1CCCc2cc(Oc3ccccc3C(F)(F)F)ccc21]

The title compound was prepared in 15% yield from Preparation 62c according to the general procedure for Example 13. $^1$H NMR (400 MHz, DMSO-d$_6$): δ 1.66-1.85 (4H, m), 2.67-2.79 (2H, m), 3.11-3.14 (1H, m), 3.44-3.63 (2H, m), 6.80-6.82 (2H, m), 6.98 (1H, d, J=8.4), 7.29 (1H, t, J=7.6 Hz), 6.37 (1H, d, J=9.2 Hz), 7.5 (1H, d, J=5.0 Hz), 7.63 (1H, t, J=7.4 Hz), 7.70 (1H, br s), 7.76 (1H, d, J=7.8 Hz), 7.83 (1H, d, J=5.0 Hz), 8.36 (1H, s), 13.34 (1H, br s). [M+H] calc'd for $C_{24}H_{21}F_3N_2O_3$, 443; Found 443.

Preparation 63a 6-(oxan-4-ylmethoxy)-1,2,3,4-tetrahydronaphthalen-1-one

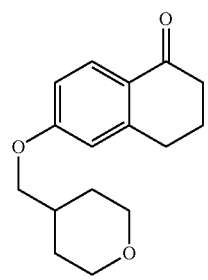 [SMILES: O=C1CCCc2cc(OCC3CCOCC3)ccc21]

To a suspension of 6-hydroxy-1-tetralone (2.0 g, 12.4 mmol), tetrahydropyran-4-methanol (1.7 g, 14.8 mmol) and triphenylphosphine (6.5 g, 24.7 mmol) in THF (40 mL) was added DEAD (4.3 g, 24.7 mmol) at 0° C. The reaction was stirred at rt overnight. The solution was concentrated and purified by silica gel chromatography (PE:EtOAc=12:1) to give 3.2 g (100%) of the title compound as a yellow oil. [M+H] Calc'd for $C_{16}H_{20}O_3$, 261; Found, 261.

Preparation 63b

[6-(oxan-4-ylmethoxy)-3,4-dihydronaphthalen-1-yl]methanamine, hydrochloride

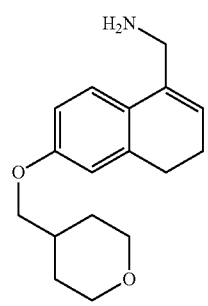 [SMILES: NCC1=CCCc2cc(OCC3CCOCC3)ccc21]

The title compound was prepared in 71% yield from Preparation 63a according to the general procedure for Preparation 3a. [M+H] Calc'd for $C_{17}H_{23}NO_2$, 274. Found, 274.

Preparation 63c

[6-(oxan-4-ylmethoxy)-1,2,3,4-tetrahydronaphthalen-1-yl]methanamine

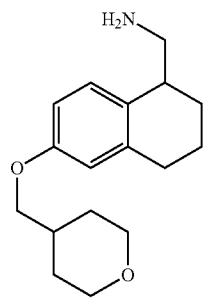 [SMILES: NCC1CCCc2cc(OCC3CCOCC3)ccc21]

The title compound was prepared in quantitative yield from Preparation 63b according to the general procedure for Preparation 3e. [M+H] Calc'd for $C_{17}H_{25}NO_2$, 276; Found, 276.

Example 63

3-({[6-(oxan-4-ylmethoxy)-1,2,3,4-tetrahydronaphthalen-1-yl]methyl}amino)pyridine-4-carboxylic acid

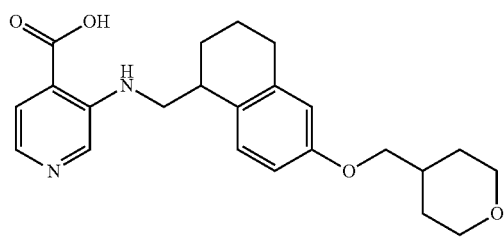 [SMILES: O=C(O)c1ccncc1NCC1CCCc2cc(OCC3CCOCC3)ccc21]

The title compound was prepared in 5% yield from Preparation 63c according to the general procedure for Example 13. $^1$H NMR (300 MHz, DMSO-$d_6$): δ 1.28-1.33 (2H, m), 1.64-1.77 (6H, m), 1.80-1.84 (1H, m), 2.67-2.70 (2H, m), 3.03-3.05 (1H, m), 3.28-3.45 (3H, m), 3.51-3.52 (1H, m), 3.77 (2H, d, J=6.3 Hz), 3.84-3.89 (2H, m), 6.65-6.71 (2H, m), 7.20 (1H, d, J=8.4 Hz), 7.55 (1H, d, J=5.4 Hz), 7.82 (1H, d, J=5.4 Hz), 8.35 (1H, s). [M+H] Calc'd for $C_{23}H_{28}N_2O_4$, 397; Found, 397.

Preparation 64a 6-(4-fluoro-2-methylphenoxy)-1,2,3,4-tetrahydronaphthalen-1-one

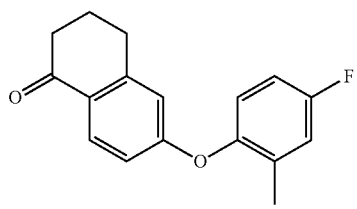 [SMILES: Cc1cc(F)ccc1Oc1ccc2c(c1)CCCC2=O]

To a suspension of 6-bromo-1,2,3,4-tetrahydronaphthalen-1-one (2.0 g, 8.9 mmol), 4-fluoro-2-methylphenol (1.7 g, 13.3 mmol), 1-pyridin-2-ylacetone (240 mg, 1.8 mmol) and $Cs_2CO_3$ (5.8 g, 17.8 mmol) in DMSO (40 mL) was added CuBr (127 mg, 0.9 mmol) at rt under $N_2$. The reaction was stirred at 100° C. overnight. The reaction was cooled, diluted with water (50 mL), and extracted with EtOAc (3×50 mL). Organics were washed with water (3×50 mL) and brine (50 mL), dried ($Na_2SO_4$), and concentrated. Purification by silica gel chromatography (PE:EtOAc=30:1) gave 2.3 g (95%) of the title compound as a colorless oil. [M+H] Calc'd for $C_{17}H_{15}FO_2$, 271; Found, 271.

Preparation 64b 6-(4-fluoro-2-methylphenoxy)-3,4-dihydronaphthalene-1-carboxamide

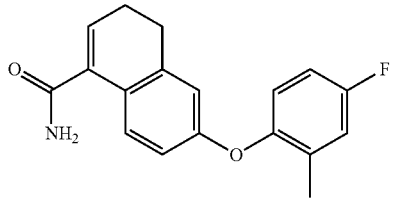 [SMILES: Cc1cc(F)ccc1Oc1ccc2c(c1)CCC=C2C(N)=O]

To a solution of Preparation 64a (2.3 g, 8.4 mmol) in toluene (20 mL) was added $ZnI_2$ (20 mg) and TMSCN (2.2 mL, 16.8 mmol) at rt, and the solution was stirred at 60° C. overnight. The reaction was cooled to rt. $H_2SO_4$ (1.0 mL) was added, followed by AcOH (12 mL), $H_2SO_4$ (4.3 mL), and $H_2O$ (1.3 mL). The reaction was heated to 130° C. for 6 h. The solution was cooled, diluted with $H_2O$ (50 mL), and extracted with EtOAc (3×50 mL). Organics were washed with brine (50 mL), dried ($Na_2SO_4$), and concentrated. Purification by silica gel chromatography (PE:THF=1:1) gave 500 mg (20%) of the title compound as a white solid. [M+H] Calc'd for $C_{18}H_{16}FNO_2$, 298; Found, 298.

Preparation 64c (1R)-6-(4-fluoro-2-methylphenoxy)-1,2,3,4-tetrahydronaphthalene-1-carboxamide

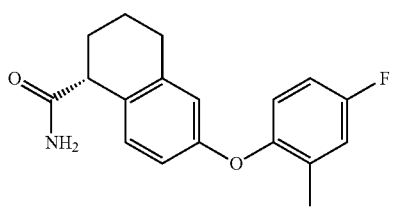 [SMILES: Cc1cc(F)ccc1Oc1ccc2c(c1)CCC[C@H]2C(N)=O]

To a solution of Preparation 64b (400 mg, 1.4 mmol) in MeOH (10 mL) and THF (10 mL) was added Ru(OAc)$_2$[s-binap] (5 mg) at rt. The mixture was heated at 50° C. for 2 days with 2.5 MPa $H_2$. The reaction was concentrated and the resulting solid was re-crystallized from EtOAc to give 120 mg (30%) of the title compound as a white solid. [M+H] Calc'd for $C_{18}H_{18}FNO_2$, 300; Found, 300. Column: Chiralcel AS-H, Mobile phase: 70:30 $CO_2$:MeOH (0.2 DEA), ee=97%, 3.04 min.

Preparation 64d

[(1R)-6-(4-fluoro-2-methylphenoxy)-1,2,3,4-tetrahydronaphthalen-1-yl]methanamine

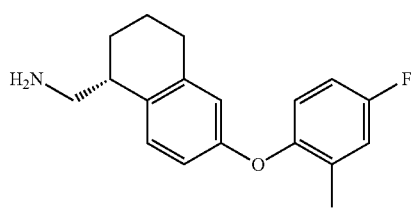 [SMILES: Cc1cc(F)ccc1Oc1ccc2c(c1)CCC[C@H]2CN]

To a solution of Preparation 64c (150 mg, 0.50 mmol) in THF (10 mL) was added BH$_3$.THF (2.5 mL, 1.0 M, 2.5 mmol) at rt. The mixture was heated at 55° C. for 6 h. The reaction was cooled, diluted with water (10 mL), basified to pH 9 with sat. Na$_2$CO$_3$, and extracted with EtOAc (3×50 mL). Organics were washed with brine (50 mL), dried (Na$_2$SO$_4$), and concentrated to give 160 mg (quant.) of the crude title compound as a yellow oil. [M+H] Calc'd for C$_{18}$H$_{20}$FNO, 286; Found, 286.

Preparation 64e methyl 3-({[(1R)-6-(4-fluoro-2-methylphenoxy)-1,2,3,4-tetrahydronaphthalen-1-yl]methyl}amino)pyridine-4-carboxylate

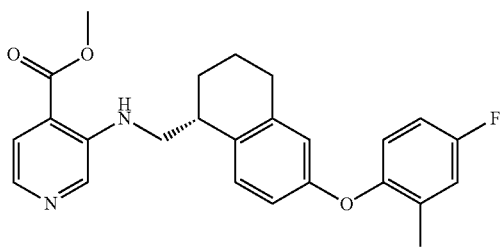 [SMILES: COC(=O)c1ccncc1NC[C@@H]1CCCc2cc(Oc3ccc(F)cc3C)ccc21]

To a suspension of Preparation 64d (0.50 mmol), methyl 3-bromoisonicotinate (119 mg, 0.55 mmol), Xantphos (43 mg, 0.08 mmol) and Cs$_2$CO$_3$ (228 mg, 0.70 mmol) in toluene (15 mL) was added Pd$_2$dba$_3$ (23 mg, 0.03 mmol) at rt under N$_2$. The reaction was stirred at 100° C. for 2 h. The reaction was filtered and concentrated. Purification by silica gel chromatography (PE:EtOAc=5:1) gave 88 mg (42%) of the title compound as a yellow oil. [M+H] Calc'd for C$_{25}$H$_{25}$FN$_2$O$_3$, 421; Found, 421.

Example 64

3-({[(1R)-6-(4-fluoro-2-methylphenoxy)-1,2,3,4-tetrahydronaphthalen-1-yl]methyl}amino)pyridine-4-carboxylic acid

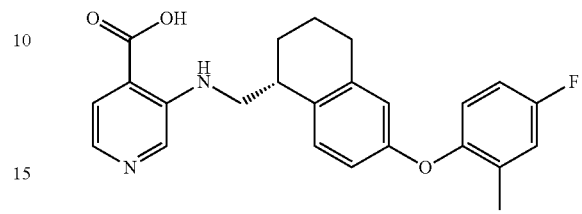

The title compound was prepared in 60% yield from Preparation 64e according to the procedure for Example 1. $^1$H NMR (400 MHz, DMSO-d$_6$): δ 1.64-1.67 (1H, m), 1.77-1.83 (3H, m), 2.16 (3H, s), 2.65-2.68 (2H, m), 3.05-3.09 (1H, m), 3.40-3.46 (1H, m), 3.54-3.59 (1H, m), 6.59 (1H, s), 6.63 (1H, dd, J=2.8, 8.4 Hz), 6.92 (1H, dd, J=5.2, 8.8 Hz), 7.04 (1H, td, J=2.8, 8.4 Hz), 7.19 (1H, dd, J=2.8, 8.2 Hz), 7.28 (1H, d, J=8.4 Hz), 7.56 (1H, d, J=5.2 Hz), 7.82 (1H, d, J=4.8 Hz), 8.34 (1H, s). [M+H] Calc'd for C$_{24}$H$_{23}$FN$_2$O$_3$, 407; Found, 407.

Preparation 65a 6-(2,4-difluorophenoxy)-1,2,3,4-tetrahydronaphthalen-1-one

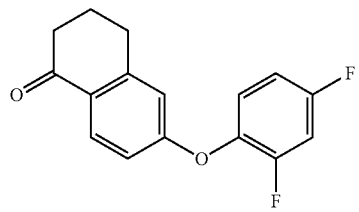 [SMILES: O=C1CCCc2cc(Oc3ccc(F)cc3F)ccc21]

The title compound was prepared in 65% yield from 2,4-difluorophenol according to the procedure for Preparation 64a. [M+H] Calc'd for C$_{16}$H$_{12}$F$_2$O$_2$, 275; Found, 275.

Preparation 65b 6-(2,4-difluorophenoxy)-3,4-dihydronaphthalene-1-carboxamide

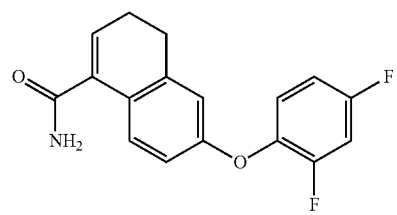 [SMILES: NC(=O)C1=CCCc2cc(Oc3ccc(F)cc3F)ccc21]

The title compound was prepared in 44% yield from Preparation 65a according to the procedure for Preparation 64b. [M+H] Calc'd for $C_{17}H_{13}F_2NO_2$, 302; Found, 302.

Preparation 65c (1R)-6-(2,4-difluorophenoxy)-1,2,3,4-tetrahydronaphthalene-1-carboxamide

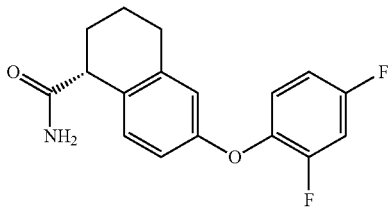 [SMILES: NC(=O)[C@@H]1CCCc2cc(Oc3ccc(F)cc3F)ccc21]

The title compound was prepared in 46% yield from Preparation 65b according to the procedure for Preparation 64c. [M+H] Calc'd for $C_{17}H_{15}F_2NO_2$, 304; Found, 304.

Preparation 65d

[(1R)-6-(2,4-difluorophenoxy)-1,2,3,4-tetrahydronaphthalen-1-yl]methanamine

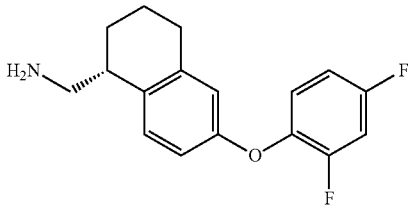 [SMILES: NC[C@@H]1CCCc2cc(Oc3ccc(F)cc3F)ccc21]

The title compound was prepared in 89% yield from Preparation 65c according to the procedure for Preparation 64d. [M+H] Calc'd for $C_{17}H_{17}F_2NO$, 290; Found, 290.

Preparation 65e methyl 3-({[(1R)-6-(2,4-difluorophenoxy)-1,2,3,4-tetrahydronaphthalen-1-yl]methyl}amino)pyridine-4-carboxylate

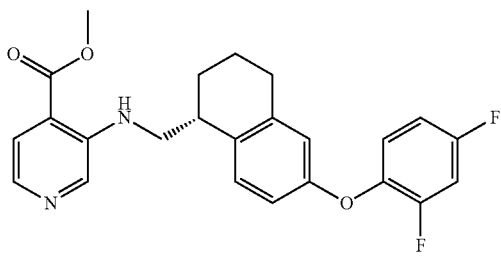

The title compound was prepared in 52% yield from Preparation 65d according to the procedure for Preparation 64e. [M+H] Calc'd for $C_{24}H_{22}F_2N_2O_3$, 425; Found, 425.

Preparation 65

3-({[(1R)-6-(2,4-difluorophenoxy)-1,2,3,4-tetrahydronaphthalen-1-yl]methyl}amino)pyridine-4-carboxylic acid

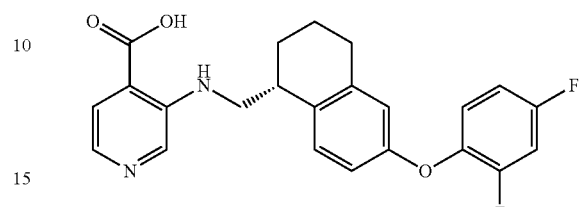

The title compound was prepared in 67% yield from Preparation 65e according to the procedure for Example 1. $^1$H NMR (400 MHz, DMSO-$d_6$): δ 1.64-1.67 (1H, m), 1.80-1.83 (3H, m), 2.66-2.69 (2H, m), 3.06-3.09 (1H, m), 3.40-3.45 (1H, m), 3.53-3.58 (1H, m), 6.67 (1H, d, J=2.4 Hz), 6.71-6.74 (1H, m), 7.11-7.13 (1H, m), 7.19-7.25 (1H, s), 7.30 (1H, d, J=8.4 Hz), 7.44-7.49 (1H, m), 7.55 (1H, d, J=5.2 Hz), 7.81 (1H, d, J=5.2 Hz), 8.33 (1H, s). [M+H] Calc'd for $C_{23}H_{20}F_2N_2O_3$, 411; Found, 411.

Preparation 66a 6-(2-fluoro-4-methylphenoxy)-1,2,3,4-tetrahydronaphthalen-1-one

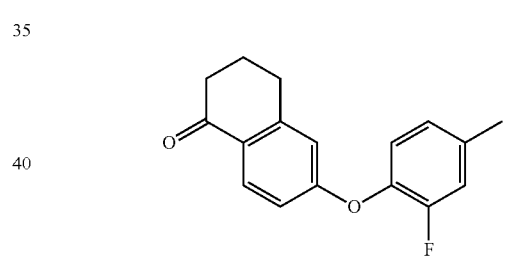

The title compound was prepared in 54% yield from 2-fluoro-4-methylphenol according to the procedure for Preparation 64a. [M+H] Calc'd for $C_{17}H_{15}FO_2$, 271; Found, 271.

Preparation 66b

[6-(2-fluoro-4-methylphenoxy)-3,4-dihydronaphthalen-1-yl]methanamine, hydrochloride

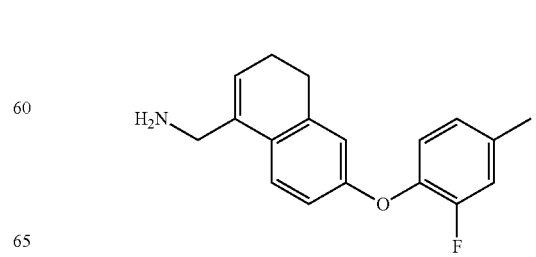

The title compound was prepared in 78% yield from Preparation 66a according to the procedure for Preparation 3a. [M+H] Calc'd for $C_{18}H_{18}FNO$, 284; Found, 284.

Preparation 66c

[6-(2-fluoro-4-methylphenoxy)-1,2,3,4-tetrahydronaphthalen-1-yl]methanamine

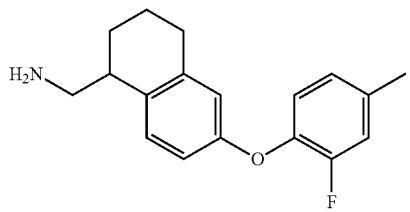 [SMILES: Cc1ccc(Oc2ccc3c(c2)CCCC3CN)c(F)c1]

The title compound was prepared in 92% yield from Preparation 66b according to the procedure for Preparation 3e. [M+H] Calc'd for $C_{18}H_{20}FNO$, 286; Found, 286.

Preparation 66d methyl 3-({[(1S)-6-(2-fluoro-4-methylphenoxy)-1,2,3,4-tetrahydronaphthalen-1-yl]methyl}amino)pyridine-4-carboxylate; and Preparation 66e methyl 3-({[(1R)-6-(2-fluoro-4-methylphenoxy)-1,2,3,4-tetrahydronaphthalen-1-yl]methyl}amino)pyridine-4-carboxylate

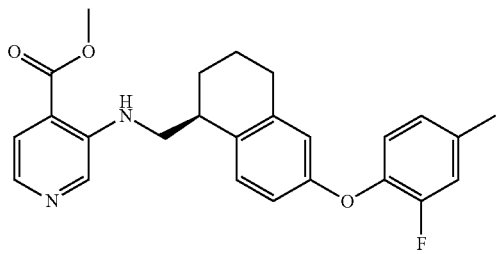

66d

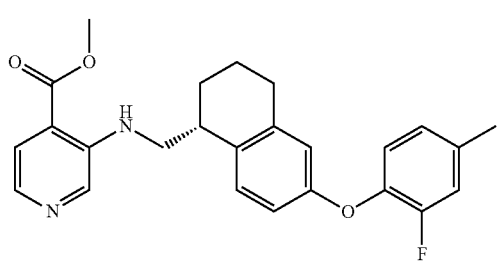

66e

The racemate of the title compounds was prepared in 57% yield from Preparation 66c according to the general procedure for Preparation 1e. Separation by chiral HPLC (Column: Chiralcel: IA 5 um 4.6*250 mm, Mobile phase: Hex:EtOH=70:30, F: 1.0 mL/min, W: 230 nm, T: 30° C.) gave 29% yield of Preparation 66e (6.855 min) and 29% of Preparation 66d (8.064 min), each as a yellow oil. [M+H] Calc'd for $C_{25}H_{25}FN_2O_3$, 421; Found, 421.

Example 66

3-({[(1R)-6-(2-fluoro-4-methylphenoxy)-1,2,3,4-tetrahydronaphthalen-1-yl]methyl}amino)pyridine-4-carboxylic acid

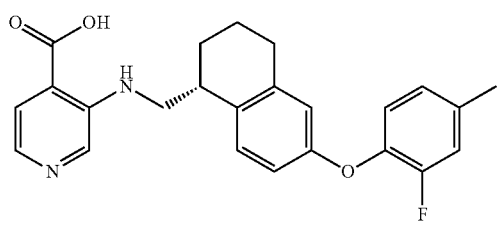 [SMILES: Cc1ccc(Oc2ccc3c(c2)CCC[C@H]3CNc2cnccc2C(=O)O)c(F)c1]

The title compound was prepared in 83% yield from Preparation 66e according to the procedure for Example 1. $^1$H NMR (400 MHz, DMSO-d$_6$): δ 1.64-1.83 (4H, m), 2.32 (3H, s), 2.65-2.69 (2H, m), 3.06-3.09 (1H, m), 3.41-3.47 (1H, m), 3.54-3.59 (1H, m), 6.64 (1H, s), 6.69-6.72 (1H, m), 7.03-7.06 (2H, m), 7.20 (1H, d, J=12.0 Hz), 7.29 (1H, d, J=8.4 Hz), 7.57 (1H, d, J=5.2 Hz), 7.84 (1H, d, J=5.2 Hz), 8.37 (1H, s). [M+H] Calc'd for $C_{24}H_{23}FN_2O_3$, 407; Found, 407.

Preparation 67a 6-(2-chlorophenoxy)-1,2,3,4-tetrahydronaphthalen-1-one

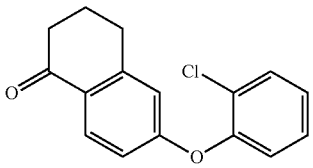 [SMILES: O=C1CCCc2cc(Oc3ccccc3Cl)ccc21]

The title compound was prepared in 64% yield from 2-chlorophenol according to the procedure for Preparation 64a. $^1$H NMR (400 MHz, CDCl$_3$): δ 2.09-2.15 (m, 2H), 2.62 (t, J=6.4 Hz, 2H), 2.90 (t, J=6.0 Hz, 2H), 6.71 (d, J=2.4 Hz, 1H), 6.81 (dd, J=8.4 Hz, 2.4 Hz, 1H), 7.11 (dd, J=8.4 Hz, 1.2 Hz, 1H), 7.17-7.22 (m, 1H), 7.28-7.33 (m, 1H), 7.50 (dd, J=8.0 Hz, 1.6 Hz, 1H), 8.02 (d, J=8.4 Hz, 1H). [M+H] Calc'd for $C_{16}H_{13}ClO_2$, 273; Found, 273.

Preparation 67b 6-(2-chlorophenoxy)-3,4-dihydronaphthalene-1-carboxamide

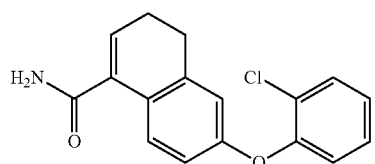

The title compound was prepared in 32% yield from Preparation 67a according to the procedure for Preparation 64b. [M+H] Calc'd for $C_{17}H_{14}ClNO_2$, 300; Found, 300.

Preparation 67c (1R)-6-(2-chlorophenoxy)-1,2,3,4-tetrahydronaphthalene-1-carboxamide

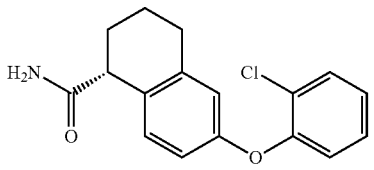 [SMILES: NC(=O)[C@@H]1CCCc2cc(Oc3ccccc3Cl)ccc21]

The title compound was prepared in 52% yield from Preparation 67b according to the procedure for Preparation 64c. [M+H] Calc'd for $C_{17}H_{16}ClNO_2$, 302; Found, 302.

Preparation 67d

[(1R)-6-(2-chlorophenoxy)-1,2,3,4-tetrahydronaphthalen-1-yl]methanamine

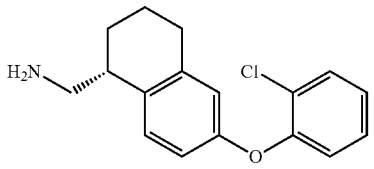 [SMILES: NC[C@@H]1CCCc2cc(Oc3ccccc3Cl)ccc21]

The title compound was prepared in 88% yield from Preparation 67c according to the procedure for Preparation 64d. [M+H] Calc'd for $C_{17}H_{18}ClNO$, 288; Found, 288.

Preparation 67e methyl 3-({[(1R)-6-(2-chlorophenoxy)-1,2,3,4-tetrahydronaphthalen-1-yl]methyl}amino)pyridine-4-carboxylate

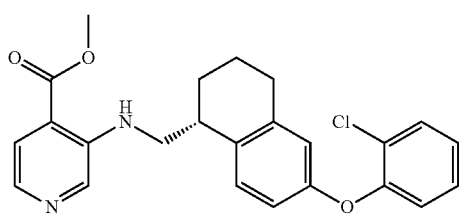 [SMILES: COC(=O)c1ccncc1NC[C@@H]1CCCc2cc(Oc3ccccc3Cl)ccc21]

The title compound was prepared in 31% yield from Preparation 67d according to the procedure for Preparation 64e. [M+H] Calc'd for $C_{24}H_{23}ClN_2O_3$, 423; Found, 423.

Example 67

3-({[(1R)-6-(2-chlorophenoxy)-1,2,3,4-tetrahydronaphthalen-1-yl]methyl}amino)pyridine-4-carboxylic acid

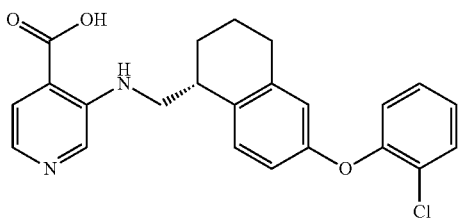 [SMILES: O=C(O)c1ccncc1NC[C@@H]1CCCc2cc(Oc3ccccc3Cl)ccc21]

The title compound was prepared in 41% yield from Preparation 67e according to the procedure for Example 1. $^1$H NMR (400 MHz, DMSO-$d_6$): δ 1.66-1.70 (m, 1H), 1.78-1.85 (m, 3H), 2.65-2.75 (m, 2H), 3.09-3.13 (m, 1H), 3.41-3.49 (m, 1H), 3.56-3.61 (m, 1H), 670-6.74 (m, 2H), 7.04 (dd, J=8.4 Hz, 0.8 Hz, 1H), 7.18-7.22 (m, 1H), 7.32-7.37 (m, 2H), 7.56 (d, J=5.2 Hz, 1H), 7.59 (dd, J=8.0 Hz, 1.2 Hz, 1H), 7.83 (d, J=5.2 Hz, 1H), 8.36 (s, 1H). [M+H] Calc'd for $C_{23}H_{21}ClN_2O_3$, 409; Found, 409.

Preparation 68a

6-[(3-methylphenyl)sulfanyl]-1,2,3,4-tetrahydronaphthalen-1-one

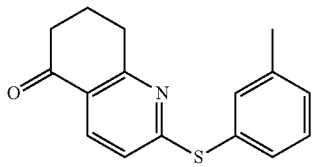 [SMILES: Cc1cccc(Sc2ccc3c(n2)CCCC3=O)c1]

The suspension of 5-oxo-5,6,7,8-tetrahydronaphthalen-2-yl trifluoromethanesulfonate (1.8 g, 6.1 mmol), 3-methylbenzene-1-thiol (0.76 g, 6.1 mmol), Pd$_2$(dba)$_3$ (142 mg, 0.153 mmol), Xantphos (177 mg, 0.306 mmol) and DIEA (1.58 g, 12.2 mmol) in 1,4-dioxane (60 mL) was stirred at reflux overnight under N$_2$. The reaction was filtered and concentrated. Purification by silica gel chromatography (PE: EtOAc=5:1) gave 1.8 g (100%) of the title compound as an orange oil. [M+H] Calc'd for $C_{17}H_{16}OS$, 269; Found, 269.

Preparation 68b

{6-[(3-methylphenyl)sulfanyl]-3,4-dihydronaphthalen-1-yl}methanamine, hydrochloride

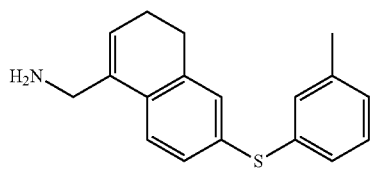

The title compound was prepared in 69% yield from Preparation 68a according to the general procedure for Preparation 3a. [M+H] Calc'd for $C_{18}H_{19}NS$, 282. Found, 282.

Preparation 68c

{6-[(3-methylphenyl)sulfanyl]-1,2,3,4-tetrahydronaphthalen-1-yl}methenamine

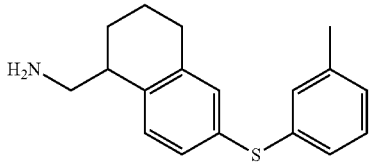 [SMILES: Cc1cccc(Sc2ccc3c(c2)CCCC3CN)c1]

The title compound was prepared in 92% yield from Preparation 68b according to the general procedure for Preparation 3e. [M+H] Calc'd for $C_{18}H_{21}NS$, 284; Found, 284.

Preparation 68d methyl 3-({[(1S)-6-[(3-methylphenyl)sulfanyl]-1,2,3,4-tetrahydronaphthalen-1-yl]methyl}amino)pyridine-4-carboxylate; and Preparation 69d methyl 3-({[(1R)-6-[(3-methylphenyl)sulfanyl]-1,2,3,4-tetrahydronaphthalen-1-yl]methyl}amino)pyridine-4-carboxylate

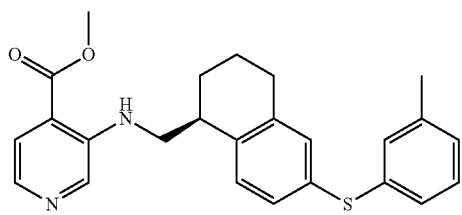

68d

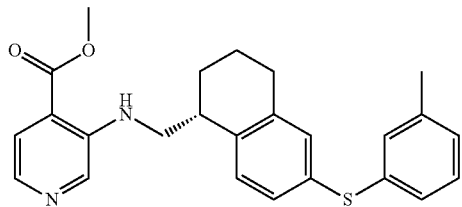

69d

The racemate of the title compounds was prepared in 25% yield from Preparation 68c according to the general procedure for Preparation 1e. [M+H] Calc'd for $C_{25}H_{26}N_2O_2S$, 419; Found, 419.
Separation by chiral HPLC (Column: Chiralcel: IA 5 um 4.6*250 mm, Mobile phase: Hex:EtOH=50:50, F: 1.0 mL/min, W: 230 nm, T: 30° C.) gave 38% yield of Preparation 68d (6.259 min) and 37% of Preparation 69d (6.802 min), each as a yellow oil.

Example 68

3-({[(1S)-6-[(3-methylphenyl)sulfanyl]-1,2,3,4-tetrahydronaphthalen-1-yl]methyl}amino)pyridine-4-carboxylic acid

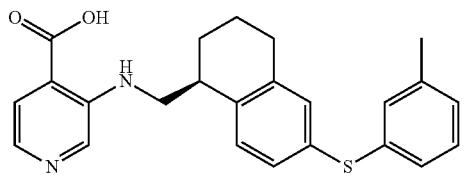 [SMILES: Cc1cccc(Sc2ccc3c(c2)CCC[C@@H]3CNc2cnccc2C(=O)O)c1]

The title compound was prepared in 80% yield from Preparation 68d according to the general procedure for Example 1. $^1$H NMR (300 MHz, DMSO-d$_6$): δ 1.65-1.85 (4H, m), 2.27 (3H, s), 2.67-2.73 (2H, m), 3.10-3.12 (1H, m), 3.46-3.49 (1H, m), 3.56-3.57 (1H, m), 7.05-7.15 (5H, m), 7.22-7.27 (1H, m), 7.32-7.35 (1H, m), 7.55 (1H, d, J=5.1 Hz), 7.83-7.84 (1H, m), 8.35 (1H, s). [M+H] Calc'd for $C_{24}H_{24}N_2O_2S$, 405; Found, 405.

Example 69

3-({[(1R)-6-[(3-methylphenyl)sulfanyl]-1,2,3,4-tetrahydronaphthalen-1-yl]methyl}amino)pyridine-4-carboxylic acid

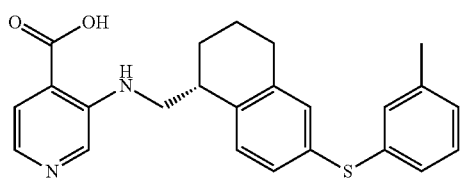 [SMILES: Cc1cccc(Sc2ccc3c(c2)CCC[C@H]3CNc2cnccc2C(=O)O)c1]

The title compound was prepared in 83% yield from Preparation 69d according to the general procedure for Example 1. $^1$H NMR (400 MHz, DMSO-d$_6$): δ 1.65-1.85 (4H, m), 2.27 (3H, s), 2.67-2.71 (2H, m), 3.09-3.14 (1H, m), 3.46-3.50 (1H, m), 3.56-3.57 (1H, m), 7.05-7.15 (5H, m), 7.22-7.27 (1H, m), 7.33 (1H, d, J=7.8 Hz), 7.55 (1H, d, J=4.8 Hz), 7.83 (1H, d, J=4.8 Hz), 8.36 (1H, s). [M+H] Calc'd for $C_{24}H_{24}N_2O_2S$, 405; Found, 405.

Preparation 70a

6-[(2-methylphenyl)sulfanyl]-1,2,3,4-tetrahydronaphthalen-1-one

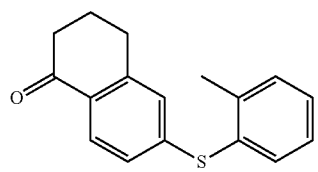

The title compound was prepared in 92% yield from 3-methylbenzene-1-thiol according to the general procedure for Preparation 68a. [M+H] Calc'd for $C_{17}H_{16}OS$, 269; Found, 269.

Preparation 70b

{6-[(2-methylphenyl)sulfanyl]-3,4-dihydronaphthalen-1-yl}methanamine, hydrochloride

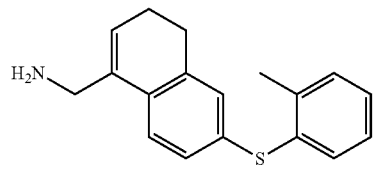

The title compound was prepared in 89% yield from Preparation 68a according to the general procedure for Preparation 3a. [M+H] Calc'd for $C_{18}H_{19}NS$, 282; Found, 282.

Preparation 70c

{6-[(2-methylphenyl)sulfanyl]-1,2,3,4-tetrahydronaphthalen-1-yl}methenamine

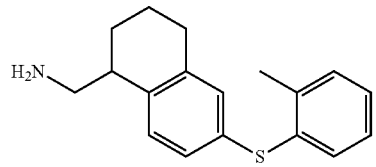 [SMILES: Cc1ccccc1Sc1ccc2c(c1)CCCC2CN]

The title compound was prepared in 88% yield from Preparation 70b according to the general procedure for Preparation 3e. [M+H] Calc'd for $C_{18}H_{21}NS$, 284; Found, 284.

Preparation 70d methyl 3-({[(1S)-6-[(2-methylphenyl)sulfanyl]-1,2,3,4-tetrahydronaphthalen-1-yl]methyl}amino)pyridine-4-carboxylate; and

Preparation 70d methyl 3-({[(1R)-6-[(2-methylphenyl)sulfanyl]-1,2,3,4-tetrahydronaphthalen-1-yl]methyl}amino)pyridine-4-carboxylate

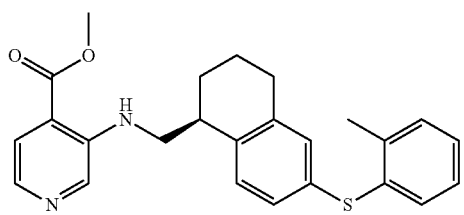

70d

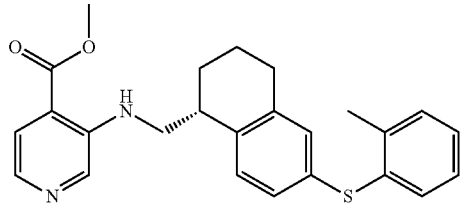

71d

The racemate (550 mg) of the title compounds was prepared in 37% yield from Preparation 70c according to the general procedure for Preparation 1e. [M+H] Calc'd for $C_{25}H_{26}N_2O_2S$, 419; Found, 419.

Separation by chiral HPLC (Column: Chiralcel: IC 5 um 4.6*250 mm, Mobile phase: Hex:EtOH=70:30, F: 1.0 mL/min, W: 230 nm, T: 30° C.) 160 mg (11%) of Preparation 70d (6.645 min) and 150 mg (10%) of Preparation 71d (7.659 min), each as a yellow oil.

Example 70

3-({[(1S)-6-[(2-methylphenyl)sulfanyl]-1,2,3,4-tetrahydronaphthalen-1-yl]methyl}amino)pyridine-4-carboxylic acid

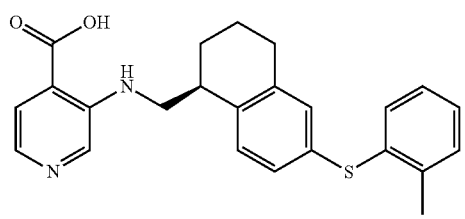

The title compound was prepared in 84% yield from Preparation 70d according to the general procedure for Example 1. $^1$H NMR (300 MHz, DMSO-d$_6$): δ 1.64-1.68 (1H, m), 1.77-1.84 (3H, m), 2.31 (3H, s), 2.67-2.70 (2H, m), 3.08-3.12 (1H, m), 3.42-3.49 (1H, m), 3.55-3.60 (1H, m), 6.95 (1H, d, J=7.8 Hz), 7.02 (1H, s), 7.12-7.25 (3H, m), 7.29-7.33 (2H, m), 7.55 (1H, d, J=5.1 Hz), 7.83 (1H, d, J=5.1 Hz), 8.35 (1H, s). [M+H] Calc'd for $C_{24}H_{24}N_2O_2S$, 405; Found, 405.

Example 71

3-({[(1R)-6-[(2-methylphenyl)sulfanyl]-1,2,3,4-tetrahydronaphthalen-1-yl]methyl}amino)pyridine-4-carboxylic acid

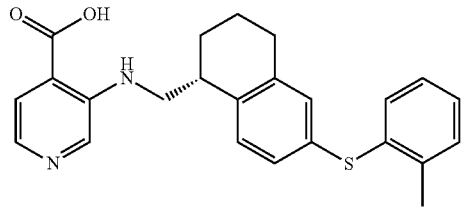

The title compound was prepared in 93% yield from Preparation 71d according to the general procedure for Example 1. $^1$H NMR (300 MHz, DMSO-d$_6$): δ 1.64-1.68 (1H, m), 1.77-1.84 (3H, m), 2.31 (3H, s), 2.67-2.70 (2H, m), 3.08-3.12 (1H, m), 3.42-3.49 (1H, m), 3.55-3.60 (1H, m), 6.95 (1H, d, J=7.8 Hz), 7.02 (1H, s), 7.12-7.25 (3H, m), 7.29-7.33 (2H, m), 7.55 (1H, d, J=5.1 Hz), 7.83 (1H, d, J=5.1 Hz), 8.35 (1H, s). [M+H] Calc'd for C$_{24}$H$_{24}$N$_2$O$_2$S, 405; Found, 405.

Preparation 72a

6-[(2-fluorophenyl)sulfanyl]-1,2,3,4-tetrahydronaphthalen-1-one

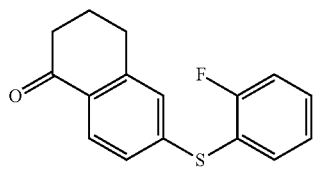 [SMILES: O=C1CCCc2cc(Sc3ccccc3F)ccc21]

To a suspension of 5-oxo-5,6,7,8-tetrahydronaphthalen-2-yl 4-methylbenzene-1-sulfonate (3.0 g, 10.2 mmol), 2,2'-difluorodiphenyldisulfide (1.0 mL, 5.1 mmol) and Zn (800 mg, 12.2 mmol) in THF (30 mL) was added Pd(dppf)Cl$_2$ (374 mg, 0.51 mmol) at rt under N$_2$. The reaction was stirred at reflux overnight. The reaction was filtered and concentrated. Purification by silica gel chromatography (PE:EtOAc=30:1 to 10:1) gave 2.4 g (86%) of the title compound as an off-white solid. $^1$H NMR (400 MHz, CDCl$_3$): δ 2.07-2.13 (m, 2H), 2.62 (t, J=6.4 Hz, 2H), 2.87 (t, J=6.0 Hz, 2H), 7.01-7.03 (m, 2H), 7.17-7.21 (m, 2H), 7.40-7.46 (m, 1H), 7.51 (dt, J=8.0 Hz, 1.2 Hz, 1H), 7.90 (d, J=8.8 Hz, 1H). [M+H] Calc'd for C$_{16}$H$_{13}$FOS, 273; Found, 273.

Preparation 72b

{6-[(2-fluorophenyl)sulfanyl]-3,4-dihydronaphthalen-1-yl}methanamine, hydrochloride

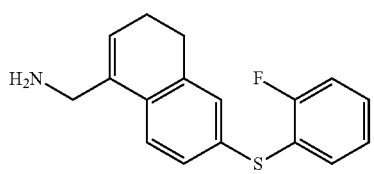

The title compound was prepared in 80% yield from Preparation 72a according to the general procedure for Preparation 3a. [M+H] Calc'd for C$_{17}$H$_{16}$FNS, 286; Found, 286.

Preparation 72c

{6-[(2-fluorophenyl)sulfanyl]-1,2,3,4-tetrahydronaphthalen-1-yl}methanamine

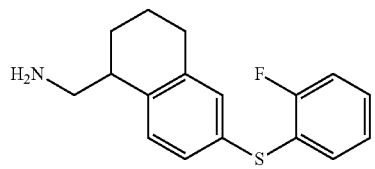 [SMILES: NCC1CCCc2cc(Sc3ccccc3F)ccc21]

The title compound was prepared in 71% yield from Preparation 72b according to the general procedure for Preparation 3e. [M+H] Calc'd for C$_{17}$H$_{18}$FNS, 288; Found, 288.

Preparation 72d methyl 3-({[(1S)-6-[(2-fluorophenyl)sulfanyl]-1,2,3,4-tetrahydronaphthalen-1-yl]methyl}amino)pyridine-4-carboxylate; and

Preparation 73d methyl 3-({[(1R)-6-[(2-fluorophenyl)sulfanyl]-1,2,3,4-tetrahydronaphthalen-1-yl]methyl}amino)pyridine-4-carboxylate

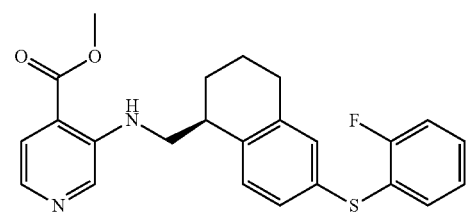

72d

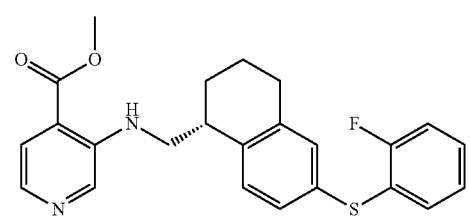

73d

The racemate (410 mg) of the title compounds was prepared in 28% yield from Preparation 72c according to the general procedure for Preparation 1e. [M+H] Calc'd for C$_{24}$H$_{23}$FN$_2$O$_2$S, 423; Found, 423.

Separation by chiral HPLC (Column: Chiralcel: IC 5 um 4.6*250 mm, Mobile phase: Hex:EtOH=70:30, F: 1.0 mL/min, W: 230 nm, T: 30° C.) gave 115 mg (28%) of Preparation 71d (7.352 min) and 114 mg (28%) of Preparation 72d (8.388 min), each as a colorless oil.

Example 72

3-({[(1S)-6-[(2-fluorophenyl)sulfanyl]-1,2,3,4-tetrahydronaphthalen-1-yl]methyl}amino)pyridine-4-carboxylic acid

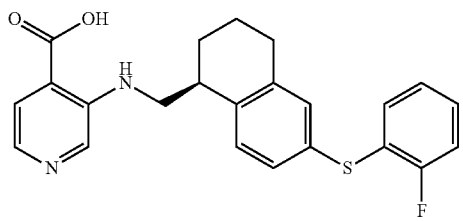 [SMILES: O=C(O)c1ccncc1NC[C@H]1CCCc2cc(Sc3ccccc3F)ccc21]

The title compound was prepared in 88% yield from Preparation 72d according to the general procedure for Example 1. $^1$H NMR (400 MHz, DMSO-$d_6$): δ 1.64-1.70 (m, 1H), 1.76-1.86 (m, 3H), 2.65-2.76 (m, 2H), 3.09-3.15 (m, 1H), 3.44-3.49 (m, 1H), 3.57-3.61 (m, 1H), 7.06-7.09 (m, 1H), 7.12 (s, 1H), 7.20-7.22 (m, 2H), 7.28-7.39 (m, 3H), 7.55 (d, J=4.8 Hz, 1H), 7.83 (d, J=4.8 Hz, 1H), 8.36 (s, 1H). [M+H] Calc'd for $C_{23}H_{21}FN_2O_2S$, 409; Found, 409.

Example 73

3-({[(1R)-6-[(2-fluorophenyl) sulfanyl]-1,2,3,4-tetrahydronaphthalen-1-yl]methyl}amino)pyridine-4-carboxylic acid

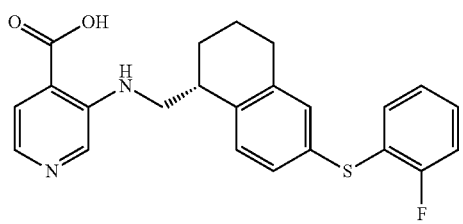 [SMILES: O=C(O)c1ccncc1NC[C@@H]1CCCc2cc(Sc3ccccc3F)ccc21]

The title compound was prepared in 50% yield from Preparation 73d according to the general procedure for Example 1. $^1$H NMR (400 MHz, DMSO-$d_6$): δ 1.64-1.69 (m, 1H), 1.78-1.85 (m, 3H), 2.65-2.76 (m, 2H), 3.10-3.14 (m, 1H), 3.44-3.50 (m, 1H), 3.57-3.61 (m, 1H), 7.07-7.09 (m, 1H), 7.12 (s, 1H), 7.18-7.24 (m, 2H), 7.28-7.41 (m, 3H), 7.55 (d, J=4.8 Hz, 1H), 7.83 (d, J=4.8 Hz, 1H), 8.36 (s, 1H). [M+H] Calc'd for $C_{23}H_{21}FN_2O_2S$, 409; Found, 409.

Preparation 74a

6-[(3-fluorophenyl)sulfanyl]-1,2,3,4-tetrahydronaphthalen-1-one

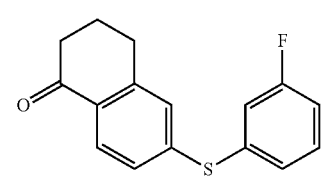

The title compound was prepared in 76% yield from 3,3'-difluorodiphenyldisulfide according to the general procedure for Preparation 72a. [M+H] Calc'd for $C_{16}H_{13}FOS$, 273; Found, 273.

Preparation 74b

{6-[(3-fluorophenyl)sulfanyl]-3,4-dihydronaphthalen-1-yl}methanamine, hydrochloride

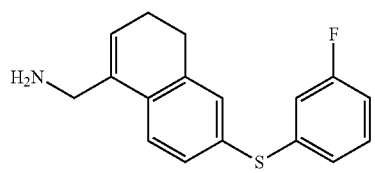

The title compound was prepared in 54% yield from Preparation 74a according to the general procedure for Preparation 3a. [M+H] Calc'd for $C_{17}H_{16}FNS$, 286; Found, 286.

Preparation 74c

{6-[(3-fluorophenyl)sulfanyl]-1,2,3,4-tetrahydronaphthalen-1-yl}methanamine

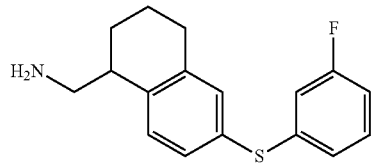 [SMILES: NCC1CCCc2cc(Sc3cccc(F)c3)ccc21]

The title compound was prepared in 75% yield from Preparation 74b according to the general procedure for Preparation 3e. [M+H] Calc'd for $C_{17}H_{18}FNS$, 288; Found, 288.

Preparation 74d methyl 3-({[(1S)-6-[(3-fluorophenyl) sulfanyl]-1,2,3,4-tetrahydronaphthalen-1-yl]methyl}amino)pyridine-4-carboxylate; and

Preparation 75d methyl 3-({[(1R)-6-[(3-fluorophenyl) sulfanyl]-1,2,3,4-tetrahydronaphthalen-1-yl]methyl}amino)pyridine-4-carboxylate

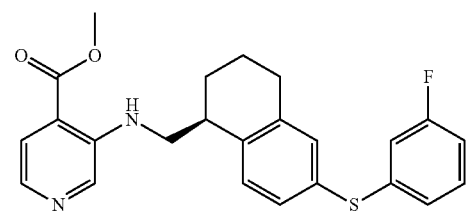

-continued

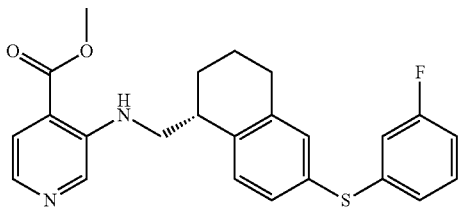

The racemate (600 mg) of the title compounds was prepared in 43% yield from Preparation 74c according to the general procedure for Preparation 1e. [M+H] Calc'd for C$_{24}$H$_{23}$FN$_2$O$_2$S, 423; Found, 423.
Separation by chiral HPLC (Column: Chiralcel: OD-H 5 um 4.6*250 mm, Mobile phase: Hex: EtOH:DEA=70:30:0.2, F: 1.0 mL/min, W: 230 nm, T: 30° C.) gave 80 mg (13%) of Preparation 74d (6.571 min) and 70 mg (12%) of Preparation 75d (7.213 min), each as a yellow oil.

Example 74

3-({[(1S)-6-[(3-fluorophenyl)sulfanyl]-1,2,3,4-tetrahydronaphthalen-1-yl]methyl}amino)pyridine-4-carboxylic acid

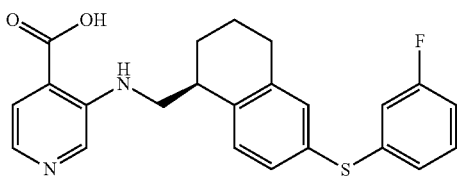

The title compound was prepared in 64% yield from Preparation 74d according to the general procedure for Example 1. $^1$H NMR (400 MHz, DMSO-d$_6$): δ 1.67-1.69 (1H, m), 1.79-1.83 (3H, m), 2.68-2.75 (2H, m), 3.10-3.12 (1H, m), 3.36-3.42 (1H, m), 3.53-3.58 (1H, m), 7.01-7.08 (3H, m), 7.19-7.22 (2H, m), 7.35-7.42 (2H, m), 7.57 (1H, d, J=4.4 Hz), 7.78 (1H, d, J=4.8 Hz), 8.23 (1H, s). [M+H] Calc'd for C$_{23}$H$_{21}$FN$_2$O$_2$S, 409; Found, 409.

Example 75

3-({[(1R)-6-[(3-fluorophenyl)sulfanyl]-1,2,3,4-tetrahydronaphthalen-1-yl]methyl}amino)pyridine-4-carboxylic acid

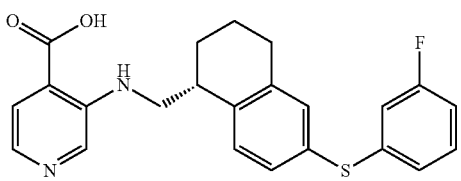

The title compound was prepared in 74% yield from Preparation 75d according to the general procedure for Example 1. $^1$H NMR (400 MHz, DMSO-d$_6$): δ 1.67-1.69 (1H, m), 1.79-1.83 (3H, m), 2.68-2.75 (2H, m), 3.10-3.12 (1H, m), 3.36-3.42 (1H, m), 3.53-3.58 (1H, m), 7.01-7.08 (3H, m), 7.19-7.22 (2H, m), 7.35-7.42 (2H, m), 7.57 (1H, d, J=4.4 Hz), 7.78 (1H, d, J=4.8 Hz), 8.23 (1H, s). [M+H] Calc'd for C$_{23}$H$_{21}$FN$_2$O$_2$S, 409; Found, 409.

Preparation 76a

6-[(4-fluorophenyl)sulfanyl]-1,2,3,4-tetrahydronaphthalen-1-one

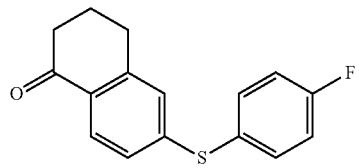 [SMILES: O=C1CCCc2cc(Sc3ccc(F)cc3)ccc21]

To a solution of 5-oxo-5,6,7,8-tetrahydronaphthalen-2-yl 4-methylbenzene-1-sulfonate (5.0 g, 17.0 mmol) in dioxane (75 mL) was added 4-fluorothiophenol (2.6 g, 20.4 mmol), Pd$_2$(dba)$_3$ (392 mg, 0.43 mmol), Xantphos (492 mg, 0.85 mmol) and DIEA (4.4 g, 34.0 mmol). The mixture was heated to reflux overnight under nitrogen. The mixture was filtered and concentrated. The residue was purified by silica gel chromatography (PE:EtOAc=20:1 to 5:1) to give 3.6 g (77%) of the title compound as an off-white solid. $^1$H NMR (400 MHz, CDCl$_3$): δ 2.08-2.13 (m, 2H), 2.61 (t, J=6.4 Hz, 2H), 2.85 (t, J=6.0 Hz, 2H), 6.94 (br s, 1H), 6.98 (dd, J=8.4 Hz, 1.6 Hz, 1H), 7.10-7.14 (m, 2H), 7.49-7.53 (m, 2H), 7.88 (d, J=8.4 Hz, 1H). [M+H] Calc'd for C$_{16}$H$_{13}$FOS, 273; Found, 273.

Preparation 76b

{6-[(4-fluorophenyl) sulfanyl]-3,4-dihydronaphthalen-1-yl}methanamine, hydrochloride

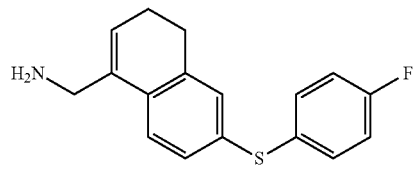 [SMILES: NCC1=CCCc2cc(Sc3ccc(F)cc3)ccc21]

The title compound was prepared in 69% yield from Preparation 76a according to the general procedure for Preparation 3a. [M+H] Calc'd for C$_{17}$H$_{16}$FNS, 286; Found, 286.

Preparation 76c

{6-[(4-fluorophenyl)sulfanyl]-1,2,3,4-tetrahydronaphthalen-1-yl}methanamine

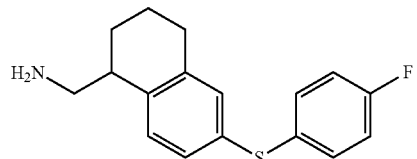

The title compound was prepared in 97% yield from Preparation 76b according to the general procedure for Preparation 3e. [M+H] Calc'd for $C_{17}H_{18}FNS$, 288; Found, 288.

Preparation 76d methyl 3-({[(1S)-6-[(4-fluorophenyl)sulfanyl]-1,2,3,4-tetrahydronaphthalen-1-yl]methyl}amino)pyridine-4-carboxylate; and Preparation 77d methyl 3-({[(1R)-6-[(4-fluorophenyl)sulfanyl]-1,2,3,4-tetrahydronaphthalen-1-yl]methyl}amino)pyridine-4-carboxylate

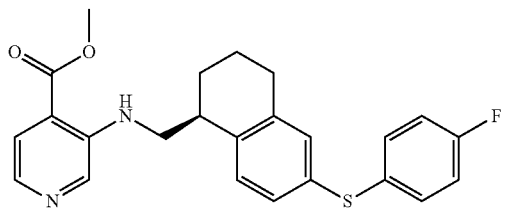

76d

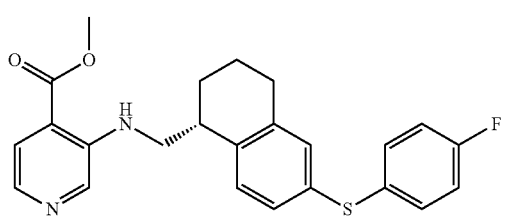

77d

The racemate (330 mg) of the title compounds was prepared in 20% yield from Preparation 76c according to the general procedure for Preparation 1e. [M+H] Calc'd for $C_{24}H_{23}FN_2O_2S$, 423; Found, 423.
Separation by chiral HPLC (Column: Chiralcel: IC 5 um 4.6*250 mm, Mobile phase: Hex:EtOH=70:30, F: 1.0 mL/min, W: 230 nm, T: 30° C.) gave 84 mg (25%) of Preparation 76d (6.916 min) and 91 mg (28%) of Preparation 77d (7.681 min), each as a colorless oil.

Example 76

3-({[(1S)-6-[(4-fluorophenyl)sulfanyl]-1,2,3,4-tetrahydronaphthalen-1-yl]methyl}amino)pyridine-4-carboxylic acid

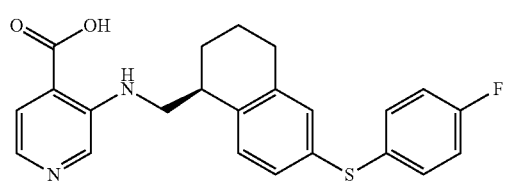 [SMILES: O=C(O)c1ccncc1NC[C@H]1CCCc2cc(Sc3ccc(F)cc3)ccc21]

The title compound was prepared in 48% yield from Preparation 76d according to the general procedure for Example 1. $^1$H NMR (400 MHz, DMSO-$d_6$): δ 1.65-1.68 (m, 1H), 1.78-1.83 (m, 3H), 2.64-2.75 (m, 2H), 3.18-3.12 (m, 1H), 3.43-3.48 (m, 1H), 3.56-3.62 (m, 1H), 7.04-7.07 (m, 1H), 7.09 (s, 1H), 7.21-7.25 (m, 2H), 7.32-7.39 (m, 3H), 7.55 (d, J=5.2 Hz, 1H), 7.83 (d, J=5.2 Hz, 1H), 8.35 (s, 1H). [M+H] Calc'd for $C_{23}H_{21}FN_2O_2S$, 409; Found, 409.

Example 77

3-({[(1R)-6-[(4-fluorophenyl) sulfanyl]-1,2,3,4-tetrahydronaphthalen-1-yl]methyl}amino)pyridine-4-carboxylic acid

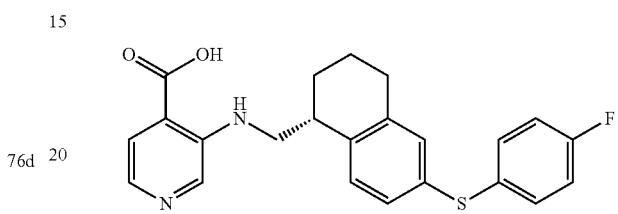

The title compound was prepared in 57% yield from Preparation 77d according to the general procedure for Example 1. $^1$H NMR (400 MHz, DMSO-$d_6$): δ 1.64-1.69 (m, 1H), 1.77-1.84 (m, 3H), 2.65-2.75 (m, 2H), 3.07-3.12 (m, 1H), 3.42-3.48 (m, 1H), 3.56-3.60 (m, 1H), 7.04-7.06 (m, 1H), 7.09 (s, 1H), 7.21-7.25 (m, 2H), 7.32-7.39 (m, 3H), 7.55 (d, J=5.2 Hz, 1H), 7.83 (d, J=5.2 Hz, 1H), 8.35 (s, 1H). [M+H] Calc'd for $C_{23}H_{21}FN_2O_2S$, 409; Found, 409.

Preparation 78a

6-[(4-methylphenyl)sulfanyl]-1,2,3,4-tetrahydronaphthalen-1-one

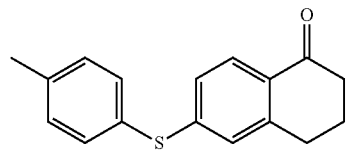 [SMILES: Cc1ccc(Sc2ccc3c(c2)CCCC3=O)cc1]

The title compound was prepared in 96% yield from 4-tolyl disulfide according to the general procedure for Preparation 72a. [M+H] Calc'd for $C_{17}H_{16}OS$, 269; Found, 269.

Preparation 78b

{6-[(4-methylphenyl)sulfanyl]-3,4-dihydronaphthalen-1-yl}methanamine, hydrochloride

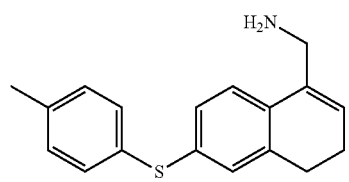 [SMILES: Cc1ccc(Sc2ccc3c(c2)CCC=C3CN)cc1]

The title compound was prepared in 77% yield from Preparation 76a according to the general procedure for Preparation 3a. [M+H] Calc'd for $C_{18}H_{19}NS$, 282; Found, 282.

Preparation 78c

{6-[(4-methylphenyl)sulfanyl]-1,2,3,4-tetrahydronaphthalen-1-yl}methenamine

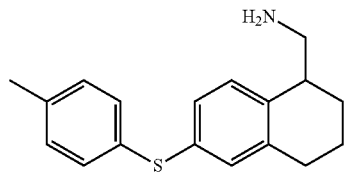 [SMILES: Cc1ccc(Sc2ccc3c(c2)CCCC3CN)cc1]

The title compound was prepared in 68% yield from Preparation 78b according to the general procedure for Preparation 3e. [M+H] Calc'd for $C_{18}H_{21}NS$, 284; Found, 284.

Preparation 78d methyl 3-({[(1S)-6-[(4-methylphenyl)sulfanyl]-1,2,3,4-tetrahydronaphthalen-1-yl]methyl}amino)pyridine-4-carboxylate; and Preparation 79d methyl 3-({[(1R)-6-[(4-methylphenyl)sulfanyl]-1,2,3,4-tetrahydronaphthalen-1-yl]methyl}amino)pyridine-4-carboxylate

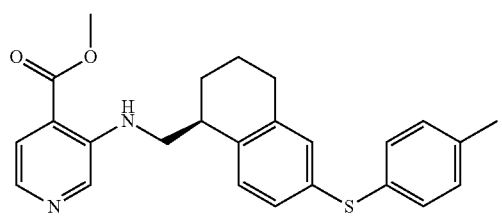

78d

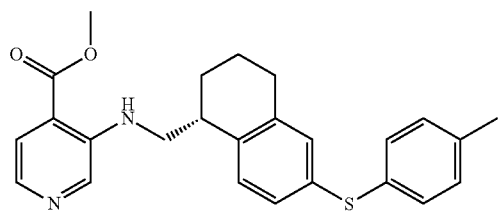

79d

The racemate (200 mg) of the title compounds was prepared in 20% yield from Preparation 78c according to the general procedure for Preparation 1e. [M+H] Calc'd for $C_{25}H_{26}N_2O_2S$, 419; Found, 419.
Separation by chiral HPLC (Column: Chiralcel IC, 250 mm*4.6 mm 5 um; Mobile phase: Hex:EtOH=80:20; F: 1.0 mL/min; W: 230 nm; T=30° C.) gave 66 mg (33%) of Preparation 78d (9.08 min) and 66 mg (33%) of Preparation 79d (10.33 min), each as a yellow oil.

Example 78

3-({[(1S)-6-[(4-methylphenyl)sulfanyl]-1,2,3,4-tetrahydronaphthalen-1-yl]methyl}amino)pyridine-4-carboxylic acid

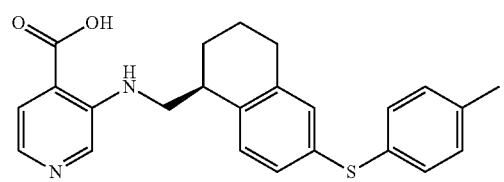 [SMILES: Cc1ccc(Sc2ccc3c(c2)CCC[C@@H]3CNc2cnccc2C(=O)O)cc1]

The title compound was prepared in 40% yield from Preparation 78d according to the general procedure for Example 1. $^1$H NMR (300 MHz, DMSO-d$_6$): δ 1.62-1.67 (1H, m), 1.75-1.85 (3H, m), 2.29 (3H, s), 2.64-2.71 (2H, m), 3.06-3.11 (1H, m), 3.41-3.48 (1H, m), 3.54-3.60 (1H, m), 6.99-7.04 (2H, m), 7.17-7.31 (5H, m), 7.55 (1H, d, J=5.1 Hz), 7.82 (1H, d, J=5.1 Hz), 8.35 (1H, s). [M+H] Calc'd for $C_{24}H_{24}N_2O_2S$, 405; Found, 405.

Example 79

3-({[(1R)-6-[(4-methylphenyl)sulfanyl]-1,2,3,4-tetrahydronaphthalen-1-yl]methyl}amino)pyridine-4-carboxylic acid

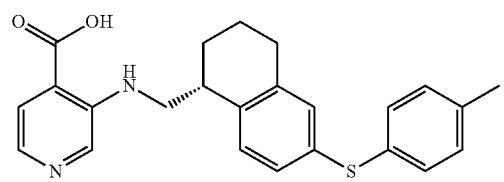 [SMILES: Cc1ccc(Sc2ccc3c(c2)CCC[C@H]3CNc2cnccc2C(=O)O)cc1]

The title compound was prepared in 40% yield from Preparation 79d according to the general procedure for Example 1. $^1$H NMR (300 MHz, DMSO-d$_6$): δ 1.63-1.67 (1H, m), 1.76-1.85 (3H, m), 2.29 (3H, s), 2.64-2.68 (2H, m), 3.07-3.10 (1H, m), 3.40-3.47 (1H, m), 3.53-3.59 (1H, m), 6.99-7.04 (2H, m), 7.17-7.31 (5H, m), 7.54 (1H, d, J=5.1 Hz), 7.82 (1H, d, J=4.8 Hz), 8.34 (1H, s). [M+H] Calc'd for $C_{24}H_{24}N_2O_2S$, 405; Found, 405.

Preparation 80a 6-bromo-1,2,3,4-tetrahydronaphthalen-1-ol

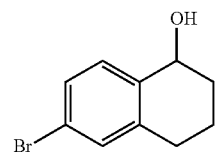 [SMILES: OC1CCCc2cc(Br)ccc21]

To a solution of 6-bromo-1,2,3,4-tetrahydronaphthalen-1-one (2.0 g, 8.9 mmol) in EtOH (20 mL) was added NaBH$_4$ (1.6 g, 42.7 mmol) at rt, and the reaction was stirred for 30 min. The reaction was diluted with water (10 mL) and extracted with EtOAc (3×50 mL). Organics were washed with brine (50 mL), dried (Na$_2$SO$_4$) and concentrated to give 1.9 g (94%) of the title compound as a brown oil. [M+H] calc'd for C$_{10}$H$_{11}$BrO$_2$, 227, 229; Found 227, 229.

Preparation 80b triethyl (6-bromo-1,2,3,4-tetrahydronaphthalen-1-yl)methanetricarboxylate

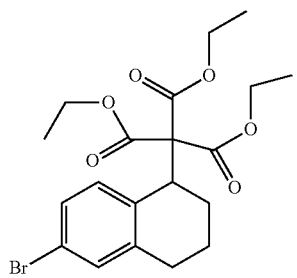 [SMILES: CCOC(=O)C(C(=O)OCC)(C(=O)OCC)C1CCCc2cc(Br)ccc21]

To a solution of Preparation 80a (1.83 g, 8.1 mmol) and triethylmethane tricarboxylate (3.76 g, 16.2 mmol) in toluene (20 mL) was added n-Bu$_3$P (4.0 mL, 16.2 mmol), and the solution was cooled to −50° C. under N$_2$. DIAD (3.2 mL, 16.2 mmol) was added dropwise, and the reaction mixture stirred for 30 min. The reaction was concentrated. Water (50 mL) and 3N NaOH (50 mL) were added, and the solution was extracted with ether. Organics were washed with 3N NaOH, water, 1N HCl, and brine. The solution was dried (Na$_2$SO$_4$) and concentrated. Purification by silica gel chromatography (10% EtOAc/hexanes) gave 2.84 g (79%) of the title compound as a white solid. [M+H] calc'd for C$_{20}$H$_{25}$BrO$_6$, 441, 443; Found 441, 443.

Preparation 80c 2-(6-bromo-1,2,3,4-tetrahydronaphthalen-1-yl)acetic acid

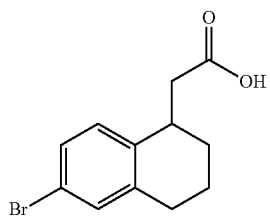

To a solution of Preparation 80b (2.84 g, 6.4 mmol) in methanol (10 mL) was added 1.5 N NaOH (50 mL) at rt, and the mixture was refluxed for 20 h. The reaction mixture was concentrated. Glacial acetic acid (50 mL) was added, and the reaction was refluxed for 3 h. The reaction mixture was concentrated and the residue was taken up in water and extracted with ether. Organics were dried (Na$_2$SO$_4$) and concentrated to give 1.58 g (91%) of the title compound as a yellow oil. [M+H] calc'd for C$_{12}$H$_{13}$BrO$_2$, 269, 271; Found 269, 271.

Preparation 80d (6-bromo-1,2,3,4-tetrahydronaphthalen-1-yl)methanamine

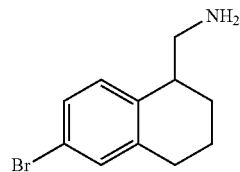

To a solution of Preparation 80c (0.8 g, 3.0 mmol) in DCM (20 mL) was added oxalyl chloride (0.4 mL, 4.5 mmol) and DMF (5 drops) at rt, and the mixture was stirred for 1 h. The solvent was removed in vacuo, and the residue was dissolved in acetone (20 mL). A solution of NaN$_3$ (390 mg, 6.0 mmol) in H$_2$O (3 mL) was added slowly at 0° C. After 10 min, the mixture was diluted with water and brine, and extracted with toluene. Organics were washed with brine, dried (Na$_2$SO$_4$), and then heated to reflux for 30 min. The solution was concentrated and re-dissolved in dioxane (10 mL). The solution was added dropwise to conc. HCl (20 mL) at 100° C. After 20 min, the reaction mixture was concentrated. The residue was dissolved in DCM/MeOH (1:1), basified to pH 8 with sat. Na$_2$CO$_3$, filtered, and concentrated to give the title compound as pale brown oil which was used for next reaction without further purification. [M+H] calc'd for C$_{11}$H$_{14}$BrN, 240, 242; Found 240, 242.

Preparation 80e methyl 3-{[(7-bromo-3,4-dihydro-2H-1-benzopyran-4-yl)methyl]amino}pyridine-4-carboxylate

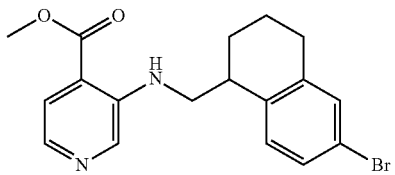 [SMILES: COC(=O)c1ccncc1NCC1CCCc2cc(Br)ccc21]

The title compound was prepared in 6% yield from Preparation 80d according to the procedure for Preparation 1e. [M+H] calc'd for C$_{18}$H$_{19}$BrN$_2$O$_2$, 375, 377; Found 375, 377.

Example 80

3-({[6-(pyridin-2-ylsulfanyl)-1,2,3,4-tetrahydronaphthalen-1-yl]methyl}amino)pyridine-4-carboxylic acid

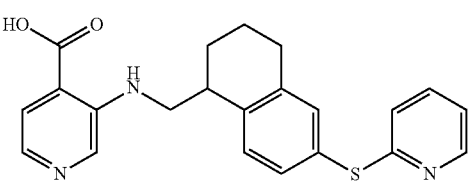 [SMILES: O=C(O)c1ccncc1NCC1CCCc2cc(Sc3ccccn3)ccc21]

To a suspension of Preparation 80e (72 mg, 0.19 mmol), 2,2'-dipyridyl disulfide (84 mg, 0.38 mmol) and Zn (60 mg, 0.91 mmol) in DMF (5 mL) was added Pd(dppf)Cl₂ (30 mg, 0.038 mmol) at rt under N₂, and the reaction was stirred at 60° C. overnight. The reaction was diluted with EtOAc, filtered, and concentrated. The residue was purified by prep-TLC (PE:EA=2:1) to give a pale brown oil. This oil was dissolved in THF (3 mL) and H₂O (1 mL). LiOH.H₂O (2 mg) was added, and the reaction was stirred at rt for 2 h. The reaction mixture was acidified to pH=3 with 1.0 N aqueous HCl solution, concentrated and purified by prep-HPLC to give 4.8 mg (6%) of the title compound as a yellow solid. ¹H NMR (400 MHz, CD₃OD): δ 1.81-1.86 (m, 1H), 1.91-2.08 (m, 3H), 2.86-2.91 (m, 2H), 3.35-3.38 (m, 1H), 3.65-3.73 (m, 2H), 7.19 (d, J=8.4 Hz, 1H), 7.44 (d, J=7.6 Hz, 1H), 7.49-7.55 (m, 3H), 7.98 (d, J=6.0 Hz, 1H), 8.06 (t, J=7.6 Hz, 1H), 8.31 (d, J=6.0 Hz, 1H), 8.44 (s, 1H), 8.55 (d, J=5.6 Hz, 1H). [M+H] Calc'd for $C_{22}H_{21}N_3O_2S$, 392; Found, 392.

Preparation 81a 6-(phenylsulfanyl)-1,2,3,4-tetrahydronaphthalen-1-one

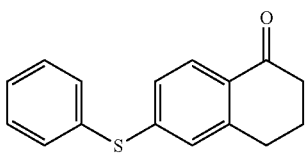 [SMILES: O=C1CCCc2cc(Sc3ccccc3)ccc21]

To a solution of 5-oxo-5,6,7,8-tetrahydronaphthalen-2-yl 4-methylbenzene-1-sulfonate (8.83 g, 30 mmol) and diphenyl disulphide (3.27 g, 15 mmol) in THF (20 mL) was added Zn powder (2.34 g, 36 mmol) and Pd(dppf)Cl₂ (1.22 g, 1.5 mmol) under nitrogen, and the reaction was refluxed overnight. The mixture was filtered and concentrated. The residue was purified by silica gel chromatography to give 5.93 g (77%) of the title compound as an orange solid. ¹H NMR (400 MHz, CDCl₃): δ 2.06-2.12 (2H, m), 2.61 (2H, t, J=6.6 Hz), 2.85 (2H, t, J=6.0 Hz), 7.01-7.04 (2H, m), 7.39-7.42 (3H, m), 7.49-7.51 (2H, m), 7.89 (1H, d, J=8.0 Hz). [M+H] Calc'd for $C_{16}H_{14}OS$, 255; Found, 255.

Preparation 81b 6-(benzenesulfonyl)-1,2,3,4-tetrahydronaphthalen-1-one

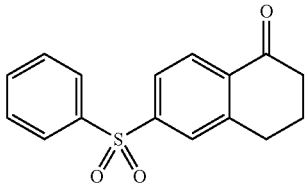 [SMILES: O=C1CCCc2cc(S(=O)(=O)c3ccccc3)ccc21]

To a solution of Preparation 81a (1.72 g, 6.77 mmol) in MeOH/MeCN (1:1, 30 mL) was added another solution of OXONE (16.6 g, 27 mmol) in water. The mixture was stirred for 2 h at rt. The reaction was diluted with EtOAc and filtered, washed with brine, dried (Na₂SO₄), and concentrated to give 1.9 g (98%) of the title compound as colorless gum. [M+H] Calc'd for $C_{16}H_{14}O_3S$, 287; Found, 287.

Preparation 81c

[6-(benzenesulfonyl)-3,4-dihydronaphthalen-1-yl]methanamine

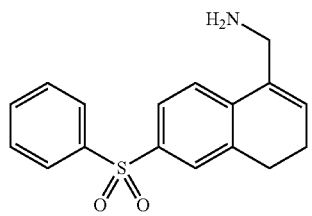 [SMILES: NCC1=CCCc2cc(S(=O)(=O)c3ccccc3)ccc21]

The title compound was prepared in 31% yield from Preparation 81b according to the procedure for Preparation 3a. [M+H] Calc'd for $C_{17}H_{17}NO_2S$, 300; Found, 300.

Preparation 81d

[6-(benzenesulfonyl)-1,2,3,4-tetrahydronaphthalen-1-yl]methanamine

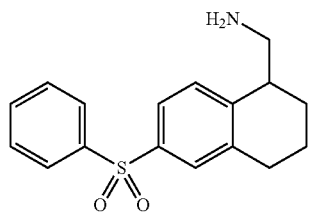 [SMILES: NCC1CCCc2cc(S(=O)(=O)c3ccccc3)ccc21]

The title compound was prepared in 91% yield from Preparation 81c according to the procedure for Preparation 3e. [M+H] Calc'd for $C_{17}H_{19}NO_2S$, 302; Found, 302.

Preparation 81e methyl 3-({[6-(benzenesulfonyl)-3,4-dihydronaphthalen-1-yl]methyl}amino)pyridine-4-carboxylate

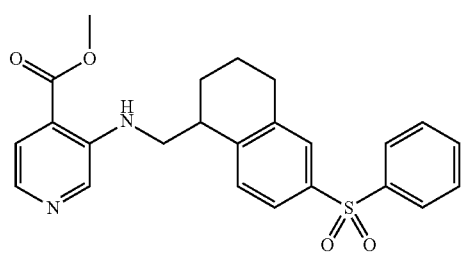 [SMILES: COC(=O)c1ccncc1NCC1CCCc2cc(S(=O)(=O)c3ccccc3)ccc21]

The title compound was prepared in 43% yield from Preparation 81d according to the procedure for Preparation 1e. [M+H] Calc'd for $C_{24}H_{24}N_2O_4S$, 437; Found, 437.

Preparation 81f methyl 3-({[(1S)-6-(benzene sulfonyl)-1,2,3,4-tetrahydronaphthalen-1-yl]methyl}amino)pyridine-4-carboxylate; and

Preparation 82f methyl 3-({[(1R)-6-(benzene sulfonyl)-1,2,3,4-tetrahydronaphthalen-1-yl]methyl}amino)pyridine-4-carboxylate

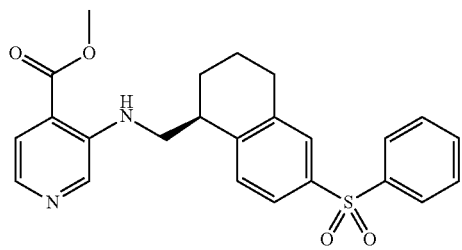
81e

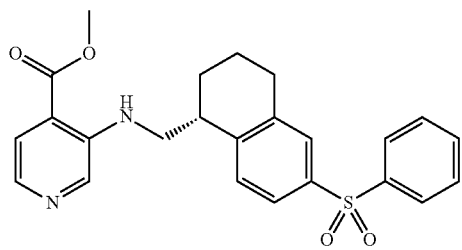
82e

Preparation 81e (360 mg) was separated by chiral HPLC (Column: Chiralcel AS-H, 250 mm*4.6 mm 5 um; Mobile phase: Hex:EtOH=50:50; F: 1.0 mL/min; W: 230 nm; T=30° C.) to give 116 mg (32%) of Preparation 81e (10.39 min) and 107 mg (30%) of Preparation 82e (20.88 min), each as a yellow oil.

Example 81

3-({[(1S)-6-(benzenesulfonyl)-1,2,3,4-tetrahydronaphthalen-1-yl]methyl}amino)pyridine-4-carboxylic acid

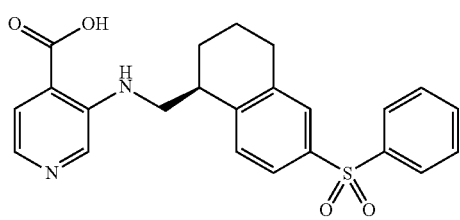 [SMILES: O=C(O)c1ccncc1NC[C@H]1CCCc2cc(S(=O)(=O)c3ccccc3)ccc21]

The title compound was prepared in 81% yield from Preparation 81f according to the general procedure for Example 1. $^1$H NMR (400 MHz, DMSO-d$_6$): δ 1.66-1.70 (1H, m), 1.77-1.86 (3H, m), 2.75-2.88 (2H, m), 3.18-3.19 (1H, m), 3.44-3.50 (1H, m), 3.56-3.61 (1H, m), 7.55-7.71 (7H, m), 7.86 (1H, d, J=5.6 Hz), 7.94 (2H, d, J=7.2 Hz), 8.41 (1H, s). [M+H] Calc'd for $C_{23}H_{22}N_2O_4S$, 423; Found, 423.

Example 82

3-({[(1R)-6-(benzenesulfonyl)-1,2,3,4-tetrahydronaphthalen-1-yl]methyl}amino)pyridine-4-carboxylic acid

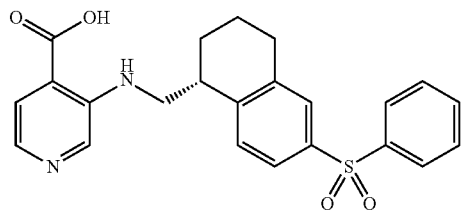 [SMILES: O=C(O)c1ccncc1NC[C@@H]1CCCc2cc(S(=O)(=O)c3ccccc3)ccc21]

The title compound was prepared in 90% yield from Preparation 82f according to the general procedure for Example 1. $^1$H NMR (400 MHz, DMSO-d$_6$): δ 1.66-1.70 (1H, m), 1.77-1.85 (3H, m), 2.78-2.83 (2H, m), 3.18-3.21 (1H, m), 3.45-3.51 (1H, m), 3.57-3.61 (1H, m), 7.55-7.76 (7H, m), 7.89 (1H, d, J=5.2 Hz), 7.94 (2H, d, J=7.2 Hz), 8.42 (1H, s). [M+H] Calc'd for $C_{23}H_{22}N_2O_4S$, 423; Found, 423.

Preparation 83a 6-(4-methylbenzenesulfonyl)-1,2,3,4-tetrahydronaphthalen-1-one

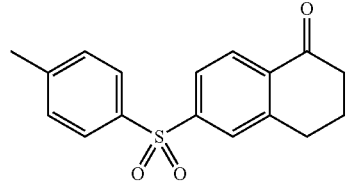 [SMILES: Cc1ccc(S(=O)(=O)c2ccc3c(c2)CCCC3=O)cc1]

The title compound was prepared in 97% yield from Preparation 78a according to the general procedure for Preparation 81b. [M+H] Calc'd for $C_{17}H_{16}O_3S$, 301; Found, 301.

Preparation 83b

[6-(4-methylbenzenesulfonyl)-3,4-dihydronaphthalen-1-yl]methanamine, hydrochloride

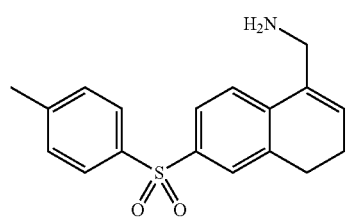 [SMILES: Cc1ccc(S(=O)(=O)c2ccc3c(c2)CCC=C3CN)cc1]

The title compound was prepared in 60% yield from Preparation 83a according to the general procedure for Preparation 3a. [M−H] Calc'd for $C_{18}H_{19}NO_2S$, 314; Found, 314.

Preparation 83c

[6-(4-methylbenzenesulfonyl)-1,2,3,4-tetrahydronaphthalen-1-yl]methanamine

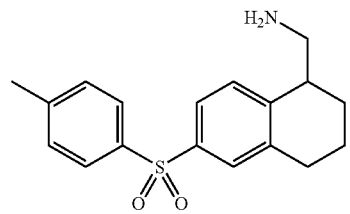 [SMILES: Cc1ccc(S(=O)(=O)c2ccc3c(c2)CCCC3CN)cc1]

The title compound was prepared in 78% yield from Preparation 83b according to the procedure for Preparation 3e. [M+H] Calc'd for $C_{18}H_{21}NO_2S$, 316; Found, 316.

Preparation 83d methyl 3-({[(1S)-6-(4-methylbenzenesulfonyl)-1,2,3,4-tetrahydronaphthalen-1-yl]methyl}amino)pyridine-4-carboxylate; and Preparation 84d methyl 3-({[(1R)-6-(4-methylbenzenesulfonyl)-1,2,3,4-tetrahydronaphthalen-1-yl]methyl}amino)pyridine-4-carboxylate 83d

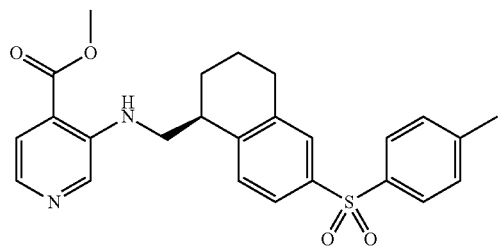

84d

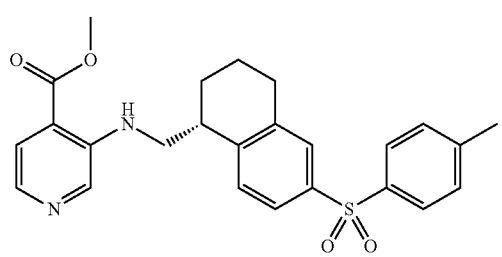

The racemate (226 mg) of the title compounds was prepared in 24% yield from Preparation 83c according to the general procedure for Preparation 1e. [M+H] Calc'd for $C_{25}H_{26}N_2O_4S$, 451; Found, 451.
Separation by chiral HPLC (Column: Chiralcel AS-H, 250 mm*4.6 mm 5 um; Mobile phase: MeOH:EtOH=50:50; F: 1.0 mL/min; W: 230 nm; T=30° C.) gave 95 mg (42%) of Preparation 83d (9.67 min), and 86 mg (38%) of Preparation 84d (16.75 min), each as colorless oil.

Example 83

3-({[(1S)-6-(4-methylbenzenesulfonyl)-1,2,3,4-tetrahydronaphthalen-1-yl]methyl}amino)pyridine-4-carboxylic acid

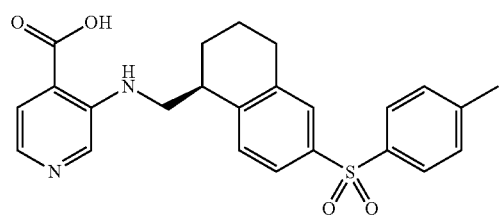 [SMILES: Cc1ccc(S(=O)(=O)c2ccc3c(c2)CCC[C@@H]3CNc2cnccc2C(=O)O)cc1]

The title compound was prepared in 56% yield from Preparation 83d according to the general procedure for Example 1. $^1$H NMR (400 MHz, DMSO-$d_6$): δ 1.66-1.69 (1H, m), 1.76-1.84 (3H, m), 2.35 (3H, s), 2.76-2.83 (2H, m), 3.15-3.18 (1H, m), 3.35-3.48 (1H, m), 3.55-3.60 (1H, m), 7.40 (2H, d, J=8.4 Hz), 7.53-7.57 (2H, m), 7.62-7.67 (2H, m), 7.81-7.84 (3H, m), 8.37 (1H, s). [M+H] Calc'd for $C_{24}H_{24}N_2O_4S$, 437; Found, 437.

Example 84

3-({[(1R)-6-(4-methylbenzenesulfonyl)-1,2,3,4-tetrahydronaphthalen-1-yl]methyl}amino)pyridine-4-carboxylic acid

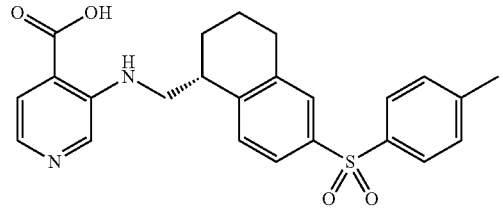 [SMILES: Cc1ccc(S(=O)(=O)c2ccc3c(c2)CCC[C@H]3CNc2cnccc2C(=O)O)cc1]

The title compound was prepared in 63% yield from Preparation 84d according to the general procedure for Example 1. $^1$H NMR (400 MHz, DMSO-$d_6$): δ 1.65-1.69 (1H, m), 1.76-1.86 (3H, m), 2.36 (3H, s), 2.76-2.86 (2H, m), 3.15-3.18 (1H, m), 3.35-3.48 (1H, m), 3.55-3.60 (1H, m), 7.40 (2H, d, J=8.0 Hz), 7.53-7.57 (2H, m), 7.62-7.67 (2H, m), 7.81-7.84 (3H, m), 8.37 (1H, s). [M+H] Calc'd for $C_{24}H_{24}N_2O_4S$, 437; Found, 437.

Preparation 85a 6-(3-methylbenzenesulfonyl)-1,2,3,4-tetrahydronaphthalen-1-one

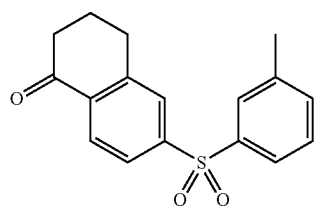 [SMILES: Cc1cccc(S(=O)(=O)c2ccc3c(c2)CCCC3=O)c1]

The title compound was prepared in 84% yield from Preparation 68a according to the general procedure for Preparation 81b. [M+H] Calc'd for $C_{17}H_{16}O_3S$, 301; Found, 301.

Preparation 85b

[6-(3-methylbenzenesulfonyl)-3,4-dihydronaphthalen-1-yl]methanamine, hydrochloride

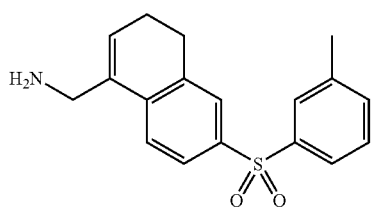

The title compound was prepared in 95% yield from Preparation 85a according to the general procedure for Preparation 3a. [M+H] Calc'd for $C_{18}H_{19}NO_2S$, 314; Found, 314.

Preparation 85c

[6-(3-methylbenzenesulfonyl)-1,2,3,4-tetrahydronaphthalen-1-yl]methanamine

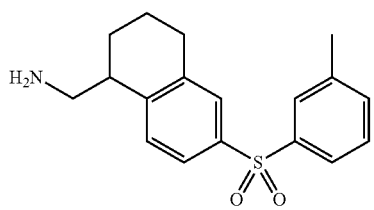 [SMILES: Cc1cccc(S(=O)(=O)c2ccc3c(c2)CCCC3CN)c1]

The title compound was prepared in 64% yield from Preparation 85b according to the procedure for Preparation 3e. [M+H] Calc'd for $C_{18}H_{21}NO_2S$, 316; Found, 316.

Preparation 85d methyl 3-({[(1S)-6-(3-methylbenzenesulfonyl)-1,2,3,4-tetrahydronaphthalen-1-yl]methyl}amino)pyridine-4-carboxylate; and Preparation 86d methyl 3-({[(1R)-6-(3-methylbenzenesulfonyl)-1,2,3,4-tetrahydronaphthalen-1-yl]methyl}amino)pyridine-4-carboxylate

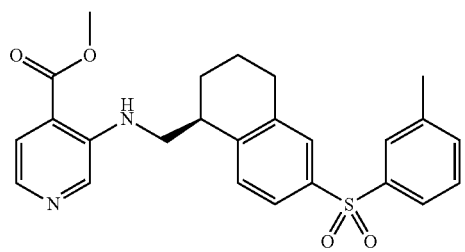

85d

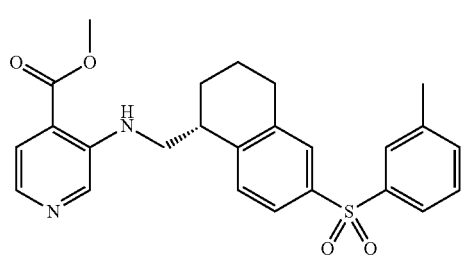

86d

The racemate (230 mg) of the title compounds was prepared in 16% yield from Preparation 85c according to the general procedure for Preparation 1e. [M+H] Calc'd for $C_{25}H_{26}N_2O_4S$, 451; Found, 451.

Separation by chiral HPLC (Column: Chiralcel: AS 5 um 4.6*250 mm, Mobile phase: Hex:EtOH=50:50, F: 1.0 mL/min, W: 230 nm, T: 30° C.) to give 77 mg (33%) of Preparation 85d (9.653 min) and 77 mg (33%) of Preparation 86d (15.046 min), each as a yellow oil.

Example 85

3-({[(1S)-6-(3-methylbenzenesulfonyl)-1,2,3,4-tetrahydronaphthalen-1-yl]methyl}amino)pyridine-4-carboxylic acid

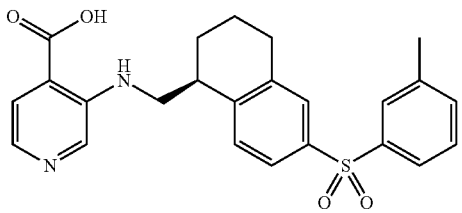 [SMILES: Cc1cccc(S(=O)(=O)c2ccc3c(c2)CCC[C@@H]3CNc2cnccc2C(=O)O)c1]

The title compound was prepared in 95% yield from Preparation 85d according to the general procedure for Example 1. $^1$H NMR (400 MHz, DMSO-$d_6$): δ 1.65-1.87 (4H, m), 2.38 (3H, s), 2.76-2.88 (2H, m), 3.18-3.21 (1H, m), 3.46-3.51 (1H, m), 3.58-3.63 (1H, m), 7.49-7.58 (3H, m), 7.66-7.85 (5H, m), 7.89 (1H, d, J=5.2 Hz), 8.44 (1H, s). [M+M] Calc'd for $C_{24}H_{24}N_2O_4S$, 437; Found, 437.

Example 86

3-({[(1R)-6-(3-methylbenzenesulfonyl)-1,2,3,4-tetrahydronaphthalen-1-yl]methyl}amino)pyridine-4-carboxylic acid

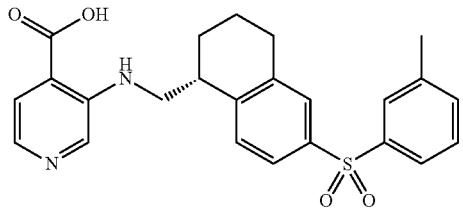 [SMILES: Cc1cccc(S(=O)(=O)c2ccc3c(c2)CCC[C@H]3CNc2cnccc2C(=O)O)c1]

The title compound was prepared in 78% yield from Preparation 86d according to the general procedure for Example 1. $^1$H NMR (400 MHz, DMSO-d$_6$): δ 1.67-1.83 (4H, m), 2.38 (3H, s), 2.78-2.88 (2H, m), 3.18-3.21 (1H, m), 3.45-3.50 (1H, m), 3.57-3.62 (1H, m), 7.49-7.57 (3H, m), 7.66-7.83 (5H, m), 7.88 (1H, d, J=5.2 Hz), 8.42 (1H, s). [M+M] Calc'd for $C_{24}H_{24}N_2O_4S$, 437; Found, 437.

Preparation 87a 6-(3-fluorobenzenesulfonyl)-1,2,3,4-tetrahydronaphthalen-1-one

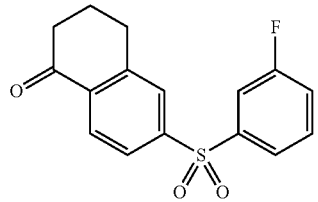 [SMILES: O=C1CCCc2cc(S(=O)(=O)c3cccc(F)c3)ccc21]

The title compound was prepared in 40% yield from Preparation 74a according to the general procedure for Preparation 81b. [M+H] Calc'd for $C_{16}H_{13}FO_3S$, 305; Found, 305.

Preparation 87b

[6-(3-fluorobenzenesulfonyl)-3,4-dihydronaphthalen-1-yl]methanamine, hydrochloride

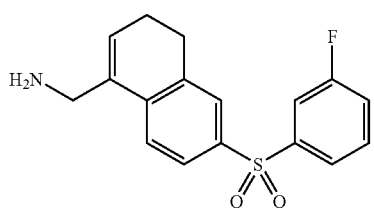

The title compound was prepared in 87% yield from Preparation 87a according to the general procedure for Preparation 3a. [M+H] Calc'd for $C_{17}H_{16}FNO_2S$, 318; Found, 318.

Preparation 87c

[6-(3-fluorobenzenesulfonyl)-1,2,3,4-tetrahydronaphthalen-1-yl]methanamine

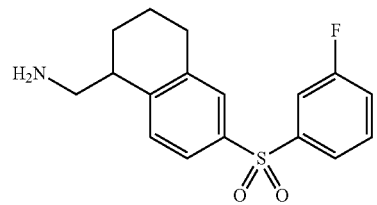 [SMILES: NCC1CCCc2cc(S(=O)(=O)c3cccc(F)c3)ccc21]

The title compound was prepared in 73% yield from Preparation 87b according to the procedure for Preparation 3e. [M+H] Calc'd for $C_{17}H_{18}FNO_2S$, 320; Found, 320.

Preparation 87d methyl 3-({[6-(3-fluorobenzenesulfonyl)-1,2,3,4-tetrahydronaphthalen-1-yl]methyl}amino)pyridine-4-carboxylate

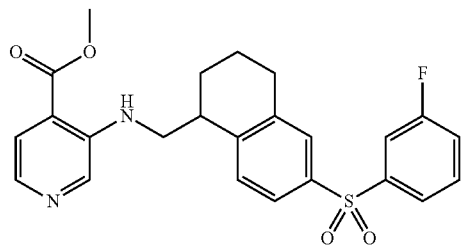 [SMILES: COC(=O)c1ccncc1NCC1CCCc2cc(S(=O)(=O)c3cccc(F)c3)ccc21]

The title compound was prepared in 6% yield from Preparation 87c according to the procedure for Preparation 1e. [M+H] Calc'd for $C_{24}H_{23}FN_2O_4S$, 455; Found, 455.

Example 87

3-({[6-(3-fluorobenzenesulfonyl)-1,2,3,4-tetrahydronaphthalen-1-yl]methyl}amino)pyridine-4-carboxylic acid

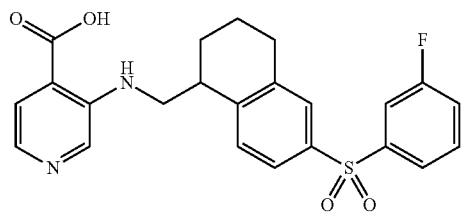 [SMILES: O=C(O)c1ccncc1NCC1CCCc2cc(S(=O)(=O)c3cccc(F)c3)ccc21]

The title compound was prepared in 73% yield from Preparation 87d according to the general procedure for

267

Example 1. $^1$H NMR (400 MHz, DMSO-d$_6$): δ 1.67-1.86 (4H, m), 2.78-2.85 (2H, m), 3.18-3.22 (1H, m), 3.45-3.51 (1H, m), 3.57-3.62 (1H, m), 7.54-7.59 (2H, m), 7.65-7.87 (8H, m), 8.40 (1H, s). [M+H] Calc'd for C$_{23}$H$_{21}$FN$_2$O$_4$S, 441; Found, 441.

Preparation 88a 6-(3,6-dihydro-2H-pyran-4-yl)-1,2,3,4-tetrahydronaphthalen-1-one

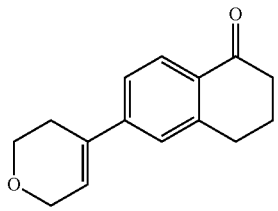 [SMILES: O=C1CCCc2cc(C3=CCOCC3)ccc21]

To a solution of 5-oxo-5,6,7,8-tetrahydronaphthalen-2-yl trifluoromethanesulfonate (1.4 g, 4.76 mmol) in dioxane (6 mL) was added 3,6-dihydro-2H-pyran-4-boronic acid pinacol ester (1.0 g, 4.76 mmol), Pd(dppf)Cl$_2$DCM (408 mg, 0.5 mmol) and sat. NaHCO$_3$ solution (2 mL). The mixture was stirred at 100° C. for 2 h under nitrogen. The mixture was cooled to rt and diluted with EtOAc, filtered, and concentrated. The residue was purified by silica gel chromatography (PE:EtOAc=4:1) to give 930 mg (86%) of the title compound as yellow solid. $^1$H NMR (400 MHz, CDCl$_3$): δ 2.13-2.16 (2H, m), 2.53 (2H, s), 2.65 (2H, t, J=6.4 Hz), 2.96 (2H, t, J=6.0 Hz), 3.94 (2H, t, J=5.6 Hz), 4.34 (2H, s), 6.26 (1H, s), 7.25 (1H, d, J=5.6 Hz), 7.33 (1H, d, J=8.4 Hz), 7.99 (1H, d, J=8.0 Hz). [M+H] Calc'd for C$_{15}$H$_{16}$O$_2$, 229; Found, 229.

Preparation 88b

[6-(oxan-4-yl)-3,4-dihydronaphthalen-1-yl]methanamine

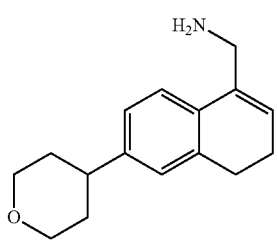 [SMILES: NCC1=CCCc2cc(C3CCOCC3)ccc21]

The title compound was prepared in 40% yield from Preparation 88a according to the procedure for Preparation 3a. [M+H] Calc'd for C$_{16}$H$_{21}$NO, 244; Found, 244.

268

Preparation 88c

[6-(oxan-4-yl)-1,2,3,4-tetrahydronaphthalen-1-yl]methanamine

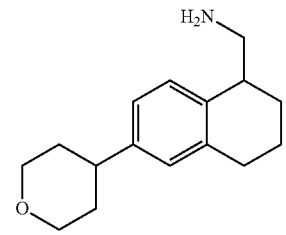 [SMILES: NCC1CCCc2cc(C3CCOCC3)ccc21]

The title compound was prepared in 86% yield from Preparation 88b according to the procedure for Preparation 3e. [M+H] Calc'd for C$_{16}$H$_{23}$NO, 246; Found, 246.

Preparation 88d methyl 3-({[6-(oxan-4-yl)-1,2,3,4-tetrahydronaphthalen-1-yl]methyl}amino)pyridine-4-carboxylate

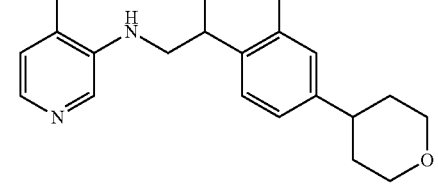

The title compound was prepared in 17% yield from Preparation 88c according to the procedure for Preparation 1e. [M+H] Calc'd for C$_{23}$H$_{28}$N$_2$O$_3$, 381; Found, 381.

Example 88

3-({[6-(oxan-4-yl)-1,2,3,4-tetrahydronaphthalen-1-yl]methyl}amino)pyridine-4-carboxylic acid

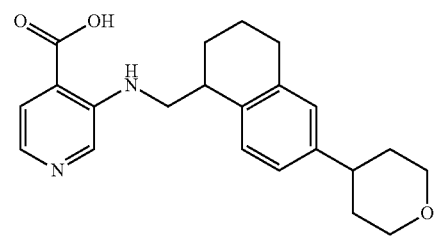 [SMILES: O=C(O)c1ccncc1NCC1CCCc2cc(C3CCOCC3)ccc21]

The title compound was prepared in 69% yield from Preparation 88d according to the general procedure for Example 1. $^1$H NMR (400 MHz, DMSO-d$_6$): δ 1.61-1.68 (5H, m), 1.77-1.83 (3H, m), 2.65-2.72 (3H, m), 3.04-3.07 (1H, m), 3.37-3.45 (3H, m), 3.54-3.59 (1H, m), 3.91-3.94 (2H, m), 6.96 (1H, s), 7.00 (1H, d, J=8.4 Hz), 7.24 (1H, d, J=8.0 Hz), 7.56 (1H, d, J=5.2 Hz), 7.83 (1H, d, J=5.2 Hz), 8.37 (1H, s). [M+H] Calc'd for C$_{22}$H$_{26}$N$_2$O$_3$, 367; Found, 367.

Preparation 89a 6-(2-methylpyridin-4-yl)-1,2,3,4-tetrahydronaphthalen-1-one

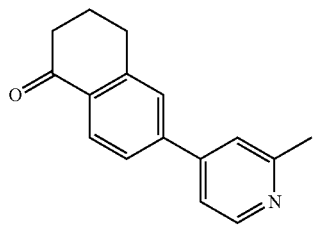 [SMILES: Cc1cc(-c2ccc3c(c2)CCCC3=O)ccn1]

To a suspension of 5-oxo-5,6,7,8-tetrahydronaphthalen-2-yl 4-methylbenzene-1-sulfonate (1.3 g, 4.4 mmol), 2-methylpyridine-4-boronic acid pinacol ester (800 mg, 3.7 mmol), Na$_2$CO$_3$ (773 mg, 7.3 mmol) and LiCl.H$_2$O (442 mg, 7.3 mmol) in EtOH/H$_2$O/toluene (4.4 mL/2.3 mL/20.0 mL) was added Pd(PPh$_3$)$_4$ (211 mg, 0.2 mmol) at rt under N$_2$. The reaction was stirred at 100° C. overnight. The reaction was filtered and concentrated. Purification by silica gel chromatography (PE:EtOAc=1:1) gave 865 mg (quantitative) of the title compound as a yellow solid. [M+H] Calc'd for C$_{16}$H$_{15}$NO, 238; Found, 238.

Preparation 89b

[6-(2-methylpyridin-4-yl)-3,4-dihydronaphthalen-1-yl]methanamine, hydrochloride

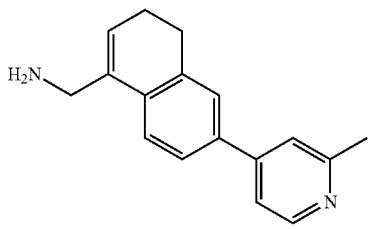 [SMILES: Cc1cc(-c2ccc3c(c2)CCC=C3CN)ccn1]

The title compound was prepared in 44% yield from Preparation 89a according to the procedure for Preparation 3a. [M+H] Calc'd for C$_{17}$H$_{18}$N, 251; Found, 251.

Preparation 89c

[6-(2-methylpyridin-4-yl)-1,2,3,4-tetrahydronaphthalen-1-yl]methanamine

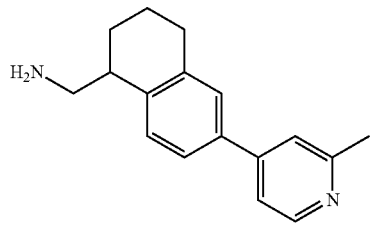 [SMILES: Cc1cc(-c2ccc3c(c2)CCCC3CN)ccn1]

The title compound was prepared in 98% yield from Preparation 89b according to the procedure for Preparation 3e. [M+H] Calc'd for C$_{17}$H$_{20}$N, 253; Found, 253.

Preparation 89d methyl 3-({[6-(2-methylpyridin-4-yl)-1,2,3,4-tetrahydronaphthalen-1-yl]methyl}amino)pyridine-4-carboxylate

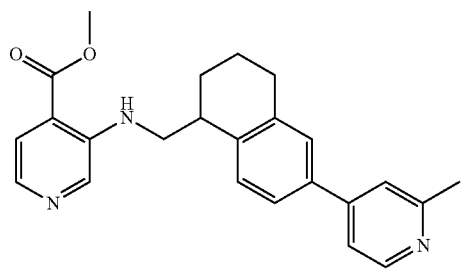 [SMILES: COC(=O)c1ccncc1NCC1CCCc2cc(-c3ccnc(C)c3)ccc21]

The title compound was prepared in 5% yield from Preparation 88c according to the procedure for Preparation 1e. [M+H] Calc'd for C$_{24}$H$_{25}$N$_3$O$_2$, 388; Found, 388.

Example 89

3-({[6-(2-methylpyridin-4-yl)-1,2,3,4-tetrahydronaphthalen-1-yl]methyl}amino)pyridine-4-carboxylic acid, hydrochloride

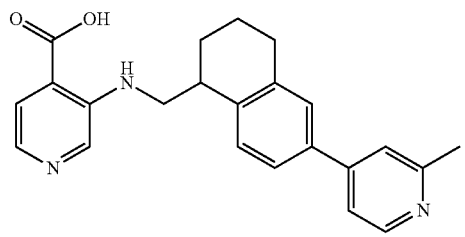 [SMILES: Cc1cc(-c2ccc3c(c2)CCCC3CNc2cnccc2C(=O)O)ccn1]

The title compound was prepared in 40% yield from Preparation 89d according to the general procedure for Example 1, and the product was purified by prep-HPLC. $^1$H NMR (400 MHz, DMSO-d$_6$): δ 1.75-1.92 (4H, m), 2.78 (3H, s), 2.85-2.89 (2H, m), 3.25-3.29 (1H, m), 3.55-3.60 (1H, m), 3.68-3.73 (1H, m), 7.59 (1H, d, J=8.0 Hz), 7.80-7.82 (2H, m), 7.95-7.97 (2H, m), 8.07 (1H, brs), 8.20-8.22 (1H, m), 8.33 (1H, s), 8.54 (1H, s), 8.78 (1H, d, J=6.4 Hz). [M+H] Calc'd for $C_{23}H_{23}N_3O_2$, 374; Found, 374.

Preparation 90a tert-butyl N-[(6-ethenyl-3,4-dihydronaphthalen-1-yl)methyl]carbamate

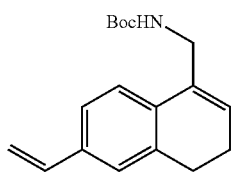 [SMILES: C=Cc1ccc2c(c1)CCC=C2CNC(=O)OC(C)(C)C]

To a solution of Preparation 3b (1.0 g, 2.97 mmol) in DMSO (20 mL) was added potassium vinyltrifluoroborate (600 mg, 4.45 mmol), $K_2CO_3$ (820 mg, 5.94 mmol) and Pd(dppf)Cl$_2$ (74 mg, 0.09 mmol). The mixture was stirred at 80° C. for 2 h under nitrogen. The mixture was poured into water and extracted with EtOAc. Organics were washed with brine, dried (Na$_2$SO$_4$), and concentrated. The residue was purified by HPLC to give 700 mg (82%) of the title compound as white solid. $^1$H NMR (400 MHz, CDCl$_3$): δ 1.48 (9H, s), 2.26-2.32 (2H, m), 2.75 (2H, t, J=8.0 Hz), 4.14 (2H, d, J=4.8 Hz), 4.57 (1H, s), 5.20 (1H, d, J=11.2 Hz), 5.71 (1H, d, J=17.6 Hz), 6.00-6.02 (1H, m), 6.63-6.71 (1H, m), 7.19-7.24 (2H, m). [M+H] Calc'd for $C_{18}H_{23}NO_2$, 286; Found, 286.

Preparation 90b (6-ethenyl-3,4-dihydronaphthalen-1-yl)methanamine, hydrochloride

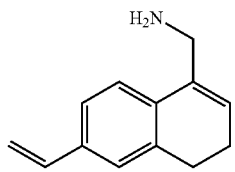

A mixture of Preparation 90a (700 mg, 2.45 mmol) in 6N HCl/EA solution (10 mL) was stirred overnight at rt. The reaction mixture was concentrated to give 400 mg (88%) of the title compound as a yellow solid. [M+H] Calc'd for $C_{13}H_{15}N$, 186; Found, 186.

Preparation 90c (6-ethyl-1,2,3,4-tetrahydronaphthalen-1-yl)methanamine

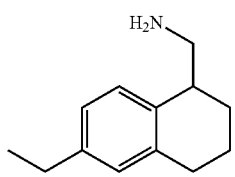

The title compound was prepared in 98% yield from Preparation 88b according to the procedure for Preparation 3e. [M+H] Calc'd for $C_{13}H_{19}N$, 190; Found, 190.

Preparation 90d methyl 3-{[(6-ethyl-1,2,3,4-tetrahydronaphthalen-1-yl)methyl]amino}pyridine-4-carboxylate

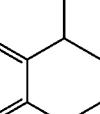

The title compound was prepared in 28% yield from Preparation 90c according to the procedure for Preparation 1e. [M+H] Calc'd for $C_{20}H_{24}N_2O_2$, 325; Found, 325.

Preparation 90e methyl 3-({[(1S)-6-ethyl-1,2,3,4-tetrahydronaphthalen-1-yl]methyl}amino)pyridine-4-carboxylate; and Preparation 91e methyl 3-({[(1R)-6-ethyl-1,2,3,4-tetrahydronaphthalen-1-yl]methyl}amino)pyridine-4-carboxylate 90e
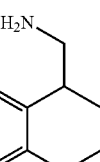

91e
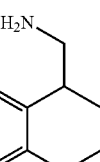

Preparation 90d (146 mg) was separated by chiral HPLC (Column: Chiralcel OJ, 250 mm*4.6 mm 5 um; Mobile phase: 70:30 CO$_2$:MeOH; F: 1.0 mL/min; W: 230 nm; T=30° C.) to give 56 mg (38%) of Preparation 91e (2.16 min) and 53 mg (36%) of Preparation 90e (2.88 min), each as a yellow gum.

Example 90

3-({[(1S)-6-ethyl-1,2,3,4-tetrahydronaphthalen-1-yl]methyl}amino)pyridine-4-carboxylic

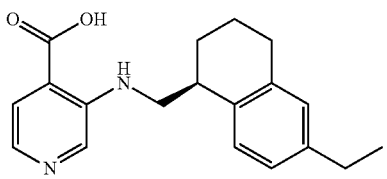 [SMILES: CCc1ccc2c(c1)CCC[C@@H]2CNc1cnccc1C(=O)O]

The title compound was prepared in 58% yield from Preparation 90e according to the general procedure for Example 1. $^1$H NMR (400 MHz, DMSO-$d_6$): δ1.15 (3H, t, J=7.6 Hz), 1.64-1.68 (1H, m), 1.77-1.83 (3H, m), 2.53-2.55 (2H, m), 2.67-2.71 (2H, m), 3.04-3.07 (1H, m), 3.39-3.44 (1H, m), 3.53-3.57 (1H, m), 6.92 (1H, s), 6.95 (1H, d, J=7.6 Hz), 7.20 (1H, d, J=8.0 Hz), 7.55 (1H, d, J=5.2 Hz), 7.82 (1H, d, J=4.0 Hz), 8.35 (1H, s). [M+H] Calc'd for $C_{19}H_{22}N_2O_2$, 311; Found, 311.

Example 91

3-({[(1R)-6-ethyl-1,2,3,4-tetrahydronaphthalen-1-yl]methyl}amino)pyridine-4-carboxylic acid

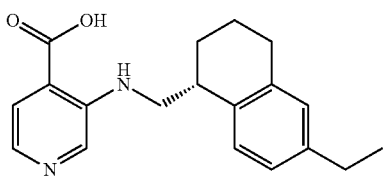 [SMILES: CCc1ccc2c(c1)CCC[C@H]2CNc1cnccc1C(=O)O]

The title compound was prepared in 72% yield from Preparation 91e according to the general procedure for Example 1. $^1$H NMR (400 MHz, DMSO-$d_6$): δ1.15 (3H, t, J=7.6 Hz), 1.63-1.69 (1H, m), 1.77-1.87 (3H, m), 2.53-2.55 (2H, m), 2.65-2.75 (2H, m), 3.04-3.07 (1H, m), 3.38-3.45 (1H, m), 3.53-3.57 (1H, m), 6.92 (1H, s), 6.95 (1H, d, J=7.2 Hz), 7.20 (1H, d, J=7.6 Hz), 7.55 (1H, d, J=5.2 Hz), 7.82 (1H, d, J=4.0 Hz), 8.36 (1H, s). [M+H] Calc'd for $C_{19}H_{22}N_2O_2$, 311; Found, 311.

Preparation 92a 4-(2,3-dihydro-1-benzofuran-7-yl)but-3-enoic acid

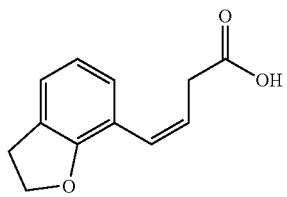 [SMILES: O=C(O)C/C=C\c1cccc2c1OCC2]

To a solution of (2-carboxyethyl)triphenylphosphonium bromide (617 mg, 1.5 mmol) in THF (20 mL) was added NaHMDS (1.5 mL, 3.0 mmol) at −20° C., and the reaction was stirred for 20 min. 2,3-Dihydro-1-benzofuran-7-carbaldehyde (200 mg, 1.4 mmol) was added to the reaction at −78° C., and the reaction was stirred overnight while warming to rt. The reaction was diluted with water (30 mL) and extracted with EtOAc (3×30 mL). Organics were washed with brine (30 mL), dried (Na$_2$SO$_4$), and concentrated to give the crude title compound as a yellow solid. [M+H] Calc'd for $C_{12}H_{12}O_3$, 205; Found, 205.

Preparation 92b 4-(2,3-dihydro-1-benzofuran-7-yl)butanoic acid

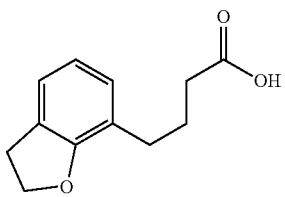 [SMILES: O=C(O)CCCc1cccc2c1OCC2]

To a solution of Preparation 92a (6.8 mmol) in MeOH (30 mL) was added 10% Pd/C (200 mg) at rt under N$_2$. The mixture was stirred at rt overnight with 50 psi H$_2$. The reaction was filtered through Celite and concentrated to give 1.2 g (86%) of the crude title compound as a yellow oil. [M+H] Calc'd for $C_{12}H_{14}O_3$, 207; Found, 207.

Preparation 92c 2H,3H,6H,7H,8H,9H-naphtho[1,2-b]furan-6-one

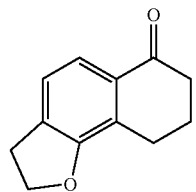 [SMILES: O=C1CCCc2c1ccc1c2OCC1]

PPA (5 mL) was added to Preparation 92b (1.2 g, 5.8 mmol) at rt, and the reaction was stirred at 95° C. for 1.5 h. The solution was poured into water (50 mL) at rt, extracted with EtOAc (3×50 mL), washed with brine (50 mL), dried (Na$_2$SO$_4$), and concentrated. Purification by silica gel chromatography (PE:EtOAc=15:1) gave 200 mg (18%) of the title compound as a yellow solid.

$^1$H NMR (300 MHz, CDCl$_3$): δ 2.11-2.15 (2H, m), 2.64 (2H, t, J=6.3 Hz), 2.85 (2H, t, J=6.3 Hz), 3.28 (2H, t, J=8.7 Hz), 4.65 (2H, t, J=8.7 Hz), 7.15 (1H, d, J=7.8 Hz), 7.62 (1H, d, J=7.8 Hz). [M+H] Calc'd for $C_{12}H_{12}O_2$, 189; Found, 189.

Preparation 92d 2H,3H,8H,9H-naphtho[1,2-b]furan-6-ylmethanamine, hydrochloride

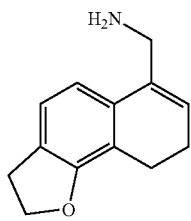 [SMILES: NCC1=CCCc2c1ccc1c2OCC1]

The title compound was prepared in 72% yield from Preparation 92c according to the general procedure for Preparation 3a. [M+H] Calc'd for $C_{13}H_{15}NO$, 202; Found, 202.

Preparation 92e 2H,3H,6H,7H,8H,9H-naphtho[1,2-b]furan-6-ylmethanamine

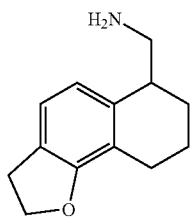 [SMILES: NCC1CCCc2c1ccc1c2OCC1]

The title compound was prepared in quantitative yield from Preparation 92d according to the general procedure for Preparation 3e. [M+H] Calc'd for $C_{13}H_{17}NO$, 204; Found, 204.

Preparation 92f methyl 3-({2H,3H,6H,7H,8H,9H-naphtho[1,2-b]furan-6-ylmethyl}amino)pyridine-4-carboxylate

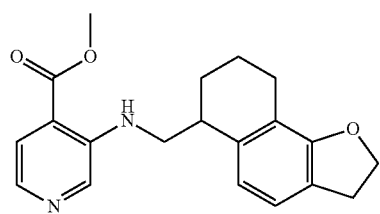 [SMILES: COC(=O)c1ccncc1NCC1CCCc2c1ccc1c2OCC1]

The title compound was prepared in 26% yield from Preparation 92f according to the general procedure for Preparation 1e. [M+H] Calc'd for $C_{20}H_{22}N_2O_3$, 339; Found, 339.

Example 92

3-({2H,3H,6H,7H,8H,9H-naphtho[1,2-b]furan-6-ylmethyl}amino)pyridine-4-carboxylic acid

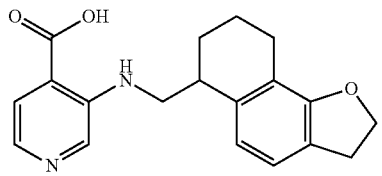 [SMILES: O=C(O)c1ccncc1NCC1CCCc2c1ccc1c2OCC1]

The title compound was prepared in 81% yield from Preparation 92f according to the general procedure for Example 1. $^1$H NMR (400 MHz, DMSO-d$_6$): δ 1.65-1.84 (4H, m), 2.44-2.50 (1H, m), 2.50-2.61 (1H, m), 3.05-3.14 (3H, m), 3.41-3.56 (2H, m), 4.99 (2H, t, J=8.4 Hz), 6.78 (1H, d, J=7.6 Hz), 6.99 (1H, d, J=7.6 Hz), 7.57 (1H, d, J=4.8 Hz), 7.83 (1H, d, J=5.2 Hz), 8.35 (1H, s). [M+H] Calc'd for $C_{19}H_{20}N_2O_3$, 325; Found, 325.

Preparation 93a (6,7-dimethyl-2H-chromen-4-yl)methanamine, hydrochloride

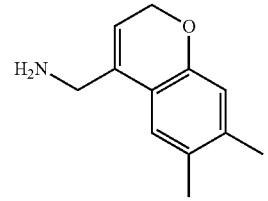

The title compound was prepared in 26% yield from 6,7-dimethyl-3,4-dihydro-2H-1-benzopyran-4-one according to the general procedure for Preparation 3a. $^1$H NMR (400 MHz, DMSO-d$_6$): δ 1.55 (2H, br s), 1.81-1.99 (2H, m), 2.09 (6H, s), 2.54-2.60 (2H, m), 2.81-2.88 (1H, m), 3.96-4.07 (2H, m), 6.50 (1H, s), 6.90 (1H, s). [M+H] calc'd for $C_{12}H_{15}NO$, 190; Found 190.

Preparation 93b (6,7-dimethyl-3,4-dihydro-2H-1-benzopyran-4-yl)methanamine

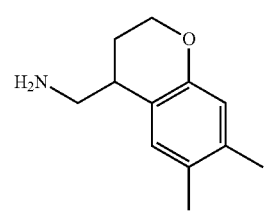

The title compound was prepared in quantitative yield from Preparation 93a according to the general procedure for Preparation 3e. $^1$H NMR (400 MHz, DMSO-d$_6$): δ 1.55 (2H, br s), 1.81-1.99 (2H, m), 2.09 (6H, s), 2.54-2.60 (2H, m), 2.81-2.88 (1H, m), 3.96-4.07 (2H, m), 6.50 (1H, s), 6.90 (1H, s). [M+H] calc'd for $C_{12}H_{17}NO$, 192; found 192.

Example 93

3-{[(6,7-dimethyl-3,4-dihydro-2H-1-benzopyran-4-yl)methyl]amino}pyridine-4-carboxylic acid

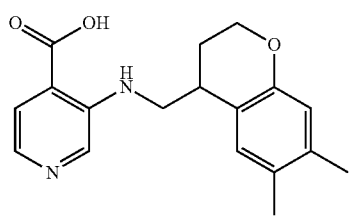 [SMILES: Cc1cc2c(cc1C)C(CNc1cnccc1C(=O)O)CCO2]

The title compound was prepared in 21% yield from Preparation 93b according to the general procedure for Example 13. $^1$H NMR (400 MHz, DMSO-d$_6$): δ 1.81-1.99 (2H, m), 2.11 (3H, s), 2.12 (3H, s), 3.02-3.06 (1H, m), 3.43-3.67 (2H, m), 4.06-4.17 (2H, m), 6.56 (1H, s), 7.04 (1H, s), 7.57 (1H, d, J=5.0 Hz), 7.69 (1H, br s), 7.85 (1H, d, J=5.0 Hz), 8.42 (s, 1H), 13.38 (1H, br s). [M+H] calc'd for $C_{18}H_{20}N_2O_3$, 313; found 313.

Preparation 94a (6-methoxy-7-methyl-3,4-dihydronaphthalen-1-yl)methanamine, hydrochloride

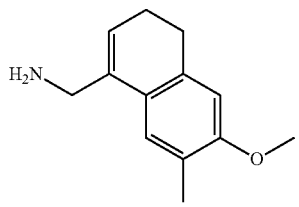

The title compound was prepared in 56% yield from 6-methoxy-7-methyl-1,2,3,4-tetrahydronaphthalen-1-one according to the general procedure for Preparation 3a. [M+H] calc'd for $C_{13}H_{17}NO$, 204; found 204.

Preparation 94b (6-methoxy-7-methyl-1,2,3,4-tetrahydronaphthalen-1-yl)methanamine

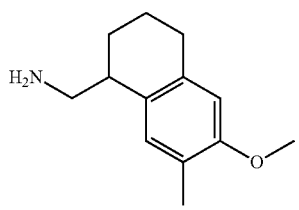

The title compound was prepared in quantitative yield from Preparation 94a according to the general procedure for Preparation 3e. $^1$H NMR (400 MHz, CDCl$_3$): δ 1.65-1.85 (6H, m), 2.17 (3H, s), 2.69-2.75 (3H, m), 2.84-2.97 (2H, m), 3.79 (3H, s), 6.53 (1H, s), 6.95 (1H, s). [M+H] calc'd for $C_{13}H_{19}NO$, 206; found 206.

Preparation 94c methyl 3-{[(6-methoxy-7-methyl-1,2,3,4-tetrahydronaphthalen-1-yl)methyl]amino}pyridine-4-carboxylate

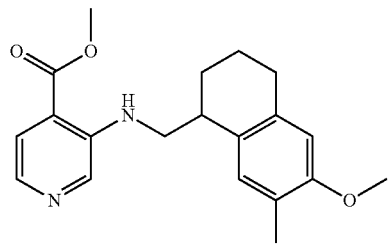 [SMILES: COC(=O)c1ccncc1NCC1CCCc2cc(OC)c(C)cc21]

The title compound was prepared in 66% yield from Preparation 94b according to the general procedure for Preparation 4d. $^1$H NMR (400 MHz, DMSO-d$_6$): δ 1.76-1.92 (4H, m), 2.18 (3H, s), 2.74-2.79 (2H, m), 3.06-3.10 (1H, m), 3.34-3.41 (1H, m), 3.52-3.59 (1H, m), 3.80 (3H, s), 3.90 (3H, s), 6.56 (1H, s), 7.00 (1H, s), 7.58 (1H, br s), 7.63 (1H, d, J=5.1 Hz), 7.90 (1H, d, J=5.1 Hz), 8.34 (1H, s). [M+H] calc'd for $C_{20}H_{24}N_2O_3$, 341; found 341.

Example 94

3-{[(6-methoxy-7-methyl-1,2,3,4-tetrahydronaphthalen-1-yl)methyl]amino}pyridine-4-carboxylic acid

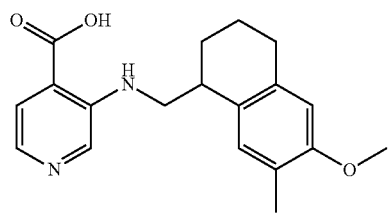 [SMILES: COc1cc2c(cc1C)C(CNc1cnccc1C(=O)O)CCC2]

The title compound was prepared in 63% yield from Preparation 94c according to the general procedure for Example 1. $^1$H NMR (400 MHz, DMSO-d$_6$): δ 1.62-1.81 (4H, m), 2.08 (3H, s), 2.66-2.71 (2H, m), 2.97-3.01 (1H, m), 3.35-3.42 (1H, m), 3.50-3.56 (1H, m), 3.73 (3H, s), 6.61 (1H, s), 7.05 (1H, s), 7.57 (1H, d, J=5.0 Hz), 7.71 (1H, br s), 7.83 (1H, d, J=5.0 Hz), 8.35 (1H, s). [M+H] calc'd for $C_{19}H_{22}N_2O_3$, 327; found 327.

Preparation 95a 4-(3,5-dimethoxyphenyl)but-3-enoic acid

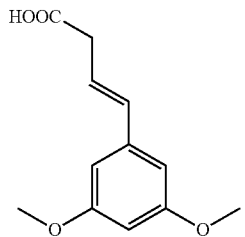

To a solution of (2-carboxyethyl)triphenylphosphonium bromide (13.7 g, 33 mmol) in dry THF (50 mL) was added NaHMDS (33 mL, 66 mmol) dropwise at −20° C. under $N_2$ and the reaction stirred for 20 min. The reaction was cooled to −78° C. and 3,5-dimethoxybenzaldehyde (5.0 g, 30 mmol) was added, and the reaction mixture stirred overnight while warming to rt. The reaction was quenched with water and extracted with EtOAc. The aqueous layer was acidified to pH=2 with dilute HCl solution and extracted with EtOAc again. The combined organic layers were washed with brine, dried ($Na_2SO_4$) and concentrated to give 2.54 g (38%) of the title compound as an orange gum. [M+H] Calc'd for $C_{12}H_{14}O_4$, 223; Found, 223.

Preparation 95b 4-(3,5-dimethoxyphenyl)butanoic acid

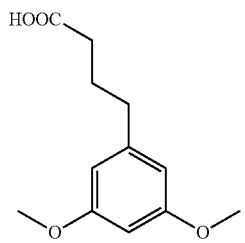

To a solution of Preparation 95a (2.54 g, 11.4 mmol) in MeOH (25 mL) and conc. HCl (three drops) under $N_2$ was added 10% Pd/C (0.5 g) at rt. The suspension was stirred for 3 h under 50 psi of $H_2$. The reaction mixture was filtered through Celite and concentrated to give 2.27 g (88%) of the title compound as colorless oil. [M+H] Calc'd for $C_{12}H_{16}O_4$, 225; Found, 225.

Preparation 95c 6,8-dimethoxy-1,2,3,4-tetrahydronaphthalen-1-one

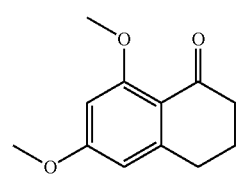

The mixture of Preparation 95b (2.27 g, 10 mmol) and PPA (30 g) was heated at 95° C. for 30 min. The gum was dissolved in water and extracted with EtOAc. Organics were washed with brine, dried ($Na_2SO_4$), and concentrated. The residue was purified by silica gel chromatography to give 1.2 g (57%) of the title compound as tan oil. $^1$H NMR (400 MHz, $CD_3OD$): δ 1.96 (2H, t, J=6.2 Hz), 2.51 (2H, t, J=6.4 Hz), 2.85 (2H, t, J=6.0 Hz), 3.81 (3H, s), 3.83 (3H, s), 6.38 (2H, d, J=2.4 Hz). [M+H] Calc'd for $C_{12}H_{14}O_3$, 207; Found, 207.

Preparation 95d (6,8-dimethoxy-3,4-dihydronaphthalen-1-yl)methanamine, hydrochloride

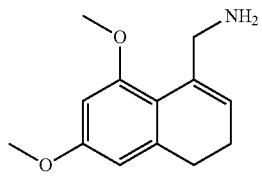 [SMILES: COc1cc2c(c(OC)c1)C(CN)=CCC2]

The title compound was prepared in 46% yield from Preparation 95c according to the general procedure for Preparation 3a. [M+H] Calc'd for $C_{13}H_{17}NO_2$, 220; Found, 220.

Preparation 95e (6,8-dimethoxy-1,2,3,4-tetrahydronaphthalen-1-yl)methanamine

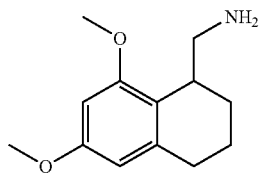 [SMILES: COc1cc2c(c(OC)c1)C(CN)CCC2]

The title compound was prepared in 87% yield from Preparation 95d according to the general procedure for Preparation 3e. [M+H] Calc'd for $C_{13}H_{19}NO_2$, 222; Found, 222.

Preparation 95f methyl 3-{[(6,8-dimethoxy-1,2,3,4-tetrahydronaphthalen-1-yl)methyl]amino}pyridine-4-carboxylate

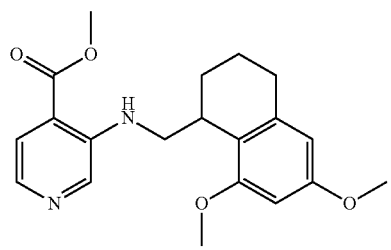 [SMILES: COC(=O)c1ccncc1NCC1CCCc2cc(OC)cc(OC)c21]

The title compound was prepared in 38% yield from Preparation 95e according to the general procedure for Preparation 1e. [M+H] Calc'd for $C_{20}H_{24}N_2O_4$, 357; Found, 357.

Example 95

3-{[(6,8-dimethoxy-1,2,3,4-tetrahydronaphthalen-1-yl)methyl]amino}pyridine-4-carboxylic acid

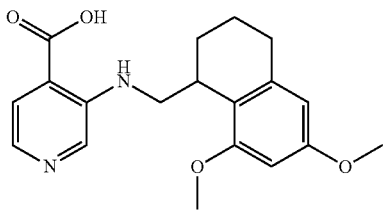 [SMILES: COc1cc2c(c(OC)c1)C(CNc1cnccc1C(=O)O)CCC2]

The title compound was prepared in 46% yield from Preparation 95f according to the general procedure for Example 1. $^1$H NMR (400 MHz, DMSO-$d_6$): δ 1.51-1.57 (1H, m), 1.63-1.67 (1H, m), 1.81-1.93 (2H, m), 2.61-2.75 (2H, m), 3.14-3.24 (2H, m), 3.47 (1H, d, J=10.8 Hz), 3.70 (3H, s), 3.84 (3H, s), 6.28 (1H, d, J=2.0 Hz), 6.39 (1H, d, J=2.0 Hz), 7.55 (1H, d, J=5.2 Hz), 7.81 (1H, d, J=5.2 Hz), 8.53 (1H, s). [M+H] Calc'd for $C_{19}H_{22}N_2O_4$, 343; Found, 343.

Preparation 96a 4-(4-fluoro-3-methoxyphenyl)but-3-enoic acid

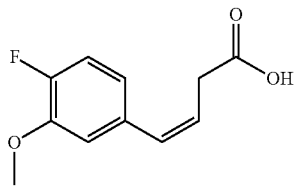

To a solution of (2-carboxyethyl)triphenylphosphonium bromide (14.8 g, 35.7 mmol) in THF (40 mL) was added NaHMDS (35.8 mL, 71.5 mmol) at −20° C., and the reaction was stirred for 20 min. 4-Fluoro-3-methoxybenzaldehyde (5.0 g, 32.5 mmol) was added to the reaction at −78° C., and the reaction was stirred overnight while warming to rt. The reaction was diluted with water (30 mL) and extracted with EtOAc (3×30 mL). Organics were washed with brine (30 mL), dried (Na$_2$SO$_4$), and concentrated to give 6.0 g (88%) of the crude title compound as a yellow solid. [M+H] Calc'd for $C_{11}H_{11}FO_3$, 211; Found, 211.

Preparation 96b 4-(4-fluoro-3-methoxyphenyl)butanoic acid

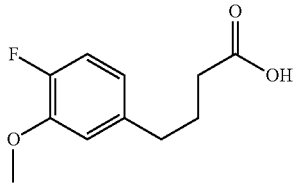

To a solution of Preparation 96a (6.0 g, 28.6 mmol) in MeOH (30 mL) under N$_2$ was added 10% Pd/C (1.2 g), and the mixture was stirred at rt overnight under 50 psi of H$_2$. The reaction mixture was filtered through Celite and concentrated to give 5.8 g (96%) of the crude title compound as an off-white solid. [M+H] Calc'd for $C_{11}H_{13}FO_3$, 213; Found, 213.

Preparation 96c 7-fluoro-6-methoxy-1,2,3,4-tetrahydronaphthalen-1-one

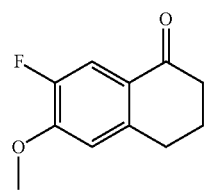

PPA (30 g) was added to Preparation 96b (5.8 g, 27.4 mmol) at rt, and the reaction was stirred at 95° C. for 0.5 h. The solution was poured into water (50 mL) at rt, and extracted with EtOAc (3×50 mL). Organics were washed with brine (50 mL), dried (Na$_2$SO$_4$), and concentrated. Purification by silica gel chromatography (PE:EtOAc=3:1) gave 3.1 g (58%) of the title compound as an off-white solid. $^1$H NMR (400 MHz, CDCl$_3$): δ 2.09-2.16 (2H, m), 2.60 (2H, t, J=6.4 Hz), 2.91 (2H, t, J=6.0 Hz), 3.94 (3H, s), 6.75 (1H, d, J=8.0 Hz), 7.32 (1H, d, J=11.6 Hz). [M+H] Calc'd for $C_{11}H_{11}FO_2$, 195; Found, 195.

Preparation 96d (7-fluoro-6-methoxy-3,4-dihydronaphthalen-1-yl)methanamine, hydrochloride

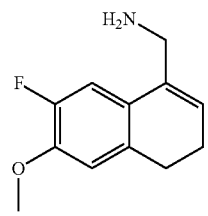

The title compound was prepared in 83% yield from Preparation 96c according to the general procedure for Preparation 3a. [M+H] Calc'd for $C_{12}H_{14}FNO$, 208; Found, 208.

Preparation 96e (7-fluoro-6-methoxy-1,2,3,4-tetrahydronaphthalen-1-yl)methanamine

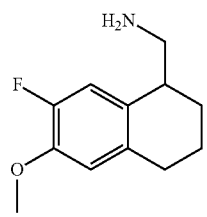

The title compound was prepared in quantitative yield from Preparation 96d according to the general procedure for Preparation 3e. [M+H] Calc'd for $C_{12}H_{16}FNO$, 210; Found, 210.

Preparation 96f methyl 3-({[(1S)-7-fluoro-6-methoxy-1,2,3,4-tetrahydronaphthalen-1-yl]methyl}amino)pyridine-4-carboxylate, and Preparation 97f methyl 3-({[(1R)-7-fluoro-6-methoxy-1,2,3,4-tetrahydronaphthalen-1-yl]methyl}amino)pyridine-4-carboxylate

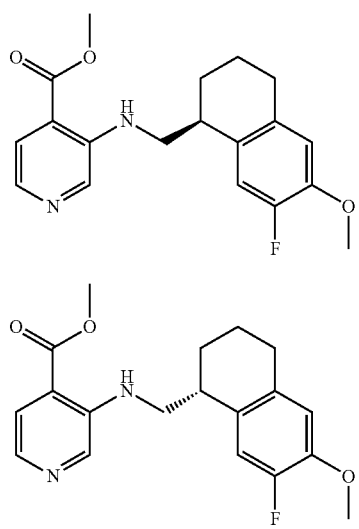

The racemate of the title compounds was prepared in 25% yield from Preparation 96e according to the general procedure for Preparation 1e. [M+H] Calc'd for $C_{19}H_{21}FN_2O_3$, 345; Found, 345.

Separation by chiral HPLC (Column: Chiralcel: IA 5 um 4.6*250 mm, Mobile phase: Hex:EtOH=70:30, F: 1.0 mL/min, W: 230 nm, T: 30° C.) gave 40% yield of Preparation 96f (7.937 min) and 37% of Preparation 97f (10.383 min), each as a colorless oil.

Example 96

3-({[(1S)-7-fluoro-6-methoxy-1,2,3,4-tetrahydronaphthalen-1-yl]methyl}amino)pyridine-4-carboxylic acid

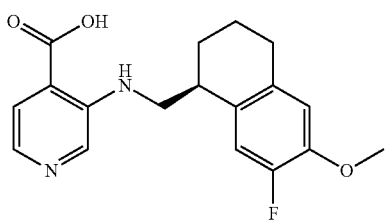 [SMILES: COc1cc2c(cc1F)[C@@H](CNc1cnccc1C(=O)O)CCC2]

The title compound was prepared in 65% yield from Preparation 96f according to the general procedure for Example 1. $^1$H NMR (400 MHz, DMSO-$d_6$): δ 1.63-1.84 (4H, m), 2.64-2.74 (2H, m), 3.01-3.06 (1H, m), 3.38-3.44 (1H, m), 3.56-3.60 (1H, m), 3.79 (3H, s), 6.85 (1H, d, J=8.8 Hz), 7.17 (1H, d, J=13.2 Hz), 7.56 (1H, d, J=5.2 Hz), 7.83 (1H, d, J=5.2 Hz), 8.38 (1H, s). [M+H] Calc'd for $C_{18}H_{19}FN_2O_3$, 331; Found, 331.

Example 97

3-({[(1R)-7-fluoro-6-methoxy-1,2,3,4-tetrahydronaphthalen-1-yl]methyl}amino)pyridine-4-carboxylic acid

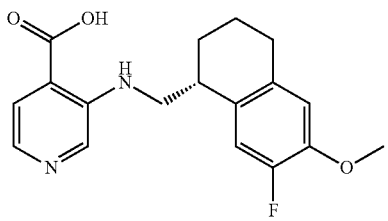 [SMILES: COc1cc2c(cc1F)[C@H](CNc1cnccc1C(=O)O)CCC2]

The title compound was prepared in 64% yield from Preparation 97f according to the general procedure for Example 1. $^1$H NMR (400 MHz, DMSO-$d_6$): δ 1.63-1.86 (4H, m), 2.63-2.74 (2H, m), 3.01-3.04 (1H, m), 3.39-3.43 (1H, m), 3.56-3.60 (1H, m), 3.79 (3H, s), 6.86 (1H, d, J=9.2 Hz), 7.17 (1H, d, J=12.8 Hz), 7.55 (1H, d, J=5.2 Hz), 7.83 (1H, d, J=5.2 Hz), 8.38 (1H, s). [M+H] Calc'd for $C_{18}H_{19}FN_2O_3$, 331; Found, 331.

Preparation 98a 5-bromo-6-methoxy-1,2,3,4-tetrahydronaphthalen-1-one

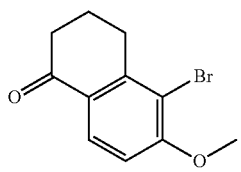

To a suspension of 6-methoxy-1-tetralone (2.0 g, 11.4 mmol) and NBS (2.0 g, 11.4 mmol) in H$_2$O (30 mL) was added conc. H$_2$SO$_4$ (1.2 mL, 22.7 mmol) at rt. The reaction was stirred at 60° C. for 3 h. The mixture was filtered, and concentrated. Purification by prep-HPLC gave 1.2 g (41%) of the title compound as a white solid. $^1$H NMR (400 MHz, CDCl$_3$): δ 2.13-2.18 (2H, m), 2.61 (2H, t, J=6.0 Hz), 3.03 (2H, t, J=6.0 Hz), 3.97 (3H, s), 6.88 (1H, d, J=8.8 Hz), 8.06 (1H, d, J=8.8 Hz). [M+H] Calc'd for C$_{11}$H$_{11}$BrO$_2$, 255, 257; Found, 255, 257.

Preparation 98b 6-methoxy-5-methyl-1,2,3,4-tetrahydronaphthalen-1-one

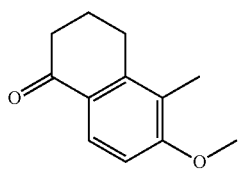

To a suspension of Preparation 98a (100 mg, 0.39 mmol), potassium methyltrifluoroborate (48 mg, 0.39 mmol) and Cs$_2$CO$_3$ (381 mg, 1.2 mmol) in H$_2$O (2 mL) and DMF (18 mL) was added Pd(dppf)Cl$_2$DCM (32 mg, 0.04 mmol) at rt under N$_2$. The reaction was stirred at 120° C. overnight. The reaction was filtered and concentrated. Purification by silica gel chromatography (PE:EtOAc=15:1) gave 40 mg (54%) of the title compound as a white solid. [M+H] Calc'd for C$_{12}$H$_{14}$O$_2$, 191; Found, 191.

Preparation 98c (6-methoxy-5-methyl-3,4-dihydronaphthalen-1-yl)methanamine, hydrochloride

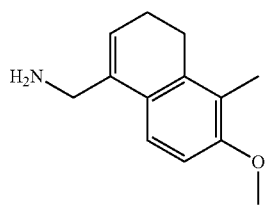

The title compound was prepared in 42% yield from Preparation 98b according to the general procedure for Preparation 3a. [M+H] Calc'd for C$_{13}$H$_{17}$NO, 204. Found, 204.

Preparation 98d (6-methoxy-5-methyl-1,2,3,4-tetrahydronaphthalen-1-yl)methanamine

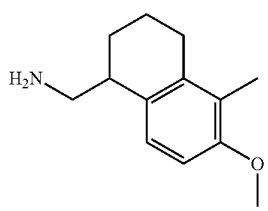

The title compound was prepared in quantitative yield from Preparation 98c according to the general procedure for Preparation 3e. [M+H] Calc'd for C$_{13}$H$_{19}$NO, 206; Found, 206.

Preparation 98d methyl 3-({[(1S)-6-methoxy-5-methyl-1,2,3,4-tetra-hydronaphthalen-1-yl]methyl}amino)pyridine-4-carboxylate, and

Preparation 99d methyl 3-({[(1R)-6-methoxy-5-methyl-1,2,3,4-tetra-hydronaphthalen-1-yl]methyl}amino)pyridine-4-carboxylate

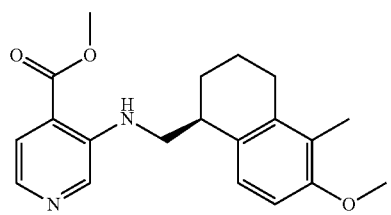

98d

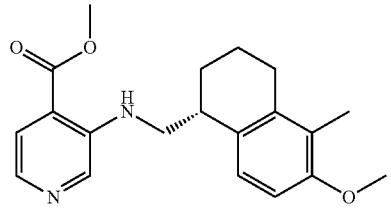

99d

The racemate of the title compounds was prepared in 43% yield from Preparation 99c according to the general procedure for Preparation 1e. [M+H] Calc'd for C$_{19}$H$_{21}$FN$_2$O$_3$, 345; Found, 345.

Separation by chiral HPLC (Column: Chiralcel: OJ-H 5 um 4.6*250 mm, Mobile phase: CO$_2$:MeOH=70:30, F: 1.0 mL/min, W: 230 nm, T: 30° C.) gave 40% yield of Preparation 99d (2.17 min) and 28% of Preparation 98d (3.10 min), each as a yellow oil.

Example 98

3-({[(1S)-6-methoxy-5-methyl-1,2,3,4-tetrahydronaphthalen-1-yl]methyl}amino)pyridine-4-carboxylic acid

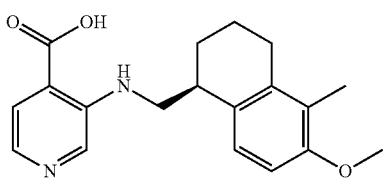 [SMILES: COc1ccc2c(c1C)CCC[C@@H]2CNc1cnccc1C(=O)O]

The title compound was prepared in 63% yield from Preparation 98d according to the general procedure for Example 1. $^1$H NMR (400 MHz, DMSO-d$_6$): δ 1.70-1.77 (3H, m), 1.83-1.86 (1H, m), 2.03 (3H, s), 2.52-2.56 (1H, m), 2.63-2.67 (1H, m), 3.03-3.06 (1H, m), 3.40-3.45 (1H, m), 3.50-3.55 (1H, m), 3.74 (3H, s), 6.78 (1H, d, J=8.4 Hz), 7.12 (1H, d, J=8.4 Hz), 7.56 (1H, d, J=4.8 Hz), 7.83 (1H, d, J=4.8 Hz), 8.36 (1H, s). [M+H] Calc'd for C$_{19}$H$_{22}$N$_2$O$_3$, 327; Found, 327.

Example 99

3-({[(1R)-6-methoxy-5-methyl-1,2,3,4-tetrahydronaphthalen-1-yl]methyl}amino)pyridine-4-carboxylic acid

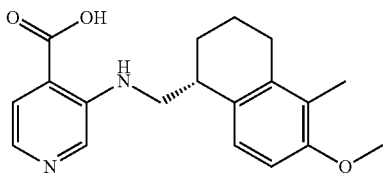 [SMILES: COc1ccc2c(c1C)CCC[C@H]2CNc1cnccc1C(=O)O]

The title compound was prepared in 93% yield from Preparation 99d according to the general procedure for Example 1. $^1$H NMR (400 MHz, DMSO-d$_6$): δ 1.70-1.77 (3H, m), 1.83-1.86 (1H, m), 2.03 (3H, s), 2.52-2.56 (1H, m), 2.63-2.67 (1H, m), 3.03-3.06 (1H, m), 3.40-3.45 (1H, m), 3.50-3.55 (1H, m), 3.74 (3H, s), 6.78 (1H, d, J=8.4 Hz), 7.12 (1H, d, J=8.4 Hz), 7.56 (1H, d, J=4.8 Hz), 7.83 (1H, d, J=4.8 Hz), 8.36 (1H, s). [M+H] Calc'd for C$_{19}$H$_{22}$N$_2$O$_3$, 327; Found, 327.

Preparation 100a 7-(2-methylphenyl)-3,4-dihydro-2H-1-benzopyran-4-one

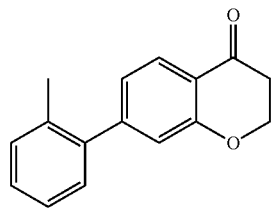 [SMILES: Cc1ccccc1-c1ccc2c(c1)OCCC2=O]

To a solution of 7-bromo-4-chromanone (2.0 g, 8.8 mmol) in dioxane (30 mL) was added 2-methylphenylboronic acid (1.8 g, 13.2 mmol), Pd(PPh$_3$)$_4$ (0.5 g, 0.44 mmol) and Na$_2$CO$_3$ (2.8 g, 26.4 mmol). The mixture was stirred at 100° C. under nitrogen overnight. The mixture was filtered and concentrated. The residue was purified by silica gel chromatography (PE:EtOAc=10:1) to give 2.1 g (quantitative) of the title compound as an off-white solid. $^1$H NMR (300 MHz, CDCl$_3$): δ2.29 (s, 3H), 2.85 (t, J=6.3 Hz, 2H), 4.59 (t, J=6.3 Hz, 2H), 6.94 (s, 1H), 7.00 (d, J=8.1 Hz, 1H), 7.19-7.32 (m, 4H), 7.93 (d, J=8.1 Hz, 1H). [M+H] Calc'd for C$_{16}$H$_{14}$O$_2$, 239; Found, 239.

Preparation 100b

[7-(2-methylphenyl)-2H-chromen-4-yl]methanamine, hydrochloride

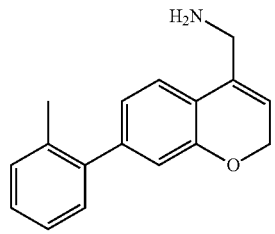 [SMILES: Cc1ccccc1-c1ccc2c(c1)OCC=C2CN]

The title compound was prepared in 47% yield from Preparation 100a according to the general procedure for Preparation 3a. [M+H] Calc'd for C$_{17}$H$_{17}$NO, 252; Found, 252.

Preparation 100c

[7-(2-methylphenyl)-3,4-dihydro-2H-1-benzopyran-4-yl]methanamine

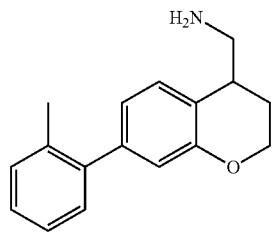 [SMILES: Cc1ccccc1-c1ccc2c(c1)OCCC2CN]

The title compound was prepared in quantitative yield from Preparation 100b according to the general procedure for Preparation 3e. [M+H] Calc'd for $C_{17}H_{19}NO$, 254; Found, 254.

Preparation 100d methyl 3-({[(4S)-7-(2-methylphenyl)-3,4-dihydro-2H-1-benzopyran-4-yl]methyl}amino)pyridine-4-carboxylate; and Preparation 101d methyl 3-({[(4R)-7-(2-methylphenyl)-3,4-dihydro-2H-1-benzopyran-4-yl]methyl}amino)pyridine-4-carboxylate

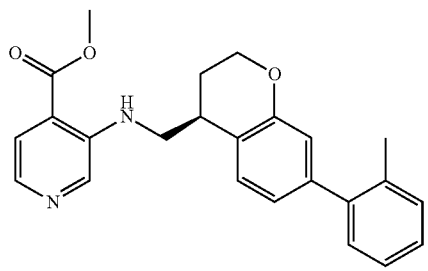

100d

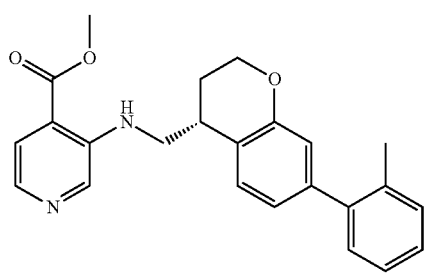

101d

The racemate (440 mg) of the title compounds was prepared in 25% yield from Preparation 100c according to the general procedure for Preparation 1e. [M+H] Calc'd for $C_{24}H_{24}N_2O_3$, 389; Found, 389.
Separation by chiral HPLC (Column: Chiralcel: IC 5 um 4.6*250 mm, Mobile phase: Hex:EtOH=70:30, F: 1.0 mL/min, W: 230 nm, T: 30° C.) gave 179 mg (41%) of Preparation 100d (7.49 min) and 189 mg (43%) of Preparation 101d (8.82 min), each as a colorless oil.

Example 100

3-({[(4S)-7-(2-methylphenyl)-3,4-dihydro-2H-1-benzopyran-4-yl]methyl}amino)pyridine-4-carboxylic acid

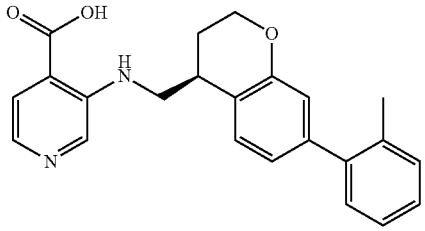 [SMILES: Cc1ccccc1-c1ccc2c(c1)OCC[C@@H]2CNc1cnccc1C(=O)O]

The title compound was prepared in 80% yield from Preparation 100d according to the general procedure for Example 1. $^1$H NMR (400 MHz, DMSO-d$_6$): δ 1.88-1.96 (m, 1H), 2.02-2.09 (m, 1H), 2.23 (s, 3H), 3.16-3.21 (m, 1H), 3.54-3.59 (m, 1H), 3.74-3.79 (m, 1H), 4.17-4.28 (m, 2H), 6.72 (d, J=1.6 Hz, 1H), 6.82 (dd, J=7.6 Hz, 1.6 Hz, 1H), 7.16-7.17 (m, 1H), 7.20-7.28 (m, 3H), 7.37 (d, J=7.6 Hz, 1H), 7.58 (d, J=4.8 Hz, 1H), 7.86 (d, J=4.8 Hz, 1H), 8.45 (s, 1H). [M+H] Calc'd for $C_{23}H_{22}N_2O_3$, 375; Found, 375.

Example 101

3-({[(4R)-7-(2-methylphenyl)-3,4-dihydro-2H-1-benzopyran-4-yl]methyl}amino)pyridine-4-carboxylic acid

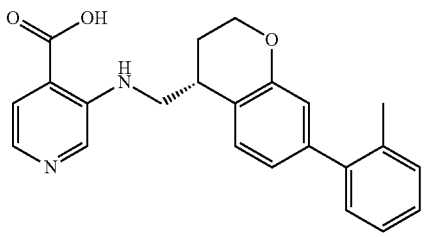 [SMILES: Cc1ccccc1-c1ccc2c(c1)OCC[C@H]2CNc1cnccc1C(=O)O]

The title compound was prepared in 74% yield from Preparation 101d according to the general procedure for Example 1. $^1$H NMR (400 MHz, DMSO-d$_6$): δ 1.88-1.96 (m, 1H), 2.00-2.09 (m, 1H), 2.23 (s, 3H), 3.17-3.22 (m, 1H), 3.54-3.62 (m, 1H), 3.74-3.79 (m, 1H), 4.17-4.29 (m, 2H), 6.72 (d, J=1.6 Hz, 1H), 6.82 (dd, J=7.6 Hz, 1.6 Hz, 1H), 7.15-7.17 (m, 1H), 7.20-7.29 (m, 3H), 7.37 (d, J=7.6 Hz, 1H), 7.58 (d, J=4.8 Hz, 1H), 7.86 (d, J=4.8 Hz, 1H), 8.45 (s, 1H). [M+H] Calc'd for $C_{23}H_{22}N_2O_3$, 375; Found, 375.

Preparation 102a tert-butyl N-{[(4R)-7-(5-fluoro-2-methoxyphenyl)-3,4-dihydro-2H-1-benzopyran-4-yl]methyl}carbamate

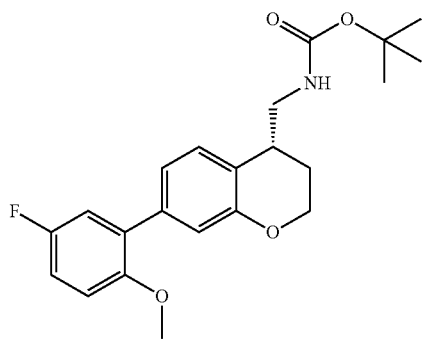 [SMILES: COc1ccc(F)cc1-c1ccc2c(c1)OCC[C@H]2CNC(=O)OC(C)(C)C]

The title compound was prepared in 80% yield from 5-fluoro-2-methoxyphenylboronic acid and Preparation 18d according to the procedures for Preparation 43a. [M+H] Calc'd for $C_{22}H_{26}FNO_4$, 388; Found, 388.

Preparation 102b

[(4R)-7-(5-fluoro-2-methoxyphenyl)-3,4-dihydro-2H-1-benzopyran-4-yl]methanamine

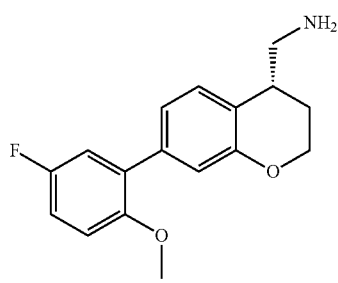 [SMILES: COc1ccc(F)cc1-c1ccc2c(c1)OCC[C@H]2CN]

The title compound was prepared in 78% yield from Preparation 102a according to the procedure for Preparation 43b. [M+H] Calc'd for $C_{17}H_{18}FNO_2$, 288; Found, 288.

Preparation 102c methyl 3-({[(4R)-7-(5-fluoro-2-methoxyphenyl)-3,4-dihydro-2H-1-benzopyran-4-yl]methyl}amino)pyridine-4-carboxylate

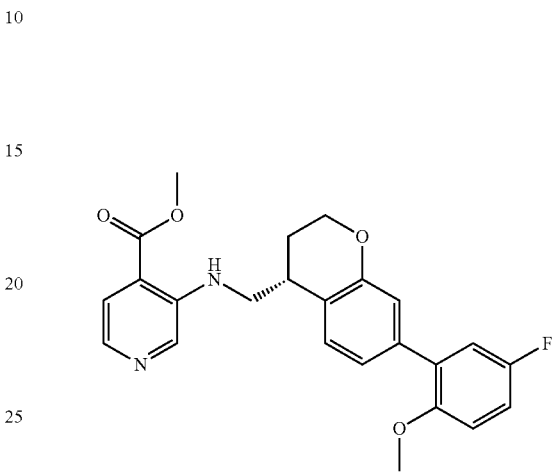

The title compound was prepared in 56% yield from Preparation 102b according to the procedure for Preparation 4d. [M+H] Calc'd for $C_{24}H_{23}FN_2O_4$, 423. Found, 423.

Example 102

3-({[(4R)-7-(5-fluoro-2-methoxyphenyl)-3,4-dihydro-2H-1-benzopyran-4-yl]methyl}amino)pyridine-4-carboxylic acid

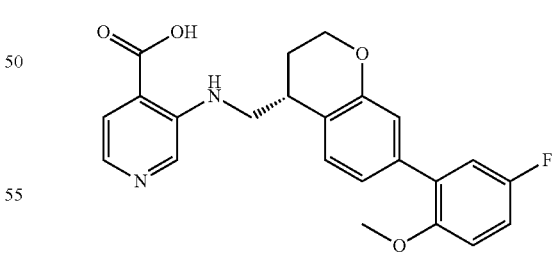

The title compound was prepared in 90% yield from Preparation 102c according to the procedure for Example 1. $^1$H NMR (400 MHz, DMSO-$d_6$): δ 1.90-1.94 (1H, m), 2.00-2.04 (1H, m), 3.15-3.19 (1H, m), 3.51-3.56 (1H, m), 3.72-3.76 (4H, m), 4.19-4.25 (2H, m), 6.91 (1H, s), 6.97 (1H, d, J=8.4 Hz), 7.07-7.17 (3H, m), 7.35 (1H, d, J=7.6 Hz), 7.59 (1H, d, J=5.2 Hz), 7.86 (1H, d, J=4.4 Hz), 8.44 (1H, s). [M+H] Calc'd for $C_{23}H_{21}FN_2O_4$, 409; Found, 409.

Preparation 103a tert-butyl N-{[(1R)-6-[(4-cyanophenyl)(methyl)amino]-1,2,3,4-tetrahydronaphthalen-1-yl]methyl}carbamate

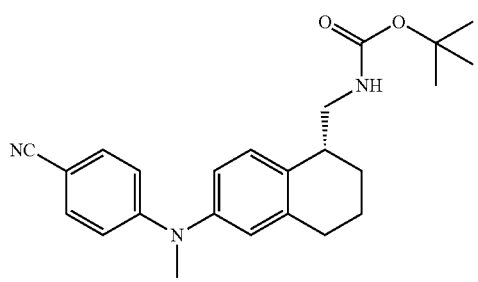 [SMILES: CN(c1ccc(C#N)cc1)c1ccc2c(c1)CCC[C@H]2CNC(=O)OC(C)(C)C]

The title compound was prepared in 47% yield from Preparation 6d and 4-cyano-N-methylaniline according to the general procedure for Preparation 6e. [M+H] calc'd for $C_{24}H_{29}N_3O_2$, 392; found 392.

Preparation 103b

4-{[(5R)-5-(aminomethyl)-5,6,7,8-tetrahydronaphthalen-2-yl](methyl)amino}benzonitrile

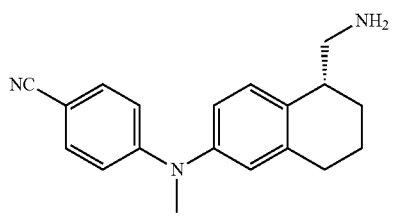 [SMILES: CN(c1ccc(C#N)cc1)c1ccc2c(c1)CCC[C@H]2CN]

The title compound was prepared in 95% yield from Preparation 103a according to the procedure for Preparation 43b. [M+H] Calc'd for $C_{19}H_{21}N_3$, 292; Found, 292.

Preparation 103c methyl 3-({[(1R)-6-[(4-cyanophenyl)(methyl)amino]-1,2,3,4-tetrahydronaphthalen-1-yl]methyl}amino)pyridine-4-carboxylate

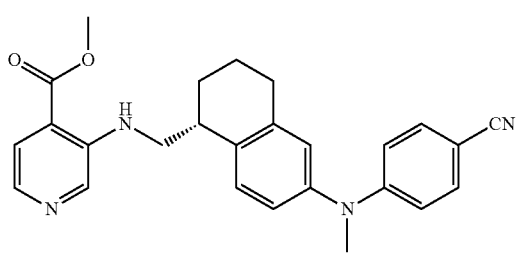 [SMILES: COC(=O)c1ccncc1NC[C@@H]1CCCc2cc(N(C)c3ccc(C#N)cc3)ccc21]

The title compound was prepared in 68% yield from Preparation 103b according to the procedure for Preparation 4d. [M+H] Calc'd for $C_{26}H_{26}N_4O_2$, 427; Found, 427.

Example 103

3-({[(1R)-6-[(4-cyanophenyl)(methyl)amino]-1,2,3,4-tetrahydronaphthalen-1-yl]methyl}amino)pyridine-4-carboxylic acid

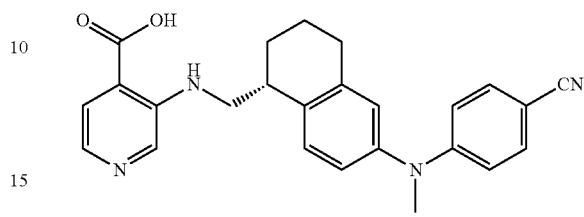

The title compound was prepared in 48% yield from Preparation 103c according to the procedure for Example 1. $^1$H NMR (400 MHz, DMSO-d$_6$): δ 1.62-1.87 (4H, m), 2.69-2.75 (2H, m), 3.05-3.11 (1H, m), 3.28 (3H, s), 3.45-3.51 (1H, m), 3.60-3.68 (1H, m), 6.74 (2H, d, J=8.9 Hz), 6.98-7.03 (2H, m), 7.40 (1H, d, J=8.9 Hz), 7.53 (2H, d, J=8.9 Hz), 7.55 (1H, d, J=5.0 Hz), 7.72 (1H, br s), 7.84 (1H, d, J=5.0 Hz), 8.37 (1H, s), 13.37 (1H, br s). [M+H] Calc'd for $C_{25}H_{24}N_4O_2$, 436; Found, 413.

Preparation 104a tert-butyl N-{[(4R)-7-[(2,4-difluorophenyl)(methyl)amino]-3,4-dihydro-2H-1-benzopyran-4-yl]methyl}carbamate

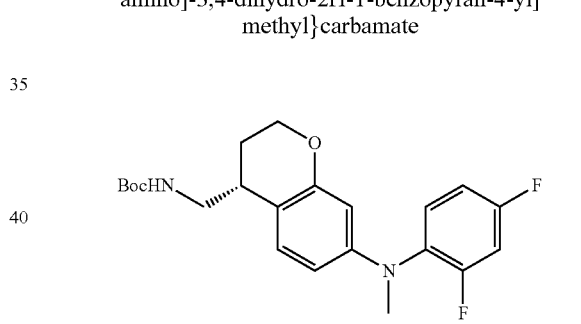

The title compound was prepared in 29% yield from Preparation 18d and 2,4-difluoro-N-methylaniline according to the general procedure for Preparation 6e. [M+H] calc'd for $C_{22}H_{26}F_2N_2O_3$, 405; Found 405.

Preparation 104b (4R)-4-(aminomethyl)-N-(2,4-difluorophenyl)-N-methyl-3,4-dihydro-2H-1-benzopyran-7-amine

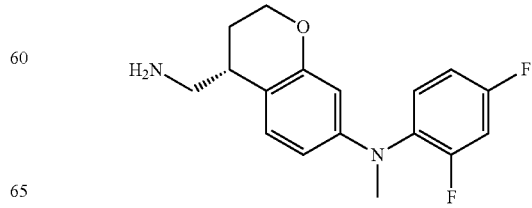

The title compound was prepared in 78% yield from Preparation 104a according to the procedure for Preparation 43b. [M+H] Calc'd for $C_{17}H_{18}F_2N_2O$, 305; Found, 305.

Preparation 104c methyl 3-({[(4R)-7-[(2,4-difluorophenyl)(methyl)amino]-3,4-dihydro-2H-1-benzopyran-4-yl]methyl}amino)pyridine-4-carboxylate

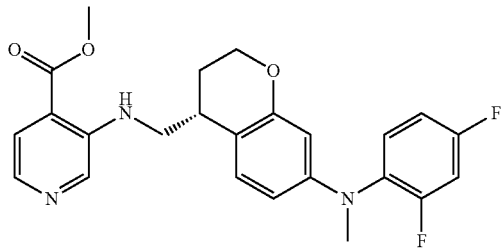 [SMILES: COC(=O)c1ccncc1NC[C@@H]1CCOc2cc(N(C)c3ccc(F)cc3F)ccc21]

The title compound was prepared in 70% yield from Preparation 104b according to the procedure for Preparation 4d. [M+H] Calc'd for $C_{24}H_{213}F_2N_3O_3$, 440; Found, 440.

Example 104

3-({[(4R)-7-[(2,4-difluorophenyl)(methyl)amino]-3,4-dihydro-2H-1-benzopyran-4-yl]methyl}amino)pyridine-4-carboxylic acid

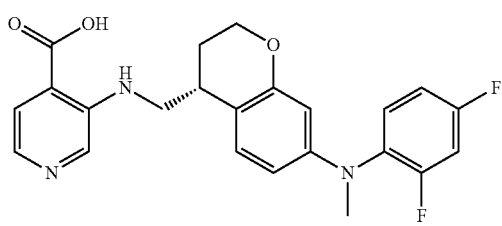 [SMILES: CN(c1ccc2c(c1)OCC[C@H]2CNc1cnccc1C(=O)O)c1ccc(F)cc1F]

The title compound was prepared in 34% yield from Preparation 104c according to the procedure for Example 1. $^1$H NMR (300 MHz, DMSO-$d_6$): δ 1.84-1.86 (1H, m), 1.93-1.95 (1H, m), 2.99-3.03 (1H, m), 3.14 (3H, s), 3.42-3.46 (1H, m), 3.58-3.62 (1H, m), 4.08-4.15 (2H, m), 6.00 (1H, d, J=2.4 Hz), 6.14 (1H, d, J=6.3 Hz), 7.07-7.16 (2H, m), 7.31-7.40 (2H, m), 7.55 (1H, d, J=5.1 Hz), 7.82 (1H, d, J=4.8 Hz), 8.38 (1H, s). [M+H] Calc'd for $C_{23}H_{21}F_2N_3O_3$, 426; Found, 426.

Preparation 105a tert-butyl N-{[(4R)-7-[methyl(3-methylphenyl)amino]-3,4-dihydro-2H-1-benzpyran-4-yl]methyl}carbamate

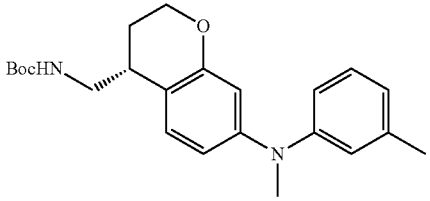 [SMILES: Cc1cccc(N(C)c2ccc3c(c2)OCC[C@H]3CNC(=O)OC(C)(C)C)c1]

The title compound was prepared in 33% yield from Preparation 18d and 3-methyl-N-methylaniline according to the general procedure for Preparation 6e. [M+H] calc'd for $C_{23}H_{30}N_2O_3$, 383; found 383.

Preparation 105b (4R)-4-(aminomethyl)-N-methyl-N-(3-methylphenyl)-3,4-dihydro-2H-1-benzopyran-7-amine

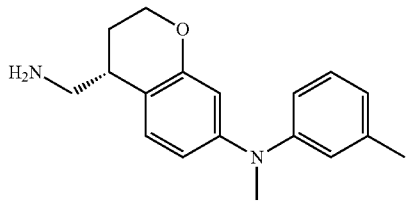 [SMILES: Cc1cccc(N(C)c2ccc3c(c2)OCC[C@H]3CN)c1]

The title compound was prepared in 93% yield from Preparation 105a according to the procedure for Preparation 43b. [M+H] Calc'd for $C_{18}H_{22}N_2O$, 283; Found, 283.

Preparation 105c 3-({[(4R)-7-[methyl(3-methylphenyl)amino]-3,4-dihydro-2H-1-benzopyran-4-yl]methyl}amino)pyridine-4-carboxylate

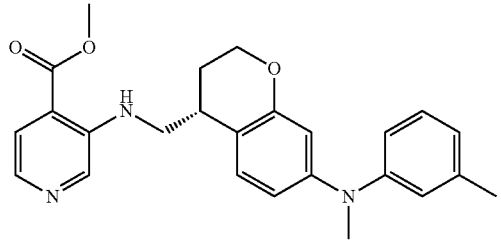 [SMILES: COC(=O)c1ccncc1NC[C@@H]1CCOc2cc(N(C)c3cccc(C)c3)ccc21]

The title compound was prepared in 77% yield from Preparation 105b according to the procedure for Preparation 4d. [M+H] Calc'd for $C_{25}H_{27}N_3O_3$, 418; Found, 418.

Example 105

3-({[(4R)-7-[methyl(3-methylphenyl)amino]-3,4-dihydro-2H-1-benzopyran-4-yl]methyl}amino)pyridine-4-carboxylic acid

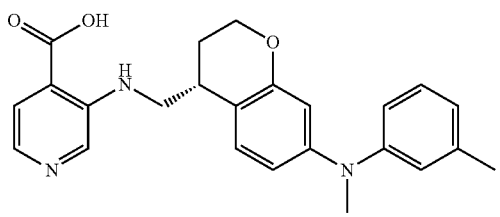 [SMILES: Cc1cccc(N(C)c2ccc3c(c2)OCC[C@H]3CNc2cnccc2C(=O)O)c1]

The title compound was prepared in 39% yield from Preparation 105c according to the procedure for Example 1. ¹H NMR (400 MHz, DMSO-d₆): δ 1.86-1.87 (1H, m), 1.96-1.98 (1H, m), 2.25 (3H, s), 3.04-3.07 (1H, m), 3.18 (3H, s), 3.43-3.50 (1H, m), 3.64-3.69 (1H, m), 4.11-4.18 (2H, m), 6.33 (1H, d, J=2.0 Hz), 6.46 (1H, d, J=6.0 Hz), 6.76-6.83 (3H, m), 7.13-7.18 (2H, m), 7.57 (1H, d, J=5.2 Hz), 7.84 (1H, d, J=5.2 Hz), 8.40 (1H, s). [M+H] Calc'd for $C_{24}H_{25}N_3O_3$, 404; Found, 404.

Preparation 106a tert-butyl N-{[(1R)-6-(pyrrolidin-1-yl)-1,2,3,4-tetrahydronaphthalen-1-yl]methyl}carbamate

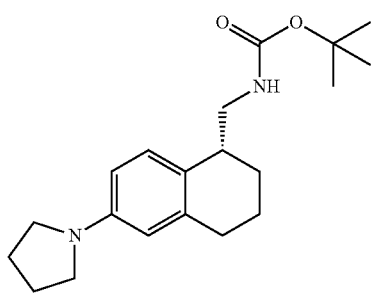 [SMILES: CC(C)(C)OC(=O)NC[C@@H]1CCCc2cc(N3CCCC3)ccc21]

To a suspension of Preparation 6d (200 mg, 0.59 mmol), pyrrolidine (84 mg, 1.18 mmol), JohnPhos (27 mg, 0.09 mmol) and t-BuONa (57 mg, 0.59 mmol) in toluene (10 mL) was added Pd₂dba₃ (55 mg, 0.06 mmol) under N₂, and the reaction was refluxed for 3 h. The reaction was filtered and concentrated. Purification by HPLC gave 144 mg (73%) of the title compound as a yellow oil. [M+H] Calc'd for $C_{20}H_{30}N_2O_2$, 331; Found, 331.

Preparation 106b

[(1R)-6-(pyrrolidin-1-yl)-1,2,3,4-tetrahydronaphthalen-1-yl]methanamine

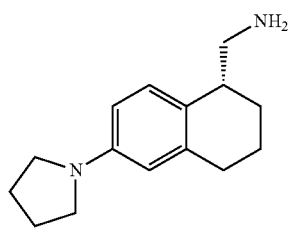 [SMILES: NC[C@@H]1CCCc2cc(N3CCCC3)ccc21]

The title compound was prepared in 95% yield from Preparation 106a according to the procedure for Preparation 43b. [M+H] Calc'd for $C_{15}H_{22}N_2$, 231; Found, 231.

Preparation 106c methyl 3-({[(1R)-6-(pyrrolidin-1-yl)-1,2,3,4-tetrahydronaphthalen-1-yl]methyl}amino)pyridine-4-carboxylate

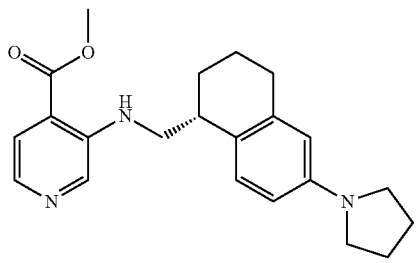 [SMILES: COC(=O)c1ccncc1NC[C@@H]1CCCc2cc(N3CCCC3)ccc21]

The title compound was prepared in 19% yield from Preparation 106b according to the procedure for Preparation 4d. [M+H] Calc'd for $C_{22}H_{27}N_3O_2$, 366; Found, 366.

Example 106

3-({[(1R)-6-(pyrrolidin-1-yl)-1,2,3,4-tetrahydronaphthalen-1-yl]methyl}amino)pyridine-4-carboxylic acid

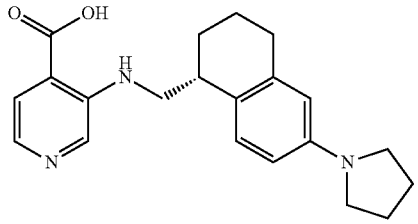 [SMILES: O=C(O)c1ccncc1NC[C@@H]1CCCc2cc(N3CCCC3)ccc21]

The title compound was prepared in 15% yield from Preparation 106c according to the general procedure for Example 1. ¹H NMR (300 MHz, DMSO-d₆): δ 1.61-1.62 (1H, m), 1.74-1.78 (3H, m), 1.89-1.94 (4H, m), 2.63-2.66 (2H, m), 2.95-2.97 (1H, m), 3.14-3.20 (2H, m), 3.25-3.35 (2H, m), 3.38-3.49 (2H, m), 6.23 (1H, s), 6.34 (1H, d, J=6.0

Hz), 7.07 (1H, d, J=8.7 Hz), 7.55-7.56 (1H, d, J=4.5 Hz), 7.77-7.78 (1H, d, J=4.8 Hz), 8.23 (1H, s). [M+H] Calc'd for $C_{21}H_{25}N_3O_2$, 352; Found, 352.

Preparation 107a tert-butyl N-{[(4R)-7-(2-chloro-5-methoxyphenyl)-3,4-dihydro-2H-1-benzopyran-4-yl]methyl}carbamate

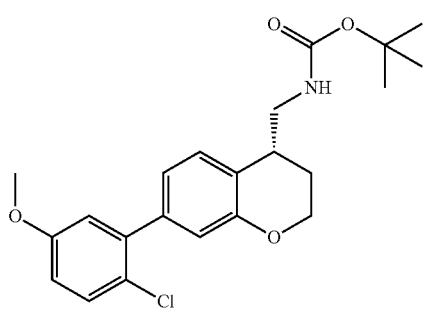 [SMILES: COc1ccc(Cl)c(-c2ccc3c(c2)OCC[C@H]3CNC(=O)OC(C)(C)C)c1]

The title compound was prepared in 68% yield from 2-chloro-5-methoxyphenylboronic acid and Preparation 18d according to the procedures for Preparation 43a. [M+H] Calc'd for $C_{22}H_{26}ClNO_4$, 404; Found, 404.

Preparation 107b

[(4R)-7-(2-chloro-5-methoxyphenyl)-3,4-dihydro-2H-1-benzopyran-4-yl]methanamine

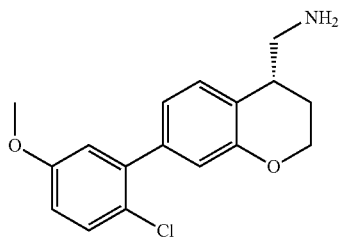 [SMILES: COc1ccc(Cl)c(-c2ccc3c(c2)OCC[C@H]3CN)c1]

The title compound was prepared in 79% yield from Preparation 107a according to the procedure for Preparation 43b. [M+H] Calc'd for $C_{17}H_{18}ClNO_2$, 304; Found, 304.

Preparation 107c methyl 3-({[(4R)-7-(2-chloro-5-methoxyphenyl)-3,4-dihydro-2H-1-benzopyran-4-yl]methyl}amino)pyridine-4-carboxylate

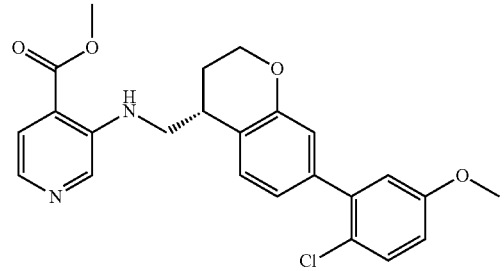 [SMILES: COC(=O)c1ccncc1NC[C@@H]1CCOc2cc(-c3cc(OC)ccc3Cl)ccc21]

The title compound was prepared in 48% yield from Preparation 107b according to the procedure for Preparation 4d. [M+H] Calc'd for $C_{24}H_{23}ClN_2O_4$, 439; Found, 439.

Example 107

3-({[(4R)-7-(2-chloro-5-methoxyphenyl)-3,4-dihydro-2H-1-benzopyran-4-yl]methyl}amino)pyridine-4-carboxylic acid

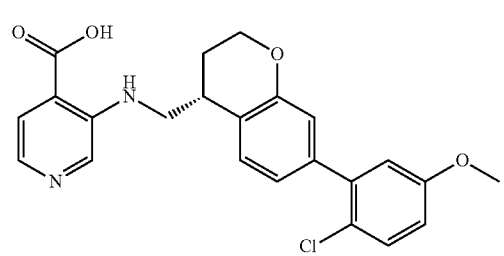 [SMILES: COc1ccc(Cl)c(-c2ccc3c(c2)OCC[C@H]3CNc2cnccc2C(=O)O)c1]

The title compound was prepared in 84% yield from Preparation 107c according to the procedure for Example 1. $^1$H NMR (400 MHz, DMSO-$d_6$): δ 1.90-1.95 (1H, m), 2.02-2.06 (1H, m), 3.18-3.21 (1H, m), 3.53-3.59 (1H, m), 3.74-3.79 (4H, m), 4.19-4.28 (2H, m), 6.84 (1H, s), 6.90-6.97 (3H, m), 7.40-7.44 (2H, m), 7.60 (1H, d, J=5.2 Hz), 7.87 (1H, d, J=5.2 Hz), 8.47 (1H, s). [M+H] Calc'd for $C_{23}H_{21}ClN_2O_4$, 425; Found, 425.

Preparation 108a tert-butyl N-{[(1R)-6-(3,4-dihydro-2H-1,4-benzoxazin-4-yl)-1,2,3,4-tetrahydronaphthalen-1-yl]methyl}carbamate

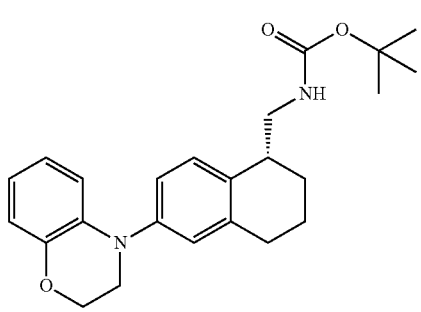 [SMILES: CC(C)(C)OC(=O)NC[C@@H]1CCCc2cc(N3CCOc4ccccc43)ccc21]

The title compound was prepared in 58% yield from Preparation 6d and 3,4-dihydro-2H-1,4-benzoxazine according to the general procedure for Preparation 9a. [M+H] Calc'd for $C_{24}H_{30}N_2O_3$, 395; Found, 395.

Preparation 108b

[(1R)-6-(3,4-dihydro-2H-1,4-benzoxazin-4-yl)-1,2,3,4-tetrahydronaphthalen-1-yl]methanamine

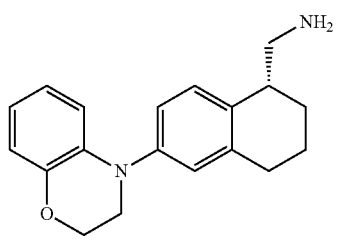 [SMILES: NC[C@@H]1CCCc2cc(N3CCOc4ccccc43)ccc21]

The title compound was prepared in 93% yield from Preparation 108a according to the procedure for Preparation 43b. [M+H] Calc'd for $C_{19}H_{22}N_2O$, 295; Found, 295.

Preparation 108c methyl 3-({[(1R)-6-(3,4-dihydro-2H-1,4-benzoxazin-4-yl)-1,2,3,4-tetrahydronaphthalen-1-yl]methyl}amino)pyridine-4-carboxylate

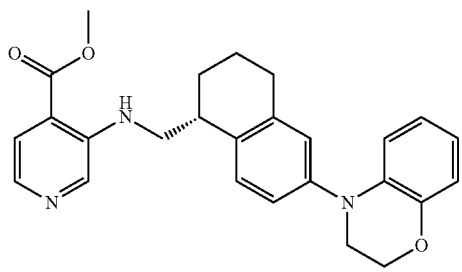 [SMILES: COC(=O)c1ccncc1NC[C@@H]1CCCc2cc(N3CCOc4ccccc43)ccc21]

The title compound was prepared in 55% yield from Preparation 108b according to the procedure for Preparation 4d. [M+H] Calc'd for $C_{26}H_{27}N_3O_3$, 430; Found, 430.

Example 108

3-({[(1R)-6-(3,4-dihydro-2H-1,4-benzoxazin-4-yl)-1,2,3,4-tetrahydronaphthalen-1-yl]methyl}amino)pyridine-4-carboxylic acid

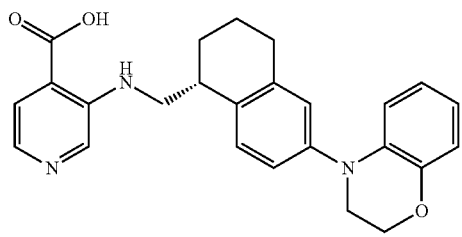

The title compound was prepared in 86% yield from Preparation 108c according to the procedure for Example 1. $^1$H NMR (400 MHz, DMSO-$d_6$): δ 1.65-1.70 (1H, m), 1.79-1.85 (3H, m), 2.69-2.73 (2H, m), 3.08-3.11 (1H, m), 3.43-3.49 (1H, m), 3.58-3.65 (3H, m), 4.22 (2H, t, J=4.0 Hz), 6.67-6.71 (2H, m), 6.76-6.81 (2H, m), 6.97-7.01 (2H, m), 7.31 (1H, d, J=8.0 Hz), 7.57 (1H, d, J=4.8 Hz), 7.84 (1H, d, J=4.8 Hz), 8.37 (1H, s). [M+H] Calc'd for $C_{25}H_{25}N_3O_3$, 416; Found, 416.

Preparation 109a 3,5-difluoro-N-methylaniline

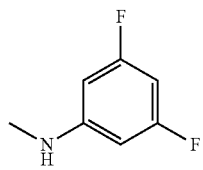

A solution of 3,5-difluoroaniline (5.0 g, 38.7 mmol) in HCOOH (15 mL) was heated to reflux for 4 h. The mixture was poured into ice-water and stirred for 0.5 h. The white solid was collected by filtration, and dried under vacuum to give 4.8 g (79%) of crude N-(3,5-difluorophenyl)formamide. To the solution of LiAlH$_4$ (3.0 g, 78.9 mmol) in dry THF (50 mL) was added a solution of N-(3,5-difluorophenyl)formamide (4.8 g, 30.6 mmol) in dry THF (50 mL) at r.t. The mixture was stirred overnight and then quenched with addition of water (3.0 mL), aqueous 10% NaOH (3.0 mL), and water (9.0 ml). The reaction mixture was filtered and extracted with EtOAc. Organics were dried (Na$_2$SO$_4$), and concentrated to give 3.8 g (86%) of the title compound as a pale brown oil.

Preparation 109b tert-butyl N-{[(4R)-7-[(3,5-difluorophenyl)(methyl)amino]-3,4-dihydro-2H-1-benzopyran-4-yl]methyl}carbamate

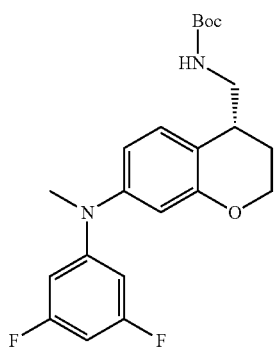 [SMILES: CN(c1cc(F)cc(F)c1)c1ccc2c(c1)OCC[C@H]2CNC(=O)OC(C)(C)C]

The title compound was prepared in 74% yield from Preparation 18d and Preparation 109a according to the general procedure for Preparation 6e. [M+H] calc'd for $C_{22}H_{267}F_2N_2O_3$, 405. found 405.

Preparation 109c (4R)-4-(aminomethyl)-N-(3,5-difluorophenyl)-N-methyl-3,4-dihydro-2H-1-benzopyran-7-amine

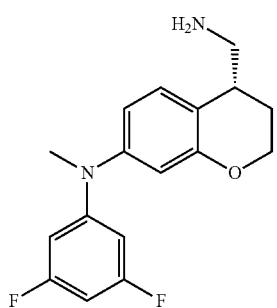 [SMILES: CN(c1cc(F)cc(F)c1)c1ccc2c(c1)OCC[C@H]2CN]

The title compound was prepared in 94% yield from Preparation 109b according to the procedure for Preparation 43b. [M+H] Calc'd for $C_{17}H_{18}F_2N_2O$, 305; Found, 305.

Preparation 109d 3-({[(4R)-7-[(3,5-difluorophenyl)(methyl)amino]-3,4-dihydro-2H-1-benzopyran-4-yl]methyl}amino)pyridine-4-carboxylate

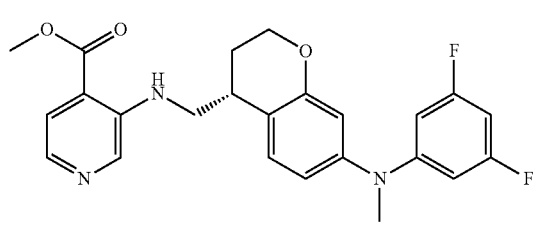 [SMILES: COC(=O)c1ccncc1NC[C@@H]1CCOc2cc(N(C)c3cc(F)cc(F)c3)ccc21]

The title compound was prepared in 38% yield from Preparation 109c according to the procedure for Preparation 4d. [M+H] Calc'd for $C_{24}H_{23}F_2N_3O_3$, 440; Found, 440.

Example 109

3-({[(4R)-7-[(3,5-difluorophenyl)(methyl)amino]-3,4-dihydro-2H-1-benzopyran-4-yl]methyl}amino)pyridine-4-carboxylic acid

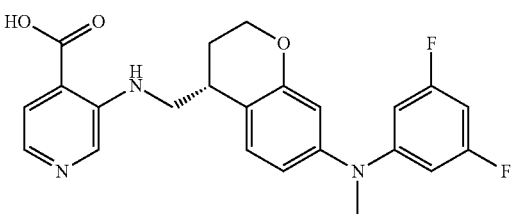 [SMILES: CN(c1cc(F)cc(F)c1)c1ccc2c(c1)OCC[C@H]2CNc1cnccc1C(=O)O]

The title compound was prepared in 86% yield from Preparation 109c according to the procedure for Example 1. $^1$H NMR (400 MHz, DMSO-$d_6$): δ 1.88-1.92 (1H, m), 1.98-2.05 (1H, m), 3.12-3.18 (1H, m), 3.21 (3H, s), 3.51-3.56 (1H, m), 3.71-3.75 (1H, m), 4.15-4.27 (2H, m), 6.34-6.37 (2H, m), 6.45-6.50 (1H, m), 6.63 (1H, d, J=2.4 Hz), 6.71 (1H, dd, J=2.0, 8.0 Hz), 7.35 (1H, d, J=8.4 Hz), 7.57 (1H, d, J=5.2 Hz), 7.84 (1H, d, J=5.2 Hz), 8.42 (1H, s). [M+H] Calc'd for $C_{23}H_{21}F_2N_3O_3$, 426; Found, 426.

Preparation 110a tert-butyl N-{[(4R)-7-[(3-chlorophenyl)(methyl)amino]-3,4-dihydro-2H-1-benzopyran-4-yl]methyl}carbamate

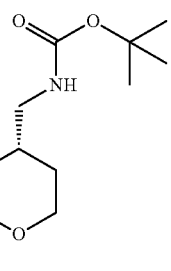

The title compound was prepared in 37% yield from Preparation 18d and 3-chloro-N-methylaniline according to the general procedure for Preparation 6e. [M+H] calc'd for $C_{22}H_{27}ClN_2O_3$, 403; Found 403.

Preparation 110b (4R)-4-(aminomethyl)-N-(3-chlorophenyl)-N-methyl-3,4-dihydro-2H-1-benzopyran-7-amine

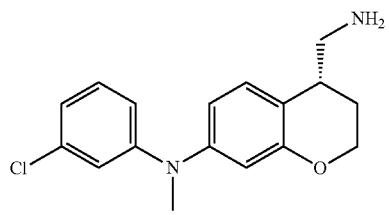 [SMILES: CN(c1cccc(Cl)c1)c1ccc2c(c1)OCC[C@H]2CN]

The title compound was prepared in 79% yield from Preparation 110a according to the procedure for Preparation 43b. [M+H] Calc'd for $C_{17}H_{19}ClN_2O$, 303; Found, 303.

Preparation 110c 3-({[(4R)-7-[(3-chlorophenyl)(methyl)amino]-3,4-dihydro-2H-1-benzopyran-4-yl]methyl}amino)pyridine-4-carboxylate

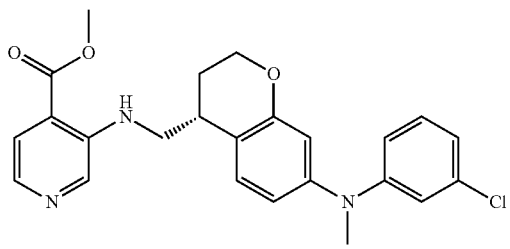 [SMILES: COC(=O)c1ccncc1NC[C@@H]1CCOc2cc(N(C)c3cccc(Cl)c3)ccc21]

The title compound was prepared in 50% yield from Preparation 110b according to the procedure for Preparation 4d. [M+H] Calc'd for $C_{24}H_{24}ClN_3O_3$, 438; Found, 438.

Example 110

3-({[(4R)-7-[(3-chlorophenyl)(methyl)amino]-3,4-dihydro-2H-1-benzopyran-4-yl]methyl}amino)pyridine-4-carboxylic acid

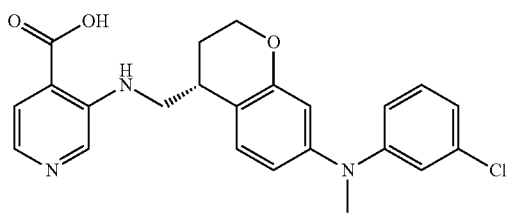 [SMILES: CN(c1cccc(Cl)c1)c1ccc2c(c1)OCC[C@H]2CNc1cnccc1C(=O)O]

The title compound was prepared in 82% yield from Preparation 110c according to the procedure for Example 1. $^1$H NMR (400 MHz, DMSO-d$_6$): δ 1.86-1.90 (1H, m), 1.98-2.02 (1H, m), 3.10-3.14 (1H, m), 3.21 (3H, s), 3.48-3.54 (1H, m), 3.68-3.73 (1H, m), 4.16-4.24 (2H, m), 6.52 (1H, s), 6.62-6.64 (1H, m), 6.79-6.85 (3H, m), 7.21 (1H, t, J=8.0 Hz), 7.29 (1H, d, J=8.0 Hz), 7.57 (1H, d, J=5.2 Hz), 7.85 (1H, d, J=5.2 Hz), 8.42 (1H, s). [M+H] Calc'd for $C_{23}H_{22}ClN_3O_3$, 424; Found, 424.

Preparation 111a tert-butyl N-{[(4R)-7-[methyl(2-methylphenyl)amino]-3,4-dihydro-2H-1-benzopyran-4-yl]methyl}carbamate

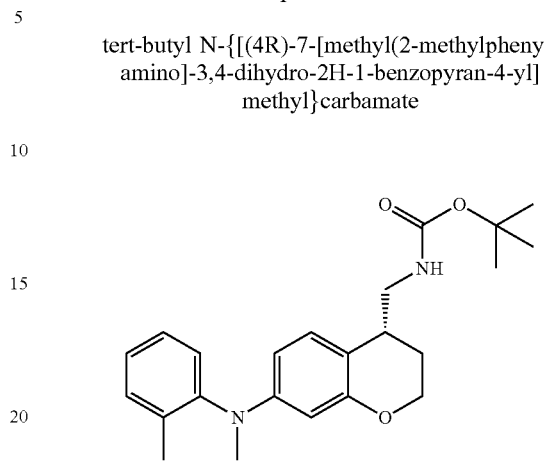

The title compound was prepared in 27% yield from Preparation 18d and N,2-dimethylaniline according to the general procedure for Preparation 9a. [M+H] calc'd for $C_{23}H_{30}N_2O_3$, 383; Found 383.

Preparation 111b (4R)-4-(aminomethyl)-N-methyl-N-(2-methylphenyl)-3,4-dihydro-2H-1-benzopyran-7-amine

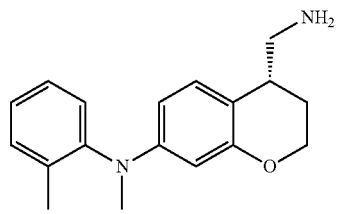 [SMILES: Cc1ccccc1N(C)c1ccc2c(c1)OCC[C@H]2CN]

The title compound was prepared in 96% yield from Preparation 111a according to the procedure for Preparation 43b. [M+H] Calc'd for $C_{18}H_{22}N_2O$, 283; Found, 283.

Preparation 111c methyl 3-({[(4R)-7-[methyl(2-methylphenyl)amino]-3,4-dihydro-2H-1-benzopyran-4-yl]methyl}amino)pyridine-4-carboxylate

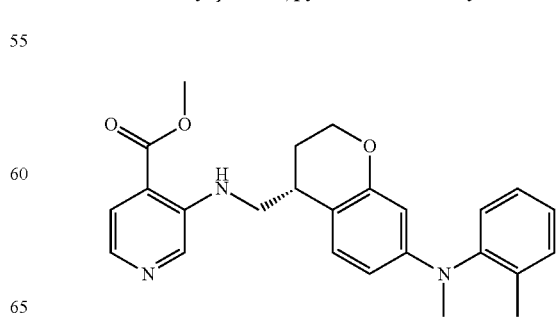

The title compound was prepared in 11% yield from Preparation 111b according to the procedure for Preparation 4d. [M+H] Calc'd for $C_{25}H_{27}N_3O_3$, 418; Found, 418.

Example 111

3-({[(4R)-7-[methyl(2-methylphenyl)amino]-3,4-dihydro-2H-1-benzopyran-4-yl]methyl}amino)pyridine-4-carboxylic acid

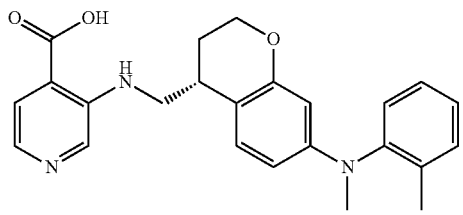 [SMILES: Cc1ccccc1N(C)c1ccc2c(c1)OCC[C@H]2CNc1cnccc1C(=O)O]

The title compound was prepared in 58% yield from Preparation 111c according to the procedure for Example 1. $^1$H NMR (400 MHz, DMSO-d$_6$): δ 1.83-1.93 (1H, m), 1.94-1.96 (1H, m), 2.07 (3H, m), 2.97-3.01 (1H, m), 3.11 (3H, s), 3.37-3.45 (1H, m), 3.58-3.62 (1H, m), 4.05-4.15 (2H, m), 5.84 (1H, s), 5.98-6.00 (1H, m), 7.04 (1H, d, J=8.8 Hz), 7.09-7.11 (1H, m), 7.18-7.32 (3H, m), 7.56 (1H, t, J=5.2 Hz), 7.83 (1H, d, J=4.8 Hz), 8.38 (1H, s). [M+H] Calc'd for $C_{24}H_{25}N_3O_3$, 404; Found, 404.

Preparation 112a 4-fluoro-3-methoxy-N-methylaniline

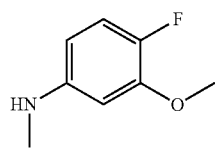

The title compound was prepared in 75% yield from 4-fluoro-3-methoxy-aniline according to the general procedure for Preparation 109a.

Preparation 112b tert-butyl N-{[(4R)-7-[(4-fluoro-3-methoxyphenyl)(methyl)amino]-3,4-dihydro-2H-1-benzopyran-4-yl]methyl}carbamate

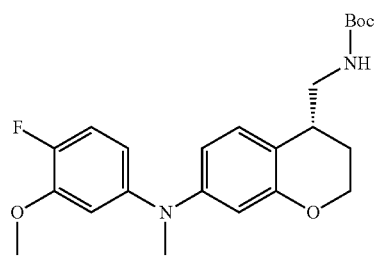 [SMILES: COc1cc(N(C)c2ccc3c(c2)OCC[C@H]3CNC(=O)OC(C)(C)C)ccc1F]

The title compound was prepared in 49% yield from Preparation 18d and Preparation 112a according to the general procedure for Preparation 9a. [M+H] calc'd for $C_{23}H_{29}FN_2O_4$, 417; Found 417.

Preparation 112c (4R)-4-(aminomethyl)-N-(4-fluoro-3-methoxyphenyl)-N-methyl-3,4-dihydro-2H-1-benzopyran-7-amine

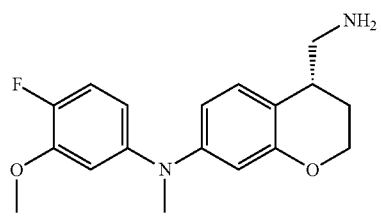

The title compound was prepared in 94% yield from Preparation 112b according to the procedure for Preparation 43b. [M+H] Calc'd for $C_{18}H_{21}FN_2O_2$, 317; Found, 317.

Preparation 112d methyl 3-({[(4R)-7-[(4-fluoro-3-methoxyphenyl)(methyl)amino]-3,4-dihydro-2H-1-benzopyran-4-yl]methyl}amino)pyridine-4-carboxylate

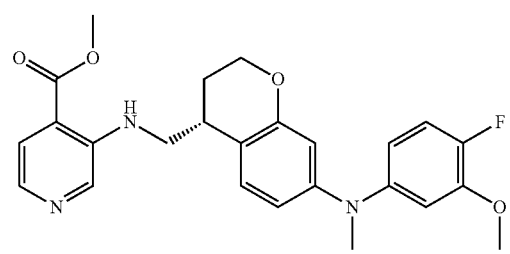 [SMILES: COC(=O)c1ccncc1NC[C@@H]1CCOc2cc(N(C)c3ccc(F)c(OC)c3)ccc21]

The title compound was prepared in 66% yield from Preparation 112c according to the procedure for Preparation 4d. [M+H] Calc'd for $C_{25}H_{26}FN_3O_4$, 450; Found, 450.

Example 112

3-({[(4R)-7-[(4-fluoro-3-methoxyphenyl)(methyl)amino]-3,4-dihydro-2H-1-benzopyran-4-yl]methyl}amino)pyridine-4-carboxylic acid

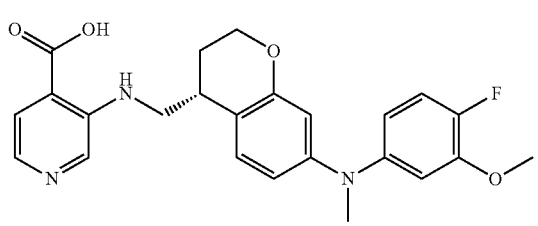

The title compound was prepared in 78% yield from Preparation 112d according to the procedure for Example 1. $^1$H NMR (400 MHz, DMSO-d$_6$): δ 1.82-1.87 (1H, m), 1.91-2.00 (1H, m), 3.03-3.07 (1H, m), 3.18 (3H, s), 3.43-3.50 (1H, m), 3.61-3.68 (1H, m), 3.78 (3H, s), 4.08-4.18 (2H, m), 6.27 (1H, d, J=2.4 Hz), 6.41 (1H, dd, J=8.4, 2.4 Hz), 6.54-6.58 (1H, m), 6.82-6.85 (1H, m), 7.09-7.16 (2H, m), 7.56 (1H, d J=5.2 Hz), 7.84 (1H, d, J=5.2 Hz), 8.39 (1H, s). [M+H] Calc'd for C$_{24}$H$_{24}$FN$_3$O$_4$, 438; Found, 438.

Preparation 113a tert-butyl N-{[(1R)-6-[methyl(oxan-4-yl)amino]-1,2,3,4-tetrahydronaphthalen-1-yl]methyl}carbamate

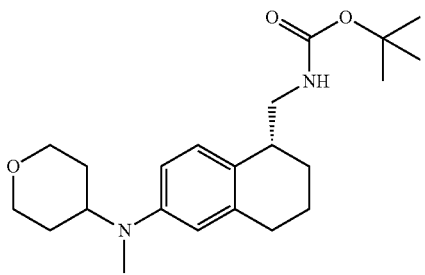 [SMILES: CN(c1ccc2c(c1)CCC[C@H]2CNC(=O)OC(C)(C)C)C1CCOCC1]

To a solution of Preparation 6d (400 mg, 1.18 mmol) in toluene (10 mL) was added N-methyloxan-4-amine (270 mg, 2.36 mmol), Cs$_2$CO$_3$ (770 mg, 2.36 mmol), BINAP (38 mg, 0.06 mmol) and Pd(OAc)$_2$ (14 mg, 0.06 mmol). The mixture was stirred overnight at 100° C. under N$_2$. The mixture was filtered and concentrated, and the residue was purified by HPLC to give 70 mg (15%) of the title compound as a yellow gum. [M+H] Calc'd for C$_{22}$H$_{34}$N$_2$O$_3$, 375; Found, 375.

Preparation 113b

N-[(5R)-5-(aminomethyl)-5,6,7,8-tetrahydronaphthalen-2-yl]-N-methyloxan-4-amine

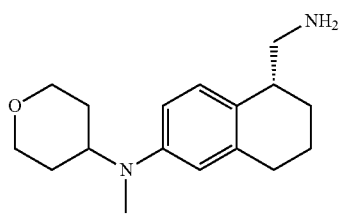 [SMILES: CN(c1ccc2c(c1)CCC[C@H]2CN)C1CCOCC1]

The title compound was prepared in 99% yield from Preparation 113a according to the procedure for Preparation 43b. [M+H] Calc'd for C$_{17}$H$_{26}$N$_2$O, 275; Found, 275.

Preparation 113c methyl 3-({[(1R)-6-[methyl(oxan-4-yl)amino]-1,2,3,4-tetrahydronaphthalen-1-yl]methyl}amino)pyridine-4-carboxylate

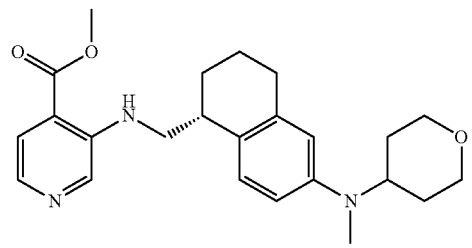 [SMILES: COC(=O)c1ccncc1NC[C@@H]1CCCc2cc(N(C)C3CCOCC3)ccc21]

The title compound was prepared in 26% yield from Preparation 113b according to the procedure for Preparation 4d. [M+H] Calc'd for C$_{24}$H$_{31}$N$_3$O$_3$, 410; Found, 410.

Example 113

3-({[(1R)-6-[methyl(oxan-4-yl)amino]-1,2,3,4-tetrahydronaphthalen-1-yl]methyl}amino)pyridine-4-carboxylic acid

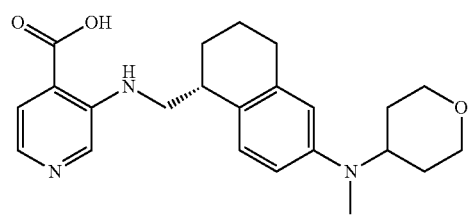 [SMILES: CN(c1ccc2c(c1)CCC[C@H]2CNc1cnccc1C(=O)O)C1CCOCC1]

The title compound was prepared in 10% yield from Preparation 113c according to the procedure for Example 1. $^1$H NMR (300 MHz, DMSO-d$_6$): δ 1.61-1.68 (3H, m), 1.83-2.06 (6H, m), 2.87-2.94 (2H, m), 3.25 (3H, s), 3.34-3.44 (2H, m), 3.62-3.65 (2H, m), 3.81-3.90 (1H, m), 4.01-4.06 (2H, m), 7.28-7.30 (2H, m), 7.51 (1H, d, J=7.8 Hz), 7.89-7.91 (1H, m), 8.08 (1H, d, J=5.4 Hz), 8.26 (1H, d, J=1.8 Hz). [M+H] Calc'd for C$_{23}$H$_{29}$N$_3$O$_3$, 396; Found, 396.

Preparation 114a tert-butyl N-{[(1R)-6-[(4-fluoro-3-methoxyphenyl)(methyl)amino]-1,2,3,4-tetrahydronaphthalen-1-yl]methyl}carbamate

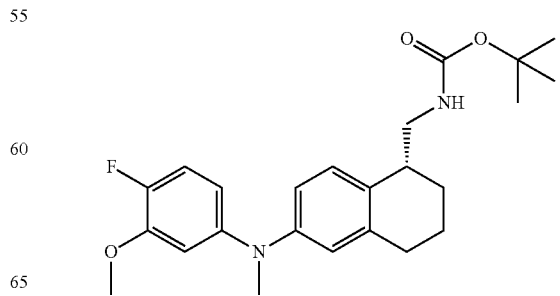

The title compound was prepared in 41% yield from Preparation 6d and Preparation 112a according to the general procedure for Preparation 6e. [M+H] calc'd for $C_{24}H_{31}FN_2O_3$, 415; Found 415.

Preparation 114b (5R)-5-(aminomethyl)-N-(4-fluoro-3-methoxyphenyl)-N-methyl-5,6,7,8-tetrahydronaphthalen-2-amine

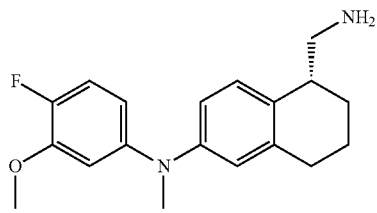 [SMILES: COc1cc(N(C)c2ccc3c(c2)CCC[C@H]3CN)ccc1F]

The title compound was prepared in 85% yield from Preparation 114a according to the procedure for Preparation 43b. [M+H] Calc'd for $C_{19}H_{23}FN_2O$, 315; Found, 315.

Preparation 114c methyl 3-({[(1R)-6-[(4-fluoro-3-methoxyphenyl)(methyl)amino]-1,2,3,4-tetrahydronaphthalen-1-yl]methyl}amino)pyridine-4-carboxylate

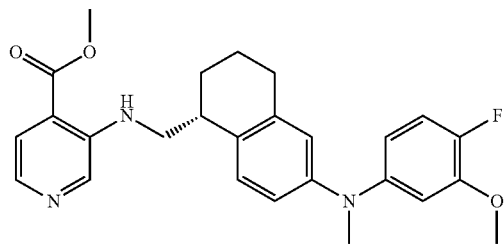

The title compound was prepared in 62% yield from Preparation 114b according to the procedure for Preparation 4d. [M+H] Calc'd for $C_{26}H_{28}FN_3O_3$, 450; Found, 450.

Example 114

3-({[(1R)-6-[(4-fluoro-3-methoxyphenyl)(methyl)amino]-1,2,3,4-tetrahydronaphthalen-1-yl]methyl}amino)pyridine-4-carboxylic acid

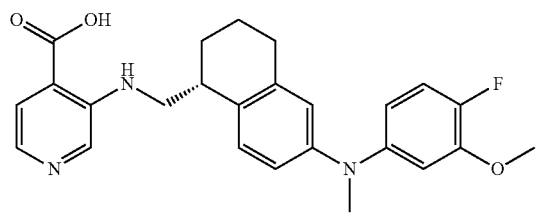 [SMILES: COc1cc(N(C)c2ccc3c(c2)CCC[C@H]3CNc2cnccc2C(=O)O)ccc1F]

The title compound was prepared in 98% yield from Preparation 114c according to the procedure for Example 1.

$^1$H NMR (400 MHz, DMSO-d$_6$): δ 1.64-1.84 (4H, m), 2.64-2.68 (2H, m), 3.03-3.06 (1H, m), 3.21 (3H, s), 3.38-3.45 (1H, m), 3.54-3.58 (1H, m), 3.76 (3H, s), 6.46-6.50 (1H, m), 6.70-6.78 (3H, m), 7.06-7.11 (1H, m), 7.20 (1H, d, J=8.4 Hz), 7.56 (1H, t, J=5.2 Hz), 7.82 (1H, d, J=5.2 Hz), 8.34 (1H, s). [M+H] Calc'd for $C_{25}H_{26}FN_3O_3$, 436; Found, 436.

Preparation 115a tert-butyl N-{[(1R)-6-[(3-cyanophenyl)(methyl)amino]-1,2,3,4-tetrahydronaphthalen-1-yl]methyl}carbamate

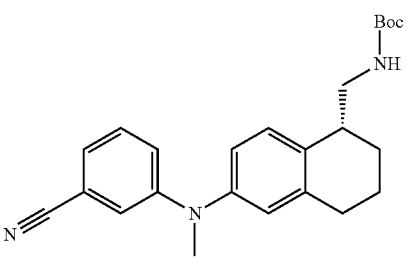 [SMILES: CN(c1cccc(C#N)c1)c1ccc2c(c1)CCC[C@H]2CNC(=O)OC(C)(C)C]

The title compound was prepared in 36% yield from Preparation 6e and 3-cyano-N-methylaniline according to the general procedure for Preparation 9a. [M+H] calc'd for $C_{24}H_{29}N_3O_2$, 392. found 392.

Preparation 115b

3-{[(5R)-5-(aminomethyl)-5,6,7,8-tetrahydronaphthalen-2-yl](methyl)amino}benzonitrile

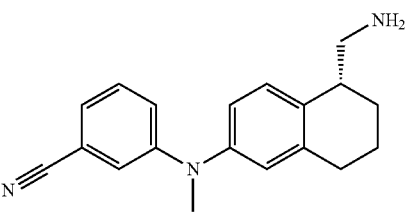 [SMILES: CN(c1cccc(C#N)c1)c1ccc2c(c1)CCC[C@H]2CN]

The title compound was prepared in 97% yield from Preparation 115a according to the procedure for Preparation 43b. [M+H] Calc'd for $C_{19}H_{21}N_3$, 292; Found, 292.

Preparation 115c methyl 3-({[(1R)-6-[(3-cyanophenyl)(methyl)amino]-1,2,3,4-tetrahydronaphthalen-1-yl]methyl}amino)pyridine-4-carboxylate

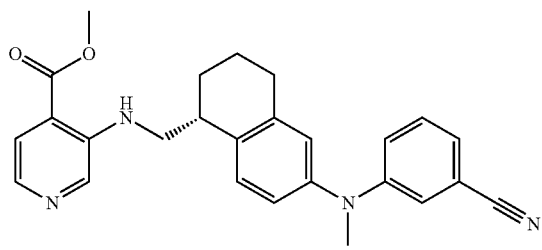 [SMILES: COC(=O)c1ccncc1NC[C@@H]1CCCc2cc(N(C)c3cccc(C#N)c3)ccc21]

The title compound was prepared in 69% yield from Preparation 115b according to the procedure for Preparation 4d. [M+H] Calc'd for $C_{26}H_{26}N_4O_2$, 427; Found, 427.

Example 115

3-({[(1R)-6-[(3-cyanophenyl)(methyl)amino]-1,2,3,4-tetrahydronaphthalen-1-yl]methyl}amino)pyridine-4-carboxylic acid

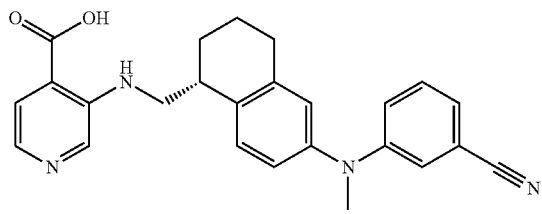

The title compound was prepared in 76% yield from Preparation 115c according to the procedure for Example 1. $^1$H NMR (400 MHz, DMSO-d$_6$): δ 1.66-1.87 (4H, m), 2.72-2.74 (2H, m), 3.11-3.17 (1H, m), 3.25 (3H, s), 3.51-3.53 (1H, m), 3.62-3.65 (1H, m), 6.95-6.96 (2H, m), 7.02-7.04 (1H, m), 7.12-7.16 (2H, m), 7.32-7.37 (2H, m), 7.77 (1H, d, J=5.2 Hz), 7.91 (1H, t, J=5.6 Hz), 8.42 (1H, s). [M+H] Calc'd for $C_{25}H_{24}N_4O_2$, 413; Found, 413.

Preparation 116a tert-butyl N-{[(4R)-7-(2-methoxyphenyl)-3,4-dihydro-2H-1-benzopyran-4-yl]methyl}carbamate

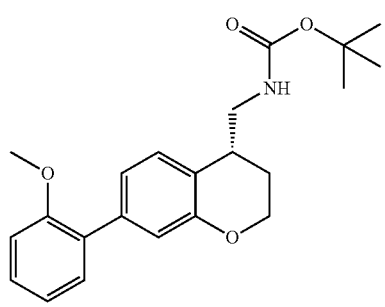 [SMILES: COc1ccccc1-c1ccc2c(c1)OCC[C@H]2CNC(=O)OC(C)(C)C]

The title compound was prepared in 83% yield from 2-methoxyphenylboronic acid and Preparation 18d according to the procedures for Preparation 43a. [M+H] Calc'd for $C_{22}H_{27}NO_4$, 370. Found, 370.

Preparation 116b

[(4R)-7-(2-methoxyphenyl)-3,4-dihydro-2H-1-benzopyran-4-yl]methanamine

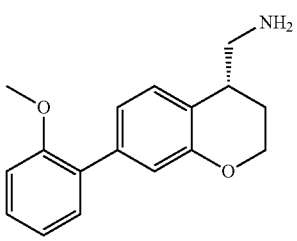 [SMILES: COc1ccccc1-c1ccc2c(c1)OCC[C@H]2CN]

The title compound was prepared in quantitative yield from Preparation 116a according to the procedure for Preparation 43b. [M+H] Calc'd for $C_{17}H_{19}NO_2$, 270; Found, 270.

Preparation 116c methyl 3-({[(4R)-7-(2-methoxyphenyl)-3,4-dihydro-2H-1-benzopyran-4-yl]methyl}amino)pyridine-4-carboxylate

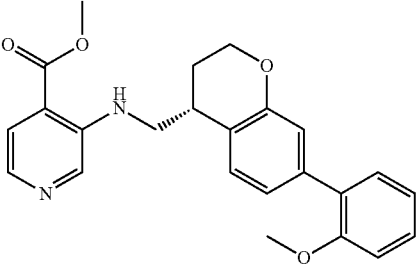 [SMILES: COC(=O)c1ccncc1NC[C@@H]1CCOc2cc(-c3ccccc3OC)ccc21]

The title compound was prepared in 57% yield from Preparation 116b according to the procedure for Preparation 4d. [M+H] Calc'd for $C_{24}H_{24}N_2O_4$, 405; Found, 405.

Example 116

3-({[(4R)-7-(2-methoxyphenyl)-3,4-dihydro-2H-1-benzopyran-4-yl]methyl}amino)pyridine-4-carboxylic acid

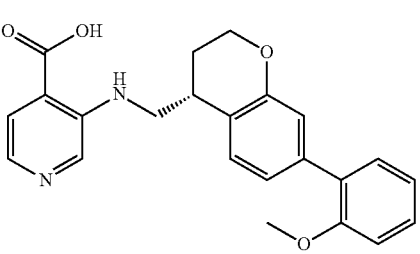 [SMILES: COc1ccccc1-c1ccc2c(c1)OCC[C@H]2CNc1cnccc1C(=O)O]

The title compound was prepared in 75% yield from Preparation 116c according to the procedure for Example 1. ¹H NMR (400 MHz, DMSO-d₆): δ 1.90-1.93 (1H, m), 2.00-2.05 (1H, m), 3.15-3.18 (1H, m), 3.51-3.57 (1H, m), 3.72-3.76 (4H, m), 4.17-4.26 (2H, m), 6.87 (1H, s), 6.94-7.02 (2H, m), 7.09 (1H, d, J=8.0 Hz), 7.24-7.26 (1H, m), 7.30-7.35 (2H, m), 7.58 (1H, d, J=4.8 Hz), 7.86 (1H, d, J=5.2 Hz), 8.45 (1H, s). [M+H] Calc'd for $C_{23}H_{22}N_2O_4$, 391; Found, 391.

Preparation 117a tert-butyl N-{[(4R)-7-[(3-cyanophenyl)(methyl)amino]-3,4-dihydro-2H-1-benzopyran-4-yl]methyl}carbamate

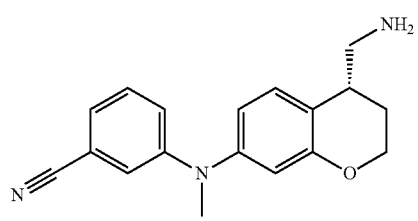

The title compound was prepared in 55% yield from Preparation 18d and 3-cyano-N-methylaniline according to the general procedure for Preparation 9a. [M+H] Calc'd for $C_{23}H_{27}N_3O_3$, 394; Found, 394.

Preparation 117b

3-{[(4R)-4-(aminomethyl)-3,4-dihydro-2H-1-benzopyran-7-yl](methyl)amino}benzonitrile

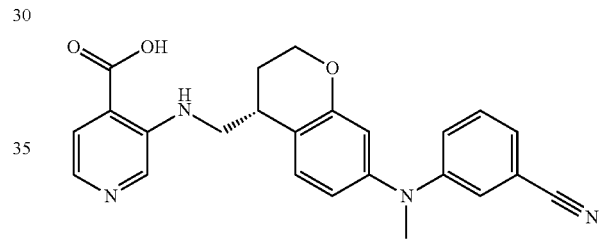

The title compound was prepared in quantitative yield from Preparation 117a according to the procedure for Preparation 43b. [M+H] Calc'd for $C_{18}H_{19}N_3O$, 294; Found, 294.

Preparation 117c methyl 3-({[(4R)-7-[(3-cyanophenyl)(methyl)amino]-3,4-dihydro-2H-1-benzopyran-4-yl]methyl}amino)pyridine-4-carboxylate

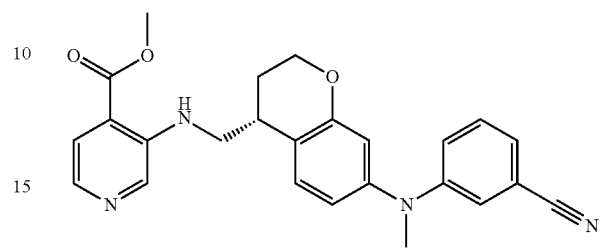

The title compound was prepared in 56% yield from Preparation 117b according to the procedure for Preparation 4d. [M+H] Calc'd for $C_{25}H_{24}N_4O_3$, 429; Found, 429.

Example 117

3-({[(4R)-7-[(3-cyanophenyl)(methyl)amino]-3,4-dihydro-2H-1-benzopyran-4-yl]methyl}amino)pyridine-4-carboxylic acid

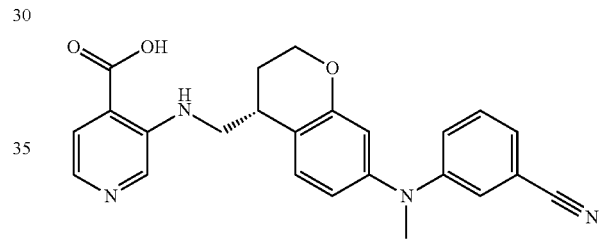

The title compound was prepared in 85% yield from Preparation 117c according to the procedure for Example 1. ¹H NMR (400 MHz, DMSO-d₆): δ 1.88-1.98 (1H, m), 1.99-2.03 (1H, m), 3.11-3.15 (1H, m), 3.26 (3H, s), 3.49-3.54 (1H, m), 3.69-3.74 (1H, m), 4.15-4.25 (2H, m), 6.57 (1H, d, J=2.4 Hz), 6.65-6.68 (1H, m), 7.09-7.12 (1H, m), 7.18-7.20 (2H, m), 7.32-7.38 (2H, m), 7.57 (1H, d, J=5.2 Hz), 7.85 (1H, d, J=5.2 Hz), 8.41 (1H, s). [M+H] Calc'd for $C_{24}H_{22}N_4O_3$, 415; Found, 415.

Preparation 118a tert-butyl N-{[(4R)-7-(4-fluoro-2-methoxyphenyl)-3,4-dihydro-2H-1-benzopyran-4-yl]methyl}carbamate

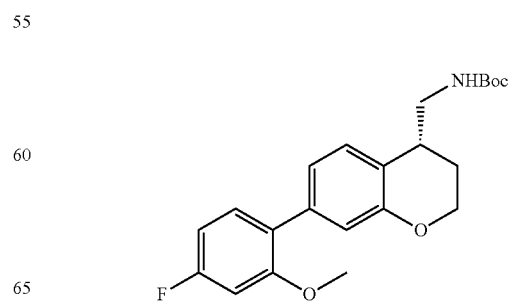

The title compound was prepared in 60% yield from 4-fluoro-2-methoxyphenylboronic acid and Preparation 18d according to the procedures for Preparation 43a. [M+H] Calc'd for $C_{22}H_{26}FNO_4$, 388; Found, 388. [M+H] Calc'd for $C_{22}H_{26}FNO_4$, 388; Found, 388.

Preparation 118b

[(4R)-7-(4-fluoro-2-methoxyphenyl)-3,4-dihydro-2H-1-benzopyran-4-yl]methanamine

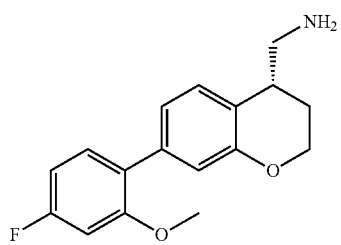 [SMILES: COc1cc(F)ccc1-c1ccc2c(c1)OCC[C@H]2CN]

The title compound was prepared in 95% yield from Preparation 118a according to the procedure for Preparation 43b. [M+H] Calc'd for $C_{17}H_{18}FN_2O_4$, 288; Found, 288.

Preparation 118c methyl 3-({[(4R)-7-(4-fluoro-2-methoxyphenyl)-3,4-dihydro-2H-1-benzopyran-4-yl]methyl}amino)pyridine-4-carboxylate

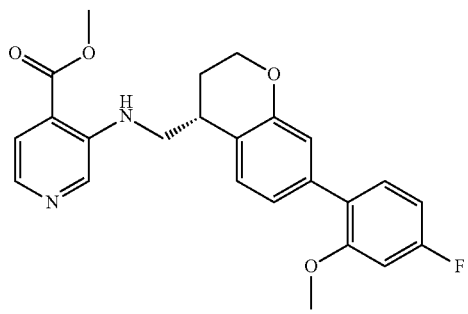 [SMILES: COC(=O)c1ccncc1NC[C@@H]1CCOc2cc(-c3ccc(F)cc3OC)ccc21]

The title compound was prepared in 63% yield from Preparation 118b according to the procedure for Preparation 4d. [M+H] Calc'd for $C_{24}H_{23}FN_2O_4$, 423; Found, 423.

Example 118

3-({[(4R)-7-(4-fluoro-2-methoxyphenyl)-3,4-dihydro-2H-1-benzopyran-4-yl]methyl}amino)pyridine-4-carboxylic acid

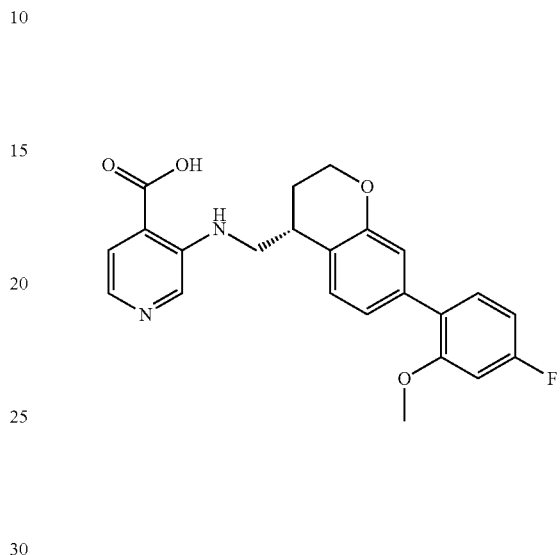

The title compound was prepared in 67% yield from Preparation 118c according to the procedure for Example 1. $^1$H NMR (400 MHz, DMSO-$d_6$): δ 1.91-2.03 (2H, m), 3.15-3.18 (1H, m), 3.51-3.60 (1H, m), 3.72-3.77 (4H, m), 4.16-4.24 (2H, m), 6.80-6.85 (2H, m), 6.92 (1H, dd, J=1.6, 7.8 Hz), 6.99 (1H, dd, J=2.4, 11.2 Hz), 7.25-7.29 (1H, m), 3.34 (1H, d, J=8.0 Hz), 7.55 (1H, d, J=5.2 Hz), 7.87 (1H, d, J=5.2 Hz), 8.45 (1H, s). [M+H] Calc'd for $C_{23}H_{21}FN_2O_4$, 409; Found, 409.

Preparation 119a tert-butyl N-{[(4R)-7-[(4-cyanophenyl)(methyl)amino]-3,4-dihydro-2H-1-benzopyran-4-yl]methyl}carbamate

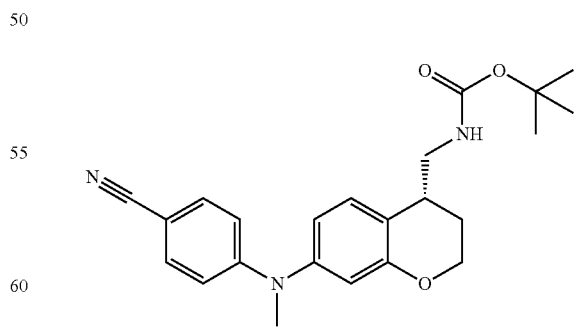

The title compound was prepared in 57% yield from Preparation 18d and 4-cyano-N-methylaniline according to the general procedure for Preparation 9a. [M+H] Calc'd for $C_{23}H_{27}N_3O_3$, 394; Found, 394.

Preparation 119b

4-{[(4R)-4-(aminomethyl)-3,4-dihydro-2H-1-benzopyran-7-yl](methyl)amino}benzonitrile

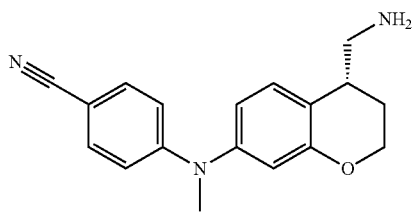 [SMILES: CN(c1ccc(C#N)cc1)c1ccc2c(c1)OCC[C@H]2CN]

The title compound was prepared in quantitative yield from Preparation 119a according to the procedure for Preparation 43b. [M+H] Calc'd for $C_{18}H_{19}N_3O$, 294; Found, 294.

Preparation 119c methyl 3-({[(4R)-7-[(4-cyanophenyl)(methyl)amino]-3,4-dihydro-2H-1-benzopyran-4-yl]methyl}amino)pyridine-4-carboxylate

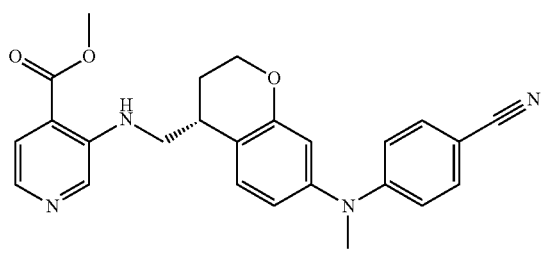 [SMILES: COC(=O)c1ccncc1NC[C@@H]1CCOc2cc(N(C)c3ccc(C#N)cc3)ccc21]

The title compound was prepared in 50% yield from Preparation 119b according to the procedure for Preparation 4d. [M+H] Calc'd for $C_{25}H_{24}N_4O_3$, 429; Found, 429.

Example 119

3-({[(4R)-7-[(4-cyanophenyl)(methyl)amino]-3,4-dihydro-2H-1-benzopyran-4-yl]methyl}amino)pyridine-4-carboxylic acid

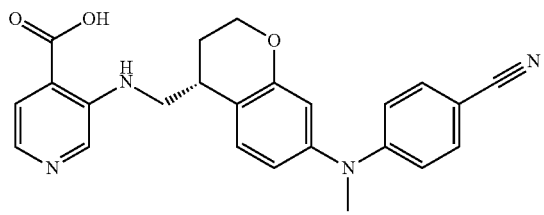 [SMILES: CN(c1ccc(C#N)cc1)c1ccc2c(c1)OCC[C@H]2CNc1cnccc1C(=O)O]

The title compound was prepared in 88% yield from Preparation 119c according to the procedure for Example 1. $^1$H NMR (400 MHz, DMSO-$d_6$): δ 1.92-1.94 (1H, m), 2.01-2.04 (1H, m), 3.15-3.18 (1H, m), 3.27 (3H, s), 3.52-3.57 (1H, m), 3.72-3.76 (1H, m), 4.19-4.25 (2H, m), 6.67 (1H, d, J=2.0 Hz), 6.73-6.79 (3H, m), 7.39 (1H, d, J=8.0 Hz), 7.54-7.59 (3H, m), 7.86 (1H, d, J=5.2 Hz), 8.43 (1H, s). [M+H] Calc'd for $C_{24}H_{22}N_4O_3$, 415; Found, 415.

Preparation 120a tert-butyl N-{[(1R)-6-[(cyclopropylmethyl)(methyl)amino]-1,2,3,4-tetrahydronaphthalen-1-yl]methyl}carbamate

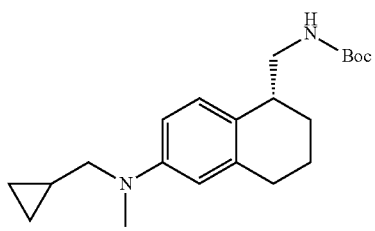 [SMILES: CN(CC1CC1)c1ccc2c(c1)CCC[C@H]2CNC(=O)OC(C)(C)C]

To a solution of Preparation 6d (0.5 g, 1.47 mmol) in toluene (10 mL) was added N-(cyclopropylmethyl)-N-methylamine hydrochloride (0.36 g, 2.94 mmol), $Pd_2(dba)_3$ (28 mg, 0.029 mmol), Xantphos (51 mg, 0.088 mmol) and $Cs_2CO_3$ (2.4 g, 7.35 mmol). The mixture was heated in a sealed tube at 130° C. for 4 h. The mixture was filtered and concentrated, and the residue was purified by silica gel chromatography (PE:EtOAc=9:1 to 4:1) to give 48 mg (9%) of the title compound as a brown oil. [M+H] Calc'd for $C_{21}H_{32}N_2O_2$, 345; Found, 345.

Preparation 120b (5R)-5-(aminomethyl)-N-(cyclopropylmethyl)-N-methyl-5,6,7,8-tetrahydronaphthalen-2-amine

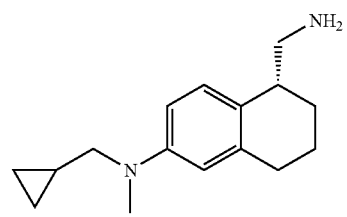 [SMILES: CN(CC1CC1)c1ccc2c(c1)CCC[C@H]2CN]

The title compound was prepared in 90% yield from Preparation 120a according to the procedure for Preparation 43b. [M+H] Calc'd for $C_{16}H_{24}N_2$, 245; Found, 245.

Preparation 120c methyl 3-({[(1R)-6-[(cyclopropylmethyl)(methyl)amino]-1,2,3,4-tetrahydronaphthalen-1-yl]methyl}amino)pyridine-4-carboxylate

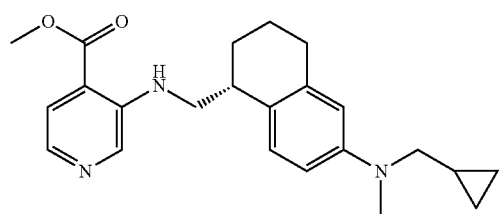 [SMILES: COC(=O)c1ccncc1NC[C@@H]1CCCc2cc(N(C)CC3CC3)ccc21]

321

The title compound was prepared in 38% yield from Preparation 120b according to the procedure for Preparation 4d. [M+H] Calc'd for $C_{23}H_{29}N_3O_2$, 380; Found, 380.

Example 120

3-({[(1R)-6-[(cyclopropylmethyl)(methyl)amino]-1,2,3,4-tetrahydronaphthalen-1-yl]methyl}amino)pyridine-4-carboxylic acid

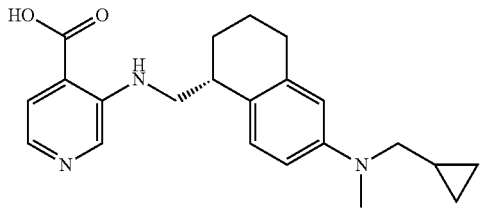 [SMILES: CN(CC1CC1)c1ccc2c(c1)CCC[C@H]2CNc1cnccc1C(=O)O]

The title compound was prepared in 50% yield from Preparation 120c according to the procedure for Example 1. $^1$H NMR (400 MHz, DMSO-d$_6$): δ 0.33-0.37 (2H, m), 0.60-0.65 (2H, m), 0.81-0.88 (1H, m), 1.80-1.87 (1H, m), 1.91-2.05 (3H, m), 2.83-2.98 (2H, m), 3.26 (3H, s), 3.30-3.32 (1H, m), 3.46 (2H, d, J=7.2 Hz), 3.59-3.68 (2H, m), 7.36-7.40 (2H, m), 7.53 (1H, d, J=8.4 Hz), 7.94 (1H, s) 8.19 (1H, d, J=5.2 Hz), 8.36 (1H, s). [M+H] Calc'd for $C_{22}H_{27}N_3O_2$, 366; Found, 366.

Preparation 121a tert-butyl N-{[(1R)-6-[(6-methoxypyridin-2-yl)(methyl)amino]-1,2,3,4-tetrahydronaphthalen-1-yl]methyl}carbamate

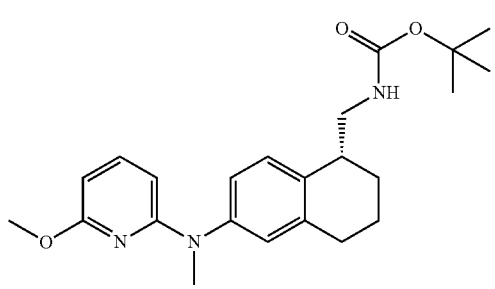 [SMILES: COc1cccc(N(C)c2ccc3c(c2)CCC[C@H]3CNC(=O)OC(C)(C)C)n1]

The title compound was prepared in 58% yield from Preparation 6d and 6-methoxy-N-methylpyridin-2-amine according to the general procedure for Preparation 9a. [M+H] Calc'd for $C_{23}H_{31}N_3O_3$, 398; Found, 398.

Preparation 121b

N-[(5R)-5-(aminomethyl)-5,6,7,8-tetrahydronaphthalen-2-yl]-6-methoxy-N-methylpyridin-2-amino

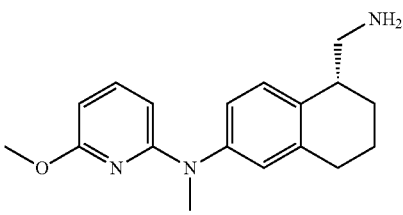 [SMILES: COc1cccc(N(C)c2ccc3c(c2)CCC[C@H]3CN)n1]

The title compound was prepared in quantitative yield from Preparation 121a according to the procedure for Preparation 43b. [M+H] Calc'd for $C_{18}H_{23}N_3O$, 298; Found, 298.

Preparation 121c methyl 3-({[(1R)-6-[(6-methoxypyridin-2-yl)(methyl)amino]-1,2,3,4-tetrahydronaphthalen-1-yl]methyl}amino)pyridine-4-carboxylate

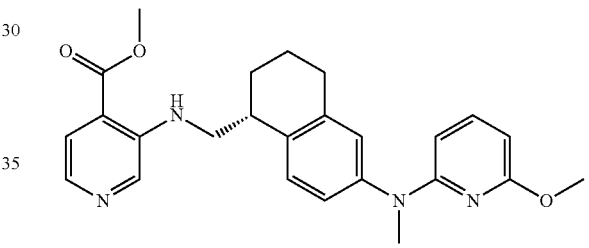

The title compound was prepared in 28% yield from Preparation 121b according to the procedure for Preparation 4d. [M+H] Calc'd for $C_{25}H_{28}N_4O_3$, 433; Found, 433.

Example 121

3-({[(1R)-6-[(6-methoxypyridin-2-yl)(methyl)amino]-1,2,3,4-tetrahydronaphthalen-1-yl]methyl}amino)pyridine-4-carboxylic acid

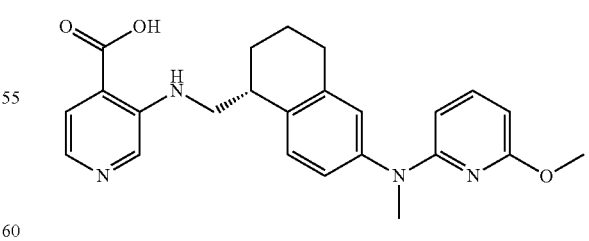

The title compound was prepared in 50% yield from Preparation 121c according to the procedure for Example 1. $^1$H NMR (400 MHz, DMSO-d$_6$): δ 1.67-1.87 (4H, m), 2.70-2.74 (2H, m), 3.07-3.09 (1H, m), 3.34-3.36 (4H, m), 3.55-3.61 (1H, m), 3.80 (3H, s), 5.99-6.06 (2H, m), 7.03-7.07 (2H, m), 7.30-7.38 (2H, m), 7.57 (1H, d, J=4.8 Hz), 7.82 (1H, d, J=4.8 Hz), 8.54 (1H, s). [M+H] Calc'd for $C_{24}H_{26}N_4O_3$, 419; Found, 419.

Preparation 122a methyl 3-({[(1R)-6-bromo-1,2,3,4-tetrahydronaphthalen-1-yl]methyl}amino)pyridine-4-carboxylate

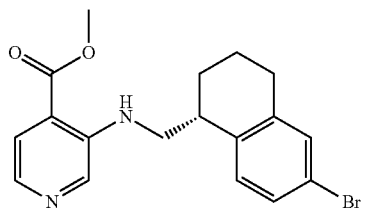 [SMILES: COC(=O)c1ccncc1NC[C@@H]1CCCc2cc(Br)ccc21]

To a solution of Preparation 6c (3.2 g, 13.39 mmol) in toluene (50 mL) was added methyl 3-bromo-isonicotinate (3.47 g, 16.07 mmol), $Cs_2CO_3$ (8.73 g, 26.78 mmol), Xantphos (462 mg, 0.8 mmol) and $Pd_2(dba)_3$ (250 mg, 0.27 mmol). The mixture was stirred overnight at 120° C. under nitrogen. The mixture was filtered and concentrated, and the residue was purified by prep-HPLC to give 2.53 g (50%) of the title compound as a yellow gum. [M+H] Calc'd for $C_{18}H_{19}BrN_2O_2$, 375, 377; Found, 375, 377.

Example 122

3-({[(1R)-6-[methyl(5-methylpyridin-2-yl)amino]-1,2,3,4-tetrahydronaphthalen-1-yl]methyl}amino)pyridine-4-carboxylic acid

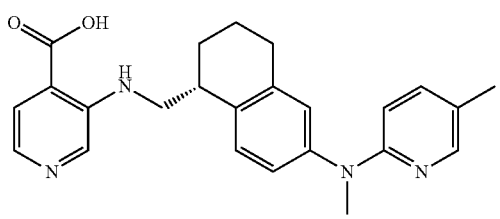 [SMILES: Cc1ccc(N(C)c2ccc3c(c2)CCC[C@H]3CNc2cnccc2C(=O)O)nc1]

To a solution of Preparation 122a (550 mg, 1.47 mmol) in toluene (10 mL) was added N,5-dimethylpyridin-2-amine (178 mg, 1.47 mmol), t-BuONa (282 mg, 2.94 mmol), JohnPhos (66 mg, 0.22 mmol) and $Pd_2(dba)_3$ (138 mg, 0.15 mmol). The mixture was stirred overnight at 110° C. under nitrogen. The mixture was filtered and concentrated, and the residue was purified by prep-HPLC to 101 mg (16%) as a yellow solid. (Hydrolysis of the ester had occurred during the course of this reaction.) $^1$H NMR (300 MHz, DMSO-$d_6$): δ 1.64-1.70 (1H, m), 1.77-1.86 (3H, m), 2.10 (3H, s), 2.70-2.72 (2H, m), 3.07-3.11 (1H, m), 3.31 (3H, s), 3.40-3.48 (1H, m), 3.57-3.63 (1H, m), 6.45 (1H, d, J=8.4 Hz), 6.97 (1H, s), 7.00 (1H, d, J=1.5 Hz), 7.23 (1H, d, J=2.4 Hz), 7.32 (1H, d, J=8.1 Hz), 7.55 (1H, d, J=5.1 Hz), 7.81 (1H, d, J=4.8 Hz), 7.96 (1H, s), 8.33 (1H, s). [M+H] Calc'd for $C_{24}H_{26}N_4O_2$, 403; Found, 403.

Preparation 123a tert-butyl N-{[(1R)-6-[methyl(6-methylpyridin-2-yl)amino]-1,2,3,4-tetrahydronaphthalen-1-yl]methyl}carbamate

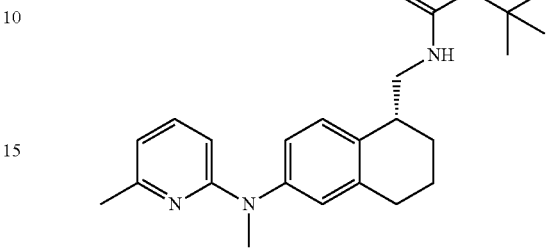

The title compound was prepared in 30% yield from Preparation 6d and N,6-dimethylpyridin-2-amine according to the general procedure for Preparation 9a. [M+H] Calc'd for $C_{23}H_{31}N_3O_2$, 382; Found, 382.

Preparation 123b

N-[(5R)-5-(aminomethyl)-5,6,7,8-tetrahydronaphthalen-2-yl]-N,6-dimethylpyridin-2-amine

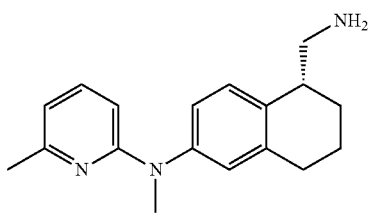 [SMILES: Cc1cccc(N(C)c2ccc3c(c2)CCC[C@H]3CN)n1]

The title compound was prepared in quantitative yield from Preparation 123a according to the procedure for Preparation 43b. [M+H] Calc'd for $C_{18}H_{23}N_3$, 282; Found, 282.

Preparation 123c methyl 3-({[(1R)-6-[methyl(6-methylpyridin-2-yl)amino]-1,2,3,4-tetrahydronaphthalen-1-yl]methyl}amino)pyridine-4-carboxylate

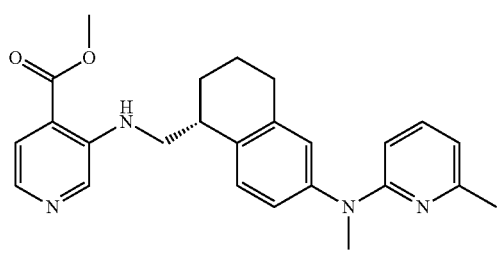 [SMILES: COC(=O)c1ccncc1NC[C@@H]1CCCc2cc(N(C)c3cccc(C)n3)ccc21]

The title compound was prepared in 56% yield from Preparation 123b according to the procedure for Preparation 4d. [M+H] Calc'd for $C_{25}H_{28}N_4O_2$, 417; Found, 417.

Example 123

3-({[(1R)-6-[methyl(6-methylpyridin-2-yl)amino]-1,2,3,4-tetrahydronaphthalen-1-yl]methyl}amino)pyridine-4-carboxylic acid

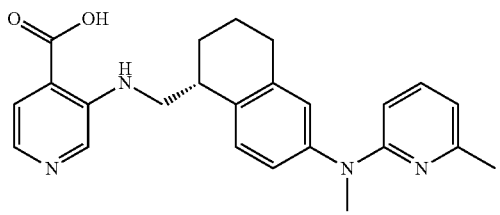 [SMILES: Cc1cccc(N(C)c2ccc3c(c2)CCC[C@H]3CNc2cnccc2C(=O)O)n1]

The title compound was prepared in 35% yield from Preparation 123c according to the procedure for Example 1. $^1$H NMR (400 MHz, DMSO-d$_6$): δ 1.67-1.70 (1H, m), 1.82-1.84 (3H, m), 2.34 (3H, s), 2.70-2.74 (2H, m), 3.07-3.09 (1H, m), 3.34-3.36 (4H, m), 3.53-3.58 (1H, m), 6.27 (1H, d, J=8.4 Hz), 6.49 (1H, d, J=7.2 Hz), 6.99-7.02 (2H, m), 7.27 (1H, dd, J=7.2, 8.0 Hz), 7.36 (1H, d, J=8.0 Hz), 7.57 (1H, d, J=4.4 Hz), 7.60 (1H, d, J=4.8 Hz), 8.20 (1H, s). [M+H] Calc'd for C$_{24}$H$_{26}$N$_4$O$_2$, 403; Found, 403.

Preparation 124a tert-butyl N-{[(4R)-7-(2-cyanophenyl)-3,4-dihydro-2H-1-benzopyran-4-yl]methyl}carbamate

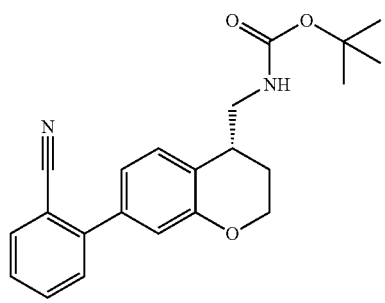 [SMILES: CC(C)(C)OC(=O)NC[C@@H]1CCOc2cc(-c3ccccc3C#N)ccc21]

The title compound was prepared in 29% yield from Preparation 18d and 2-cyanophenylboronic acid according to the general procedure outlined for Preparation 43a. [M+H] Calc'd for C$_{22}$H$_{24}$N$_2$O$_3$, 365; Found, 365.

Preparation 124b

2-[(4R)-4-(aminomethyl)-3,4-dihydro-2H-1-benzopyran-7-yl]benzonitrile

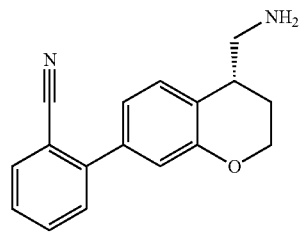 [SMILES: N#Cc1ccccc1-c1ccc2c(c1)OCC[C@H]2CN]

The title compound was prepared in quantitative yield from Preparation 124a according to the procedure for Preparation 43b. [M+H] Calc'd for C$_{17}$H$_{16}$N$_2$O, 265; Found, 265.

Preparation 124c methyl 3-({[(4R)-7-(2-cyanophenyl)-3,4-dihydro-2H-1-benzopyran-4-yl]methyl}amino)pyridine-4-carboxylate

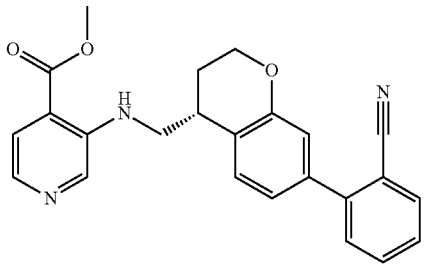 [SMILES: COC(=O)c1ccncc1NC[C@@H]1CCOc2cc(-c3ccccc3C#N)ccc21]

The title compound was prepared in 24% yield from Preparation 124b according to the procedure for Preparation 4d. [M+H] Calc'd for C$_{24}$H$_{21}$N$_3$O$_3$, 400; Found, 400.

Example 124

3-({[(4R)-7-(2-cyanophenyl)-3,4-dihydro-2H-1-benzopyran-4-yl]methyl}amino)pyridine-4-carboxylic acid

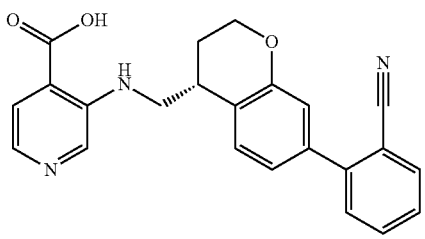 [SMILES: N#Cc1ccccc1-c1ccc2c(c1)OCC[C@H]2CNc1cnccc1C(=O)O]

The title compound was prepared in 54% yield from Preparation 124c according to the procedure for Example 1. $^1$H NMR (400 MHz, DMSO-d$_6$): δ 1.92-2.06 (2H, m), 3.21-3.26 (1H, m), 3.54-3.60 (1H, m), 3.76-3.81 (1H, m), 4.21-4.28 (2H, m), 6.99 (1H, d, J=1.6 Hz), 7.06-7.09 (1H, m), 7.50 (1H, d, J=8.4 Hz), 7.55-7.61 (3H, m), 7.75-7.79 (1H, m), 7.87 (1H, d, J=4.8 Hz), 7.93 (1H, d, J=6.4 Hz), 8.47 (1H, s). [M+H] Calc'd for C$_{23}$H$_{19}$N$_3$O$_3$, 386; Found, 386.

Preparation 125a tert-butyl N-{[(1R)-6-[methyl(1-methyl-1H-pyrazol-3-yl)amino]-1,2,3,4-tetrahydronaphthalen-1-yl]methyl}carbamate

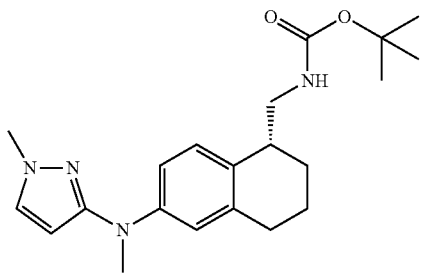 [SMILES: CN(c1ccc2c(c1)CCC[C@H]2CNC(=O)OC(C)(C)C)c1ccn(C)n1]

The title compound was prepared in 62% yield from Preparation 6d and N,1-dimethyl-1H-pyrazol-3-amine according to the general procedure for Preparation 9a. [M+H] Calc'd for $C_{21}H_{30}N_4O_2$, 371; Found, 371.

Preparation 125b

N-[(5R)-5-(aminomethyl)-5,6,7,8-tetrahydronaphthalen-2-yl]-N,1-dimethyl-1H-pyrazol-3-amine

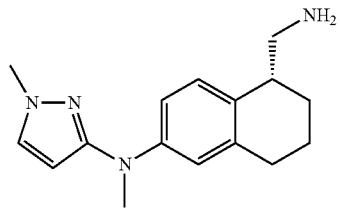 [SMILES: CN(c1ccc2c(c1)CCC[C@H]2CN)c1ccn(C)n1]

The title compound was prepared in quantitative yield from Preparation 125a according to the procedure for Preparation 43b. [M+H] Calc'd for $C_{16}H_{22}N_4$, 271; Found, 271.

Preparation 125c methyl 3-({[(1R)-6-[methyl(1-methyl-1H-pyrazol-3-yl)amino]-1,2,3,4-tetrahydronaphthalen-1-yl]methyl}amino)pyridine-4-carboxylate

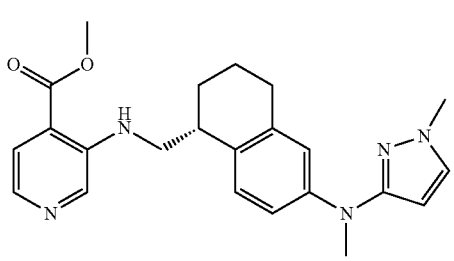 [SMILES: COC(=O)c1ccncc1NC[C@@H]1CCCc2cc(N(C)c3ccn(C)n3)ccc21]

The title compound was prepared in 24% yield from Preparation 125b according to the procedure for Preparation 4d. [M+H] Calc'd for $C_{23}H_{27}N_5O_2$, 406; Found, 406.

Example 125

3-({[(1R)-6-[methyl(1-methyl-1H-pyrazol-3-yl)amino]-1,2,3,4-tetrahydronaphthalen-1-yl]methyl}amino)pyridine-4-carboxylic acid

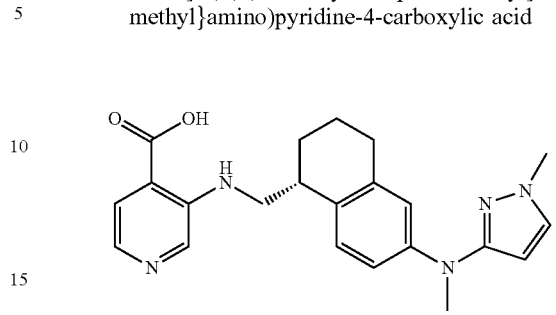

The title compound was prepared in 90% yield from Preparation 125c according to the procedure for Example 1. $^1$H NMR (400 MHz, DMSO-$d_6$): δ 1.62-1.82 (4H, m), 2.64-2.71 (2H, m), 3.00-3.05 (1H, m), 3.22 (3H, s), 3.37-3.44 (1H, m), 3.52-3.58 (1H, m), 3.72 (3H, s), 5.81 (1H, s), 6.81 (1H, s), 6.90 (1H, d, J=8.3 Hz), 7.17 (1H, d, J=8.3 Hz), 7.51 (1H, s), 7.57 (1H, br s), 7.83 (1H, br s), 8.35 (1H, br s). [M+H] Calc'd for $C_{22}H_{25}N_5O_2$, 392; Found, 392.

Preparation 126a

N-methyl-4-[2-(trimethylsilyl)ethynyl]aniline

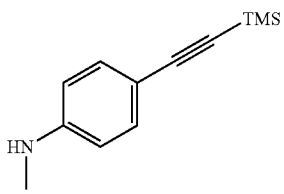

To a suspension of 4-bromo-N-methylaniline (500 mg, 2.7 mmol), trimethylsilyl acetylene (527 mg, 5.4 mmol), CuI (92 mg, 0.5 mmol) and PPh$_3$ (233 mg, 0.9 mmol) in TEA (20 mL) was added PdCl$_2$(PPh$_3$)$_2$ (94 mg, 0.1 mmol) at r.t. under N$_2$. The reaction was stirred at reflux overnight. The reaction was filtered, concentrated, and purified by silica gel chromatography (PE:EtOAc=20:1) to give 200 mg (37%) of the title compound as a yellow oil. [M+H] Calc'd for $C_{12}H_{17}NSi$, 204; Found, 204.

Preparation 126b methyl 3-({[(4R)-7-bromo-3,4-dihydro-2H-1-benzopyran-4-yl]methyl}amino)pyridine-4-carboxylate

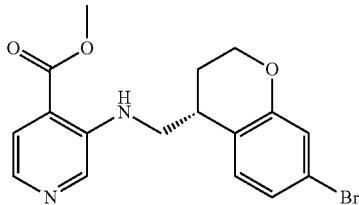 [SMILES: COC(=O)c1ccncc1NC[C@@H]1CCOc2cc(Br)ccc21]

The title compound was prepared from Preparation 18c and methyl 3-bromo-isonicotinate according to the general procedure outline for Preparation 122a. [M+H] Calc'd for $C_{17}H_{17}BrN_2O_3$, 377, 379; Found, 377, 379.

Preparation 126c methyl 3-({[(4R)-7-[methyl({4-[2-(trimethylsilyl) ethynyl]phenyl})amino]-3,4-dihydro-2H-1-benzopyran-4-yl]methyl}amino)pyridine-4-carboxylate

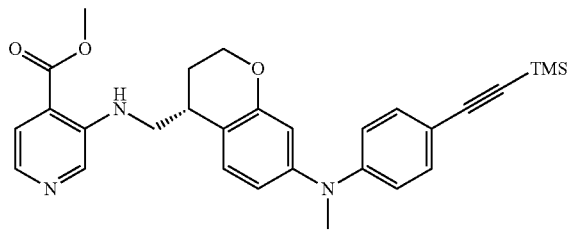 [SMILES: COC(=O)c1ccncc1NC[C@@H]1CCOc2cc(N(C)c3ccc(C#C[Si](C)(C)C)cc3)ccc21]

To a suspension of Preparation 126b (100 mg, 0.27 mmol), N-methyl-4-[2-(trimethylsilyl)-ethynyl]aniline (54 mg, 0.27 mmol), Xantphos (23 mg, 0.04 mmol) and $Cs_2CO_3$ (123 mg, 0.38 mmol) in toluene (10 mL) was added $Pd_2dba_3$ (12 mg, 0.01 mmol) at r.t. under $N_2$. The reaction was stirred at 110° C. overnight. The reaction was filtered, concentrated, and purified by silica gel chromatography (PE:EtOAc=5:1) to give 30 mg (23%) of the title compound as a yellow oil. [M+H] Calc'd for $C_{29}H_{33}N_3O_3Si$, 500; Found, 500.

Preparation 126d methyl 3-({[(4R)-7-[(4-ethynylphenyl)(methyl) amino]-3,4-dihydro-2H-1-benzopyran-4-yl] methyl}amino)pyridine-4-carboxylate

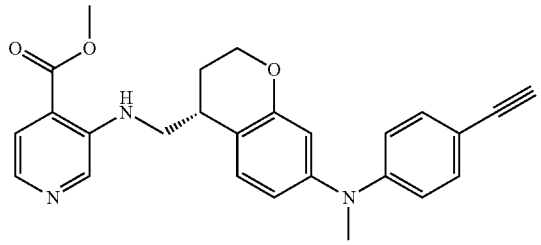 [SMILES: C#Cc1ccc(N(C)c2ccc3c(c2)OCC[C@H]3CNc2cnccc2C(=O)OC)cc1]

To a solution of Preparation 126c (50 mg, 0.10 mmol) in THF (5 mL) was added TBAF (0.20 mL, 1.0 M in THF, 0.20 mmol), and the reaction was stirred at r.t. for 1 h. The solution was concentrated and dried under vacuum. This material was used for the next step directly without purification. [M+H] Calc'd for $C_{26}H_{25}N_3O_3$, 428; Found, 428.

Example 126

3-({[(4R)-7-[(4-ethynylphenyl)(methyl)amino]-3,4-dihydro-2H-1-benzopyran-4-yl]methyl}amino)pyridine-4-carboxylic acid

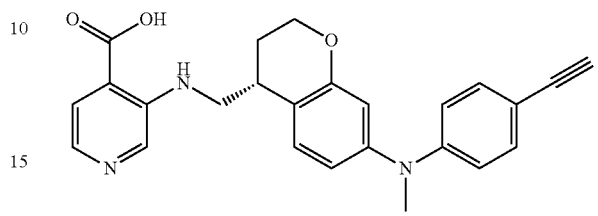

The title compound was prepared in 49% yield from Preparation 126d according to the procedure for Example 1. $^1$H NMR (300 MHz, DMSO-$d_6$): δ 1.83-1.88 (1H, m), 1.94-2.03 (1H, m), 3.09-3.12 (1H, m), 3.19 (3H, s), 3.49-3.51 (1H, m), 3.67-3.72 (1H, m), 3.94 (1H, s), 4.17-4.21 (2H, m), 6.55 (1H, d, J=1.8 Hz), 6.63 (1H, dd, J=1.8, 8.1 Hz), 6.80 (2H, d, J=8.7 Hz), 7.28-7.31 (3H, m), 7.57 (1H, d, J=4.8 Hz), 7.84 (1H, d, J=5.1 Hz), 8.40 (1H, s). [M+H] Calc'd for $C_{25}H_{23}N_3O_3$, 414; Found, 414.

Preparation 127a

N-methyl-1,3-dihydro-2-benzofuran-5-amine

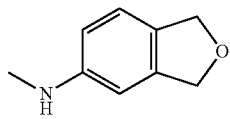

1,3-Dihydro-2-benzofuran-5-amine (300 mg, 2.2 mmol) was added to HCOOH (10 mL), and the reaction was stirred at reflux overnight. The reaction was concentrated, basified to pH=8 with sat $Na_2CO_3$, and extracted with EtOAc. Organics were washed with brine, dried ($Na_2SO_4$), and concentrated to give 250 mg (69%) of N-(1,3-dihydro-2-benzofuran-5-yl)formamide as a yellow oil.

To a solution of N-(1,3-dihydro-2-benzofuran-5-yl)formamide (250 mg, 1.5 mmol) in THF (20 mL) was added LAH (1.9 mL, 2.4 M in THF, 4.6 mmol) at 0° C. The reaction was stirred at r.t. for 2 h. The solution was diluted with water (0.5 mL) and EtOAc (30 mL), dried ($Na_2SO_4$), and concentrated to give 220 mg (96%) of the title compound as a yellow oil. [M+H] Calc'd for $C_9H_{11}NO$, 150; Found, 150.

Preparation 127b methyl 3-({[(4R)-7-[(1,3-dihydro-2-benzofuran-5-yl)(methyl)amino]-3,4-dihydro-2H-1-benzopyran-4-yl]methyl}amino)pyridine-4-carboxylate

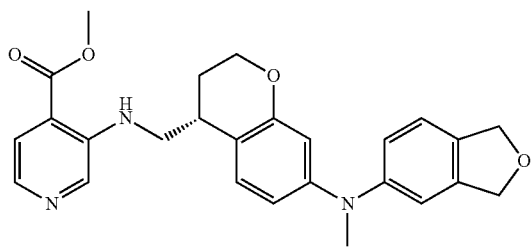

The title compound was prepared in 40% yield from Preparation 126b and N-methyl-1,3-dihydro-2-benzofuran-5-amine according to the general procedure outlined for Preparation 126c. [M+H] Calc'd for $C_{26}H_{27}N_3O_4$, 446; Found, 446.

Example 127

3-({[(4R)-7-[(1,3-dihydro-2-benzofuran-5-yl)(methyl)amino]-3,4-dihydro-2H-1-benzopyran-4-yl]methyl}amino)pyridine-4-carboxylic acid

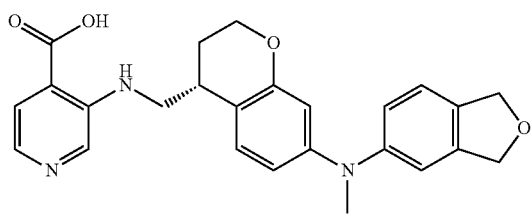 [SMILES: CN(c1ccc2c(c1)COC2)c1ccc2c(c1)OCC[C@H]2CNc1cnccc1C(=O)O]

The title compound was prepared in 90% yield from Preparation 127b according to the procedure for Example 1. $^1$H NMR (400 MHz, DMSO-$d_6$): δ 1.84-1.87 (1H, m), 1.96-1.99 (1H, m), 3.04-3.08 (1H, m), 3.19 (3H, s), 3.44-3.50 (1H, m), 3.64-3.69 (1H, m), 4.10-4.18 (2H, m), 4.95 (4H, s), 6.32 (1H, d, J=2.8 Hz), 6.45 (1H, dd, J=2.4, 8.4 Hz), 6.91-6.97 (2H, m), 7.16-7.22 (2H, m), 7.57 (1H, d, J=4.8 Hz), 7.84 (1H, d, J=5.2 Hz), 8.40 (1H, s). [M+H] Calc'd for $C_{25}H_{25}N_3O_4$, 432; Found, 432.

Preparation 128a tert-butyl N-{[(4R)-7-{methyl[4-(trifluoromethyl)phenyl]amino}-3,4-dihydro-2H-1-benzopyran-4-yl]methyl}carbamate

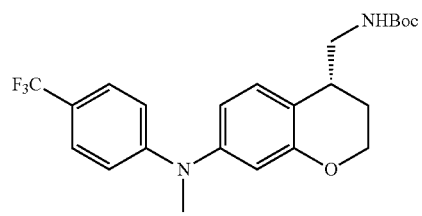 [SMILES: CN(c1ccc(C(F)(F)F)cc1)c1ccc2c(c1)OCC[C@H]2CNC(=O)OC(C)(C)C]

The title compound was prepared in 23% yield from Preparation 18d and N-methyl-4-(trifluoromethyl)aniline according to the general procedure outlined for Preparation 9a. [M+H] Calc'd for $C_{23}H_{27}F_3N_2O_3$, 437; Found, 437.

Preparation 128b (4R)-4-(aminomethyl)-N-methyl-N-[4-(trifluoromethyl)phenyl]-3,4-dihydro-2H-1-benzopyran-7-amine

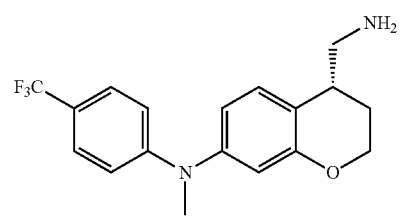 [SMILES: CN(c1ccc(C(F)(F)F)cc1)c1ccc2c(c1)OCC[C@H]2CN]

The title compound was prepared in 95% yield from Preparation 128a according to the procedure for Preparation 43b. [M+H] Calc'd for $C_{18}H_{19}F_3N_2O$, 337; Found, 337.

Preparation 128c methyl 3-({[(4R)-7-{methyl[4-(trifluoromethyl)phenyl]amino}-3,4-dihydro-2H-1-benzopyran-4-yl]methyl}amino)pyridine-4-carboxylate

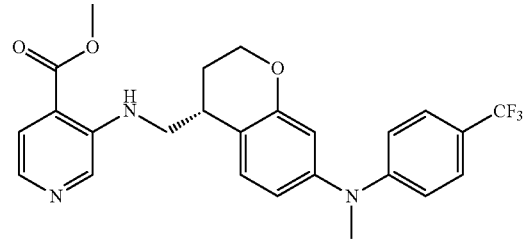 [SMILES: COC(=O)c1ccncc1NC[C@@H]1CCOc2cc(N(C)c3ccc(C(F)(F)F)cc3)ccc21]

The title compound was prepared in 60% yield from Preparation 128b according to the procedure for Preparation 4d. [M+H] Calc'd for $C_{25}H_{24}F_3N_3O_3$, 472; Found, 472.

Preparation 128

3-({[(4R)-7-{methyl[4-(trifluoromethyl)phenyl]amino}-3,4-dihydro-2H-1-benzopyran-4-yl]methyl}amino)pyridine-4-carboxylic acid

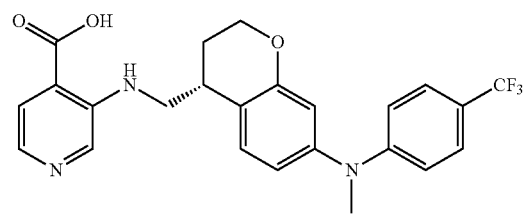 [SMILES: CN(c1ccc(C(F)(F)F)cc1)c1ccc2c(c1)OCC[C@H]2CNc1cnccc1C(=O)O]

The title compound was prepared in 16% yield from Preparation 128c according to the procedure for Example 1. ¹H NMR (400 MHz, DMSO-d₆): δ 1.88-1.92 (1H, m), 1.96-2.05 (1H, m), 3.13-3.18 (1H, m), 3.37 (3H, s), 3.51-3.56 (1H, m), 3.71-3.76 (1H, m), 4.15-4.27 (2H, m), 6.64 (1H, s), 6.71-6.74 (1H, m), 6.88 (2H, d, J=8.4 Hz), 7.37-7.34 (1H, m), 7.48 (2H, d, J=8.8 Hz), 7.58 (1H, d, J=4.8 Hz), 7.85 (1H, d, J=5.2 Hz), 8.43 (1H, s). [M+H] Calc'd for $C_{24}H_{22}F_3N_3O_3$, 458; Found, 458.

Preparation 129a

N-(2,2,2-trifluoroethyl)aniline

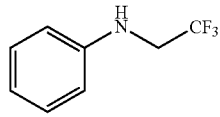 [SMILES: FC(F)(F)CNc1ccccc1]

To a solution of aniline (10.0 g, 107 mmol) in DCM (50 mL) was added TFAA (24.8 g, 118 mmol) and TEA (22 mL, 160 mmol). The mixture was stirred at r.t. for 2 h. The reaction was washed with water, dried (Na₂SO₄), and concentrated to give 17.7 g (87%) of 2,2,2-trifluoro-N-phenylacetamide as a white solid.

To a solution of 2,2,2-trifluoro-N-phenylacetamide (5.0 g, 26 mmol) in THF (10 mL) was added BH₃ in THF (130 mL, 130 mmol, 1.0 M). The resulting mixture was refluxed overnight. The mixture was quenched with water and methanol, concentrated to remove most of THF, and extracted with EtOAc. Organics were washed with brine, dried (Na₂SO₄), and concentrated to give 4.17 g (92%) of the title compound as a colorless oil. ¹H NMR (400 MHz, CDCl₃): δ 3.71-3.75 (2H, m), 6.66 (2H, d, J=8.0 Hz), 6.79 (1H, t, J=7.2 Hz), 7.20 (2H, t, J=8.0 Hz).

Preparation 129b methyl 3-[({7-[phenyl(2,2,2-trifluoroethyl)amino]-3,4-dihydro-2H-1-benzopyran-4-yl}methyl)amino]pyridine-4-carboxylate

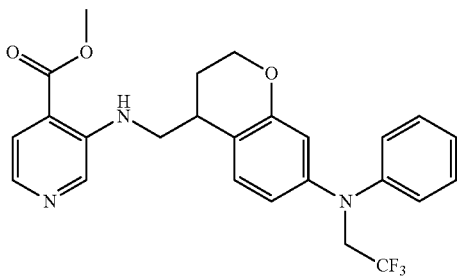 [SMILES: COC(=O)c1ccncc1NCC1CCOc2cc(N(CC(F)(F)F)c3ccccc3)ccc21]

The title compound was prepared in 4% yield from Preparation 14c and Preparation 129a according to the general procedure for Preparation 15a. [M+H] Calc'd for $C_{25}H_{26}F_3N_3O_3$, 472; Found, 472.

Example 129

3-[({7-[phenyl(2,2,2-trifluoroethyl)amino]-3,4-dihydro-2H-1-benzopyran-4-yl}methyl)amino]pyridine-4-carboxylic acid

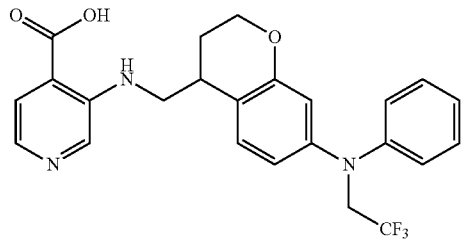 [SMILES: O=C(O)c1ccncc1NCC1CCOc2cc(N(CC(F)(F)F)c3ccccc3)ccc21]

The title compound was prepared in 44% yield from Preparation 129b according to the procedure for Example 1. ¹H NMR (400 MHz, MeOD-d₄): δ 1.90-1.95 (1H, m), 2.05-2.11 (1H, m), 3.08-3.12 (1H, m), 3.43-3.48 (1H, m), 3.58-3.63 (1H, m), 4.06-4.14 (1H, m), 4.24-4.30 (1H, m), 5.24 (2H, t, J=4.6 Hz), 6.29 (1H, d, J=3.2 Hz), 6.36 (1H, d, J=6.0 Hz), 6.92-6.98 (3H, m), 7.04 (1H, d, J=8.1 Hz), 7.18-7.22 (2H, m), 7.80-7.82 (1H, m), 8.03-8.05 (1H, m), 8.23 (1H, d, J=2.0 Hz). [M+H] Calc'd for $C_{24}H_{22}F_3N_3O_3$, 458; Found, 458.

Preparation 130a tert-butyl N-({7-[benzyl(methyl)amino]-3,4-dihydro-2H-1-benzopyran-4-yl}methyl)carbamate

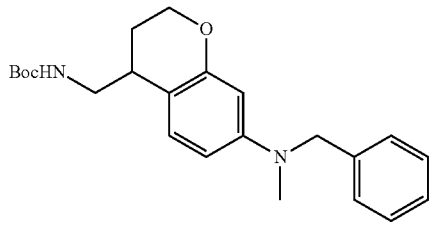 [SMILES: CN(Cc1ccccc1)c1ccc2c(c1)OCCC2CNC(=O)OC(C)(C)C]

To a solution of tert-butyl N-[(7-bromo-3,4-dihydro-2H-1-benzopyran-4-yl)methyl]carbamate (500 mg, 1.46 mmol) in toluene (10 mL) was added N-methyl-benzylamine (212 mg, 1.75 mmol), Cs₂CO₃ (950 mg, 2.92 mmol), BINAP (44 mg, 0.07 mmol) and Pd(OAc)₂ (16 mg, 0.07 mmol). The mixture was stirred overnight at 100° C. under nitrogen. The mixture was filtered and concentrated, and the residue was purified by prep-HPLC to give 362 mg (65%) of the title compound as a colorless gum. [M+H] Calc'd for $C_{23}H_{30}N_2O_3$, 383; Found, 383.

Preparation 130b 4-(aminomethyl)-N-benzyl-N-methyl-3,4-dihydro-2H-1-benzopyran-7-amine

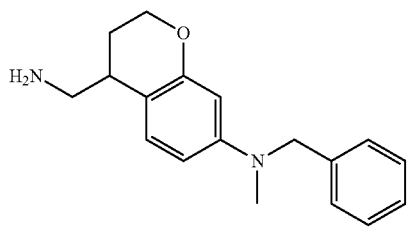 [SMILES: CN(Cc1ccccc1)c1ccc2c(c1)OCCC2CN]

The title compound was prepared in 97% yield from Preparation 130a according to the procedure for Preparation 43b. [M+H] Calc'd for $C_{18}H_{22}N_2O$, 283; Found, 283.

Preparation 130c methyl 3-({[(1R)-6-[benzyl(methyl)amino]-1,2,3,4-tetrahydronaphthalen-1-yl]methyl}amino)pyridine-4-carboxylate

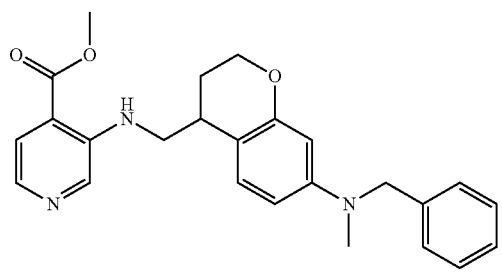 [SMILES: COC(=O)c1ccncc1NCC1CCOc2cc(N(C)Cc3ccccc3)ccc21]

The title compound was prepared in 4% yield from Preparation 130b according to the general procedure for Preparation 1e. [M+H] Calc'd for $C_{25}H_{27}N_3O_3$, 418; Found, 418.

Example 130

3-({[(1R)-6-[benzyl(methyl)amino]-1,2,3,4-tetrahydronaphthalen-1-yl]methyl}amino)pyridine-4-carboxylic acid

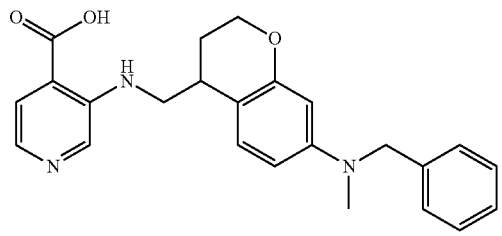 [SMILES: CN(Cc1ccccc1)c1ccc2c(c1)OCCC2CNc1cnccc1C(=O)O]

The title compound was prepared in 76% yield from Preparation 130c according to the procedure for Example 1. $^1$H NMR (400 MHz, MeOD-$d_4$): δ 1.84-1.93 (1H, m), 2.00-2.09 (1H, m), 3.04 (3H, s), 3.10-3.15 (1H, m), 3.44- 3.50 (1H, m), 3.57-3.62 (1H, m), 4.08-4.18 (2H, m), 4.51 (2H, s), 6.47 (1H, d, J=2.0 Hz), 6.53 (1H, d, J=6.0 Hz), 7.12-7.14 (3H, m), 7.20-7.22 (3H, m), 7.84 (1H, s), 8.15 (1H, d, J=4.4 Hz), 8.29 (1H, m). [M+H] Calc'd for $C_{24}H_{25}N_3O_3$, 404; Found, 404.

Preparation 131a

N-methyl-2,3-dihydro-1H-inden-5-amine

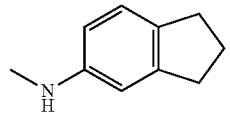

The title compound was prepared in 16% overall yield from 2,3-dihydro-1H-inden-5-amine according to the general procedure outlined for Preparation 127a. [M+H] Calc'd for $C_{10}H_{13}N$, 148; Found, 148.

Preparation 131b tert-butyl N-{[(4R)-7-[(2,3-dihydro-1H-inden-5-yl)(methyl)amino]-3,4-dihydro-2H-1-benzopyran-4-yl]methyl}carbamate

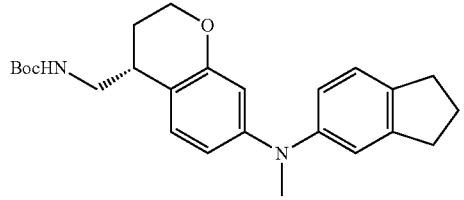 [SMILES: CN(c1ccc2c(c1)CCC2)c1ccc2c(c1)OCC[C@H]2CNC(=O)OC(C)(C)C]

The title compound was prepared in 73% yield from Preparation 18d and Preparation 131a according to the general procedure outlined for Preparation 6e. [M+H] Calc'd for $C_{25}H_{32}N_2O_3$, 409; Found, 409.

Preparation 131c (4R)-4-(aminomethyl)-N-(2,3-dihydro-1H-inden-5-yl)-N-methyl-3,4-dihydro-2H-1-benzopyran-7-amine

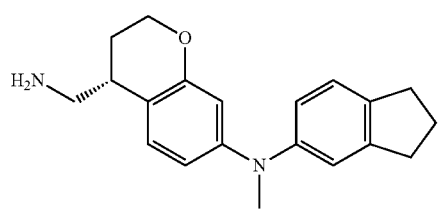 [SMILES: CN(c1ccc2c(c1)CCC2)c1ccc2c(c1)OCC[C@H]2CN]

The title compound was prepared in 98% yield from Preparation 131b according to the procedure for Preparation 43b. [M+H] Calc'd for $C_{20}H_{24}N_2O$, 309; Found, 309.

Preparation 131d methyl 3-({[(4R)-7-[(2,3-dihydro-1H-inden-5-yl)(methyl)amino]-3,4-dihydro-2H-1-benzopyran-4-yl]methyl}amino)pyridine-4-carboxylate

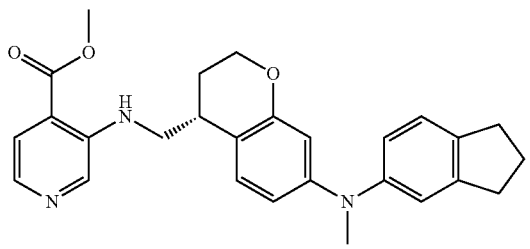 [SMILES: COC(=O)c1ccncc1NC[C@@H]1CCOc2cc(N(C)c3ccc4c(c3)CCC4)ccc21]

The title compound was prepared in 51% yield from Preparation 131c according to the procedure for Preparation 4d. [M+H] Calc'd for $C_{27}H_{29}N_3O_3$, 444; Found, 444.

Example 131

3-({[(4R)-7-[(2,3-dihydro-1H-inden-5-yl)(methyl)amino]-3,4-dihydro-2H-1-benzopyran-4-yl]methyl}amino)pyridine-4-carboxylic acid

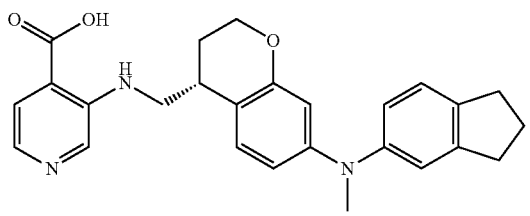 [SMILES: CN(c1ccc2c(c1)CCC2)c1ccc2c(c1)OCC[C@H]2CNc1cnccc1C(=O)O]

The title compound was prepared in 24% yield from Preparation 131d according to the procedure for Example 1. $^1$H NMR (400 MHz, DMSO-$d_6$): δ 1.84-1.85 (1H, m), 1.95-2.05 (3H, m), 2.79-2.83 (4H, m), 3.03-3.05 (1H, m), 3.15 (3H, s), 3.43-3.48 (1H, m), 3.62-3.66 (1H, m), 4.09-4.16 (2H, m), 6.20 (1H, d, J=2.4 Hz), 6.35 (1H, d, J=6.0 Hz), 6.81 (1H, d, J=6.0 Hz), 6.94 (1H, s), 7.09-7.16 (2H, m), 7.59 (1H, d, J=5.2 Hz), 7.84 (1H, d, J=4.8 Hz), 8.40 (1H, s). [M+H] Calc'd for $C_{26}H_{27}N_3O_3$, 430; Found, 430.

Preparation 132a tert-butyl N-{[(1R)-6-[(1,3-dihydro-2-benzofuran-5-yl)(methyl)amino]-1,2,3,4-tetrahydronaphthalen-1-yl]methyl}carbamate

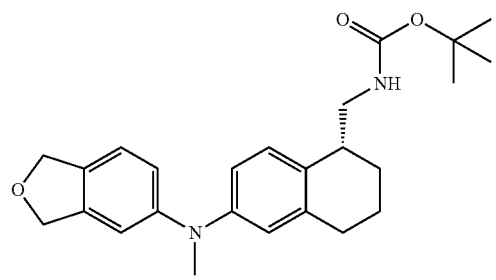 [SMILES: CN(c1ccc2c(c1)COC2)c1ccc2c(c1)CCC[C@H]2CNC(=O)OC(C)(C)C]

The title compound was prepared in 48% yield from Preparation 18d and Preparation 127a according to the general procedure outlined for Preparation 9a. [M+H] Calc'd for $C_{25}H_{32}N_2O_3$, 409; Found, 409.

Preparation 132b

N-[(5R)-5-(aminomethyl)-5,6,7,8-tetrahydronaphthalen-2-yl]-N-methyl-1,3-dihydro-2-benzofuran-5-amine

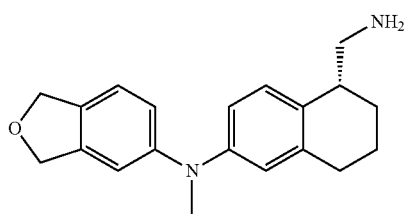 [SMILES: CN(c1ccc2c(c1)COC2)c1ccc2c(c1)CCC[C@H]2CN]

The title compound was prepared in quantitative yield from Preparation 132a according to the procedure for Preparation 43b. [M+H] Calc'd for $C_{20}H_{24}N_2O$, 309; Found, 309.

Preparation 132c methyl 3-({[(1R)-6-[(1,3-dihydro-2-benzofuran-5-yl)(methyl)amino]-1,2,3,4-tetrahydronaphthalen-1-yl]methyl}amino)pyridine-4-carboxylate

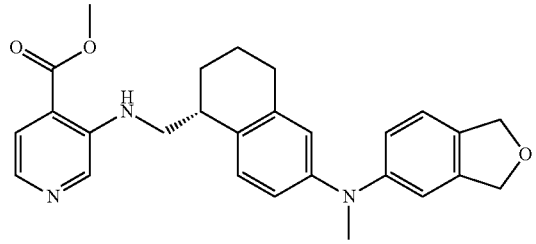

The title compound was prepared in 60% yield from Preparation 132b according to the procedure for Preparation 4d. [M+H] Calc'd for $C_{27}H_{29}N_3O_3$, 444; Found, 444.

Example 132

3-({[(1R)-6-[(1,3-dihydro-2-benzofuran-5-yl)(methyl)amino]-1,2,3,4-tetrahydronaphthalen-1-yl]methyl}amino)pyridine-4-carboxylic acid

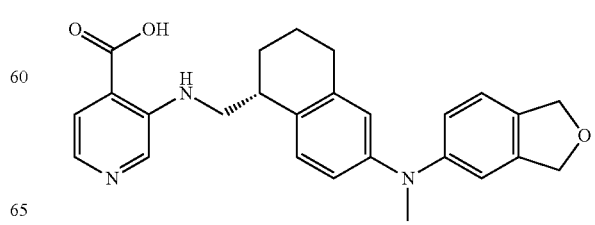

The title compound was prepared in 84% yield from Preparation 132c according to the procedure for Example 1. $^1$H NMR (400 MHz, DMSO-$d_6$): δ 1.65-1.84 (4H, m), 2.64-2.68 (2H, m), 3.03-3.06 (1H, m), 3.21 (3H, s), 3.40-3.46 (1H, m), 3.55-3.60 (1H, m), 4.93 (4H, s), 6.74-6.78 (2H, m), 6.84-6.89 (2H, m), 7.15-7.23 (2H, m), 7.56 (1H, d, J=4.8 Hz), 7.83 (1H, d, J=5.2 Hz), 8.34 (1H, s). [M+H] Calc'd for $C_{26}H_{27}N_3O_3$, 430; Found, 430.

Preparation 133a methyl 3-({[(1R)-6-[cyclopentyl(methyl)amino]-1,2,3,4-tetrahydronaphthalen-1-yl]methyl}amino)pyridine-4-carboxylate

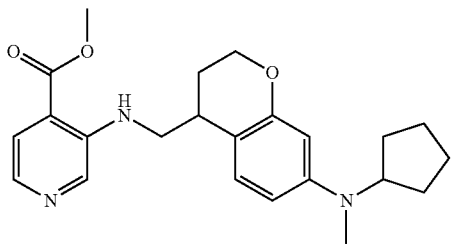 [SMILES: COC(=O)c1ccncc1NCC1CCOc2cc(N(C)C3CCCC3)ccc21]

To a suspension of Preparation 14a (300 mg, 0.80 mmol), N-methylcyclopentanamine (87 mg, 0.88 mmol), Xantphos (69 mg, 0.12 mmol) and $Cs_2CO_3$ (365 mg, 1.12 mmol) in toluene (20 mL) was added $Pd_2dba_3$ (37 mg, 0.04 mmol) at r.t. under $N_2$. The reaction was stirred at 110° C. overnight. The reaction was filtered, concentrated, and purified by silica gel chromatography (PE:EtOAc=5:1) to give 20 mg (6%) of the title compound as a yellow oil. [M+H] Calc'd for $C_{23}H_{29}FN_3O_3$, 396; Found, 396.

Example 133

3-({[(1R)-6-[cyclopentyl(methyl)amino]-1,2,3,4-tetrahydronaphthalen-1-yl]methyl}amino)pyridine-4-carboxylic acid

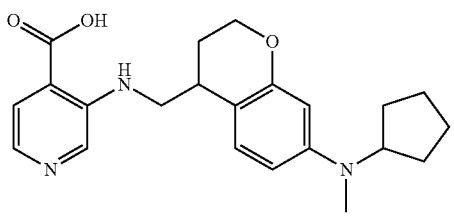 [SMILES: CN(c1ccc2c(c1)OCCC2CNc1cnccc1C(=O)O)C1CCCC1]

The title compound was prepared in 48% yield from Preparation 133a according to the procedure for Example 1. $^1$H NMR (300 MHz, $CD_3OD$): δ 1.32-1.34 (2H, m), 1.68-1.72 (3H, m), 1.84-1.87 (3H, m), 2.06-2.11 (1H, m), 2.20-2.22 (1H, m), 3.28 (3H, s), 3.34-3.40 (1H, m), 3.66-3.71 (1H, m), 3.79-3.84 (1H, m), 4.16-4.19 (1H, m), 4.33-4.38 (2H, m), 7.16-7.18 (2H, m), 7.76 (1H, d, J=5.7 Hz), 8.02 (1H, d, J=4.2 Hz), 8.32 (1H, d, J=4.2 Hz), 8.50 (1H, s). [M+H] Calc'd for $C_{22}H_{27}FN_3O_3$, 382. Found, 382.

Preparation 134a 4-cyclopropyl-N-methylaniline

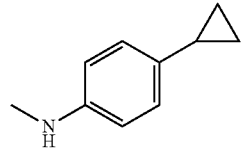

To a suspension of 4-bromo-N-methylaniline (500 mg, 2.69 mmol), cyclopropylboronic acid (462 mg, 5.38 mmol), (cyclohexyl)$_3$P$^+$HBF$_4^-$ (99 mg, 0.27 mmol) and $K_3PO_4$ (2.0 g, 9.4 mmol) in toluene (20 mL) and $H_2O$ (1 mL) was added $Pd(OAc)_2$ (36 mg, 0.16 mmol) at r.t. under $N_2$. The reaction was stirred at reflux overnight. The reaction was filtered, concentrated, and purified by silica gel chromatography (PE:EtOAc=10:1) to give 268 mg (68%) of the title compound as a brown oil. [M+H] Calc'd for $C_{10}H_{23}N$, 148; Found, 148.

Preparation 134b methyl 3-({[(4R)-7-[(4-cyclopropylphenyl)(methyl)amino]-3,4-dihydro-2H-1-benzopyran-4-yl]methyl}amino)pyridine-4-carboxylate

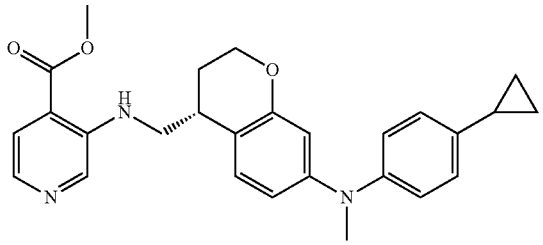 [SMILES: COC(=O)c1ccncc1NC[C@@H]1CCOc2cc(N(C)c3ccc(C4CC4)cc3)ccc21]

The title compound was prepared in 4% yield from Preparation 126b and 4-cyclopropyl-N-methylaniline according to the general procedure outlined for Preparation 126c. [M+H] Calc'd for $C_{27}H_{29}N_3O_3$, 444; Found, 444.

Example 134

3-({[(4R)-7-[(4-cyclopropylphenyl)(methyl)amino]-3,4-dihydro-2H-1-benzopyran-4-yl]methyl}amino)pyridine-4-carboxylic acid

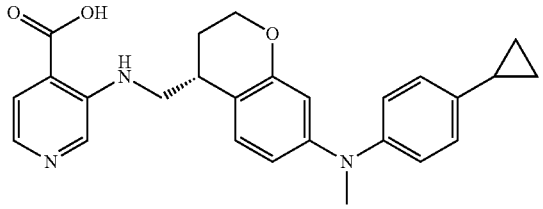 [SMILES: CN(c1ccc(C2CC2)cc1)c1ccc2c(c1)OCC[C@H]2CNc1cnccc1C(=O)O]

The title compound was prepared in 28% yield from Preparation 134b according to the procedure for Example 1.

¹H NMR (300 MHz, DMSO-d₆): δ 0.60-0.63 (2H, m), 0.88-0.92 (2H, m), 1.85-1.89 (3H, m), 3.03-3.05 (1H, m), 3.19 (3H, s), 3.45-3.48 (1H, m), 3.62-3.66 (1H, m), 4.10-4.16 (2H, m), 6.24 (1H, d, J=2.4 Hz), 6.24-6.39 (1H, m), 6.93-7.03 (4H, m), 7.12 (1H, d, J=8.4 Hz), 7.56 (1H, d, J=5.2 Hz), 7.84 (1H, d, J=5.2 Hz), 8.38 (1H, s). [M+H] Calc'd for $C_{26}H_{27}N_3O_3$, 430; Found, 430.

Preparation 135a

N-methyl-1-benzofuran-6-amine

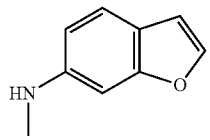

A mixture of 6-bromo-1-benzofuran (1.0 g, 5.1 mmol), methylamine (2N, 25 mL, 50 mmol), CuI (1.16 g, 6.1 mmol) and KOAc (1.25 g, 12.7 mmol) in DMF (10 mL) was stirred overnight at 100° C. under nitrogen in a sealed tube. The mixture was cooled to r.t., diluted with aqueous ammonium hydroxide, and extracted with EtOAc. The organic layer was concentrated, and the residue was purified by silica gel chromatography to give 250 mg (33%) of the title compound as a yellow oil. [M+H] Calc'd for $C_9H_9NO$, 148; Found, 148.

Preparation 135b tert-butyl N-{[(1R)-6-[(1-benzofuran-6-yl)(methyl)amino]-1,2,3,4-tetrahydronaphthalen-1-yl]methyl}carbamate

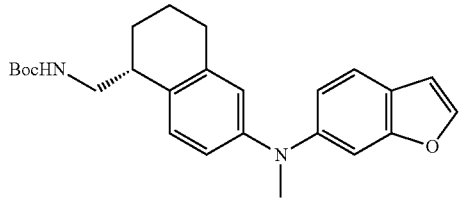 [SMILES: CN(c1ccc2c(c1)CCC[C@H]2CNC(=O)OC(C)(C)C)c1ccc2ccoc2c1]

The title compound was prepared in 61% yield from Preparation 6d and Preparation 135a according to the general procedure outlined for Preparation 6e. [M+H] Calc'd for $C_{25}H_{30}N_2O$, 407. Found, 407.

Preparation 135c

N-[(5R)-5-(aminomethyl)-5,6,7,8-tetrahydronaphthalen-2-yl]-N-methyl-1-benzofuran-6-amine

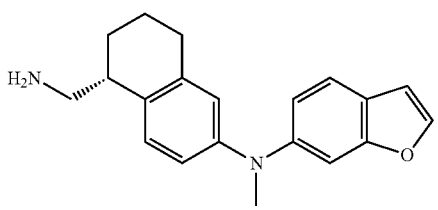 [SMILES: CN(c1ccc2c(c1)CCC[C@H]2CN)c1ccc2ccoc2c1]

The title compound was prepared in 95% yield from Preparation 135b according to the procedure for Preparation 43b. [M+H] Calc'd for $C_{20}H_{22}N_2O$, 307; Found, 307.

Preparation 135d methyl 3-({[(1R)-6-[(1-benzofuran-6-yl)(methyl)amino]-1,2,3,4-tetrahydronaphthalen-1-yl]methyl}amino)pyridine-4-carboxylate

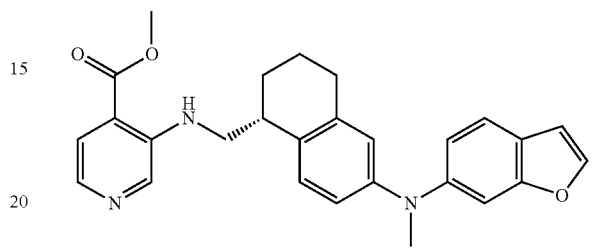

The title compound was prepared in 50% yield from Preparation 135c according to the procedure for Preparation 4d. [M+H] Calc'd for $C_{27}H_{27}N_3O_3$, 442; Found, 442.

Example 135

3-({[(1R)-6-[(1-benzofuran-6-yl)(methyl)amino]-1,2,3,4-tetrahydronaphthalen-1-yl]methyl}amino)pyridine-4-carboxylic acid

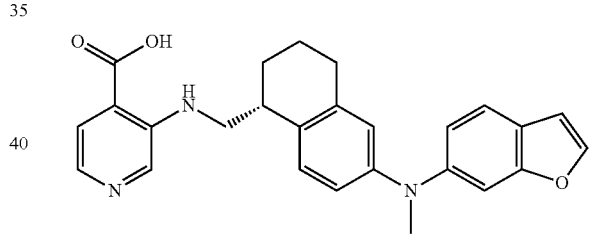

The title compound was prepared in 43% yield from Preparation 135d according to the procedure for Example 1. ¹H NMR (400 MHz, MeOD-d₄): δ 1.73-1.96 (4H, m), 2.69-2.76 (2H, m), 3.11-3.16 (1H, m), 3.28 (3H, s), 3.36-3.60 (2H, m), 6.10 (1H, s), 6.73-6.79 (3H, m), 6.90 (1H, d, J=8.4 Hz), 7.08 (1H, s), 7.16 (1H, d, J=8.2 Hz), 7.42 (1H, d, J=8.4 Hz), 7.62 (1H, s), 7.78-7.83 (2H, m), 8.15 (1H, s). [M+H] Calc'd for $C_{26}H_{26}N_3O_3$, 428; Found, 428.

Preparation 136a

N-methyl-1-benzofuran-5-amine

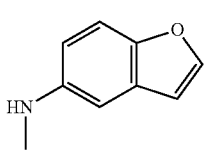

The title compound was prepared in 76% overall yield from 1-benzofuran-5-amine according to the general procedure outlined for Preparation 127a. [M+H] Calc'd for $C_9H_9NO$, 148. Found, 148.

Preparation 136b tert-butyl N-{[(4R)-7-[(1-benzofuran-5-yl)(methyl)amino]-3,4-dihydro-2H-1-benzopyran-4-yl]methyl}carbamate

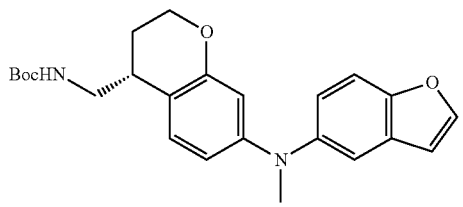 [SMILES: CN(c1ccc2c(c1)OCC[C@H]2CNC(=O)OC(C)(C)C)c1ccc2occc2c1]

The title compound was prepared in 14% yield from Preparation 18d and Preparation 136a according to the general procedure outlined for Preparation 6e. [M+H] Calc'd for $C_{24}H_{28}N_2O_4$, 409; Found, 409.

Preparation 136c (4R)-4-(aminomethyl)-N-(1-benzofuran-5-yl)-N-methyl-3,4-dihydro-2H-1-benzopyran-7-amine

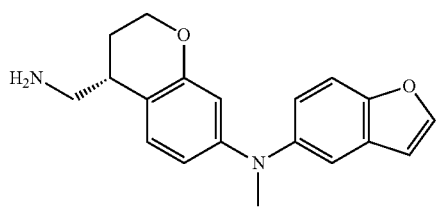 [SMILES: CN(c1ccc2c(c1)OCC[C@H]2CN)c1ccc2occc2c1]

The title compound was prepared in 75% yield from Preparation 136b according to the procedure for Preparation 43b. [M+H] Calc'd for $C_{19}H_{20}N_2O_2$, 309; Found, 309.

Preparation 136d methyl 3-({[(4R)-7-[(1-benzofuran-5-yl)(methyl)amino]-3,4-dihydro-2H-1-benzopyran-4-yl]methyl}amino)pyridine-4-carboxylate

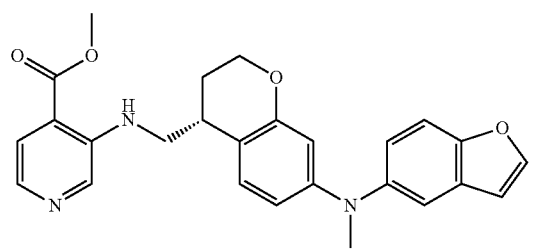 [SMILES: COC(=O)c1ccncc1NC[C@@H]1CCOc2cc(N(C)c3ccc4occc4c3)ccc21]

The title compound was prepared in 53% yield from Preparation 136c according to the procedure for Preparation 4d. [M+H] Calc'd for $C_{26}H_{25}N_3O_4$, 444; Found, 444.

Example 136

3-({[(4R)-7-[(1-benzofuran-5-yl)(methyl)amino]-3,4-dihydro-2H-1-benzopyran-4-yl]methyl}amino)pyridine-4-carboxylic acid

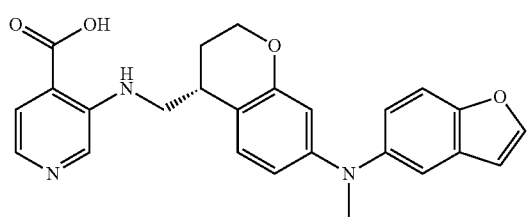 [SMILES: CN(c1ccc2c(c1)OCC[C@H]2CNc1cnccc1C(=O)O)c1ccc2occc2c1]

The title compound was prepared in 50% yield from Preparation 136d according to the procedure for Example 1. $^1$H NMR (400 MHz, MeOD-d$_4$): δ 1.83-1.88 (1H, m), 1.99-2.09 (1H, m), 3.03-3.06 (1H, m), 3.14 (3H, s), 3.41-3.47 (1H, m), 3.55-3.60 (1H, m), 4.02-4.14 (2H, m), 6.10 (1H, s), 6.17 (1H, d, J=5.6 Hz), 6.69 (1H, s), 6.90-6.95 (2H, m), 7.25 (1H, s), 7.34 (1H, d, J=8.4 Hz), 7.63 (1H, s), 7.81 (1H, s), 8.13 (1H, d, J=5.6 Hz), 8.22 (1H, s). [M+H] Calc'd for $C_{25}H_{23}N_3O_4$, 430; Found, 430.

Preparation 137a methyl 3-({[(1R)-6-[(1-benzofuran-5-yl)(methyl)amino]-1,2,3,4-tetrahydronaphthalen-1-yl]methyl}amino)pyridine-4-carboxylate

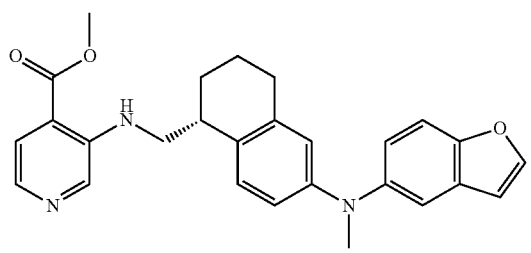 [SMILES: COC(=O)c1ccncc1NC[C@@H]1CCCc2cc(N(C)c3ccc4occc4c3)ccc21]

The title compound was prepared in 15% yield from Preparation 122a and Preparation 136a according to the general procedure outlined for Preparation 126c. [M+H] Calc'd for $C_{27}H_{27}N_3O_3$, 442; Found, 442.

Example 137

3-({[(1R)-6-[(1-benzofuran-5-yl)(methyl)amino]-1,2,3,4-tetrahydronaphthalen-1-yl]methyl}amino)pyridine-4-carboxylic acid

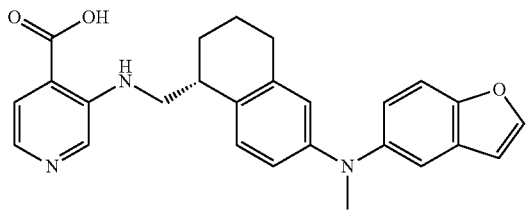 [SMILES: CN(c1ccc2c(c1)CCC[C@H]2CNc1cnccc1C(=O)O)c1ccc2occc2c1]

The title compound was prepared in 23% yield from Preparation 137a according to the procedure for Example 1. $^1$H NMR (400 MHz, DMSO-$d_6$): δ 1.76-1.79 (1H, m), 1.86-2.06 (3H, m), 2.70-2.75 (2H, m), 3.13-3.17 (1H, m), 3.28 (3H, s), 3.51-3.63 (2H, m), 6.60 (2H, s), 6.80 (1H, s), 7.02-7.09 (2H, m), 7.33 (1H, s), 7.44 (1H, d, J=8.4 Hz), 7.90 (1H, s), 7.75 (1H, s), 8.18 (1H, d, J=2.0 Hz), 8.26 (1H, s). [M+H] Calc'd for $C_{26}H_{25}N_3O_3$, 428; Found, 428.

Example 138

3-({[(4R)-7-(2-hydroxyphenyl)-3,4-dihydro-2H-1-benzopyran-4-yl]methyl}amino)pyridine-4-carboxylic acid

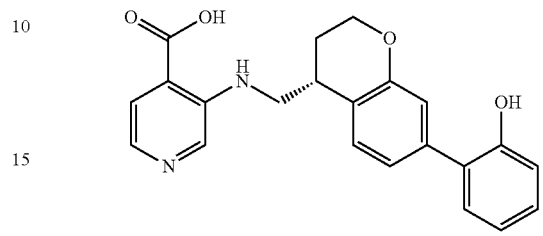

The title compound was prepared in 40% yield from Preparation 138a according to the procedure for Example 1. $^1$H NMR (400 MHz, DMSO-$d_6$): δ 1.92-1.93 (1H, m), 1.98-2.03 (1H, m), 3.14-3.17 (1H, m), 3.50-3.56 (1H, m), 3.71-3.75 (1H, m), 4.17-4.23 (2H, m), 6.82-7.22 (6H, m), 7.31 (1H, d, J=8.0 Hz), 7.57 (1H, d, J=4.8 Hz), 7.85 (1H, d, J=5.2 Hz), 8.44 (1H, s), 9.44 (1H, s). [M+H] Calc'd for $C_{22}H_{20}N_2O_4$, 377; Found, 377.

Preparation 138a methyl 3-({[(4R)-7-(2-hydroxyphenyl)-3,4-dihydro-2H-1-benzopyran-4-yl]methyl}amino)pyridine-4-carboxylate

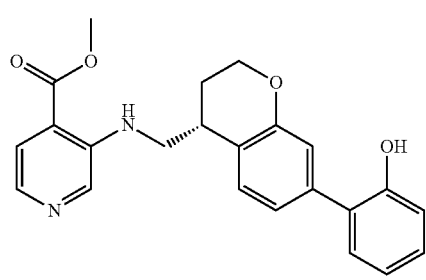 [SMILES: COC(=O)c1ccncc1NC[C@@H]1CCOc2cc(-c3ccccc3O)ccc21]

To a solution of Preparation 126b (180 mg, 0.48 mmol) in DMF (5 mL) was added 2-hydroxyphenylboronic acid (80 mg, 0.57 mmol), $K_2CO_3$ (133 mg, 0.96 mmol) and Pd(PPh$_3$)$_4$ (58 mg, 0.05 mmol). The mixture was stirred for 4 h at 105° C. under nitrogen. The mixture was cooled, diluted with water, and extracted with EtOAc. Organics were washed with brine, dried (Na$_2$SO$_4$), and concentrated to give 147 mg (79%) of the title compound as a yellow solid. [M+H] Calc'd for $C_{23}H_{22}N_2O_4$, 391; Found, 391.

Preparation 139a tert-butyl N-{[(1R)-6-(methylamino)-1,2,3,4-tetrahydronaphthalen-1-yl]methyl}carbamate

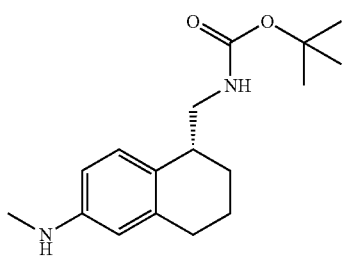 [SMILES: CNc1ccc2c(c1)CCC[C@H]2CNC(=O)OC(C)(C)C]

Preparation 6d (300 mg, 0.88 mmol), CuI (201 mg, 1.06 mmol), KOAc (216 mg, 2.2 mmol), and CuOAc (176 mg, 0.88 mmol) were combined in DMF (3 mL) in a microwave tube. Methylamine (0.7 mL, 40% in water, 8.8 mmol) was added, and the reaction stirred at 100° C. in the microwave for 2 h. The reaction was diluted with EtOAc, washed with water and brine, dried (MgSO$_4$), and concentrated. The residue was purified by silica gel chromatography (20% to 80% EtOAc/hexanes) to give 186 mg (73%) of the title compound as a yellow oil. [M+H] Calc'd for $C_{17}H_{26}N_2O_2$, 291; Found, 291.

Preparation 139b tert-butyl N-{[(1R)-6-[methyl(2-methyl-1,3-thiazol-4-yl)amino]-1,2,3,4-tetrahydronaphthalen-1-yl]methyl}carbamate

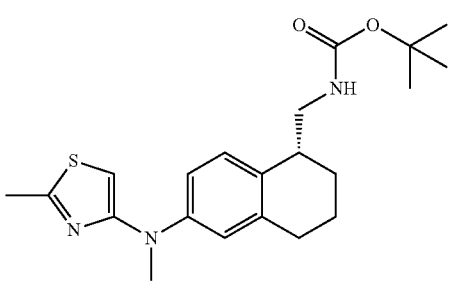 [SMILES: Cc1nc(N(C)c2ccc3c(c2)CCC[C@H]3CNC(=O)OC(C)(C)C)cs1]

To a suspension of Preparation 139a (200 mg, 0.69 mmol), 4-bromo-2-methyl-1,3-thiazole (184 mg, 1.03 mmol), Xantphos (60 mg, 0.10 mmol) and Cs$_2$CO$_3$ (315 mg, 0.97 mmol) in toluene (20 mL) was added Pd$_2$dba$_3$ (32 mg, 0.04 mmol) at r.t. under N$_2$. The reaction was stirred at reflux overnight. The reaction was cooled, filtered, and concentrated. The residue was purified by silica gel chromatography (PE:EtOAc=3:1) to give 60 mg (23%) of the title compound as a yellow oil. [M+H] Calc'd for C$_{21}$H$_{29}$N$_3$O$_2$S, 388; Found, 388.

Preparation 139c

N-[(5R)-5-(aminomethyl)-5,6,7,8-tetrahydronaphthalen-2-yl]-N,2-dimethyl-1,3-thiazol-4-amine

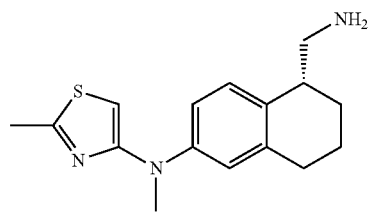 [SMILES: Cc1nc(N(C)c2ccc3c(c2)CCC[C@H]3CN)cs1]

The title compound was prepared in quantitative yield from Preparation 136b according to the procedure for Preparation 43b. [M+H] Calc'd for C$_{16}$H$_{21}$N$_3$S, 288; Found, 288.

Preparation 139d methyl 3-({[(1R)-6-[methyl(2-methyl-1,3-thiazol-4-yl)amino]-1,2,3,4-tetrahydronaphthalen-1-yl]methyl}amino)pyridine-4-carboxylate

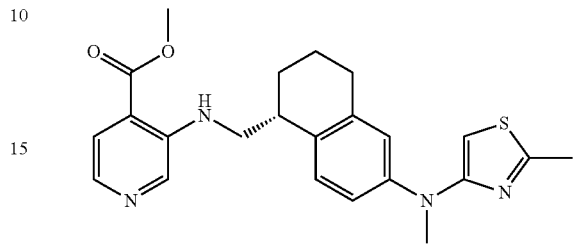

The title compound was prepared in 23% yield from Preparation 139c according to the procedure for Preparation 4d. [M+H] Calc'd for C$_{23}$H$_{26}$N$_4$O$_2$S, 423; Found, 423.

Example 139

3-({[(1R)-6-[methyl(2-methyl-1,3-thiazol-4-yl)amino]-1,2,3,4-tetrahydronaphthalen-1-yl]methyl}amino)pyridine-4-carboxylic acid

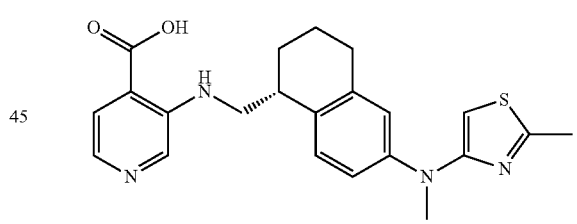

The title compound was prepared in 63% yield from Preparation 139d according to the procedure for Example 1. $^1$H NMR (400 MHz, DMSO-d$_6$): δ 1.65-1.69 (1H, m), 1.81-1.85 (3H, m), 2.57 (3H, s), 2.67-2.70 (2H, m), 3.05-3.07 (1H, m), 3.25 (3H, s), 3.42-3.45 (1H, m), 3.55-3.60 (1H, m), 6.32 (1H, s), 6.84 (1H, d, J=2.8 Hz), 6.90 (1H, dd, J=2.4, 8.4 Hz), 7.21 (1H, d, J=8.4 Hz), 7.56 (1H, d, J=4.4 Hz), 7.83 (1H, d, J=5.2 Hz), 8.36 (1H, s). [M+H] Calc'd for C$_{22}$H$_{24}$N$_4$O$_2$S, 409; Found, 409.

Preparation 140a tert-butyl N-{[(1R)-6-[methyl(4-methylphenyl)amino]-1,2,3,4-tetrahydronaphthalen-1-yl]methyl}carbamate

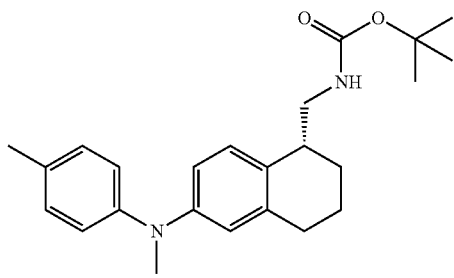 [SMILES: Cc1ccc(N(C)c2ccc3c(c2)CCC[C@H]3CNC(=O)OC(C)(C)C)cc1]

The title compound was prepared in 38% yield from Preparation 6d and N,4-dimethylaniline according to the general procedure outlined for Preparation 9a. [M+H] Calc'd for $C_{26}H_{32}N_2O_2$, 381; Found, 381.

Preparation 140b (5R)-5-(aminomethyl)-N-methyl-N-(4-methylphenyl)-5,6,7,8-tetrahydronaphthalen-2-amine

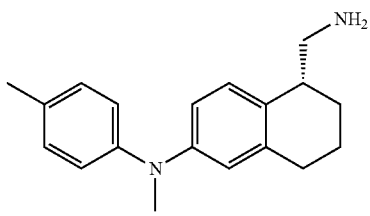 [SMILES: Cc1ccc(N(C)c2ccc3c(c2)CCC[C@H]3CN)cc1]

The title compound was prepared in quantitative yield from Preparation 140a according to the procedure for Preparation 43b. [M+H] Calc'd for $C_{19}H_{24}N_2$, 281; Found, 281.

Preparation 140c methyl 3-({[(1R)-6-[methyl(4-methylphenyl)amino]-1,2,3,4-tetrahydronaphthalen-1-yl]methyl}amino)pyridine-4-carboxylate

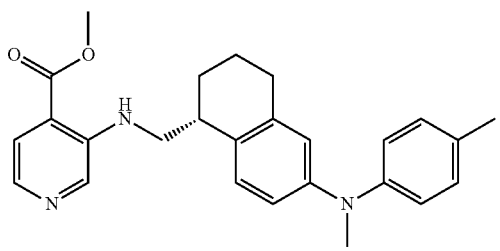 [SMILES: COC(=O)c1ccncc1NC[C@@H]1CCCc2cc(N(C)c3ccc(C)cc3)ccc21]

The title compound was prepared in 76% yield from Preparation 140b according to the procedure for Preparation 4d. [M+H] Calc'd for $C_{26}H_{29}N_3O_2$, 416; Found, 416.

Example 140

3-({[(1R)-6-[methyl(4-methylphenyl)amino]-1,2,3,4-tetrahydronaphthalen-1-yl]methyl}amino)pyridine-4-carboxylic acid

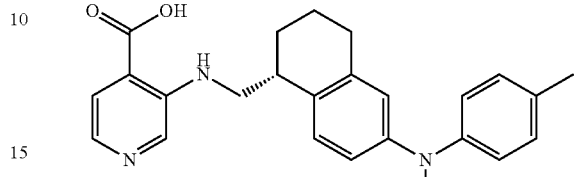

The title compound was prepared in 98% yield from Preparation 140c according to the procedure for Example 1. $^1$H NMR (300 MHz, DMSO-$d_6$): δ 1.63-1.81 (4H, m), 2.24 (3H, s), 2.64-2.65 (2H, m), 2.99-3.05 (1H, m), 3.18 (3H, s), 3.38-3.42 (1H, m), 3.53-3.59 (1H, m), 6.66-6.71 (2H, m), 6.88-6.90 (2H, m), 7.09 (2H, d, J=2.4 Hz), 7.17 (1H, d, J=8.1 Hz), 7.55 (1H, d, J=5.1 Hz), 7.82 (1H, d, J=5.1 Hz), 8.34 (1H, s). [M+H] Calc'd for $C_{25}H_{27}N_3O_2$, 402; Found, 402.

Preparation 141a methyl 3-({[(4R)-7-[(1-benzofuran-6-yl)(methyl)amino]-3,4-dihydro-2H-1-benzopyran-4-yl]methyl}amino)pyridine-4-carboxylate

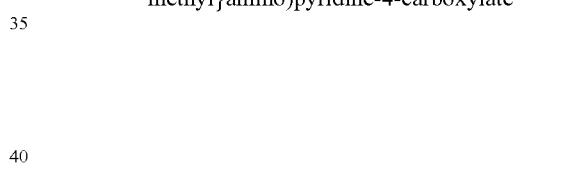

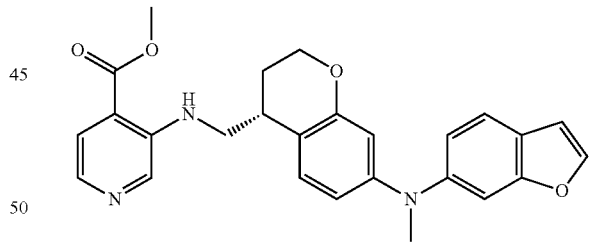

To a solution of Preparation 135a (250 mg, 1.71 mmol) in toluene (10 mL) was added Preparation 126b (536 mg, 1.42 mmol), $Cs_2CO_3$ (926 mg, 2.84 mmol), BINAP (44 mg, 0.07 mmol) and $Pd(OAc)_2$ (16 mg, 0.07 mmol). The mixture was stirred overnight at 120° C. under nitrogen. The mixture was filtered and concentrated. The residue was purified by silica gel chromatography to give 160 mg (25%) of the title compound as a white solid. [M+H] Calc'd for $C_{26}H_{25}N_3O_4$, 444; Found, 444.

Example 141

3-({[(4R)-7-[(1-benzofuran-6-yl)(methyl)amino]-3,4-dihydro-2H-1-benzopyran-4-yl]methyl}amino)pyridine-4-carboxylic acid

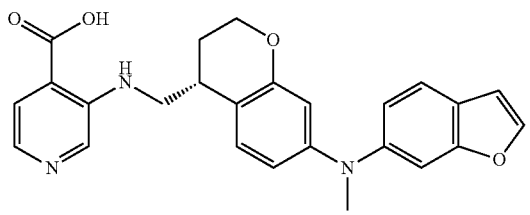 [SMILES: CN(c1ccc2c(c1)OCC[C@H]2CNc1cnccc1C(=O)O)c1ccc2ccoc2c1]

The title compound was prepared in 40% yield from Preparation 141a according to the procedure for Example 1. $^1$H NMR (400 MHz, DMSO-d$_6$): δ 1.83-1.87 (1H, m), 1.96-2.00 (1H, m), 3.05-3.08 (1H, m), 3.24 (3H, s), 3.46-3.51 (1H, m), 3.64-3.69 (1H, m), 4.10-4.20 (2H, m), 6.33 (1H, s), 6.45 (1H, d, J=6.0 Hz), 6.88 (1H, s), 6.94 (1H, d, J=6.8 Hz), 7.15 (1H, d, J=8.4 Hz), 7.25 (1H, s), 7.51 (1H, d, J=8.8 Hz), 7.62 (1H, d, J=4.8 Hz), 7.86-7.89 (2H, m), 8.41 (1H, s). [M+H] Calc'd for C$_{25}$H$_{23}$N$_3$O$_4$, 430; Found, 430.

Preparation 142a methyl 3-[(3,4-dihydro-1H-2-benzopyran-1-ylmethyl)amino]pyridine-4-carboxylate

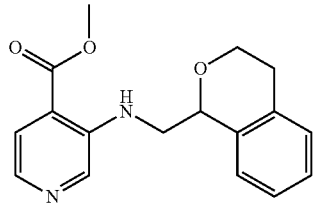 [SMILES: COC(=O)c1ccncc1NCC1OCCc2ccccc21]

The title compound was prepared in 70% yield from 3,4-dihydro-1H-2-benzopyran-1-ylmethanamine according to the procedure for Preparation 4d. $^1$H NMR (400 MHz, CDCl$_3$): δ 2.72-2.78 (1H, m), 3.00-3.09 (1H, m), 3.53-3.60 (1H, m), 3.78-3.87 (5H, m), 4.18-4.24 (1H, m), 5.07 (1H, d, J=6.4 Hz), 7.15-7.22 (4H, m), 7.60 (1H, d, J=5.0 Hz), 7.72 (1H, br s), 7.91 (1H, d, J=5.0 Hz), 8.31 (1H, s). [M+H] Calc'd for C$_{17}$H$_{18}$N$_2$O$_3$, 299; Found, 299.

Example 142

3-[(3,4-dihydro-1H-2-benzopyran-1-ylmethyl)amino]pyridine-4-carboxylic acid

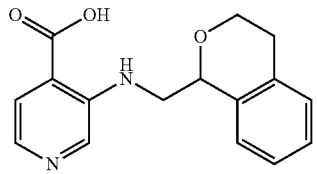 [SMILES: O=C(O)c1ccncc1NCC1OCCc2ccccc21]

The title compound was prepared in 53% yield from Preparation 142a according to the procedure for Example 1. $^1$H NMR (400 MHz, DMSO-d$_6$): δ 2.69-2.74 (1H, m), 2.86-2.94 (1H, m), 3.54-3.60 (1H, m), 3.71-3.85 (2H, m), 4.08-4.12 (1H, m), 4.98 (1H, d, J=5.8 Hz), 7.16-7.21 (3H, m), 7.34 (1H, d, J=4.2 Hz), 7.52 (1H, d, J=4.8 Hz), 7.81 (1H, d, J=4.8 Hz), 7.90 (1H, br s), 8.34 (1H, s), 12.52 (1H, br s). [M+H] Calc'd for C$_{16}$H$_{16}$N$_2$O$_3$, 285; Found, 285.

Example 143

3-({[(1R)-6-[methyl(3-methylphenyl)amino]-1,2,3,4-tetrahydronaphthalen-1-yl]methyl}amino)pyridine-4-carboxylic acid

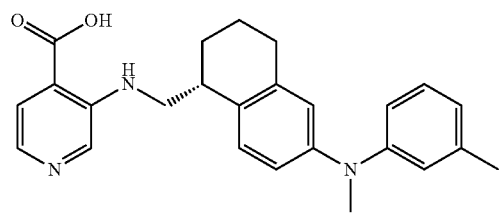 [SMILES: Cc1cccc(N(C)c2ccc3c(c2)CCC[C@H]3CNc2cnccc2C(=O)O)c1]

To a solution of Preparation 122a (374 mg, 1.0 mmol) in toluene (10 mL) was added N,3-dimethylaniline (242 mg, 2.0 mmol), t-BuONa (192 mg, 2.0 mmol), JohnPhos (45 mg, 0.15 mmol) and Pd$_2$(dba)$_3$ (92 mg, 0.1 mmol). The mixture was refluxed for 3 h under N$_2$. The reaction was cooled, filtered and concentrated. The residue was purified by prep-HPLC to give 21 mg (5%) of the title compound as a yellow solid. (Ester hydrolysis occurred during the course of the reaction.) $^1$H NMR (300 MHz, MeOD-d$_4$): δ 1.76-1.80 (1H, m), 1.83-2.02 (3H, m), 2.26 (3H, s), 2.71-2.75 (2H, m), 3.15-3.19 (1H, m), 3.22 (3H, s), 3.56-3.60 (2H, m), 6.73-6.78 (5H, m), 7.08-7.16 (2H, m), 7.89-7.91 (1H, m), 8.21 (1H, d, J=5.4 Hz), 8.29 (1H, s). [M+H] Calc'd for C$_{25}$H$_{27}$N$_3$O$_2$, 402; Found, 402.

Preparation 144a tert-butyl N-{[(1R)-6-[methyl(thiophen-2-yl)amino]-1,2,3,4-tetrahydronaphthalen-1-yl]methyl}carbamate

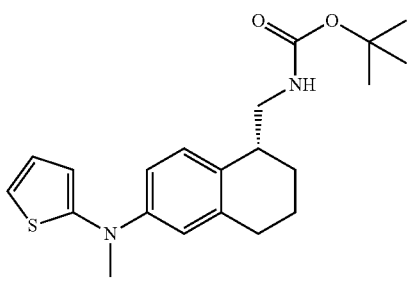 [SMILES: CN(c1ccc2c(c1)CCC[C@H]2CNC(=O)OC(C)(C)C)c1cccs1]

To a suspension of Preparation 139a (50 mg, 0.17 mmol), 2-bromo-thiophene (56 mg, 0.34 mmol), JohnPhos (8 mg, 0.03 mmol) and t-BuONa (33 mg, 0.34 mmol) in toluene (10 mL) was added Pd$_2$dba$_3$ (16 mg, 0.02 mmol) at r.t. under N$_2$. The reaction was stirred at reflux overnight. The reaction was cooled, filtered, and concentrated. The residue was purified by silica gel chromatography (PE:EtOAc=8:1) to give 40 mg (63%) of the title compound as a yellow oil. [M+H] Calc'd for $C_{21}H_{28}N_2O_2S$, 373; Found, 373.

Preparation 144b

N-[(5R)-5-(aminomethyl)-5,6,7,8-tetrahydronaphthalen-2-yl]-N-methylthiophen-2-amine

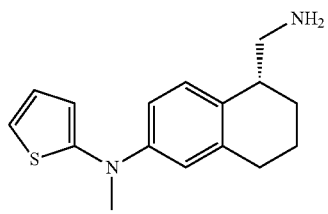 [SMILES: CN(c1ccc2c(c1)CCC[C@H]2CN)c1cccs1]

The title compound was prepared in quantitative yield from Preparation 144a according to the procedure for Preparation 43b. [M+H] Calc'd for $C_{16}H_{20}N_2S$, 273; Found, 273.

Preparation 144c methyl 3-({[(1R)-6-[methyl(thiophen-2-yl)amino]-1,2,3,4-tetrahydronaphthalen-1-yl]methyl}amino)pyridine-4-carboxylate

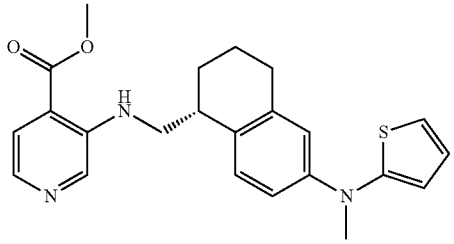 [SMILES: COC(=O)c1ccncc1NC[C@@H]1CCCc2cc(N(C)c3cccs3)ccc21]

The title compound was prepared in 22% yield from Preparation 144b according to the procedure for Preparation 4d. [M+H] Calc'd for $C_{23}H_{25}N_3O_2S$, 408; Found, 408.

Example 144

3-({[(1R)-6-[methyl(thiophen-2-yl)amino]-1,2,3,4-tetrahydronaphthalen-1-yl]methyl}amino)pyridine-4-carboxylic acid

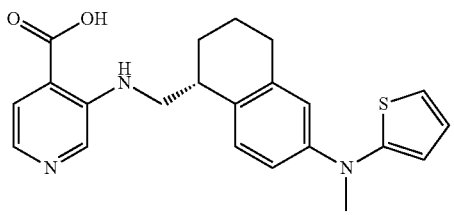 [SMILES: CN(c1ccc2c(c1)CCC[C@H]2CNc1cnccc1C(=O)O)c1cccs1]

The title compound was prepared in 53% yield from Preparation 144c according to the procedure for Example 1. $^1$H NMR (300 MHz, DMSO-d$_6$): δ 1.59-1.64 (1H, m), 1.76-1.84 (3H, m), 2.65-2.69 (2H, m), 2.98-3.05 (1H, m), 3.23 (3H, s), 3.41-3.43 (1H, m), 3.51-3.57 (1H, m), 6.59 (1H, d, J=2.7 Hz), 6.75-6.78 (2H, m), 6.88 (1H, dd, J=3.9, 5.1 Hz), 7.03 (1H, dd, J=0.6, 5.1 Hz), 7.19 (1H, d, J=8.1 Hz), 7.55 (1H, d, J=4.2 Hz), 7.83 (1H, d, J=4.5 Hz), 8.34 (1H, s). [M+H] Calc'd for $C_{22}H_{23}N_3O_2S$, 394; Found, 394.

Preparation 145a tert-butyl N-{[(4R)-7-[methyl(5-methylpyridin-2-yl)amino]-3,4-dihydro-2H-1-benzopyran-4-yl]methyl}carbamate

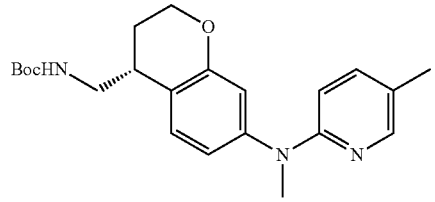 [SMILES: Cc1ccc(N(C)c2ccc3c(c2)OCC[C@H]3CNC(=O)OC(C)(C)C)nc1]

The title compound was prepared in 9% yield from Preparation 18d and N,5-dimethylpyridin-2-amine according to the general procedure outlined for Preparation 6e. [M+H] Calc'd for $C_{22}H_{29}N_3O_3$, 384; Found, 384.

Preparation 145b

N-[(4R)-4-(aminomethyl)-3,4-dihydro-2H-1-benzopyran-7-yl]-N,5-dimethylpyridin-2-amine

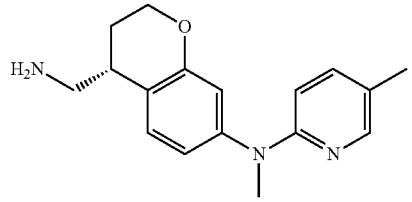 [SMILES: Cc1ccc(N(C)c2ccc3c(c2)OCC[C@H]3CN)nc1]

The title compound was prepared in quantitative yield from Preparation 145a according to the procedure for Preparation 43b. [M+H] Calc'd for $C_{17}H_{21}N_3O$, 284; Found, 284.

Preparation 145c methyl 3-({[(4R)-7-[methyl(5-methylpyridin-2-yl)amino]-3,4-dihydro-2H-1-benzopyran-4-yl]methyl}amino)pyridine-4-carboxylate

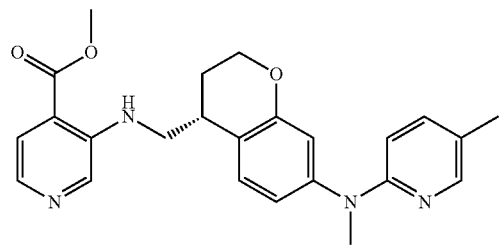 [SMILES: COC(=O)c1ccncc1NC[C@@H]1CCOc2cc(N(C)c3ccc(C)cn3)ccc21]

The title compound was prepared in 78% yield from Preparation 145b according to the procedure for Preparation 4d. [M+H] Calc'd for $C_{24}H_{26}N_4O_3$, 419; Found, 419.

Example 145

3-({[(4R)-7-[methyl(5-methylp yridin-2-yl)amino]-3,4-dihydro-2H-1-benzopyran-4-yl]methyl}amino) pyridine-4-carboxylic acid

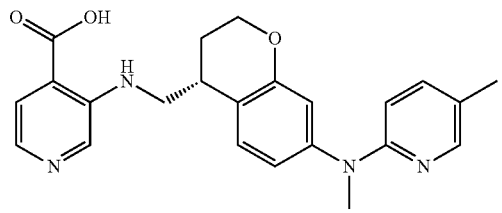 [SMILES: Cc1ccc(N(C)c2ccc3c(c2)OCC[C@H]3CNc2cnccc2C(=O)O)nc1]

The title compound was prepared in 65% yield from Preparation 145c according to the procedure for Example 1. $^1$H NMR (300 MHz, DMSO-d$_6$): δ 1.88-1.91 (1H, m), 1.96-2.03 (1H, m), 2.14 (3H, s), 3.10-3.14 (1H, m), 3.25 (3H, s), 3.43-3.55 (1H, m), 3.68-3.74 (1H, m), 4.13-4.21 (2H, m), 6.52 (1H, d, J=8.4 Hz), 6.63 (1H, s), 6.72 (1H, d, J=8.1 Hz), 7.26-7.32 (2H, m), 7.56 (1H, d, J=5.1 Hz), 7.84 (1H, d, J=6.9 Hz), 7.98 (1H, s), 8.41 (1H, s). [M+H] Calc'd for $C_{23}H_{24}N_4O_3$, 405; Found, 405.

Preparation 146a

2-{3-[methyl(phenyl)amino]phenyl}ethan-1-ol

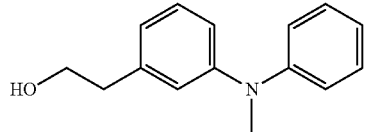 [SMILES: CN(c1ccccc1)c1cccc(CCO)c1]

1-Bromo-3-[2-(tert-butyldimethylsilyloxy)ethyl]benzene (2.5 g, 7.96 mmol), N-methylaniline (1.02 g, 9.55 mmol), Pd$_2$dba$_3$ (364 mg, 0.4 mmol), Xantphos (691 mg, 1.19 mmol) and NaOtBu (727 mg, 9.55 mmol) were combined in toluene (12 mL), and the reaction was heated at 100° C. in the microwave for 90 min. The reaction was diluted with EtOAc, washed with brine, dried (MgSO$_4$), and concentrated. The residue was stirred in 70% TFA/DCM (10 mL) for 2 h. The solution was concentrated and purified by silica gel chromatography (30% to 100% EtOAc/hexanes) to give 1.3 g (72%) of the title compound as a clear oil. $^1$H NMR (400 MHz, CDCl$_3$): δ 1.53 (1H, br s), 2.81 (2H, t, J=6.5 Hz), 3.31 (3H, s), 3.83 (2H, t, J=6.5 Hz), 6.81 (1H, d, J=7.4 Hz), 6.86-6.89 (2H, m), 6.97 (1H, t, J=7.3 Hz), 7.04 (d, 2H, J=7.8 Hz), 7.18-7.29 (3H, m). [M+H] Calc'd for $C_{15}H_{17}NO$, 228; Found, 228.

Preparation 146b 1-(aminomethyl)-N-methyl-N-phenyl-3,4-dihydro-1H-2-benzopyran-6-amine

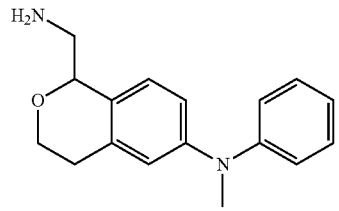 [SMILES: CN(c1ccccc1)c1ccc2c(c1)CCOC2CN]

2-{3-[Methyl(phenyl)amino]phenyl}ethan-1-ol (1.0 g, 4.4 mmol) was stirred in 4N HCl/dioxane (8 mL) at 0° C. Aminoacetaldehyde diethyl acetal (880 mg, 6.6 mmol) was added, and the reaction stirred for at r.t. for 1 h and then at 108° C. in the microwave for 1 h. The solution was concentrated and purified by silica gel chromatography (0% to 20% MeOH/DCM) to give 150 mg (13%) of the title compound as a yellow oil. [M+H] Calc'd for $C_{17}H_{20}N_2O$, 269; Found, 269.

Example 146

3-[({6-[methyl(phenyl)amino]-3,4-dihydro-1H-2-benzopyran-1-yl}methyl)amino]pyridine-4-carboxylic acid

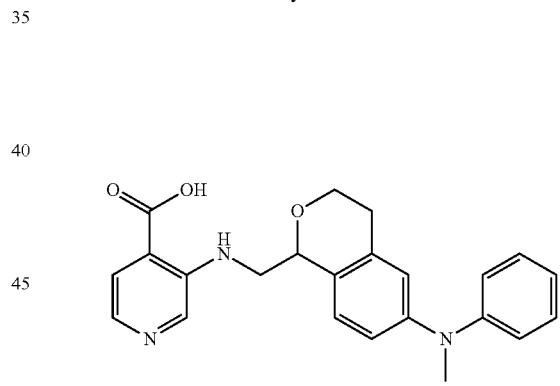

3-Flouroisonicotinic acid (79 mg, 0.56 mmol), Preparation 146b (150 mg, 0.56 mmol), and DIEA (0.098 mL, 0.56 mmol) were combined in DMA (4 mL) and heated at 168° C. in the microwave for 1 h. The solution was concentrated, and the residue was purified by prep-HPLC to give 18 mg (8%) of the title compound as a tan solid. $^1$H NMR (400 MHz, DMSO-d$_6$): δ 2.60-2.83 (1H, m), 2.79-2.86 (1H, m), 3.23 (3H, s), 3.53-3.59 (1H, m), 3.70-3.82 (2H, m), 4.04-4.10 (1H, m), 4.90-4.96 (1H, m), 6.78-6.98 (5H, m), 7.22-7.28 (3H, m), 7.53 (1H, d, J=4.8 Hz), 7.74 (1H, br s), 7.81 (1H, d, J=4.8 Hz), 8.36 (1H, s), 13.25 (1H, br s). [M+H] Calc'd for $C_{23}H_{23}N_3O_3$, 390; Found, 390.

Preparation 147a

N-{2-[(tert-butyldimethylsilyl)oxy]ethyl}aniline

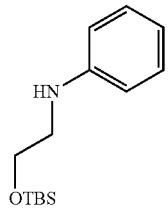

To a solution of 2-(phenylamino)ethan-1-ol (2.0 g, 14.6 mmol) and imidazole (2.9 g, 43.7 mmol) in DCM (20 mL) was added TBSCl (2.6 g, 16.0 mmol) at r.t., and the reaction was stirred for 2 h. The reaction was diluted with water (50 mL) and extracted with DCM (50 mL×3). Organics were washed with brine (50 mL), dried (Na$_2$SO$_4$), and concentrated. Purification by silica gel chromatography (PE:EtOAc=40:1) gave 3.0 g (82%) of the title compound as a yellow oil.

Preparation 147b methyl 3-({[(1R)-6-({2-[(tert-butyldimethylsilyl)oxy]ethyl}(phenyl)amino)-1,2,3,4-tetrahydronaphthalen-1-yl]methyl}amino)pyridine-4-carboxylate

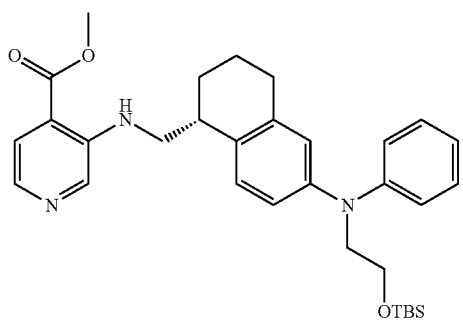 [SMILES: COC(=O)c1ccncc1NC[C@@H]1CCCc2cc(N(CCO[Si](C)(C)C(C)(C)C)c3ccccc3)ccc21]

The title compound was prepared in 28% yield from Preparation 122a and N-{2-[(tert-butyldimethylsilyl)oxy]ethyl}aniline according to the general procedure outlined for Preparation 126c. [M+H] Calc'd for C$_{32}$H$_{43}$N$_3$O$_3$Si, 546; Found, 546.

Example 147

3-({[(1R)-6-[(2-hydroxyethyl)(phenyl)amino]-1,2,3,4-tetrahydronaphthalen-1-yl]methyl}amino)pyridine-4-carboxylic acid

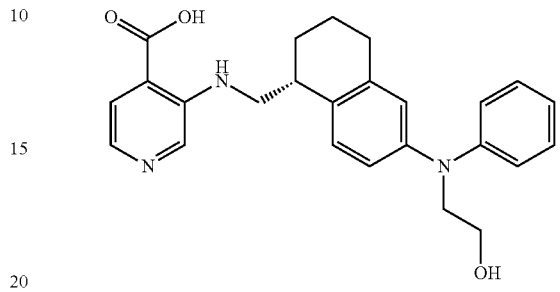

To a solution of Preparation 147b (80 mg, 0.15 mmol) in THF (5 mL) was added TBAF (0.29 mL, 1.0 M in THF, 0.29 mmol) at r.t., and the reaction was stirred for 1 h. To the reaction mixture was added H$_2$O (5 mL) and LiOH H$_2$O (13 mg, 0.30 mmol). The reaction was stirred at r.t. for 2 h. The solution was concentrated to remove THF, and the residue was acidified to pH=5 with 1.0 N aqueous HCl solution. The solid was collected by filtration and then purified by prep-HPLC to give compound 30 mg (48%) of the title compound as a yellow solid. $^1$H NMR (300 MHz, DMSO-d$_6$): δ 1.65-1.68 (1H, m), 1.74-1.84 (3H, m), 2.62-2.67 (2H, m), 3.04-3.07 (1H, m), 3.41-3.46 (1H, m), 3.54-3.60 (3H, m), 3.72 (2H, d, J=4.8 Hz), 4.73 (1H, br s), 6.80-6.93 (3H, m), 6.92 (2H, d, J=5.7 Hz), 7.19-7.24 (3H, m), 7.55 (1H, d, J=3.9 Hz), 7.83 (1H, d, J=3.6 Hz), 8.36 (1H, s). [M+H] Calc'd for C$_{25}$H$_{27}$N$_3$O$_3$, 418. Found, 418.

Preparation 148a tert-butyl N-{[(4R)-7-[methyl(6-methylpyridin-2-yl)amino]-3,4-dihydro-2H-1-benzopyran-4-yl]methyl}carbamate

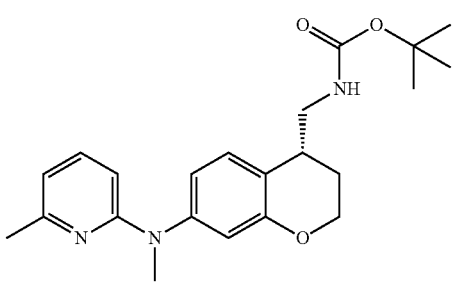 [SMILES: Cc1cccc(N(C)c2ccc3c(c2)OCC[C@H]3CNC(=O)OC(C)(C)C)n1]

The title compound was prepared in 27% yield from Preparation 18d and N,6-dimethylpyridin-2-amine according to the general procedure outlined for Preparation 6e. [M+H] Calc'd for C$_{22}$H$_{29}$N$_3$O$_3$, 384; Found, 384.

Preparation 148b

N-[(4R)-4-(aminomethyl)-3,4-dihydro-2H-1-benzopyran-7-yl]-N,6-dimethylpyridin-2-amine

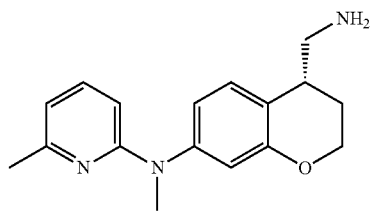 [SMILES: Cc1cccc(N(C)c2ccc3c(c2)OCC[C@H]3CN)n1]

The title compound was prepared in quantitative yield from Preparation 148a according to the procedure for Preparation 43b. [M+H] Calc'd for $C_{17}H_{21}N_3O$, 284; Found, 284.

Preparation 148c methyl 3-({[(4R)-7-[methyl(6-methylpyridin-2-yl)amino]-3,4-dihydro-2H-1-benzopyran-4-yl]methyl}amino)pyridine-4-carboxylate

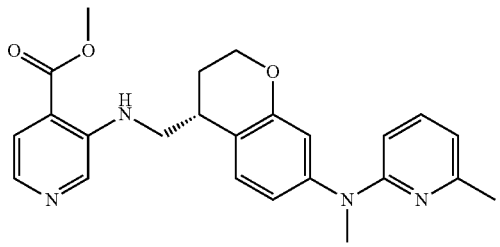

The title compound was prepared in 77% yield from Preparation 148b according to the procedure for Preparation 4d. [M+H] Calc'd for $C_{24}H_{26}N_4O_3$, 419; Found, 419.

Example 148

3-({[(4R)-7-[methyl(6-methylpyridin-2-yl)amino]-3,4-dihydro-2H-1-benzopyran-4-yl]methyl}amino)pyridine-4-carboxylic acid

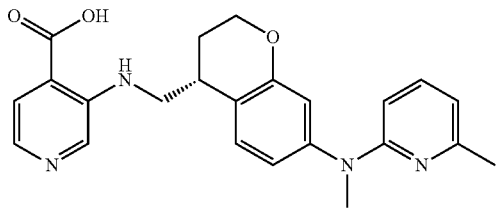 [SMILES: Cc1cccc(N(C)c2ccc3c(c2)OCC[C@H]3CNc2cnccc2C(=O)O)n1]

The title compound was prepared in 78% yield from Preparation 148c according to the procedure for Example 1. $^1$H NMR (300 MHz, DMSO-d$_6$): δ 1.88-2.01 (2H, m), 2.32 (3H, s), 3.09-3.16 (1H, m), 3.32 (3H, s), 3.46-3.54 (1H, m), 3.67-3.73 (1H, m), 4.13-4.21 (1H, m), 6.31 (1H, d, J=8.4 Hz), 6.50 (1H, d, J=7.2 Hz), 6.64 (1H, d, J=2.4 Hz), 6.72-6.75 (1H, m), 7.25-7.33 (2H, m), 7.55 (1H, d, J=5.1 Hz), 7.83 (1H, d, J=4.8 Hz), 8.39 (1H, s). [M+H] Calc'd for $C_{23}H_{24}N_4O_3$, 405; Found, 405.

Preparation 149a tert-butyl 1-(aminomethyl)-1,2,3,4-tetrahydroisoquinoline-2-carboxylate

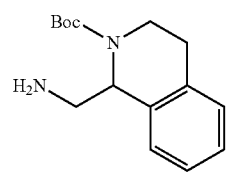 [SMILES: CC(C)(C)OC(=O)N1CCc2ccccc2C1CN]

Methanesulfonyl chloride (0.324 mL, 4.18 mmol) was added to a solution of tert-butyl 1-(hydroxymethyl)-1,2,3,4-tetrahydroisoquinoline-2-carboxylate (1.0 g, 3.8 mmol) and DIEA (0.812 mL, 4.56 mmol) in DCM (20 mL) at r.t., and the solution was stirred overnight. The solution was washed with brine, dried (MgSO$_4$), and concentrated to give the crude mesylate intermediate. This mesylate intermediate was stirred in DMF (8 mL) with sodium azide (1.5 g, 22.8 mmol) at 52° C. overnight. The reaction was diluted with EtOAc (30 mL), filtered, and concentrated. The residue was dissolved in MeOH (30 mL) and hydrogenated under a balloon of H$_2$ in the presence of 10% Pd/C overnight. The reaction was filtered through Celite and concentrated. Purification by silica gel chromatography (0% to 20% MeOH/DCM) gave 250 mg (25%) of the title compound as a clear oil. [M+H] Calc'd for $C_{15}H_{22}N_2O_2$, 263; Found, 263.

Example 149

3-[(1,2,3,4-tetrahydroisoquinolin-1-ylmethyl)amino]pyridine-4-carboxylic acid

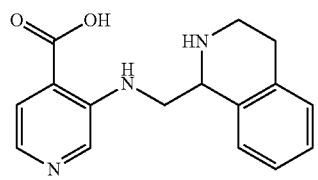

3-Flouroisonicotinic acid (135 mg, 0.95 mmol), Preparation 149a (250 mg, 0.95 mmol), and DIEA (0.17 mL, 0.95 mmol) were combined in DMA (4 mL) and heated at 168° C. in the microwave for 1 h. The solution was concentrated, and then the residue stirred in 50% TFA/DCM (4 mL) for 1 h. The solution was concentrated, and the residue was purified by prep-HPLC to give 28 mg (7%) of the title compound as a pale yellow solid. $^1$H NMR (400 MHz, DMSO-d$_6$): δ 3.00-3.05 (2H, m), 3.28-3.33 (1H, m), 3.54-3.60 (1H, m), 3.80-3.86 (1H, m), 4.05-4.09 (1H, m), 4.87 (1H, br s), 7.26-7.35 (3H, m), 7.50 (1H, d, J=6.2 Hz), 7.71 (1H, d, J=5.0 Hz), 7.80-7.85 (1H, m), 7.99 (1H, d, J=4.8 Hz), 8.55 (1H, s), 8.90 (1H, br s), 9.40 (1H, br s). [M+H] Calc'd for $C_{16}H_{17}N_3O_2$, 284; Found, 284.

Preparation 150a methyl 3-({[(1R)-6-[(3-methoxyphenyl)(methyl)amino]-1,2,3,4-tetrahydronaphthalen-1-yl]methyl}amino)pyridine-4-carboxylate

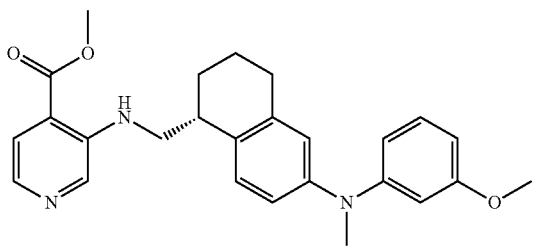 [SMILES: COC(=O)c1ccncc1NC[C@@H]1CCCc2cc(N(C)c3cccc(OC)c3)ccc21]

The title compound was prepared in 43% yield from Preparation 122a and 3-fluoro-N,4-dimethylaniline according to the general procedure outlined for Preparation 126c. [M+H] Calc'd for $C_{26}H_{29}N_3O_3$, 432; Found, 432.

Example 150

3-({[(1R)-6-[(3-methoxyphenyl)(methyl)amino]-1,2,3,4-tetrahydronaphthalen-1-yl]methyl}amino)pyridine-4-carboxylic acid

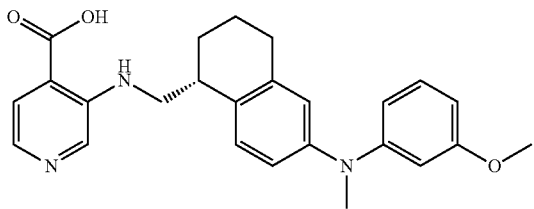 [SMILES: COc1cccc(N(C)c2ccc3c(c2)CCC[C@H]3CNc2cnccc2C(=O)O)c1]

The title compound was prepared in 92% yield from Preparation 150a according to the procedure for Example 1. $^1$H NMR (300 MHz, DMSO-d$_6$): δ 1.64-1.67 (1H, m), 1.76-1.83 (3H, m), 2.65-2.67 (2H, m), 3.01-3.06 (1H, m), 3.19 (3H, s), 3.41-3.44 (1H, m), 3.53-3.59 (1H, m), 3.67 (3H, s), 6.40-6.45 (3H, m), 6.80-6.84 (2H, m), 7.09 (1H, t, J=8.1 Hz), 7.24 (1H, d, J=8.4 Hz), 7.54 (1H, d, J=4.5 Hz), 7.80 (1H, d, J=3.9 Hz), 8.32 (1H, s). [M+H] Calc'd for $C_{25}H_{27}N_3O_3$, 418; Found, 418.

Preparation 151a 3-fluoro-N,4-dimethylaniline

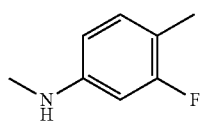

To a suspension of 4-bromo-2-fluoro-1-methylbenzene (1.0 g, 5.3 mmol), KOAc (1.3 g, 13.2 mmol), and CuI (1.2 g, 6.4 mmol) in DMF (20 mL) was added methylamine (26.5 mL, 2.0M in THF, 53.0 mmol) at r.t. under N$_2$. The reaction was stirred at 100° C. overnight in a sealed tube. The reaction mixture was filtered, diluted with water (50 mL), and extracted with EtOAc (50 mL×3). The organic layers were washed with ammonium hydroxide (50 mL×3) and brine (50 mL), dried (Na$_2$SO$_4$), and concentrated. The residue was purified by silica gel chromatography (PE:EtOAc=20:1) to give 310 mg (42%) of the title compound as a yellow oil. [M+H] Calc'd for $C_8H_{10}FN$, 140; Found, 140.

Preparation 151b methyl 3-({[(4R)-7-[(3-fluoro-4-methylphenyl)(methyl)amino]-3,4-dihydro-2H-1-benzopyran-4-yl]methyl}amino)pyridine-4-carboxylate

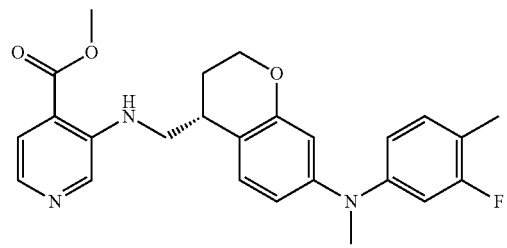 [SMILES: COC(=O)c1ccncc1NC[C@@H]1CCOc2cc(N(C)c3ccc(C)c(F)c3)ccc21]

The title compound was prepared in 58% yield from Preparation 126b and 3-fluoro-N,4-dimethylaniline according to the general procedure outlined for Preparation 126c. [M+H] Calc'd for $C_{25}H_{26}FN_3O_3$, 436; Found, 436.

Example 151

3-({[(4R)-7-[(3-fluoro-4-methylphenyl)(methyl)amino]-3,4-dihydro-2H-1-benzopyran-4-yl]methyl}amino)pyridine-4-carboxylic acid

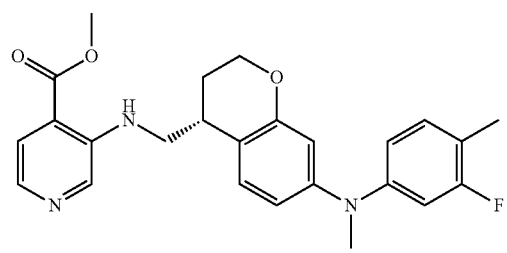 [SMILES: COC(=O)c1ccncc1NC[C@@H]1CCOc2cc(N(C)c3ccc(C)c(F)c3)ccc21]

The title compound was prepared in 93% yield from Preparation 151b according to the procedure for Example 1. $^1$H NMR (300 MHz, DMSO-d$_6$): δ 1.83-1.89 (1H, m), 1.93-1.98 (1H, m), 2.12 (3H, s), 3.04-3.08 (1H, m), 3.16 (3H, s), 3.42-3.49 (1H, m), 3.63-3.69 (1H, m), 4.09-4.18 (2H, m), 6.41 (1H, d, J=2.4 Hz), 6.53 (1H, dd, J=2.4, 8.4 Hz), 6.62-6.70 (2H, m), 7.06-7.12 (1H, m), 7.21 (1H, d, J=8.4 Hz), 7.55 (1H, d, J=5.1 Hz), 7.81 (1H, d, J=5.1 Hz), 8.37 (1H, s). [M+H] Calc'd for $C_{24}H_{24}FN_3O_3$, 422; Found, 422.

Preparation 152a tert-butyl N-{[(4R)-7-(methylamino)-3,4-dihydro-2H-1-benzopyran-4-yl]methyl}carbamate

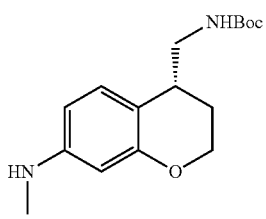 [SMILES: CNc1ccc2c(c1)OCC[C@H]2CNC(=O)OC(C)(C)C]

To a suspension of Preparation 18d (1.00 g, 2.91 mmol), KOAc (710 mg, 7.25 mmol), methylamine (15 mL, 2 M in THF) in DMF (30 mL) was added CuI (663 mg, 3.49 mmol) at r.t. under $N_2$. The reaction was sealed and stirred at 100° C. overnight. The reaction was diluted with EtOAc, filtered, and washed with sat $NaHCO_3$ (10 mL). The organic layer was concentrated, and the residue was purified by silica gel chromatography (PE:EtOAc=5:1) to give 286 mg (34%) of the title compound as a yellow solid. [M+H] Calc'd for $C_{16}H_{24}N_2O_3$, 293; Found, 293.

Preparation 152b tert-butyl N-{[(4R)-7-[(5-chloropyridin-2-yl)(methyl)amino]-3,4-dihydro-2H-1-benzopyran-4-yl]methyl}carbamate

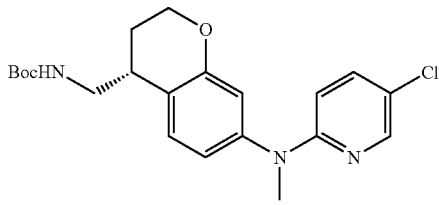 [SMILES: CN(c1ccc2c(c1)OCC[C@H]2CNC(=O)OC(C)(C)C)c1ccc(Cl)cn1]

To a suspension of Preparation 152a (116 mg, 0.40 mmol), 5-bromo-2-chloropyridine (153 mg, 0.80 mmol), S-phos (24 mg, 0.06 mmol) and $Cs_2CO_3$ (182 mg, 0.56 mmol) in toluene (20 mL) was added $Pd_2dba_3$ (36 mg, 0.04 mmol) at r.t. under $N_2$. The reaction was stirred at 120° C. overnight. The reaction was filtered and concentrated. The residue was purified by silica gel chromatography (PE:EtOAc=5:1) to give 63 mg (39%) of the title compound as a yellow solid. [M+H] Calc'd for $C_{21}H_{26}ClN_3O_3$, 404; Found, 404.

Preparation 152c

N-[(4R)-4-(aminomethyl)-3,4-dihydro-2H-1-benzopyran-7-yl]-5-chloro-N-methylpyridin-2-amine

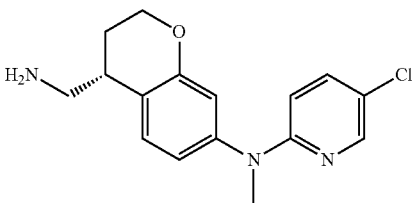 [SMILES: CN(c1ccc2c(c1)OCC[C@H]2CN)c1ccc(Cl)cn1]

The title compound was prepared in 97% yield from Preparation 152b according to the procedure for Preparation 43b. [M+H] Calc'd for $C_{16}H_{18}ClN_3O$, 304; Found, 304.

Preparation 152d methyl 3-({[(4R)-7-[(5-chloropyridin-2-yl)(methyl)amino]-3,4-dihydro-2H-1-benzopyran-4-yl]methyl}amino)pyridine-4-carboxylate

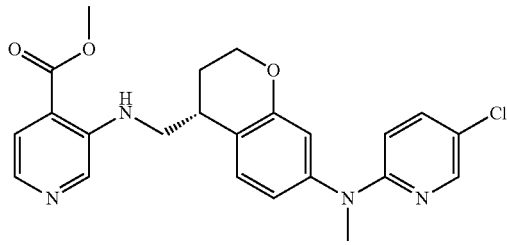 [SMILES: COC(=O)c1ccncc1NC[C@@H]1CCOc2cc(N(C)c3ccc(Cl)cn3)ccc21]

The title compound was prepared in 47% yield from Preparation 152c according to the procedure for Preparation 4d. [M+H] Calc'd for $C_{23}H_{23}ClN_4O_3$, 439; Found, 439.

Example 152

3-({[(4R)-7-[(5-chloropyridin-2-yl)(methyl)amino]-3,4-dihydro-2H-1-benzopyran-4-yl]methyl}amino)pyridine-4-carboxylic acid

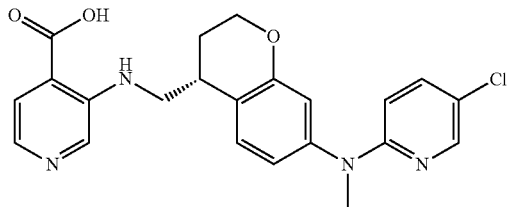 [SMILES: CN(c1ccc2c(c1)OCC[C@H]2CNc1cnccc1C(=O)O)c1ccc(Cl)cn1]

The title compound was prepared in 70% yield from Preparation 152d according to the procedure for Example 1. $^1$H NMR (300 MHz, DMSO-$d_6$): δ 1.88-2.21 (2H, m), 3.15-3.25 (1H, m), 3.33 (3H, s), 3.49-3.56 (1H, m), 3.71-3.74 (1H, m), 4.20-4.24 (2H, m), 6.52 (1H, d, J=9.3 Hz), 6.71 (1H, s), 6.78 (1H, dd, J=7.8 Hz), 7.38 (1H, d, J=6.6 Hz), 7.50 (1H, d, J=9.3 Hz), 7.58 (1H, d, J=3.0 Hz), 7.85 (1H, dd, J=4.5, 1.5 Hz), 8.15 (1H, s), 8.41 (1H, s). [M+H] Calc'd for C$_{22}$H$_{21}$ClN$_4$O$_3$, 425; Found, 425.

Preparation 153a 2-chloro-5-cyclopropylpyridine

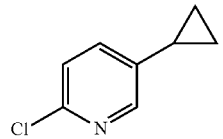

To a suspension of 5-bromo-2-chloropyridine (990 mg, 5.15 mmol), cyclopropylboronic acid (893 mg, 10.39 mmol) and Cs$_2$CO$_3$ (5.082 g, 15.45 mmol) in 1,4-dioxane (25 mL) was added Pd(PPh$_3$)$_4$ (601 mg, 0.52 mmol) at r.t. under N$_2$. The reaction was stirred at 100° C. for 1 h. After filtration, the solvent was removed in vacuo, and the residue was purified by silica gel chromatography (PE:EtOAc=50:1) to give 452 mg (57%) of the title compound as a colorless oil. [M+H] Calc'd for C$_8$H$_8$NCl, 154; Found, 154.

Preparation 153b tert-butyl N-{[(4R)-7-[(5-cyclopropylpyridin-2-yl)(methyl)amino]-3,4-dihydro-2H-1-benzopyran-4-yl]methyl}carbamate

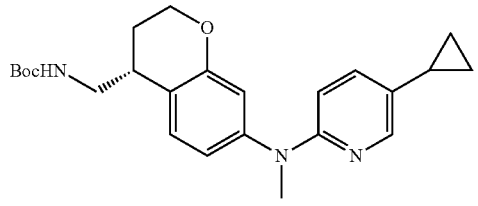 [SMILES: CN(c1ccc2c(c1)OCC[C@H]2CNC(=O)OC(C)(C)C)c1ccc(C2CC2)cn1]

To a suspension of 2-chloro-5-cyclopropylpyridine (333 mg, 2.18 mmol), Preparation 152a (317 mg, 1.09 mmol), S-phos (70 mg, 0.17 mmol) and Cs$_2$CO$_3$ (499 mg, 1.53 mmol) in toluene (20 mL) was added Pd$_2$dba$_3$ (101 mg, 0.11 mmol) at r.t. under N$_2$. The reaction was stirred at 120° C. overnight. After filtration, the solvent was removed in vacuo, and the residue was purified by silica gel chromatography (PE:EtOAc=10:1) to give 330 mg (75%) of the title compound as a yellow oil. [M+H] Calc'd for C$_{24}$H$_{31}$N$_3$O$_3$, 410; Found, 410.

Preparation 153c

N-[(4R)-4-(aminomethyl)-3,4-dihydro-2H-1-benzopyran-7-yl]-5-cyclopropyl-N-methylpyridin-2-amine

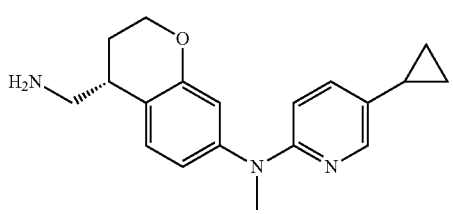 [SMILES: CN(c1ccc2c(c1)OCC[C@H]2CN)c1ccc(C2CC2)cn1]

The title compound was prepared in 94% yield from Preparation 153b according to the procedure for Preparation 43b. [M+H] Calc'd for C$_{19}$H$_{23}$N$_3$O, 310; Found, 310.

Preparation 153d methyl 3-({[(4R)-7-[(5-cyclopropylpyridin-2-yl)(methyl)amino]-3,4-dihydro-2H-1-benzopyran-4-yl]methyl}amino)pyridine-4-carboxylate

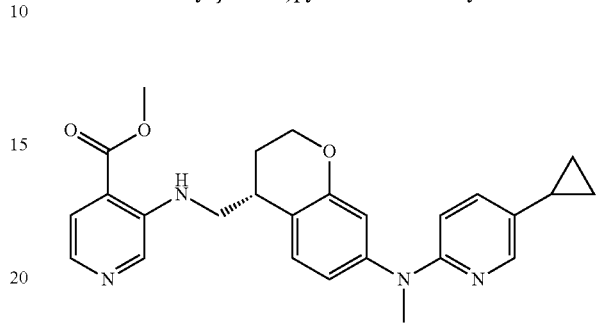

The title compound was prepared in 86% yield from Preparation 153d according to the procedure for Preparation 4d. [M+H] Calc'd for C$_{26}$H$_{28}$N$_4$O$_3$, 445; Found, 445.

Example 153

3-({[(4R)-7-[(5-cyclopropylpyridin-2-yl)(methyl)amino]-3,4-dihydro-2H-1-benzopyran-4-yl]methyl}amino)pyridine-4-carboxylic acid

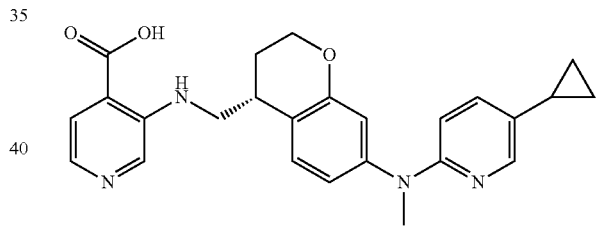

The title compound was prepared in 39% yield from Preparation 153d according to the procedure for Example 1. $^1$H NMR (300 MHz, DMSO-d$_6$): δ 0.55-0.59 (2H, m), 0.83-0.89 (2H, m), 1.78-2.02 (3H, m), 3.12-3.15 (1H, m), 3.31 (3H, s), 3.48-3.55 (1H, m), 3.72 (1H, dd, J=4.2, 13.5 Hz), 4.14-4.22 (2H, m), 6.53 (1H, d, J=8.4 Hz), 6.63 (1H, s), 6.74-6.71 (1H, m), 7.12 (1H, dd, J=2.1, 8.4 Hz), 7.31 (1H, d, J=8.4 Hz), 7.57 (1H, d, J=4.8 Hz), 7.85 (1H, d, J=5.1 Hz), 8.00 (1H, s), 8.41 (1H, s). [M+H] Calc'd for C$_{25}$H$_{26}$N$_4$O$_3$, 431; Found, 431.

Preparation 154a 4-ethyl-N-methylaniline

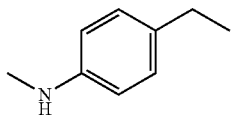

The title compound was prepared in 60% overall yield from 4-ethylaniline according to the general procedure outlined for Preparation 127a. [M+H] Calc'd for $C_9H_{13}N$, 136; Found, 136.

Preparation 154b methyl 3-({[(4R)-7-[(4-ethylphenyl)(methyl)amino]-3,4-dihydro-2H-1-benzopyran-4-yl]methyl}amino)pyridine-4-carboxylate

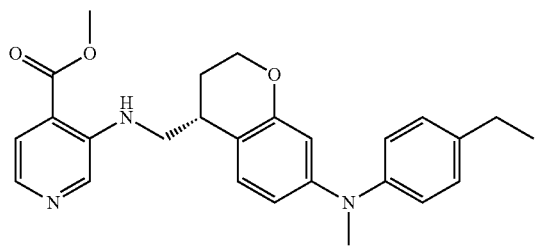

The title compound was prepared in 48% yield from Preparation 126b and 4-ethyl-N-methylaniline according to the general procedure outlined for Preparation 126c. [M+H] Calc'd for $C_{26}H_{29}N_3O_3$, 432; Found, 432.

Example 154

3-({[(4R)-7-[(4-ethylphenyl)(methyl)amino]-3,4-dihydro-2H-1-benzopyran-4-yl]methyl}amino)pyridine-4-carboxylic acid

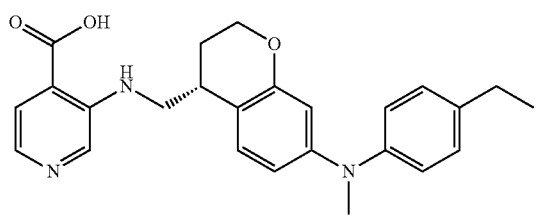 [SMILES: CCc1ccc(N(C)c2ccc3c(c2)OCC[C@H]3CNc2cnccc2C(=O)O)cc1]

The title compound was prepared in 82% yield from Preparation 154b according to the procedure for Example 1. $^1$H NMR (300 MHz, DMSO-$d_6$): δ 1.15 (3H, t, J=7.5 Hz), 1.80-1.85 (1H, m), 1.90-1.97 (1H, m), 2.54 (2H, q, J=7.5 Hz), 3.00-3.04 (1H, m), 3.15 (3H, s), 3.40-3.47 (1H, m), 3.62 (1H, dd, J=5.1, 13.5 Hz), 4.06-4.14 (2H, m), 6.23 (1H, d, J=2.1 Hz), 6.38 (1H, dd, J=8.1, 2.4 Hz), 6.95 (2H, d, J=8.1 Hz), 7.12 (3H, dd, J=3.6, 8.1 Hz), 7.55 (1H, d, J=4.8 Hz), 7.82 (1H, d, J=4.8 Hz), 8.37 (1H, s). [M+H] Calc'd for $C_{25}H_{27}N_3O_3$, 418; Found, 418.

Preparation 155a tert-butyl N-{[(1R)-6-[methyl(1-methyl-2-oxo-1,2-dihydropyridin-4-yl)amino]-1,2,3,4-tetrahydronaphthalen-1-yl]methyl}carbamate

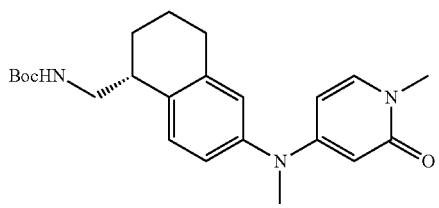 [SMILES: CN(c1ccc2c(c1)CCC[C@H]2CNC(=O)OC(C)(C)C)c1ccn(C)c(=O)c1]

To a suspension of Preparation 139a (200 mg, 0.69 mmol), 4-bromo-1-methyl-1,2-dihydropyridin-2-one (259 mg, 1.38 mmol), S-phos (45 mg, 0.11 mmol) and $Cs_2CO_3$ (315 mg, 0.97 mmol) in toluene (20 mL) was added $Pd_2dba_3$ (64 mg, 0.07 mmol) at r.t. under $N_2$. The reaction was stirred at 120° C. overnight. The reaction was cooled, filtered, and concentrated. The residue was purified by silica gel chromatography (DCM:MeOH=15:1) to give 162 mg (59%) of the title compound as a yellow oil. [M+H] Calc'd for $C_{23}H_{31}N_3O_3$, 398; Found, 398.

Preparation 155b

4-{[(5R)-5-(aminomethyl)-5,6,7,8-tetrahydronaphthalen-2-yl](methyl)amino}-1-methyl-1,2-dihydropyridin-2-one

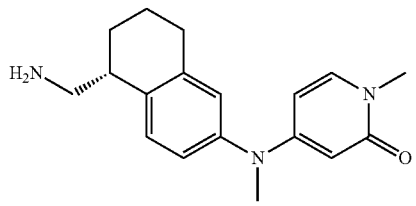 [SMILES: CN(c1ccc2c(c1)CCC[C@H]2CN)c1ccn(C)c(=O)c1]

The title compound was prepared in 54% yield from Preparation 155a according to the procedure for Preparation 43b. [M+H] Calc'd for $C_{18}H_{23}N_3O$, 298; Found, 298.

Preparation 155c methyl 3-({[(1R)-6-[methyl(1-methyl-2-oxo-1,2-dihydropyridin-4-yl)amino]-1,2,3,4-tetrahydronaphthalen-1-yl]methyl}amino)pyridine-4-carboxylate

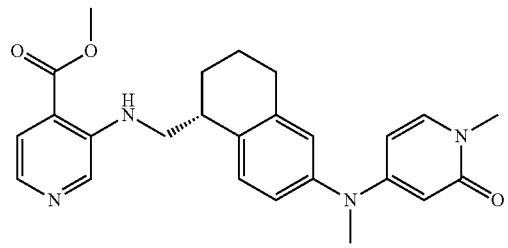 [SMILES: COC(=O)c1ccncc1NC[C@@H]1CCCc2cc(N(C)c3ccn(C)c(=O)c3)ccc21]

The title compound was prepared in 65% yield from Preparation 155b according to the procedure for Preparation 4d. [M+H] Calc'd for $C_{25}H_{28}N_4O_3$, 433; Found, 433.

Example 155

3-({[(1R)-6-[methyl(1-methyl-2-oxo-1,2-dihydro-pyridin-4-yl)amino]-1,2,3,4-tetrahydronaphthalen-1-yl]methyl}amino)pyridine-4-carboxylic acid

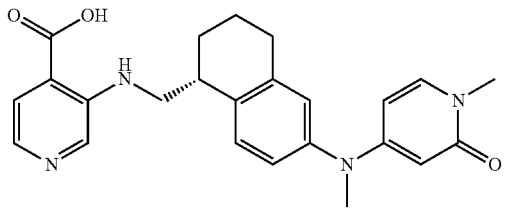 [SMILES: CN(c1ccc2c(c1)CCC[C@H]2CNc1cnccc1C(=O)O)c1ccn(C)c(=O)c1]

The title compound was prepared in 42% yield from Preparation 155c according to the procedure for Example 1. $^1$H NMR (400 MHz, DMSO-d$_6$): δ 1.76-1.87 (4H, m), 2.67-2.78 (2H, m), 3.28 (3H, s), 3.41 (3H, s), 3.42-3.51 (2H, m), 3.60-3.65 (1H, m), 5.45 (1H, s), 5.65-5.67 (1H, m), 6.67 (2H, m), 7.31-7.38 (2H, m), 7.55 (1H, m), 7.82 (1H, s), 8.34 (1H, s). [M+H] Calc'd for $C_{24}H_{26}N_4O_3$, 418. Found, 419.

Preparation 156a tert-butyl N-{[(1R)-6-[methyl(5-methylpyrimidin-2-yl)amino]-1,2,3,4-tetrahydronaphthalen-1-yl]methyl}carbamate

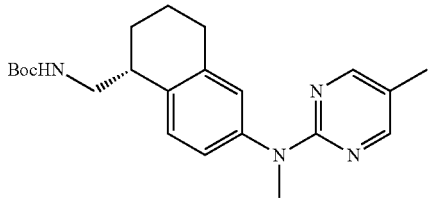 [SMILES: Cc1cnc(N(C)c2ccc3c(c2)CCC[C@H]3CNC(=O)OC(C)(C)C)nc1]

The title compound was prepared in 21% yield form Preparation 139a and 2-chloro-5-methylpyrimidine according to the general procedure outlined for Preparation 155a. [M+H] Calc'd for $C_{22}H_{30}N_4O_2$, 383; Found, 383.

Preparation 156b

N-[(5R)-5-(aminomethyl)-5,6,7,8-tetrahydronaphthalen-2-yl]-N,5-dimethylpyrimidin-2-amine

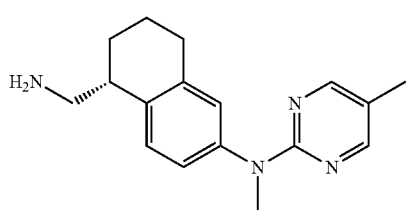 [SMILES: Cc1cnc(N(C)c2ccc3c(c2)CCC[C@H]3CN)nc1]

The title compound was prepared in 98% yield from Preparation 156a according to the procedure for Preparation 43b. [M+H] Calc'd for $C_{17}H_{22}N_4$, 283; Found, 283.

Preparation 156c methyl 3-({[(1R)-6-[methyl(5-methylpyrimidin-2-yl)amino]-1,2,3,4-tetrahydronaphthalen-1-yl]methyl}amino)pyridine-4-carboxylate

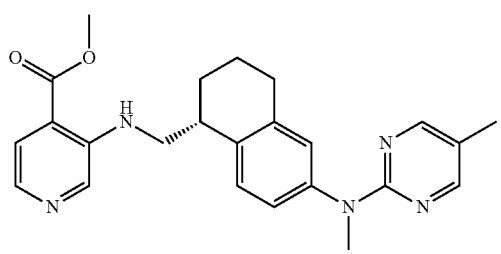 [SMILES: COC(=O)c1ccncc1NC[C@@H]1CCCc2cc(N(C)c3ncc(C)cn3)ccc21]

The title compound was prepared in 59% yield from Preparation 156b according to the procedure for Preparation 4d. [M+H] Calc'd for $C_{24}H_{27}N_5O_2$, 418; Found, 418.

Example 156

3-({[(1R)-6-[methyl(5-methylpyrimidin-2-yl)amino]-1,2,3,4-tetrahydronaphthalen-1-yl]methyl}amino)pyridine-4-carboxylic acid

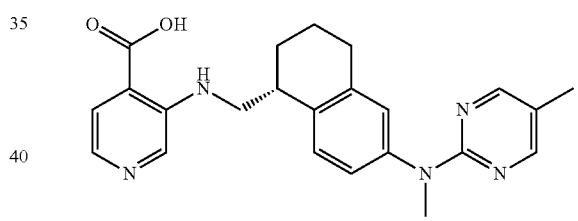

The title compound was prepared in 57% yield from Preparation 156c according to the procedure for Example 1. $^1$H NMR (300 MHz, DMSO-d$_6$): δ 1.68-1.71 (1H, m), 1.83-1.86 (3H, m), 2.09 (3H, s), 2.67-2.73 (2H, m), 3.09-3.12 (1H, m), 3.39 (3H, s), 3.42-3.48 (1H, m), 3.62 (1H, dd, J=4.8, 12.8 Hz), 7.02 (1H, s), 7.06 (1H, d, J=8.4 Hz), 7.32 (1H, d, J=8.4 Hz), 7.58 (1H, d, J=4.8 Hz), 7.84 (1H, d, J=4.8 Hz), 8.21 (2H, s), 8.38 (1H, s). [M+H] Calc'd for $C_{23}H_{25}N_5O_2$, 403; Found, 404.

Preparation 157a 5-ethyl-N-methylpyridin-2-amine

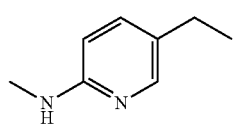

A solution of 5-ethylpyridin-2-amine (330 mg, 2.70 mmol) in THF (10 mL) was cooled to −78° C. and n-BuLi (1.2 mL, 3.0 mmol) was added. The reaction stirred at −78° C. for 30 min, and then MeI (423 mg, 2.97 mmol) was added. The reaction was stirred for 2 h while warming to r.t. Water (10 mL) was added, and the solution was extracted with EtOAc (20 mL). The organic layer was dried (Na$_2$SO$_4$) and concentrated. The residue was purified by silica gel chromatography (PE:EtOAc=5:1) to give 35 mg (9%) of the title compound as a yellow oil. [M+H] Calc'd for C$_8$H$_{12}$N$_2$, 137; Found, 137.

Preparation 157b methyl 3-({[(4R)-7-[(5-ethylpyridin-2-yl)(methyl) amino]-3,4-dihydro-2H-1-benzopyran-4-yl] methyl}amino)pyridine-4-carboxylate

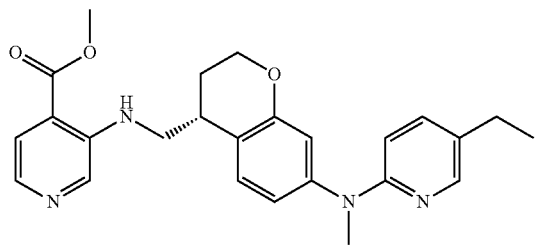 [SMILES: CCc1ccc(N(C)c2ccc3c(c2)OCC[C@H]3CNc2cnccc2C(=O)OC)nc1]

The title compound was prepared in 42% yield from Preparation 126b and 5-ethyl-N-methylpyridin-2-amine according to the general procedure outlined for Preparation 126c. [M+H] Calc'd for C$_{25}$H$_{28}$N$_4$O$_3$, 433; Found, 433.

Example 157

3-({[(4R)-7-[(5-ethylpyridin-2-yl)(methyl)amino]-3, 4-dihydro-2H-1-benzopyran-4-yl]methyl}amino) pyridine-4-carboxylic acid

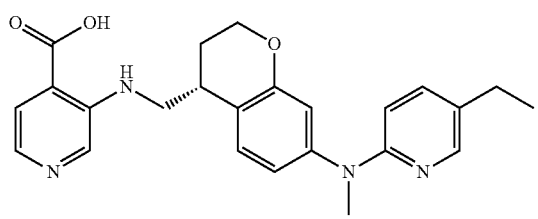

The title compound was prepared in 80% yield from Preparation 157b according to the procedure for Example 1. $^1$H NMR (300 MHz, DMSO-d$_6$): δ 1.13 (3H, t, J=7.5 Hz), 1.88-2.03 (2H, m), 2.44-2.50 (2H, m), 3.11-3.13 (1H, m), 3.49 (3H, s), 3.47-3.50 (1H, m), 3.67-3.74 (1H, m), 4.17-4.23 (2H, m), 6.56 (1H, d, J=8.7 Hz), 6.64 (1H, m), 6.72-6.76 (1H, m), 7.33 (2H, d, J=8.1 Hz), 7.58 (1H, d, J=5.1 Hz), 7.83 (1H, d, J=4.8 Hz), 8.01 (1H, d, J=1.8 Hz), 8.37 (1H, s). [M+H] Calc'd for C$_{24}$H$_{26}$N$_4$O$_3$, 419; Found, 419.

Preparation 158a

[4-(methylamino)phenyl]methanol

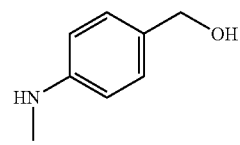

To a solution of methyl 4-(methylamino)benzoate (2.0 g, 12.1 mmol) in THF (30 mL) was added LAH (6.1 mL, 2.4 M in THF, 14.5 mmol) at 0° C. The reaction was stirred at r.t. for 2 h. The reaction was quenched with EtOAc (50 mL) and water (2 mL). The mixture was dried (Na$_2$SO$_4$) and concentrated. Purification by silica gel chromatography (PE: EtOAc=3:1) gave 1.0 g (60%) of the title compound as a yellow oil. [M+H] Calc'd for C$_8$H$_{11}$NO, 138; Found 138.

Preparation 158b

4-{[(tert-butyldimethylsilyl)oxy]methyl}-N-methyl-aniline

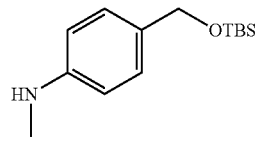 [SMILES: CNc1ccc(CO[Si](C)(C)C(C)(C)C)cc1]

To a solution of [4-(methylamino)phenyl]methanol (500 mg, 3.7 mmol) and imidazole (248 mg, 3.7 mmol) in DCM (20 mL) was added TBSCl (548 mg, 3.7 mmol) at r.t., and the reaction was stirred for 2 h. The reaction was diluted with water (50 mL) and extracted with DCM (50 mL×3). Organics were washed with brine (50 mL), dried (Na$_2$SO$_4$), and concentrated. The residue was purified by silica gel chromatography (PE:EtOAc=40:1) to give 600 mg (66%) of the title compound as a yellow oil. [M+H] Calc'd for C$_{14}$H$_{15}$NOSi, 252; Found 252.

Preparation 158c methyl 3-({[(1R)-6-[(4-{[(tert-butyldimethylsilyl) oxy]methyl}phenyl)-(methyl)amino]-1,2,3,4-tetrahydronaphthalen-1-yl]methyl}amino)pyridine-4-carboxylate

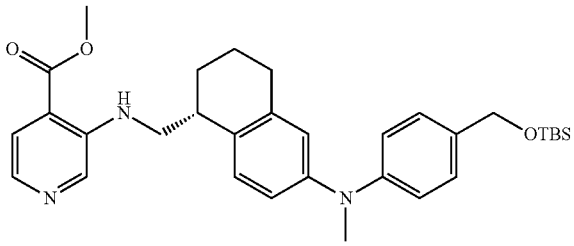 [SMILES: COC(=O)c1ccncc1NC[C@@H]1CCCc2cc(N(C)c3ccc(CO[Si](C)(C)C(C)(C)C)cc3)ccc21]

Example 158

3-({[(1R)-6-{[4-(hydroxymethyl)phenyl](methyl)amino}-1,2,3,4-tetrahydronaphthalen-1-yl]methyl}amino)pyridine-4-carboxylic acid

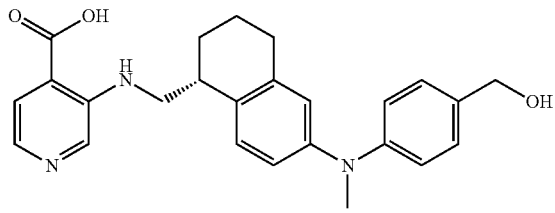 [SMILES: CN(c1ccc(CO)cc1)c1ccc2c(c1)CCC[C@H]2CNc1cnccc1C(=O)O]

The title compound was prepared in 28% yield from Preparation 126b and Preparation 158b according to the general procedure outlined for Preparation 126c. [M+H] Calc'd for $C_{32}H_{43}N_3O_3Si$, 546; Found, 546.

To a solution of Preparation 158c (80 mg, 0.15 mmol) in THF (5 mL) was added TBAF (0.29 mL, 1.0 M in THF, 0.29 mmol) at r.t., and the reaction was stirred for 1 h. Water (5 mL) and LiOH H$_2$O (26 mg, 0.60 mmol) were added, and the reaction was stirred at r.t. for 2 h. THF was removed in vacuo, and the residue was acidified to pH=5 with 1.0 N aqueous HCl solution. The precipitate was filtered and purified by prep-HPLC to give 40 mg (65%) of the title compound as a yellow solid. $^1$H NMR (400 MHz, DMSO-d$_6$): δ 1.65-1.68 (1H, m), 1.77-1.84 (3H, m), 2.64-2.67 (2H, m), 3.03-3.06 (1H, m), 3.20 (3H, s), 3.41-3.46 (1H, m), 3.55-3.60 (1H, m), 4.41 (2H, s), 5.01 (1H, br s), 6.72-6.76 (2H, m), 6.92 (2H, d, J=8.4 Hz), 7.19-7.21 (3H, m), 7.56 (1H, d, J=4.8 Hz), 7.83 (1H, d, J=5.2 Hz), 8.35 (1H, s). [M+H] Calc'd for $C_{25}H_{27}N_3O_3$, 418; Found, 418.

Preparation 159a methyl 3-({[(1R)-6-[methyl(1-methyl-1H-pyrazol-4-yl)amino]-1,2,3,4-tetrahydronaphthalen-1-yl]methyl}amino)pyridine-4-carboxylate

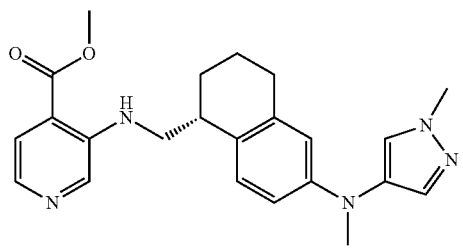 [SMILES: COC(=O)c1ccncc1NC[C@@H]1CCCc2cc(N(C)c3cnn(C)c3)ccc21]

To a suspension of Preparation 122a (300 mg, 0.796 mmol), N,1-dimethyl-1H-pyrazol-4-amine (106 mg, 0.955 mmol), S-phos (49 mg, 0.119 mmol) and Cs$_2$CO$_3$ (363 mg, 1.114 mmol) in toluene (30 mL) was added Pd$_2$dba$_3$ (73 mg, 0.080 mmol) at r.t. under N$_2$. The reaction was stirred at 120° C. overnight. The reaction was cooled, filtered, and concentrated. The residue was purified by silica gel chromatography (PE:EtOAc=5:1) to give 100 mg (32%) of the title compound as a yellow oil. [M+H] Calc'd for $C_{23}H_{27}N_5O_2$, 406; Found, 406.

Example 159

3-({[(1R)-6-[methyl(1-methyl-1H-pyrazol-4-yl)amino]-1,2,3,4-tetrahydronaphthalen-1-yl]methyl}amino)pyridine-4-carboxylic acid

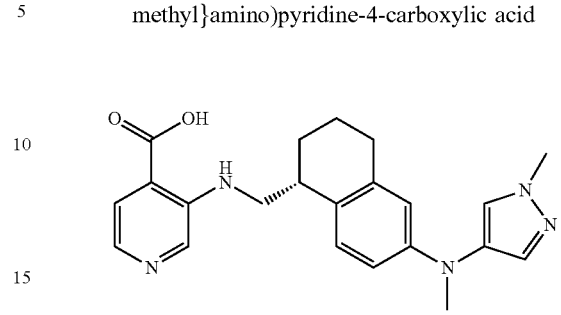

The title compound was prepared in 52% yield from Preparation 159a according to the procedure for Example 1. $^1$H NMR (400 MHz, DMSO-d$_6$): δ 1.73-1.76 (4H, m), 2.62 (2H, m), 2.91 (1H, s), 3.09 (3H, s), 3.44-3.50 (2H, m), 3.64-3.69 (1H, m), 3.78 (3H, s), 6.51-6.52 (1H, m), 6.60 (1H, m), 7.07-7.10 (1H, m), 7.29 (1H, s), 7.53-7.54 (1H, d, J=4.8 Hz), 7.60 (1H, s), 7.78-7.80 (1H, m), 8.29 (1H, s). [M+H] Calc'd for $C_{22}H_{25}N_5O_2$, 392; Found, 392.

Preparation 160a

1-N,1-N,4-N-trimethylbenzene-1,4-diamine

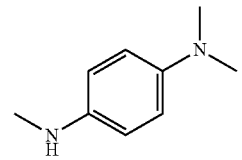

The title compound was prepared in 52% overall yield from 1-N,1-N-dimethylbenzene-1,4-diamine according to the general procedure outlined for Preparation 127a. [M+H] Calc'd for $C_9H_{14}N_2$, 151; Found, 151.

Preparation 160b methyl 3-({[(1R)-6-{[4-(dimethylamino)phenyl](methyl)amino}-1,2,3,4-tetrahydronaphthalen-1-yl]methyl}amino)pyridine-4-carboxylate

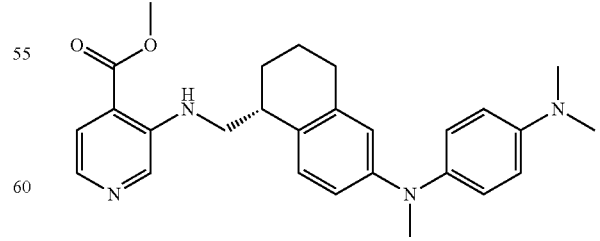

The title compound was prepared in 23% yield from Preparation 122a and Preparation 160a according to the general procedure outlined for Preparation 126c. [M+H] Calc'd for $C_{27}H_{32}N_4O_2$, 445; Found, 445.

Example 160

3-({[(1R)-6-{[4-(dimethylamino)phenyl](methyl)amino}-1,2,3,4-tetrahydronaphthalen-1-yl]methyl}amino)pyridine-4-carboxylic acid

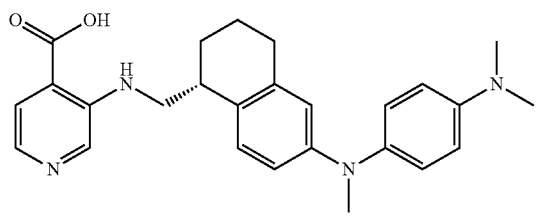 [SMILES: CN(C)c1ccc(N(C)c2ccc3c(c2)CCC[C@H]3CNc2cnccc2C(=O)O)cc1]

The title compound was prepared in 11% yield from Preparation 164b according to the procedure for Example 1. $^1$H NMR (400 MHz, DMSO-$d_6$): δ 1.61-1.64 (1H, m), 1.75-1.80 (3H, m), 2.60-2.61 (2H, m), 2.88 (6H, s), 2.97-2.98 (1H, m), 3.12 (3H, s), 3.48-3.52 (2H, m), 6.42-6.49 (2H, m), 6.73 (2H, d, J=6.8 Hz), 6.97 (2H, d, J=6.8 Hz), 7.07 (1H, d, J=8.0 Hz), 7.55 (1H, d, J=4.8 Hz), 7.81 (1H, d, J=4.8 Hz), 8.30 (1H, s). [M+H] Calc'd for $C_{26}H_{30}N_4O_2$, 431; Found, 431.

Preparation 161a methyl 3-({[(1R)-6-[(4-cyclopropylphenyl)(methyl)amino]-1,2,3,4-tetrahydronaphthalen-1-yl]methyl}amino)pyridine-4-carboxylate

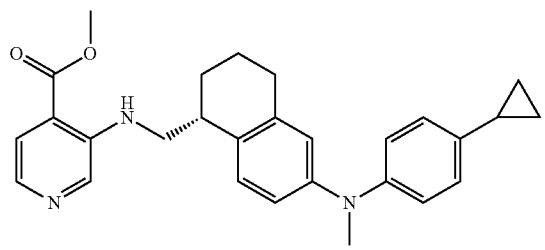

The title compound was prepared in 28% yield from Preparation 122a and 4-cyclopropyl-N-methylaniline according to the general procedure outlined for Preparation 126c. [M+H] Calc'd for $C_{28}H_{31}N_3O_2$, 442; Found, 442.

Example 161

3-({[(1R)-6-[(4-cyclopropylphenyl)(methyl)amino]-1,2,3,4-tetrahydronaphthalen-1-yl]methyl}amino)pyridine-4-carboxylic acid

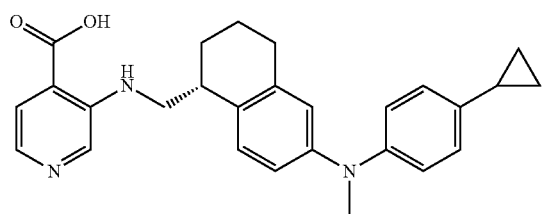

The title compound was prepared in 93% yield from Preparation 161a according to the procedure for Example 1. $^1$H NMR (300 MHz, DMSO-$d_6$): δ 0.56-0.60 (2H, m), 0.84-0.90 (2H, m), 1.60-1.63 (1H, m), 1.75-1.86 (4H, m), 2.62-2.64 (2H, m), 2.97-3.01 (1H, m), 3.15 (3H, s), 3.34-3.41 (1H, m), 3.50-3.56 (1H, m), 6.65-6.69 (2H, m), 6.86 (2H, d, J=8.1 Hz), 6.97 (2H, d, J=8.7 Hz), 7.15 (1H, d, J=8.4 Hz), 7.54 (1H, d, J=4.8 Hz), 7.80 (1H, d, J=4.8 Hz), 8.31 (1H, s). [M+H] Calc'd for $C_{27}H_{29}N_3O_2$, 428; Found, 428.

Preparation 162a tert-butyl N-{[(1R)-6-(2,3,4,5-tetrahydro-1H-1-benzazepin-1-yl)-1,2,3,4-tetrahydronaphthalen-1-yl]methyl}carbamate

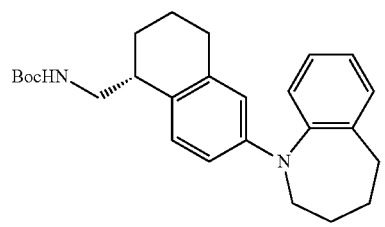 [SMILES: CC(C)(C)OC(=O)NC[C@@H]1CCCc2cc(N3CCCCc4ccccc43)ccc21]

The title compound was prepared in 69% yield from Preparation 6d and 2,3,4,5-tetrahydro-1H-1-benzazepine according to the general procedure outlined for Preparation 9a. [M+H] Calc'd for $C_{26}H_{34}N_2O_2$, 407; Found, 407.

Preparation 162b

[(1R)-6-(2,3,4,5-tetrahydro-1H-1-benzazepin-1-yl)-1,2,3,4-tetrahydronaphthalen-1-yl]methanamine

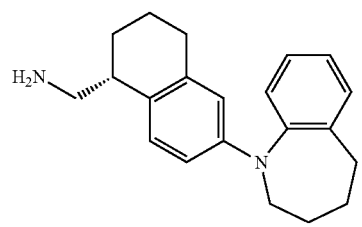 [SMILES: NC[C@@H]1CCCc2cc(N3CCCCc4ccccc43)ccc21]

The title compound was prepared in quantitative yield from Preparation 162a according to the procedure for Preparation 43b. [M+H] Calc'd for $C_{21}H_{26}N_2$, 307; Found, 307.

Preparation 162c methyl 3-({[(1R)-6-(2,3,4,5-tetrahydro-1H-1-benzazepin-1-yl)-1,2,3,4-tetrahydronaphthalen-1-yl]methyl}amino)pyridine-4-carboxylate

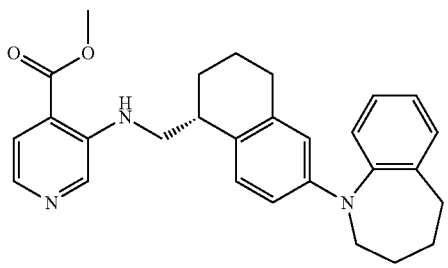 [SMILES: COC(=O)c1ccncc1NC[C@@H]1CCCc2cc(N3CCCCc4ccccc43)ccc21]

The title compound was prepared in 76% yield from Preparation 162b according to the procedure for Preparation 4d. [M+H] Calc'd for $C_{28}H_{31}N_3O_2$, 442; Found, 442.

Example 162

3-({[(1R)-6-(2,3,4,5-tetrahydro-1H-1-benzazepin-1-yl)-1,2,3,4-tetrahydronaphthalen-1-yl]methyl}amino)pyridine-4-carboxylic acid

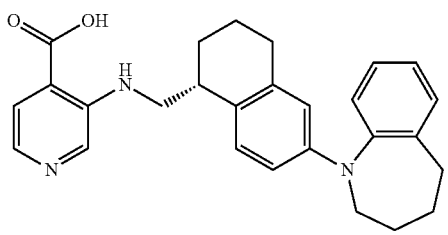 [SMILES: O=C(O)c1ccncc1NC[C@@H]1CCCc2cc(N3CCCCc4ccccc43)ccc21]

The title compound was prepared in 65% yield from Preparation 145c according to the procedure for Example 1. $^1$H NMR (400 MHz, DMSO-$d_6$): δ 1.56-1.89 (8H, m), 2.58 (4H, br s), 2.93-2.99 (1H, m), 3.32-3.39 (1H, m), 3.47-3.60 (3H, m), 6.28 (1H, s), 6.33-6.37 (1H, m), 7.04-7.11 (2H, m), 7.14-7.26 (2H, m), 7.30-7.36 (1H, m), 7.56 (d, 1H, J=5.0 Hz), 7.82 (1H, d, J=5.0 Hz), 8.36 (1H, s). [M+H] Calc'd for $C_{27}H_{29}N_3O_2$, 428; Found, 428.

Preparation 163a 4-cyclopropyl-N-(2-methoxyethyl)aniline

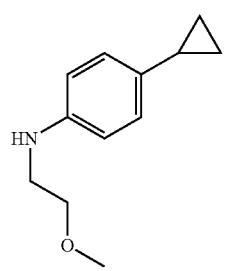

Methoxyacetyl chloride (0.55 mL, 6.0 mmol) was added to a solution of 4-cyclopropylaniline (800 mg, 6.0 mmol) and DIEA (1.05 mL, 6.0 mmol) in DCM, and the reaction was stirred at r.t. for 2 h. The reaction was washed with brine, dried (MgSO$_4$), and concentrated to give crude N-(4-cyclopropylphenyl)-2-methoxyacetamide.

To a solution of this N-(4-cyclopropylphenyl)-2-methoxyacetamide in THF (20 mL) was added LAH (5.0 mL, 2.4 M in THF, 12 mmol) at 0° C. The reaction was stirred at r.t. for 2 h. The solution was diluted with water (0.5 mL) and EtOAc (30 mL), dried (Na$_2$SO$_4$), and concentrated. Purification by silica gel chromatography (0% to 15% MeOH/DCM) gave 912 mg (79%) of the title compound as a yellow oil. [M+H] Calc'd for $C_{12}H_{17}NO$, 192; Found, 192.

Preparation 163b tert-butyl N-{[(1R)-6-[(4-cyclopropylphenyl)(2-methoxyethyl)amino]-1,2,3,4-tetrahydronaphthalen-1-yl]methyl}carbamate

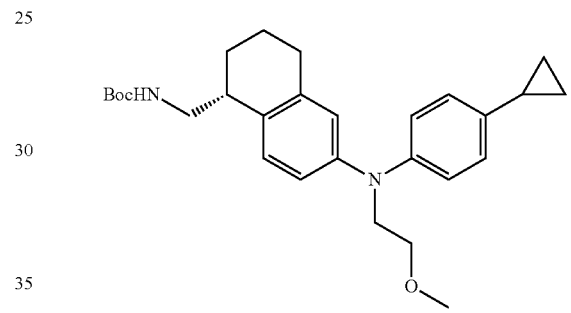

The title compound was prepared in 69% yield from Preparation 6d and 4-cyclopropyl-N-(2-methoxyethyl)aniline according to the general procedure outlined for Preparation 9a. [M+H] Calc'd for $C_{28}H_{38}N_2O_3$, 451; Found, 451.

Preparation 163c (5R)-5-(aminomethyl)-N-(4-cyclopropylphenyl)-N-(2-methoxyethyl)-5,6,7,8-tetrahydronaphthalen-2-amine

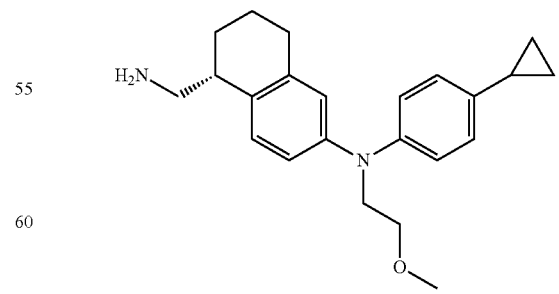

The title compound was prepared in quantitative yield from Preparation 163b according to the procedure for Preparation 43b. [M+H] Calc'd for $C_{23}H_{30}N_2O$, 351; Found, 351.

Preparation 163d methyl 3-({[(1R)-6-[(4-cyclopropylphenyl)(2-methoxyethyl)amino]-1,2,3,4-tetrahydronaphthalen-1-yl]methyl}amino)pyridine-4-carboxylate

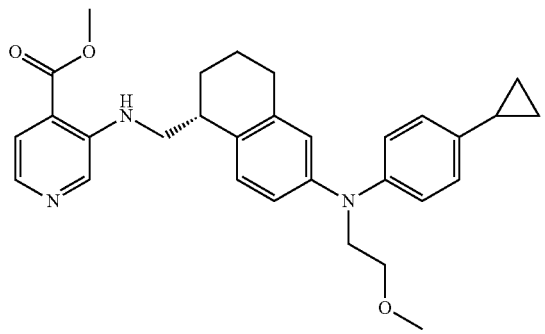 [SMILES: COCCN(c1ccc(C2CC2)cc1)c1ccc2c(c1)CCC[C@H]2CNc1cnccc1C(=O)OC]

The title compound was prepared in 72% yield from Preparation 163c according to the procedure for Preparation 4d. [M+H] Calc'd for $C_{30}H_{35}N_3O_3$, 486; Found, 486.

Example 163

3-({[(1R)-6-[(4-cyclopropylphenyl)(2-methoxyethyl)amino]-1,2,3,4-tetrahydronaphthalen-1-yl]methyl}amino)pyridine-4-carboxylic acid

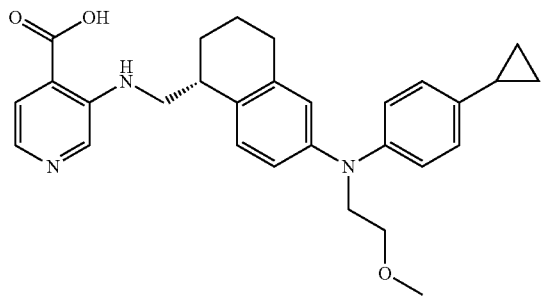 [SMILES: COCCN(c1ccc(C2CC2)cc1)c1ccc2c(c1)CCC[C@H]2CNc1cnccc1C(=O)O]

The title compound was prepared in 65% yield from Preparation 163d according to the procedure for Example 1. $^1$H NMR (400 MHz, DMSO-d$_6$): δ 0.58-0.62 (2H, m), 0.85-0.91 (2H, m), 1.61-1.67 (1H, m), 1.71-1.85 (4H, m), 2.60-2.65 (2H, m), 2.99-3.03 (1H, m), 3.23 (3H, s), 3.37-3.57 (4H, m), 3.75-3.80 (2H, m), 6.65 (1H, s), 6.68 (1H, d, J=8.6 Hz), 6.89 (2H, d, J=7.0 Hz), 6.97 (2H, d, J=7.8 Hz), 7.16 (1H, d, J=8.2 Hz), 7.55 (1H, d, J=4.5 Hz), 7.81 (1H, d, J=4.5 Hz), 8.32 (1H, s). [M+H] Calc'd for $C_{29}H_{33}N_3O_3$, 472; Found, 472.

Preparation 164a 4-(methoxymethyl)-N-methylaniline

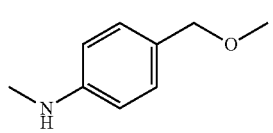

The title compound was prepared in 22% overall yield from 4-methoxymethylaniline according to the general procedure outlined for Preparation 127a. [M+H] Calc'd for $C_9H_{13}NO$, 152. Found, 152.

Preparation 164b methyl 3-({[(1R)-6-{[4-(methoxymethyl)phenyl](methyl)amino}-1,2,3,4-tetrahydronaphthalen-1-yl]methyl}amino)pyridine-4-carboxylate

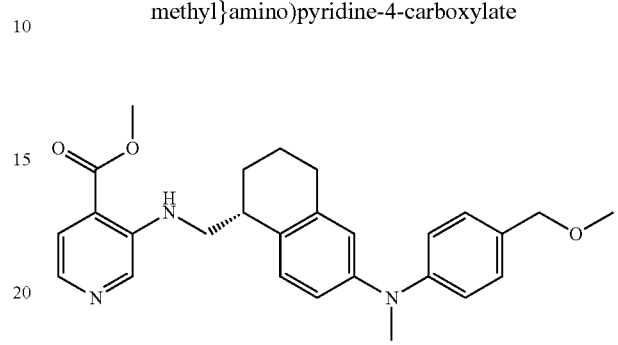

The title compound was prepared in 23% yield from Preparation 122a and 4-(methoxymethyl)-N-methylaniline according to the general procedure outlined for Preparation 126c. [M+H] Calc'd for $C_{27}H_{31}N_3O_3$, 446; Found, 446.

Example 164

3-({[(1R)-6-{[4-(methoxymethyl)phenyl](methyl)amino}-1,2,3,4-tetrahydronaphthalen-1-yl]methyl}amino)pyridine-4-carboxylic acid

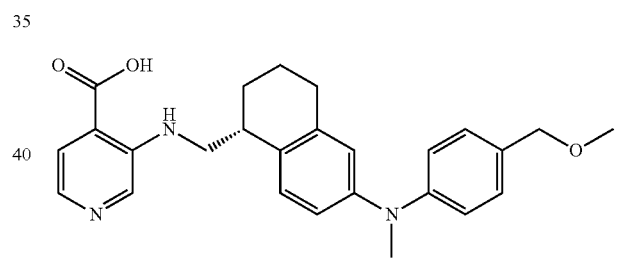

The title compound was prepared in 33% yield from Preparation 164b according to the procedure for Example 1. $^1$H NMR (300 MHz, DMSO-d$_6$): δ 1.59-1.79 (4H, m), 2.61-2.67 (2H, m), 3.02-3.04 (1H, m), 3.20 (3H, s), 3.23 (3H, s), 3.31-3.40 (1H, m), 3.51-3.54 (1H, m), 4.28 (2H, s), 6.77-6.88 (4H, m), 7.14-7.24 (3H, m), 7.54 (1H, d, J=4.2 Hz), 7.80 (1H, d, J=4.8 Hz), 8.31 (1H, s). Calc'd for $C_{26}H_{29}N_3O_3$, 432; Found, 432.

Preparation 165a 4-((tert-butyldimethylsilyl)oxy)-N-methylaniline

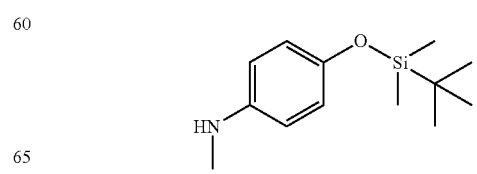

A solution of 4-(methylamino)phenol (5.0 g, 29 mmol), TBDMSCl (4.8 g, 32 mmol) and imidazole (9.9 g, 0.15 mol) in DCM was stirred at r.t. for 1 h. Water was added, and the mixture was extracted with EtOAc. The organic layer was dried (Na$_2$SO$_4$), concentrated and purified by silica gel chromatography (PE:EtOAc=10:1) to give 3.0 g (43%) of the title compound as a dark green oil. [M+H] Calc'd for C$_{13}$H$_{23}$NOSi, 238; Found, 238.

Preparation 165b methyl 3-({[(1R)-6-{(4-[tert-butyldimethylsilyl)oxy]phenyl}-(methyl)amino)-1,2,3,4-tetrahydronaphthalen-1-yl]methyl}amino)pyridine-4-carboxylate

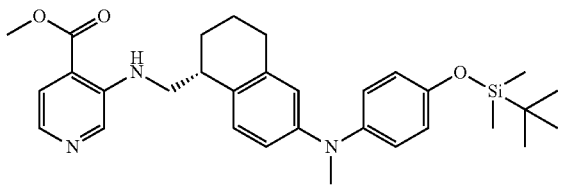 [SMILES: COC(=O)c1ccncc1NC[C@@H]1CCCc2cc(N(C)c3ccc(O[Si](C)(C)C(C)(C)C)cc3)ccc21]

The title compound was prepared in 36% yield from Preparation 122a and 4-((tert-butyldimethylsilyl)oxy)-N-methylaniline according to the general procedure outlined for Preparation 126c. [M+H] Calc'd for C$_{31}$H$_{41}$N$_3$O$_3$Si, 532; Found, 532.

Preparation 165c methyl 3-({[(1R)-6-[(4-hydroxyphenyl)(methyl)amino]-1,2,3,4-tetrahydronaphthalen-1-yl]methyl}amino)pyridine-4-carboxylate

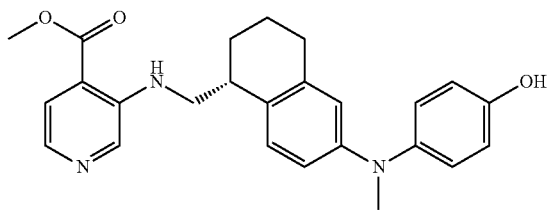 [SMILES: COC(=O)c1ccncc1NC[C@@H]1CCCc2cc(N(C)c3ccc(O)cc3)ccc21]

To a solution of Preparation 165b (733 mg, 1.37 mmol) in THF (10 mL) was added TBAF (3 mL, 3 mmol, 1 M) slowly. The mixture was stirred at r.t. for 20 min. EtOAc (10 mL) and then water (10 mL) was added to the solution. The organic layer was separated, dried over Na$_2$SO$_4$, concentrated, and purified by silica gel chromatography (PE:EtOAc=2:1) to give 576 mg (100%) of the title compound as a yellow oil. [M+H] Calc'd for C$_{25}$H$_{27}$N$_3$O$_3$, 418; Found, 418.

Example 165

3-({[(1R)-6-[(4-hydroxyphenyl)(methyl)amino]-1,2,3,4-tetrahydronaphthalen-1-yl]methyl}amino)pyridine-4-carboxylic acid

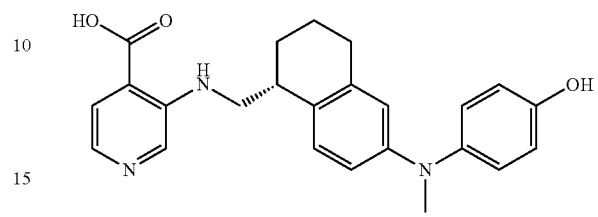

The title compound was prepared in 88% yield from Preparation 165c according to the procedure for Example 1. $^1$H NMR (300 MHz, DMSO-d$_6$): δ 1.59-1.81 (4H, m), 2.48-2.58 (2H, m), 2.92-3.00 (1H, m), 3.10 (3H, s), 3.27-3.51 (2H, m), 6.41 (1H, s), 6.46 (1H, dd, J=8.7, 1.5 Hz), 7.33 (2H, d, J=8.7 Hz), 6.91 (2H, d, J=8.7 Hz), 7.06 (1H, d, J=8.1 Hz), 7.53 (1H, d, J=4.8 Hz), 7.78 (1H, d, J=4.8 Hz), 8.27 (1H, s), 9.26 (1H, br s). [M+H] Calc'd for C$_{24}$H$_{25}$N$_3$O$_3$, 404; Found, 404.

Preparation 166a

N,3,5-trimethyl-1,2-oxazol-4-amine

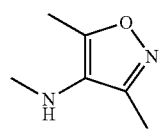

The title compound was prepared in 33% overall yield from dimethyl-1,2-oxazol-4-amine according to the general procedure outlined for Preparation 127a. [M+H] Calc'd for C$_6$H$_{10}$N$_2$O, 127. Found, 127.

Preparation 166b methyl 3-({[(1R)-6-[(dimethyl-1,2-oxazol-4-yl)(methyl)amino]-1,2,3,4-tetrahydronaphthalen-1-yl]methyl}amino)pyridine-4-carboxylate

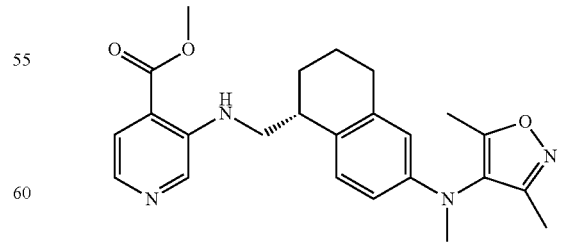

The title compound was prepared in 36% yield from Preparation 122a and N,3,5-trimethyl-1,2-oxazol-4-amine according to the general procedure outlined for Preparation 126c. [M+H] Calc'd for C$_{24}$H$_{28}$N$_4$O$_3$, 421; Found, 421.

Example 166

3-({[(1R)-6-[(dimethyl-1,2-oxazol-4-yl)(methyl)amino]-1,2,3,4-tetrahydronaphthalen-1-yl]methyl}amino)pyridine-4-carboxylic acid

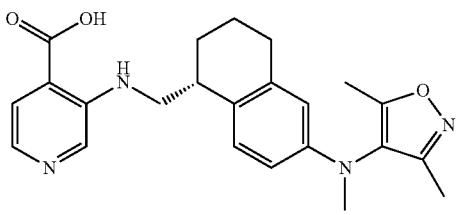 [SMILES: Cc1noc(C)c1N(C)c1ccc2c(c1)CCC[C@H]2CNc1cnccc1C(=O)O]

The title compound was prepared in 91% yield from Preparation 166b according to the procedure for Example 1. $^1$H NMR (300 MHz, DMSO-$d_6$): δ 1.61-1.64 (1H, m), 1.73-1.82 (3H, m), 1.95 (3H, s), 2.19 (3H, s), 2.62-2.66 (2H, m), 2.96-3.00 (1H, m), 3.09 (3H, s), 3.38-3.41 (1H, m), 3.47-3.53 (1H, m), 6.31-6.33 (2H, m), 7.10 (1H, d, J=8.4 Hz), 7.53 (1H, d, J=5.1 Hz), 7.80 (1H, d, J=5.1 Hz), 8.31 (1H, s). [M+H] Calc'd for $C_{23}H_{26}N_4O_3$, 407; Found, 407.

Preparation 167a

N-methyl-4-(pyrrolidin-1-yl)aniline

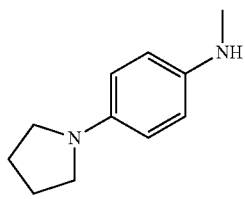

The title compound was prepared in 74% overall yield from 4-(pyrrolidin-1-yl)aniline according to the general procedure outlined for Preparation 127a. [M+H] Calc'd for $C_{11}H_{16}N_2$, 177. Found, 177.

Preparation 167b methyl 3-({[(1R)-6-{methyl[4-(pyrrolidin-1-yl)phenyl]amino}-1,2,3,4-tetrahydronaphthalen-1-yl]methyl}amino)pyridine-4-carboxylate

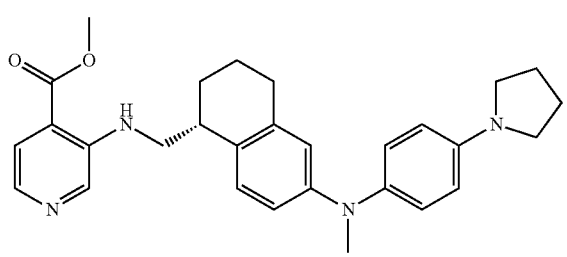

The title compound was prepared in 55% yield from Preparation 122a and N-methyl-4-(pyrrolidin-1-yl)aniline according to the general procedure outlined for Preparation 126c. [M+H] Calc'd for $C_{29}H_{34}N_4O_2$, 471; Found, 471.

Example 167

3-({[(1R)-6-{methyl[4-(pyrrolidin-1-yl)phenyl]amino}-1,2,3,4-tetrahydronaphthalen-1-yl]methyl}amino)pyridine-4-carboxylic acid

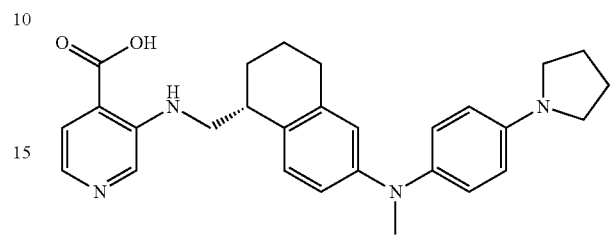

The title compound was prepared in 77% yield from Preparation 167b according to the procedure for Example 1. $^1$H NMR (300 MHz, DMSO-$d_6$): δ 1.58-1.62 (1H, m) 1.69-1.78 (3H, m), 1.89-1.94 (4H, m), 2.55-2.58 (2H, m), 2.92-2.96 (1H, m), 3.09 (3H, s), 3.30-3.33 (4H, m), 3.37-3.43 (1H, m), 3.46-3.49 (1H, m), 6.36 (1H, s), 6.42 (1H, d, J=9.0 Hz), 6.52 (2H, d, J=8.7 Hz), 6.94 (2H, d, J=8.4 Hz), 7.03 (1H, d, J=9.0 Hz), 7.53 (1H, d, J=4.8 Hz), 7.79 (1H, d, J=4.5 Hz), 8.29 (1H, s). [M+H] Calc'd for $C_{28}H_{32}N_4O_2$, 457; Found, 457.

Preparation 168a

[1-(4-bromophenyl)ethoxy](tert-butyl)dimethylsilane

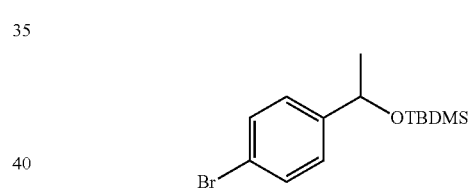

To a solution of 1-(4-bromophenyl)ethan-1-ol (2.8 g, 13.93 mmol) and imidazole (2.84 g, 41.79 mmol) in DMF (35 mL) was added TBDMSCl (4.18 g, 27.86 mmol) at r.t., and the reaction was stirred overnight. The reaction was diluted with water (70 mL) and extracted with EtOAc (50 mL×3). Organics were washed with brine (50 mL), dried (Na$_2$SO$_4$), and concentrated. The residue was purified by silica gel chromatography (PE:EtOAc=100:1) to give 4.08 g (95%) of the title compound as a colorless oil.

Preparation 168b

4-{1-[(tert-butyldimethylsilyl)oxy]ethyl}-N-methylaniline

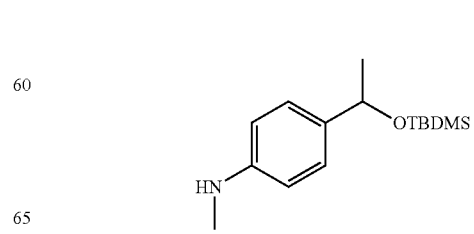

To a suspension of Preparation 168a (1.0 g, 3.18 mmol), KOAc (780 mg, 7.96 mmol), and methylamine (16 mL, 2 M in THF) in DMF (30 mL) was added CuI (728 mg, 3.83 mmol) at r.t. under $N_2$. The reaction vessel was sealed and stirred at 100° C. overnight. After filtration, the solution was diluted with ammonium hydroxide (10 mL) and extracted with EtOAc. The organic layer was concentrated in vacuo, and the residue was purified by silica gel chromatography (PE:EtOAc=5:1) to give 490 mg (58%) of the title compound as a colorless oil. [M+H] Calc'd for $C_{15}H_{27}NOSi$, 266; Found, 266.

Preparation 168c methyl 3-[({6-[(4-{1-[(tert-butyldimethylsilyl)oxy]ethyl}phenyl)-(methyl)amino]-1,2,3,4-tetrahydronaphthalen-1-yl}methyl)amino]pyridine-4-carboxylate

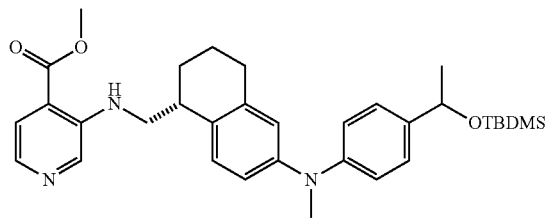 [SMILES: COC(=O)c1ccncc1NC[C@@H]1CCCc2cc(N(C)c3ccc(C(C)O[Si](C)(C)C(C)(C)C)cc3)ccc21]

The title compound was prepared in 32% yield from Preparation 122a and Preparation 168b according to the general procedure outlined for Preparation 126c. [M+H] Calc'd for $C_{33}H_{45}N_3O_3Si$, 560; Found, 560.

Preparation 168d methyl 3-({[6-({4-[(1R)-1-hydroxyethyl]phenyl}(methyl)amino)-1,2,3,4-tetrahydronaphthalen-1-yl]methyl}amino)pyridine-4-carboxylate; and Preparation 169d methyl 3-({[6-({4-[(1S)-1-hydroxyethyl]phenyl}(methyl)amino)-1,2,3,4-tetrahydronaphthalen-1-yl]methyl}amino)pyridine-4-carboxylate

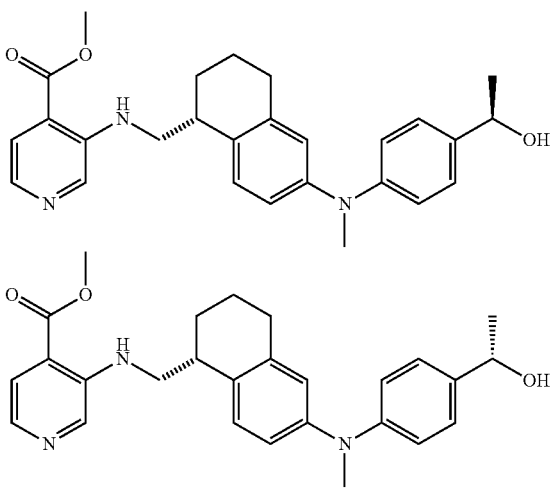

To a solution of Preparation 168c (333 mg, 0.60 mmol) in THF (5 mL) was added TBAF (1.2 mL, 1.0 M in THF, 1.2 mmol) at r.t., and the reaction was stirred for 1 h. The solution was diluted with EtOAc (30 mL) and water (10 mL), and acidified to pH=5 with 5N HCl. This mixture was extracted with EtOAc (50 mL×3), washed with brine (50 mL), dried ($Na_2SO_4$), and concentrated. The residue was purified by silica gel chromatography (PE:EtOAc=1:1) to give 142 mg (54%) of the racemate as a yellow solid. [M+H] Calc'd for $C_{27}H_{31}N_3O_3$, 446; Found, 446.

Separation by chiral prep-HPLC (Column: Chiralcel IA 5 um 4.6*250 mm, Mobile phase: Hex:EtOH=80:20; F: 1.0 mL/min; W: 230 nm; T: 30° C.) gave 50 mg (30%) of Preparation 168d (8.622 min) and 55 mg (33%) of Preparation 169d (9.751 min), each as a yellow solid. Assignment of the hydroxyethyl stereocenter is arbitrary.

Example 168

3-({[6-({4-[(1R)-1-hydroxyethyl]phenyl}(methyl)amino)-1,2,3,4-tetrahydronaphthalen-1-yl]methyl}amino)pyridine-4-carboxylic acid

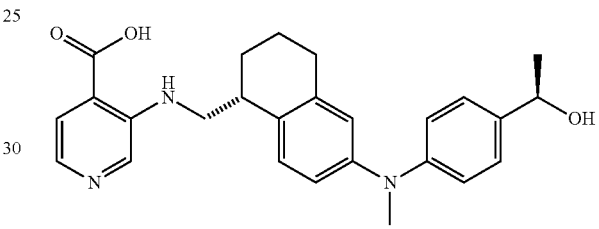

The title compound was prepared in 15% yield from Preparation 168d according to the procedure for Example 1. $^1$H NMR (400 MHz, DMSO-$d_6$): δ1.30 (3H, d, J=6.4 Hz), 1.63-1.67 (1H, m), 1.77-1.84 (3H, m), 2.64-2.67 (2H, m), 3.03-3.05 (1H, m), 3.20 (3H, s), 3.39-3.41 (1H, m), 3.42-3.44 (1H, m), 3.54-3.58 (1H, m), 4.64-4.66 (1H, m), 5.01 (1H, s), 6.71-6.75 (2H, m), 6.92 (2H, d, J=8.0 Hz), 7.19-7.24 (3H, m), 7.56 (1H, d, J=5.2 Hz), 7.82 (1H, d, J=4.8 Hz), 8.33 (1H, s). [M+H] Calc'd for $C_{26}H_{29}N_3O_3$, 432; Found, 432.

Example 169

3-({[6-({4-[(1S)-1-hydroxyethyl]phenyl}(methyl)amino)-1,2,3,4-tetrahydronaphthalen-1-yl]methyl}amino)pyridine-4-carboxylic acid

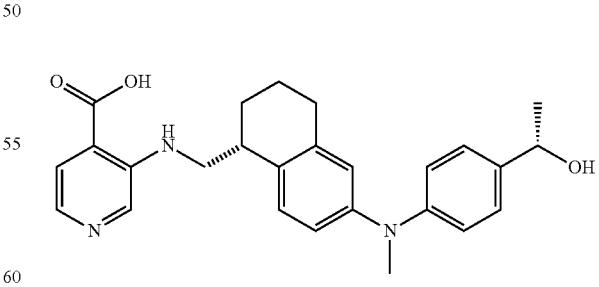

The title compound was prepared in 17% yield from Preparation 169d according to the procedure for Example 1. $^1$H NMR (400 MHz, DMSO-$d_6$): δ1.30 (3H, d, J=6.4 Hz), 1.63-1.67 (1H, m), 1.75-1.82 (3H, m), 2.64-2.67 (2H, m), 2.99-3.04 (1H, m), 3.20 (3H, s), 3.34-3.38 (2H, m), 3.50-3.55 (1H, m), 4.63-4.67 (1H, m), 5.01 (1H, s), 6.71-6.75

(2H, m), 6.92 (2H, d, J=8.4 Hz), 7.20-7.23 (3H, m), 7.57 (1H, d, J=5.2 Hz), 7.78 (1H, d, J=4.8 Hz), 8.24 (1H, s). [M+H] Calc'd for $C_{26}H_{29}N_3O_3$, 432. Found, 432.

Preparation 170a

N-methyl-4-(morpholin-4-yl)aniline

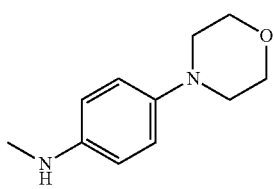

The title compound was prepared in 48% overall yield from 4-(morpholin-4-yl)aniline according to the general procedure outlined for Preparation 127a. [M+H] Calc'd for $C_{11}H_{16}N_2O$, 193. Found, 193.

Preparation 170b methyl 3-({[(1R)-6-{methyl[4-(morpholin-4-yl)phenyl]amino}-1,2,3,4-tetrahydronaphthalen-1-yl]methyl}amino)pyridine-4-carboxylate

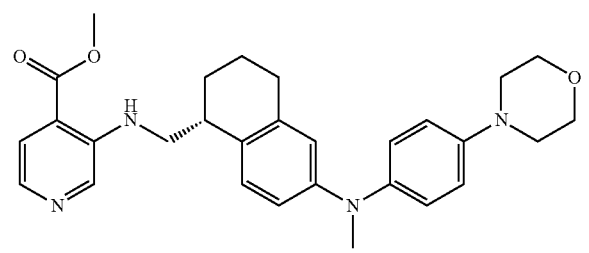

The title compound was prepared in 46% yield from Preparation 122a and N-methyl-4-(morpholin-4-yl)aniline according to the general procedure outlined for Preparation 126c. [M+H] Calc'd for $C_{29}H_{34}N_4O_3$, 487; Found, 487.

Example 170

3-({[(1R)-6-{methyl[4-(morpholin-4-yl)phenyl]amino}-1,2,3,4-tetrahydronaphthalen-1-yl]methyl}amino)pyridine-4-carboxylic acid

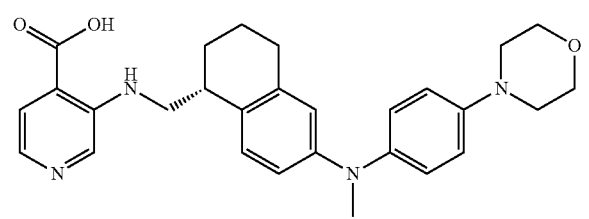 [SMILES: CN(c1ccc(N2CCOCC2)cc1)c1ccc2c(c1)CCC[C@H]2CNc1cnccc1C(=O)O]

The title compound was prepared in 66% yield from Preparation 166b according to the procedure for Example 1. $^1$H NMR (400 MHz, DMSO-d$_6$): δ 1.62-1.63 (1H, m), 1.79-1.80 (3H, m), 2.60-2.63 (2H, m) 2.97-2.99 (1H, m), 3.05-3.07 (4H, m), 3.14 (3H, s), 3.31-3.36 (1H, m), 3.48-3.52 (1H, m), 3.72-3.74 (4H, m), 6.51 (1H, m), 6.55-6.57 (1H, m), 6.91-6.99 (4H, m), 7.11 (1H, d, J=8.4 Hz), 7.56 (1H, d, J=4.8 Hz), 7.79 (1H, d, J=4.8 Hz), 8.26 (1H, s). [M+H] Calc'd for $C_{28}H_{32}N_4O_3$, 473. Found, 473.

Preparation 171a tert-butyl N-{[(1R)-6-[methyl(5-methyl-1,2-oxazol-3-yl)amino]-1,2,3,4-tetrahydronaphthalen-1-yl]methyl}carbamate

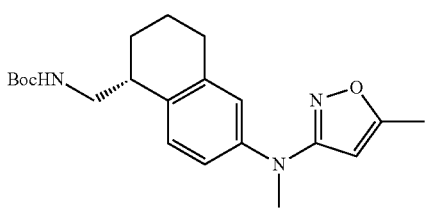 [SMILES: Cc1cc(N(C)c2ccc3c(c2)CCC[C@H]3CNC(=O)OC(C)(C)C)no1]

The title compound was prepared in 55% yield from Preparation 6d and N,5-dimethyl-1,2-oxazol-3-amine according to the general procedure outlined for Preparation 9a. [M+H] Calc'd for $C_{21}H_{29}N_3O_3$, 372; Found, 372.

Preparation 171b

N-[(5R)-5-(aminomethyl)-5,6,7,8-tetrahydronaphthalen-2-yl]-N,5-dimethyl-1,2-oxazol-3-amine

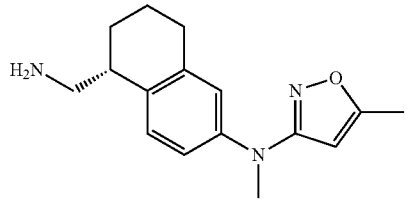 [SMILES: Cc1cc(N(C)c2ccc3c(c2)CCC[C@H]3CN)no1]

The title compound was prepared in quantitative yield from Preparation 171a according to the procedure for Preparation 43b. [M+H] Calc'd for $C_{16}H_{21}N_3O$, 272; Found, 272.

Preparation 171c methyl 3-({[(1R)-6-[methyl(5-methyl-1,2-oxazol-3-yl)amino]-1,2,3,4-tetrahydronaphthalen-1-yl]methyl}amino)pyridine-4-carboxylate

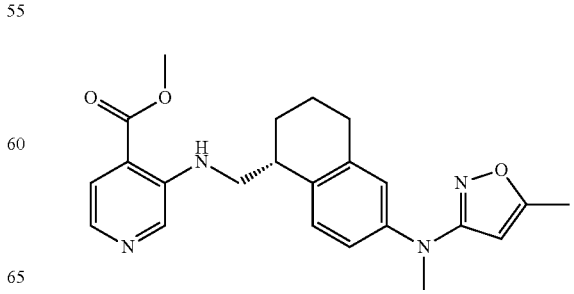

The title compound was prepared in 69% yield from Preparation 171b according to the procedure for Preparation 4d. [M+H] Calc'd for $C_{23}H_{26}N_4O_3$, 407; Found, 407.

Example 171

3-({[(1R)-6-[methyl(5-methyl-1,2-oxazol-3-yl) amino]-1,2,3,4-tetrahydronaphthalen-1-yl] methyl}amino)pyridine-4-carboxylic acid

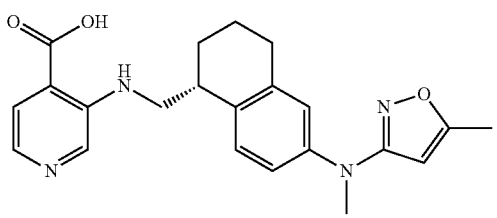 [SMILES: Cc1cc(N(C)c2ccc3c(c2)CCC[C@H]3CNc2cnccc2C(=O)O)no1]

The title compound was prepared in 72% yield from Preparation 171c according to the procedure for Example 1. $^1$H NMR (400 MHz, DMSO-d$_6$): δ 1.67-1.86 (4H, m), 2.26 (3H, s), 2.63-2.71 (2H, m), 3.02-3.11 (1H, m), 3.24 (3H, s), 3.33-3.65 (2H, m), 5.80 (1H, s), 6.98-7.04 (2H, m), 7.31 (1H, d, J=6.1 Hz), 7.66 (1H, d, J=4.4 Hz), 7.87 (1H, d, J=4.4 Hz), 8.39 (1H, s). [M+H] Calc'd for $C_{22}H_{24}N_4O_3$, 393; Found, 393.

Preparation 172a tert-butyl N-{[(1R)-6-[(2-methoxyphenyl)(methyl) amino]-1,2,3,4-tetrahydronaphthalen-1-yl] methyl}carbamate

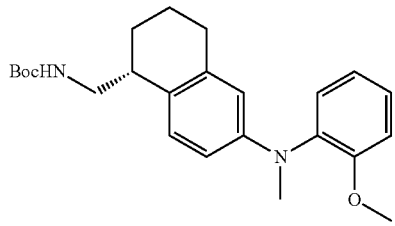 [SMILES: COc1ccccc1N(C)c1ccc2c(c1)CCC[C@H]2CNC(=O)OC(C)(C)C]

The title compound was prepared in 39% yield from Preparation 6d and 2-methoxy-N-methylaniline according to the general procedure outlined for Preparation 9a. [M+H] Calc'd for $C_{24}H_{32}N_2O_3$, 397; Found, 397.

Preparation 172b (5R)-5-(aminomethyl)-N-(2-methoxyphenyl)-N-methyl-5,6,7,8-tetrahydronaphthalen-2-amine

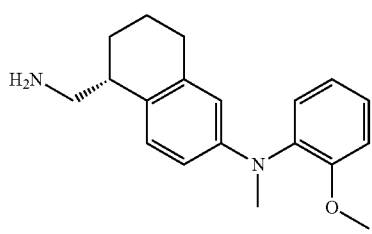 [SMILES: COc1ccccc1N(C)c1ccc2c(c1)CCC[C@H]2CN]

The title compound was prepared in quantitative yield from Preparation 172a according to the procedure for Preparation 43b. [M+H] Calc'd for $C_{19}H_{24}N_2O$, 297; Found, 297.

Preparation 172c methyl 3-({[(1R)-6-[(2-methoxyphenyl)(methyl) amino]-1,2,3,4-tetrahydronaphthalen-1-yl] methyl}amino)pyridine-4-carboxylate

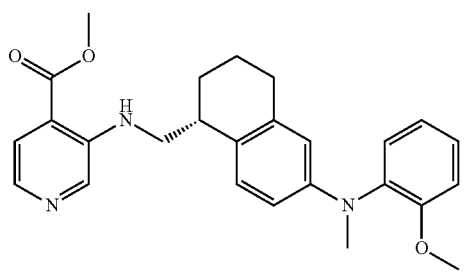 [SMILES: COC(=O)c1ccncc1NC[C@@H]1CCCc2cc(N(C)c3ccccc3OC)ccc21]

The title compound was prepared in 44% yield from Preparation 172b according to the procedure for Preparation 4d. [M+H] Calc'd for $C_{26}H_{29}N_3O_3$, 432; Found, 432.

Example 172

3-({[(1R)-6-[(2-methoxyphenyl)(methyl)amino]-1,2,3,4-tetrahydronaphthalen-1-yl]methyl}amino)pyridine-4-carboxylic acid

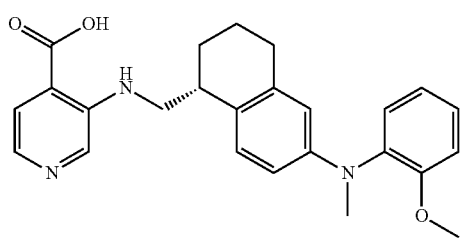 [SMILES: COc1ccccc1N(C)c1ccc2c(c1)CCC[C@H]2CNc1cnccc1C(=O)O]

The title compound was prepared in 47% yield from Preparation 172c according to the procedure for Example 1. $^1$H NMR (400 MHz, DMSO-d$_6$): δ 1.55-1.65 (1H, m), 1.71-1.82 (3H, m), 2.57-2.62 (2H, m), 2.87-2.91 (1H, m), 3.10 (3H, s), 3.25-3.35 (2H, m), 3.73 (3H, s), 6.26-6.31 (2H, m), 6.95-7.15 (4H, m), 7.22-7.29 (1H, m), 7.52 (1H, d, J=4.4 Hz), 7.65 (1H, d, J=4.4 Hz), 7.96 (s, 1H). [M+H] Calc'd for $C_{25}H_{27}N_3O_3$, 418; Found, 418.

Preparation 173a tert-butyl N-{[(1R)-6-[methyl(pyridin-4-yl)amino]-1,2,3,4-tetrahydronaphthalen-1-yl]methyl}carbamate

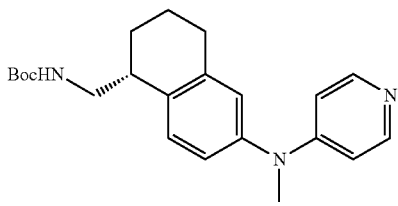 [SMILES: CN(c1ccncc1)c1ccc2c(c1)CCC[C@H]2CNC(=O)OC(C)(C)C]

The title compound was prepared in 59% yield from Preparation 6d and 4-methylaminopyridine according to the general procedure outlined for Preparation 9a. [M+H] Calc'd for $C_{22}H_{29}N_3O_2$, 368; Found, 368.

Preparation 173b

N-[(5R)-5-(aminomethyl)-5,6,7,8-tetrahydronaphthalen-2-yl]-N-methylpyridin-4-amine

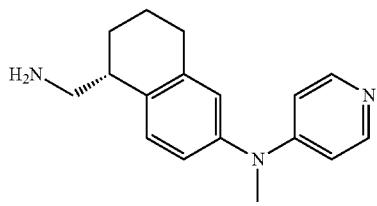 [SMILES: CN(c1ccncc1)c1ccc2c(c1)CCC[C@H]2CN]

The title compound was prepared in quantitative yield from Preparation 173a according to the procedure for Preparation 43b. [M+H] Calc'd for $C_{17}H_{21}N_3$, 268; Found, 268.

Preparation 173c methyl 3-({[(1R)-6-[methyl(pyridin-4-yl)amino]-1,2,3,4-tetrahydronaphthalen-1-yl]methyl}amino)pyridine-4-carboxylate

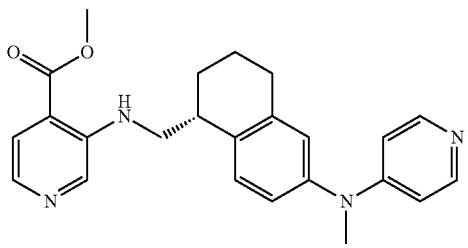 [SMILES: COC(=O)c1ccncc1NC[C@@H]1CCCc2cc(N(C)c3ccncc3)ccc21]

The title compound was prepared in 42% yield from Preparation 173b according to the procedure for Preparation 4d. [M+H] Calc'd for $C_{24}H_{26}N_4O_2$, 403; Found, 403.

Example 173

3-({[(1R)-6-[methyl(pyridin-4-yl)amino]-1,2,3,4-tetrahydro naphthalen-1-yl]methyl}amino)pyridine-4-carboxylic acid

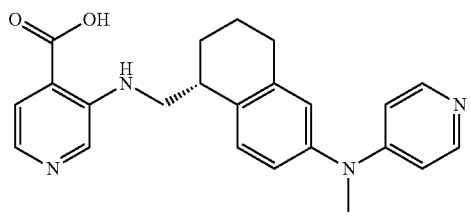 [SMILES: CN(c1ccncc1)c1ccc2c(c1)CCC[C@H]2CNc1cnccc1C(=O)O]

The title compound was prepared in 23% yield from Preparation 173c according to the procedure for Example 1. $^1$H NMR (400 MHz, MeOD): δ 1.75-1.84 (1H, m), 1.96-2.05 (3H, m), 2.78-2.95 (2H, m), 3.27-3.32 (1H, m), 3.49 (3H, s), 3.55-3.60 (2H, m), 6.84-6.87 (2H, m), 7.04 (1H, d, J=8.1 Hz), 7.08 (1H, s), 7.47 (1H, d, J=8.1 Hz), 7.78 (2H, br s), 8.09-8.13 (3H, m). [M+H] Calc'd for $C_{23}H_{24}N_4O_2$, 389; Found, 389.

Preparation 174a 4-(3,6-dihydro-2H-pyran-4-yl)-N-methylaniline

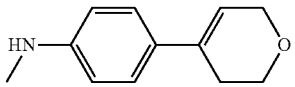

To a solution of 4-(4,4,5,5-tetramethyl-[1,3,2]dioxaborolan-2-yl)-3,6-dihydro-2H-pyran (800 mg, 3.8 mmol), S-Phos (160 mg, 0.38 mmol), Pd$_2$(dba)$_3$ (72 mg, 0.08 mmol), and K$_3$PO$_4$ (96 mg, 3.8 mmol) in toluene/H$_2$O (100 mL/20 mL) was added 4-bromo-N-methylaniline (712 mg, 3.84 mmol) under N$_2$. After stirring at 115° C. overnight, the reaction mixture was filtered and concentrated. The residue was purified by silica gel chromatography (PE:EtOAc=10:1) to give 550 mg (76%) of the title compound as a yellow solid. [M+H] Calc'd for $C_{12}H_{15}NO$, 190; Found, 190.

Preparation 174b methyl 3-({[(1R)-6-{[4-(3,6-dihydro-2H-pyran-4-yl)phenyl](methyl)amino}-1,2,3,4-tetrahydronaphthalen-1-yl]methyl}amino)pyridine-4-carboxylate

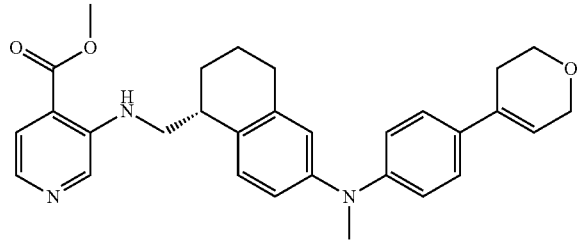 [SMILES: COC(=O)c1ccncc1NC[C@@H]1CCCc2cc(N(C)c3ccc(C4=CCOCC4)cc3)ccc21]

The title compound was prepared in 15% yield from Preparation 122a and 4-(3,6-dihydro-2H-pyran-4-yl)-N-methylaniline according to the general procedure outlined for Preparation 126c. [M+H] Calc'd for $C_{30}H_{33}N_3O_3$, 484; Found, 484.

Example 174

3-({[(1R)-6-{[4-(3,6-dihydro-2H-pyran-4-yl)phenyl](methyl)amino}-1,2,3,4-tetrahydronaphthalen-1-yl]methyl}amino)pyridine-4-carboxylic acid

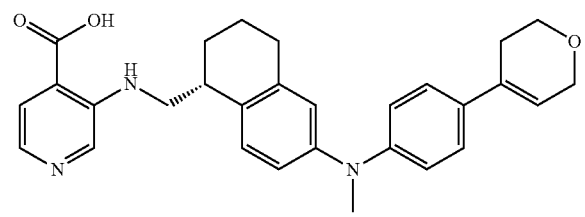 [SMILES: CN(c1ccc(C2=CCOCC2)cc1)c1ccc2c(c1)CCC[C@H]2CNc1cnccc1C(=O)O]

The title compound was prepared in 32% yield from Preparation 174b according to the procedure for Example 1. $^1$H NMR (300 MHz, DMSO-$d_6$): δ 1.62-1.63 (1H, m), 1.75-1.82 (2H, m), 2.38-2.42 (2H, m), 2.67-2.69 (2H, m), 3.05-3.08 (1H, m), 3.20 (3H, s), 3.46-3.49 (2H, m), 3.76-3.84 (4H, m), 4.17-4.18 (2H, m), 6.09 (1H, s), 6.80-6.86 (4H, t, J=9.0 Hz), 7.22-7.24 (1H, d, J=8.1 Hz), 7.28-7.31 (2H, d, J=8.4 Hz), 7.73-7.75 (1H, d, J=5.7 Hz), 7.87-7.89 (1H, d, J=5.1 Hz), 8.39 (1H, s). [M+H] Calc'd for $C_{29}H_{31}N_3O_3$, 470; Found, 470.

Preparation 175a

N-methyl-4-(oxan-4-yl)aniline

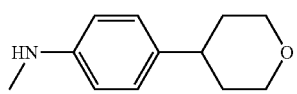

To a solution of compound 4-(3,6-dihydro-2H-pyran-4-yl)-N-methylaniline (200 mg, 1.05 mmol) in EtOAc (20 mL) under $N_2$ was added 10% Pd/C (50 mg) at r.t. The reaction was stirred overnight under 1 atm $H_2$. The reaction was filtered through Celite and concentrated to give 180 mg (89%) as a yellow solid. [M+H] Calc'd for $C_{12}H_{15}NO$, 190; Found, 190.

Preparation 175b methyl 3-({[(1R)-6-{methyl[4-(oxan-4-yl)phenyl]amino}-1,2,3,4-tetrahydronaphthalen-1-yl]methyl}amino)pyridine-4-carboxylate

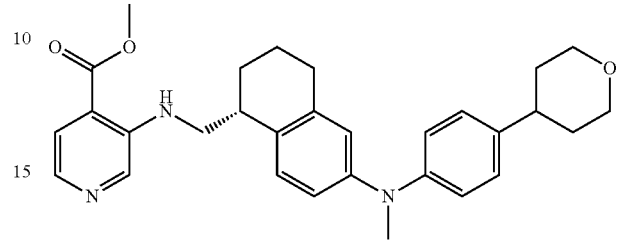

The title compound was prepared in 44% yield from Preparation 122a and N-methyl-4-(oxan-4-yl)aniline according to the general procedure outlined for Preparation 126c. [M+H] Calc'd for $C_{30}H_{35}N_3O_3$, 486; Found, 486.

Example 175

3-({[(1R)-6-{methyl[4-(oxan-4-yl)phenyl]amino}-1,2,3,4-tetrahydronaphthalen-1-yl]methyl}amino)pyridine-4-carboxylic acid

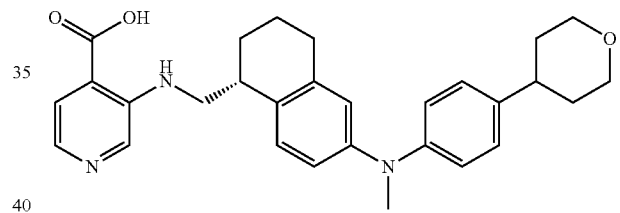

The title compound was prepared in 93% yield from Preparation 175b according to the procedure for Example 1. $^1$H NMR (300 MHz, DMSO-$d_6$): δ 1.57-1.64 (5H, m) 1.75-1.78 (3H, m), 2.62-2.65 (3H, m), 3.00-3.03 (1H, m), 3.17 (3H, s), 3.35-3.44 (3H, m), 3.51-3.53 (1H, m), 3.89-3.93 (2H, m), 6.70-6.73 (2H, m), 6.88 (2H, d, J=8.4 Hz), 7.11 (2H, d, J=8.4 Hz), 7.18 (1H, d, J=8.4 Hz), 7.54 (1H, d, J=5.1 Hz), 7.1 (1H, d, J=5.1 Hz), 8.33 (1H, s). [M+H] Calc'd for $C_{29}H_{33}N_3O_3$, 472; Found, 472.

Preparation 176a 4-ethenyl-N-methylaniline

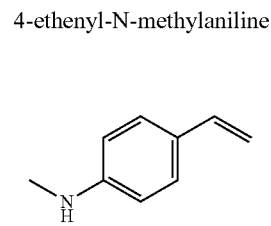

The title compound was prepared in 13% overall yield from 4-ethenylaniline according to the general procedure outlined for Preparation 127a. [M+H] Calc'd for $C_9H_{11}N$, 134; Found, 134.

Preparation 176b methyl 3-({[(4R)-7-[(4-ethenylphenyl)(methyl)amino]-3,4-dihydro-2H-1-benzopyran-4-yl]methyl}amino)pyridine-4-carboxylate

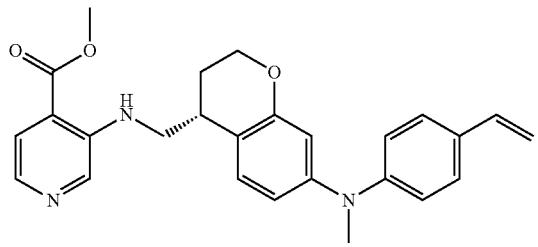 [SMILES: C=Cc1ccc(N(C)c2ccc3c(c2)OCC[C@H]3CNc2cnccc2C(=O)OC)cc1]

The title compound was prepared in 38% yield from Preparation 126b and 4-ethenyl-N-methylaniline according to the general procedure outlined for Preparation 126c. [M+H] Calc'd for $C_{26}H_{27}N_3O_3$, 430; Found, 430.

Example 176

3-({[(4R)-7-[(4-ethenylphenyl)(methyl)amino]-3,4-dihydro-2H-1-benzopyran-4-yl]methyl}amino)pyridine-4-carboxylic acid

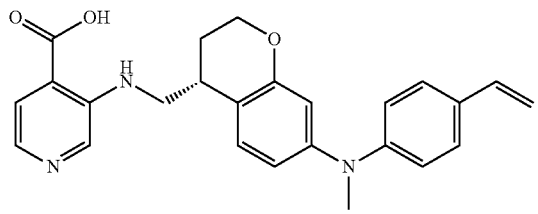 [SMILES: C=Cc1ccc(N(C)c2ccc3c(c2)OCC[C@H]3CNc2cnccc2C(=O)O)cc1]

The title compound was prepared in 98% yield from Preparation 176b according to the procedure for Example 1. $^1$H NMR (300 MHz, DMSO-$d_6$): δ 1.87-1.97 (2H, m), 3.05-3.08 (1H, m), 3.20 (3H, s) 3.42-3.49 (1H, m), 3.63-3.69 (1H, m), 4.11-4.18 (2H, m), 5.06-5.10 (1H, m), 5.60-5.66 (1H, m), 6.42-6.43 (1H, m), 6.53-6.67 (2H, m), 6.90 (2H, d, J=8.4 Hz), 7.21 (1H, d, J=8.1 Hz), 7.33 (2H, d, J=8.7 Hz), 7.55 (1H, d, J=4.8 Hz), 7.82 (1H, d, J=4.8 Hz), 8.36 (1H, s). [M+H] Calc'd for $C_{25}H_{25}N_3O_3$, 416; Found, 416.

Preparation 177a methyl 3-({[(1R)-6-[(4-methoxyphenyl)(methyl)amino]-1,2,3,4-tetrahydronaphthalen-1-yl]methyl}amino)pyridine-4-carboxylate

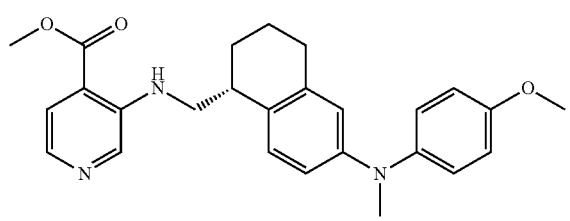

The title compound was prepared in 52% yield from Preparation 122a and 4-methoxy-N-methylaniline according to the general procedure outlined for Preparation 126c. [M+H] Calc'd for $C_{26}H_{29}N_3O_3$, 432; Found, 432.

Example 177

3-({[(1R)-6-[(4-methoxyphenyl)(methyl)amino]-1,2,3,4-tetrahydronaphthalen-1-yl]methyl}amino)pyridine-4-carboxylic acid

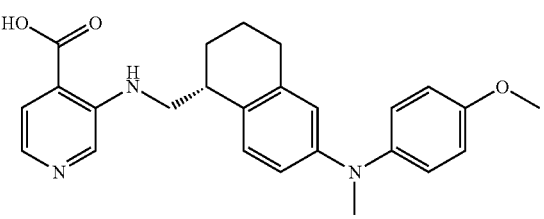 [SMILES: COc1ccc(N(C)c2ccc3c(c2)OCC[C@H]3CNc2cnccc2C(=O)O)cc1]

The title compound was prepared in 84% yield from Preparation 177a according to the procedure for Example 1. $^1$H NMR (300 MHz, DMSO-$d_6$): δ 1.60-1.81 (4H, m), 2.59-2.63 (2H, m), 2.99-3.01 (1H, m), 3.13 (3H, s), 3.37-3.56 (2H, m), 3.72 (3H, s), 6.49-6.54 (2H, m), 6.87-6.90 (2H, m), 6.99-7.02 (2H, m), 7.09 (1H, d, J=8.4 Hz), 7.77 (1H, d, J=5.1 Hz), 7.87 (1H, d, J=5.4 Hz), 8.38 (1H, s). [M+H] Calc'd for $C_{25}H_{27}N_3O_3$, 418; Found, 418.

Preparation 178a methyl 3-({[(4R)-7-[(4-methoxyphenyl)(methyl)amino]-3,4-dihydro-2H-1-benzopyran-4-yl]methyl}amino)pyridine-4-carboxylate

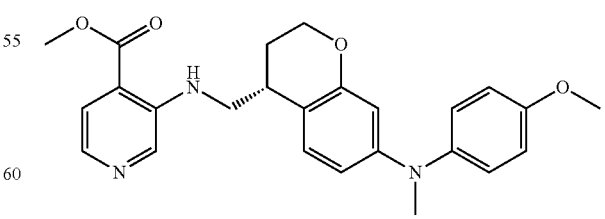

The title compound was prepared in 51% yield from Preparation 126b and 4-methoxy-N-methylaniline according to the general procedure outlined for Preparation 126c. [M+H] Calc'd for $C_{25}H_{27}N_3O_4$, 434; Found, 434.

Example 178

3-({[(4R)-7-[(4-methoxyphenyl)(methyl)amino]-3,4-dihydro-2H-1-benzopyran-4-yl]methyl}amino)pyridine-4-carboxylic acid

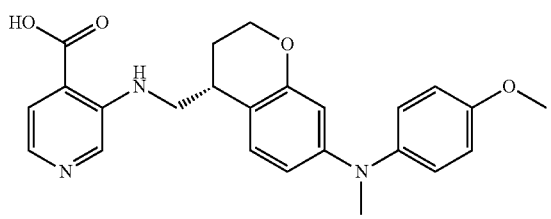

The title compound was prepared in 84% yield from Preparation 178a according to the procedure for Example 1. $^1$H NMR (300 MHz, DMSO-d$_6$): δ 1.80-1.94 (2H, m), 2.97-3.01 (1H, m), 3.11 (3H, s), 3.31-3.38 (1H, m), 3.41-3.46 (1H, m), 3.73 (3H, s), 4.04-4.12 (2H, m), 6.08 (1H, s), 6.22-6.25 (1H, m), 6.89-6.92 (2H, m), 7.02-7.07 (3H, m), 7.56 (1H, d, J=4.8 Hz), 7.82 (1H, d, J=5.1 Hz), 8.37 (1H, s). [M+H] Calc'd for C$_{24}$H$_{25}$N$_3$O$_4$, 420; Found, 420.

Preparation 179a methyl 3-({[(4R)-7-{methyl[4-(pyrrolidin-1-yl)phenyl]amino}-3,4-dihydro-2H-1-benzopyran-4-yl]methyl}amino)pyridine-4-carboxylate

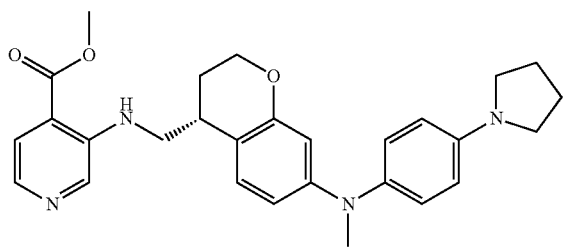 [SMILES: COC(=O)c1ccncc1NC[C@@H]1CCOc2cc(N(C)c3ccc(N4CCCC4)cc3)ccc21]

The title compound was prepared in 35% yield from Preparation 126b and N-methyl-4-(pyrrolidin-1-yl)aniline according to the general procedure outlined for Preparation 126c. [M+H] Calc'd for C$_{28}$H$_{32}$N$_4$O$_3$, 473; Found, 473.

Example 179

3-({[(4R)-7-{methyl[4-(pyrrolidin-1-yl)phenyl]amino}-3,4-dihydro-2H-1-benzopyran-4-yl]methyl}amino)pyridine-4-carboxylic acid

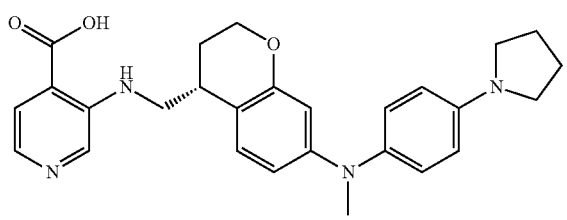 [SMILES: CN(c1ccc(N2CCCC2)cc1)c1ccc2c(c1)OCC[C@H]2CNc1cnccc1C(=O)O]

The title compound was prepared in 87% yield from Preparation 179a according to the procedure for Example 1. $^1$H NMR (300 MHz, DMSO-d$_6$): δ 1.79-1.80 (1H, m), 1.86-1.87 (5H, m), 2.97-2.98 (1H, m), 3.25-3.26 (3H, m), 3.38-3.39 (4H, m), 3.40-3.43 (1H, m), 3.55-3.56 (1H, m), 3.59-3.61 (2H, m), 5.96-5.97 (1H, m) 6.12-6.14 (1H, m), 6.52-6.56 (2H, m), 6.99-7.02 (3H, m), 7.53-7.55 (1H, d, J=4.8 Hz), 7.80-7.82 (1H, d, J=5.1 Hz), 8.36 (1H, s). [M+H] Calc'd for C$_{27}$H$_{30}$N$_4$O$_3$, 459. Found, 459.

Preparation 180a 1-(4-nitrophenyl)azetidine O$_2$N

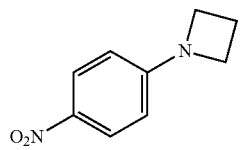

1-Fluoro-4-nitrobenzene (5.0 g, 35.5 mmol) was added to a suspension of azetidine HCl (3.98 g, 42.55 mmol) and K$_2$CO$_3$ (7.34 g, 53.19 mmol) in EtOH (100 mL) at r.t., and the reaction was stirred at 40° C. overnight. The reaction mixture was filtered and concentrated. The residue was purified by silica gel chromatography (PE:EtOAc=10:1) to give compound 700 mg (11%) of the title compound as a yellow solid. [M+H] Calc'd for C$_9$H$_{10}$N$_2$O$_2$, 180; Found, 180.

Preparation 180b 4-(azetidin-1-yl)aniline

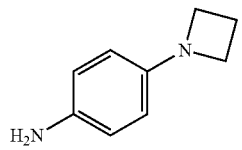 [SMILES: O=[N+]([O-])c1ccc(N2CCC2)cc1]

10% Pd/C (70 mg) was added to a solution of 1-(4-nitrophenyl)azetidine (0.7 g, 3.9 mmol) in EtOH (15 mL) at r.t. under N$_2$. After stirring under 50 psi H$_2$ overnight, the reaction mixture was filtered through Celite and concentrated to give 580 mg (99%) of the title compound as a brown oil. [M+H] Calc'd for C$_9$H$_{12}$N$_2$, 149; Found, 149.

Preparation 180c 4-(azetidin-1-yl)-N-methylaniline

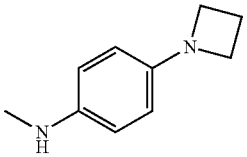

The title compound was prepared in 73% overall yield from 4-(azetidin-1-yl)aniline according to the general procedure outlined for Preparation 127a. [M+H] Calc'd for $C_{10}H_{14}N_2$, 163. Found, 163.

Preparation 180d methyl 3-({[(1R)-6-{[4-(azetidin-1-yl)phenyl](methyl)amino}-1,2,3,4-tetrahydronaphthalen-1-yl]methyl}amino)pyridine-4-carboxylate

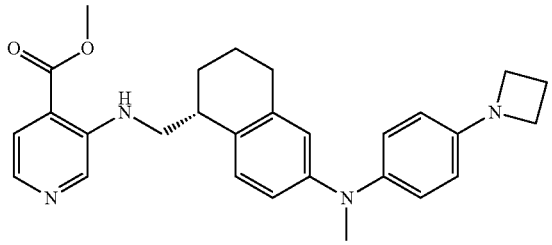 [SMILES: COC(=O)c1ccncc1NC[C@@H]1CCCc2cc(N(C)c3ccc(N4CCC4)cc3)ccc21]

The title compound was prepared in 50% yield from Preparation 122a and 4-(azetidin-1-yl)-N-methylaniline according to the general procedure outlined for Preparation 126c. [M+H] Calc'd for $C_{28}H_{32}N_4O_2$, 457; Found, 457.

Example 180

3-({[(1R)-6-{[4-(azetidin-1-yl)phenyl](methyl)amino}-1,2,3,4-tetrahydronaphthalen-1-yl]methyl}amino)pyridine-4-carboxylic acid

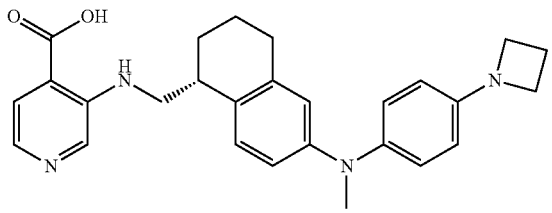 [SMILES: CN(c1ccc(N2CCC2)cc1)c1ccc2c(c1)CCC[C@H]2CNc1cnccc1C(=O)O]

The title compound was prepared in 73% yield from Preparation 180d according to the procedure for Example 1. $^1$H NMR (300 MHz, DMSO-$d_6$): δ 1.59-1.64 (1H, m) 1.70-1.81 (3H, m), 2.24-2.29 (2H, m), 2.56-2.60 (2H, m), 2.95-3.06 (1H, m), 3.11 (3H, s), 3.30-3.42 (1H, m), 3.48-3.52 (1H, m), 3.3-3.79 (4H, m), 6.42-6.45 (4H, m), 6.93-6.95 (2H, m), 7.06-7.08 (1H, m), 7.57 (1H, d, J=4.5 Hz), 7.83 (1H, d, J=5.1 Hz), 8.34 (1H, s). [M+H] Calc'd for $C_{27}H_{30}N_4O_2$, 443; Found, 443.

Preparation 181a

N-methyl-4-(trifluoromethoxy)aniline

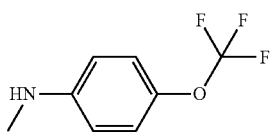

The title compound was prepared in 68% overall yield from 4-(trifluoromethoxy)aniline according to the general procedure outlined for Preparation 127a. [M+H] Calc'd for $C_8H_8F_3NO$, 192. Found, 192.

Preparation 181b methyl 3-({[(1R)-6-{methyl[4-(trifluoromethoxy)phenyl]amino}-1,2,3,4-tetrahydronaphthalen-1-yl]methyl}amino)pyridine-4-carboxylate

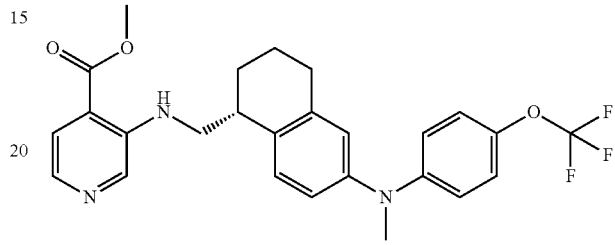

The title compound was prepared in 67% yield from Preparation 122a and N-methyl-4-(trifluoromethoxy)aniline according to the general procedure outlined for Preparation 126c. [M+H] Calc'd for $C_{26}H_{26}F_3N_3O_3$, 486; Found, 486.

Example 181

3-({[(1R)-6-{methyl[4-(trifluoromethoxy)phenyl]amino}-1,2,3,4-tetrahydronaphthalen-1-yl]methyl}amino)pyridine-4-carboxylic acid

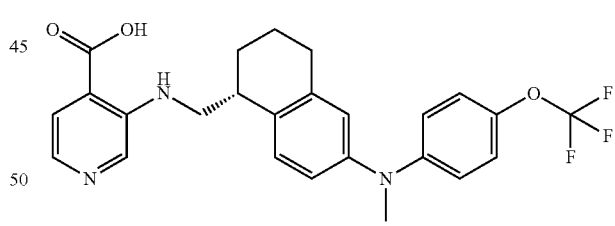

The title compound was prepared in 94% yield from Preparation 181b according to the procedure for Example 1. $^1$H NMR (300 MHz, DMSO-$d_6$): δ 1.63-1.84 (4H, m), 2.65-2.69 (2H, m), 3.18-3.20 (1H, m), 3.25 (3H, s) 3.40-3.47 (1H, m), 3.55-3.61 (1H, m), 6.85-6.88 (4H, m), 7.16 (2H, d, J=8.7 Hz), 7.29 (1H, d, J=8.4 Hz), 7.55 (1H, d, J=5.1 Hz), 7.82 (1H, d, J=5.1 Hz), 8.35 (1H, s). [M+H] Calc'd for $C_{25}H_{24}F_3N_3O_3$, 472; Found, 472.

Preparation 182a methyl 3-({[(4R)-7-{methyl[4-(trifluoromethoxy)phenyl]amino}-3,4-dihydro-2H-1-benzopyran-4-yl]methyl}amino)pyridine-4-carboxylate

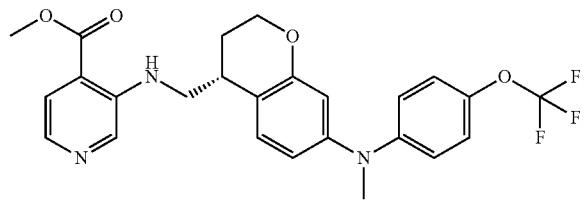 [SMILES: COC(=O)c1ccncc1NC[C@@H]1CCOc2cc(N(C)c3ccc(OC(F)(F)F)cc3)ccc21]

The title compound was prepared in 32% yield from Preparation 126b and N-methyl-4-(trifluoromethoxy)aniline according to the general procedure outlined for Preparation 126c. [M+H] Calc'd for $C_{25}H_{24}F_3N_3O_4$, 488; Found, 488.

Example 182

3-({[(4R)-7-{methyl[4-(trifluoromethoxy)phenyl]amino}-3,4-dihydro-2H-1-benzopyran-4-yl]methyl}amino)pyridine-4-carboxylic acid

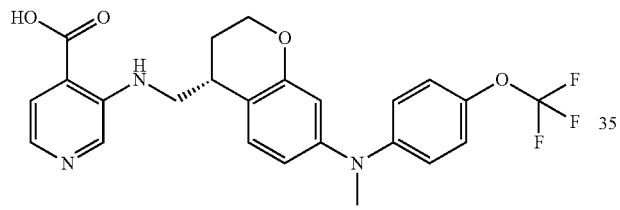

The title compound was prepared in 89% yield from Preparation 182a according to the procedure for Example 1. $^1$H NMR (300 MHz, DMSO-d$_6$): δ 1.87-1.98 (2H, m), 3.05-3.10 (1H, m), 3.24 (3H, s), 3.44-3.51 (1H, m), 3.64-3.70 (1H, m), 4.12-4.19 (2H, m), 6.45 (1H, d, J=2.4 Hz), 6.55-6.59 (1H, m), 6.94-6.96 (2H, m), 7.18-7.26 (3H, m), 7.55 (1H, d, J=5.1 Hz), 7.82 (1H, d, J=5.1 Hz), 8.38 (1H, s). [M+H] Calc'd for $C_{24}H_{22}F_3N_3O_4$, 474; Found, 474.

Preparation 183a methyl 3-({[(4R)-7-{[4-(azetidin-1-yl)phenyl](methyl)amino}-3,4-dihydro-2H-1-benzopyran-4-yl]methyl}amino)pyridine-4-carboxylate

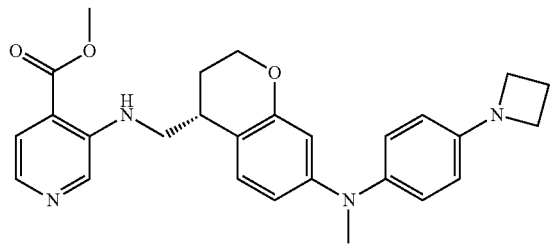 [SMILES: COC(=O)c1ccncc1NC[C@@H]1CCOc2cc(N(C)c3ccc(N4CCC4)cc3)ccc21]

The title compound was prepared in 51% yield from Preparation 126b and 4-(azetidin-1-yl)-N-methylaniline according to the general procedure outlined for Preparation 126c. [M+H] Calc'd for $C_{27}H_{30}N_4O_3$, 459; Found, 459.

Example 183

3-({[(4R)-7-{[4-(azetidin-1-yl)phenyl](methyl)amino}-3,4-dihydro-2H-1-benzopyran-4-yl]methyl}amino)pyridine-4-carboxylic acid

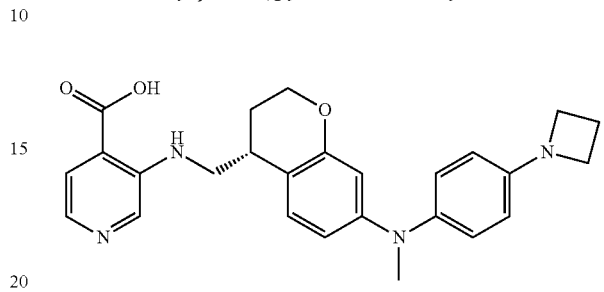

The title compound was prepared in 81% yield from Preparation 183a according to the procedure for Example 1. $^1$H NMR (300 MHz, DMSO-d$_6$): δ 1.82-1.95 (2H, m), 2.24-2.31 (2H, m), 2.94-2.97 (1H, m), 3.07 (3H, s), 3.29-3.37 (1H, m), 3.50-3.58 (1H, m), 3.74-3.79 (4H, m), 4.02-4.13 (2H, m), 5.99 (1H, d, J=2.4 Hz), 6.16 (1H, dd, J=8.7 Hz, 2.4 Hz), 6.40 (2H, d, J=8.4 Hz), 6.94 (2H, d, J=8.7 Hz), 7.03 (1H, d, J=8.4 Hz), 7.54 (1H, d, J=4.8 Hz), 7.77 (1H, d, J=4.8 Hz), 8.25 (1H, s). [M+H] Calc'd for $C_{26}H_{28}N_4O_3$, 445; Found, 445.

Preparation 184a 4-(difluoromethoxy)-N-methylaniline

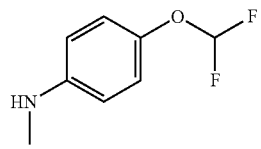

The title compound was prepared in 82% yield from 4-(difluoromethoxy)aniline according to the general procedure outlined for Preparation 127a. $^1$H NMR (400 MHz, CDCl$_3$): δ 2.82 (3H, s), 3.75 (1H, br s), 6.37 (1H, t, J=75.0 Hz), 6.56 (2H, d, J=7.1 Hz), 6.98 (2H, d, J=8.4 Hz). [M+H] Calc'd for $C_8H_9F_2NO$, 174; Found, 174.

Preparation 184b tert-butyl N-{[(1R)-6-{[4-(difluoromethoxy)phenyl](methyl)amino}-1,2,3,4-tetrahydronaphthalen-1-yl]methyl}carbamate

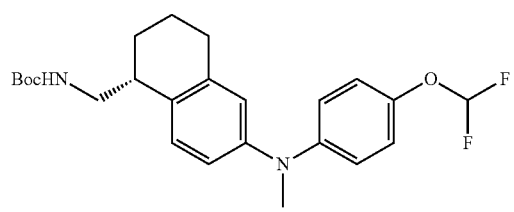 [SMILES: CN(c1ccc(OC(F)F)cc1)c1ccc2c(c1)CCC[C@H]2CNC(=O)OC(C)(C)C]

The title compound was prepared in 59% yield from Preparation 6d and Preparation 184a according to the general procedure outlined for Preparation 9a. [M+H] Calc'd for $C_{24}H_{30}F_2N_2O_3$, 433. Found, 433.

Preparation 184c (5R)-5-(aminomethyl)-N-[4-(difluoromethoxy)phenyl]-N-methyl-5,6,7,8-tetrahydronaphthalen-2-amine

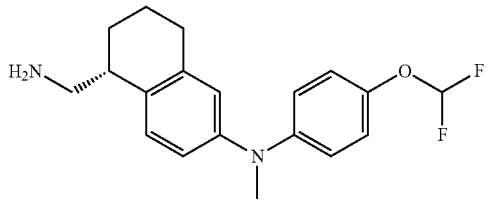 [SMILES: CN(c1ccc(OC(F)F)cc1)c1ccc2c(c1)CCC[C@H]2CN]

The title compound was prepared in quantitative yield from Preparation 184b according to the procedure for Preparation 43b. [M+H] Calc'd for $C_{19}H_{22}F_2N_2O$, 333; Found, 333.

Preparation 184d methyl 3-({[(1R)-6-{[4-(difluoromethoxy)phenyl](methyl)amino}-1,2,3,4-tetrahydronaphthalen-1-yl]methyl}amino)pyridine-4-carboxylate

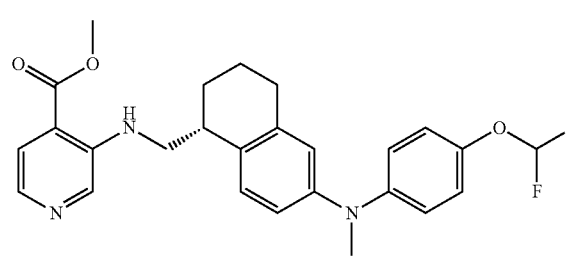

The title compound was prepared in 76% yield from Preparation 184c according to the procedure for Preparation 4d. [M+H] Calc'd for $C_{26}H_{27}F_2N_3O_3$, 468; Found, 468.

Example 184

3-({[(1R)-6-{[4-(difluoromethoxy)phenyl](methyl)amino}-1,2,3,4-tetrahydronaphthalen-1-yl]methyl}amino)pyridine-4-carboxylic acid

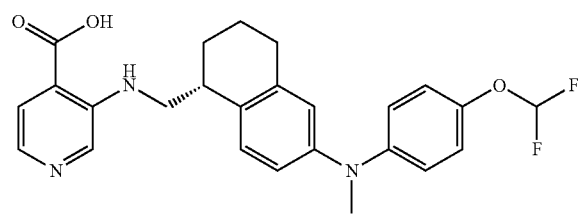

The title compound was prepared in 84% yield from Preparation 184d according to the procedure for Example 1.

$^1$H NMR (400 MHz, DMSO-$d_6$): δ 1.64-1.91 (4H, m), 2.65-2.70 (2H, m), 3.03-3.07 (1H, m), 3.32 (3H, s), 3.40-3.46 (1H, m), 3.54-3.59 (1H, m), 6.76-6.80 (2H, m), 6.90-7.28 (6H, m), 7.56 (1H, d, J=4.5 Hz), 7.77 (1H, br s), 7.82 (1H, d, J=4.5 Hz), 8.33 (1H, s). [M+H] Calc'd for $C_{25}H_{25}F_2N_3O_3$, 454; Found, 454.

Preparation 185a 4-ethoxy-N-methylaniline

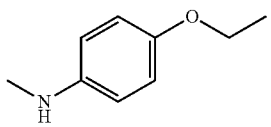

The title compound was prepared in 61% overall yield from 4-ethoxyaniline according to the general procedure outlined for Preparation 127a. [M+H] Calc'd for $C_9H_{13}NO$, 152; Found, 152.

Preparation 185b methyl 3-({[(1R)-6-[(4-ethoxyphenyl)(methyl)amino]-1,2,3,4-tetrahydronaphthalen-1-yl]methyl}amino)pyridine-4-carboxylate

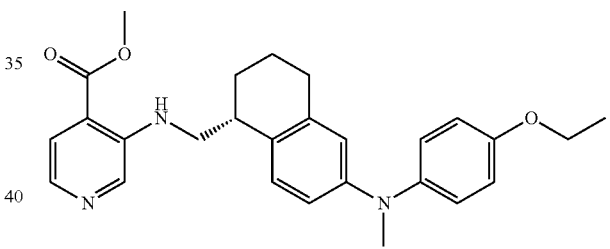

The title compound was prepared in 28% yield from Preparation 122a and 4-ethoxy-N-methylaniline according to the general procedure outlined for Preparation 126c. [M+H] Calc'd for $C_{27}H_{31}N_3O_3$, 446; Found, 446.

Example 185

3-({[(1R)-6-[(4-ethoxyphenyl)(methyl)amino]-1,2,3,4-tetrahydronaphthalen-1-yl]methyl}amino)pyridine-4-carboxylic acid

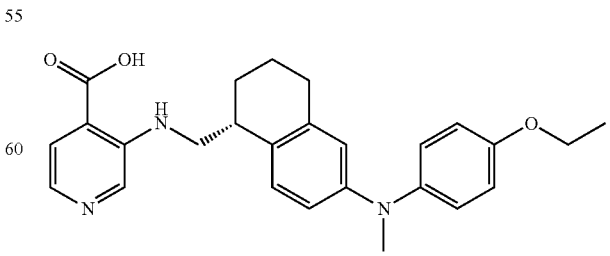

The title compound was prepared in 33% yield from Preparation 185b according to the procedure for Example 1.

¹H NMR (300 MHz, DMSO-d₆): δ 1.32 (3H, t, J=6.9 Hz), 1.62-1.78 (4H, m), 2.62-2.63 (2H, m), 2.95-2.97 (1H, m), 3.15 (3H, s), 3.26-3.33 (1H, m), 3.45-3.51 (1H, m), 3.99 (2H, q, J=6.9 Hz), 6.51-6.57 (2H, m), 6.88 (2H, d, J=8.7 Hz), 7.00 (2H, d, J=8.7 Hz), 7.12 (1H, d, J=8.4 Hz), 7.57 (1H, d, J=5.1 Hz), 7.77 (1H, d, J=5.1 Hz), 8.20 (1H, s). [M+H] Calc'd for $C_{26}H_{29}N_3O_3$, 432. Found, 432.

Preparation 186a methyl 3-({[(4R)-7-[(4-ethoxyphenyl)(methyl)amino]-3,4-dihydro-2H-1-benzopyran-4-yl]methyl}amino)pyridine-4-carboxylate

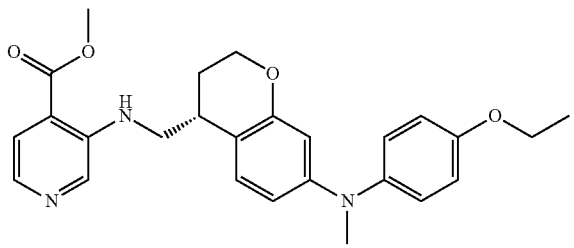 [SMILES: CCOc1ccc(N(C)c2ccc3c(c2)OCC[C@H]3CNc2cnccc2C(=O)OC)cc1]

The title compound was prepared in 58% yield from Preparation 126b and 4-ethoxy-N-methylaniline according to the general procedure outlined for Preparation 126c. [M+H] Calc'd for $C_{26}H_{29}N_3O_4$, 448; Found, 448.

Example 186

3-({[(4R)-7-[(4-ethoxyphenyl)(methyl)amino]-3,4-dihydro-2H-1-benzopyran-4-yl]methyl}amino)pyridine-4-carboxylic acid

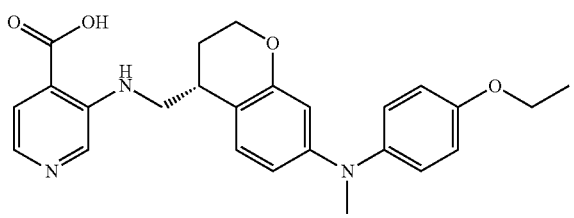 [SMILES: CCOc1ccc(N(C)c2ccc3c(c2)OCC[C@H]3CNc2cnccc2C(=O)O)cc1]

The title compound was prepared in 94% yield from Preparation 186a according to the procedure for Example 1. ¹H NMR (400 MHz, DMSO-d₆): δ 1.32 (3H, t, J=6.8 Hz), 1.81-1.84 (1H, m), 1.92-1.98 (1H, m), 2.99-3.02 (1H, m), 3.13 (3H, s), 3.39-3.45 (1H, m), 3.59-3.63 (1H, m), 4.00 (2H, q, J=6.8 Hz), 4.06-4.16 (2H, m), 6.10 (1H, d, J=2.0 Hz), 6.25 (2H, dd, J=8.8 Hz, 2.0 Hz), 6.91 (2H, d, J=8.8 Hz), 7.04 (2H, d, J=8.8 Hz), 7.07 (2H, d, J=8.8 Hz), 7.03-7.09 (3H, m), 7.56 (1H, d, J=4.8 Hz), 7.83 (1H, d, J=4.8 Hz), 8.37 (1H, s). [M+H] Calc'd for $C_{25}H_{27}N_3O_4$, 434; Found, 434.

Preparation 187a

N-methyl-4-(propan-2-yl)aniline

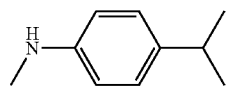

A mixture of 1-bromo-4-isopropylbenzene (1.0 g, 5.03 mmol), methylamine (25 mL, 50.0 mmol), CuI (1.15 g, 6.0 mmol), KOAc (1.24 g, 12.6 mmol) and DMF (30 mL) in a sealed tube under $N_2$ was heated to 100° C. overnight. The mixture was cooled to r.t., diluted with water (100 mL), and extracted with EtOAc. The organic layer was dried ($Na_2SO_4$), concentrated, and purified by silica gel chromatography (PE:EtOAc=10:1) to give 254 mg (34%) of the title compound as a yellow oil. [M+H] Calc'd for $C_{10}H_{15}N$, 150; Found, 150.

Preparation 187b methyl 3-({[(4R)-7-{methyl[4-(propan-2-yl)phenyl]amino}-3,4-dihydro-2H-1-benzopyran-4-yl]methyl}amino)pyridine-4-carboxylate

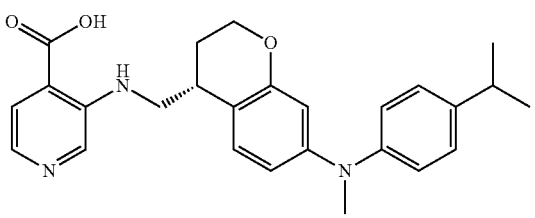 [SMILES: CC(C)c1ccc(N(C)c2ccc3c(c2)OCC[C@H]3CNc2cnccc2C(=O)O)cc1]

The title compound was prepared in 57% yield from Preparation 126b and N-methyl-4-(propan-2-yl)aniline according to the general procedure outlined for Preparation 126c. [M+H] Calc'd for $C_{27}H_{31}N_3O_3$, 446; Found, 446.

Example 187

3-({[(4R)-7-{methyl[4-(propan-2-yl)phenyl]amino}-3,4-dihydro-2H-1-benzopyran-4-yl]methyl}amino)pyridine-4-carboxylic acid

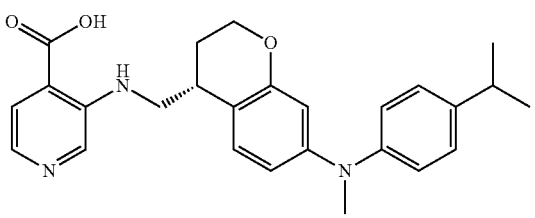 [SMILES: CC(C)c1ccc(N(C)c2ccc3c(c2)OCC[C@H]3CNc2cnccc2C(=O)O)cc1]

The title compound was prepared in 90% yield from Preparation 187b according to the procedure for Example 1. ¹H NMR (400 MHz, DMSO-d₆): δ 1.19 (6H, d, J=6.8 Hz), 1.83-1.99 (2H, m), 2.81-2.88 (1H, m), 3.02-3.05 (1H, m), 3.17 (3H, s), 3.44-3.48 (1H, m), 3.62-3.66 (1H, m), 4.09-

4.19 (2H, m), 6.25 (1H, d, J=1.6 Hz), 6.40 (1H, dd, J=8.4 Hz, 1.6 Hz), 6.97 (2H, d, J=8.0 Hz), 7.13 (1H, d, J=8.4 Hz), 7.17 (2H, d, J=8.0 Hz), 7.57 (1H, d, J=5.2 Hz), 7.83 (1H, d, J=5.2 Hz), 8.38 (1H, s). [M+H] Calc'd for $C_{26}H_{29}N_3O_3$, 432; Found, 432.

Preparation 188a

N-methyl-4-(1H-pyrazol-1-yl)aniline

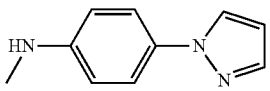

The title compound was prepared in 98% overall yield from 4-(1H-pyrazol-1-yl)aniline according to the general procedure outlined for Preparation 127a. [M+H] Calc'd for $C_{10}H_{11}N_3$, 174. Found, 174.

Preparation 188b methyl 3-({[(1R)-6-{methyl[4-(1H-pyrazol-1-yl)phenyl]amino}-1,2,3,4-tetrahydronaphthalen-1-yl]methyl}amino)pyridine-4-carboxylate

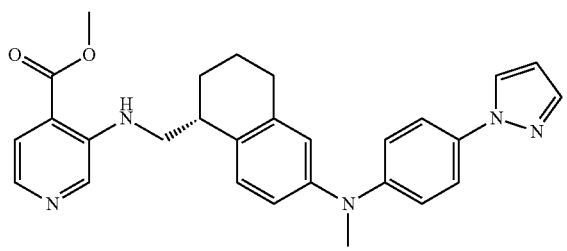 [SMILES: COC(=O)c1ccncc1NC[C@@H]1CCCc2cc(N(C)c3ccc(-n4cccn4)cc3)ccc21]

The title compound was prepared in 32% yield from Preparation 122a and N-methyl-4-(1H-pyrazol-1-yl)aniline according to the general procedure outlined for Preparation 126c. [M+H] Calc'd for $C_{28}H_{29}N_5O_2$, 468; Found, 468.

Example 188

3-({[(1R)-6-{methyl[4-(1H-pyrazol-1-yl)phenyl]amino}-1,2,3,4-tetrahydronaphthalen-1-yl]methyl}amino)pyridine-4-carboxylic acid

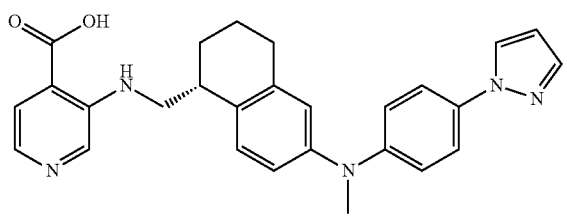 [SMILES: CN(c1ccc(-n2cccn2)cc1)c1ccc2c(c1)CCC[C@H]2CNc1cnccc1C(=O)O]

The title compound was prepared in 57% yield from Preparation 188b according to the procedure for Example 1. $^1$H NMR (400 MHz, DMSO-$d_6$): δ 1.64-1.69 (1H, m), 1.79-1.85 (3H, m), 2.67-2.70 (2H, m), 3.07-3.08 (1H, m), 3.26 (3H, s), 3.42-3.47 (1H, m), 3.57-3.61 (1H, m), 6.49 (1H, s), 6.84 (1H, s), 6.86 (1H, d, J=8.4 Hz), 6.99 (2H, d, J=8.8 Hz), 7.27 (1H, d, J=8.4 Hz), 7.57 (1H, d, J=4.8 Hz), 7.66 (2H, d, J=8.8 Hz), 7.68 (1H, s), 7.83 (1H, d, J=4.8 Hz), 8.35 (2H, s). [M+H] Calc'd for $C_{27}H_{27}N_5O_2$, 454; Found, 454.

Preparation 189a methyl 3-({[(4R)-7-{methyl[4-(1H-pyrazol-1-yl)phenyl]amino}-3,4-dihydro-2H-1-benzopyran-4-yl]methyl}amino)pyridine-4-carboxylate

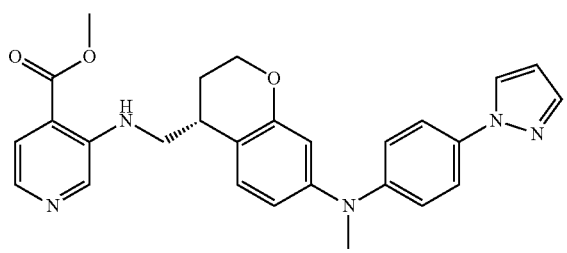 [SMILES: COC(=O)c1ccncc1NC[C@@H]1CCOc2cc(N(C)c3ccc(-n4cccn4)cc3)ccc21]

The title compound was prepared in 52% yield from Preparation 126b and N-methyl-4-(1H-pyrazol-1-yl)aniline according to the general procedure outlined for Preparation 126c. [M+H] Calc'd for $C_{27}H_{27}N_5O_3$, 470; Found, 470.

Example 189

3-({[(4R)-7-{methyl[4-(1H-pyrazol-1-yl)phenyl]amino}-3,4-dihydro-2H-1-benzopyran-4-yl]methyl}amino)pyridine-4-carboxylic acid

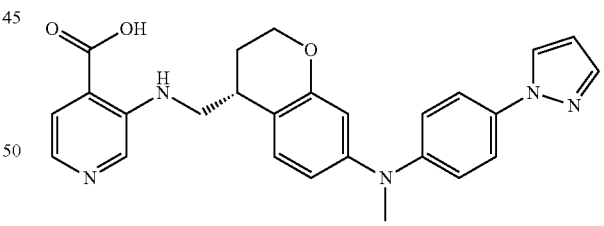

The title compound was prepared in 83% yield from Preparation 189a according to the procedure for Example 1. $^1$H NMR (400 MHz, DMSO-$d_6$): δ 1.85-1.90 (1H, m), 1.97-2.02 (1H, m), 3.07-3.10 (1H, m), 3.24 (3H, s), 3.46-3.52 (1H, m), 3.66-3.71 (1H, m), 4.11-4.22 (2H, m), 6.43 (1H, s), 6.50 (1H, s), 6.55 (1H, d, J=8.4 Hz), 7.08 (2H, d, J=8.8 Hz), 7.23 (1H, d, J=8.4 Hz), 7.57 (1H, d, J=5.2 Hz), 7.69 (1H, s), 7.70 (2H, d, J=8.8 Hz), 7.85 (1H, d, J=5.2 Hz), 8.38 (1H, s), 8.41 (1H, s). [M+H] Calc'd for $C_{26}H_{25}N_5O_3$, 456; Found, 456.

Preparation 190a

4-(difluoromethoxy)-N-methylaniline

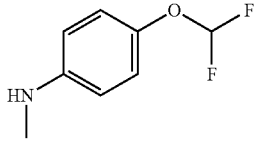

The title compound was prepared in 29% overall yield from 4-(difluoromethoxy)aniline according to the general procedure outlined for Preparation 127a. [M+H] Calc'd for $C_8H_9F_2NO$, 174. Found, 174.

Preparation 190b methyl 3-({[(4R)-7-{[4-(difluoromethoxy)phenyl](methyl)amino}-3,4-dihydro-2H-1-benzopyran-4-yl]methyl}amino)pyridine-4-carboxylate

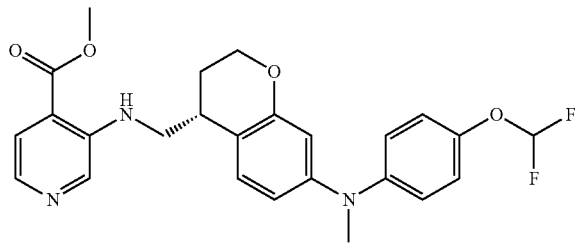

The title compound was prepared in 75% yield from Preparation 126b and 4-(difluoromethoxy)-N-methylaniline according to the general procedure outlined for Preparation 126c. [M+H] Calc'd for $C_{25}H_{25}F_2N_3O_4$, 470; Found, 470.

Example 190

3-({[(4R)-7-{[4-(difluoromethoxy)phenyl](methyl)amino}-3,4-dihydro-2H-1-benzopyran-4-yl]methyl}amino)pyridine-4-carboxylic acid

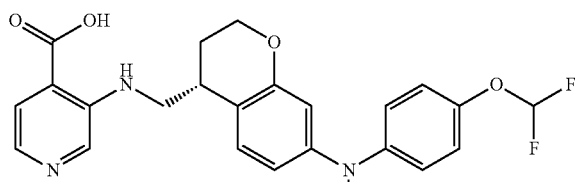

The title compound was prepared in 89% yield from Preparation 190b according to the procedure for Example 1. $^1$H NMR (400 MHz, DMSO-$d_6$): δ 1.83-1.87 (1H, m), 1.94-2.01 (1H, m), 3.04-3.08 (1H, m), 3.19 (3H, s), 3.43-3.49 (1H, m), 3.63-3.68 (1H, m), 4.10-4.20 (2H, m), 6.34 (1H, s), 6.47 (1H, d, J=8.0 Hz), 7.03 (2H, d, J=8.8 Hz), 7.10 (2H, d, J=8.8 Hz), 7.13 (1H, t, J=74.8 Hz), 7.19 (1H, d, J=8.8 Hz), 7.57 (1H, d, J=4.8 Hz), 7.83 (1H, d, J=4.8 Hz), 8.38 (1H, s). [M+H] Calc'd for $C_{24}H_{23}F_2N_3O_4$, 456; Found, 456.

Preparation 191a tert-butyl N-{[(1R)-6-[methyl(phenyl)amino]-1,2,3,4-tetrahydronaphthalen-1-yl]methyl}carbamate

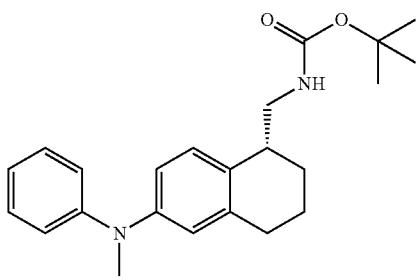 [SMILES: CN(c1ccccc1)c1ccc2c(c1)CCC[C@H]2CNC(=O)OC(C)(C)C]

The title compound was prepared in 69% yield from Preparation 6d and N-methylaniline according to the general procedure for Preparation 9a. [M+H] Calc'd for $C_{23}H_{30}N_2O_2$, 367; Found, 367.

Preparation 191b

(5R)-5-(aminomethyl)-N-methyl-N-phenyl-5,6,7,8-tetrahydronaphthalen-2-amine

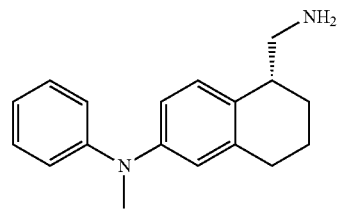 [SMILES: CN(c1ccccc1)c1ccc2c(c1)CCC[C@H]2CN]

The title compound was prepared in 96% yield from Preparation 191a according to the procedure for Preparation 43b. [M+H] Calc'd for $C_{18}H_{22}N_2$, 267; Found, 267.

Preparation 191c

6-chloro-3-({[(1R)-6-[methyl(phenyl)amino]-1,2,3,4-tetrahydronaphthalen-1-yl]methyl}amino)pyridazine-4-carboxylic acid

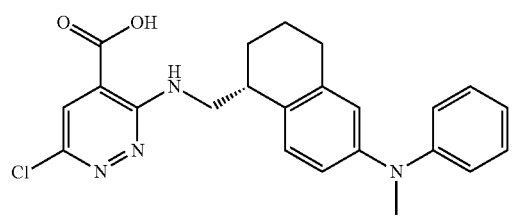 [SMILES: CN(c1ccccc1)c1ccc2c(c1)CCC[C@H]2CNc1nnc(Cl)cc1C(=O)O]

A 0.3 M solution of Preparation 191b (132 mg, 0.5 mmol) in 1-butanol was combined with 3,6-dichloropyridazine-4-carboxylic acid (97 mg, 0.5 mmol) and DIEA (304 μL, 1.8 mmol). The reaction mixture was capped and heated to 80° C. for 14 h. The mixture was diluted with water (10 mL) and extracted with EtOAc (3×15 mL). The combined organic layers were washed with saturated bicarbonate solution (30 mL) and brine (30 mL), dried (Na$_2$SO$_4$), filtered, and concentrated in vacuo. The resulting orange solid (190 mg) was carried forward without any further purification. $^1$H NMR (400 MHz, DMSO-d$_6$) δ 1.59-1.90 (m, 4 H) 2.62-2.73 (m, 2 H) 3.10-3.17 (m, 1 H) 3.22 (s, 3 H) 3.56-3.69 (m, 1 H) 3.80-3.92 (m, 1 H) 6.76-6.94 (m, 5 H) 7.19-7.27 (m, 3 H) 7.75-7.79 (m, 1 H) 8.15-8.28 (m, 1 H). [M+H] Calc'd for C$_{23}$H$_{23}$ClN$_4$O$_2$, 423; Found, 423.

Example 191

3-({[(1R)-6-[methyl(phenyl)amino]-1,2,3,4-tetrahydronaphthalen-1-yl]methyl}amino)pyridazine-4-carboxylic acid

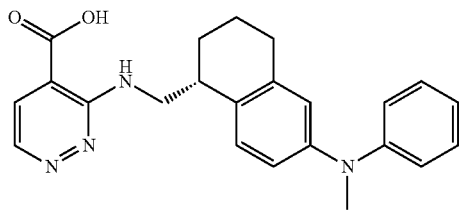 [SMILES: CN(c1ccccc1)c1ccc2c(c1)CCC[C@H]2CNc1nnccc1C(=O)O]

A solution of Preparation 191c (171 mg, 0.4 mmol) in MeOH (7.1 mL) was treated with ammonium formate (51 mg, 0.8 mmol), and 10% Pd/C (Degussa) (25 mg). The reaction mixture was heated to 50° C. using microwave irradiation for 2 h. The crude reaction mixture was filtered through a short plug of Celite, washing with MeOH (~30 mL). The resulting filtrate was concentrated in vacuo. The residue was diluted with EtOAc (25 ml), washed with water, dried (MgSO$_4$), filtered, and concentrated in vacuo. The resulting residue was purified by prep-HPLC to give 21 mg (14%) of the title compound as a tan solid. $^1$H NMR (400 MHz, DMSO-d$_6$) δ 1.61-1.91 (m, 4 H) 2.61-2.74 (m, 2 H) 3.06-3.18 (m, 1 H) 3.22 (s, 3 H) 3.53-3.68 (m, 1 H) 3.85-3.96 (m, 1 H) 6.75-6.89 (m, 3 H) 6.89-6.95 (m, 2 H) 7.19-7.28 (m, 3 H) 7.67-7.75 (m, 1 H) 8.10-8.17 (m, 1 H) 8.57-8.63 (m, 1 H). [M+H] Calc'd for C$_{23}$H$_{24}$N$_4$O$_2$, 389; Found, 389.

Preparation 192a

N-methyl-4-(2,2,2-trifluoroethyl)aniline

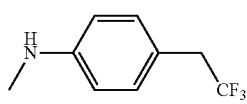

The title compound was prepared in 77% yield from 1-bromo-4-(2,2,2-trifluoroethyl)benzene according to the procedure Preparation 187a. [M+H] Calc'd for C$_9$H$_{10}$F$_3$N, 190. Found, 190.

Preparation 192b methyl 3-({[(4R)-7-{methyl[4-(2,2,2-trifluoroethyl)phenyl]amino}-3,4-dihydro-2H-1-benzopyran-4-yl]methyl}amino)pyridine-4-carboxylate

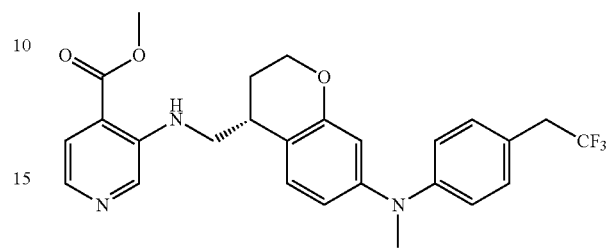

The title compound was prepared in 47% yield from Preparation 126b and N-methyl-4-(2,2,2-trifluoroethyl)aniline according to the general procedure outlined for Preparation 126c. [M+H] Calc'd for C$_{26}$H$_{26}$F$_3$N$_3$O$_3$, 486; Found, 486.

Example 192

3-({[(4R)-7-{methyl[4-(2,2,2-trifluoroethyl)phenyl]amino}-3,4-dihydro-2H-1-benzopyran-4-yl]methyl}amino)pyridine-4-carboxylic acid

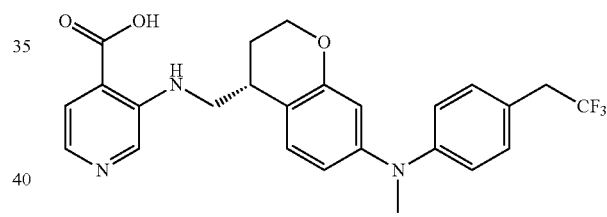

The title compound was prepared in 88% yield from Preparation 192b according to the procedure for Example 1. $^1$H NMR (300 MHz, DMSO-d$_6$): δ 1.84-1.88 (1H, m), 1.95-2.02 (1H, m), 3.06-3.10 (1H, m), 3.20 (3H, s), 3.46-3.58 (3H, m), 3.66-3.70 (1H, m), 4.11-4.22 (2H, m), 6.42 (1H, s), 6.54 (1H, d, J=8.8 Hz), 6.95 (2H, d, J=8.0 Hz), 7.20-7.23 (3H, m), 7.57 (1H, d, J=4.8 Hz), 7.85 (1H, d, J=4.8 Hz), 8.40 (1H, s). [M+H] Calc'd for C$_{25}$H$_{24}$F$_3$N$_3$O$_3$, 472; Found, 472.

Preparation 193a 4-(1H-imidazol-1-yl)-N-methylaniline

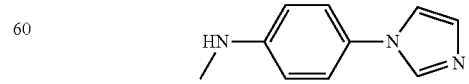

The title compound was prepared in 33% overall yield from 4-(1H-imidazol-1-yl)aniline according to the general procedure outlined for Preparation 127a. [M+H] Calc'd for C$_{10}$H$_{11}$N$_3$, 174. Found, 174.

Preparation 193b methyl 3-({[(1R)-6-{[4-(1H-imidazol-1-yl)phenyl](methyl)amino}-1,2,3,4-tetrahydronaphthalen-1-yl]methyl}amino)pyridine-4-carboxylate

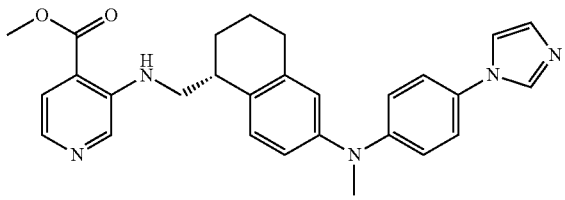 [SMILES: COC(=O)c1ccncc1NC[C@@H]1CCCc2cc(N(C)c3ccc(-n4ccnc4)cc3)ccc21]

The title compound was prepared in 43% yield from Preparation 122a and 4-(1H-imidazol-1-yl)-N-methylaniline according to the general procedure outlined for Preparation 126c. [M+H] Calc'd for $C_{28}H_{29}N_5O_2$, 468; Found, 468.

Example 193

3-({[(1R)-6-{[4-(1H-imidazol-1-yl)phenyl](methyl)amino}-1,2,3,4-tetrahydronaphthalen-1-yl]methyl}amino)pyridine-4-carboxylic acid

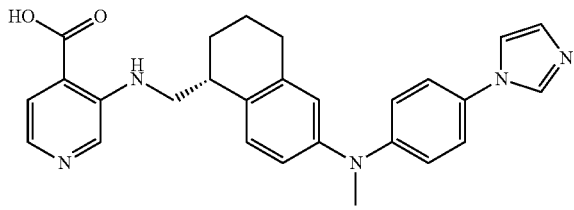 [SMILES: CN(c1ccc(-n2ccnc2)cc1)c1ccc2c(c1)CCC[C@H]2CNc1cnccc1C(=O)O]

The title compound was prepared in 82% yield from Preparation 193b according to the procedure for Example 1. $^1$H NMR (300 MHz, DMSO-d$_6$): δ 1.64-1.69 (1H, m), 1.79-1.85 (3H, m), 2.66-2.71 (2H, m), 3.07-3.08 (1H, m), 3.26 (3H, s), 3.39-3.44 (1H, m), 3.56-3.60 (1H, m), 6.86-6.90 (2H, m), 6.97-6.99 (2H, m), 7.07 (1H, s), 7.30 (1H, d, J=6.3 Hz), 7.46 (2H, d, J=6.3 Hz), 7.57-7.62 (2H, m), 7.81 (1H, d, J=3.6 Hz), 8.11 (1H, s), 8.31 (1H, s). [M+H] Calc'd for $C_{27}H_{27}N_5O_2$, 454; Found, 454.

Preparation 194 a: methyl 3-({[(4R)-7-{[4-(1H-imidazol-1-yl)phenyl](methyl)amino}-3,4-dihydro-2H-1-benzopyran-4-yl]methyl}amino)pyridine-4-carboxylate

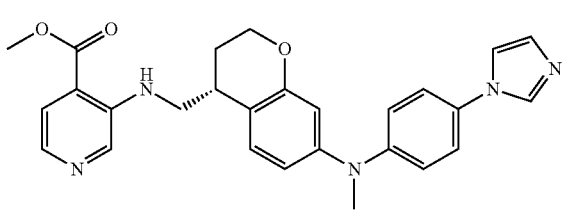 [SMILES: COC(=O)c1ccncc1NC[C@@H]1CCOc2cc(N(C)c3ccc(-n4ccnc4)cc3)ccc21]

The title compound was prepared in 72% yield from Preparation 126b and 4-(1H-imidazol-1-yl)-N-methylaniline according to the general procedure outlined for Preparation 126c. [M+H] Calc'd for $C_{27}H_{27}N_5O_3$, 470; Found, 470.

Example 194

3-({[(4R)-7-{[4-(1H-imidazol-1-yl)phenyl](methyl)amino}-3,4-dihydro-2H-1-benzopyran-4-yl]methyl}amino)pyridine-4-carboxylic acid

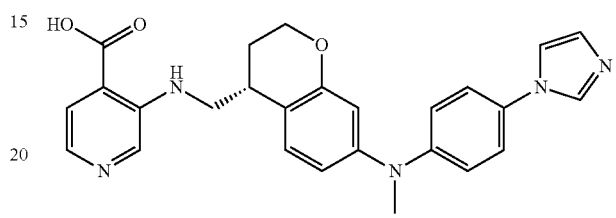

The title compound was prepared in 81% yield from Preparation 194a according to the procedure for Example 1. $^1$H NMR (300 MHz, DMSO-d$_6$): δ 1.87-1.90 (1H, m), 1.98-2.00 (1H, m), 3.06-3.09 (1H, m), 3.25 (3H, s), 3.43-3.48 (1H, m), 3.64-3.69 (1H, m), 4.13-4.20 (2H, m), 6.46 (1H, s), 6.58 (1H, d, J=6.0 Hz), 7.04-7.08 (3H, m), 7.25 (1H, d, J=6.3 Hz), 7.50 (2H, d, J=6.3 Hz), 7.58 (1H, d, J=3.6 Hz), 7.64 (1H, s), 7.82 (1H, d, J=3.3 Hz), 8.13 (1H, s), 8.35 (1H, s). [M+H] Calc'd for $C_{26}H_{25}N_5O_3$, 456; Found, 456.

Preparation 195a 4-(3,3-difluoroazetidin-1-yl)-N-methylaniline

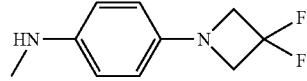

The title compound was prepared in 10% overall yield from 3,3-difluoroazetidine hydrochloride according to the general scheme outlined for Preparations 180a, 180b, and 180c. [M+H] Calc'd for $C_{10}H_{12}F_2N_2$, 199; Found, 199.

Preparation 195b methyl 3-({[(1R)-6-{[4-(3,3-difluoroazetidin-1-yl)phenyl](methyl)amino}-1,2,3,4-tetrahydronaphthalen-1-yl]methyl}amino)pyridine-4-carboxylate

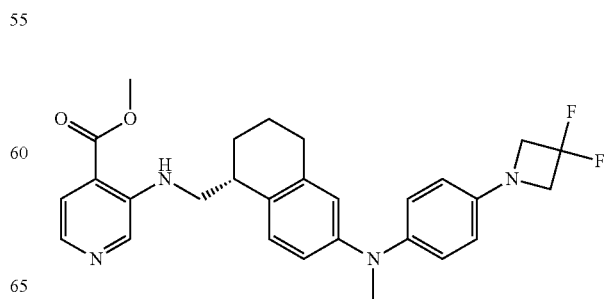

The title compound was prepared in 39% yield from Preparation 122a and 4-(3,3-difluoroazetidin-1-yl)-N-methylaniline according to the general procedure outlined for Preparation 126c. [M+H] Calc'd for $C_{27}H_{28}F_2N_4O_2$, 479; Found, 479.

Example 195

3-({[(1R)-6-{[4-(3,3-difluoroazetidin-1-yl)phenyl](methyl)amino}-1,2,3,4-tetrahydronaphthalen-1-yl]methyl}amino)pyridine-4-carboxylic acid

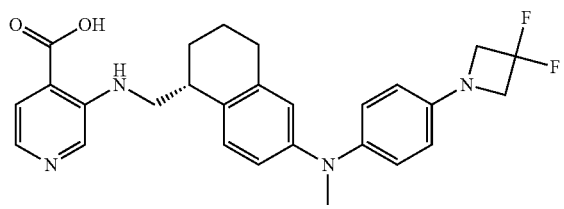 [SMILES: CN(c1ccc(N2CC(F)(F)C2)cc1)c1ccc2c(c1)CCC[C@H]2CNc1cnccc1C(=O)O]

The title compound was prepared in 90% yield from Preparation 195b according to the procedure for Example 1. $^1$H NMR (300 MHz, DMSO-d$_6$): δ 1.59-1.65 (1H, m), 1.76-1.81 (3H, m), 2.57-2.63 (2H, m), 2.96-3.01 (1H, m), 3.14 (3H, s), 3.33-3.41 (1H, m), 3.47-3.54 (1H, m), 4.24 (4H, t, J=12.3 Hz), 6.48 (1H, s), 6.51 (1H, d, J=8.8 Hz), 6.57 (2H, d, J=8.4 Hz), 7.00 (2H, d, J=8.4 Hz), 7.09 (1H, d, J=8.8 Hz), 7.55 (1H, d, J=4.8 Hz), 7.81 (1H, d, J=4.8 Hz), 8.32 (1H, s). [M+H] Calc'd for $C_{27}H_{28}F_2N_4O_2$, 479; Found, 479.

Preparation 196a methyl 3-({[(4R)-7-{[4-(3,3-difluoroazetidin-1-yl)phenyl](methyl)amino}-3,4-dihydro-2H-1-benzopyran-4-yl]methyl}amino)pyridine-4-carboxylate

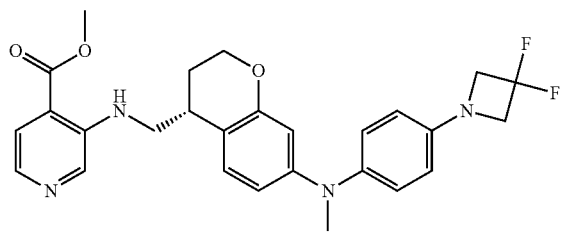 [SMILES: COC(=O)c1ccncc1NC[C@@H]1CCOc2cc(N(C)c3ccc(N4CC(F)(F)C4)cc3)ccc21]

The title compound was prepared in 35% yield from Preparation 126b and 4-(3,3-difluoroazetidin-1-yl)-N-methylaniline according to the general procedure outlined for Preparation 126c. [M+H] Calc'd for $C_{27}H_{28}F_2N_4O_3$, 495; Found, 495.

Example 196

3-({[(4R)-7-{[4-(3,3-difluoroazetidin-1-yl)phenyl](methyl)amino}-3,4-dihydro-2H-1-benzopyran-4-yl]methyl}amino)pyridine-4-carboxylic acid

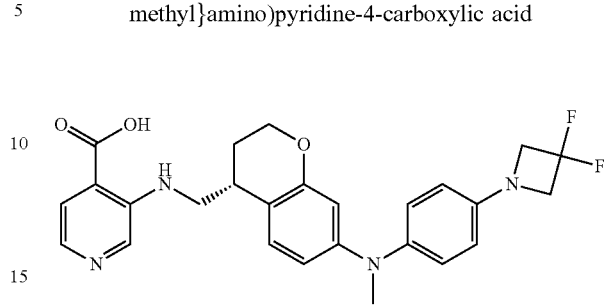

The title compound was prepared in 86% yield from Preparation 196a according to the procedure for Example 1. $^1$H NMR (300 MHz, DMSO-d$_6$): δ 1.78-1.86 (1H, m), 1.90-1.98 (1H, m), 2.97-3.02 (1H, m), 3.12 (3H, s), 3.40-3.47 (1H, m), 3.59-3.65 (1H, m), 4.05-4.14 (2H, m), 4.25 (4H, t, J=12.0 Hz), 6.07 (1H, s), 6.23 (1H, d, J=6.6 Hz), 6.58 (2H, d, J=8.4 Hz), 7.03 (2H, d, J=8.4 Hz), 7.06 (1H, d, J=6.6 Hz), 7.56 (1H, d, J=3.9 Hz), 7.84 (1H, d, J=3.9 Hz), 8.37 (1H, s). [M+H] Calc'd for $C_{26}H_{26}F_2N_4O_3$, 481; Found, 481.

Preparation 197a 4-(2-methoxyethoxy)-N-methylaniline

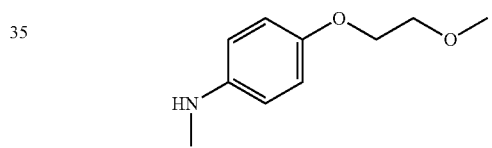

The title compound was prepared in 88% yield from 4-(2-methoxyethoxy)aniline according to the general procedure outlined for Preparation 127a. [M+H] Calc'd for $C_{10}H_{15}NO_2$, 182. Found, 182.

Preparation 197b tert-butyl N-{[(1R)-6-{[4-(2-methoxyethoxy)phenyl](methyl)amino}-1,2,3,4-tetrahydronaphthalen-1-yl]methyl}carbamate

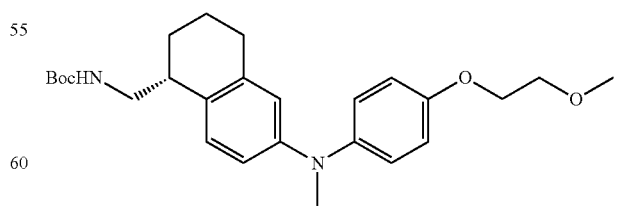

The title compound was prepared in 53% yield from Preparation 6d and Preparation 197a according to the general procedure outlined for Preparation 9a. [M+H] Calc'd for $C_{26}H_{36}N_2O_4$, 441. Found, 441.

Preparation 197c (5R)-5-(aminomethyl)-N-[4-(2-methoxyethoxy)phenyl]-N-methyl-5,6,7,8-tetrahydronaphthalen-2-amine

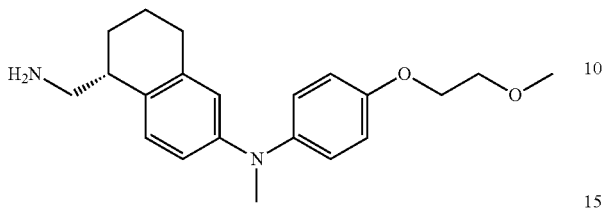

The title compound was prepared in quantitative yield from Preparation 197b according to the procedure for Preparation 43b. [M+H] Calc'd for $C_{21}H_{28}N_2O_2$, 341; Found, 341.

Preparation 197d methyl 3-({[(1R)-6-{[4-(2-methoxyethoxy)phenyl](methyl)amino}-1,2,3,4-tetrahydronaphthalen-1-yl]methyl}amino)pyridine-4-carboxylate

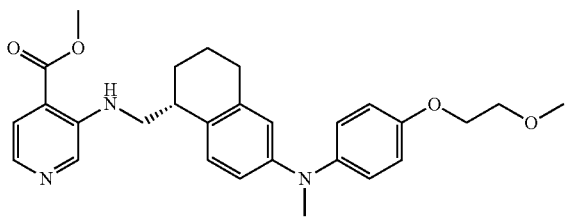 [SMILES: COCCOc1ccc(N(C)c2ccc3c(c2)CCC[C@H]3CNc2cnccc2C(=O)OC)cc1]

The title compound was prepared in 52% yield from Preparation 197c according to the procedure for Preparation 4d. [M+H] Calc'd for $C_{28}H_{33}N_3O_4$, 476; Found, 476.

Example 197

3-({[(1R)-6-{[4-(2-methoxyethoxy)phenyl](methyl)amino}-1,2,3,4-tetrahydronaphthalen-1-yl]methyl}amino)pyridine-4-carboxylic acid

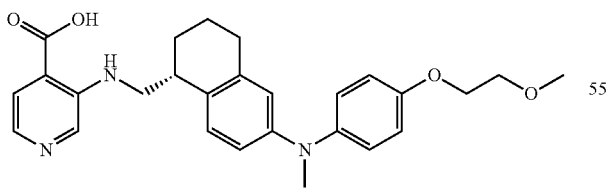

The title compound was prepared in 62% yield from Preparation 197d according to the procedure for Example 1. $^1$H NMR (400 MHz, DMSO-$d_6$): δ 1.60-1.79 (4H, m), 2.0-2.65 (2H, m), 2.98-3.02 (1H, m), 3.15 (3H, s), 3.30 (3H, s), 3.38-3.54 (2H, m), 3.65 (2H, s), 4.06 (2H, s), 6.51-6.58 (2H, m), 6.91 (2H, d, J=8.0 Hz), 7.00 (2H, d, J=7.8 Hz), 7.12 (1H, d, J=8.3 Hz), 7.56 (1H, br s), 7.82 (1H, br s), 7.84 (1H, br s), 8.32 (1H, br s), 13.4 (1H, br s). [M+H] Calc'd for $C_{27}H_{31}N_3O_4$, 462; Found, 462.

Preparation 198a methyl 3-({[(4R)-7-(1-phenylethenyl)-3,4-dihydro-2H-1-benzopyran-4-yl]methyl}amino)pyridine-4-carboxylate

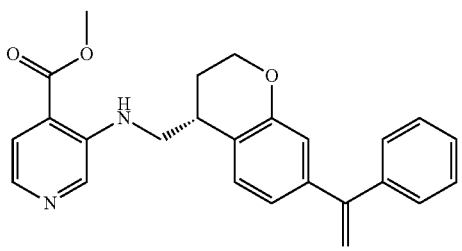 [SMILES: C=C(c1ccccc1)c1ccc2c(c1)OCC[C@H]2CNc1cnccc1C(=O)OC]

To a solution of 4,4,5,5-tetramethyl-2-(1-phenyl-vinyl)-[1,3,2]dioxaborolane (612 mg, 2.66 mmol), S-Phos (55 mg, 0.13 mmol), Pd(OAc)$_2$ (15 mg, 0.0665 mmol) and K$_3$PO$_4$ (708 mg, 3.33 mmol) in ACN/H$_2$O (30 mL/10 mL) was added Preparation 126b (500 mg, 1.33 mmol). The reaction mixture was stirred at 120° C. under N$_2$ overnight. The solvent was removed by vacuum, and the residue was purified by silica gel chromatography (PE: EtOAc=3:1) to give 200 mg (38%) of the title compound. [M+H] Calc'd for $C_{25}H_{24}N_2O_3$, 401; Found, 401.

Preparation 198b methyl 3-({[(4R)-7-(1-phenylethyl)-3,4-dihydro-2H-1-benzopyran-4-yl]methyl}amino)pyridine-4-carboxylate

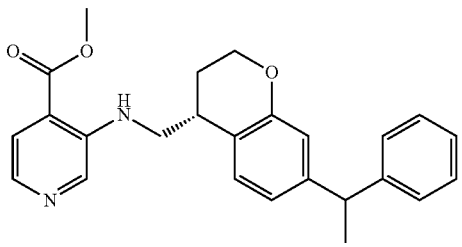 [SMILES: COC(=O)c1ccncc1NC[C@@H]1CCOc2cc(C(C)c3ccccc3)ccc21]

10% Pd/C (20 mg) was added to a solution of Preparation 198a (0.1 g, 0.25 mmol) in EtOH (15 mL) under N$_2$ at r.t. After stirring under 50 psi of H$_2$ overnight, the reaction mixture was filtered through Celite and concentrated. The residue was purified by prep-HPLC to give 50 mg (50%) of the title compound as a brown oil. [M+H] Calc'd for $C_{25}H_{26}N_2O_3$, 403; Found, 403.

Example 198

3-({[(4R)-7-(1-phenylethyl)-3,4-dihydro-2H-1-benzopyran-4-yl]methyl}amino)pyridine-4-carboxylic acid

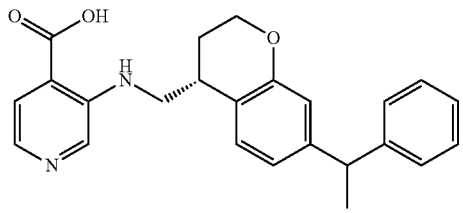 [SMILES: CC(c1ccccc1)c1ccc2c(c1)OCC[C@H]2CNc1cnccc1C(=O)O]

The title compound was prepared in 83% yield from Preparation 198b according to the procedure for Example 1. $^1$H NMR (400 MHz, DMSO-d$_6$): δ 1.52 (3H, d, J=7.2 Hz) 1.80-1.90 (1H, m), 1.91-1.99 (1H, m), 3.03-3.09 (1H, m), 3.43-3.49 (1H, m), 3.62-3.68 (1H, m), 4.04 (1H, t, J=7.2 Hz), 4.09-4.18 (2H, m), 6.64 (1H, s), 6.75 (1H, d, J=8.0 Hz), 7.14-7.29 (6H, m), 7.58 (1H, d, J=5.2 Hz), 7.84 (1H, d, J=5.2 Hz), 8.40 (1H, s). [M+H] Calc'd for C$_{24}$H$_{24}$N$_2$O$_3$, 389; Found, 389.

Preparation 199a 5-isopropyl-N-methylpyridin-2-amine

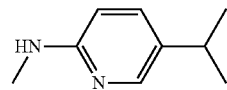

A solution of 5-isopropyl-pyridin-2-ylamine (0.5 g, 3.67 mmol) in dry THF was purged with N$_2$ and cooled to −78° C. n-BuLi (1.62 mL, 4.04 mmol) was added dropwise. The reaction was stirred at 0° C. for 0.5 h, and then iodomethane (0.25 mL, 4.04 mmol) was added dropwise. The resulting mixture was stirred overnight while warming to r.t. Water (20 mL) was added, and the mixture was extracted with EtOAc. The organic layer was dried over Na$_2$SO$_4$, concentrated, and purified by silica gel chromatography (10% to 30% EtOAc in PE) to give 200 mg (36%) of the title compound as a brown oil. [M+H] Calc'd for C$_9$H$_{14}$N$_2$, 151; Found, 151.

Preparation 199b methyl 3-({[(4R)-7-{methyl[5-(propan-2-yl)pyridin-2-yl]amino}-3,4-dihydro-2H-1-benzopyran-4-yl]methyl}amino)pyridine-4-carboxylate

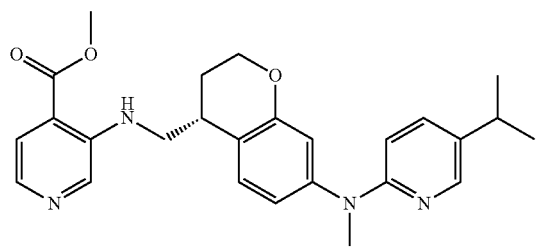 [SMILES: COC(=O)c1ccncc1NC[C@@H]1CCOc2cc(N(C)c3ccc(C(C)C)cn3)ccc21]

The title compound was prepared in 65% yield from Preparation 126b and 5-isopropyl-N-methylpyridin-2-amine according to the general procedure outlined for Preparation 126c. [M+H] Calc'd for C$_{26}$H$_{30}$N$_4$O$_3$, 447; Found, 447.

Example 199

3-({[(4R)-7-{methyl[5-(propan-2-yl)pyridin-2-yl]amino}-3,4-dihydro-2H-1-benzopyran-4-yl]methyl}amino)pyridine-4-carboxylic acid

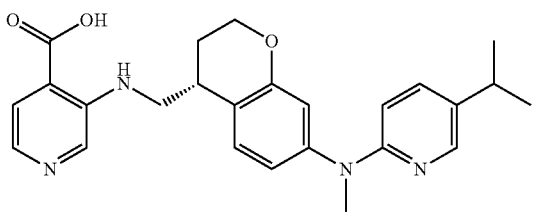

The title compound was prepared in 82% yield from Preparation 199b according to the procedure for Example 1. $^1$H NMR (300 MHz, DMSO-d$_6$): δ 1.16 (6H, d, J=7.2 Hz), 1.85-1.93 (1H, m), 1.95-2.06 (1H, m), 2.73-2.84 (1H, m), 3.09-3.16 (1H, m), 3.32 (3H, s), 3.48-3.56 (1H, m), 3.69-3.75 (1H, m), 4.12-4.26 (2H, m), 6.57 (1H, d, J=8.1 Hz), 6.64 (1H, d, J=2.4 Hz), 6.74 (1H, dd, J=8.1 Hz, 1.8 Hz), 7.32 (1H, d, J=8.4 Hz), 7.36 (1H, dd, J=8.4 Hz, 2.4 Hz), 7.57 (1H, d, J=5.1 Hz), 7.85 (1H, d, J=5.1 Hz), 8.04 (1H, d, J=1.8 Hz), 8.42 (1H, s). [M+H] Calc'd for C$_{25}$H$_{28}$N$_4$O$_3$, 433; Found, 433.

Preparation 200a methyl 3-({[(1R)-6-{methyl[4-(trifluoromethanesulfonyloxy)phenyl]amino}-1,2,3,4-tetrahydronaphthalen-1-yl]methyl}amino)pyridine-4-carboxylate

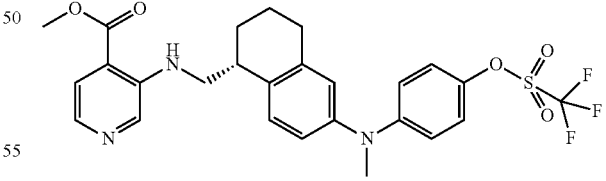

To a solution of Preparation 165c (576 mg, 1.37 mmol) and pyridine (217 mg, 2.75 mmol) in THF (10 mL) was added Tf$_2$O (407 mg, 1.44 mmol) slowly at 0° C. The mixture was stirred at rt for 2 h. The mixture was concentrated and purified by silica gel chromatography (PE:EtOAc=2:1) to give 553 mg (73%) of the title compound as a yellow oil. [M+H] Calc'd for C$_{26}$H$_{26}$F$_3$N$_3$O$_5$S, 550. Found, 550.

Preparation 200b methyl 3-({[(1R)-6-[(4-{3-[(tert-butyldimethylsilyl)oxy]azetidin-1-yl}phenyl)(methyl)amino]-1,2,3,4-tetrahydronaphthalen-1-yl]methyl}amino)pyridine-4-carboxylate

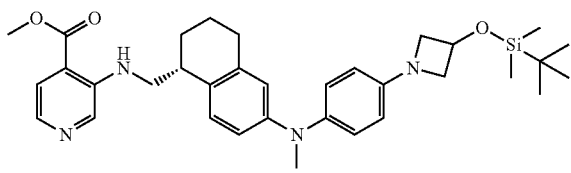 [SMILES: COC(=O)c1ccncc1NC[C@@H]1CCCc2cc(N(C)c3ccc(N4CC(O[Si](C)(C)C(C)(C)C)C4)cc3)ccc21]

The title compound was prepared in 55% yield from Preparation 200a and 3-[(tert-butyldimethylsilanyl)oxy]azetidine according to the procedure for Preparation 126c. [M+H] Calc'd for $C_{34}H_{46}N_4O_3Si$, 587; Found, 587.

Preparation 200c methyl 3-({[(1R)-6-{[4-(3-hydroxyazetidin-1-yl)phenyl](methyl)amino}-1,2,3,4-tetrahydronaphthalen-1-yl]methyl}amino)pyridine-4-carboxylate

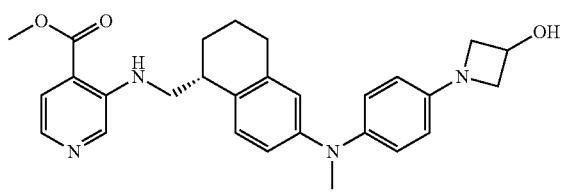 [SMILES: COC(=O)c1ccncc1NC[C@@H]1CCCc2cc(N(C)c3ccc(N4CC(O)C4)cc3)ccc21]

The title compound was prepared in 89% yield from Preparation 200b according to the procedure for Preparation 165c. [M+H] Calc'd for $C_{28}H_{32}N_4O_3$, 473; Found, 473.

Example 200

3-({[(1R)-6-{[4-(3-hydroxyazetidin-1-yl)phenyl](methyl)amino}-1,2,3,4-tetrahydronaphthalen-1-yl]methyl}amino)pyridine-4-carboxylic acid

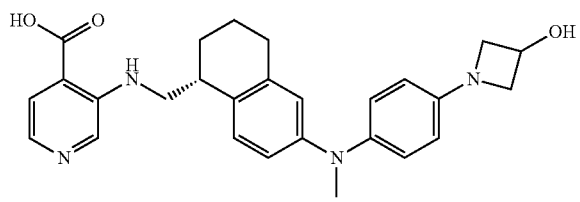 [SMILES: CN(c1ccc(N2CC(O)C2)cc1)c1ccc2c(c1)CCC[C@H]2CNc1cnccc1C(=O)O]

The title compound was prepared in 95% yield from Preparation 200c according to the procedure for Example 1. $^1$H NMR (300 MHz, DMSO-d$_6$): δ 1.58-1.79 (4H, m), 2.56-2.60 (2H, m), 2.92-2.95 (1H, m), 3.09 (3H, s) 3.26-3.32 (1H, m), 3.35-3.58 (4H, m), 4.02 (2H, t, J=6.6 Hz), 4.50-4.54 (1H, m), 6.39-6.45 (4H, m), 6.92 (2H, d, J=6.0 Hz), 7.05 (1H, d, J=8.4 Hz), 7.54 (1H, d, J=5.1 Hz), 7.78 (1H, d, J=4.8 Hz), 8.26 (1H, s). [M+H] Calc'd for $C_{27}H_{30}N_4O_3$, 459; Found, 459.

Preparation 201a methyl 3-({[(4R)-7-{[4-(3,6-dihydro-2H-pyran-4-yl)phenyl](methyl)amino}-3,4-dihydro-2H-1-benzopyran-4-yl]methyl}amino)pyridine-4-carboxylate

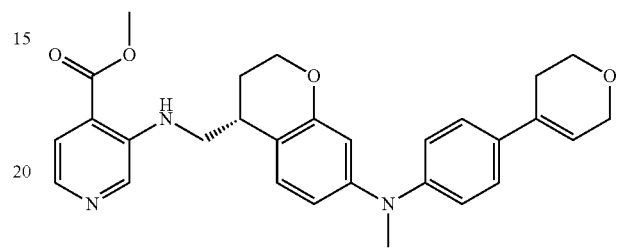

The title compound was prepared in 49% yield from Preparation 126b and Preparation 174a according to the general procedure outlined for Preparation 126c. [M+H] Calc'd for $C_{29}H_{31}N_3O_4$, 486; Found, 486.

Example 201

3-({[(4R)-7-{[4-(3,6-dihydro-2H-pyran-4-yl)phenyl](methyl)amino}-3,4-dihydro-2H-1-benzopyran-4-yl]methyl}amino)pyridine-4-carboxylic acid

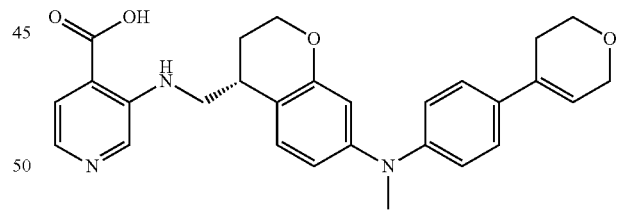

The title compound was prepared in 83% yield from Preparation 201a according to the procedure for Example 1. $^1$H NMR (300 MHz, DMSO-d$_6$): δ 1.86-1.98 (2H, m), 2.38-2.40 (2H, m), 3.03-3.08 (1H, m), 3.19 (3H, s), 3.42-3.50 (1H, m), 3.63-3.68 (1H, m), 3.77-3.80 (2H, m), 4.11-4.19 (4H, m), 6.12 (1H, m), 6.39 (1H, d, J=2.1 Hz), 6.50-6.53 (1H, m), 6.93 (2H, d, J=8.7 Hz), 7.18 (1H, d, J=8.1 Hz), 7.33 (2H, d, J=8.1 Hz), 7.55 (1H, d, J=4.8 Hz), 7.82 (1H, d, J=5.1 Hz), 8.37 (1H, s). [M+H] Calc'd for $C_{28}H_{29}N_3O_4$, 472; Found, 472.

Preparation 202a methyl 3-({[(4R)-7-{methyl[4-(oxan-4-yl)phenyl]amino}-3,4-dihydro-2H-1-benzopyran-4-yl]methyl}amino)pyridine-4-carboxylate

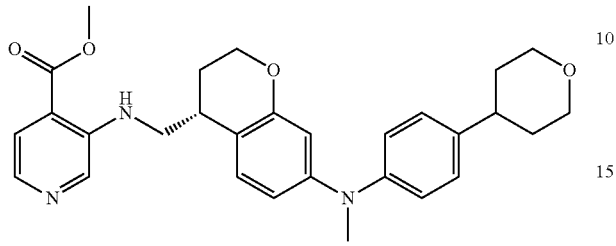

The title compound was prepared in 42% yield from Preparation 126b and Preparation 175a according to the general procedure outlined for Preparation 126c. [M+H] Calc'd for $C_{29}H_{33}N_3O_4$, 488; Found, 488.

Example 202

3-({[(4R)-7-{methyl[4-(oxan-4-yl)phenyl]amino}-3,4-dihydro-2H-1-benzopyran-4-yl]methyl}amino)pyridine-4-carboxylic acid

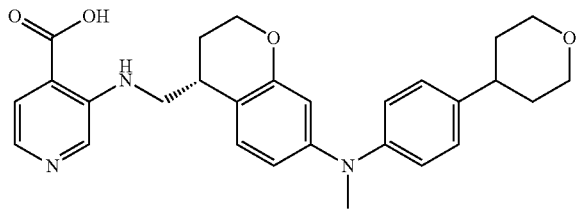 [SMILES: CN(c1ccc(C2CCOCC2)cc1)c1ccc2c(c1)OCC[C@H]2CNc1cnccc1C(=O)O]

The title compound was prepared in 96% yield from Preparation 202a according to the procedure for Example 1. $^1$H NMR (300 MHz, DMSO-$d_6$): δ 1.59-1.67 (4H, m), 1.85-1.94 (2H, m), 2.67-2.70 (1H, m), 3.00-3.04 (1H, m), 3.22 (3H, s), 3.39-3.46 (3H, m), 3.59-3.65 (1H, m), 3.90-3.94 (2H, m), 4.09-4.14 (2H, m), 6.26 (1H, d, J=2.8 Hz), 6.27-6.43 (1H, m), 6.94-6.97 (2H, m), 7.12-7.17 (3H, m), 7.54 (1H, d, J=4.8 Hz), 7.80 (1H, d, J=4.8 Hz), 8.34 (1H, s). [M+H] Calc'd for $C_{28}H_{31}N_3O_4$, 474; Found, 474.

Preparation 203a tert-butyl N-{[(4R)-7-(1-phenylethenyl)-3,4-dihydro-2H-1-benzopyran-4-yl]methyl}carbamate

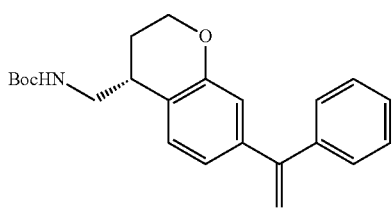

The title compound was prepared in 87% yield from Preparation 18d and 4,4,5,5-tetramethyl-2-(1-phenyl-vinyl)-[1,3,2]dioxaborolane according to the procedure for Preparation 198a. Calc'd for $C_{22}H_{27}NO_3$, 309; Found, 309.

Preparation 203b tert-butyl N-{[(4R)-7-(1-phenylcyclopropyl)-3,4-dihydro-2H-1-benzopyran-4-yl]methyl}carbamate

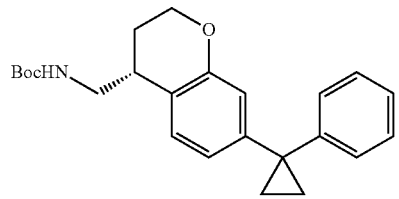 [SMILES: CC(C)(C)OC(=O)NC[C@@H]1CCOc2cc(C3(c4ccccc4)CC3)ccc21]

A solution of Preparation 203a (0.2 g, 0.548 mmol) in DCE (5 mL) was purged with $N_2$ and cooled to 0° C. Diethyl zinc (3.3 mL, 3.3 mmol) was added to the reaction mixture dropwise. After stirring for 10 min, diiodomethane (1.76 g, 6.576 mmol) was added dropwise. The reaction mixture was stirred overnight while warming to r.t. Water (10 mL) was added, and the mixture was extracted with EtOAc. The organic layer was dried ($Na_2SO_4$) and concentrated. The residue was purified by silica gel chromatography (PE:EtOAc=10:1) to give 13 mg (6%) of the title compound as a brown oil. Calc'd for $C_{24}H_{29}NO_3$, 323; Found, 323.

Preparation 203c

[(4R)-7-(1-phenylcyclopropyl)-3,4-dihydro-2H-1-benzopyran-4-yl]methanamine

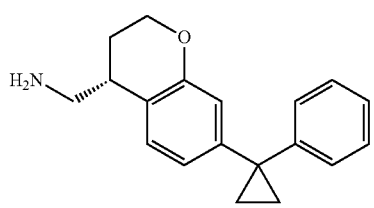 [SMILES: NC[C@@H]1CCOc2cc(C3(c4ccccc4)CC3)ccc21]

A mixture of Preparation 203b (30 mg) in HCl solution (2.0 M in EtOAc, 10 mL) was stirred for 2 h at r.t. The solution was concentrated and used for next reaction without further purification. Calc'd for $C_{19}H_{21}NO$, 263; Found, 263.

Preparation 203d methyl 3-({[(4R)-7-(1-phenylcyclopropyl)-3,4-di-hydro-2H-1-benzopyran-4-yl]methyl}amino)pyridine-4-carboxylate

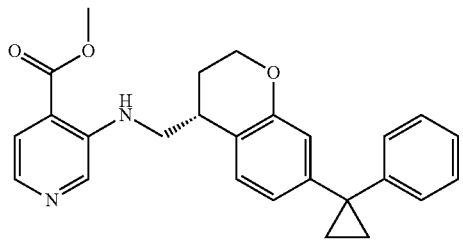 [SMILES: COC(=O)c1ccncc1NC[C@@H]1CCOc2cc(C3(c4ccccc4)CC3)ccc21]

The title compound was prepared in 40% yield from Preparation 203c according to the procedure for Preparation 4d. [M+H] Calc'd for $C_{26}H_{26}N_2O_3$, 415; Found, 415.

Example 203

3-({[(4R)-7-(1-phenylcyclopropyl)-3,4-dihydro-2H-1-benzopyran-4-yl]methyl}amino)pyridine-4-carboxylic acid

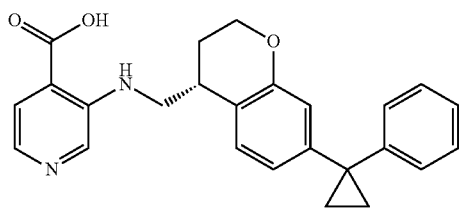 [SMILES: O=C(O)c1ccncc1NC[C@@H]1CCOc2cc(C3(c4ccccc4)CC3)ccc21]

The title compound was prepared in 63% yield from Preparation 203d according to the procedure for Example 1. $^1$H NMR (300 MHz, DMSO-$d_6$): δ 1.19 (4H, s), 1.80-1.87 (1H, m), 1.91-2.01 (1H, m), 3.04-3.09 (1H, m) 3.42-3.51 (1H, m), 3.62-3.69 (1H, m), 4.08-4.20 (2H, m), 6.57 (1H, d, J=1.8 Hz), 6.70 (1H, dd, J=7.8 Hz, 1.8 Hz), 7.15-7.30 (6H, m), 7.57 (1H, d, J=5.1 Hz), 7.84 (1H, d, J=5.1 Hz), 8.40 (1H, s). [M+H] Calc'd for $C_{25}H_{24}N_2O_3$, 401; Found, 401.

Preparation 204a

N-methyl-4-(1-methyl-1,2,3,6-tetrahydropyridin-4-yl)aniline

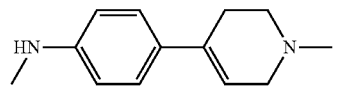

The title compound was prepared in 37% yield, using 1-methyl-1,2,3,6-tetrahydropyridine-4-boronic acid pinacol ester, according to the general procedure for the preparation of Preparation 174a. [M+H] Calc'd for $C_{13}H_{18}N_2$, 203; Found, 203.

Preparation 204b methyl 3-({[(4R)-7-{methyl[4-(1-methyl-1,2,3,6-tetrahydropyridin-4-yl)phenyl]amino}-3,4-dihydro-2H-1-benzopyran-4-yl]methyl}amino)pyridine-4-carboxylate

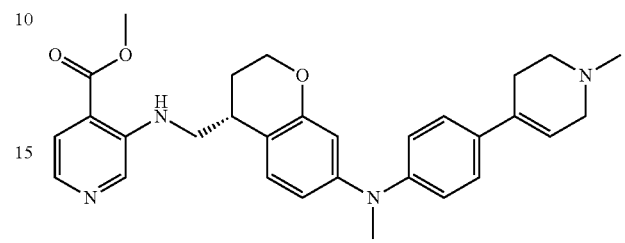

The title compound was prepared in 20% yield from Preparation 126b and Preparation 204a according to the general procedure outlined for Preparation 126c. [M+H] Calc'd for $C_{30}H_{34}N_4O_3$, 499; Found, 499.

Example 204

3-({[(4R)-7-{methyl[4-(1-methyl-1,2,3,6-tetrahydropyridin-4-yl)phenyl]amino}-3,4-dihydro-2H-1-benzopyran-4-yl]methyl}amino)pyridine-4-carboxylic acid

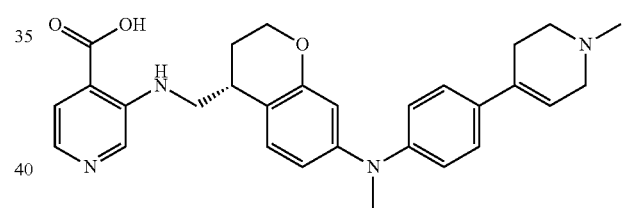

The title compound was prepared in 16% yield from Preparation 204b according to the procedure for Example 1. $^1$H NMR (300 MHz, DMSO-$d_6$): δ 1.82-1.98 (m, 2H), 2.77-3.04 (m, 6H), 3.04-3.08 (m, 1H), 3.20 (s, 3H), 3.30-3.76 (m, 5H), 4.11-4.16 (m, 2H), 6.05 (s, 1H), 6.43 (d, 1H, J=2.1 Hz,), 6.55 (dd, 1H, J=2.1 Hz, 8.1 Hz), 6.91 (d, 2H, J=8.7 Hz), 7.21 (d, 1H, J=7.8 Hz), 7.35 (d, 2H, J=8.7 Hz), 7.55 (d, 1H, J=5.4 Hz), 7.81 (d, 1H, J=4.8 Hz), 8.36 (s, 1H). [M+H] Calc'd for $C_{29}H_{32}N_4O_3$, 485; Found, 485.

Preparation 205a

N-methyl-4-(1-methylpiperidin-4-yl)aniline

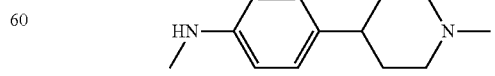

The title compound was prepared in 90% yield from Preparation 204a according to the general procedure for Preparation 175a. [M+H] Calc'd for $C_{13}H_{20}N_2$, 205; Found, 205.

Preparation 205b methyl 3-({[(4R)-7-{methyl[4-(1-methylpiperidin-4-yl)phenyl]amino}-3,4-dihydro-2H-1-benzopyran-4-yl]methyl}amino)pyridine-4-carboxylate

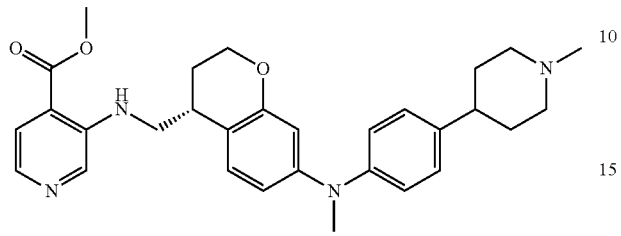

The title compound was prepared in 18% yield from Preparation 126b and Preparation 205a according to the general procedure outlined for Preparation 126c. [M+H] Calc'd for $C_{30}H_{36}N_4O_3$, 501; Found, 501.

Example 205

3-({[(4R)-7-{methyl[4-(1-methylpiperidin-4-yl)phenyl]amino}-3,4-dihydro-2H-1-benzopyran-4-yl]methyl}amino)pyridine-4-carboxylic acid

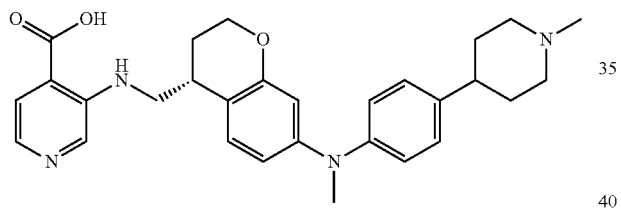

The title compound was prepared in 14% yield from Preparation 205b according to the procedure for Example 1. $^1$H NMR (300 MHz, DMSO-$d_6$): δ 1.90-1.93 (m, 6H), 2.72 (s, 3H), 3.00-3.03 (m, 3H), 3.16 (s, 3H), 3.39-3.61 (m, 5H), 4.09-4.10 (m, 2H), 6.29 (d, 1H, J=2.1 Hz), 6.43 (dd, 1H, J=2.1, 8.7 Hz), 6.96 (d, 2H, J=8.4 Hz), 7.14 (d, 3H, J=8.7 Hz), 7.56 (d, 1H, J=5.4 Hz), 7.82 (d, 1H, J=5.1 Hz), 8.36 (s, 1H). [M+H] Calc'd for $C_{29}H_{34}N_4O_3$, 487; Found, 487.

Preparation 206a

N,3,4-trimethylaniline

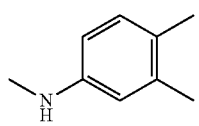

The title compound was prepared in 33% overall yield from 3,4-dimethylaniline according to the general procedure outlined for Preparation 127a. [M+H] Calc'd for $C_9H_{13}N$, 136. Found, 136.

Preparation 206b methyl 3-({[(4R)-7-[(3,4-dimethylphenyl)(methyl)amino]-3,4-dihydro-2H-1-benzopyran-4-yl]methyl}amino)pyridine-4-carboxylate

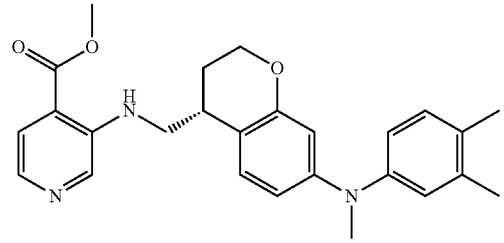 [SMILES: COC(=O)c1ccncc1NC[C@@H]1CCOc2cc(N(C)c3ccc(C)c(C)c3)ccc21]

The title compound was prepared in 43% yield from Preparation 126b and N,3,4-trimethylaniline according to the general procedure outlined for Preparation 126c. [M+H] Calc'd for $C_{26}H_{29}N_3O_3$, 432; Found, 432.

Example 206

3-({[(4R)-7-[(3,4-dimethylphenyl)(methyl)amino]-3,4-dihydro-2H-1-benzopyran-4-yl]methyl}amino) pyridine-4-carboxylic acid

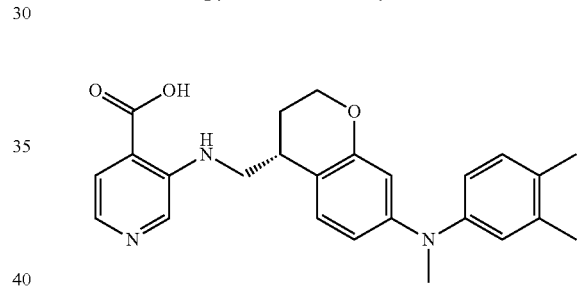

The title compound was prepared in 87% yield from Preparation 206b according to the procedure for Example 1. $^1$H NMR (300 MHz, DMSO-$d_6$): δ 1.79-1.97 (2H, m), 2.16 (6H, s) 2.99-3.03 (1H, m), 3.13 (3H, s), 3.39-3.48 (1H, m), 3.59-3.65 (1H, m), 4.05-4.17 (2H, m), 6.19 (1H, d, J=2.4 Hz), 6.32-6.36 (1H, m), 6.75-6.79 (1H, m), 6.85 (1H, d, J=1.8 Hz), 7.03-7.10 (2H, m), 7.54 (1H, d, J=4.8 Hz), 7.82 (1H, d, J=4.8 Hz), 8.36 (1H, s). [M+H] Calc'd for $C_{25}H_{27}N_3O_3$, 418; Found, 418.

Preparation 207a 4-(2-((tert-butyldimethylsilyl)oxy)ethyl)aniline

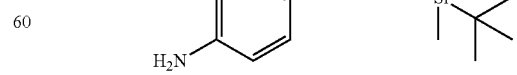

The title compound was prepared in quantitative yield from 2-(4-aminophenyl)ethan-1-ol according to the procedure for Preparation 165a. [M+H] Calc'd for $C_{14}H_{25}NOSi$, 252; Found, 252.

Preparation 207b 4-(2-((tert-butyldimethylsilyl)oxy)ethyl)-N-methyl-aniline

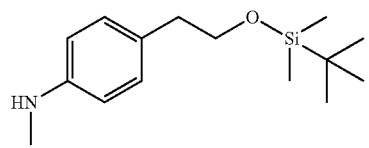 [SMILES: CNc1ccc(CCO[Si](C)(C)C(C)(C)C)cc1]

The title compound was prepared in 49% overall yield from 4-(2-((tert-butyldimethylsilyl)oxy)ethyl)aniline according to the general procedure outlined for Preparation 127a. [M+H] Calc'd for $C_{15}H_{27}NOSi$, 266; Found, 266.

Preparation 207c methyl 3-({[(4R)-7-[(4-{2-[(tert-butyldimethylsilyl)oxy]ethyl}phenyl)-(methyl)amino]-3,4-dihydro-2H-1-benzopyran-4-yl]methyl}amino)pyridine-4-carboxylate

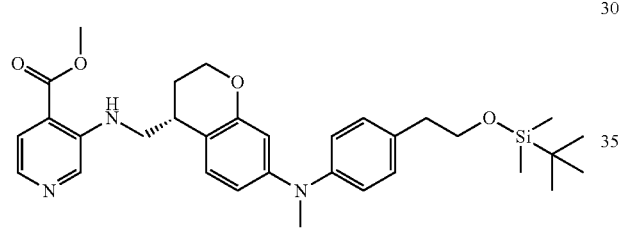

The title compound was prepared in 39% yield from Preparation 126b and Preparation 207b according to the general procedure outlined for Preparation 126c. [M+H] Calc'd for $C_{32}H_{43}N_3O_4Si$, 562; Found, 562.

Preparation 207d methyl 3-({[(4R)-7-{[4-(2-hydroxyethyl)phenyl](methyl)amino}-3,4-dihydro-2H-1-benzopyran-4-yl]methyl}amino)pyridine-4-carboxylate

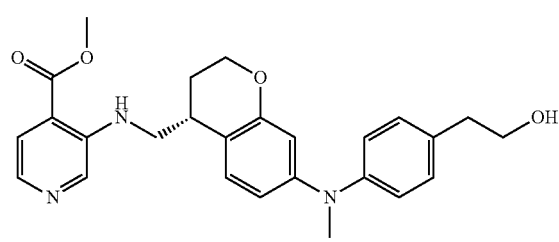 [SMILES: COC(=O)c1ccncc1NC[C@@H]1CCOc2cc(N(C)c3ccc(CCO)cc3)ccc21]

The title compound was prepared in 80% yield from Preparation 207c according to the procedure for Preparation 165c. [M+H] Calc'd for $C_{26}H_{29}N_3O_4$, 448; Found, 448.

Example 207

3-({[(4R)-7-{[4-(2-hydroxyethyl)phenyl](methyl)amino}-3,4-dihydro-2H-1-benzopyran-4-yl]methyl}amino)pyridine-4-carboxylic acid

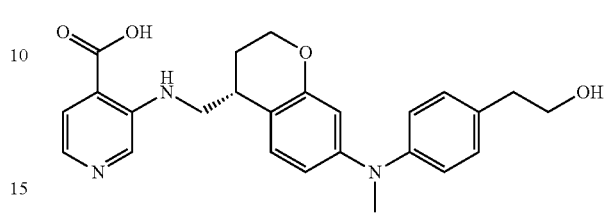

The title compound was prepared in 95% yield from Preparation 207d according to the procedure for Example 1. $^1$H NMR (300 MHz, DMSO-$d_6$): δ 1.79-1.95 (2H, m), 2.65 (2H, t, J=7.2 Hz), 3.01-3.04 (1H, m), 3.12 (3H, s) 3.43-3.48 (1H, m), 3.53-3.66 (3H, m), 4.08-4.15 (2H, m), 6.24 (1H, d, J=2.4 Hz), 6.37-6.40 (1H, m), 6.92-6.95 (2H, m), 7.11-7.13 (3H, m), 7.56 (1H, d, J=5.1 Hz), 7.83 (1H, d, J=4.8 Hz), 8.38 (1H, s). [M+H] Calc'd for $C_{25}H_{27}N_3O_4$, 434; Found, 434.

Preparation 208a

N-methyl-4-propylaniline

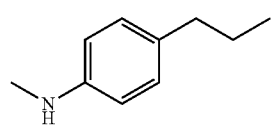

The title compound was prepared in 95% overall yield from 4-propylaniline according to the general procedure outlined for Preparation 127a. [M+H] Calc'd for $C_{10}H_{15}N$, 150; Found, 150.

Preparation 208b methyl 3-({[(4R)-7-[methyl(4-propylphenyl)amino]-3,4-dihydro-2H-1-benzopyran-4-yl]methyl}amino)pyridine-4-carboxylate

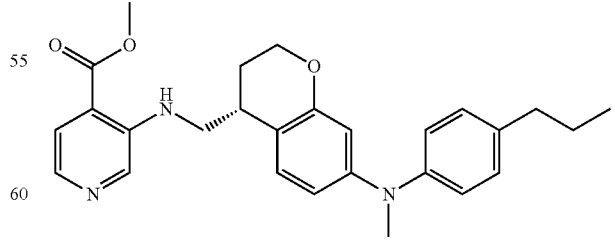

The title compound was prepared in 24% yield from Preparation 126b and N-methyl-4-propylaniline according to the general procedure outlined for Preparation 126c. [M+H] Calc'd for $C_{27}H_{31}N_3O_3$, 446; Found, 446.

Example 208

3-({[(4R)-7-[methyl(4-propylphenyl)amino]-3,4-dihydro-2H-1-benzopyran-4-yl]methyl}amino)pyridine-4-carboxylic acid

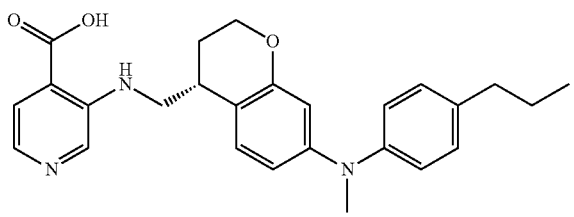 [SMILES: CCCc1ccc(N(C)c2ccc3c(c2)OCC[C@H]3CNc2cnccc2C(=O)O)cc1]

The title compound was prepared in 88% yield from Preparation 208b according to the procedure for Example 1. $^1$H NMR (300 MHz, DMSO-d$_6$): δ 0.89 (3H, t, J=7.2 Hz), 1.50-1.63 (2H, m), 1.81-1.87 (1H, m), 1.91-2.01 (1H, m), 2.99-3.12 (1H, m), 3.17 (3H, s), 3.40-3.50 (3H, m), 3.61-3.68 (1H, m), 4.06-4.21 (2H, m), 6.25 (1H, d, J=2.4 Hz), 6.40 (1H, dd, J=8.4 Hz, 2.4 Hz), 6.96 (2H, d, J=8.4 Hz), 7.11 (2H, d, J=8.4 Hz), 7.13 (1H, d, J=8.4 Hz), 7.56 (1H, d, J=5.1 Hz), 7.84 (1H, d, J=5.1 Hz), 8.39 (1H, s). [M+H] Calc'd for C$_{26}$H$_{29}$N$_3$O$_3$, 432; Found, 432.

Preparation 209a tert-butyl N-{[(1R)-6-{[4-(cyclopropylmethoxy)phenyl](methyl)amino}-1,2,3,4-tetrahydronaphthalen-1-yl]methyl}carbamate

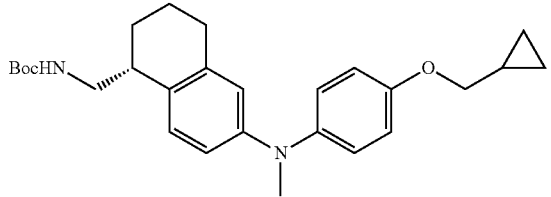 [SMILES: CN(c1ccc(OCC2CC2)cc1)c1ccc2c(c1)CCC[C@H]2CNC(=O)OC(C)(C)C]

The title compound was prepared in 66% yield from 4-(cyclopropylmethoxy)-N-methylaniline and Preparation 6d according to the general procedure outlined for Preparation 9a. [M+H] Calc'd for C$_{27}$H$_{36}$N$_2$O$_3$, 437; Found, 437.

Preparation 209b (5R)-5-(aminomethyl)-N-[4-(cyclopropylmethoxy)phenyl]-N-methyl-5,6,7,8-tetrahydronaphthalen-2-amine

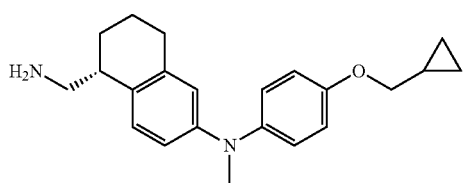 [SMILES: CN(c1ccc(OCC2CC2)cc1)c1ccc2c(c1)CCC[C@H]2CN]

The title compound was prepared in quantitative yield from Preparation 209a according to the procedure for Preparation 43b. [M+H] Calc'd for C$_{22}$H$_{28}$N$_2$O, 337; Found, 337.

Preparation 209c methyl 3-({[(1R)-6-{[4-(cyclopropylmethoxy)phenyl](methyl)amino}-1,2,3,4-tetrahydronaphthalen-1-yl]methyl}amino)pyridine-4-carboxylate

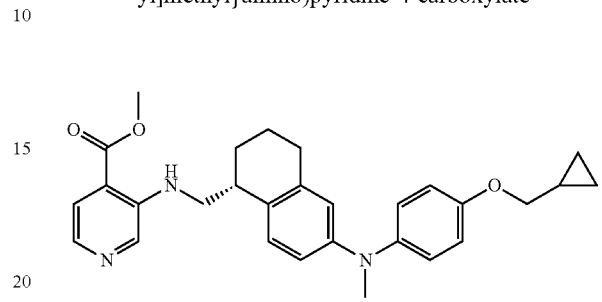

The title compound was prepared in 72% yield from Preparation 209b according to the procedure for Preparation 4d. [M+H] Calc'd for C$_{29}$H$_{33}$N$_3$O$_3$, 472; Found, 472.

Example 209

3-({[(1R)-6-{[4-(cyclopropylmethoxy)phenyl](methyl)amino}-1,2,3,4-tetrahydronaphthalen-1-yl]methyl}amino)pyridine-4-carboxylic acid

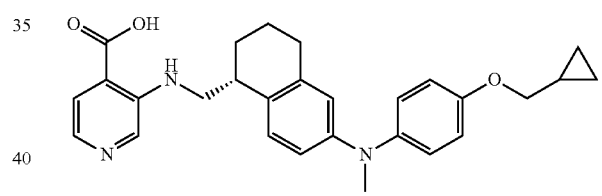

The title compound was prepared in 89% yield from Preparation 209c according to the procedure for Example 1. $^1$H NMR (400 MHz, DMSO-d$_6$): δ 0.24 (2H, s), 0.49 (2H, d, J=6.0 Hz), 1.11-1.17 (1H, m), 1.52-1.58 (1H, m), 1.68-1.75 (3H, m), 2.53-2.58 (2H, m), 2.90-2.95 (1H, s), 3.07 (3H, s), 3.25-3.46 (2H, m), 3.71 (2H, d, J=6.7 Hz), 6.43 (1H, s), 6.48 (1H, d, J=7.4 Hz), 6.81 (2H, d, J=8.4 Hz), 6.92 (2H, d, J=8.4 Hz), 7.04 (1H, d, J=8.2 Hz), 7.50 (1H, s), 7.74 (1H, s), 8.22 (1H, s). [M+H] Calc'd for C$_{28}$H$_{31}$N$_3$O$_3$, 458; Found, 458.

Preparation 210a 4-isopropoxy-N-methylaniline

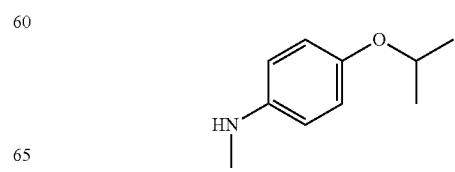

The title compound was prepared in 96% overall yield from 4-isopropoxyaniline according to the general procedure outlined for Preparation 127a. [M+H] Calc'd for $C_{10}H_{15}NO$, 166. Found, 166.

Preparation 210b methyl 3-({[(4R)-7-{methyl[4-(propan-2-yloxy)phenyl]amino}-3,4-dihydro-2H-1-benzopyran-4-yl]methyl}amino)pyridine-4-carboxylate

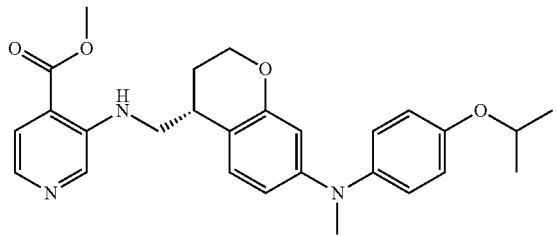

The title compound was prepared in 45% yield from Preparation 126b and 4-isopropoxy-N-methylaniline according to the general procedure outlined for Preparation 126c. [M+H] Calc'd for $C_{27}H_{31}N_3O_4$, 462; Found, 462.

Example 210

3-({[(4R)-7-{methyl[4-(propan-2-yloxy)phenyl]amino}-3,4-dihydro-2H-1-benzopyran-4-yl]methyl}amino)pyridine-4-carboxylic acid

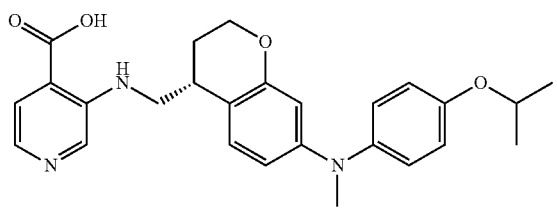

The title compound was prepared in 78% yield from Preparation 210b according to the procedure for Example 1. $^1$H NMR (400 MHz, DMSO-d$_6$): δ 1.26 (6H, d, J=6.0 Hz), 1.79-1.86 (1H, m), 1.91-2.01 (1H, m), 2.97-3.05 (1H, m), 3.13 (3H, s), 3.40-3.46 (1H, m), 3.59-3.64 (1H, m), 4.05-4.17 (2H, m), 4.50-4.60 (1H, m), 6.10 (1H, d, J=2.4 Hz), 6.26 (1H, dd, J=8.4 Hz, 2.4 Hz), 6.89 (2H, d, J=8.4 Hz), 7.02 (2H, d, J=8.4 Hz), 7.08 (1H, d, J=8.4 Hz), 7.56 (1H, d, J=5.2 Hz), 7.83 (1H, d, J=5.2 Hz), 8.37 (1H, s). [M+H] Calc'd for $C_{26}H_{29}N_3O_4$, 448; Found, 448.

Preparation 211a 1-(cyclopropylmethoxy)-4-nitrobenzene

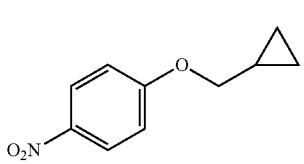

4-Nitrophenol (5.0 g, 35.9 mmol) was added to a suspension of (bromomethyl)cyclopropane (10.7 g, 79.07 mmol) and $K_2CO_3$ (19.9 g, 143.76 mmol) in DMF (80 mL), and the reaction was stirred at 40° C. overnight. The reaction mixture was diluted with water (300 mL) and extracted with EtOAc (100 mL×3). Organics were washed with brine (50 mL), dried (Na$_2$SO$_4$), and concentrated. The residue was purified by silica gel chromatography (0-5% EtOAc/PE) to give 6.77 g (98%) of the title compound as a colorless oil. [M+H] Calc'd for $C_{10}H_{11}NO_3$, 194; Found, 194.

Preparation 211b 4-(cyclopropylmethoxy)aniline

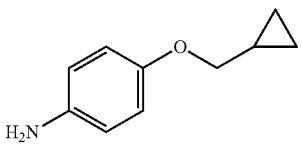 [SMILES: O=[N+]([O-])c1ccc(OCC2CC2)cc1]

10% Pd/C (680 mg) was added to a solution of Preparation 211a (6.77 g, 35.1 mmol) in EtOAc (70 mL) under N$_2$, and the reaction mixture stirred under H$_2$ at r.t. overnight. The reaction mixture was filtered through Celite and concentrated to give 5.72 g (100%) of the title compound as a brown oil. [M+H] Calc'd for $C_{10}H_{13}NO$, 164; Found, 164.

Preparation 211c 4-(cyclopropylmethoxy)-N-methylaniline

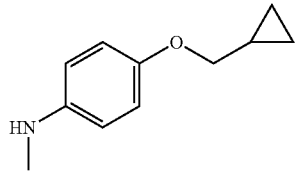

The title compound was prepared in 91% overall yield from Preparation 211b according to the general procedure outlined for Preparation 127a. [M+H] Calc'd for $C_{11}H_{15}NO$, 178; Found, 178.

Preparation 211d methyl 3-({[(4R)-7-{[4-(cyclopropylmethoxy)phenyl](methyl)amino}-3,4-dihydro-2H-1-benzopyran-4-yl]methyl}amino)pyridine-4-carboxylate

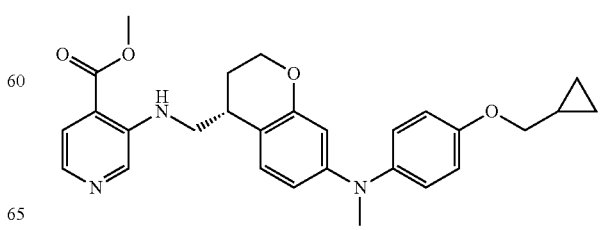

Example 211

3-({[(4R)-7-{[4-(cyclopropylmethoxy)phenyl](methyl)amino}-3,4-dihydro-2H-1-benzopyran-4-yl]methyl}amino)pyridine-4-carboxylic acid

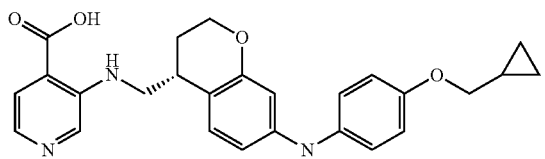

The title compound was prepared in 89% yield from Preparation 210b according to the procedure for Example 1. $^1$H NMR (300 MHz, DMSO-d$_6$): δ 0.29-0.34 (2H, m), 0.53-0.60 (2H, m), 1.16-1.24 (1H, m), 1.77-2.01 (2H, m), 2.96-3.05 (1H, m), 3.13 (3H, s), 3.39-3.47 (1H, m), 3.58-3.65 (1H, m), 3.79 (2H, d, J=6.9 Hz), 4.03-4.19 (2H, m), 6.09 (1H, d, J=2.4 Hz), 6.25 (1H, dd, J=8.4 Hz, 2.4 Hz), 6.91 (2H, d, J=9.0 Hz), 7.03 (2H, d, J=9.0 Hz), 7.07 (1H, d, J=8.4 Hz), 7.56 (1H, d, J=5.1 Hz), 7.83 (1H, d, J=5.1 Hz), 8.37 (1H, s). [M+H] Calc'd for C$_{27}$H$_{29}$N$_3$O$_4$, 460; Found, 460.

Preparation 212a 1-nitro-4-propoxybenzene O$_2$N

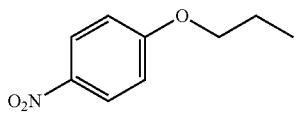

The title compound was prepared in 98% yield according to the procedure for Preparation 211a. [M+H] Calc'd for C$_9$H$_{11}$NO$_3$, 182; Found, 182.

Preparation 212b 4-propoxyaniline

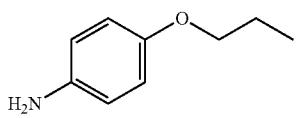

The title compound was prepared in 100% yield from Preparation 212a according to the procedure for Preparation 211b. [M+H] Calc'd for C$_9$H$_{13}$NO, 152; Found, 152.

The title compound was prepared in 55% yield from Preparation 126b and Preparation 211c according to the general procedure outlined for Preparation 126c. [M+H] Calc'd for C$_{28}$H$_{31}$N$_3$O$_4$, 474; Found, 474.

Preparation 212c

N-methyl-4-propoxyaniline

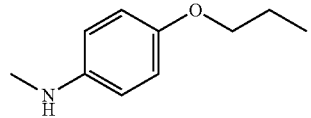

The title compound was prepared in 86% overall yield from 4-propoxyaniline according to the general procedure outlined for Preparation 127a. [M+H] Calc'd for C$_{10}$H$_{15}$NO, 166; Found, 166.

Preparation 212d methyl 3-({[(4R)-7-[methyl(4-propoxyphenyl)amino]-3,4-dihydro-2H-1-benzopyran-4-yl]methyl}amino)pyridine-4-carboxylate

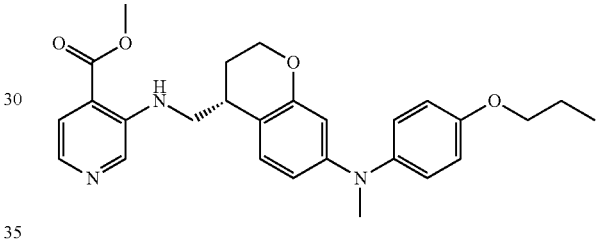

The title compound was prepared in 56% yield from Preparation 126b and Preparation 212c according to the general procedure outlined for Preparation 126c. [M+H] Calc'd for C$_{28}$H$_{31}$N$_3$O$_4$, 462; Found, 462.

Example 212

3-({[(4R)-7-[methyl(4-propoxyphenyl)amino]-3,4-dihydro-2H-1-benzopyran-4-yl]methyl}amino)pyridine-4-carboxylic acid

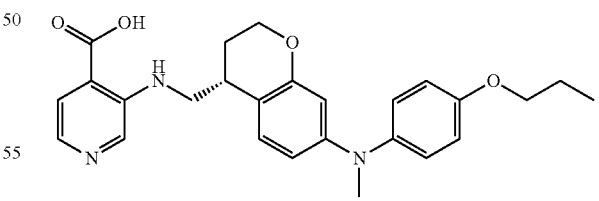

The title compound was prepared in 88% yield from Preparation 212d according to the procedure for Example 1. $^1$H NMR (300 MHz, DMSO-d$_6$): δ 0.95 (3H, t, J=7.5 Hz), 1.68-1.96 (4H, m), 2.99-3.03 (1H, m), 3.12 (3H, s), 3.40-3.47 (1H, m), 3.59-3.65 (1H, m), 3.90 (2H, t, J=6.3 Hz), 4.09-4.14 (2H, m), 6.10 (1H, s), 6.25 (1H, dd, J=8.4 Hz, 1.5 Hz), 6.89-6.92 (2H, m), 7.02-7.08 (3H, m), 7.59 (1H, d, J=5.1 Hz), 7.84 (1H, d, J=4.8 Hz), 8.39 (1H, s). [M+H] Calc'd for C$_{26}$H$_{29}$N$_3$O$_4$, 448; Found, 448.

Preparation 213a

4-cyclopropoxy-N-methylaniline

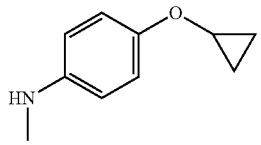

The title compound was prepared in 17% yield from 1-bromo-4-cyclopropoxybenzene according to the procedure for Preparation 187a. [M+H] Calc'd for $C_{10}H_{13}NO$, 164; Found, 164.

Preparation 213b methyl 3-({[(4R)-7-[(4-cyclopropoxyphenyl)(methyl)amino]-3,4-dihydro-2H-1-benzopyran-4-yl]methyl}amino)pyridine-4-carboxylate

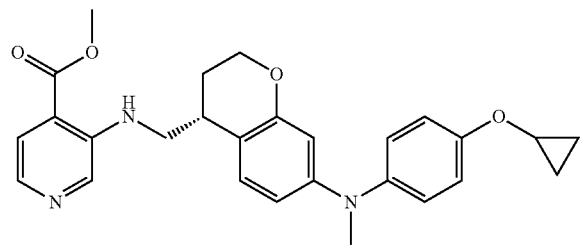 [SMILES: COC(=O)c1ccncc1NC[C@@H]1CCOc2cc(N(C)c3ccc(OC4CC4)cc3)ccc21]

The title compound was prepared in 22% yield from Preparation 126b and Preparation 213a according to the general procedure outlined for Preparation 126c. [M+H] Calc'd for $C_{27}H_{29}N_3O_4$, 460; Found, 460.

Example 213

3-({[(4R)-7-[(4-cyclopropoxyphenyl)(methyl)amino]-3,4-dihydro-2H-1-benzopyran-4-yl]methyl}amino)pyridine-4-carboxylic acid

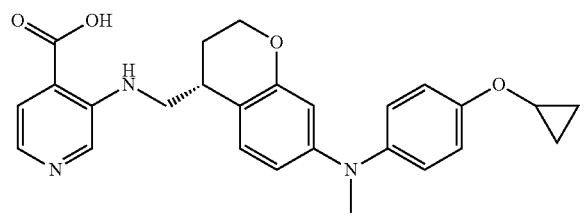

The title compound was prepared in 59% yield from Preparation 213b according to the procedure for Example 1. $^1$H NMR (300 MHz, DMSO-d$_6$): δ 0.62-0.68 (2H, m), 0.73-0.80 (2H, m), 1.77-2.01 (2H, m), 2.96-3.05 (1H, m), 3.14 (3H, s), 3.39-3.47 (1H, m), 3.59-3.65 (1H, m), 3.78-3.85 (1H, m), 4.04-4.19 (2H, m), 6.11 (1H, d, J=1.5 Hz), 6.31 (1H, dd, J=8.4 Hz, 1.5 Hz), 7.01-7.10 (5H, m), 7.56 (1H, d, J=4.8 Hz), 7.83 (1H, d, J=4.8 Hz), 8.37 (1H, s). [M+H] Calc'd for $C_{26}H_{27}N_3O_4$, 446; Found, 446.

Preparation 214a

N-methyl-4-(2,2,2-trifluoroethoxy)aniline

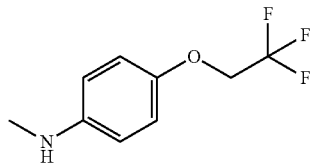

The title compound was prepared in 98% overall yield from 4-(2,2,2-trifluoroethoxy)aniline according to the general procedure outlined for Preparation 127a. [M+H] Calc'd for $C_9H_{10}F_3NO$, 206; Found, 206.

Preparation 214b methyl 3-({[(4R)-7-{methyl[4-(2,2,2-trifluoroethoxy)phenyl]amino}-3,4-dihydro-2H-1-benzopyran-4-yl]methyl}amino)pyridine-4-carboxylate

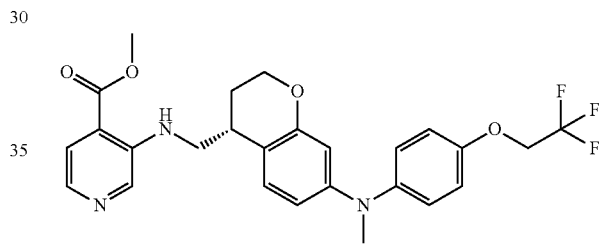

The title compound was prepared in 35% yield from Preparation 126b and Preparation 214a according to the general procedure outlined for Preparation 126c. [M+H] Calc'd for $C_{26}H_{26}F_3N_3O_4$, 502; Found, 502.

Example 214

3-({[(4R)-7-{methyl[4-(2,2,2-trifluoroethoxy)phenyl]amino}-3,4-dihydro-2H-1-benzopyran-4-yl]methyl}amino)pyridine-4-carboxylic acid

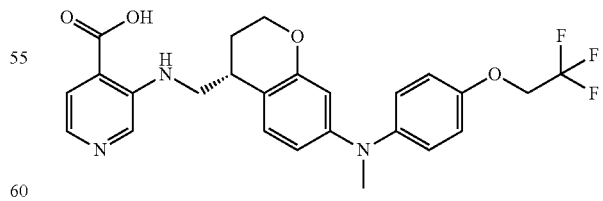

The title compound was prepared in 62% yield from Preparation 214b according to the procedure for Example 1. $^1$H NMR (300 MHz, DMSO-d$_6$): δ 1.78-2.03 (2H, m), 2.98-3.07 (1H, m), 3.15 (3H, s), 3.41-3.49 (1H, m), 3.60-3.67 (1H, m), 4.05-4.20 (2H, m), 4.73 (2H, q, J=9.0 Hz), 6.17 (1H, d, J=2.1 Hz), 6.31 (1H, dd, J=8.4 Hz, 2.1 Hz), 7.01-7.12 (5H, m), 7.56 (1H, d, J=4.8 Hz), 7.84 (1H, d, J=4.8 Hz), 8.39 (1H, s). [M+H] Calc'd for $C_{25}H_{24}F_3N_3O_4$, 488; Found, 488.

Preparation 215a cyclopropyl(4-(methylamino)phenyl)methanone

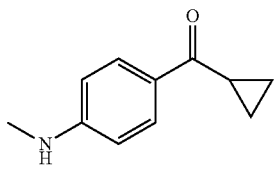

The title compound was prepared in 57% yield from 4-bromophenyl cyclopropyl ketone according to the procedure for Preparation 187a. [M+H] Calc'd for $C_{11}H_{13}NO$, 176; Found, 176.

Preparation 215b 4-(cyclopropylmethyl)-N-methylaniline

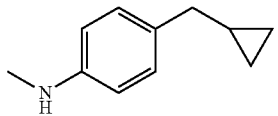

Preparation 215a (0.5 g, 2.85 mmol), hydrazine monohydrate (0.3 ml) and potassium hydroxide (0.4 g) were added to ethylene glycol (5 ml), and the mixture was heated to reflux for 1 h. The hydrazine monohydrate and water were then boiled off by heating open for 2 h. The reaction mixture was cooled and partitioned between water (20 ml) and ethyl acetate (30 ml), and the organic layer was separated. The aqueous layer was extracted with ethyl acetate (30 ml) and the combined organic phases were washed with water (15 ml) and brine (15 ml), dried ($Na_2SO_4$), and concentrated. The residue was purified by silica gel chromatography (0-10% EtOAc/PE) to give 0.22 g (48%) of the title compound as a colorless oil. [M+H] Calc'd for $C_{11}H_{15}N$, 162; Found, 162.

Preparation 215c methyl 3-({[(4R)-7-{[4-(cyclopropylmethyl)phenyl](methyl)amino}-3,4-dihydro-2H-1-benzopyran-4-yl]methyl}amino)pyridine-4-carboxylate

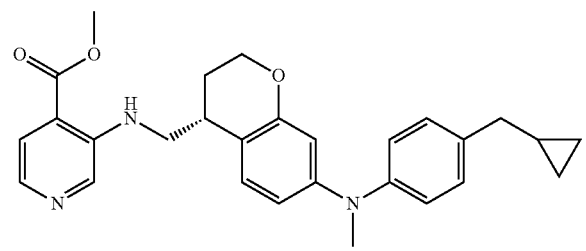 [SMILES: COC(=O)c1ccncc1NC[C@@H]1CCOc2cc(N(C)c3ccc(CC4CC4)cc3)ccc21]

The title compound was prepared in 40% yield from Preparation 126b and Preparation 215b according to the general procedure outlined for Preparation 126c. [M+H] Calc'd for $C_{28}H_{31}N_3O_3$, 458; Found, 458.

Example 215

3-({[(4R)-7-{[4-(cyclopropylmethyl)phenyl](methyl)amino}-3,4-dihydro-2H-1-benzopyran-4-yl]methyl}amino)pyridine-4-carboxylic acid

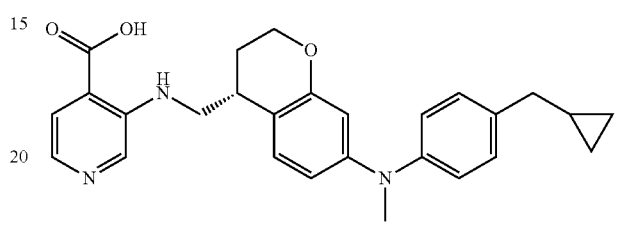

The title compound was prepared in 85% yield from Preparation 215c according to the procedure for Example 1. $^1$H NMR (300 MHz, DMSO-$d_6$): δ 0.15-0.21 (2H, m), 0.43-0.50 (2H, m), 0.90-1.01 (1H, m), 1.80-1.90 (1H, m), 1.91-2.03 (1H, m), 2.45 (2H, d, J=7.2 Hz), 3.01-3.07 (1H, m), 3.18 (3H, s), 3.41-3.50 (1H, m), 3.61-3.68 (1H, m), 4.06-4.21 (2H, m), 6.26 (1H, d, J=2.1 Hz), 6.41 (1H, dd, J=8.4 Hz, 2.1 Hz), 6.97 (2H, d, J=7.8 Hz), 7.14 (1H, d, J=8.4 Hz), 7.19 (2H, d, J=8.7 Hz), 7.56 (1H, d, J=4.8 Hz), 7.56 (1H, d, J=4.8 Hz), 8.38 (1H, s). [M+H] Calc'd for $C_{27}H_{29}N_3O_3$, 444. Found, 444.

Preparation 216a methyl 3-({[(4R)-7-[(4-cyclopropanecarbonylphenyl)(methyl)amino]-3,4-dihydro-2H-1-benzopyran-4-yl]methyl}amino)pyridine-4-carboxylate

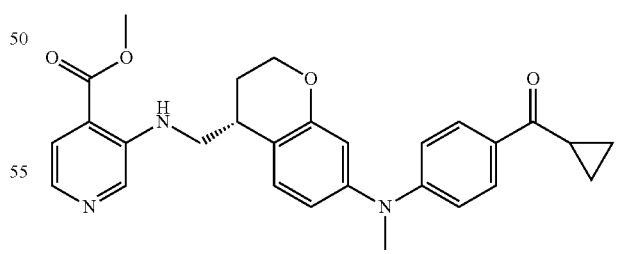

The title compound was prepared in 58% yield from Preparation 126b and Preparation 215a according to the general procedure outlined for Preparation 126c. [M+H] Calc'd for $C_{28}H_{29}N_3O_4$, 472; Found, 472.

Example 216

3-({[(4R)-7-[(4-cyclopropanecarbonylphenyl)(methyl)amino]-3,4-dihydro-2H-1-benzopyran-4-yl]methyl}amino)pyridine-4-carboxylic acid

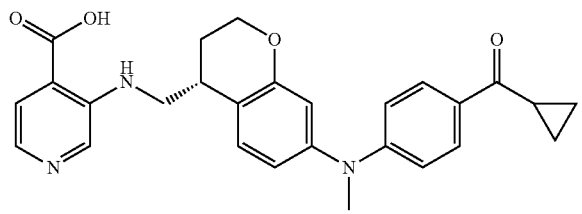 [SMILES: CN(c1ccc(C(=O)C2CC2)cc1)c1ccc2c(c1)OCC[C@H]2CNc1cnccc1C(=O)O]

The title compound was prepared in 92% yield from Preparation 215c according to the procedure for Example 1. $^1$H NMR (300 MHz, DMSO-$d_6$): δ 0.92-0.95 (4H, m), 1.88-2.07 (2H, m), 2.72-2.82 (1H, m), 3.11-3.20 (1H, m), 3.30 (3H, s), 3.49-3.57 (1H, m), 3.70-3.76 (1H, m), 4.15-4.27 (2H, m), 6.67 (1H, s), 6.75 (1H, d, J=7.5 Hz), 6.81 (2H, d, J=8.4 Hz), 7.38 (1H, d, J=8.4 Hz), 7.58 (1H, d, J=4.8 Hz), 7.85 (1H, d, J=4.8 Hz), 7.89 (2H, d, J=8.4 Hz), 8.41 (1H, s). [M+H] Calc'd for $C_{27}H_{27}N_3O_4$, 458; Found, 458.

Preparation 217a (6-bromo-1H-inden-3-yl)methanamine, hydrochloride

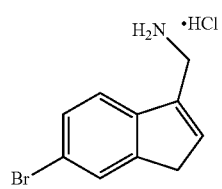 [SMILES: Cl ; NCC1=CCc2cc(Br)ccc21]

To a solution of 5-bromo-1-indanone (10.0 g, 47.4 mmol) and ZnI$_2$ (100 mg) in toluene (100 mL) was added TMSCN (15.0 mL, 94.8 mmol) at rt. The solution was heated at 60° C. overnight. The reaction was cooled to rt, and THF (50 mL) was added. LAH (40.0 mL, 2.4 M, 94.8 mmol) was added dropwise at rt, and the reaction was heated at 40° C. for 3 h. EtOAc (50 mL) was added at rt, the reaction mixture was stirred for 30 min. Water (10 mL) was added, and the reaction stirred for 30 min and then was dried (Na$_2$SO$_4$), filtered, and concentrated in vacuo to a brown oil.

To a solution of this brown oil in toluene (50 mL) was added HCl/dioxane (30 mL, 1.0 M), and the reaction was stirred at reflux for 10 min. The reaction was cooled to rt, and the solid was collected by filtration to give 8.6 g (70%) of the crude title compound as a yellow solid. [M+H] Calc'd for $C_{10}H_{10}BrN$, 224, 226; Found, 224, 226.

Preparation 217b (5-bromo-2,3-dihydro-1H-inden-1-yl)methanamine

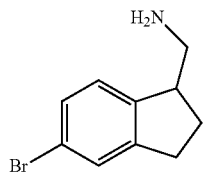

To a solution of Preparation 217a (3.0 g, 11.5 mmol) in MeOH (50 mL) and AcOH (5 mL) was added Raney Ni (300 mg) at rt. The mixture was stirred at 50° C. overnight under 50 psi of H$_2$. After filtration, the solvent was removed under vacuum. The residue was diluted with EtOAc and basified to pH 8 with K$_2$CO$_3$. The organic layer was separated, washed with brine, dried (Na$_2$SO$_4$) and concentrated to give 2.2 g (85%) of the title compound as a brown oil. [M+H] Calc'd for $C_{10}H_{12}BrN$, 226, 228; Found, 226, 228.

Preparation 217c methyl 3-{[(5-bromo-2,3-dihydro-1H-inden-1-yl)methyl]amino}pyridine-4-carboxylate To a suspension of Preparation 217b (500 mg, 2.2 mmol), methyl 3-bromoisonicotinate (717 mg, 3.3 mmol), Xantphos (192 mg, 0.3 mmol) and Cs$_2$CO$_3$ (1.0 g, 3.1 mmol) in toluene (30 mL) was added Pd$_2$dba$_3$ (102 mg, 0.1 mmol) at rt under N$_2$. The reaction was stirred at reflux overnight. After filtration, the solvent was removed in vacuo, and the residue was purified by silica gel chromatography (PE:EtOAc=5:1) to give 380 mg (48%) of the title compound as a yellow oil. [M+H] Calc'd for $C_{17}H_{17}BrN_2O_2$, 360, 362; Found, 360, 362.

Preparation 217d methyl 3-({[(1S)-5-[methyl(phenyl)amino]-2,3-dihydro-1H-inden-1-yl]methyl}amino)pyridine-4-carboxylate; and Preparation 217e methyl 3-({[(1R)-5-[methyl(phenyl)amino]-2,3-dihydro-1H-inden-1-yl]methyl}amino)pyridine-4-carboxylate

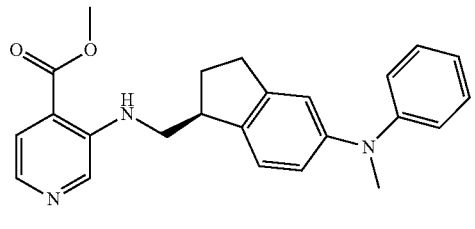

217d

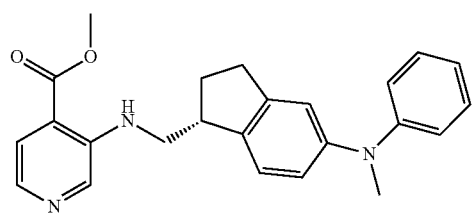

217e

To a suspension of Preparation 217c (380 mg, 1.05 mmol), N-methyl aniline (135 mg, 1.26 mmol), Xantphos (91 mg, 0.16 mmol) and Cs$_2$CO$_3$ (479 mg, 1.47 mmol) in toluene (30 mL) was added Pd$_2$dba$_3$ (48 mg, 0.053 mmol) at rt under N$_2$. The reaction was stirred at reflux overnight. After filtration, the solvent was removed in vacuo, and the residue was purified by silica gel chromatography (PE:EtOAc=5:1) to give 150 mg (37%) of the product racemate as a yellow oil. [M+H] Calc'd for C$_{24}$H$_{25}$N$_3$O$_2$, 388; Found, 388.

Separation by chiral prep-HPLC (Column: Chiralcel: IC 5 um 4.6*250 mm, Mobile phase: Hex:EtOH=80:20, F: 1.0 mL/min, W: 230 nm, T: ambient) gave 60 mg (40%) of Preparation 217d (10.726 min) and 50 mg (33%) of Preparation 217e (13.051 min), each as a yellow oil.

Example 217

3-({[(1S)-5-[methyl(phenyl)amino]-2,3-dihydro-1H-inden-1-yl]methyl}amino)pyridine-4-carboxylic acid

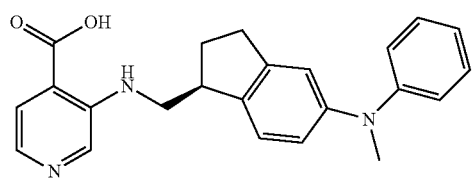 [SMILES: CN(c1ccccc1)c1ccc2c(c1)CC[C@@H]2CNc1cnccc1C(=O)O]

To a solution of Preparation 217d (40 mg, 0.10 mmol) in THF (5 mL) and H$_2$O (5 mL) was added LiOH.H$_2$O (4 mg, 0.20 mmol) at rt, and the reaction was stirred for 2 h. THF was removed in vacuo, the residue was acidified to pH=5 with 1.0 N aqueous HCl solution. The precipitate was collected by filtration to give 30 mg (77%) of the title compound as a yellow solid. $^1$H NMR (300 MHz, DMSO-d$_6$): δ 1.79-1.86 (1H, m), 2.22-2.28 (1H, m), 2.74-2.82 (1H, m), 2.87-2.94 (1H, m), 3.20 (3H, s), 3.27-3.42 (2H, m), 3.59-3.62 (1H, m), 6.81-6.92 (5H, m), 7.17-7.27 (3H, m), 7.54 (1H, d, J=4.8 Hz), 7.81 (1H, d, J=5.1 Hz), 8.32 (1H, s). [M+H] Calc'd for C$_{23}$H$_{23}$N$_3$O$_2$, 374; Found, 374.

Example 218

3-({[(1R)-5-[methyl(phenyl)amino]-2,3-dihydro-1H-inden-1-yl]methyl}amino)pyridine-4-carboxylic acid

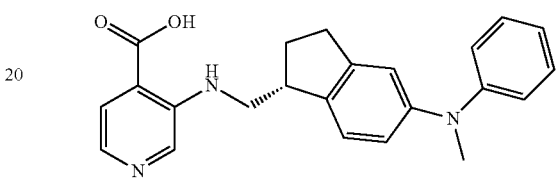

The title compound was prepared in 90% yield from Preparation 217e according to the procedure for Example 217. $^1$H NMR (300 MHz, DMSO-d$_6$): δ 1.79-1.86 (1H, m), 2.22-2.28 (1H, m), 2.74-2.82 (1H, m), 2.87-2.94 (1H, m), 3.20 (3H, s), 3.27-3.42 (2H, m), 3.59-3.62 (1H, m), 6.81-6.92 (5H, m), 7.17-7.27 (3H, m), 7.54 (1H, d, J=4.8 Hz), 7.81 (1H, d, J=5.1 Hz), 8.32 (1H, s). [M+H] Calc'd for C$_{23}$H$_{23}$N$_3$O$_2$, 374; Found, 374.

Preparation 219a methyl 3-({[(1S)-5-[methyl(4-methylphenyl)amino]-2,3-dihydro-1H-inden-1-yl]methyl}amino)pyridine-4-carboxylate; and Preparation 219b methyl 3-({[(1R)-5-[methyl(4-methylphenyl)amino]-2,3-dihydro-1H-inden-1-yl]methyl}amino)pyridine-4-carboxylate

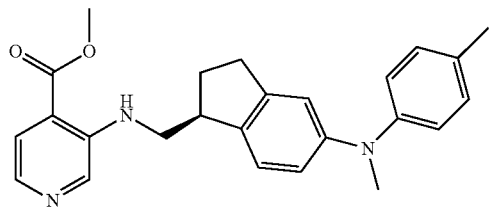

219a

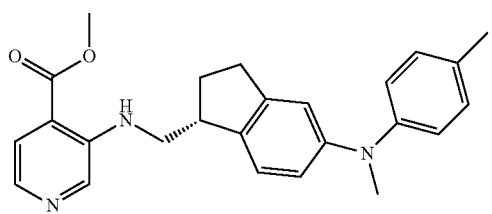

219b

The racemate of the title compounds was prepared in 42% yield from Preparation 217c and N-methyl-p-toluidine according to the procedure for Preparation 217d and 217e. [M+H] Calc'd for $C_{25}H_{27}N_3O_2$, 402; Found, 402.

Separation by chiral prep-HPLC (Column: Chiralcel: IC 5 um 4.6*250 mm, Mobile phase: Hex:EtOH=60:40, F: 1.0 mL/min, W: 230 nm, T: ambient) gave Preparation 219a (6.536 min, 43% yield) and Preparation 219b (7.378 min, 40% yield), each as a yellow oil.

Example 219

3-({[(1S)-5-[methyl(4-methylphenyl)amino]-2,3-dihydro-1H-inden-1-yl]methyl}amino)pyridine-4-carboxylic acid

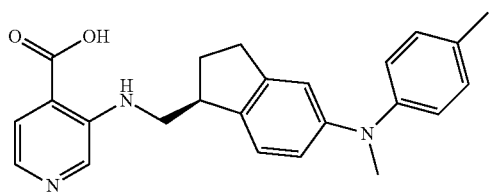

The title compound was prepared in 89% yield from Preparation 219b according to the procedure for Example 217. $^1$H NMR (300 MHz, DMSO-$d_6$): δ 1.77-1.83 (1H, m), 2.16-2.28 (4H, m), 2.69-2.93 (2H, m), 3.16 (3H, s), 3.29-3.39 (2H, m), 3.57-3.59 (1H, m), 6.70-6.73 (1H, m), 6.80-6.87 (3H, m), 7.05 (2H, d, J=8.1 Hz), 7.20 (1H, d, J=8.4 Hz), 7.54 (1H, d, J=5.1 Hz), 7.81 (1H, d, J=5.1 Hz), 8.32 (1H, s). [M+H] Calc'd for $C_{24}H_{25}N_3O_2$, 388; Found, 388.

Example 220

3-({[(1R)-5-[methyl(4-methylphenyl)amino]-2,3-dihydro-1H-inden-1-yl]methyl}amino)pyridine-4-carboxylic acid

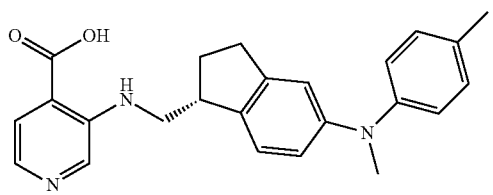 [SMILES: Cc1ccc(N(C)c2ccc3c(c2)CC[C@H]3CNc2cnccc2C(=O)O)cc1]

The title compound was prepared in 75% yield from Preparation 219a according to the procedure for Example 217. $^1$H NMR (300 MHz, DMSO-$d_6$): δ 1.77-1.83 (1H, m), 2.16-2.28 (4H, m), 2.69-2.93 (2H, m), 3.16 (3H, s), 3.29-3.39 (2H, m), 3.57-3.59 (1H, m), 6.70-6.73 (1H, m), 6.80-6.87 (3H, m), 7.05 (2H, d, J=8.1 Hz), 7.20 (1H, d, J=8.4 Hz), 7.54 (1H, d, J=5.1 Hz), 7.81 (1H, d, J=5.1 Hz), 8.32 (1H, s). [M+H] Calc'd for $C_{24}H_{25}N_3O_2$, 388; Found, 388.

Preparation 221a methyl 3-({[(1S)-5-{[4-(dimethylamino)phenyl](methyl)amino}-2,3-dihydro-1H-inden-1-yl]methyl}amino)pyridine-4-carboxylate; and Preparation 221b methyl 3-({[(1R)-5-{[4-(dimethylamino)phenyl](methyl)amino}-2,3-dihydro-1H-inden-1-yl]methyl}amino)pyridine-4-carboxylate

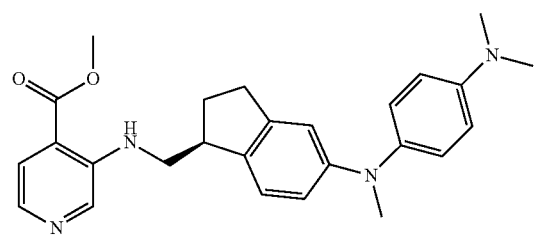

221a

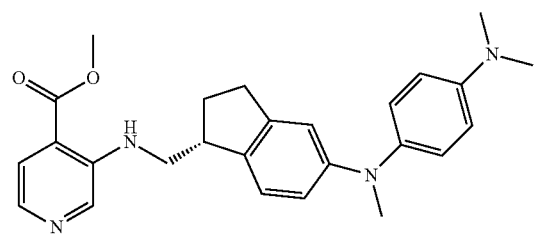

221b

The racemate of the title compounds was prepared in 34% yield from Preparation 217c and 1-N,1-N,4-N-trimethylbenzene-1,4-diamine according to the procedure for Preparation 217d and 217e. [M+H] Calc'd for $C_{26}H_{30}N_4O_2$, 431; Found, 431.

Separation by chiral prep-HPLC (Column: Chiralcel: ID 5 um 4.6*250 mm, Mobile phase: Hex:IPA=50:50, W: 230 nm, T: 30° C.) gave Preparation 221a (10.573 min, 40% yield) and Preparation 221b (13.379 min, 42% yield), each as a yellow oil.

Example 221

3-({[(1S)-5-{[4-(dimethylamino)phenyl](methyl)amino}-2,3-dihydro-1H-inden-1-yl]methyl}amino)pyridine-4-carboxylic acid

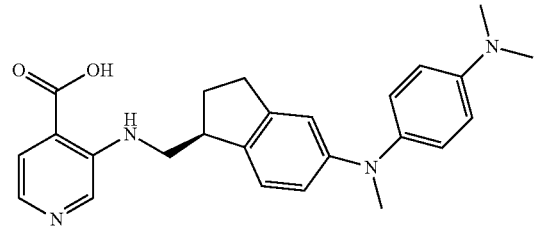 [SMILES: CN(C)c1ccc(N(C)c2ccc3c(c2)CC[C@@H]3CNc2cnccc2C(=O)O)cc1]

The title compound was prepared in 77% yield from Preparation 221a according to the procedure for Example 217. ¹H NMR (300 MHz, DMSO-d₆): δ 1.74-1.80 (1H, m), 2.16-2.22 (1H, m), 2.65-3.31 (13H, m), 3.49-3.51 (1H, m), 6.46-7.14 (7H, m), 7.53 (1H, d, J=4.8 Hz), 7.80 (1H, d, J=4.8 Hz), 8.29 (1H, s). [M+H] Calc'd for C₂₅H₂₆N₄O₂, 417; Found, 417.

Example 222

3-({[(1R)-5-{[4-(dimethylamino)phenyl](methyl)amino}-2,3-dihydro-1H-inden-1-yl]methyl}amino)pyridine-4-carboxylic acid

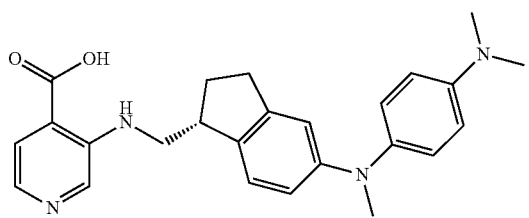 [SMILES: CN(C)c1ccc(N(C)c2ccc3c(c2)CC[C@H]3CNc2cnccc2C(=O)O)cc1]

The title compound was prepared in 78% yield from Preparation 221b according to the procedure for Example 217. ¹H NMR (300 MHz, DMSO-d₆): δ 1.74-1.80 (1H, m), 2.16-2.22 (1H, m), 2.65-3.31 (13H, m), 3.49-3.51 (1H, m), 6.46-7.14 (7H, m), 7.53 (1H, d, J=4.8 Hz), 7.80 (1H, d, J=4.8 Hz), 8.29 (1H, s). [M+H] Calc'd for C₂₅H₂₆N₄O₂, 417; Found, 417.

Preparation 223a methyl 3-({[(1S)-5-[(4-cyclopropylphenyl)(methyl)amino]-2,3-dihydro-1H-inden-1-yl]methyl}amino)pyridine-4-carboxylate; and Preparation 223b methyl 3-({[(1R)-5-[(4-cyclopropylphenyl)(methyl)amino]-2,3-dihydro-1H-inden-1-yl]methyl}amino)pyridine-4-carboxylate 223a

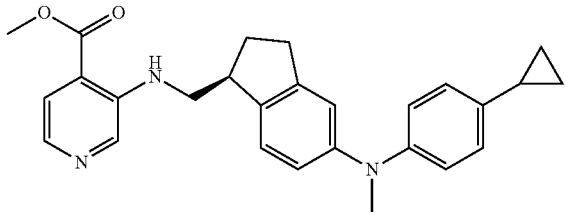

223b

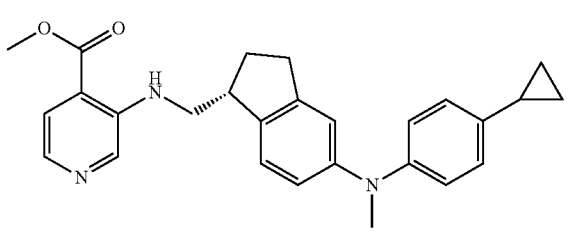

The racemate of the title compounds was prepared in 41% yield from Preparation 217c and 4-cyclopropyl-N-methyl-aniline according to the procedure for Preparation 217d and 217e. [M+H] Calc'd for C₂₇H₂₉N₃O₂, 428; Found, 428.

Separation by chiral HPLC (Column: Chiralcel: ID 5 um 4.6*250 mm, Mobile phase: Hex:IPA=70:30, F: 1.0 mL/min, W: 230 nm, T: 30° C.) gave Preparation 223a (9.737 min, 32% yield) and Preparation 223b (11.171 min, 29% yield), each as a yellow oil.

Example 223

3-({[(1S)-5-[(4-cyclopropylphenyl)(methyl)amino]-2,3-dihydro-1H-inden-1-yl]methyl}amino)pyridine-4-carboxylic acid

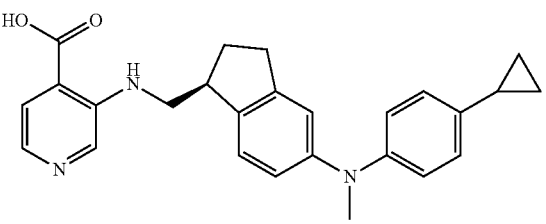 [SMILES: CN(c1ccc(C2CC2)cc1)c1ccc2c(c1)CC[C@@H]2CNc1cnccc1C(=O)O]

The title compound was prepared in 78% yield from Preparation 223a according to the procedure for Example 217. ¹H NMR (400 MHz, DMSO-d₆): δ 0.52-0.61 (2H, m), 0.86-0.91 (2H, m), 1.23 (1H, s), 1.81-1.87 (2H, m), 2.22-2.25 (1H, m), 2.76-2.78 (1H, m), 2.86-2.90 (1H, m), 3.18 (3H, s), 3.32-3.40 (1H, m), 3.58-3.62 (1H, m), 6.73 (1H, d, J=6.3 Hz), 6.82-6.88 (3H, m), 6.97-6.99 (2H, m), 7.21 (1H, d, J=6.0 Hz), 7.56 (1H, d, J=3.6 Hz), 7.84 (1H, d, J=3.9 Hz), 8.34 (1H, s).

[M+H] Calc'd for C₂₆H₂₇N₃O₂, 414; Found, 414.

Example 224

3-({[(1R)-5-[(4-cyclopropylphenyl)(methyl)amino]-2,3-dihydro-1H-inden-1-yl]methyl}amino)pyridine-4-carboxylic acid

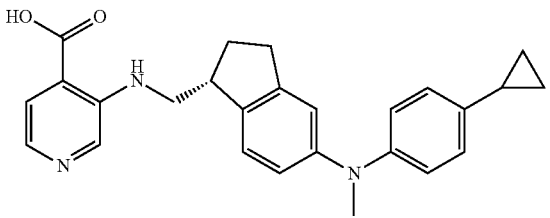 [SMILES: CN(c1ccc(C2CC2)cc1)c1ccc2c(c1)CC[C@H]2CNc1cnccc1C(=O)O]

The title compound was prepared in 91% yield from Preparation 223b according to the procedure for Example 217. ¹H NMR (400 MHz, DMSO-d₆): δ 0.52-0.61 (2H, m), 0.86-0.91 (2H, m), 1.23 (1H, s), 1.81-1.87 (2H, m), 2.22-2.25 (1H, m), 2.76-2.78 (1H, m), 2.86-2.90 (1H, m), 3.18 (3H, s), 3.32-3.40 (1H, m), 3.58-3.62 (1H, m), 6.73 (1H, d, J=6.3 Hz), 6.82-6.88 (3H, m), 6.97-6.99 (2H, m), 7.21 (1H, d, J=6.0 Hz), 7.56 (1H, d, J=3.6 Hz), 7.84 (1H, d, J=3.9 Hz), 8.34 (1H, s). [M+H] Calc'd for C₂₆H₂₇N₃O₂, 414; Found, 414.

Preparation 225a 1,3-dimethyl 2-(4-bromo-2-nitrophenyl)propanedioate

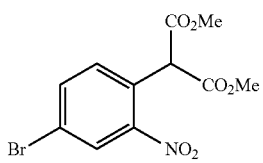

To a solution of dimethyl malonate (7.8 mL, 68.2 mmol) in DME (100 mL) at 0° C. was added $K_2CO_3$ (12.6 g, 91.0 mmol). The reaction mixture was stirred for 30 min, and then 4-bromo-1-fluoro-2-nitrobenzene (10.0 g, 45.5 mmol) was added. The reaction mixture stirred at 40° C. overnight. The reaction was cooled, diluted with water (200 mL), and extracted with EtOAc (100 mL×3). The combined organic layers were washed with brine (100 mL), dried ($Na_2SO_4$) and concentrated. The residue was triturated with PE:EtOAc=8:1 (30 mL) to 13.0 g (86%) of the title compound as a yellow solid. [M+H] Calc'd for $C_{11}H_{10}BrNO_6$, 332, 334; Found, 332, 334.

Preparation 225b 2-(4-bromo-2-nitrophenyl)propane-1,3-diol

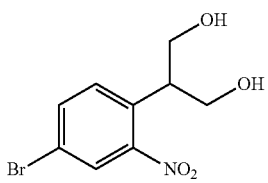

To a solution of Preparation 225a (500 mg, 1.5 mmol) in dioxane (20 mL) was added $BH_3\text{-}Me_2S$ (2.3 mL, 1.0 M in THF, 2.3 mmol) at rt. The reaction was stirred at 70° C. overnight. The reaction was cooled, diluted with water (20 mL), basified to pH 5 with sat. $Na_2CO_3$, and extracted with EtOAc (50 mL×3). The combined organic layers were washed with brine (100 mL), dried ($Na_2SO_4$), and concentrated. The residue was purified by silica gel chromatography (PE:EtOAc=3:2) to give 200 mg (48%) of the title compound as a yellow solid. [M+H] Calc'd for $C_9H_{10}BrNO_4$, 276, 278; Found, 276, 278.

Preparation 225c 2-(2-amino-4-bromophenyl)propane-1,3-diol

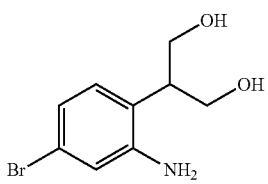

To a suspension of Preparation 225b (100 mg, 0.36 mmol) and $NH_4Cl$ (10 mg, 0.18 mmol) in dioxane (20 mL) was added Fe (203 mg, 3.60 mmol) at rt. The reaction was stirred at 80° C. for 2 h. The reaction was filtered through Celite. The filtrate was diluted with EtOAc (50 mL), washed with water (50 mL) and brine (50 mL), dried ($Na_2SO_4$), and concentrated. The residue was purified by silica gel chromatography (PE:EtOAc=1:1) to give 80 mg (90%) of the title compound as a yellow solid. [M+H] Calc'd for $C_9H_{12}BrNO_2$, 246, 248; Found, 246, 248.

Preparation 225d (6-bromo-2,3-dihydro-1-benzofuran-3-yl)methanol

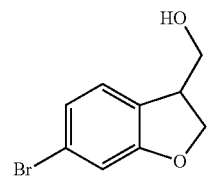

To a solution of Preparation 225c (200 mg, 0.81 mmol) in water (4 mL) and conc. $H_2SO_4$ (1 mL) was added a solution of $NaNO_2$ (61 mg, 0.89 mmol) in water (2 mL) at 0° C. The reaction was stirred at rt for 1.5 h, and at 50° C. for 10 min. The reaction was diluted with EtOAc (20 mL), basified to pH 5 with sat. $Na_2CO_3$, and extracted with EtOAc (30 mL×3). The combined organic layers were washed with brine (50 mL), dried ($Na_2SO_4$), and concentrated. The residue was purified by silica gel chromatography (PE:EtOAc=3:2) to give 81 mg (44%) of the title compound as a yellow oil. $^1$H NMR (300 MHz, $CDCl_3$): δ 3.56-3.61 (1H, m), 3.78 (2H, dd, J=0.9, 5.7 Hz), 4.47-4.52 (1H, m), 4.66 (1H, t, J=9.0 Hz), 6.95-7.01 (2H, m), 7.07 (1H, d, J=8.1 Hz).

Preparation 225e (6-bromo-2,3-dihydro-1-benzofuran-3-yl)methyl methanesulfonate

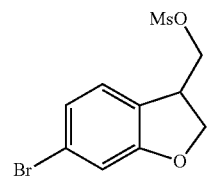

To a solution of Preparation 225d (520 mg, 2.3 mmol) in pyridine (0.5 mL) and DCM (20 mL) was added MsCl (0.2 mL, 2.7 mmol) at 0° C. The reaction was stirred at rt overnight. The reaction was diluted with water (30 mL), and extracted with DCM (30 mL×3). The combined organic layers were washed with 0.1N HCl (10 mL×2) and brine (50 mL), dried ($Na_2SO_4$), and concentrated to give 650 mg (93%) of the crude title compound as a yellow solid.

Preparation 225f 3-(azidomethyl)-6-bromo-2,3-dihydro-1-benzofuran

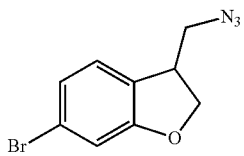 [SMILES: [N-]=[N+]=NCC1COc2cc(Br)ccc21]

To a solution of Preparation 225e (200 mg, 0.65 mmol) in DMF (10 mL) was added NaN$_3$ (47 mg, 0.72 mmol) at rt. The reaction was stirred at 55° C. overnight. The solution was diluted with water (50 mL) and extracted with EtOAc (30 mL×3). The combined organic layers were washed with brine (50 mL), dried (Na$_2$SO$_4$) and concentrated. The residue was purified by silica gel chromatography (PE:EA=10:1) to give 107 mg (65%) of the title compound as a yellow oil. $^1$H NMR (300 MHz, CDCl$_3$): δ 3.44-3.63 (3H, m), 4.37-4.42 (1H, m), 4.65 (1H, t, J=9.0 Hz), 6.97-7.03 (2H, m), 7.08 (1H, d, J=7.8 Hz).

Preparation 225g (6-bromo-2,3-dihydro-1-benzofuran-3-yl)methanamine

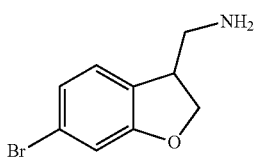 [SMILES: NCC1COc2cc(Br)ccc21]

To a solution of Preparation 225f (70 mg, 0.28 mmol) in THF (10 mL) and water (0.5 mL) was added PPh$_3$ (110 mg, 0.42 mmol) at rt, and the reaction was stirred overnight. The reaction was diluted with water (30 mL), acidified to pH=3 with 1N HCl, and washed with EtOAc (30 mL×2). The aqueous layer was basified to pH=9 with sat. Na$_2$CO$_3$ and extracted with EtOAc (30 mL×3). The combined organic layers were dried (Na$_2$SO$_4$) and concentrated to give 50 mg (78%) of the title compound as a yellow oil. [M+H] Calc'd for C$_9$H$_{10}$BrNO, 228, 230; Found, 228, 230.

Preparation 225h methyl 3-{[(6-bromo-2,3-dihydro-1-benzofuran-3-yl)methyl]amino}pyridine-4-carboxylate

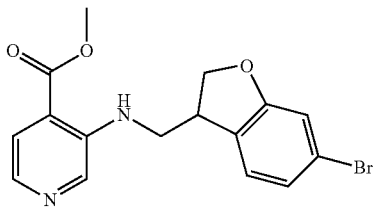 [SMILES: COC(=O)c1ccncc1NCC1COc2cc(Br)ccc21]

The title compound was prepared in 63% yield from Preparation 225g according to the procedure for Preparation 217c. [M+H] Calc'd for C$_{16}$H$_{15}$BrN$_2$O$_3$, 363; Found, 363.

Preparation 225j methyl 3-({[(3S)-6-[methyl(4-methylphenyl)amino]-2,3-dihydro-1-benzofuran-3-yl]methyl}amino)pyridine-4-carboxylate; and Preparation 225k methyl 3-({[(3R)-6-[methyl(4-methylphenyl)amino]-2,3-dihydro-1-benzofuran-3-yl]methyl}amino)pyridine-4-carboxylate

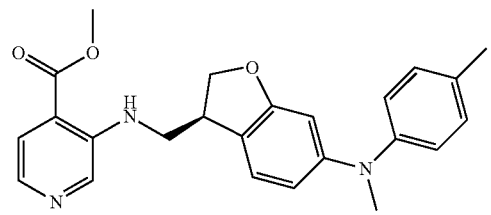

225j

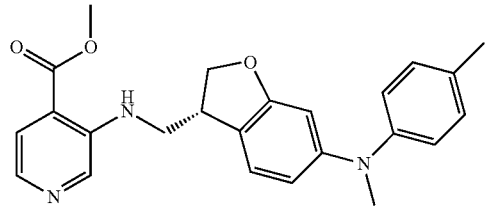

225k

The racemate of the title compounds was prepared in 60% yield from Preparation 225h and N-methyl-p-toluidine according to the procedure for Preparation 217d and 217e. [M+H] Calc'd for C$_{24}$H$_{25}$N$_3$O$_3$, 404; Found, 404.

Separation by chiral prep-HPLC (Column: Chiralcel: IC 5 um 4.6*250 mm, Mobile phase: Hex:EtOH=50:50, F: 1.0 mL/min, W: 230 nm, T: 30° C.) gave Preparation 225j (7.814 min, 33% yield) and Preparation 225k (10.720 min, 38% yield), each as a yellow oil.

Example 225

3-({[(3S)-6-[methyl(4-methylphenyl)amino]-2,3-dihydro-1-benzofuran-3-yl]methyl}amino)pyridine-4-carboxylic acid

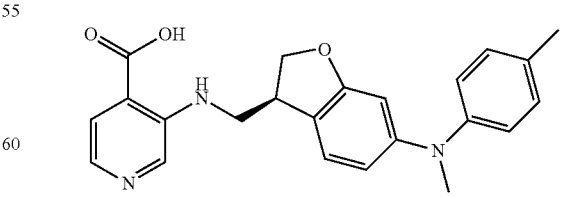

The title compound was prepared in 97% yield from Preparation 225j according to the procedure for Example 217. $^1$H NMR (300 MHz, DMSO-d$_6$): δ 2.24 (3H, s), 3.15 (3H, s), 3.47 (2H, d, J=6.9 Hz), 3.67-3.71 (1H, m), 4.29-4.34

(1H, m), 4.57 (1H, t, J=8.7 Hz), 6.27-6.34 (2H, m), 6.92 (2H, d, J=8.1 Hz), 7.08-7.14 (3H, m), 7.54 (1H, d, J=5.4 Hz), 7.83 (1H, d, J=5.1 Hz), 8.33 (1H, s). [M+H] Calc'd for C$_{23}$H$_{23}$N$_3$O$_3$, 390; Found, 390.

Example 226

3-({[(3R)-6-[methyl(4-methylphenyl)amino]-2,3-dihydro-1-benzofuran-3-yl]methyl}amino)pyridine-4-carboxylic acid

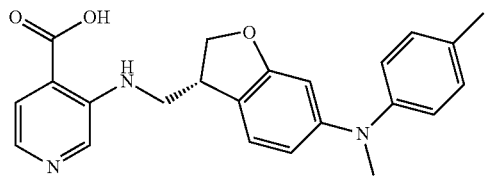 [SMILES: Cc1ccc(N(C)c2ccc3c(c2)OC[C@H]3CNc2cnccc2C(=O)O)cc1]

The title compound was prepared in 98% yield from Preparation 225k according to the procedure for Example 217. $^1$H NMR (300 MHz, DMSO-d$_6$): δ 2.24 (3H, s), 3.15 (3H, s), 3.47 (2H, d, J=6.9 Hz), 3.67-3.71 (1H, m), 4.29-4.34 (1H, m), 4.57 (1H, t, J=8.7 Hz), 6.27-6.34 (2H, m), 6.92 (2H, d, J=8.1 Hz), 7.08-7.14 (3H, m), 7.54 (1H, d, J=5.4 Hz), 7.83 (1H, d, J=5.1 Hz), 8.33 (1H, s). [M+H] Calc'd for C$_{23}$H$_{23}$N$_3$O$_3$, 390; Found, 390.

Preparation 227a methyl 3-({[(3S)-6-[(4-cyclopropylphenyl)(methyl)amino]-2,3-dihydro-1-benzofuran-3-yl]methyl}amino)pyridine-4-carboxylate; and Preparation 227b methyl 3-({[(3R)-6-[(4-cyclopropylphenyl)(methyl)amino]-2,3-dihydro-1-benzofuran-3-yl]methyl}amino)pyridine-4-carboxylate

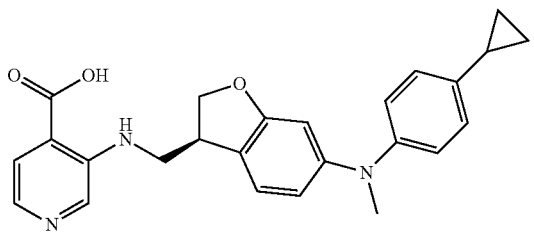 [SMILES: CN(c1ccc(C2CC2)cc1)c1ccc2c(c1)OC[C@@H]2CNc1cnccc1C(=O)O]

The racemate of the title compounds was prepared in 70% yield from Preparation 225h and 4-cyclopropyl-N-methyl-aniline according to the procedure for Preparation 217d and 217e. [M+H] Calc'd for C$_{24}$H$_{25}$N$_3$O$_3$, 404; Found, 404. [M+H] Calc'd for C$_{26}$H$_{27}$N$_3$O$_3$, 430; Found, 430.
Separation by chiral prep-HPLC (Column: Chiralcel: IC 5 um 4.6*250 mm, Mobile phase: Hex:EtOH=50:50, F: 1.0 mL/min, W: 230 nm, T: 30° C.) gave Preparation 227a (8.246 min, 17% yield) and Preparation 227b (11.339 min, 19% yield), each as a yellow oil.

Example 227

3-({[(3S)-6-[(4-cyclopropylphenyl)(methyl)amino]-2,3-dihydro-1-benzofuran-3-yl]methyl}amino)pyridine-4-carboxylic acid

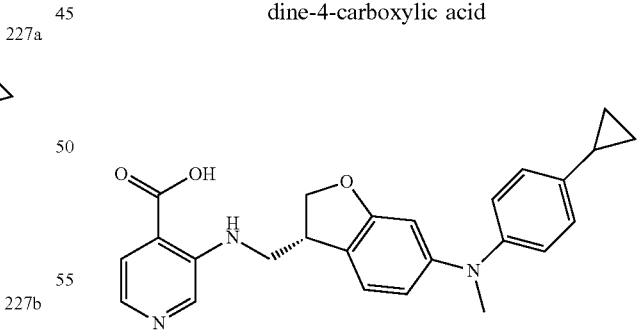

The title compound was prepared in 98% yield from Preparation 227a according to the procedure for Example 217. $^1$H NMR (300 MHz, DMSO-d$_6$): δ 0.57-0.62 (2H, m), 0.85-0.91 (2H, m), 1.82-1.87 (1H, m), 3.14 (3H, s), 3.48 (2H, d, J=6.3 Hz), 3.67-3.71 (1H, m), 4.29-4.34 (1H, m), 4.57 (1H, t, J=9.0 Hz), 6.26-6.33 (2H, m), 6.91 (2H, d, J=8.7 Hz), 6.98 (2H, d, J=8.7 Hz), 7.12 (1H, d, J=7.8 Hz), 7.54 (1H, d, J=4.8 Hz), 7.83 (1H, d, J=4.8 Hz), 8.35 (1H, s). [M+H] Calc'd for C$_{25}$H$_{25}$N$_3$O$_3$, 416; Found, 416.

Example 228

3-({[(3R)-6-[(4-cyclopropylphenyl)(methyl)amino]-2,3-dihydro-1-benzofuran-3-yl]methyl}amino)pyridine-4-carboxylic acid The title compound was prepared in 94% yield from Preparation 227b according to the procedure for Example 217. $^1$H NMR (300 MHz, DMSO-d$_6$): δ 0.57-0.62 (2H, m), 0.85-0.91 (2H, m), 1.82-1.87 (1H, m), 3.14 (3H, s), 3.48 (2H, d, J=6.3 Hz), 3.67-3.71 (1H, m), 4.29-4.34 (1H, m), 4.57 (1H, t, J=9.0 Hz), 6.26-6.33 (2H, m), 6.91 (2H, d, J=8.7 Hz), 6.98 (2H, d, J=8.7 Hz), 7.12 (1H, d, J=7.8 Hz), 7.54 (1H, d, J=4.8 Hz), 7.83 (1H, d, J=4.8 Hz), 8.35 (1H, s). [M+H] Calc'd for C$_{25}$H$_{25}$N$_3$O$_3$, 416; Found, 416.

Preparation 229a 4-bromo-2-(chloromethyl)-1-iodobenzene

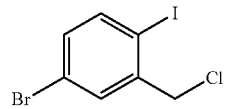

To a solution of (5-bromo-2-iodophenyl)methanol (1.4 g, 4.5 mmol) in DCM (20 mL) was added $SOCl_2$ (3.2 g, 26.9 mmol) at 0° C., and the reaction was stirred at rt overnight. The solution was concentrated, and the residue was purified silica gel chromatography (PE) to give 1.2 g (81%) of the title compound as a brown solid.

Preparation 229b

[(5-bromo-1,3-dihydro-2-benzofuran-1-yl)methoxy](tert-butyl)dimethylsilane

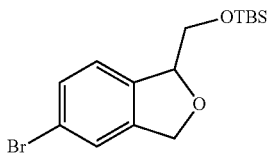 [SMILES: CC(C)(C)[Si](C)(C)OCC1OCc2cc(Br)ccc21]

To a solution of Preparation 229a (1.0 g, 3.0 mmol) in THF (25 mL) was added i-PrMgBr (1.6 mL, 2.0 M in THF, 3.2 mmol) at −10° C., and the mixture was stirred for 2 min. (tert-Butyl-dimethylsiloxy)acetaldehyde (578 g, 3.3 mmol) was added at −10° C. The reaction mixture was stirred at rt for 1 h, and then was heated at reflux overnight. The reaction was cooled, diluted with water (30 mL), and extracted with EtOAc (50 mL×3). The combined organic layers were washed with brine (100 mL), dried ($Na_2SO_4$), and concentrated. The residue was purified by silica gel chromatography (PE) to give 680 mg (66%) of the title compound as a yellow oil. $^1$H NMR (300 MHz, $CDCl_3$): δ 0.02 (3H, s), 0.04 (3H, s), 0.86 (9H, s), 3.72-3.78 (1H, m), 3.82-3.87 (1H, m), 5.02-5.18 (3H, m), 7.15 (1H, d, J=8.1 Hz), 7.35-7.39 (2H, m). [M+H] Calc'd for $C_{15}H_{23}BrO_2Si$, 343, 345; Found, 343, 345.

Preparation 229c (5-bromo-1,3-dihydro-2-benzofuran-1-yl)methanol

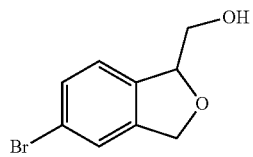 [SMILES: OCC1OCc2cc(Br)ccc21]

To a solution of Preparation 229b (5.0 g, 14.6 mmol) in THF (100 mL) was added TBAF (27.4 mL, 1.0 M in THF, 24.7 mmol) at rt, and the reaction was stirred for 30 min. The reaction was diluted with water (100 mL), and extracted with EtOAc (50 mL×3). The combined organic layers were washed with brine (50 mL), dried ($Na_2SO_4$), and concentrated to give 3.0 g (90%) of the title compound as a white solid. [M+H] Calc'd for $C_9H_9BrO_2$, 229, 231; Found, 229, 231.

Preparation 229d (5-bromo-1,3-dihydro-2-benzofuran-1-yl)methyl methanesulfonate

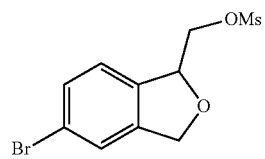 [SMILES: CS(=O)(=O)OCC1OCc2cc(Br)ccc21]

To a solution of Preparation 229c (5.0 g, 13.2 mmol) in pyridine (3 mL) and DCM (100 mL) was added MsCl (1.2 mL, 15.8 mmol) at 0° C., and the reaction was stirred at rt overnight. The solution was diluted with water (100 mL) and extracted with DCM (50 mL×3). The combined organic layers were washed with 0.1 N HCl (20 mL×2) and brine (50 mL), dried ($Na_2SO_4$), and concentrated to give 4.0 g (100%) of the title compound as a colorless oil.

Preparation 229e 1-(azidomethyl)-5-bromo-1,3-dihydro-2-benzofuran

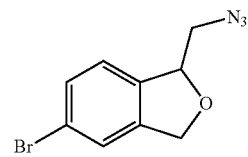 [SMILES: [N-]=[N+]=NCC1OCc2cc(Br)ccc21]

To a solution of Preparation 229d (4.0 g, 13.1 mmol) in DMF (50 mL) was added $NaN_3$ (898 mg, 13.8 mmol) at rt, and the reaction was stirred at 60° C. overnight. The reaction was diluted with water (100 mL) and extracted with EtOAc (80 mL×3). The combined organic layers were washed with brine (100 mL), dried ($Na_2SO_4$), and concentrated. The residue was purified by silica gel chromatography (PE: EA=10:1) to give 1.9 g (57%) of the title compound as a yellow oil.

Preparation 229f (5-bromo-1,3-dihydro-2-benzofuran-1-yl)methanamine

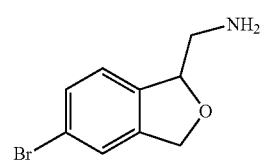 [SMILES: NCC1OCc2cc(Br)ccc21]

To a solution of Preparation 229e (1.9 g, 7.5 mmol) in THF (50 mL) and water (8 mL) was added $PPh_3$ (3.0 g, 11.3 mmol) at rt, and the reaction was stirred at 60° C. overnight. The reaction was diluted with water (50 mL), acidified to pH=3 with 1N HCl, and washed with EtOAc (50 mL×2). The aqueous layer was basified to pH=9 with sat. Na$_2$CO$_3$ and extracted with EtOAc (50 mL×3). The combined organic layers were dried (Na$_2$SO$_4$) concentrated to give 1.0 g (59%) of the title compound as a yellow oil. [M+H] Calc'd for C$_9$H$_{10}$BrNO, 228, 230; Found, 228, 230.

Preparation 229g methyl 3-{[(5-bromo-1,3-dihydro-2-benzofuran-1-yl)methyl]amino}pyridine-4-carboxylate

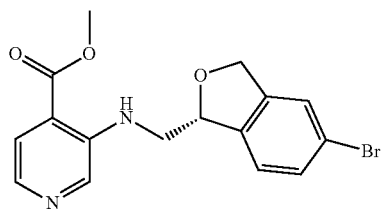 [SMILES: COC(=O)c1ccncc1NC[C@@H]1OCc2cc(Br)ccc21]

The title compound was prepared in 53% yield from Preparation 229f according to the procedure for Preparation 217c. [M+H] Calc'd for C$_{16}$H$_{15}$BrN$_2$O$_3$, 363,365; Found, 363, 365.

Preparation 229h methyl 3-({[(1S)-5-[methyl(4-methylphenyl)amino]-1,3-dihydro-2-benzofuran-1-yl]methyl}amino)pyridine-4-carboxylate; and Preparation 229j methyl 3-({[(1S)-5-[methyl(4-methylphenyl)amino]-1,3-dihydro-2-benzofuran-1-yl]methyl}amino)pyridine-4-carboxylate

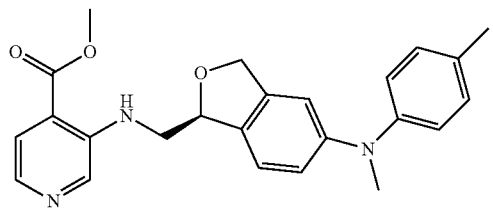

229h

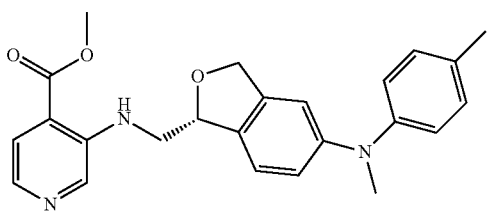

229j

The racemate of the title compounds was prepared in 75% yield from Preparation 229g and N-methyl-p-toluidine according to the procedure for Preparation 217d and 217e. [M+H] Calc'd for C$_{24}$H$_{25}$N$_3$O$_3$, 404; Found, 404.

Separation by chiral prep-HPLC (Column: Chiralcel: IE 5 um 4.6*250 mm, Mobile phase: Hex:EtOH=50:50, F: 1.0 mL/min, W: 230 nm, T: 30° C.) gave Preparation 229h (9.673 min, 16% yield) and Preparation 229j (11.741 min, 18% yield), each as a yellow oil.

Example 229

3-({[(1S)-5-[methyl(4-methylphenyl)amino]-1,3-dihydro-2-benzofuran-1-yl]methyl}amino)pyridine-4-carboxylic acid

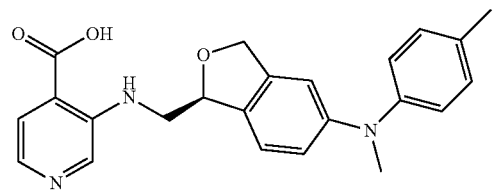

The title compound was prepared in 90% yield from Preparation 229h according to the procedure for Example 217. $^1$H NMR (300 MHz, DMSO-d$_6$): δ 2.26 (3H, s), 3.20 (3H, s), 3.48-3.54 (1H, m), 3.74-3.78 (1H, m), 4.90-4.99 (2H, m), 5.33-5.35 (1H, m), 6.78-6.80 (2H, m), 6.94 (2H, d, J=8.1 Hz), 7.12 (2H, d, J=8.1 Hz), 7.24 (1H, d, J=8.4 Hz), 7.54 (1H, d, J=5.1 Hz), 7.82 (1H, d, J=5.1 Hz), 8.38 (1H, s). [M+H] Calc'd for C$_{23}$H$_{23}$N$_3$O$_3$, 390; Found, 390.

Example 230

3-({[(1R)-5-[methyl(4-methylphenyl)amino]-1,3-dihydro-2-benzofuran-1-yl]methyl}amino)pyridine-4-carboxylic acid

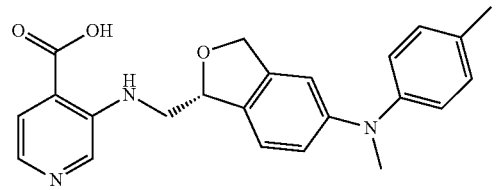

The title compound was prepared in 93% yield from Preparation 229j according to the procedure for Example 217. $^1$H NMR (300 MHz, DMSO-d$_6$): δ 2.26 (3H, s), 3.20 (3H, s), 3.48-3.54 (1H, m), 3.74-3.78 (1H, m), 4.90-4.99 (2H, m), 5.33-5.35 (1H, m), 6.78-6.80 (2H, m), 6.94 (2H, d, J=8.1 Hz), 7.12 (2H, d, J=8.1 Hz), 7.24 (1H, d, J=8.4 Hz), 7.54 (1H, d, J=5.1 Hz), 7.82 (1H, d, J=5.1 Hz), 8.38 (1H, s). [M+H] Calc'd for C$_{23}$H$_{23}$N$_3$O$_3$, 390; Found, 390.

Preparation 231a 6-bromo-1H-indene-3-carboxamide

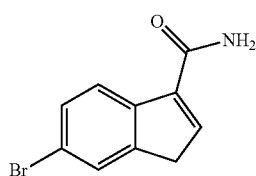 [SMILES: NC(=O)C1=CCc2cc(Br)ccc21]

To a solution of 5-bromo-1-indanone (50 g, 0.23 mol) in toluene (2000 mL) was added $ZnI_2$ (1.5 g), and the mixture was stirred at 40° C. until dissolved. TMSCN (76 mL, 0.57 mol) was added, and the reaction was stirred at reflux for 6 h. The solution was concentrated, and the residue was dissolved in 300 mL HOAc. While keeping the temperature under 25° C., concentrated $H_2SO_4$ (100 mL) was added, followed by water (30 mL), and then the reaction mixture was heated at 130° C. for 2 h. The solution was cooled to rt, diluted with water, and the solid was collected by filtration. The filter cake was triturated in THF and collected by filtration to give 25 g (44%) of the title compound as yellow solid. [M+H] Calc'd for $C_{10}H_8BrNO$, 238, 240; Found, 238, 240.

Preparation 231b (1R)-5-bromo-2,3-dihydro-1H-indene-1-carboxamide

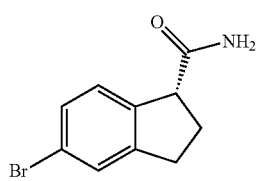 [SMILES: NC(=O)[C@@H]1CCc2cc(Br)ccc21]

To a solution of Preparation 231a (5.0 g, 21 mmol) in MeOH/THF (200 mL, 1:1) was added $Ru(OAc)_2$[s-binap] (250 mg). The mixture was stirred overnight at 60° C. under 5.0 M Pa of hydrogen. The mixture was filtered and concentrated to give 5.3 g (100%) of the crude title compound as a brown solid (ee >95%). [M+H] Calc'd for $C_{10}H_{10}BrNO$, 240, 242; Found, 240, 242. Analytical Column: Chiralcel: AS-H, Mobile phase: Hex: EtOH=60:40.

Preparation 231c

[(1R)-5-bromo-2,3-dihydro-1H-inden-1-yl]methanamine

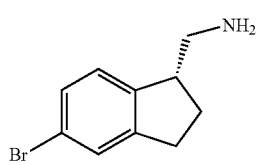

To a solution of Preparation 231b (5.3 g, 22 mmol) in THF (50 mL) was added $BH_3$-THF (110 mL, 110 mmol, 1.0 M). The resulting mixture was stirred at rt overnight. The mixture was poured into water and extracted with EtOAc. The combined organic layers were washed with brine, dried ($Na_2SO_4$), and concentrated to give 4.27 g (85%) of the title compound as a brown oil. [M+H] Calc'd for $C_{10}H_{12}BrN$, 226, 228; Found, 226, 228.

Preparation 231d methyl 3-({[(1R)-5-bromo-2,3-dihydro-1H-inden-1-yl]methyl}amino)pyridine-4-carboxylate

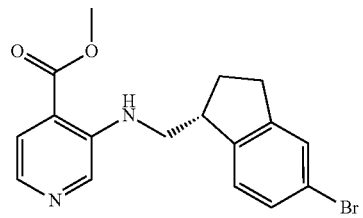 [SMILES: COC(=O)c1ccncc1NC[C@@H]1CCc2cc(Br)ccc21]

To a solution of Preparation 231c (4.27 g, 18.9 mmol) in toluene (100 mL) was added methyl 3-bromoisonicotinate (4.9 g, 23 mmol), $Cs_2CO_3$ (8.6 g, 26 mmol), Xantphos (655 mg, 1.13 mmol) and $Pd_2(dba)_3$ (348 mg, 0.378 mmol). The mixture was stirred overnight at 120° C. under nitrogen. After filtration and concentration, the residue was purified by silica gel chromatography (PE:EtOAc=2:1) to give 1.8 g (26%) of the title compound as a brown oil. [M+H] Calc'd for $C_{17}H_{17}BrN_2O_2$, 361, 363; Found, 361, 363.

Preparation 231e methyl 3-({[(1R)-5-[methyl(3-methylphenyl)amino]-2,3-dihydro-1H-inden-1-yl]methyl}amino)pyridine-4-carboxylate

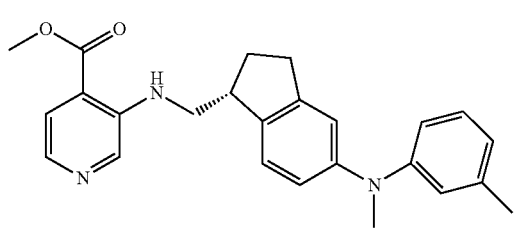

To a solution of Preparation 231d (200 mg, 0.554 mmol) in toluene (15 mL) was added compound N-methyl-m-toluidine (80 mg, 0.66 mmol), $Cs_2CO_3$ (253 mg, 0.776 mmol), Xantphos (48 mg, 0.083 mmol) and $Pd_2(dba)_3$ (26 mg, 0.028 mmol). The mixture was stirred overnight at 120° C. under nitrogen. After filtration and concentration, the residue was purified by prep-HPLC to give 62 mg (28%) of the title compound as a yellow oil. [M+H] Calc'd for $C_{25}H_{27}N_3O_3$, 402; Found, 402.

Example 231

3-({[(1R)-5-[methyl(3-methylphenyl)amino]-2,3-dihydro-1H-inden-1-yl]methyl}amino)pyridine-4-carboxylic acid

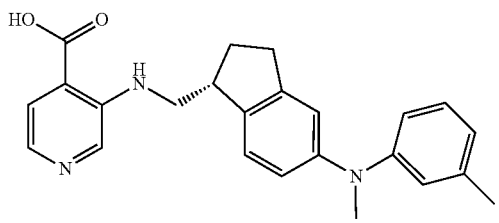 [SMILES: Cc1cccc(N(C)c2ccc3c(c2)CC[C@H]3CNc2cnccc2C(=O)O)c1]

The title compound was prepared in 75% yield from Preparation 231d according to the procedure for Example 217. $^1$H NMR (300 MHz, DMSO-d$_6$): δ 1.79-1.85 (1H, m), 2.21-2.27 (4H, m), 2.72-2.96 (2H, m), 3.15 (3H, s), 3.37-3.41 (2H, m), 3.58-3.62 (1H, m), 6.65-6.72 (3H, m), 6.80 (1H, d, J=8.1 Hz), 6.89 (1H, s), 7.06-7.11 (1H, m), 7.24 (1H, d, J=8.1 Hz), 7.54 (1H, d, J=4.8 Hz), 7.82 (1H, d, J=5.4 Hz), 8.33 (1H, s). [M+H] Calc'd for C$_{24}$H$_{25}$N$_3$O$_2$, 388; Found, 388.

Preparation 232a methyl 3-({[(1R)-5-[(4-ethylphenyl)(methyl)amino]-2,3-dihydro-1H-inden-1-yl]methyl}amino)pyridine-4-carboxylate

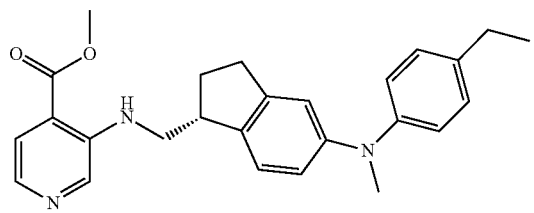 [SMILES: CCc1ccc(N(C)c2ccc3c(c2)CC[C@H]3CNc2cnccc2C(=O)OC)cc1]

The title compound was prepared in 26% yield from Preparation 231d and 4-ethyl-N-methylaniline according to the procedure for Preparation 231e. [M+H] Calc'd for C$_{26}$H$_{29}$N$_3$O$_2$, 416. Found, 416.

Example 232

3-({[(1R)-5-[(4-ethylphenyl)(methyl)amino]-2,3-dihydro-1H-inden-1-yl]methyl}amino)pyridine-4-carboxylic acid

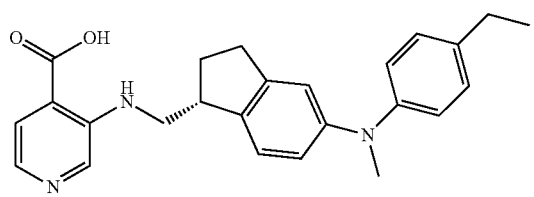 [SMILES: CCc1ccc(N(C)c2ccc3c(c2)CC[C@H]3CNc2cnccc2C(=O)O)cc1]

The title compound was prepared in 77% yield from Preparation 232a according to the procedure for Example 217. $^1$H NMR (300 MHz, DMSO-d$_6$): δ 1.14 (3H, t, J=7.5 Hz), 1.77-1.84 (1H, m), 2.16-2.25 (1H, m), 2.53 (2H, m), 2.72-2.79 (1H, m), 2.84-2.92 (1H, m), 3.17 (3H, s), 3.24-3.30 (2H, m), 3.55-3.60 (1H, m), 6.73 (1H, dd, J=1.5, 8.4 Hz), 6.82-6.88 (3H, m), 7.08 (2H, d, J=8.4 Hz), 7.20 (1H, d, J=7.8 Hz), 7.55 (1H, d, J=5.1 Hz), 7.82 (1H, d, J=5.1 Hz), 8.32 (1H, s). [M+H] Calc'd for C$_{25}$H$_{27}$N$_3$O$_2$, 402; Found, 402.

Preparation 233a methyl 3-({[(1R)-5-{methyl[4-(pyrrolidin-1-yl)phenyl]amino}-2,3-dihydro-1H-inden-1-yl]methyl}amino)pyridine-4-carboxylate

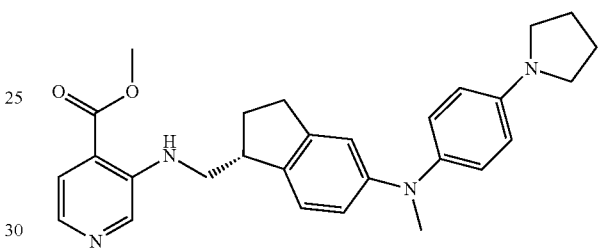

The title compound was prepared in 28% yield from Preparation 231d and N-methyl-4-(pyrrolidin-1-yl)aniline according to the procedure for Preparation 231e. [M+H] Calc'd for C$_{28}$H$_{32}$N$_4$O$_2$, 457; Found, 457.

Example 233

3-({[(1R)-5-{methyl[4-(pyrrolidin-1-yl)phenyl]amino}-2,3-dihydro-1H-inden-1-yl]methyl}amino)pyridine-4-carboxylic acid

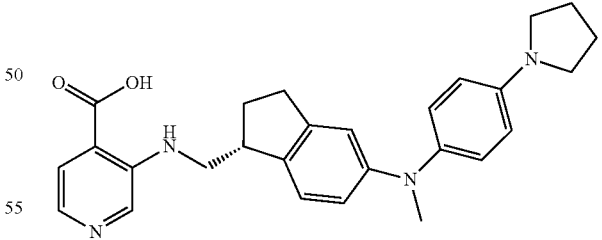

The title compound was prepared in 47% yield from Preparation 233a according to the procedure for Example 217. $^1$H NMR (300 MHz, DMSO-d$_6$): 1.77 (1H, m), 1.79 (4H, m), 2.20-2.22 (1H, m), 2.70-2.73 (1H, m), 2.82-2.84 (1H, m), 3.13 (3H, s), 3.22 (4H, m), 3.32 (2H, m), 3.47-3.49 (1H, m), 6.48 (4H, m), 6.95-6.97 (2H, d, J=6.0 Hz), 7.09-7.12 (1H, m), 7.55-7.57 (1H, d, J=6.9 Hz), 7.79 (1H, d, J=5.1 Hz), 8.24 (1H, s). [M+H] Calc'd for C$_{27}$H$_{30}$N$_4$O$_2$, 442; Found, 443.

II. Biological Evaluation

Example 1a

In Vitro Enzyme Inhibition Assay for JMJD2C Activity

This assay determines the ability of a test compound to inhibit JMJD2C demethylase activity. Baculovirus expressed JMJD2C (GenBank Accession #BC143571, AA 2-372) was purchased from BPS Bioscience (Cat#50105).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 µl of the mixture of 900 nM H3K9me3-biotin labeled peptide and 6 µM alpha-ketoglutaric acid with 2 µl of 11-point serial diluted inhibitor in 3% DMSO were added to each well of the plate, followed by the addition of 2 µl of 0.9 nM JMJD2C to initiate the reaction. The reaction mixture was incubated at room temperature for 30 minutes, and terminated by the addition of 6 µl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

Example 1b: In Vitro Enzyme Inhibition Assay for JMJD3 Activity

This assay determines the ability of a test compound to inhibit JMJD3 demethylase activity. Baculovirus expressed JMJD3 (GenBank Accession #NM-001080424, AA1043-end) was purchased from BPS Bioscience (Cat#50115).

JMJD3 Assay

The enzymatic assay of JMJD3 activity is based upon Time Resolved-Fluorescence Resonance Energy Transfer (TR-FRET) detection. The ability of test compounds to inhibit the activity of JMJD3 was determined in 384-well plate format under the following reaction conditions: 5 nM JMJD3, 250 nM H3K27me3-biotin labeled peptide (Anaspec cat #64367), 0.4 to 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 5 µM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 27 (H3K27me2) antibody (PerkinElmer) in the presence of 5 mM EDTA in LANCE detection buffer (PerkinElmer) at a final concentration of 50 nM and 1 nM, respectively.

The assay reaction was initiated by the following: 2 µl of the mixture of 750 nM H3K27me3-biotin labeled peptide and 1.2 to 6 µM alpha-ketoglutaric acid with 2 pt of 11-point serial diluted inhibitor in 3% DMSO were added to each well of plate, followed by the addition of 2 µl of 15 nM JMJD3 to initiate the reaction. The reaction mixture was incubated at room temperature for 30 minutes, and terminated by the addition of 6 µL of 5 mM EDTA in LANCE detection buffer containing 100 nM Phycolink Streptavidin-allophycocyanin and 2 nM Europium-anti-H3K27me2 antibody. Plates were read by EnVisionMultilabel Reader in TR-FRET mode (excitation at 320 nm, emission at 615 nm and 665 nm) after 1 hour incubation at room temperature. A ratio from the readout of 665/615 was calculated for each well and fitted to determine inhibition constant ($IC_{50}$).

The ability of the compounds disclosed herein to inhibit demethylase activity was quantified and the respective $IC_{50}$ value was determined. Table 3 provides the $IC_{50}$ values of various compounds disclosed herein.

TABLE 3

| Chemical Synthesis Example | Name | JMJD2C $IC_{50}$ (nM) | JMJD3 $IC_{50}$ (nM) |
|---|---|---|---|
| 1 | 3-({[(1S)-6-[methyl(phenyl)amino]-1,2,3,4-tetrahydronaphthalen-1-yl]methyl}amino)pyridine-4-carboxylic acid | C | C |
| 2 | 3-({[(1S)-6-[methyl(phenyl)amino]-1,2,3,4-tetrahydronaphthalen-1-yl]methyl}amino)pyridine-4-carboxylic acid | B | C |
| 3 | 3-({[6-(2-oxopyrrolidin-1-yl)-1,2,3,4-tetrahydronaphthalen-1-yl]methyl}amino)pyridine-4-carboxylic acid | B | |
| 4 | 3-({[6-(1,2,3,4-tetrahydroquinolin-1-yl)-1,2,3,4-tetrahydronaphthalen-1-yl]methyl}amino)pyridine-4-carboxylic acid | C | |
| 5 | 3-({[6-(2,3-dihydro-1H-indol-1-yl)-1,2,3,4-tetrahydronaphthalen-1-yl]methyl}amino)pyridine-4-carboxylic acid | C | |
| 6 | 3-({[(1R)-6-[(2-fluorophenyl)(methyl)amino]-1,2,3,4-tetrahydronaphthalen-1-yl]methyl}amino)pyridine-4-carboxylic acid | B | |
| 7 | 3-({[(1R)-6-[(3-fluorophenyl)(methyl)amino]-1,2,3,4-tetrahydronaphthalen-1-yl]methyl}amino)pyridine-4-carboxylic acid | B | |
| 8 | 3-({[(1R)-6-[(4-fluorophenyl)(methyl)amino]-1,2,3,4-tetrahydronaphthalen-1-yl]methyl}amino)pyridine-4-carboxylic acid | B | |
| 9 | 3-({[(1R)-6-[(4-chlorophenyl)(methyl)amino]-1,2,3,4-tetrahydronaphthalen-1-yl]methyl}amino)pyridine-4-carboxylic acid | C | |
| 10 | 3-({[(1R)-6-[ethyl(phenyl)amino]-1,2,3,4-tetrahydronaphthalen-1-yl]methyl}amino)pyridine-4-carboxylic acid | B | |

TABLE 3-continued

| Chemical Synthesis Example | Name | JMJD2C IC$_{50}$ (nM) | JMJD3 IC$_{50}$ (nM) |
|---|---|---|---|
| 11 | 3-({[(1R)-6-[methyl(pyridin-2-yl)amino]-1,2,3,4-tetrahydronaphthalen-1-yl]methyl}amino)pyridine-4-carboxylic acid | B | C |
| 12 | 3-({[(1R)-6-[methyl(pyridin-3-yl)amino]-1,2,3,4-tetrahydronaphthalen-1-yl]methyl}amino)pyridine-4-carboxylic acid | A | |
| 13 | 3-({[(1R)-6-[(6-methoxypyridin-3-yl)(methyl)amino]-1,2,3,4-tetrahydronaphthalen-1-yl]methyl}amino)pyridine-4-carboxylic acid | B | |
| 14 | 3-{[(7-bromo-3,4-dihydro-2H-1-benzopyran-4-yl)methyl]amino}pyridine-4-carboxylic acid | B | |
| 15 | 3-({[7-(phenylamino)-3,4-dihydro-2H-1-benzopyran-4-yl]methyl}amino)pyridine-4-carboxylic acid | B | |
| 16 | 3-({[7-(1,2,3,4-tetrahydroquinolin-1-yl)-3,4-dihydro-2H-1-benzopyran-4-yl]methyl}amino)pyridine-4-carboxylic acid | B | C |
| 17 | 3-({[7-(2,3-dihydro-1H-indol-1-yl)-3,4-dihydro-2H-1-benzopyran-4-yl]methyl}amino)pyridine-4-carboxylic acid | B | C |
| 18 | 3-({[(4R)-7-[methyl(phenyl)amino]-3,4-dihydro-2H-1-benzopyran-4-yl]methyl}amino)pyridine-4-carboxylic acid | B | B |
| 19 | 3-({[(4R)-7-[(2-fluorophenyl)(methyl)amino]-3,4-dihydro-2H-1-benzopyran-4-yl]methyl}amino)pyridine-4-carboxylic acid | B | |
| 20 | 3-({[(4R)-7-[(3-fluorophenyl)(methyl)amino]-3,4-dihydro-2H-1-benzopyran-4-yl]methyl}amino)pyridine-4-carboxylic acid | B | C |
| 21 | 3-({[(4R)-7-[(4-fluorophenyl)(methyl)amino]-3,4-dihydro-2H-1-benzopyran-4-yl]methyl}amino)pyridine-4-carboxylic acid | B | C |
| 22 | 3-({[(4R)-7-[methyl(4-methylphenyl)amino]-3,4-dihydro-2H-1-benzopyran-4-yl]methyl}amino)pyridine-4-carboxylic acid | B | C |
| 23 | 3-({[(4R)-7-[(4-chlorophenyl)(methyl)amino]-3,4-dihydro-2H-1-benzopyran-4-yl]methyl}amino)pyridine-4-carboxylic acid | B | C |
| 24 | 3-({[(4R)-7-[ethyl(phenyl)amino]-3,4-dihydro-2H-1-benzopyran-4-yl]methyl}amino)pyridine-4-carboxylic acid | B | C |
| 25 | 3-{[(2-phenyl-5,6,7,8-tetrahydroquinolin-5-yl)methyl]amino}pyridine-4-carboxylic acid | B | B |
| 26 | 3-[({2-[methyl(phenyl)amino]-5,6,7,8-tetrahydroquinolin-5-yl}methyl)amino]pyridine-4-carboxylic acid | B | C |
| 27 | 3-[({7-[4-(trifluoromethyl)phenyl]-3,4-dihydro-2H-1-benzopyran-4-yl}methyl)amino]pyridine-4-carboxylic acid | C | |
| 28 | 3-({[7-(furan-3-yl)-3,4-dihydro-2H-1-benzopyran-4-yl]methyl}amino)pyridine-4-carboxylic acid | B | A |
| 29 | 3-({[(4S)-7-(3-methylphenyl)-3,4-dihydro-2H-1-benzopyran-4-yl]methyl}amino)pyridine-4-carboxylic acid | C | B |
| 30 | 3-({[(4R)-7-(3-methylphenyl)-3,4-dihydro-2H-1-benzopyran-4-yl]methyl}amino)pyridine-4-carboxylic acid | B | |
| 31 | 3-({[(4S)-7-(4-methylphenyl)-3,4-dihydro-2H-1-benzopyran-4-yl]methyl}amino)pyridine-4-carboxylic acid | C | B |
| 32 | 3-({[(4R)-7-(4-methylphenyl)-3,4-dihydro-2H-1-benzopyran-4-yl]methyl}amino)pyridine-4-carboxylic acid | B | |
| 33 | 3-({[(4S)-7-(thiophen-3-yl)-3,4-dihydro-2H-1-benzopyran-4-yl]methyl}amino)pyridine-4-carboxylic acid | C | A |
| 34 | 3-({[(4R)-7-(thiophen-3-yl)-3,4-dihydro-2H-1-benzopyran-4-yl]methyl}amino)pyridine-4-carboxylic acid | B | C |
| 35 | 3-({[(4R)-7-cyclohexyl-3,4-dihydro-2H-1-benzopyran-4-yl]methyl}amino)pyridine-4-carboxylic acid | B | |
| 36 | 3-({[(4S)-7-(2-methylthiophen-3-yl)-3,4-dihydro-2H-1-benzopyran-4-yl]methyl}amino)pyridine-4-carboxylic acid | C | B |
| 37 | 3-({[(4R)-7-(2-methylthiophen-3-yl)-3,4-dihydro-2H-1-benzopyran-4-yl]methyl}amino)pyridine-4-carboxylic acid | C | C |
| 38 | 3-({[7-(3-methylbut-1-yn-1-yl)-3,4-dihydro-2H-1-benzopyran-4-yl]methyl}amino)pyridine-4-carboxylic acid | B | |
| 39 | 3-({[(4S)-7-(2-chlorophenyl)-3,4-dihydro-2H-1-benzopyran-4-yl]methyl}amino)pyridine-4-carboxylic acid | C | B |
| 40 | 3-({[(4R)-7-(2-chlorophenyl)-3,4-dihydro-2H-1-benzopyran-4-yl]methyl}amino)pyridine-4-carboxylic acid | B | C |
| 41 | 3-({[(4S)-7-(3-fluoro-2-methylphenyl)-3,4-dihydro-2H-1-benzopyran-4-yl]methyl}amino)pyridine-4-carboxylic acid | C | |
| 42 | 3-({[(4R)-7-(3-fluoro-2-methylphenyl)-3,4-dihydro-2H-1-benzopyran-4-yl]methyl}amino)pyridine-4-carboxylic acid | B | |
| 43 | 3-({[(4R)-7-(5-fluoro-2-methylphenyl)-3,4-dihydro-2H-1-benzopyran-4-yl]methyl}amino)pyridine-4-carboxylic acid | B | |
| 44 | 3-({[(4R)-7-(2-chloro-3-fluorophenyl)-3,4-dihydro-2H-1-benzopyran-4-yl]methyl}amino)pyridine-4-carboxylic acid | B | |
| 45 | 3-({[(4R)-7-(2-chloro-5-fluorophenyl)-3,4-dihydro-2H-1-benzopyran-4-yl]methyl}amino)pyridine-4-carboxylic acid | B | |
| 46 | 3-({[(4R)-7-[2-(trifluoromethyl)phenyl]-3,4-dihydro-2H-1-benzopyran-4-yl]methyl}amino)pyridine-4-carboxylic acid | B | |
| 47 | 3-({[(4S)-7-phenoxy-3,4-dihydro-2H-1-benzopyran-4-yl]methyl}amino)pyridine-4-carboxylic acid | C | |
| 48 | 3-({[(4R)-7-phenoxy-3,4-dihydro-2H-1-benzopyran-4-yl]methyl}amino)pyridine-4-carboxylic acid | B | |

TABLE 3-continued

| Chemical Synthesis Example | Name | JMJD2C IC$_{50}$ (nM) | JMJD3 IC$_{50}$ (nM) |
|---|---|---|---|
| 49 | 3-({[7-(thiophen-2-ylsulfanyl)-3,4-dihydro-2H-1-benzopyran-4-yl]methyl}amino)pyridine-4-carboxylic acid | B | |
| 50 | 3-({[(4S)-7-[(2-methylphenyl)sulfanyl]-3,4-dihydro-2H-1-benzopyran-4-yl]methyl}amino)pyridine-4-carboxylic acid | C | |
| 51 | 3-({[(4R)-7-[(2-methylphenyl)sulfanyl]-3,4-dihydro-2H-1-benzopyran-4-yl]methyl}amino)pyridine-4-carboxylic acid | B | |
| 52 | 3-({[(4S)-7-[(3-fluorophenyl)sulfanyl]-3,4-dihydro-2H-1-benzopyran-4-yl]methyl}amino)pyridine-4-carboxylic acid | C | B |
| 53 | 3-({[(4R)-7-[(3-fluorophenyl)sulfanyl]-3,4-dihydro-2H-1-benzopyran-4-yl]methyl}amino)pyridine-4-carboxylic acid | B | |
| 54 | 3-({[(4S)-7-[(4-fluorophenyl)sulfanyl]-3,4-dihydro-2H-1-benzopyran-4-yl]methyl}amino)pyridine-4-carboxylic acid | C | B |
| 55 | 3-({[(4R)-7-[(4-fluorophenyl)sulfanyl]-3,4-dihydro-2H-1-benzopyran-4-yl]methyl}amino)pyridine-4-carboxylic acid | B | C |
| 56 | 3-[({6-[(6-methylpyridin-2-yl)oxy]-1,2,3,4-tetrahydronaphthalen-1-yl}methyl)amino]pyridine-4-carboxylic acid | B | |
| 57 | 3-({[(1S)-6-(2-methylphenoxy)-1,2,3,4-tetrahydronaphthalen-1-yl]methyl}amino)pyridine-4-carboxylic acid | C | |
| 58 | 3-({[(1R)-6-(2-methylphenoxy)-1,2,3,4-tetrahydronaphthalen-1-yl]methyl}amino)pyridine-4-carboxylic acid | B | |
| 59 | 3-{[(6-propoxy-1,2,3,4-tetrahydronaphthalen-1-yl)methyl]amino}pyridine-4-carboxylic acid | B | |
| 60 | 3-({[(1S)-6-(difluoromethoxy)-1,2,3,4-tetrahydronaphthalen-1-yl]methyl}amino)pyridine-4-carboxylic acid | C | |
| 61 | 3-({[(1R)-6-(difluoromethoxy)-1,2,3,4-tetrahydronaphthalen-1-yl]methyl}amino)pyridine-4-carboxylic acid | B | |
| 62 | 3-[({6-[2-(trifluoromethyl)phenoxy]-1,2,3,4-tetrahydronaphthalen-1-yl}methyl)amino]pyridine-4-carboxylic acid | C | |
| 63 | 3-({[6-(oxan-4-ylmethoxy)-1,2,3,4-tetrahydronaphthalen-1-yl]methyl}amino)pyridine-4-carboxylic acid | B | |
| 64 | 3-({[(1R)-6-(4-fluoro-2-methylphenoxy)-1,2,3,4-tetrahydronaphthalen-1-yl]methyl}amino)pyridine-4-carboxylic acid | B | |
| 65 | 3-({[(1R)-6-(2,4-difluorophenoxy)-1,2,3,4-tetrahydronaphthalen-1-yl]methyl}amino)pyridine-4-carboxylic acid | B | |
| 66 | 3-({[(1R)-6-(2-fluoro-4-methylphenoxy)-1,2,3,4-tetrahydronaphthalen-1-yl]methyl}amino)pyridine-4-carboxylic acid | B | C |
| 67 | 3-({[(1R)-6-(2-chlorophenoxy)-1,2,3,4-tetrahydronaphthalen-1-yl]methyl}amino)pyridine-4-carboxylic acid | B | |
| 68 | 3-({[(1S)-6-[(3-methylphenyl)sulfanyl]-1,2,3,4-tetrahydronaphthalen-1-yl]methyl}amino)pyridine-4-carboxylic acid | C | |
| 69 | 3-({[(1R)-6-[(3-methylphenyl)sulfanyl]-1,2,3,4-tetrahydronaphthalen-1-yl]methyl}amino)pyridine-4-carboxylic acid | C | |
| 70 | 3-({[(1S)-6-[(2-methylphenyl)sulfanyl]-1,2,3,4-tetrahydronaphthalen-1-yl]methyl}amino)pyridine-4-carboxylic acid | C | |
| 71 | 3-({[(1R)-6-[(2-methylphenyl)sulfanyl]-1,2,3,4-tetrahydronaphthalen-1-yl]methyl}amino)pyridine-4-carboxylic acid | C | |
| 72 | 3-({[(1S)-6-[(2-fluorophenyl)sulfanyl]-1,2,3,4-tetrahydronaphthalen-1-yl]methyl}amino)pyridine-4-carboxylic acid | C | |
| 73 | 3-({[(1R)-6-[(2-fluorophenyl)sulfanyl]-1,2,3,4-tetrahydronaphthalen-1-yl]methyl}amino)pyridine-4-carboxylic acid | B | |
| 74 | 3-({[(1S)-6-[(3-fluorophenyl)sulfanyl]-1,2,3,4-tetrahydronaphthalen-1-yl]methyl}amino)pyridine-4-carboxylic acid | C | |
| 75 | 3-({[(1R)-6-[(3-fluorophenyl)sulfanyl]-1,2,3,4-tetrahydronaphthalen-1-yl]methyl}amino)pyridine-4-carboxylic acid | B | |
| 76 | 3-({[(1S)-6-[(4-fluorophenyl)sulfanyl]-1,2,3,4-tetrahydronaphthalen-1-yl]methyl}amino)pyridine-4-carboxylic acid | C | |
| 77 | 3-({[(1R)-6-[(4-fluorophenyl)sulfanyl]-1,2,3,4-tetrahydronaphthalen-1-yl]methyl}amino)pyridine-4-carboxylic acid | B | |
| 78 | 3-({[(1S)-6-l(4-methylphenyl)sulfanyl]-1,2,3,4-tetrahydronaphthalen-1-yl]methyl}amino)pyridine-4-carboxylic acid | C | |
| 79 | 3-({[(1R)-6-[(4-methylphenyl)sulfanyl]-1,2,3,4-tetrahydronaphthalen-1-yl]methyl}amino)pyridine-4-carboxylic acid | C | |

TABLE 3-continued

| Chemical Synthesis Example | Name | JMJD2C IC$_{50}$ (nM) | JMJD3 IC$_{50}$ (nM) |
|---|---|---|---|
| 80 | 3-({[6-(pyridin-2-ylsulfanyl)-1,2,3,4-tetrahydronaphthalen-1-yl]methyl}amino)pyridine-4-carboxylic acid | B | |
| 81 | 3-({[(1S)-6-(benzenesulfonyl)-1,2,3,4-tetrahydronaphthalen-1-yl]methyl}amino)pyridine-4-carboxylic acid | B | |
| 82 | 3-({[(1R)-6-(benzenesulfonyl)-1,2,3,4-tetrahydronaphthalen-1-yl]methyl}amino)pyridine-4-carboxylic acid | B | |
| 83 | 3-({[(1S)-6-(4-methylbenzenesulfonyl)-1,2,3,4-tetrahydronaphthalen-1-yl]methyl}amino)pyridine-4-carboxylic acid | B | |
| 84 | 3-({[(1R)-6-(4-methylbenzenesulfonyl)-1,2,3,4-tetrahydronaphthalen-1-yl]methyl}amino)pyridine-4-carboxylic acid | B | |
| 85 | 3-({[(1S)-6-(3-methylbenzenesulfonyl)-1,2,3,4-tetrahydronaphthalen-1-yl]methyl}amino)pyridine-4-carboxylic acid | C | |
| 86 | 3-({[(1R)-6-(3-methylbenzenesulfonyl)-1,2,3,4-tetrahydronaphthalen-1-yl]methyl}amino)pyridine-4-carboxylic acid | B | |
| 87 | 3-({[6-(3-fluorobenzenesulfonyl)-1,2,3,4-tetrahydronaphthalen-1-yl]methyl}amino)pyridine-4-carboxylic acid | B | |
| 88 | 3-({[6-(oxan-4-yl)-1,2,3,4-tetrahydronaphthalen-1-yl]methyl}amino)pyridine-4-carboxylic acid | B | |
| 89 | 3-({[6-(2-methylpyridin-4-yl)-1,2,3,4-tetrahydronaphthalen-1-yl]methyl}amino)pyridine-4-carboxylic acid | B | |
| 90 | 3-({[(1S)-6-ethyl-1,2,3,4-tetrahydronaphthalen-1-yl]methyl}amino)pyridine-4-carboxylic acid | B | |
| 91 | 3-({[(1R)-6-ethyl-1,2,3,4-tetrahydronaphthalen-1-yl]methyl}amino)pyridine-4-carboxylic acid | B | |
| 92 | 3-({2H,3H,6H,7H,8H,9H-naphtho[1,2-b]furan-6-ylmethyl}amino)pyridine-4-carboxylic acid | B | |
| 93 | 3-{[(6,7-dimethyl-3,4-dihydro-2H-1-benzopyran-4-yl)methyl]amino}pyridine-4-carboxylic acid | B | |
| 94 | 3-{[(6-methoxy-7-methyl-1,2,3,4-tetrahydronaphthalen-1-yl)methyl]amino}pyridine-4-carboxylic acid | B | |
| 95 | 3-{[(6,8-dimethoxy-1,2,3,4-tetrahydronaphthalen-1-yl)methyl]amino}pyridine-4-carboxylic acid | B | |
| 96 | 3-({[(1S)-7-fluoro-6-methoxy-1,2,3,4-tetrahydronaphthalen-1-yl]methyl}amino)pyridine-4-carboxylic acid | B | |
| 97 | 3-({[(1R)-7-fluoro-6-methoxy-1,2,3,4-tetrahydronaphthalen-1-yl]methyl}amino)pyridine-4-carboxylic acid | B | |
| 98 | 3-({[(1S)-6-methoxy-5-methyl-1,2,3,4-tetrahydronaphthalen-1-yl]methyl}amino)pyridine-4-carboxylic acid | B | |
| 99 | 3-({[(1R)-6-methoxy-5-methyl-1,2,3,4-tetrahydronaphthalen-1-yl]methyl}amino)pyridine-4-carboxylic acid | B | B |
| 100 | 3-({[(4S)-7-(2-methylphenyl)-3,4-dihydro-2H-1-benzopyran-4-yl]methyl}amino)pyridine-4-carboxylic acid | C | |
| 101 | 3-({[(4R)-7-(2-methylphenyl)-3,4-dihydro-2H-1-benzopyran-4-yl]methyl}amino)pyridine-4-carboxylic acid | B | |
| 102 | 3-({[(4R)-7-(5-fluoro-2-methoxyphenyl)-3,4-dihydro-2H-1-benzopyran-4-yl]methyl}amino)pyridine-4-carboxylic acid | B | |
| 103 | 3-({[(1R)-6-[(4-cyanophenyl)(methyl)amino]-1,2,3,4-tetrahydronaphthalen-1-yl]methyl}amino)pyridine-4-carboxylic acid | B | |
| 104 | 3-({[(4R)-7-[(2,4-difluorophenyl)(methyl)amino]-3,4-dihydro-2H-1-benzopyran-4-yl]methyl}amino)pyridine-4-carboxylic acid | B | |
| 105 | 3-({[(4R)-7-[methyl(3-methylphenyl)amino]-3,4-dihydro-2H-1-benzopyran-4-yl]methyl}amino)pyridine-4-carboxylic acid | B | |
| 106 | 3-({[(1R)-6-(pyrrolidin-1-yl)-1,2,3,4-tetrahydronaphthalen-1-yl]methyl}amino)pyridine-4-carboxylic acid | B | |
| 107 | 3-({[(4R)-7-(2-chloro-5-methoxyphenyl)-3,4-dihydro-2H-1-benzopyran-4-yl]methyl}amino)pyridine-4-carboxylic acid | B | |
| 108 | 3-({[(1R)-6-(3,4-dihydro-2H-1,4-benzoxazin-4-yl)-1,2,3,4-tetrahydronaphthalen-1-yl]methyl}amino)pyridine-4-carboxylic acid | C | |
| 109 | 3-({[(4R)-7-[(3,5-difluorophenyl)(methyl)amino]-3,4-dihydro-2H-1-benzopyran-4-yl]methyl}amino)pyridine-4-carboxylic acid | B | |
| 110 | 3-({[(4R)-7-[(3-chlorophenyl)(methyl)amino]-3,4-dihydro-2H-1-benzopyran-4-yl]methyl}amino)pyridine-4-carboxylic acid | C | |
| 111 | 3-({[(4R)-7-[methyl(2-methylphenyl)amino]-3,4-dihydro-2H-1-benzopyran-4-yl]methyl}amino)pyridine-4-carboxylic acid | B | |
| 112 | 3-({[(4R)-7-[(4-fluoro-3-methoxyphenyl)(methyl)amino]-3,4-dihydro-2H-1-benzopyran-4-yl]methyl}amino)pyridine-4-carboxylic acid | B | |
| 113 | 3-({[(1R)-6-[methyl(oxan-4-yl)amino]-1,2,3,4-tetrahydronaphthalen-1-yl]methyl}amino)pyridine-4-carboxylic acid | B | |

TABLE 3-continued

| Chemical Synthesis Example | Name | JMJD2C IC$_{50}$ (nM) | JMJD3 IC$_{50}$ (nM) |
|---|---|---|---|
| 114 | 3-({[(1R)-6-[(4-fluoro-3-methoxyphenyl)(methyl)amino]-1,2,3,4-tetrahydronaphthalen-1-yl]methyl}amino)pyridine-4-carboxylic acid | B | |
| 115 | 3-({[(1R)-6-[(3-cyanophenyl)(methyl)amino]-1,2,3,4-tetrahydronaphthalen-1-yl]methyl}amino)pyridine-4-carboxylic acid | B | |
| 116 | 3-({[(4R)-7-(2-methoxyphenyl)-3,4-dihydro-2H-1-benzopyran-4-yl]methyl}amino)pyridine-4-carboxylic acid | B | |
| 117 | 3-({[(4R)-7-[(3-cyanophenyl)(methyl)amino]-3,4-dihydro-2H-1-benzopyran-4-yl]methyl}amino)pyridine-4-carboxylic acid | B | |
| 118 | 3-({[(4R)-7-(4-fluoro-2-methoxyphenyl)-3,4-dihydro-2H-1-benzopyran-4-yl]methyl}amino)pyridine-4-carboxylic acid | B | |
| 119 | 3-({[(4R)-7-[(4-cyanophenyl)(methyl)amino]-3,4-dihydro-2H-1-benzopyran-4-yl]methyl}amino)pyridine-4-carboxylic acid | B | |
| 120 | 3-({[(1R)-6-[(cyclopropylmethyl)(methyl)amino]-1,2,3,4-tetrahydronaphthalen-1-yl]methyl}amino)pyridine-4-carboxylic acid | B | |
| 121 | 3-({[(1R)-6-[methyl(6-methoxypyridin-2-yl)amino]-1,2,3,4-tetrahydronaphthalen-1-yl]methyl}amino)pyridine-4-carboxylic acid | B | |
| 122 | 3-({[(1R)-6-[methyl(5-methylpyridin-2-yl)amino]-1,2,3,4-tetrahydronaphthalen-1-yl]methyl}amino)pyridine-4-carboxylic acid | B | C |
| 123 | 3-({[(1R)-6-[methyl(6-methylpyridin-2-yl)amino]-1,2,3,4-tetrahydronaphthalen-1-yl]methyl}amino)pyridine-4-carboxylic acid | B | C |
| 124 | 3-({[(4R)-7-(2-cyanophenyl)-3,4-dihydro-2H-1-benzopyran-4-yl]methyl}amino)pyridine-4-carboxylic acid | B | |
| 125 | 3-({[(1R)-6-[methyl(1-methyl-1H-pyrazol-3-yl)amino]-1,2,3,4-tetrahydronaphthalen-1-yl]methyl}amino)pyridine-4-carboxylic acid | B | |
| 126 | 3-({[(4R)-7-[(4-ethynylphenyl)(methyl)amino]-3,4-dihydro-2H-1-benzopyran-4-yl]methyl}amino)pyridine-4-carboxylic acid | B | C |
| 127 | 3-({[(4R)-7-[(1,3-dihydro-2-benzofuran-5-yl)(methyl)amino]-3,4-dihydro-2H-1-benzopyran-4-yl]methyl}amino)pyridine-4-carboxylic acid | B | |
| 128 | 3-({[(4R)-7-{methyl[4-(trifluoromethyl)phenyl]amino}-3,4-dihydro-2H-1-benzopyran-4-yl]methyl}amino)pyridine-4-carboxylic acid | C | |
| 129 | 3-[({7-[phenyl(2,2,2-trifluoroethyl)amino]-3,4-dihydro-2H-1-benzopyran-4-yl}methyl)amino]pyridine-4-carboxylic acid | C | |
| 130 | 3-({[(1R)-6-[benzyl(methyl)amino]-1,2,3,4-tetrahydronaphthalen-1-yl]methyl}amino)pyridine-4-carboxylic acid | B | C |
| 131 | 3-({[(4R)-7-[(2,3-dihydro-1H-inden-5-yl)(methyl)amino]-3,4-dihydro-2H-1-benzopyran-4-yl]methyl}amino)pyridine-4-carboxylic acid | B | C |
| 132 | 3-({[(1R)-6-[(1,3-dihydro-2-benzofuran-5-yl)(methyl)amino]-1,2,3,4-tetrahydronaphthalen-1-yl]methyl}amino)pyridine-4-carboxylic acid | B | |
| 133 | 3-({[(1R)-6-[cyclopentyl(methyl)amino]-1,2,3,4-tetrahydronaphthalen-1-yl]methyl}amino)pyridine-4-carboxylic acid | B | |
| 134 | 3-({[(4R)-7-[(4-cyclopropylphenyl)(methyl)amino]-3,4-dihydro-2H-1-benzopyran-4-yl]methyl}amino)pyridine-4-carboxylic acid | B | C |
| 135 | 3-({[(1R)-6-[(1-benzofuran-6-yl)(methyl)amino]-1,2,3,4-tetrahydronaphthalen-1-yl]methyl}amino)pyridine-4-carboxylic acid | B | |
| 136 | 3-({[(4R)-7-[(1-benzofuran-5-yl)(methyl)amino]-3,4-dihydro-2H-1-benzopyran-4-yl]methyl}amino)pyridine-4-carboxylic acid | B | |
| 137 | 3-({[(1R)-6-[(1-benzofuran-5-yl)(methyl)amino]-1,2,3,4-tetrahydronaphthalen-1-yl]methyl}amino)pyridine-4-carboxylic acid | C | |
| 138 | 3-({[(4R)-7-(2-hydroxyphenyl)-3,4-dihydro-2H-1-benzopyran-4-yl]methyl}amino)pyridine-4-carboxylic acid | B | C |
| 139 | 3-({[(4R)-7-[methyl(2-methyl-1,3-thiazol-4-yl)amino]-3,4-dihydro-2H-1-benzopyran-4-yl]methyl}amino)pyridine-4-carboxylic acid | B | |
| 140 | 3-({[(1R)-6-[methyl(4-methylphenyl)amino]-1,2,3,4-tetrahydronaphthalen-1-yl]methyl}amino)pyridine-4-carboxylic acid | B | C |
| 141 | 3-({[(4R)-7-[(1-benzofuran-6-yl)(methyl)amino]-3,4-dihydro-2H-1-benzopyran-4-yl]methyl}amino)pyridine-4-carboxylic acid | B | |
| 142 | 3-[(3,4-dihydro-1H-2-benzopyran-1-ylmethyl)amino]pyridine-4-carboxylic acid | B | |
| 143 | 3-({[(1R)-6-[methyl(3-methylphenyl)amino]-1,2,3,4-tetrahydronaphthalen-1-yl]methyl}amino)pyridine-4-carboxylic acid | C | |

TABLE 3-continued

| Chemical Synthesis Example | Name | JMJD2C IC$_{50}$ (nM) | JMJD3 IC$_{50}$ (nM) |
|---|---|---|---|
| 144 | 3-({[(1R)-6-[methyl(thiophen-2-yl)amino]-1,2,3,4-tetrahydronaphthalen-1-yl]methyl}amino)pyridine-4-carboxylic acid | B | |
| 145 | 3-({[(4R)-7-[methyl(5-methylpyridin-2-yl)amino]-3,4-dihydro-2H-1-benzopyran-4-yl]methyl}amino)pyridine-4-carboxylic acid | A | C |
| 146 | 3-[({6-[methyl(phenyl)amino]-3,4-dihydro-1H-2-benzopyran-1-yl}methyl)amino]pyridine-4-carboxylic acid | B | |
| 147 | 3-({[(1R)-6-[(2-hydroxyethyl)(phenyl)amino]-1,2,3,4-tetrahydronaphthalen-1-yl]methyl}amino)pyridine-4-carboxylic acid | B | |
| 148 | 3-({[(4R)-7-[methyl(6-methylpyridin-2-yl)amino]-3,4-dihydro-2H-1-benzopyran-4-yl]methyl}amino)pyridine-4-carboxylic acid | B | |
| 149 | 3-[(1,2,3,4-tetrahydroisoquinolin-1-ylmethyl)amino]pyridine-4-carboxylic acid | B | |
| 150 | 3-({[(1R)-6-[(3-methoxyphenyl)(methyl)amino]-1,2,3,4-tetrahydronaphthalen-1-yl]methyl}amino)pyridine-4-carboxylic acid | B | |
| 151 | 3-({[(4R)-7-[(3-fluoro-4-methylphenyl)(methyl)amino]-3,4-dihydro-2H-1-benzopyran-4-yl]methyl}amino)pyridine-4-carboxylic acid | B | |
| 152 | 3-({[(4R)-7-[(5-chloropyridin-2-yl)(methyl)amino]-3,4-dihydro-2H-1-benzopyran-4-yl]methyl}amino)pyridine-4-carboxylic acid | B | |
| 153 | 3-({[(4R)-7-[(5-cyclopropylpyridin-2-yl)(methyl)amino]-3,4-dihydro-2H-1-benzopyran-4-yl]methyl}amino)pyridine-4-carboxylic acid | B | C |
| 154 | 3-({[(4R)-7-[(4-ethylphenyl)(methyl)amino]-3,4-dihydro-2H-1-benzopyran-4-yl]methyl}amino)pyridine-4-carboxylic acid | B | C |
| 155 | 3-({[(1R)-6-[methyl(1-methyl-2-oxo-1,2-dihydropyridin-4-yl)amino]-1,2,3,4-tetrahydronaphthalen-1-yl]methyl}amino)pyridine-4-carboxylic acid | B | |
| 156 | 3-({[(1R)-6-[methyl(5-methylpyrimidin-2-yl)amino]-1,2,3,4-tetrahydronaphthalen-1-yl]methyl}amino)pyridine-4-carboxylic acid | B | C |
| 157 | 3-({[(4R)-7-[(5-ethylpyridin-2-yl)(methyl)amino]-3,4-dihydro-2H-1-benzopyran-4-yl]methyl}amino)pyridine-4-carboxylic acid | B | C |
| 158 | 3-({[(1R)-6-{[4-(hydroxymethyl)phenyl](methyl)amino}-1,2,3,4-tetrahydronaphthalen-1-yl]methyl}amino)pyridine-4-carboxylic acid | B | |
| 159 | 3-({[(1R)-6-[methyl(1-methyl-1H-pyrazol-4-yl)amino]-1,2,3,4-tetrahydronaphthalen-1-yl]methyl}amino)pyridine-4-carboxylic acid | B | C |
| 160 | 3-({[(1R)-6-{[4-(dimethylamino)phenyl](methyl)amino}-1,2,3,4-tetrahydronaphthalen-1-yl]methyl}amino)pyridine-4-carboxylic acid | B | C |
| 161 | 3-({[(1R)-6-[(4-cyclopropylphenyl)(methyl)amino]-1,2,3,4-tetrahydronaphthalen-1-yl]methyl}amino)pyridine-4-carboxylic acid | C | |
| 162 | 3-({[(1R)-6-(2,3,4,5-tetrahydro-1H-1-benzazepin-1-yl)-1,2,3,4-tetrahydronaphthalen-1-yl]methyl}amino)pyridine-4-carboxylic acid | C | |
| 163 | 3-({[(1R)-6-[(4-cyclopropylphenyl)(2-methoxyethyl)amino]-1,2,3,4-tetrahydronaphthalen-1-yl]methyl}amino)pyridine-4-carboxylic acid | C | |
| 164 | 3-({[(1R)-6-{[4-(methoxymethyl)phenyl](methyl)amino}-1,2,3,4-tetrahydronaphthalen-1-yl]methyl}amino)pyridine-4-carboxylic acid | B | C |
| 165 | 3-({[(1R)-6-[(4-hydroxyphenyl)(methyl)amino]-1,2,3,4-tetrahydronaphthalen-1-yl]methyl}amino)pyridine-4-carboxylic acid | B | C |
| 166 | 3-({[(1R)-6-[(dimethyl-1,2-oxazol-4-yl)(methyl)amino]-1,2,3,4-tetrahydronaphthalen-1-yl]methyl}amino)pyridine-4-carboxylic acid | B | C |
| 167 | 3-({[(1R)-6-{methyl[4-(pyrrolidin-1-yl)phenyl]amino}-1,2,3,4-tetrahydronaphthalen-1-yl]methyl}amino)pyridine-4-carboxylic acid | B | |
| 168 | 3-({[(1R)-6-({4-[(1R)-1-hydroxyethyl]phenyl}(methyl)amino)-1,2,3,4-tetrahydronaphthalen-1-yl]methyl}amino)pyridine-4-carboxylic acid | B | |
| 169 | 3-({[(1R)-6-({4-[(1S)-1-hydroxyethyl]phenyl}(methyl)amino)-1,2,3,4-tetrahydronaphthalen-1-yl]methyl}amino)pyridine-4-carboxylic acid | B | |
| 170 | 3-({[(1R)-6-{methyl[4-(morpholin-4-yl)phenyl]amino}-1,2,3,4-tetrahydronaphthalen-1-yl]methyl}amino)pyridine-4-carboxylic acid | B | C |

TABLE 3-continued

| Chemical Synthesis Example | Name | JMJD2C IC$_{50}$ (nM) | JMJD3 IC$_{50}$ (nM) |
|---|---|---|---|
| 171 | 3-({[(1R)-6-[methyl(5-methyl-1,2-oxazol-3-yl)amino]-1,2,3,4-tetrahydronaphthalen-1-yl]methyl}amino)pyridine-4-carboxylic acid | C | |
| 172 | 3-({[(1R)-6-[(2-methoxyphenyl)(methyl)amino]-1,2,3,4-tetrahydronaphthalen-1-yl]methyl}amino)pyridine-4-carboxylic acid | B | |
| 173 | 3-({[(1R)-6-[methyl(pyridin-4-yl)amino]-1,2,3,4-tetrahydronaphthalen-1-yl]methyl}amino)pyridine-4-carboxylic acid | A | |
| 174 | 3-({[(1R)-6-{[4-(3,6-dihydro-2H-pyran-4-yl)phenyl](methyl)amino}-1,2,3,4-tetrahydronaphthalen-1-yl]methyl}amino)pyridine-4-carboxylic acid | C | |
| 175 | 3-({[(1R)-6-{methyl[4-(oxan-4-yl)phenyl]amino}-1,2,3,4-tetrahydronaphthalen-1-yl]methyl}amino)pyridine-4-carboxylic acid | C | |
| 176 | 3-({[(4R)-7-[(4-ethenylphenyl)(methyl)amino]-3,4-dihydro-2H-1-benzopyran-4-yl]methyl}amino)pyridine-4-carboxylic acid | B | |
| 177 | 3-({[(1R)-6-[(4-methoxyphenyl)(methyl)amino]-1,2,3,4-tetrahydronaphthalen-1-yl]methyl}amino)pyridine-4-carboxylic acid | B | |
| 178 | 3-({[(4R)-7-[(4-methoxyphenyl)(methyl)amino]-3,4-dihydro-2H-1-benzopyran-4-yl]methyl}amino)pyridine-4-carboxylic acid | A | |
| 179 | 3-({[(4R)-7-{methyl[4-(pyrrolidin-1-yl)phenyl]amino}-3,4-dihydro-2H-1-benzopyran-4-yl]methyl}amino)pyridine-4-carboxylic acid | B | |
| 180 | 3-({[(1R)-6-{[4-(azetidin-1-yl)phenyl](methyl)amino}-1,2,3,4-tetrahydronaphthalen-1-yl]methyl}amino)pyridine-4-carboxylic acid | B | |
| 181 | 3-({[(1R)-6-{methyl[4-(trifluoromethoxy)phenyl]amino}-1,2,3,4-tetrahydronaphthalen-1-yl]methyl}amino)pyridine-4-carboxylic acid | B | |
| 182 | 3-({[(4R)-7-{methyl[4-(trifluoromethoxy)phenyl]amino}-3,4-dihydro-2H-1-benzopyran-4-yl]methyl}amino)pyridine-4 carboxylic acid | B | C |
| 183 | 3-({[(4R)-7-{[4-(azetidin-1-yl)phenyl](methyl)amino}1-3,4-dihydro-2H-1-benzopyran-4-yl]methyl}amino)pyridine-4-carboxylic acid | B | C |
| 184 | 3-({[(1R)-6-{[4-(difluoromethoxy)phenyl](methyl)amino}-1,2,3,4-tetrahydronaphthalen-1-yl]methyl}amino)pyridine-4-carboxylic acid | B | C |
| 185 | 3-({[(1R)-6-[(4-ethoxyphenyl)(methyl)amino]-1,2,3,4-tetrahydronaphthalen-1-yl]methyl}amino)pyridine-4-carboxylic acid | B | C |
| 186 | 3-({[(4R)-7-[(4-ethoxyphenyl)(methyl)amino]-3,4-dihydro-2H-1-benzopyran-4-yl]methyl}amino)pyridine-4-carboxylic acid | B | |
| 187 | 3-({[(4R)-7-{methyl[4-(propan-2-yl)phenyl]amino}-3,4-dihydro-2H-1-benzopyran-4-yl]methyl}amino)pyridine-4-carboxylic acid | B | C |
| 188 | 3-({[(1R)-6-{methyl[4-(1H-pyrazol-1-yl)phenyl]amino}-1,2,3,4-tetrahydronaphthalen-1-yl]methyl}amino)pyridine-4-carboxylic acid | B | |
| 189 | 3-({[(4R)-7-{methyl[4-(1H-pyrazol-1-yl)phenyl]amino}-3,4-dihydro-2H-1-benzopyran-4-yl]methyl}amino)pyridine-4-carboxylic acid | B | |
| 190 | 3-({[(4R)-7-{[4-(difluoromethoxy)phenyl](methyl)amino}-3,4-dihydro-2H-1-benzopyran-4-yl]methyl}amino)pyridine-4-carboxylic acid | B | C |
| 191 | 3-({[(1R)-6-[methyl(phenyl)amino]-1,2,3,4-tetrahydronaphthalen-1-yl]methyl}amino)pyridazine-4-carboxylic acid | B | C |
| 192 | 3-({[(4R)-7-{methyl[4-(2,2,2-trifluoroethyl)phenyl]amino}-3,4-dihydro-2H-1-benzopyran-4-yl]methyl}amino)pyridine-4-carboxylic acid | B | C |
| 193 | 3-({[(1R)-6-{[4-(1H-imidazol-1-yl)phenyl](methyl)amino}-1,2,3,4-tetrahydronaphthalen-1-yl]methyl}amino)pyridine-4-carboxylic acid | B | C |
| 194 | 3-({[(4R)-7-{[4-(1H-imidazol-1-yl)phenyl](methyl)amino}-3,4-dihydro-2H-1-benzopyran-4-yl]methyl}amino)pyridine-4-carboxylic acid | B | C |
| 195 | 3-({[(1R)-6-{[4-(3,3-difluoroazetidin-1-yl)phenyl](methyl)amino}-1,2,3,4-tetrahydronaphthalen-1-yl]methyl}amino)pyridine-4-carboxylic acid | B | |
| 196 | 3-({[(4R)-7-{[4-(3,3-difluoroazetidin-1-yl)phenyl](methyl)amino}-3,4-dihydro-2H-1-benzopyran-4-yl]methyl}amino)pyridine-4-carboxylic acid | B | |
| 197 | 3-({[(1R)-6-{[4-(2-methoxyethoxy)phenyl](methyl)amino}-1,2,3,4-tetrahydronaphthalen-1-yl]methyl}amino)pyridine-4-carboxylic acid | B | |

TABLE 3-continued

| Chemical Synthesis Example | Name | JMJD2C IC$_{50}$ (nM) | JMJD3 IC$_{50}$ (nM) |
|---|---|---|---|
| 198 | 3-({[(4R)-7-(1-phenylethyl)-3,4-dihydro-2H-1-benzopyran-4-yl]methyl}amino)pyridine-4-carboxylic acid | B | |
| 199 | 3-({[(4R)-7-{methyl[5-(propan-2-yl)pyridin-2-yl]amino}-3,4-dihydro-2H-1-benzopyran-4-yl]methyl}amino)pyridine-4-carboxylic acid | B | |
| 200 | 3-({[(1R)-6-{[4-(3-hydroxyazetidin-1-yl)phenyl](methyl)amino}-1,2,3,4-tetrahydronaphthalen-1-yl]methyl}amino)pyridine-4-carboxylic acid | B | |
| 201 | 3-({[(4R)-7-{[4-(3,6-dihydro-2H-pyran-4-yl)phenyl](methyl)amino}-3,4-dihydro-2H-1-benzopyran-4-yl]methyl}amino)pyridine-4-carboxylic acid | B | |
| 202 | 3-({[(4R)-7-{methyl[4-(oxan-4-yl)phenyl]amino}-3,4-dihydro-2H-1-benzopyran-4-yl]methyl}amino)pyridine-4-carboxylic acid | B | C |
| 203 | 3-({[(4R)-7-(1-phenylcyclopropyl)-3,4-dihydro-2H-1-benzopyran-4-yl]methyl}amino)pyridine-4-carboxylic acid | B | |
| 204 | 3-({[(4R)-7-{methyl[4-(1-methyl-1,2,3,6-tetrahydropyridin-4-yl)phenyl]amino}-3,4-dihydro-2H-1-benzopyran-4-yl]methyl}amino)pyridine-4-carboxylic acid | A | |
| 205 | 3-({[(4R)-7-{methyl[4-(1-methylpiperidin-4-yl)phenyl]amino}-3,4-dihydro-2H-1-benzopyran-4-yl]methyl}amino)pyridine-4-carboxylic acid | A | |
| 206 | 3-({[(4R)-7-[(3,4-dimethylphenyl)(methyl)amino]-3,4-dihydro-2H-1-benzopyran-4-yl]methyl}amino)pyridine-4-carboxylic acid | B | |
| 207 | 3-({[(4R)-7-{[4-(2-hydroxyethyl)phenyl](methyl)amino}-3,4-dihydro-2H-1-benzopyran-4-yl]methyl}amino)pyridine-4-carboxylic acid | B | |
| 208 | 3-({[(4R)-7-[methyl(4-propylphenyl)amino]-3,4-dihydro-2H-1-benzopyran-4-yl]methyl}amino)pyridine-4-carboxylic acid | C | |
| 209 | 3-({[(1R)-6-{[4-(cyclopropylmethoxy)phenyl](methyl)amino}-1,2,3,4-tetrahydronaphthalen-1-yl]methyl}amino)pyridine-4-carboxylic acid | B | C |
| 210 | 3-({[(4R)-7-{methyl[4-(propan-2-yloxy)phenyl]amino}-3,4-dihydro-2H-1-benzopyran-4-yl]methyl}amino)pyridine-4-carboxylic acid | B | |
| 211 | 3-({[(4R)-7-{[4-(cyclopropylmethoxy)phenyl](methyl)amino}-3,4-dihydro-2H-1-benzopyran-4-yl]methyl}amino)pyridine-4-carboxylic acid | B | |
| 212 | 3-({[(4R)-7-[methyl(4-propoxyphenyl)amino]-3,4-dihydro-2H-1-benzopyran-4-yl]methyl}amino)pyridine-4-carboxylic acid | B | |
| 213 | 3-({[(4R)-7-[(4-cyclopropoxyphenyl)(methyl)amino]-3,4-dihydro-2H-1-benzopyran-4-yl]methyl}amino)pyridine-4-carboxylic acid | B | |
| 214 | 3-({[(4R)-7-{methyl[4-(2,2,2-trifluoroethoxy)phenyl]amino}-3,4-dihydro-2H-1-benzopyran-4-yl]methyl}amino)pyridine-4-carboxylic acid | B | |
| 215 | 3-({[(4R)-7-{[4-(cyclopropylmethyl)phenyl](methyl)amino}-3,4-dihydro-2H-1-benzopyran-4-yl]methyl}amino)pyridine-4-carboxylic acid | B | |
| 216 | 3-({[(4R)-7-[(4-cyclopropanecarbonylphenyl)(methyl)amino]-3,4-dihydro-2H-1-benzopyran-4-yl]methyl}amino)pyridine-4-carboxylic acid | B | |

Note:
Biochemical assay IC$_{50}$ data are designated within the following ranges:
A: ≤100 nM
B: >100 nM to ≤1000 nM
C: >1000 nM to ≤10,000 nM
D: >10,000 nM The ability of the following two compounds to inhibit JMJD3 or JMJD2C under the enzymatic assay conditions described herein was determined. 3-({[(4S)-7-phenyl-3,4-dihydro-2H-1-benzopyran-4-yl]methyl}amino)pyridine-4-carboxylic acid (Example 83 of U.S. Pat. No. 8,952,151) had a JMJD3 IC$_{50}$ of 0.019 µM and a JMJD2C IC$_{50}$ of 0.950 µM. 3-({[(4R)-7-phenyl-3,4-dihydro-2H-1-benzopyran-4-yl]methyl}amino)pyridine-4-carboxylic acid (Example 84 of U.S. Pat. No. 8,952,151) had a JMJD3 IC$_{50}$ of 2.15 µM and a JMJD2C IC$_{50}$ of 0.150 µM. The S-enantiomer was >100-fold more potent for JMJD3 than the R-enantiomer. The R-enantiomer was about 6-fold more potent for JMJD2C than the S-enantiomer.

Example 2

In Vitro Cell-Based Assay

The primary cellular assay for JMJD2C inhibition is an assay which measures cellular proliferation via Bromodeoxyuridine (BrdU) incorporation after 168 hours of compound incubation. Cell lines tested include the JMJD2C gene amplified cell line KYSE-150. This is a quantitative ELISA assay measuring DNA incorporation of BrdU during S-phase as a direct readout of cellular proliferation.

Assay Principle: This is a colorimetric immunoassay for the quantification of cell proliferation. Cells treated for 168 hours with test compounds are assayed for their ability to go through S-phase as a measure of their proliferative potential.

Assay Method: The human KYSE-150 (SMAD4 mut, TP53 mut) esophageal carcinoma cell line was seeded at 2,000 cells/well on a 96-well tissue culture treated plate. After an overnight incubation, cells were treated with compound in an 11-point dilution series with final concentrations ranging from 100 µM to 2 nM. Cells were then incubated in the presence of compound for 168 hours. After compound incubation the cells were assayed using a BrdU Cell Proliferation ELISA (Roche). The cells were first incubated with BrdU labeling reagent for 2 hours. After 2 hours, the BrdU incorporated cells were fixed and denatured, probed with an anti-BrdU-Peroxidase antibody for 1.5 hours and washed. Finally, a tetramethylbenzidine peroxidase substrate was added to each well for 15 minutes followed by a $H_2SO_4$ stop solution. The plate was read at 450 nm, and the raw optical density data was transferred into XLFit (IDBS) for $IC_{50}$ calculation using the formula:

fit=$(D+((V\max*(x\hat{}n))/((x\hat{}n)+(Km\hat{}n))))$

Table 4 provides the cellular $IC_{50}$ values of various compounds disclosed herein.

TABLE 4

| Example | Cellular $IC_{50}$ (µM) |
|---|---|
| 2 | A |
| 3 | D |
| 4 | B |
| 5 | B |
| 6 | A |
| 7 | A |
| 8 | A |
| 9 | A |
| 10 | A |
| 11 | A |
| 12 | B |
| 13 | B |
| 14 | D |
| 15 | C |
| 16 | B |
| 17 | B |
| 18 | A |
| 19 | A |
| 20 | A |
| 21 | A |
| 22 | A |
| 23 | A |
| 24 | A |
| 25 | D |
| 26 | C |
| 27 | C |
| 28 | C |
| 30 | B |
| 32 | C |
| 34 | B |
| 35 | C |
| 37 | B |
| 38 | D |
| 40 | A |
| 42 | B |
| 43 | A |
| 44 | B |
| 45 | B |
| 46 | A |
| 48 | C |
| 49 | C |
| 51 | C |
| 53 | B |
| 55 | B |
| 56 | C |
| 58 | A |
| 59 | C |
| 61 | C |
| 63 | D |
| 64 | A |
| 65 | B |
| 66 | A |
| 67 | B |
| 69 | B |
| 71 | B |
| 73 | B |
| 73 | B |
| 77 | A |
| 79 | A |
| 80 | C |
| 82 | D |
| 84 | D |
| 86 | D |
| 88 | D |
| 89 | D |
| 91 | C |
| 92 | C |
| 93 | C |
| 94 | B |
| 95 | D |
| 97 | C |
| 99 | C |
| 101 | A |
| 102 | B |
| 103 | B |
| 104 | B |
| 105 | A |
| 106 | B |
| 109 | B |
| 110 | A |
| 111 | B |
| 112 | C |
| 114 | B |
| 115 | B |
| 116 | B |
| 117 | B |
| 119 | B |
| 120 | B |
| 121 | A |
| 122 | A |
| 123 | A |
| 124 | C |
| 125 | B |
| 126 | B |
| 127 | B |
| 131 | A |
| 132 | A |
| 133 | C |
| 134 | A |
| 135 | A |
| 136 | A |
| 139 | A |
| 140 | A |
| 141 | B |
| 142 | D |
| 144 | A |
| 145 | A |
| 146 | A |
| 147 | B |
| 148 | B |
| 150 | A |
| 151 | A |
| 152 | B |
| 153 | A |
| 154 | A |
| 155 | D |
| 156 | B |
| 157 | A |
| 158 | B |
| 159 | C |
| 160 | A |
| 161 | A |
| 163 | A |
| 164 | A |
| 165 | C |
| 166 | D |
| 167 | A |
| 168 | A |
| 169 | A |

TABLE 4-continued

| Example | Cellular IC$_{50}$ (μM) |
|---|---|
| 170 | A |
| 171 | D |
| 172 | B |
| 173 | D |
| 174 | A |
| 175 | A |
| 176 | A |
| 177 | A |
| 178 | A |
| 179 | A |
| 180 | A |
| 183 | A |
| 184 | A |
| 185 | A |
| 186 | A |
| 187 | A |
| 188 | A |
| 189 | B |
| 190 | A |
| 191 | A |
| 192 | A |
| 193 | B |
| 194 | C |
| 196 | A |
| 197 | A |
| 198 | A |
| 199 | A |
| 200 | B |
| 201 | A |
| 202 | A |
| 203 | B |
| 204 | D |
| 205 | D |
| 206 | A |
| 207 | B |
| 208 | A |
| 209 | A |
| 210 | A |
| 211 | A |
| 212 | A |
| 213 | A |
| 214 | A |

Note:
Biochemical assay IC$_{50}$ data are designated within the following ranges:
A: ≤0.10 μM
B: >0.10 μM to ≤1.0 μM
C: >1.0 μM to ≤10 μM
D: >10 μM

Example 3

In Vivo Xenograph Study

Time release pellets containing 0.72 mg 1743 Estradiol are subcutaneously implanted into nu/nu mice. MCF-7 cells are grown in RPMI containing 10% FBS at 5% CO$_2$, 37° C. Cells are spun down and re-suspended in 50% RPMI (serum free) and 50% Matrigel at 1×10$^7$ cells/mL. MCF-7 cells are subcutaneously injected (100 μL/animal) on the right flank 2-3 days post pellet implantation and tumor volume (length× width$^2$/2) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1

Oral Tablet

A tablet is prepared by mixing 48% by weigh of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound, or a stereoisomer or pharmaceutically acceptable salt thereof, having the structure of Formula (I):

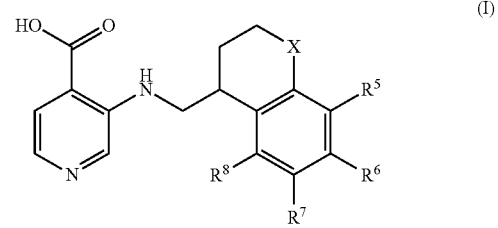

wherein,
X is O or CH$_2$;
each R$^5$, R$^6$, R$^7$ and R$^8$ is independently chosen from hydrogen, optionally substituted heterocyclyl, optionally substituted heterocyclyloxy, optionally substituted heterocyclylalkyl, optionally substituted heterocyclylalkoxy, optionally substituted C$_6$-C$_{10}$ aryl-SO$_2$—, optionally substituted heteroaryl-S—, or —N(R$^1$)(R$^2$), wherein R$^1$ is hydrogen or optionally substituted alkyl, and R$^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—;
with the provision that at least one of R$^5$, R$^6$, R$^7$ or R$^8$ is not hydrogen.

2. The compound, or a stereoisomer or pharmaceutically acceptable salt thereof, of claim 1, wherein X is O.

3. The compound, or a stereoisomer or pharmaceutically acceptable salt thereof, of claim 1, wherein X is CH$_2$.

4. The compound, or a stereoisomer or pharmaceutically acceptable salt thereof, of claim 1, wherein R$^5$ is hydrogen.

5. The compound, or a stereoisomer or pharmaceutically acceptable salt thereof, of claim 1, wherein R$^7$ is hydrogen.

6. The compound, or a stereoisomer or pharmaceutically acceptable salt thereof, of claim 1, wherein R$^8$ is hydrogen.

7. The compound, or a stereoisomer or pharmaceutically acceptable salt thereof, of claim 1, wherein R$^7$ and R$^8$ is hydrogen.

8. The compound, or a stereoisomer or pharmaceutically acceptable salt thereof, of claim 1, wherein R$^6$ is not hydrogen.

9. A compound, or a stereoisomer or pharmaceutically acceptable salt thereof, having the structure of Formula (III):

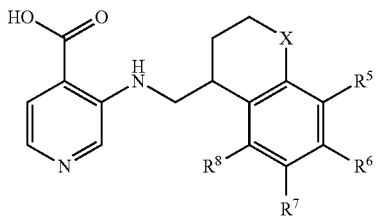

(III)

wherein,

X is O or CH2;

at least one of $R^5$, $R^6$, $R^7$ and $R^8$ is chosen from optionally substituted heterocyclyl, optionally substituted heterocyclyloxy, optionally substituted heterocyclylalkyl, optionally substituted heterocyclylalkoxy, optionally substituted $C_6$-$C_{10}$ aryl-$SO_2$—, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—; and the remaining $R^5$, $R^6$, $R^7$ and $R^8$ groups are independently chosen from hydrogen, halogen, —OH, —CN, optionally substituted $C_i$-$C_6$ alkyl, optionally substituted $C_1$-$C_6$ alkoxy, optionally substituted $C_3$-$C_7$ carbocyclyl, optionally substituted $C_3$-$C_7$ carbocyclyloxy, optionally substituted $C_4$-$C_{12}$ carbocyclylalkyl, optionally substituted $C_4$-$C_{12}$ carbocyclylalkoxy, optionally substituted $C_1$-$C_6$ alkynyl, optionally substituted $C_1$-$C_6$ alkenyl, optionally substituted $C_6$-$C_{10}$ aryl, optionally substituted $C_6$-$C_{10}$ aryloxy, optionally substituted $C_6$-$C_{10}$ aryl-S—, optionally substituted $C_7$-$C_{14}$ aralkoxy, optionally substituted heteroaryl, and optionally substituted heteroaryloxy, optionally substituted heterocyclyl, optionally substituted heterocyclyloxy, substituted heterocyclylalkyl, optionally substituted heterocyclylalkoxy, optionally substituted $C_6$-$C_{10}$ aryl-$SO_2$-, optionally substituted heteroaryl-S—, or —$N(R^1)(R^2)$, wherein $R^1$ is hydrogen or optionally substituted alkyl, and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

10. The compound, or a stereoisomer or pharmaceutically acceptable salt thereof, of claim 9, wherein X is O.

11. The compound, or a stereoisomer or pharmaceutically acceptable salt thereof, of claim 9, wherein X is $CH_2$.

12. The compound, or a stereoisomer or pharmaceutically acceptable salt thereof, of any one of claims 9, wherein $R^5$ is hydrogen.

13. The compound, or a stereoisomer or pharmaceutically acceptable salt thereof, of any one of claims 9, wherein R7 is hydrogen.

14. The compound, or a stereoisomer or pharmaceutically acceptable salt thereof, of any one of claims 9, wherein $R^8$ is hydrogen.

15. The compound, or a stereoisomer or pharmaceutically acceptable salt thereof, of any one of claims 9, wherein $R^7$ and $R^8$ are hydrogen.

16. The compound, or a stereoisomer or pharmaceutically acceptable salt thereof, of any one of claims 9, wherein $R^6$ is not hydrogen.

17. The compound, or a stereoisomer or pharmaceutically acceptable salt thereof, of any one of claims 9-16, wherein $R^6$ is optionally substituted heterocyclyl.

18. The compound, or a stereoisomer or pharmaceutically acceptable salt thereof, of any one of claims 9-16, wherein $R^6$ is optionally substituted heterocyclyloxy.

19. The compound, or a stereoisomer or pharmaceutically acceptable salt thereof, of any one of claims 9-16, wherein $R^6$ is optionally substituted heterocyclylalkyl.

20. The compound, or a stereoisomer or pharmaceutically acceptable salt thereof, of any one of claims 9-16, wherein $R^6$ is optionally substituted heterocyclylalkoxy.

21. The compound, or a stereoisomer or pharmaceutically acceptable salt thereof, of any one of claims 9-16, wherein $R^6$ is optionally substituted $C_6$-$C_{10}$ aryl-$S0_2$—, or optionally substituted heteroaryl-S—.

22. The compound, or a stereoisomer or pharmaceutically acceptable salt thereof, of any one of claims 9, wherein $R^6$ is —$N(R^1)(R^2)$, wherein $R^1$ is hydrogen and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

23. The compound, or a stereoisomer or pharmaceutically acceptable salt thereof, of any one of claims 9, wherein $R^6$ is —$N(R^1)(R^2)$, wherein $R^1$ is optionally substituted alkyl and $R^2$ is chosen from optionally substituted alkyl, optionally substituted aryl, optionally substituted heteroaryl, optionally substituted heterocyclyl, optionally substituted cycloalkyl, optionally substituted cycloalkylalkyl, optionally substituted aryl-CO—, optionally substituted heteroaryl-CO—, optionally substituted cycloalkyl-CO—, or optionally substituted alkyl-CO—.

24. The compound, or a stereoisomer or pharmaceutically acceptable salt thereof, of claim 22 or 23, wherein $R^2$ is optionally substituted alkyl.

25. The compound, or a stereoisomer or pharmaceutically acceptable salt thereof, of claim 22 or 23, wherein $R^2$ is optionally substituted aryl.

26. The compound, or a stereoisomer or pharmaceutically acceptable salt thereof, of claim 22 or 23, wherein $R^2$ is optionally substituted heteroaryl.

27. The compound, or a stereoisomer or pharmaceutically acceptable salt thereof, of claim 22 or 23, wherein $R^2$ is optionally substituted heterocyclyl.

28. The compound, or a stereoisomer or pharmaceutically acceptable salt thereof, of claim 22 or 23, wherein $R^2$ is optionally substituted cycloalkyl.

29. The compound, or a stereoisomer or pharmaceutically acceptable salt thereof, of claim 22 or 23, wherein $R^2$ is optionally substituted cycloalkylalkyl.

30. The compound, or a stereoisomer or pharmaceutically acceptable salt thereof, of claim 22 or 23, wherein $R^2$ is optionally substituted aryl-CO—.

31. The compound, or a stereoisomer or pharmaceutically acceptable salt thereof, of claim 22 or 23, wherein $R^2$ is optionally substituted heteroaryl-CO—.

32. The compound, or a stereoisomer or pharmaceutically acceptable salt thereof, of claim 22 or 23, wherein $R^2$ is optionally substituted cycloalkyl-CO—.

33. The compound, or a stereoisomer or pharmaceutically acceptable salt thereof, of claim 22 or 23, wherein $R^2$ is optionally substituted alkyl-CO—.

34. The compound, or a stereoisomer or pharmaceutically acceptable salt thereof, of claim 9, wherein each $R^5$, $R^7$ and $R^8$ is independently chosen from hydrogen, halogen, —OH, —CN, optionally substituted $C_1$-$C_6$ alkyl, or optionally substituted $C_1$-$C_6$ alkoxy.

35. A compound, or a stereoisomer or pharmaceutically acceptable salt thereof, chosen from

- 3-({[(1S)-6-[methyl(phenyl)amino]-1,2,3,4-tetrahydronaphthalen-1-yl]methyl}amino)pyridine-4-carboxylic acid;
- 3-({[(1S)-6-[methyl(phenyl)amino]-1,2,3,4-tetrahydronaphthalen-1-yl]methyl}amino)pyridine-4-carboxylic acid;
- 3-({[6-(2-oxopyrrolidin-1-yl)-1,2,3,4-tetrahydronaphthalen-1-yl]methyl}amino)pyridine-4-carboxylic acid;
- 3-({[6-(1,2,3,4-tetrahydroquinolin-1-yl)-1,2,3,4-tetrahydronaphthalen-1-yl]methyl}amino)pyridine-4-carboxylic acid;
- 3-({[6-(2,3-dihydro-1H-indol-1-yl)-1,2,3,4-tetrahydronaphthalen-1-yl]methyl}amino)pyridine-4-carboxylic acid;
- 3-({[(1R)-6-[(2-fluorophenyl)(methyl)amino]-1,2,3,4-tetrahydronaphthalen-1-yl]methyl}amino)pyridine-4-carboxylic acid;
- 3-({[(1R)-6-[(3-fluorophenyl)(methyl)amino]-1,2,3,4-tetrahydronaphthalen-1-yl]methyl}amino)pyridine-4-carboxylic acid;
- 3-({[(1R)-6-[(4-fluorophenyl)(methyl)amino]-1,2,3,4-tetrahydronaphthalen-1-yl]methyl}amino)pyridine-4-carboxylic acid;
- 3-({[(1R)-6-[(4-chlorophenyl)(methyl)amino]-1,2,3,4-tetrahydronaphthalen-1-yl]methyl}amino)pyridine-4-carboxylic acid;
- 3-[({7-[4-(trifluoromethyl)phenyl]-3,4-dihydro-2H-1-benzopyran-4-yl}methyl)amino]pyridine-4-carboxylic acid;
- 3-({[7-(furan-3-yl)-3,4-dihydro-2H-1-benzopyran-4-yl]methyl}amino)pyridine-4-carboxylic acid;
- 3-({[(4S)-7-(3-methylphenyl)-3,4-dihydro-2H-1-benzopyran-4-yl]methyl}amino)pyridine-4-carboxylic acid;
- 3-({[(4R)-7-(3-methylphenyl)-3,4-dihydro-2H-1-benzopyran-4-yl]methyl}amino)pyridine-4-carboxylic acid;
- 3-({[(4S)-7-(4-methylphenyl)-3,4-dihydro-2H-1-benzopyran-4-yl]methyl}amino)pyridine-4-carboxylic acid;
- 3-({[(4R)-7-(4-methylphenyl)-3,4-dihydro-2H-1-benzopyran-4-yl]methyl}amino)pyridine-4-carboxylic acid;
- 3-({[(4S)-7-(thiophen-3-yl)-3,4-dihydro-2H-1-benzopyran-4-yl]methyl}amino)pyridine-4-carboxylic acid;
- 3-({[(4R)-7-(thiophen-3-yl)-3,4-dihydro-2H-1-benzopyran-4-yl]methyl}amino)pyridine-4-carboxylic acid;
- 3-({[(4R)-7-cyclohexyl-3,4-dihydro-2H-1-benzopyran-4-yl]methyl}amino)pyridine-4-carboxylic acid;
- 3-({[(4S)-7-(2-methylthiophen-3-yl)-3,4-dihydro-2H-1-benzopyran-4-yl]methyl}amino)pyridine-4-carboxylic acid;
- 3-({[(4R)-7-(2-methylthiophen-3-yl)-3,4-dihydro-2H-1-benzopyran-4-yl]methyl}amino)pyridine-4-carboxylic acid;
- 3-({[7-(3-methylbut-1-yn-1-yl)-3,4-dihydro-2H-1-benzopyran-4-yl]methyl}amino)pyridine-4-carboxylic acid;
- 3-({[(4S)-7-(2-chlorophenyl)-3,4-dihydro-2H-1-benzopyran-4-yl]methyl}amino)pyridine-4-carboxylic acid;
- 3-({[4R)-7-(2-chlorophenyl)-3,4-dihydro-2H-1-benzopyran-4-yl]methyl}amino)pyridine-4-carboxylic acid;
- 3-({[R4S)-7-(3-fluoro-2-methylphenyl)-3,4-dihydro-2H-1-benzopyran-4-yl]methyl}amino)pyridine-4-carboxylic acid;
- 3-({[(4R)-7-(3-fluoro-2-methylphenyl)-3,4-dihydro-2H-1-benzopyran-4-yl]methyl}amino)pyridine-4-carboxylic acid;
- 3-({[4R)-7-(5-fluoro-2-methylphenyl)-3,4-dihydro-2H-1-benzopyran-4-yl]methyl}amino)pyridine-4-carboxylic acid;
- 3-({[4R)-7-(2-chloro-3-fluorophenyl)-3,4-dihydro-2H-1-benzopyran-4-yl]methyl}amino)pyridine-4-carboxylic acid;
- 3-({[4R)-7-(2-chloro-5-fluorophenyl)-3,4-dihydro-2H-1-benzopyran-4-yl]methyl}amino)pyridine-4-carboxylic acid;
- 3-({[(4R)-7-[2-(trifluoromethyl)phenyl]-3,4-dihydro-2H-1-benzopyran-4-yl]methyl}amino)pyridine-4-carboxylic acid;
- 3-({[(4S)-7-phenoxy-3,4-dihydro-2H-1-benzopyran-4-yl]methyl}amino)pyridine-4-carboxylic acid;
- 3-({[(4R)-7-phenoxy-3,4-dihydro-2H-1-benzopyran-4-yl]methyl}amino)pyridine-4-carboxylic acid;
- 3-({[7-(thiophen-2-ylsulfanyl)-3,4-dihydro-2H-1-benzopyran-4-yl]methyl}amino)pyridine-4-carboxylic acid;
- 3-({[4S)-7-[(2-methylphenyl)sulfanyl]-3,4-dihydro-2H-1-benzopyran-4-yl]methyl}amino)pyridine-4-carboxylic acid;
- 3-({[(4R)-7-[(2-methylphenyl)sulfanyl]-3,4-dihydro-2H-1-benzopyran-4-yl]methyl}amino)pyridine-4-carboxylic acid;
- 3-({[4S)-7-[(3-fluorophenyl)sulfanyl]-3,4-dihydro-2H-1-benzopyran-4-yl]methyl}amino)pyridine-4-carboxylic acid;
- 3-({[(4R)-7-[(3-fluorophenyl)sulfanyl]-3,4-dihydro-2H-1-benzopyran-4-yl]methyl}amino)pyridine-4-carboxylic acid;
- 3-({[(4S)-7-[(4-fluorophenyl)sulfanyl]-3,4-dihydro-2H-1-benzopyran-4-yl]methyl}amino)pyridine-4-carboxylic acid;
- 3-({[(4R)-7-[(4-fluorophenyl)sulfanyl]-3,4-dihydro-2H-1-benzopyran-4-yl]methyl}amino)pyridine-4-carboxylic acid;
- 3-[({6-[(6-methylpyridin-2-yl)oxy]-1,2,3,4-tetrahydronaphthalen-1-yl}methyl)amino]pyridine-4-carboxylic acid;
- 3-({[(1S)-6-(2-methylphenoxy)-1,2,3,4-tetrahydronaphthalen-1-yl]methyl}amino)pyridine-4-carboxylic acid;
- 3-({[(1R)-6-(2-methylphenoxy)-1,2,3,4-tetrahydronaphthalen-1-yl]methyl}amino)pyridine-4-carboxylic acid;
- 3-{[(6-propoxy-1,2,3,4-tetrahydronaphthalen-1-yl)methyl]amino}pyridine-4-carboxylic acid;
- 3-({[(1S)-6-(difluoromethoxy)-1,2,3,4-tetrahydronaphthalen-1-yl]methyl}amino)pyridine-4-carboxylic acid;
- 3-({[(1R)-6-(difluoromethoxy)-1,2,3,4-tetrahydronaphthalen-1-yl]methyl}amino)pyridine-4-carboxylic acid;
- 3-[({6-[2-(trifluoromethyl)phenoxy]-1,2,3,4-tetrahydronaphthalen-1-yl}methyl)amino]pyridine-4-carboxylic acid;
- 3-({[6-(oxan-4-ylmethoxy)-1,2,3,4-tetrahydronaphthalen-1-yl]methyl}amino)pyridine-4-carboxylic acid;
- 3-({[(1R)-6-(4-fluoro-2-methylphenoxy)-1,2,3,4-tetrahydronaphthalen-1-yl]methyl}amino)pyridine-4-carboxylic acid;

3-({[(1R)-6-(2,4-difluorophenoxy)-1,2,3,4-tetrahydronaphthalen-1-yl]methyl}amino)pyridine-4-carboxylic acid;
3-({[(1R)-6-(2-fluoro-4-methylphenoxy)-1,2,3,4-tetrahydronaphthalen-1-yl]methyl}amino)pyridine-4-carboxylic acid;
3-({[(1R)-6-(2-chlorophenoxy)-1,2,3,4-tetrahydronaphthalen-1-yl]methyl}amino)pyridine-4-carboxylic acid;
3-({[(1S)-6-[(3-methylphenyl)sulfanyl]-1,2,3,4-tetrahydronaphthalen-1-yl]methyl}amino)pyridine-4-carboxylic acid;
3-({[(1R)-6-[(3-methylphenyl)sulfanyl]-1,2,3,4-tetrahydronaphthalen-1-yl]methyl}amino)pyridine-4-carboxylic acid;
3-({[(1S)-6-[(2-methylphenyl) sulfanyl]-1,2,3,4-tetrahydronaphthalen-1-yl]methyl}amino)pyridine-4-carboxylic acid;
3-({[(1R)-6-[(2-methylphenyl)sulfanyl]-1,2,3,4-tetrahydronaphthalen-1-yl]methyl}amino)pyridine-4-carboxylic acid;
3-({[(1S)-6-[(2-fluorophenyl)sulfanyl]-1,2,3,4-tetrahydronaphthalen-1-yl]methyl}amino)pyridine-4-carboxylic acid;
3-({[(1R)-6-[(2-fluorophenyl)sulfanyl]-1,2,3,4-tetrahydronaphthalen-1-yl]methyl}amino)pyridine-4-carboxylic acid;
3-({[(1S)-6-[(3-fluorophenyl)sulfanyl]-1,2,3,4-tetrahydronaphthalen-1-yl]methyl}amino)pyridine-4-carboxylic acid;
3-({[(1R)-6-[(3-fluorophenyl)sulfanyl]-1,2,3,4-tetrahydronaphthalen-1-yl]methyl}amino)pyridine-4-carboxylic acid;
3-({[(1S)-6-[(4-fluorophenyl)sulfanyl]-1,2,3,4-tetrahydronaphthalen-1-yl]methyl}amino)pyridine-4-carboxylic acid;
3-({[(1R)-6-[(4-fluorophenyl)sulfanyl]-1,2,3,4-tetrahydronaphthalen-1-yl]methyl}amino)pyridine-4-carboxylic acid;
3-({[(1S)-6-[(4-methylphenyl) sulfanyl]-1,2,3,4-tetrahydronaphthalen-1-yl]methyl}amino)pyridine-4-carboxylic acid;
3-({[(1R)-6-[(4-methylphenyl)sulfanyl]-1,2,3,4-tetrahydronaphthalen-1-yl]methyl}amino)pyridine-4-carboxylic acid;
3-({[6-(pyridin-2-ylsulfanyl)-1,2,3,4-tetrahydronaphthalen-1-yl]methyl}amino)pyridine-4-carboxylic acid;
3-({[(1S)-6-(benzenesulfonyl)-1,2,3,4-tetrahydronaphthalen-1-yl]methyl}amino)pyridine-4-carboxylic acid;
3-({[(1R)-6-(benzenesulfonyl)-1,2,3,4-tetrahydronaphthalen-1-yl]methyl}amino)pyridine-4-carboxylic acid;
3-({[(1S)-6-(4-methylbenzenesulfonyl)-1,2,3,4-tetrahydronaphthalen-1-yl]methyl}amino)pyridine-4-carboxylic acid;
3-({[(1R)-6-(4-methylbenzenesulfonyl)-1,2,3,4-tetrahydronaphthalen-1-yl]methyl}amino)pyridine-4-carboxylic acid;
3-({[(1S)-6-(3-methylbenzenesulfonyl)-1,2,3,4-tetrahydronaphthalen-1-yl]methyl}amino)pyridine-4-carboxylic acid;
3-({[(1R)-6-(3-methylbenzenesulfonyl)-1,2,3,4-tetrahydronaphthalen-1-yl]methyl}amino)pyridine-4-carboxylic acid;
3-({[6-(3-fluorobenzenesulfonyl)-1,2,3,4-tetrahydronaphthalen-1-yl]methyl}amino)pyridine-4-carboxylic acid;
3-({[6-(oxan-4-yl)-1,2,3,4-tetrahydronaphthalen-1-yl]methyl}amino)pyridine-4-carboxylic acid;
3-({[6-(2-methylpyridin-4-yl)-1,2,3,4-tetrahydronaphthalen-1-yl]methyl}amino)pyridine-4-carboxylic acid;
3-({[(1S)-6-ethyl-1,2,3,4-tetrahydronaphthalen-1-yl]methyl}amino)pyridine-4-carboxylic acid;
3-({[(1R)-6-ethyl-1,2,3,4-tetrahydronaphthalen-1-yl]methyl}amino)pyridine-4-carboxylic acid;
3-({2H,3H,6H,7H,8H,9H-naphtho[1,2-b]furan-6-ylmethyl}amino)pyridine-4-carboxylic acid;
3-{[(6,7-dimethyl-3,4-dihydro-2H-1-benzopyran-4-yl)methyl amino}pyridine-4-carboxylic acid;
3-{[(6-methoxy-7-methyl-1,2,3,4-tetrahydronaphthalen-1-yl)methyl]amino}pyridine-4-carboxylic acid;
3-{[(6,8-dimethoxy-1,2,3,4-tetrahydronaphthalen-1-yl)methyl]amino}pyridine-4-carboxylic acid;
3-({[(1S)-7-fluoro-6-methoxy-1,2,3,4-tetrahydronaphthalen-1-yl]methyl}amino)pyridine-4-carboxylic acid;
3-({[(1R)-7-fluoro-6-methoxy-1,2,3,4-tetrahydronaphthalen-1-yl]methyl}amino)pyridine-4-carboxylic acid;
3-({[(1S)-6-methoxy-5-methyl-1,2,3,4-tetrahydronaphthalen-1-yl]methyl}amino)pyridine-4-carboxylic acid;
3-({[(1R)-6-methoxy-5-methyl-1,2,3,4-tetrahydronaphthalen-1-yl]methyl}amino)pyridine-4-carboxylic acid;
3-({[(4S)-7-(2-methylphenyl)-3,4-dihydro-2H-1-benzopyran-4-yl]methyl}amino)pyridine-4-carboxylic acid;
3-({[(4R)-7-(2-methylphenyl)-3,4-dihydro-2H-1-benzopyran-4-yl]methyl}amino)pyridine-4-carboxylic acid;
3-({[(4R)-7-(5-fluoro-2-methoxyphenyl)-3,4-dihydro-2H-1-benzopyran-4-yl]methyl}amino)pyridine-4-carboxylic acid;
3-({[(1R)-6-[(4-cyanophenyl)(methyl)amino]-1,2,3,4-tetrahydronaphthalen-1-yl]methyl}amino)pyridine-4-carboxylic acid;
3-({[(4R)-7-[(2,4-difluorophenyl)(methyl)amino]-3,4-dihydro-2H-1-benzopyran-4-yl]methyl}amino)pyridine-4-carboxylic acid;
3-({[(4R)-7-[methyl(3-methylphenyl)amino]-3,4-dihydro-2H-1-benzopyran-4-yl]methyl}amino)pyridine-4-carboxylic acid;
3-({[(1R)-6-(pyrrolidin-1-yl)-1,2,3,4-tetrahydronaphthalen-1-yl]methyl}amino)pyridine-4-carboxylic acid;
3-({[(4R)-7-(2-chloro-5-methoxyphenyl)-3,4-dihydro-2H-1-benzopyran-4-yl]methyl}amino)pyridine-4-carboxylic acid;
3-({[(1R)-6-(3,4-dihydro-2H-1,4-benzoxazin-4-yl)-1,2,3,4-tetrahydronaphthalen-1-yl]methyl}amino)pyridine-4-carboxylic acid;
3-({[(4R)-7-[(3,5-difluorophenyl)(methyl)amino]-3,4-dihydro-2H-1-benzopyran-4-yl]methyl}amino)pyridine-4-carboxylic acid;
3-({[(4R)-7-[(3-chlorophenyl)(methyl)amino]-3,4-dihydro-2H-1-benzopyran-4-yl]methyl}amino)pyridine-4-carboxylic acid;
3-({[(4R)-7-[methyl(2-methylphenyl)amino]-3,4-dihydro-2H-1-benzopyran-4-yl]methyl}amino)pyridine-4-carboxylic acid;
3-({[(4R)-7-[(4-fluoro-3-methoxyphenyl)(methyl)amino]-3,4-dihydro-2H-1-benzopyran-4-yl]methyl}amino)pyridine-4-carboxylic acid;
3-({[(1R)-6-[methyl(oxan-4-yl)amino]-1,2,3,4-tetrahydronaphthalen-1-yl]methyl}amino)pyridine-4-carboxylic acid;
3-({[(1R)-6-[(4-fluoro-3-methoxyphenyl)(methyl)amino]-1,2,3,4-tetrahydronaphthalen-1-yl]methyl}amino)pyridine-4-carboxylic acid;
3-({[(1R)-6-[(3-cyanophenyl)(methyl)amino]-1,2,3,4-tetrahydronaphthalen-1-yl]methyl}amino)pyridine-4-carboxylic acid;

3-({[(4R)-7-(2-methoxyphenyl)-3,4-dihydro-2H-1-benzopyran-4-yl]methyl}amino)pyridine-4-carboxylic acid;

3-({[(4R)-7-[(3-cyanophenyl)(methyl)amino]-3,4-dihydro-2H-1-benzopyran-4-yl]methyl}amino)pyridine-4-carboxylic acid;

3-({[(4R)-7-(4-fluoro-2-methoxyphenyl)-3,4-dihydro-2H-1-benzopyran-4-yl]methyl}amino)pyridine-4-carboxylic acid;

3-({[(4R)-7-[(4-cyanophenyl)(methyl)amino]-3,4-dihydro-2H-1-benzopyran-4-yl]methyl}amino)pyridine-4-carboxylic acid;

3-({[(1R)-6-[(4-cyclopropylmethyl)(methyl)amino]-1,2,3,4-tetrahydronaphthalen-1-yl]methyl}amino)pyridine-4-carboxylic acid;

3-({[(1R)-6-[methyl(6-methoxypyridin-2-yl)amino]-1,2,3,4-tetrahydronaphthalen-1-yl]methyl}amino)pyridine-4-carboxylic acid;

3-({[(1R)-6-[methyl(5-methylpyridin-2-yl)amino]-1,2,3,4-tetrahydronaphthalen-1-yl]methyl}amino)pyridine-4-carboxylic acid;

3-({[(1R)-6-[methyl(6-methylpyridin-2-yl)amino]-1,2,3,4-tetrahydronaphthalen-1-yl]methyl}amino)pyridine-4-carboxylic acid;

3-({[(4R)-7-(2-cyanophenyl)-3,4-dihydro-2H-1-benzopyran-4-yl]methyl}amino)pyridine-4-carboxylic acid;

3-({[(1R)-6-[methyl(1-methyl-1H-pyrazol-3-yl)amino]-1,2,3,4-tetrahydronaphthalen-1-yl]methyl}amino)pyridine-4-carboxylic acid;

3-({[(4R)-7-[(4-ethynylphenyl)(methyl)amino]-3,4-dihydro-2H-1-benzopyran-4-yl]methyl}amino)pyridine-4-carboxylic acid;

3-({[(4R)-7-[(1,3-dihydro-2-benzofuran-5-yl)(methyl)amino]-3,4-dihydro-2H-1-benzopyran-4-yl]methyl}amino)pyridine-4-carboxylic acid;

3-({[(4R)-7-{methyl[4-(trifluoromethyl)phenyl]amino}-3,4-dihydro-2H-1-benzopyran-4-yl]methyl}amino)pyridine-4-carboxylic acid;

3-[({7-[phenyl(2,2,2-trifluoroethyl)amino]-3,4-dihydro-2H-1-benzopyran-4-yl}methyl)amino]pyridine-4-carboxylic acid;

3-({[(1R)-6-[benzyl(methyl)amino]-1,2,3,4-tetrahydronaphthalen-1-yl]methyl}amino)pyridine-4-carboxylic acid;

3-({[(4R)-7-[(2,3-dihydro-1H-inden-5-yl)(methyl)amino]-3,4-dihydro-2H-1-benzopyran-4-yl]methyl}amino)pyridine-4-carboxylic acid;

3-({[(1R)-6-[(1,3-dihydro-2-benzofuran-5-yl)(methyl)amino]-1,2,3,4-tetrahydronaphthalen-1-yl]methyl}amino)pyridine-4-carboxylic acid;

3-({[(1R)-6-[cyclopentyl(methyl)amino]-1,2,3,4-tetrahydronaphthalen-1-yl]methyl}amino)pyridine-4-carboxylic acid;

3-({[(4R)-7-[(4-cyclopropylphenyl)(methyl)amino]-3,4-dihydro-2H-1-benzopyran-4-yl]methyl}amino)pyridine-4-carboxylic acid;

3-({[(1R)-6-[(1-benzofuran-6-yl)(methyl)amino]-1,2,3,4-tetrahydronaphthalen-1-yl]methyl}amino)pyridine-4-carboxylic acid;

3-({[(4R)-7-[(1-benzofuran-5-yl)(methyl)amino]-3,4-dihydro-2H-1-benzopyran-4-yl]methyl}amino)pyridine-4-carboxylic acid;

3-({[(1R)-6-[(1-benzofuran-5-yl)(methyl)amino]-1,2,3,4-tetrahydronaphthalen-1-yl]methyl}amino)pyridine-4-carboxylic acid;

3-({[(4R)-7-(2-hydroxyphenyl)-3,4-dihydro-2H-1-benzopyran-4-yl]methyl}amino)pyridine-4-carboxylic acid;

3-({[(4R)-7-[methyl(2-methyl-1,3-thiazol-4-yl)amino]-3,4-dihydro-2H-1-benzopyran-4-yl]methyl}amino)pyridine-4-carboxylic acid;

3-({[(1R)-6-[methyl(4-methylphenyl)amino]-1,2,3,4-tetrahydronaphthalen-1-yl]methyl}amino)pyridine-4-carboxylic acid;

3-({[(4R)-7-[(1-benzofuran-6-yl)(methyl)amino]-3,4-dihydro-2H-1-benzopyran-4-yl]methyl}amino)pyridine-4-carboxylic acid;

3-[(3,4-dihydro-1H-2-benzopyran-1-ylmethyl)amino]pyridine-4-carboxylic acid 3-({[(1R)-6-[methyl(3-methylphenyl)amino]-1,2,3,4-tetrahydronaphthalen-1-yl]methyl}amino)pyridine-4-carboxylic acid;

3-({[(1R)-6-[methyl(thiophen-2-yl)amino]-1,2,3,4-tetrahydronaphthalen-1-yl]methyl}amino)pyridine-4-carboxylic acid;

3-({[(4R)-7-[methyl(5-methylpyridin-2-yl)amino]-3,4-dihydro-2H-1-benzopyran-4-yl]methyl}amino)pyridine-4-carboxylic acid;

3-[({6-[methyl(phenyl)amino]-3,4-dihydro-1H-2-benzopyran-1-yl}methyl)amino]pyridine-4-carboxylic acid;

3-({[(1R)-6-[(2-hydroxyethyl)(phenyl)amino]-1,2,3,4-tetrahydronaphthalen-1-yl]methyl}amino)pyridine-4-carboxylic acid;

3-({[(4R)-7-[methyl(6-methylpyridin-2-yl)amino]-3,4-dihydro-2H-1-benzopyran-4-yl]methyl}amino)pyridine-4-carboxylic acid;

3-[(1,2,3,4-tetrahydroisoquinolin-1-ylmethyl)amino]pyridine-4-carboxylic acid 3-({[(1R)-6-[(3-methoxyphenyl)(methyl)amino]-1,2,3,4-tetrahydronaphthalen-1-yl]methyl}amino)pyridine-4-carboxylic acid;

3-({[(4R)-7-[(3-fluoro-4-methylphenyl)(methyl)amino]-3,4-dihydro-2H-1-benzopyran-4-yl]methyl}amino)pyridine-4-carboxylic acid;

3-({[(4R)-7-[(5-chloropyridin-2-yl)(methyl)amino]-3,4-dihydro-2H-1-benzopyran-4-yl]methyl}amino)pyridine-4-carboxylic acid;

3-({[(4R)-7-[(5-cyclopropylpyridin-2-yl)(methyl)amino]-3,4-dihydro-2H-1-benzopyran-4-yl]methyl}amino)pyridine-4-carboxylic acid;

3-({[(4R)-7-[(4-ethylphenyl)(methyl)amino]-3,4-dihydro-2H-1-benzopyran-4-yl]methyl}amino)pyridine-4-carboxylic acid;

3-({[(1R)-6-[methyl(1-methyl-2-oxo-1,2-dihydropyridin-4-yl)amino]-1,2,3,4-tetrahydronaphthalen-1-yl]methyl}amino)pyridine-4-carboxylic acid;

3-({[(1R)-6-[methyl(5-methylpyrimidin-2-yl)amino]-1,2,3,4-tetrahydronaphthalen-1-yl]methyl}amino)pyridine-4-carboxylic acid;

3-({[(4R)-7-[(5-ethylpyridin-2-yl)(methyl)amino]-3,4-dihydro-2H-1-benzopyran-4-yl]methyl}amino)pyridine-4-carboxylic acid;

3-({[(1R)-6-{[4-(hydroxymethyl)phenyl](methyl)amino}-1,2,3,4-tetrahydronaphthalen-1-yl]methyl}amino)pyridine-4-carboxylic acid;

3-({[(1R)-6-[methyl(1-methyl-1H-pyrazol-4-yl)amino]-1,2,3,4-tetrahydronaphthalen-1-yl]methyl}amino)pyridine-4-carboxylic acid;

3-({[(1R)-6-{[4-(dimethylamino)phenyl](methyl)amino}-1,2,3,4-tetrahydronaphthalen-1-yl]methyl}amino)pyridine-4-carboxylic acid;

3-({[(1R)-6-[(4-cyclopropylphenyl)(methyl)amino]-1,2,3,4-tetrahydronaphthalen-1-yl]methyl}amino)pyridine-4-carboxylic acid;

3-({[(1R)-6-(2,3,4,5-tetrahydro-1H-1-benzazepin-1-yl)-1,2,3,4-tetrahydronaphthalen-1-yl]methyl}amino)pyridine-4-carboxylic acid;

3-({[(1R)-6-[(4-cyclopropylphenyl)(2-methoxyethyl)amino]-1,2,3,4-tetrahydronaphthalen-1-yl]methyl}amino)pyridine-4-carboxylic acid;

3-({[(1R)-6-{[4-(methoxymethyl)phenyl](methyl)amino]-1,2,3,4-tetrahydronaphthalen-1-yl]methyl}amino)pyridine-4-carboxylic acid;

3-({[(1R)-6-[(4-hydroxyphenyl)(methyl)amino]-1,2,3,4-tetrahydronaphthalen-1-yl]methyl}amino)pyridine-4-carboxylic acid;

3-({[(1R)-6-[(dimethyl-1,2-oxazol-4-yl)(methyl)amino]-1,2,3,4-tetrahydronaphthalen-1-yl]methyl}amino)pyridine-4-carboxylic acid;

3-({[(1R)-6-1methyl[4-(pyrrolidin-1-yl)phenyl]amino}-1,2,3,4-tetrahydronaphthalen-1-yl]methyl}amino)pyridine-4-carboxylic acid;

3-({[(1R)-6-({[(1R)-1-hydroxyethyl]phenyl}(methyl)amino]-1,2,3,4-tetrahydronaphthalen-1-yl]methyl}amino)pyridine-4-carboxylic acid;

3-({[(1R)-6-({4-(1S)-1-hydroxyethyl]phenyl}(methyl)amino]-1,2,3,4-tetrahydronaphthalen-1-yl]methyl}amino)pyridine-4-carboxylic acid;

3-({[(1R)-6-{methyl[4-(morpholin-4-yl)phenyl]amino}-1,2,3,4-tetrahydronaphthalen-1-yl]methyl}amino)pyridine-4-carboxylic acid;

3-({[(1R)-6-[methyl(5-methyl-1,2-oxazol-3-yl)amino]-1,2,3,4-tetrahydronaphthalen-1-yl]methyl}amino)pyridine-4-carboxylic acid;

3-({[(1R)-6-[(2-methoxyphenyl)(methyl)amino]-1,2,3,4-tetrahydronaphthalen-1-yl]methyl}amino)pyridine-4-carboxylic acid;

3-({[(1R)-6-[methyl(pyridin-4-yl)amino]-1,2,3,4-tetrahydronaphthalen-1-yl]methyl}amino)pyridine-4-carboxylic acid;

3-({[(1R)-6-{[4-(3,6-dihydro-2H-pyran-4-yl)phenyl](methyl)amino}-1,2,3,4-tetrahydronaphthalen-1-yl]methyl}amino)pyridine-4-carboxylic acid;

3-({[(1R)-6-{methyl[4-(oxan-4-yl)phenyl]amino}-1,2,3,4-tetrahydronaphthalen-1-yl]methyl}amino)pyridine-4-carboxylic acid;

3-({[(4R)-7-[(4-ethenylphenyl)(methyl)amino]-3,4-dihydro-2H-1-benzopyran-4-yl]methyl}amino)pyridine-4-carboxylic acid;

3-({[(1R)-6-[(4-methoxyphenyl)(methyl)amino]-1,2,3,4-tetrahydronaphthalen-1-yl]methyl}amino)pyridine-4-carboxylic acid;

3-({[(4R)-7-[(4-methoxyphenyl)(methyl)amino]-3,4-dihydro-2H-1-benzopyran-4-yl]methyl}amino)pyridine-4-carboxylic acid;

3-({[(4R)-7-{methyl[4-(pyrrolidin-1-yl)phenyl]amino}-3,4-dihydro-2H-1-benzopyran-4-yl]methyl}amino)pyridine-4-carboxylic acid;

3-({[(1R)-6-{[4-(azetidin-1-yl)phenyl](methyl)amino}-1,2,3,4-tetrahydronaphthalen-1-yl]methyl}amino)pyridine-4-carboxylic acid;

3-({[(1R)-6-{methyl[4-(trifluoromethoxy)phenyl]amino}-1,2,3,4-tetrahydronaphthalen-1-yl]methyl}amino)pyridine-4-carboxylic acid;

3-({[(4R)-7-{methyl[4-(trifluoromethoxy)phenyl]amino}-3,4-dihydro-2H-1-benzopyran-4-yl]methyl}amino)pyridine-4-carboxylic acid;

3-({[(4R)-7-{[4-(azetidin-1-yl)phenyl](methyl)amino}-3,4-dihydro-2H-1-benzopyran-4-yl]methyl}amino)pyridine-4-carboxylic acid;

3-({[(1R)-6-{[4-(difluoromethoxy)phenyl](methyl)amino}-1,2,3,4-tetrahydronaphthalen-1-yl]methyl}amino)pyridine-4-carboxylic acid;

3-({[(1R)-6-[(4-ethoxyphenyl)(methyl)amino]-1,2,3,4-tetrahydronaphthalen-1-yl]methyl}amino)pyridine-4-carboxylic acid;

3-({[(4R)-7-[(4-ethoxyphenyl)(methyl)amino]-3,4-dihydro-2H-1-benzopyran-4-yl]methyl}amino)pyridine-4-carboxylic acid;

3-({[(1R)-6-{methyl[4-(1H-pyrazol-1-yl)phenyl]amino}-1,2,3,4-tetrahydronaphthalen-1-yl]methyl}amino)pyridine-4-carboxylic acid;

3-({[(4R)-7-{methyl[4-(1H-pyrazol-1-yl)phenyl]amino}-3,4-dihydro-2H-1-benzopyran-4-yl]methyl}amino)pyridine-4-carboxylic acid;

3-({[(4R)-7-{[4-(difluoromethoxy)phenyl](methyl)amino}-3,4-dihydro-2H-1-benzopyran-4-yl]methyl}amino)pyridine-4-carboxylic acid;

3-({[(1R)-6-[methyl(phenyl)amino]-1,2,3,4-tetrahydronaphthalen-1-yl]methyl}amino)pyridazine-4-carboxylic acid;

3-({[(1R)-6-{[4-(1H-imidazol-1-yl)phenyl](methyl)amino}-1,2,3,4-tetrahydronaphthalen-1-yl]methyl}amino)pyridine-4-carboxylic acid;

3-({[(4R)-7-{[4-(1H-imidazol-1-yl)phenyl](methyl)amino}-3,4-dihydro-2H-1-benzopyran-4-yl]methyl}amino)pyridine-4-carboxylic acid;

3-({[(1R)-6-{[4-(3,3-difluoroazetidin-1-yl)phenyl](methyl)amino}-1,2,3,4-tetrahydronaphthalen-1-yl]methyl}amino)pyridine-4-carboxylic acid;

3-({[(4R)-7-{[4-(3,3-difluoroazetidin-1-yl)phenyl](methyl)amino}-3,4-dihydro-2H-1-benzopyran-4-yl]methyl}amino)pyridine-4-carboxylic acid;

3-({[(1R)-6-{[4-(2-methoxyethoxy)phenyl](methyl)amino}-1,2,3,4-tetrahydronaphthalen-1-yl]methyl}amino)pyridine-4-carboxylic acid;

3-({[(4R)-7-(1-phenylethyl)-3,4-dihydro-2H-1-benzopyran-4-yl]methyl}amino)pyridine-4-carboxylic acid;

3-({[(4R)-7-{methyl[5-(propan-2-yl)pyridin-2-yl]amino}-3,4-dihydro-2H-1-benzopyran-4-yl]methyl}amino)pyridine-4-carboxylic acid;

3-({[(1R)-6-{[4-(3-hydroxyazetidin-1-yl)phenyl](methyl)amino}-1,2,3,4-tetrahydronaphthalen-1-yl]methyl}amino)pyridine-4-carboxylic acid;

3-({[(4R)-7-{[4-(3,6-dihydro-2H-pyran-4-yl)phenyl](methyl)amino}-3,4-dihydro-2H-1-benzopyran-4-yl]methyl}amino)pyridine-4-carboxylic acid;

3-({[(4R)-7-1methyl[4-(oxan-4-yl)phenyl]amino}-3,4-dihydro-2H-1-benzopyran-4-yl]methyl}amino)pyridine-4-carboxylic acid;

3-({[(4R)-7-(1-phenylcyclopropyl)-3,4-dihydro-2H-1-benzopyran-4-yl]methyl}amino)pyridine-4-carboxylic acid;

3-({[(4R)-7-{methyl[4-(1-methyl-1,2,3,6-tetrahydropyridin-4-yl)phenyl]amino}-3,4-dihydro-2H-1-benzopyran-4-yl]methyl}amino)pyridine-4-carboxylic acid;

3-({[(4R)-7-{methyl[4-(1-methylpiperidin-4-yl)phenyl]amino}-3,4-dihydro-2H-1-benzopyran-4-yl]methyl}amino)pyridine-4-carboxylic acid;

3-({[(4R)-7-[(3,4-dimethylphenyl)(methyl)amino]-3,4-dihydro-2H-1-benzopyran-4-yl]methyl}amino)pyridine-4-carboxylic acid;

3-({[(4R)-7-{[4-(2-hydroxyethyl)phenyl](methyl)amino]-3,4-dihydro-2H-1-benzopyran-4-yl]methyl}amino)pyridine-4-carboxylic acid;

3-({[(4R)-7-[methyl(4-propylphenyl)amino]-3,4-dihydro-2H-1-benzopyran-4-yl]methyl}amino)pyridine-4-carboxylic acid;

3-({[(1R)-6-{[4-(cyclopropylmethoxy)phenyl](methyl)amino}-1,2,3,4-tetrahydronaphthalen-1-yl]methyl}amino)pyridine-4-carboxylic acid;

3-({[(4R)-7-{methyl[4-(propan-2-yloxy)phenyl]amino}-3,4-dihydro-2H-1-benzopyran-4-yl]methyl}amino)pyridine-4-carboxylic acid;

3-({[(4R)-7-{[4-(cyclopropylmethoxy)phenyl](methyl)amino}-3,4-dihydro-2H-1-benzopyran-4-yl]methyl}amino)pyridine-4-carboxylic acid;

3-({[(4R)-7-[methyl(4-propoxyphenyl)amino]-3,4-dihydro-2H-1-benzopyran-4-yl]methyl}amino)pyridine-4-carboxylic acid;

3-({[(4R)-7-{methyl[4-(2,2,2-trifluoroethoxy)phenyl]amino}-3,4-dihydro-2H-1-benzopyran-4-yl]methyl}amino)pyridine-4-carboxylic acid;

3-({[(4R)-7-{[4-(cyclopropylmethyl)phenyl](methyl)amino}-3,4-dihydro-2H-1-benzopyran-4-yl]methyl}amino)pyridine-4-carboxylic acid; and 3-({[(4R)-7-[(4-cyclopropanecarbonylphenyl)(methyl)amino]-3,4-dihydro-2H-1-benzopyran-4-yl]methyl}amino)pyridine-4-carboxylic acid.

36. A pharmaceutical composition comprising a pharmaceutically acceptable carrier and a compound of claim 1 or 9, or a stereoisomer or pharmaceutically acceptable salt thereof.

\* \* \* \* \*